US008642759B2

(12) United States Patent
Rheault

(10) Patent No.: US 8,642,759 B2
(45) Date of Patent: Feb. 4, 2014

(54) BENZENE SULFONAMIDE THIAZOLE AND OXAZOLE COMPOUNDS

(71) Applicant: GlaxoSmithKline LLC, Philadelphia, PA (US)

(72) Inventor: Tara Renae Rheault, Durham, NC (US)

(73) Assignee: GlaxoSmithKline LLC, Philadelphia, PA (US)

( * ) Notice: Subject to any disclaimer, the term of this patent is extended or adjusted under 35 U.S.C. 154(b) by 0 days.

(21) Appl. No.: 13/755,466

(22) Filed: Jan. 31, 2013

(65) Prior Publication Data

US 2013/0144055 A1    Jun. 6, 2013

Related U.S. Application Data

(63) Continuation of application No. 12/991,004, filed as application No. PCT/US2009/042682 on May 4, 2009, now Pat. No. 8,415,345.

(60) Provisional application No. 61/050,744, filed on May 6, 2008.

(51) Int. Cl.
*C07D 417/04* (2006.01)

(52) U.S. Cl.
USPC .......................................................... 544/331

(58) Field of Classification Search
USPC ................. 544/60, 122, 295, 331; 514/227.8, 514/235.8, 252.14, 275, 256
See application file for complete search history.

(56) References Cited

U.S. PATENT DOCUMENTS

| | | | |
|---|---|---|---|
| 5,877,193 A | 3/1999 | Cesura et al. | |
| 6,197,779 B1 | 3/2001 | Andries et al. | |
| 6,294,558 B1 | 9/2001 | Ando et al. | |
| 6,451,794 B1 | 9/2002 | Beswick et al. | |
| 6,620,828 B2 | 9/2003 | Chu et al. | |
| 6,750,217 B2 | 6/2004 | Barrett et al. | |
| 6,831,097 B2 | 12/2004 | Beswick et al. | |
| 6,861,429 B2 | 3/2005 | Beswick et al. | |
| 7,026,336 B1 | 4/2006 | Dean et al. | |
| 7,223,772 B1 | 5/2007 | Campbell et al. | |
| 7,307,071 B2 | 12/2007 | Lyons et al. | |
| 7,713,960 B2 | 5/2010 | Sebti et al. | |
| 7,807,673 B2 | 10/2010 | Uehling et al. | |
| 7,812,022 B2 | 10/2010 | Uehling et al. | |
| 7,994,185 B2 | 8/2011 | Rheault et al. | |
| 8,415,345 B2* | 4/2013 | Adjabeng et al. ........... | 514/227.8 |
| 2002/0091116 A1 | 7/2002 | Zhu et al. | |
| 2004/0121375 A1 | 6/2004 | Eveleigh et al. | |
| 2004/0132786 A1 | 7/2004 | Chuyba et al. | |
| 2005/0267032 A1 | 12/2005 | Fulp et al. | |
| 2005/0267060 A1 | 12/2005 | Robertson et al. | |
| 2005/0277118 A1 | 12/2005 | Roth et al. | |
| 2005/0288286 A1 | 12/2005 | Flynn et al. | |
| 2006/0094747 A1 | 5/2006 | Van Zandt et al. | |
| 2006/0100251 A1 | 5/2006 | Van Zandt et al. | |
| 2006/0134068 A1 | 6/2006 | Dong et al. | |
| 2006/0235028 A1 | 10/2006 | Li et al. | |
| 2006/0241297 A1 | 10/2006 | Wang et al. | |
| 2007/0021472 A1 | 1/2007 | Zhu et al. | |
| 2007/0072833 A1 | 3/2007 | Wendt et al. | |
| 2007/0099250 A1 | 5/2007 | Hu et al. | |
| 2007/0185111 A1 | 8/2007 | Cee et al. | |
| 2007/0219239 A1 | 9/2007 | Mjalli et al. | |
| 2007/0237840 A1 | 10/2007 | Chern et al. | |
| 2007/0244135 A1 | 10/2007 | Hoelzemann et al. | |
| 2008/0221127 A1 | 9/2008 | Lin et al. | |
| 2008/0268449 A1 | 10/2008 | Hoon et al. | |
| 2008/0293706 A1 | 11/2008 | Chaudhari et al. | |
| 2009/0142302 A1 | 6/2009 | Green et al. | |
| 2009/0181371 A1 | 7/2009 | Samowitz et al. | |
| 2009/0197859 A1 | 8/2009 | Collantes et al. | |
| 2009/0208952 A1 | 8/2009 | Hoon et al. | |
| 2009/0275546 A1 | 11/2009 | Signore et al. | |
| 2009/0275596 A1 | 11/2009 | Shie et al. | |

FOREIGN PATENT DOCUMENTS

| | | |
|---|---|---|
| WO | 9736585 | 10/1997 |
| WO | 9736876 | 10/1997 |
| WO | 9736881 | 10/1997 |
| WO | 9736886 | 10/1997 |
| WO | 9736897 | 10/1997 |
| WO | 9736898 | 10/1997 |
| WO | 9800134 | 1/1998 |
| WO | WO 98/27081 | 6/1998 |
| WO | 0467248 B1 | 10/1998 |
| WO | 9912930 | 3/1999 |
| WO | 0024724 | 5/2000 |
| WO | 0026216 | 5/2000 |
| WO | 0042971 | 7/2000 |
| WO | 0052008 | 9/2000 |
| WO | 0064422 | 11/2000 |
| WO | 0105768 | 1/2001 |

(Continued)

OTHER PUBLICATIONS

Carter, J.S.; Recently Reported Inhibitors of Cyclooxygenase-2; Exp. Opin. ther. Patents; 1993; 8(1); 21-29; Ashley Publaications LTD.
Tsai J., et al.; Discovery of a selective inhibitor of oncogenic B-Raf kinase with potent antimelanoma activity.; PNAS; Feb. 26, 2008; 105/8; 3041-3046.
Vane, J.; Towards a Better Aspirin; Pharmacology; 215-216, (1994).
Talley J.T.; Review: Pulmonary-Allergy, Dermatological, Gastrointestinal & Arthritis, Selective Inhibitors of Cyclooxygenase-2; Exp. Opin. ther. Patents; 1997; 7(1); 55-62; Ashley Publications LTD.
Talley J.T.; 5 Selective Inhibitors of Cyclooxygenase-2 (COX-2); Progress in Medicinal Chemistry; 1999; 36; 201-235; Elseiver Science B.V.

(Continued)

*Primary Examiner* — Deepak Rao
(74) *Attorney, Agent, or Firm* — J. Scott Young

(57) ABSTRACT

The present invention provides thiazole sulfonamide and oxazole sulfonamide compounds, compositions containing the same, as well as processes for the preparation and methods for their use as pharmaceutical agents.

1 Claim, 6 Drawing Sheets

(56) References Cited

FOREIGN PATENT DOCUMENTS

| | | |
|---|---|---|
| WO | 0107032 | 2/2001 |
| WO | 0107401 | 2/2001 |
| WO | 0119788 | 3/2001 |
| WO | 0119798 | 3/2001 |
| WO | 0130778 | 5/2001 |
| WO | 0156989 | 8/2001 |
| WO | 0164642 | 9/2001 |
| WO | 0172745 | 10/2001 |
| WO | 0174331 | 10/2001 |
| WO | 0176582 | 10/2001 |
| WO | 0177091 | 10/2001 |
| WO | 0183479 | 11/2001 |
| WO | 0187857 | 11/2001 |
| WO | 0200647 | 1/2002 |
| WO | 0216359 | 2/2002 |
| WO | 0226712 | 4/2002 |
| WO | 0248147 | 6/2002 |
| WO | 0248148 | 6/2002 |
| WO | 02053101 | 7/2002 |
| WO | 02062792 | 8/2002 |
| WO | 02070469 | 9/2002 |
| WO | 02072581 | 9/2002 |
| WO | 02078700 | 10/2002 |
| WO | 02078701 | 10/2002 |
| WO | 02083111 | 10/2002 |
| WO | 02083672 | 10/2002 |
| WO | 02088124 | 11/2002 |
| WO | 02098363 | 12/2002 |
| WO | 03000689 | 1/2003 |
| WO | 03018536 | 3/2003 |
| WO | 03022832 | 3/2003 |
| WO | 03022845 | 3/2003 |
| WO | 03029249 | 4/2003 |
| WO | 03031446 | 4/2003 |
| WO | 03050120 | 6/2003 |
| WO | 03076441 | 9/2003 |
| WO | WO 03/076436 | 9/2003 |
| WO | 03087304 | 10/2003 |
| WO | 03090751 | 11/2003 |
| WO | 03090752 | 11/2003 |
| WO | 03095455 | 11/2003 |
| WO | 04000318 | 12/2003 |
| WO | 2004060305 | 1/2004 |
| WO | 2004055005 | 7/2004 |
| WO | 2004078114 | 9/2004 |
| WO | 2004087941 | 10/2004 |
| WO | 2004091480 | 10/2004 |
| WO | 2004092146 | 10/2004 |
| WO | 2004099168 | 11/2004 |
| WO | 2004099170 | 11/2004 |
| WO | 2004099171 | 11/2004 |
| WO | 2004099192 | 11/2004 |
| WO | 2004110418 | 12/2004 |
| WO | WO 2004/108717 | 12/2004 |
| WO | 2005000300 | 1/2005 |
| WO | 2005007090 | 1/2005 |
| WO | 2005042525 | 5/2005 |
| WO | 2005044797 | 5/2005 |
| WO | 2005047542 | 6/2005 |
| WO | 2005073225 A1 | 8/2005 |
| WO | 2005086873 A1 | 9/2005 |
| WO | 2005087236 A1 | 9/2005 |
| WO | 2005116025 A2 | 12/2005 |
| WO | 2005121142 A1 | 12/2005 |
| WO | 2006020767 A2 | 2/2006 |
| WO | 2006026305 | 3/2006 |
| WO | 2006030211 | 3/2006 |
| WO | 2006032525 | 3/2006 |
| WO | 2006044509 | 4/2006 |
| WO | 2006047772 | 5/2006 |
| WO | 2006050097 | 5/2006 |
| WO | 2006051826 | 5/2006 |
| WO | 2006055503 | 5/2006 |
| WO | 2006055553 | 5/2006 |
| WO | 2006055625 | 5/2006 |
| WO | 2006055708 | 5/2006 |
| WO | 2006055725 | 5/2006 |
| WO | 2006068826 | 6/2006 |
| WO | 2006076644 | 7/2006 |
| WO | 2006129199 | 12/2006 |
| WO | 2006130493 | 12/2006 |
| WO | 2007003934 | 1/2007 |
| WO | 2007037187 | 4/2007 |
| WO | 2007040208 | 4/2007 |
| WO | 2007056366 | 5/2007 |
| WO | 2007056496 | 5/2007 |
| WO | 2007059299 A1 | 5/2007 |
| WO | 2007065939 | 6/2007 |
| WO | 2007067506 A2 | 6/2007 |
| WO | 2007075895 | 7/2007 |
| WO | 2007084391 A2 | 7/2007 |
| WO | 2007087276 | 8/2007 |
| WO | 2007087429 A2 | 8/2007 |
| WO | 2007123516 | 11/2007 |
| WO | 2007131953 | 11/2007 |
| WO | 2008002490 | 1/2008 |
| WO | 2008003770 A1 | 1/2008 |
| WO | 2008008431 | 1/2008 |
| WO | 2008013660 | 1/2008 |
| WO | 2008013928 | 1/2008 |
| WO | 2008022281 | 2/2008 |
| WO | 2008022286 | 2/2008 |
| WO | 2008056259 | 5/2008 |
| WO | 2008073670 | 6/2008 |
| WO | WO 2008/071456 | 6/2008 |
| WO | 2008097835 | 8/2008 |
| WO | 2008104077 | 9/2008 |
| WO | 2008120004 A1 | 10/2008 |
| WO | 2008129288 | 10/2008 |
| WO | 2008141275 | 11/2008 |
| WO | 2008154642 | 12/2008 |
| WO | 2009003998 A2 | 1/2009 |
| WO | 2009010871 | 1/2009 |
| WO | 2009011850 | 1/2009 |
| WO | 2009012283 | 1/2009 |
| WO | WO2009/039397 | 3/2009 |
| WO | 2009066060 | 5/2009 |
| WO | 2009076140 A1 | 6/2009 |
| WO | 2009096198 | 8/2009 |
| WO | 2009100214 | 8/2009 |
| WO | WO 2009/106708 | 9/2009 |
| WO | 2009137391 | 11/2009 |
| WO | WO 2009/137454 | 11/2009 |
| WO | 2010005922 | 1/2010 |
| WO | 2010010154 | 1/2010 |
| WO | 2010017179 | 2/2010 |
| WO | 2010018458 | 2/2010 |
| WO | 2010020618 | 2/2010 |
| WO | 2010026365 | 3/2010 |

OTHER PUBLICATIONS

Akahane, A., et al.; Communications to the Editor: Discovery of 6-OXO-3(2-Phenylpyrazolo[1,5-a]Pyridin-3-yl)-1(6H)-Pyridazinebutanoic Acid (FR 838): A Novel Non-Xanthine Adenosine A1 Receptor Antagonist with Potent Diuretic Activity; Journal of Medicinal Chemistry; Mar. 11, 1999; 42(5); 779-782.

Pillonel, C., et al.; Evaluation of Phenylaminopyridines as Antifunal Protein Kinase Inhibitors: Pest Management Science; 2005; 61(11); 1069-1076; Elsevier Science Ltd.

Roy, P. et al.; A New Series of Selctive COX-2 Inhibitors: 5,6-Diarylimidazo[3,2.1-b]Troazp;es; Bioorganic & Medicinal Chemistry Letters; 1997; 7(1); 57-62; Elsevier Science Ltd.

Therien, M., et al.; Synthesis and Biological Evaluation of 5,6-Diarylimidazo[2.1-b]Thiazole as Selective COX-2 Inhibitors: Bioorganic & Medicinal Chemistry Letters: 1997; 7(1): 47-52; Elsevier Science Ltd.

English translation of Chilean Examiner's Report corresponding to PCT/US2009/042682, (2009).

English translation of Columbian Office Action for PCT/US2009/042682, (2009).

Simone, Oncology: Introduction, Cecil Textbook of Medicine, 20th Edition, vol. 1, pp. 1004-1010, 1996.

(56) References Cited

OTHER PUBLICATIONS

Pearce et al., Failure modes in anticancer drug discovery and development, Cancer Drug Design and Discovery Edited by Stephen Neidle, Chapter 18, pp. 424-435 (2008).
Johnson et al., Relationships between drug activity in NCI preclinical in vitro and in vivo models and early clinical trials, British Journal of Cancer, 84(10):1424-1431, 2001.
Gura et al., Systems for identifying new drugs are often faulty, Science, 278:1041-1042, 1997.
Sommerer, F., et al.; Mutations of BRAF and KRAS2 in the development of Barrett's adenocarcinoma; Oncogene; 2004; 23(2); 554-558.
Yuen, S.T., et al.; Similarity of the Phenotypic Patterns Associated with CRAF and KRAS Mutations in colorectal Neoplasia; Cancer Research; 2002; 62(22); 6451-6455.
Written Opinion of the International Searching Authority for PCT/US10/52808, (2010).
King, A.J., et al.; Demonstration of a Genetic Therapeutic Index for Tumors Expressing Oncogenic BRAF by the Kinase Inhibitors SB-590865; Cancer Research; 2006; 66(23); 11100-11105.
Kumar R., et al.; BRAF Mutaions Are Common Somatic Events in Melanocytic Nevl; Journal of Investigative Dermatology; 2004; 122(2); 342-346.
Lee, J.W., et al.; BRAF mutations in non-Hodgkin's lymphoma; British Journal of Cancer; 2003; 89; 1958-1960.
Lee, S.H., et al.; BRAF and KRAS mutations in stomach cancer; Oncogene; 2003; 22; 6942-6945.
Midgley, R.S., et al.; Ras as a target in cancer therapy: Critical Reviews in Oncology/Hematology; 2002; 44; 109-120.
Mizuchi, D., et al.; BCR/ABL activates Rap1 and B-Raf to stimulate the MED/Erk signaling pathway in hematopoletic cells; Biochemical and Biophysical Research Communications.; 2005; 326; 645-651.
Moreno-Bueno, G., et al.; Low Frequency of BRAF Mutations in Endometrial and in Cervical Carcinomas; Clin. Cancer Res.; 2006; 12(12); 3865-3866.
Nagao, S., et al.; Renal activation of extracellular signal-regulated kinase in rats with autosomal-dominant polycystic kidney disease; Kidney International; 2003; 63; 427-437.
Nagy, A., et al.; Frequent Allelic Changes at Chromosome 7q34 But Lack of Mutation of the BRAF in Papillary Rennal Cell Tumors: Int. J. Cancer: 2003; 106(6); 960-981.
Ng, M.H.L., et al.; Alterations of RAS signalling in Chinese multiple myeloma patients; absent BRAF and rare RAS mutations, but frequent inactivation of RASSF1A by transcriptional silencing or expression of a non-functional variant transcript; British Journal of Haematology; 2003; 123; 637-645.
Pardo, O.E., et al.; FGF-2 protects small cell lung cancer cells from apoptosis through a complex involving PKC, B-Raf and S6K2; The EMBO Journal; 2006; 25(13); 3078-3086.
Rodriguez-Viciana, P., et al.; Germline Mutations in Genes Within the MAPK Pathway Cause Cardio-facio-cutaneous Syndrome; Science; 2006; 311; 1287-1290.
De Martino, I., et al.; B-RAF mutations are a rare event in pituitary adenomas; J. Endocrinol. Invest.; 2007; 30(1); RC1-3.
Russell, S.E.H., et al.; A multistep model for ovarian tumorigenesis: the value of mutation analysis in the KRAS and BRAF genes; Journal of Pathology: 2004; 203; 617-619.
Weber, A., et al.; Mutations of the BRAF gene in squamous cell carcinoma of the head and neck; Oncogene; 2003; 22(30); 4757-4759.
Whitcombe, D., et al.; Detection of PCR products using self-probing amplicons and fluorescence: Nature Biotechnology; 1999; 17; 804-807.
Zebisch, A., et al.; Two Transforming C-RAF Germ-Line Mutations Identified in Patients with Therapy-Related Acute Myeloid Leukemia; Cancer Research; 2006; 66(7); 3401-3408.
Zebisch, A., et al.; Back to the roots; the remarkable RAF oncogene story; Cell. Mol. Life Sci.; 2006; 63; 1314-1330.
Brose, M.S., et al.; BRAF and RAS Mutations in Human Lung cancer and Melanoma; Cancer Research; 2002; 62(23); 6997-7000.
Cho, N-Y., et al.; BRAF and KRAS mutations in prostatic adenocarcinoma; International Journal of Cancer; 119(8); 1656-1662, (2006).
Cohen, Y., et al.; BRAF Mutations in Papillary Thyroid Carcinoma; Journal of the National Cancer Institute; 2003; 95(8); 625-627.
Downward, J.; Targeting RAS Signalling Pathways in Cancer Therapy; J. Nature Reviews Cancer; 2003; 3; 11-22.
Figl, A., et al.; Multiple Melanomas After Treatment for Hodgkin Lymphoma in a Non-Dutch p16-Leiden Mutation Carrier With 2 MC1R High-Risk Variants; Arch. Dermatol.; 2007; 143(4); 495-499.
Garnett, M.J., et al.; Guilty as charged: B-RAF is a human oncogene; Cancer Cell, 2004; 6; 313-319.
Gibson, N,J.; The use of real-time PCR methods in DNA sequence variation analysis; Clinica Chimica Acta; 2006; 363; 32-47.
Gustafsson, et al.; Mutations in the BRAF and N-ras genes in childhood acute lymphoblastic leukaemia; Leukemia; 2005; 19; 310-312.
Halilovic, E., et al.; Therapeutic strategies for inhibiting oncogenic BRAF signaling; Current Opinion in Pharmacology; 2008; 8; 419-426.
Ishimura, N., et al.; BRAF and K-ras gene mutations in human pancreatic cancers; Cancer Letters; 2003; 199(2); 169-173.
Kimura, E.T., et al.; High Prevalence of BRAF Mutations in Thyroid Cancer: Genetic Evidence for Constitutive Activation of the RET/PTC-RAS-BRAF Signaling Pathway in Papillary Thyroid Carcinoma; Cancer Research; 2003; 63; 1454-1457.
Davies, H., et al.; Mutations of the BRAF gene in human cancer; Nature; 2002; 417; 949-954.
PCT/US2009/042682; International Preliminary Report on Patentability, (2010).
Smith, R.A., et al.; Recent Advances in the Research and Development of RAF Kinase Inhibitors; Current Topics in Medicinal Chemistry; 2006; 6; 1071-1089.
Eychene A., et al.; Expression and activation of B-Raf kinase Isoforms in human and murine leukemia cell lines; Oncogene; 1995; 10; 1159-1165.
Tannapfel, A., et al.; Mutations of the BRAF gene in cholangiocarcinoma but not in hepatocellular carcinoma; Gut; 2003; 52(5); 706-712.
Kim et al. et al.; SNP Genotyping: Technologies and Biomedical Applications; Annual Review of Biomedical Engineering; 2007; 9; 289-320.
Knobbe, C.B. et al.; Mutation analysis of the Ras pathway genes NRAS, HRAS, KRAS and BRAF in glioblastomas; ACTA Neuropathol.; 2004; 108; 467-470.
Lee, S.H., et al.; BRAF mutations in acute leukemias; Leukemia; 2004; 18; 170-172.
Christiansen, D.H., et al.; Mutations of genes in the receptor tyrosine kinase (RTK)/RAF-BRAF signal transduction pathway in therapy-related myelodysplasia and acute myeloid leukemia; Leukemia; 2005; 19(12); 2232-2240.

* cited by examiner

BENZENE SULFONAMIDE THIAZOLE AND OXAZOLE COMPOUNDS

CROSS-REFERENCE TO RELATED APPLICATIONS

This application is filed as a continuation application of U.S. Ser. No. 12/991,004, filed Nov. 4, 2010, which is a National Phase Application of International Patent Application Serial No. PCT/US2009/42682 filed on May 4, 2009, which claims priority from 61/050,744 filed on May 6, 2008 in the United States.

FIELD OF THE INVENTION

The present invention relates to benzene sulfonamide thiazole and oxazole compounds, compositions containing the same, as well as processes for the preparation and methods of using such compounds and compositions.

BACKGROUND OF THE INVENTION

Both receptor tyrosine kinases and serine/threonine kinases have been implicated in cellular signaling pathways that control cell function, division, growth, differentiation, and death (apoptosis) through reversible phosphorylation of the hydroxyl groups of tyrosine or serine and threonine residues, respectively, in proteins. In signal transduction, for example, extracellular signals are transduced via membrane receptor activation, with amplification and propagation using a complex choreography of cascades of protein phosphorylation, and protein dephosphorylation events to avoid uncontrolled signaling. These signaling pathways are highly regulated, often by complex and intermeshed kinase pathways where each kinase may itself be regulated by one or more other kinases and protein phosphatases. The biological importance of these finely tuned systems is such that a variety of cell proliferative disorders have been linked to defects in one or more of the various cell signaling pathways mediated by tyrosine or serine/threonine kinases.

Receptor tyrosine kinases (RTKs) catalyze phosphorylation of certain tyrosyl amino acid residues in various proteins, including themselves, which govern cell growth, proliferation and differentiation.

Downstream of the several RTKs lie several signaling pathways, among them is the Ras-Raf-MEK-ERK kinase pathway. It is currently understood that activation of Ras GTPase proteins in response to growth factors, hormones, cytokines, etc. stimulates phosphorylation and activation of Raf kinases. These kinases then phosphorylate and activate the intracellular protein kinases MEK1 and MEK2, which in turn phosphorylate and activate other protein kinases, ERK1 and 2. This signaling pathway, also known as the mitogen-activated protein kinase (MAPK) pathway or cytoplasmic cascade, mediates cellular responses to growth signals. The ultimate function of this is to link receptor activity at the cell membrane with modification of cytoplasmic or nuclear targets that govern cell proliferation, differentiation, and survival. Mutations in various Ras GTPases and the B-Raf kinase have been identified that can lead to sustained and constitutive activation of the MAPK pathway, ultimately resulting in increased cell division and survival. As a consequence of this, these mutations have been strongly linked with the establishment, development, and progression of a wide range of human cancers. The biological role of the Raf kinases, and specifically that of B-Raf, in signal transduction is described in Davies, H., et al., *Nature* (2002) 9:1-6; Garnett, M. J. & Marais, R., *Cancer Cell* (2004) 6:313-319; Zebisch, A. & Troppmair, J., *Cell. Mol. Life. Sci.* (2006) 63:1314-1330; Midgley, R. S. & Kerr, D. J., *Crit. Rev. One/Hematol.* (2002) 44:109-120; Smith, R. A., et al., *Curr. Top. Med. Chem.* (2006) 6:1071-1089; and Downward, J., *Nat. Rev. Cancer* (2003) 3:11-22.

Naturally occurring mutations of the B-Raf kinase that activate MAPK pathway signaling have been found in a large percentage of human melanomas (Davies (2002) supra) and thyroid cancers (Cohen et al *J. Nat. Cancer Inst.* (2003) 95(8) 625-627 and Kimura et al *Cancer Res.* (2003) 63(7) 1454-1457), as well as at lower, but still significant, frequencies in the following:

Barret's adenocarcinoma (Garnett et al., *Cancer Cell* (2004) δ 313-319 and Sommerer et al *Oncogene* (2004) 23(2) 554-558), billiary tract carcinomas (Zebisch et al., *Cell. Mol. Life. Sci.* (2006) 63 1314-1330), breast cancer (Davies (2002) supra), cervical cancer (Moreno-Bueno et al *Clin. Cancer Res.* (2006) 12(12) 3865-3866), cholangiocarcinoma (Tannapfel et al *Gut* (2003) 52(5) 706-712), central nervous system tumors including primary CNS tumors such as glioblastomas, astrocytomas and ependymomas (Knobbe et al *Acta Neuropathol. (Berl.)* (2004) 108(6) 467-470, Davies (2002) supra, and Garnett et al., *Cancer Cell* (2004) supra) and secondary CNS tumors (i.e., metastases to the central nervous system of tumors originating outside of the central nervous system), colorectal cancer, including large intestinal colon carcinoma (Yuen et al *Cancer Res.* (2002) 62(22) 6451-6455, Davies (2002) supra and Zebisch et al., *Cell. Mol. Life Sci.* (2006), gastric cancer (Lee et al *Oncogene* (2003) 22(44) 6942-6945), carcinoma of the head and neck including squamous cell carcinoma of the head and neck (Cohen et al *J. Nat. Cancer Inst.* (2003) 95(8) 625-627 and Weber et al *Oncogene* (2003) 22(30) 4757-4759), hematologic cancers including leukemias (Garnett et al., *Cancer Cell* (2004) supra, particularly acute lymphoblastic leukemia (Garnett et al., *Cancer Cell* (2004) supra and Gustafsson et al *Leukemia* (2005) 19(2) 310-312), acute myelogenous leukemia (AML) (Lee et al *Leukemia* (2004) 18(1) 170-172, and Christiansen et al *Leukemia* (2005) 19(12) 2232-2240), myelodysplastic syndromes (Christiansen et al *Leukemia* (2005) supra) and chronic myelogenous leukemia (Mizuchi et al *Biochem. Biophys. Res. Commun.* (2005) 326(3) 645-651); Hodgkin's lymphoma (Figl et al *Arch. Dermatol.* (2007) 143(4) 495-499), non-Hodgkin's lymphoma (Lee et al *Br. J. Cancer* (2003) 89(10) 1958-1960), megakaryoblastic leukemia (Eychene et al *Oncogene* (1995) 10(6) 1159-1165) and multiple myeloma (Ng et al *Br. J. Haematol.* (2003) 123(4) 637-645), hepatocellular carcinoma (Garnett et al., *Cancer Cell* (2004), lung cancer (Brose et al *Cancer Res.* (2002) 62(23) 6997-7000, Cohen et al *J. Nat. Cancer Inst.* (2003) supra and Davies (2002) supra), including small cell lung cancer (Pardo et al *EMBO J.* (2006) 25(13) 3078-3088) and non-small cell lung cancer (Davies (2002) supra), ovarian cancer (Russell & McCluggage *J. Pathol.* (2004) 203(2) 617-619 and Davies (2002) supr), endometrial cancer (Garnett et al., *Cancer Cell* (2004) supra, and Moreno-Bueno et al *Clin. Cancer Res.* (2006) supra), pancreatic cancer (Ishimura et al *Cancer Lett.* (2003) 199(2) 169-173), pituitary adenoma (De Martino et al *J. Endocrinol. Invest.* (2007) 30(1) RC1-3), prostate cancer (Cho et al *Int. J. Cancer* (2006) 119(8) 1858-1862), renal cancer (Nagy et al *Int. J. Cancer* (2003) 106(6) 980-981), sarcoma (Davies (2002) supra), and skin cancers (Rodriguez-Viciana et al *Science* (2006) 311 (5765) 1287-1290 and Davies (2002) supra).

Overexpression of c-Raf has been linked to AML (Zebisch et al., *Cancer Res.* (2006) 66(7) 3401-3408, and Zebisch (*Cell. Mol. Life. Sci.* (2006)) and erythroleukemia (Zebisch et al., Cell. Mol. Life. Sci. (2006).

By virtue of the role played by the Raf family kinases in these cancers and exploratory studies with a range of preclinical and therapeutic agents, including one selectively targeted to inhibition of B-Raf kinase activity (King A. J., et al., (2006) *Cancer Res.* 66:11100-11105), it is generally accepted that inhibitors of one or more Raf family kinases will be useful for the treatment of such cancers or other condition associated with Raf kinase.

Mutation of B-Raf has also been implicated in other conditions, including cardio-facio cutaneous syndrome (Rodriguez-Viciana et al *Science* (2006) 311(5765) 1287-1290) and polycystic kidney disease (Nagao et al *Kidney Int.* (2003) 63(2) 427-437).

SUMMARY OF THE INVENTION

In a first aspect of the present invention, there is provided compounds of formula (I):

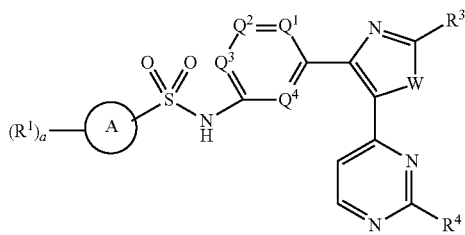

wherein:
a is 0, 1, 2 or 3;
each $R^1$ is the same or different and is independently selected from halo, alkyl, haloalkyl, —$OR^6$, —$CO_2R^6$, —$NR^6R^7$, and —CN;
Ring A is selected from $C_{3-6}$cycloalkyl, phenyl, 5-6 membered heterocycle and 5-6 membered heteroaryl, said heterocycle and said heteroaryl each having 1 or 2 heteroatoms selected from N, O and S;
each of $Q^1$, $Q^2$, $Q^3$ and $Q^4$ is CH, C—$R^2$ or N, wherein not more than one of $Q^1$, $Q^2$, $Q^3$, and $Q^4$ is N;
each $R^2$ is the same or different and is independently selected from halo, alkyl, haloalkyl, and —$OR^6$;
W is selected from —O— and —S—;
$R^3$ is selected from H, alkyl, haloalkyl-, -alkylene-OH, —$NR^6R^7$, —$C_{3-6}$cycloalkyl, -alkylene-C(O)—OH, -alkylene-$NH_2$, and Het;
wherein said $R^3$ $C_{3-6}$cycloalkyl is optionally substituted with 1 or 2 substituents which are the same or different and are independently selected from halo, $C_{1-3}$alkyl, halo$C_{1-3}$alkyl, OH, O—$C_{1-3}$alkyl, oxo, S($C_{1-3}$alkyl), $SO_2$, $NH_2$, N(H)$C_{1-3}$alkyl and N($C_{1-3}$alkyl)$_2$;
Het is a 5-6 membered heterocycle having 1 or 2 heteroatoms selected from N, O and S and optionally substituted with 1 or 2 substituents which are the same or different and are each independently selected from halo, $C_{1-3}$alkyl, halo$C_{1-3}$alkyl, O—$C_{1-3}$alkyl, $C_{1-3}$alkylene-O—$C_{1-3}$alkyl, OH, $C_{1-3}$alkylene-OH, oxo, $SO_2$($C_{1-3}$alkyl), $C_{1-3}$alkylene-$SO_2$($C_{1-3}$alkyl), $NH_2$, N(H)$C_{1-3}$alkyl, N($C_{1-3}$alkyl)$_2$, CN, and —$CH_2$CN;
$R^4$ is selected from H, alkyl, haloalkyl, alkenyl, —$OR^6$, —$R^5$—$OR^6$, —$R^5$—$CO_2R^6$, —$R^5$—$SO_2R^6$, —$R^5$—Het, —$R^5$—C(O)—Het, —N(H)$R^8$, —N($CH_3$)$R^8$, and —$R^5$—$NR^6R^7$; each $R^5$ is the same or different and is independently $C_{1-4}$alkylene;

each $R^6$ and each $R^7$ is the same or different and is independently selected from H, alkyl, haloalkyl, —C(O)-alkyl, and —C(O)-cycloalkyl;
$R^8$ is selected from H, alkyl (optionally substituted by —OH), haloalkyl, $C_{3-6}$cycloalkyl, —$R^5$—$C_{3-6}$cycloalkyl, Het$^2$, —$R^5$—Het$^2$, —$R^5$—$OR^6$, —$R^5$—O—$R^5$—$OR^6$, —$R^5$—C(O)$_2R^6$, —$R^5$—C(O)NR$^6R^7$, —$R^5$—N(H)C(O)—$R^6$, —$R^5$—N(H)C(O)—$R^5$—$OR^6$, —$R^5$—N(H)C(O)$_2$—$R^6$, —$R^5$—NR$^6R^7$, —$R^5$—S(O)$_2R^6$, —$R^5$—CN, and —$R^5$—N(H)S(O)$_2R^6$;
wherein said $R^8$ $C_{3-6}$cycloalkyl is optionally substituted with 1 or 2 substituents which are the same or different and are independently selected from halo, $C_{1-3}$alkyl, halo$C_{1-3}$alkyl, OH, O—$C_{1-3}$alkyl, oxo, S($C_{1-3}$alkyl), $SO_2$($C_{1-3}$alkyl), $NH_2$, N(H)$C_{1-3}$alkyl and N($C_{1-3}$alkyl)$_2$, and N(H)$SO_2C_{1-3}$alkyl; and
Het$^2$ is a 4-6 membered heterocycle having 1 or 2 heteroatoms selected from N, O and S and optionally substituted with 1, 2, 3, 4 or 5 $C_{1-3}$alkyl or 1 or 2 substituents which are the same or different and are each independently selected from halo, $C_{1-3}$alkyl, halo$C_{1-3}$alkyl, O—$C_{1-3}$alkyl, $C_{1-3}$alkylene-O—$C_{1-3}$alkyl, OH, $C_{1-3}$alkylene-OH, oxo, $SO_2$($C_{1-3}$alkyl), $C_{1-3}$alkylene-$SO_2$($C_{1-3}$alkyl), $NH_2$, N(H)$C_{1-3}$alkyl, N($C_{1-3}$alkyl)$_2$, N(H)$SO_2C_{1-3}$alkyl, C(O)($C_{1-3}$alkyl), $CO_2$($C_{1-4}$alkyl), CN, and —$CH_2$CN;
and $R^9$ and $R^{19}$ are independently selected from H and alkyl, and pharmaceutically acceptable salts thereof.

In a second aspect of the present invention, there is provided compounds of formula (I-i)

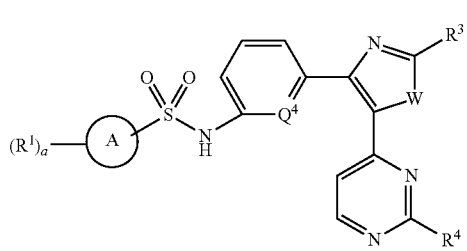

wherein $Q^4$ is CH or C—$R^2$ and all other variables are as defined above, and pharmaceutically acceptable salts thereof.

In a third aspect of the present invention, there is provided compounds of formula (I-i-b)

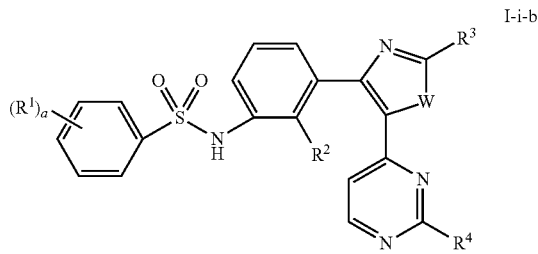

wherein all variables are as defined above, and pharmaceutically acceptable salts thereof.

In a fourth aspect of the present invention, there is provided compounds of formula (I-iii-a)

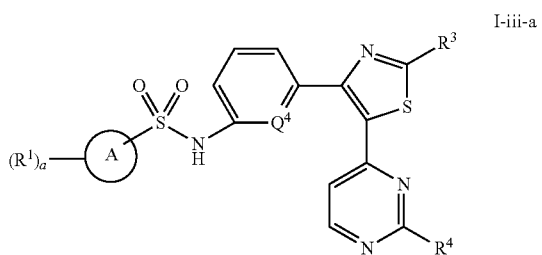

I-iii-a wherein $Q^4$ is CH or C—$R^2$ and all other variables are as defined above, and pharmaceutically acceptable salts thereof.

In a fifth aspect of the present invention, there is provided compounds of formula (I-iii-b)

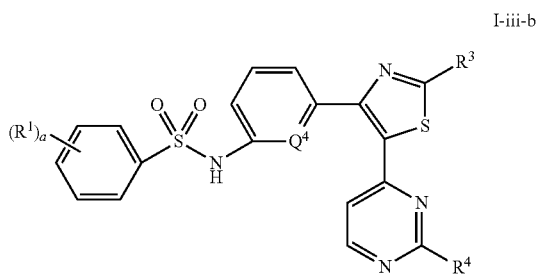

I-iii-b wherein $Q^4$ is CH or C—$R^2$ and all other variables are as defined above, and pharmaceutically acceptable salts thereof.

In a sixth aspect of the present invention, there is provided compounds of formula (I-iv):

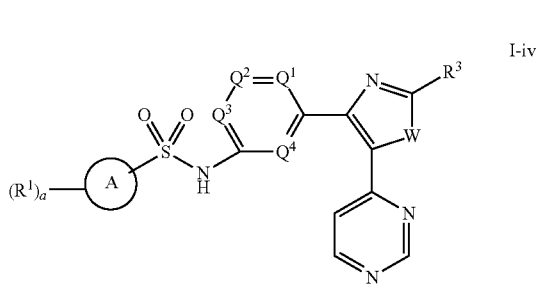

I-iv wherein $Q^4$ is CH or C—$R^2$ and all other variables are as defined above, and pharmaceutically acceptable salts thereof.

In a seventh aspect of the present invention, there is provided compounds of formula (I-v):

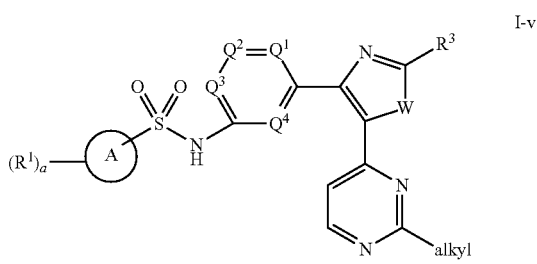

I-v wherein $Q^4$ is CH or C—$R^2$ and all other variables are as defined above, and pharmaceutically acceptable salts thereof.

In an eighth aspect of the present invention, there is provided compounds of formula (I-vii):

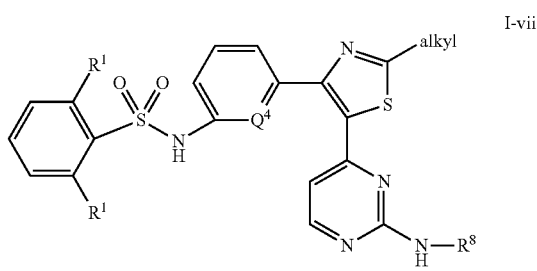

I-vii wherein $Q^4$ is CH or C—$R^2$, and all variables are as defined above, and pharmaceutically acceptable salts thereof.

In a ninth aspect of the present invention, there is provided a compound selected from:

N-{3-[5-(2-amino-4-pyrimidinyl)-2-(1,1-dimethylethyl)-1,3-thiazol-4-yl]-2-fluorophenyl}-2,6-difluorobenzenesulfonamide,

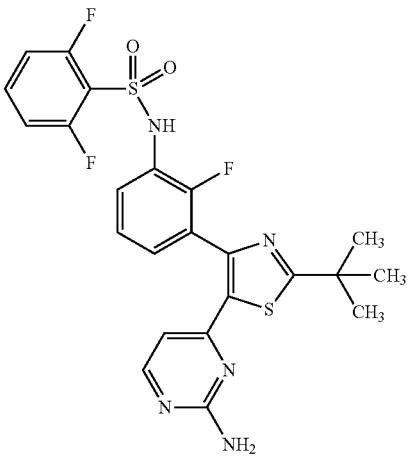 [SMILES: CC(C)(C)c1nc(-c2cccc(NS(=O)(=O)c3c(F)cccc3F)c2F)c(-c2ccnc(N)n2)s1]

N-{3-[2-(1,1-dimethylethyl)-5-(2-methyl-4-pyrimidinyl)-1,3-thiazol-4-yl]-2-fluorophenyl}-2,5-difluorobenzenesulfonamide,

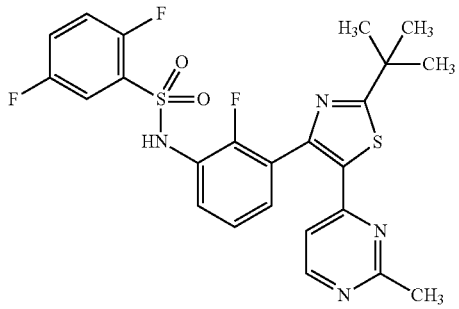 [SMILES: Cc1nccc(-c2sc(C(C)(C)C)nc2-c2cccc(NS(=O)(=O)c3cc(F)ccc3F)c2F)n1]

N-{3-[5-(2-amino-4-pyrimidinyl)-2-(tetrahydro-2H-pyran-4-yl)-1,3-thiazol-4-yl]-2-fluorophenyl}-2,6-difluorobenzenesulfonamide,

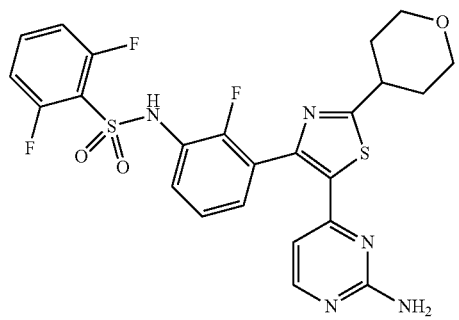 [SMILES: Nc1nccc(-c2sc(C3CCOCC3)nc2-c2cccc(NS(=O)(=O)c3c(F)cccc3F)c2F)n1]

N-{3-[5-(2-amino-4-pyrimidinyl)-2-(4-morpholinyl)-1,3-thiazol-4-yl]-2-fluorophenyl}-2,5-difluorobenzenesulfonamide,

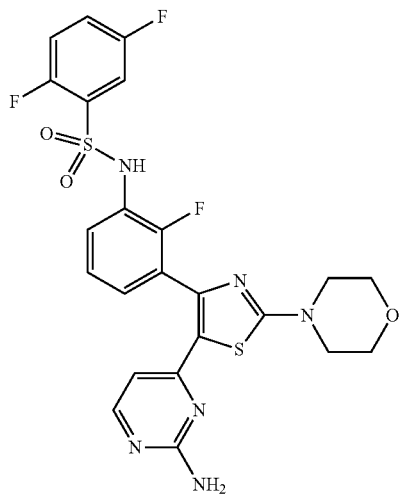 [SMILES: Nc1nccc(-c2sc(N3CCOCC3)nc2-c2cccc(NS(=O)(=O)c3cc(F)ccc3F)c2F)n1]

N-{3-[5-(2-amino-4-pyrimidinyl)-2-(4-morpholinyl)-1,3-thiazol-4-yl]-2-chlorophenyl}-2-furansulfonamide,

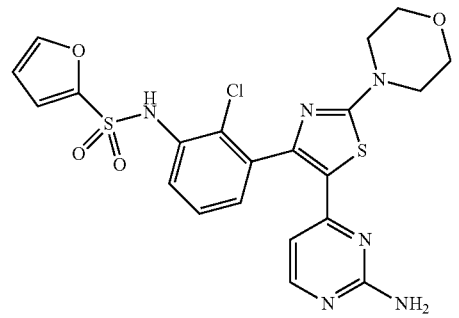 [SMILES: Nc1nccc(-c2sc(N3CCOCC3)nc2-c2cccc(NS(=O)(=O)c3ccco3)c2Cl)n1]

-continued

N-{3-[5-(2-amino-4-pyrimidinyl)-2-(4-morpholinyl)-1,3-thiazol-4-yl]-2-chlorophenyl}-2,5-difluorobenzenesulfonamide, and

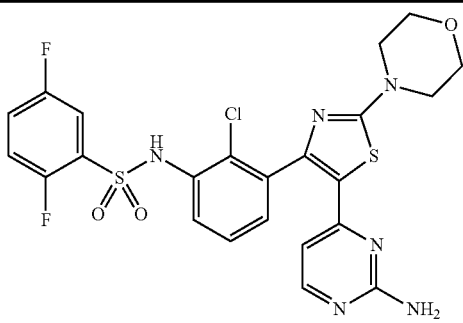

N-{3-[2-(1,1-dimethylethyl)-5-(4-pyrimidinyl)-1,3-thiazol-4-yl]-2-fluorophenyl}-2,5-difluorobenzenesulfonamide

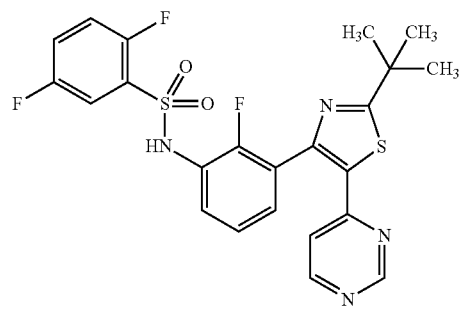 [SMILES: CC(C)(C)c1nc(-c2cccc(NS(=O)(=O)c3cc(F)ccc3F)c2F)c(-c2ccncn2)s1]

N-{3-[5-(2-amino-4-pyrimidinyl)-2-(tetrahydro-2H-pyran-4-yl)-1,3-thiazol-4-yl]-2-chlorophenyl}-3-furansulfonamide

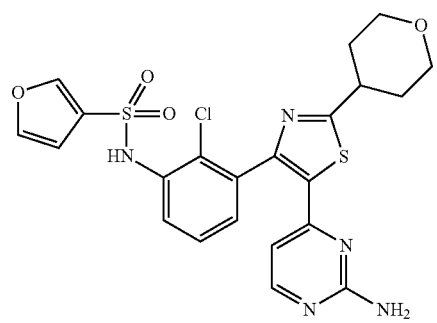

N-{3-[5-(2-amino-4-pyrimidinyl)-2-(tetrahydro-2H-pyran-4-yl)-1,3-thiazol-4-yl]-2-fluorophenyl}-3-furansulfonamide

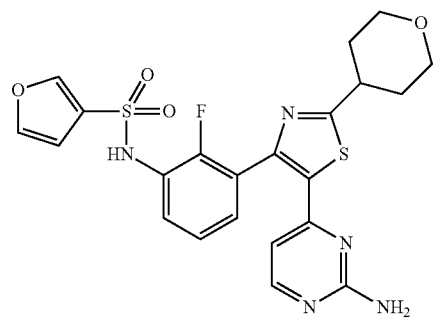

and pharmaceutically acceptable salts thereof.

And more particularly, there is provided a compound selected from:

N-{3-[5-(2-amino-4-pyrimidinyl)-2-(1,1-dimethylethyl)-1,3-thiazol-4-yl]-2-fluorophenyl}-2,6-difluorobenzenesulfonamide,

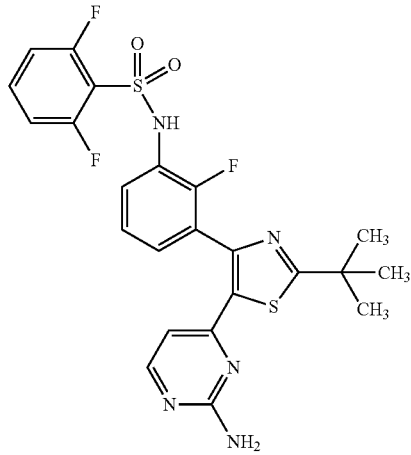 [SMILES: CC(C)(C)c1nc(-c2cccc(NS(=O)(=O)c3c(F)cccc3F)c2F)c(-c2ccnc(N)n2)s1]

N-{3-[2-(1,1-dimethylethyl)-5-(2-methyl-4-pyrimidinyl)-1,3-thiazol-4-yl]-2-fluorophenyl}-2,5-difluorobenzenesulfonamide,

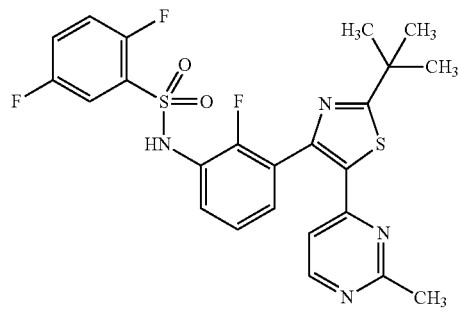 [SMILES: Cc1nccc(-c2sc(C(C)(C)C)nc2-c2cccc(NS(=O)(=O)c3cc(F)ccc3F)c2F)n1]

N-{3-[5-(2-amino-4-pyrimidinyl)-2-(tetrahydro-2H-pyran-4-yl)-1,3-thiazol-4-yl]-2-fluorophenyl}-2,6-difluorobenzenesulfonamide,

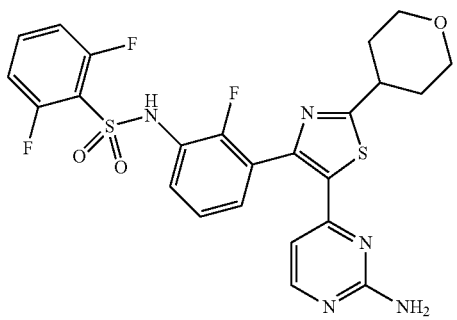 [SMILES: Nc1nccc(-c2sc(C3CCOCC3)nc2-c2cccc(NS(=O)(=O)c3c(F)cccc3F)c2F)n1]

N-{3-[5-(2-amino-4-pyrimidinyl)-2-(4-morpholinyl)-1,3-thiazol-4-yl]-2-fluorophenyl}-2,5-difluorobenzenesulfonamide,

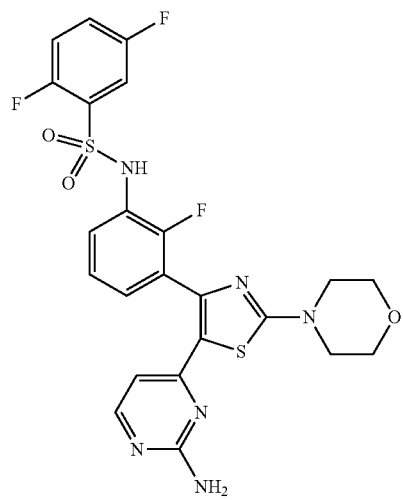 [SMILES: Nc1nccc(-c2sc(N3CCOCC3)nc2-c2cccc(NS(=O)(=O)c3cc(F)ccc3F)c2F)n1]

| | |
|---|---|
| N-{3-[5-(2-amino-4-pyrimidinyl)-2-(4-morpholinyl)-1,3-thiazol-4-yl]-2-chlorophenyl}-2-furansulfonamide, | 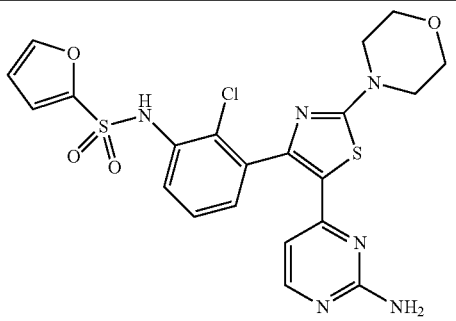 |
| N-{3-[5-(2-amino-4-pyrimidinyl)-2-(4-morpholinyl)-1,3-thiazol-4-yl]-2-chlorophenyl}-2,5-difluorobenzenesulfonamide, and | 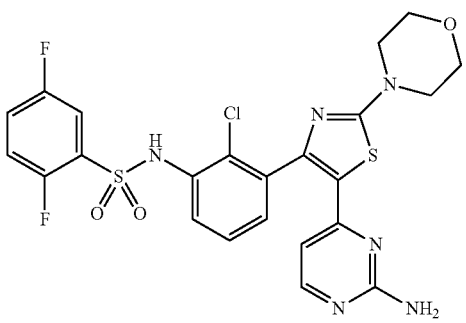 [SMILES: Nc1nccc(-c2sc(N3CCOCC3)nc2-c2cccc(NS(=O)(=O)c3cc(F)ccc3F)c2Cl)n1] |
| N-{3-[2-(1,1-dimethylethyl)-5-(4-pyrimidinyl)-1,3-thiazol-4-yl]-2-fluorophenyl}-2,5-difluorobenzenesulfonamide | 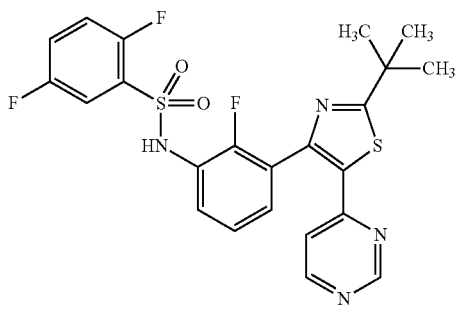 [SMILES: CC(C)(C)c1nc(-c2cccc(NS(=O)(=O)c3cc(F)ccc3F)c2F)c(-c2ccncn2)s1] | and pharmaceutically acceptable salts thereof.

In a tenth aspect of the present invention, there is provided a compound selected from
N-{3-[5-(2-amino-4-pyrimidinyl)-2-(1,1-dimethylethyl)-1,3-thiazol-4-yl]-2-fluorophenyl}-2,6-difluorobenzenesulfonamide;
N-{3-[2-(1,1-dimethylethyl)-5-(2-methyl-4-pyrimidinyl)-1,3-thiazol-4-yl]-2-fluorophenyl}-2,5-difluorobenzenesulfonamide;
N-{3-[5-(2-amino-4-pyrimidinyl)-2-(tetrahydro-2H-pyran-4-yl)-1,3-thiazol-4-yl]-2-fluorophenyl}-2,6-difluorobenzenesulfonamide;
N-{3-[5-(2-amino-4-pyrimidinyl)-2-(4-morpholinyl)-1,3-thiazol-4-yl]-2-fluorophenyl}-2,5-difluorobenzenesulfonamide;
N-{3-[5-(2-amino-4-pyrimidinyl)-2-(4-morpholinyl)-1,3-thiazol-4-yl]-2-chlorophenyl}-2-furansulfonamide;
N-{3-[5-(2-amino-4-pyrimidinyl)-2-(4-morpholinyl)-1,3-thiazol-4-yl]-2-chlorophenyl}-2,5-difluorobenzenesulfonamide; and
N-{3-[2-(1,1-dimethylethyl)-5-(4-pyrimidinyl)-1,3-thiazol-4-yl]-2-fluorophenyl}-2,5-difluorobenzenesulfonamide.

In another aspect of the present invention there is provided
N-{3-[5-(2-amino-4-pyrimidinyl)-2-(1,1-dimethylethyl)-1,3-thiazol-4-yl]-2-fluorophenyl}-2,6-difluorobenzenesulfonamide and pharmaceutically acceptable salts thereof. Particularly the free base of the compound.

In another aspect of the present invention there is provided
N-{3-[2-(1,1-dimethylethyl)-5-(2-methyl-4-pyrimidinyl)-1,3-thiazol-4-yl]-2-fluorophenyl}-2,5-difluorobenzenesulfonamide

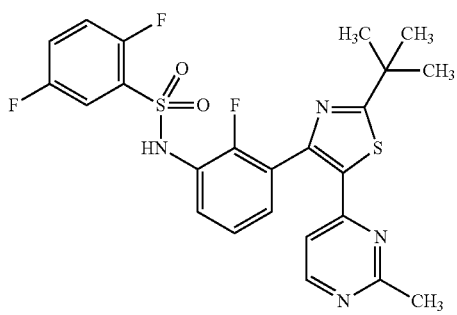 [SMILES: Cc1nccc(-c2sc(C(C)(C)C)nc2-c2cccc(NS(=O)(=O)c3cc(F)ccc3F)c2F)n1]

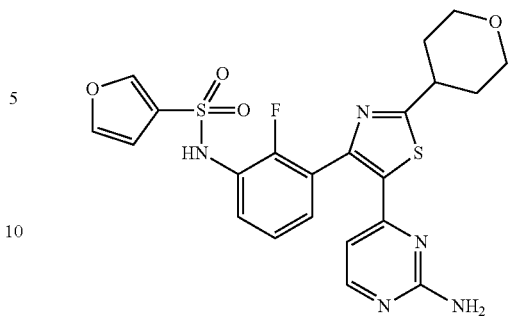

and pharmaceutically acceptable salts thereof. Particularly the free base of the compound.

In another aspect of the present invention there is provided N-{3-[5-(2-amino-4-pyrimidinyl)-2-(tetrahydro-2H-pyran-4-yl)-1,3-thiazol-4-yl]-2-fluorophenyl}-2,6-difluorobenzenesulfonamide

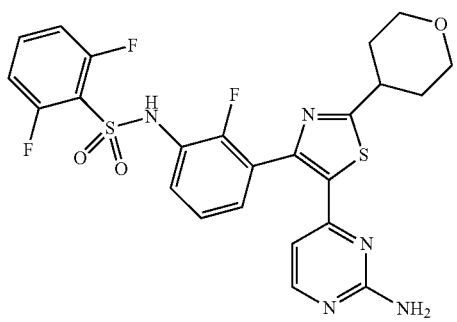 [SMILES: Nc1nccc(-c2sc(C3CCOCC3)nc2-c2cccc(NS(=O)(=O)c3c(F)cccc3F)c2F)n1]

and pharmaceutically acceptable salts thereof. Particularly the free base of the compound.

In another aspect of the present invention there is provided N-{3-[5-(2-amino-4-pyrimidinyl)-2-(tetrahydro-2H-pyran-4-yl)-1,3-thiazol-4-yl]-2-chlorophenyl}-3-furansulfonamide

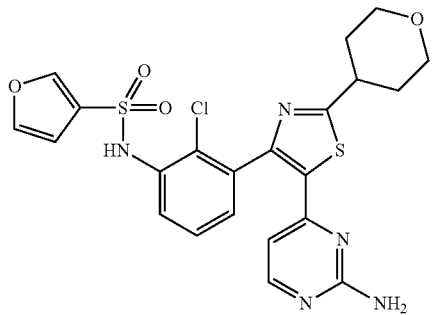

and pharmaceutically acceptable salts thereof. Particularly the free base of the compound.

In another aspect of the present invention there is provided N-{3-[5-(2-amino-4-pyrimidinyl)-2-(tetrahydro-2H-pyran-4-yl)-1,3-thiazol-4-yl]-2-fluorophenyl}-3-furansulfonamide and pharmaceutically acceptable salts thereof. Particularly the free base of the compound.

In another aspect of the present invention, there is provided a pharmaceutical composition comprising a compound of formula (I) (including any particular sub-generic formula described herein) or a pharmaceutically acceptable salt thereof. In one embodiment, the pharmaceutical composition further comprises one or more of pharmaceutically acceptable carriers, diluents or excipients. In one aspect, the present invention provides a pharmaceutical composition comprising any of N-{3-[5-(2-amino-4-pyrimidinyl)-2-(1,1-dimethylethyl)-1,3-thiazol-4-yl]-2-fluorophenyl}-2,6-difluorobenzene-sulfonamide;

N-{3-[2-(1,1-dimethylethyl)-5-(2-methyl-4-pyrimidinyl)-1,3-thiazol-4-yl]-2-fluorophenyl}-2,5-difluorobenzene-sulfonamide; or N-{3-[5-(2-amino-4-pyrimidinyl)-2-(tetrahydro-2H-pyran-4-yl)-1,3-thiazol-4-yl]-2-fluorophenyl}-2,6-difluorobenzenesulfonamide or a pharmaceutically acceptable salt thereof. Particularly the free base of any of the foregoing compounds.

In another aspect of the present invention, there is provided a method of treating a susceptible neoplasm in a mammal in need thereof, comprising administering to the mammal a therapeutically effective amount of a compound of formula (I) (including any particular sub-generic formula described herein) or a pharmaceutically acceptable salt thereof. Susceptible neoplasms include e.g., Barret's adenocarcinoma; biliary tract carcinomas; breast cancer; cervical cancer; cholangiocarcinoma; central nervous system tumors including primary CNS tumors such as glioblastomas, astrocytomas (e.g., glioblastoma multiforme) and ependymomas, and secondary CNS tumors (i.e., metastases to the central nervous system of tumors originating outside of the central nervous system); colorectal cancer including large intestinal colon carcinoma; gastric cancer; carcinoma of the head and neck including squamous cell carcinoma of the head and neck; hematologic cancers including leukemias and lymphomas such as acute lymphoblastic leukemia, acute myelogenous leukemia (AML), myelodysplastic syndromes, chronic myelogenous leukemia, Hodgkin's lymphoma, non-Hodgkin's lymphoma, megakaryoblastic leukemia, multiple myeloma and erythroleukemia; hepatocellular carcinoma; lung cancer including small cell lung cancer and non-small cell lung cancer; ovarian cancer; endometrial cancer; pancreatic cancer; pituitary adenoma; prostate cancer; renal cancer; sarcoma; skin cancers including melanomas; and thyroid cancers.

In another aspect of the present invention, there is provided a method of treating breast cancer, cholangiocarcinoma, colorectal cancer, melanoma, non-small cell lung cancer, ovarian cancer, or thyroid cancer, in a mammal, particularly a human, in need thereof, comprising administering to the mammal (e.g. human) a therapeutically effective amount of a compound of formula (I) or a pharmaceutically acceptable salt thereof.

In another aspect of the present invention, there is provided a method of treating a susceptible neoplasm in a mammal, particularly a human, in need thereof, comprising administering to the mammal (e.g. human) a therapeutically effective amount of a compound selected from N-{3-[5-(2-amino-4-pyrimidinyl)-2-(1,1-dimethylethyl)-1,3-thiazol-4-yl]-2-fluorophenyl}-2,6-difluorobenzenesulfonamide;

N-{3-[2-(1,1-dimethylethyl)-5-(2-methyl-4-pyrimidinyl)-1,3-thiazol-4-yl]-2-fluorophenyl}-2,5-difluorobenzenesulfonamide;

N-{3-[5-(2-amino-4-pyrimidinyl)-2-(tetrahydro-2H-pyran-4-yl)-1,3-thiazol-4-yl]-2-fluorophenyl}-2,6-difluorobenzenesulfonamide;

N-{3-[5-(2-amino-4-pyrimidinyl)-2-(4-morpholinyl)-1,3-thiazol-4-yl]-2-fluorophenyl}-2,5-difluorobenzenesulfonamide;

N-{3-[5-(2-amino-4-pyrimidinyl)-2-(4-morpholinyl)-1,3-thiazol-4-yl]-2-chlorophenyl}-2-furansulfonamide;

N-{3-[5-(2-amino-4-pyrimidinyl)-2-(4-morpholinyl)-1,3-thiazol-4-yl]-2-chlorophenyl}-2,5-difluorobenzenesulfonamide; and N-{3-[2-(1,1-dimethylethyl)-5-(4-pyrimidinyl)-1,3-thiazol-4-yl]-2-fluorophenyl}-2,5-difluorobenzenesulfonamide;

N-{3-[5-(2-amino-4-pyrimidinyl)-2-(tetrahydro-2H-pyran-4-yl)-1,3-thiazol-4-yl]-2-chlorophenyl}-3-furansulfonamide;

N-{3-[5-(2-amino-4-pyrimidinyl)-2-(tetrahydro-2H-pyran-4-yl)-1,3-thiazol-4-yl]-2-fluorophenyl}-3-furansulfonamide, and pharmaceutically acceptable salts thereof, and particularly selected from N-{3-[5-(2-amino-4-pyrimidinyl)-2-(1,1-dimethylethyl)-1,3-thiazol-4-yl]-2-fluorophenyl}-2,6-difluorobenzenesulfonamide;

N-{3-[2-(1,1-dimethylethyl)-5-(2-methyl-4-pyrimidinyl)-1,3-thiazol-4-yl]-2-fluorophenyl}-2,5-difluorobenzenesulfonamide;

N-{3-[5-(2-amino-4-pyrimidinyl)-2-(tetrahydro-2H-pyran-4-yl)-1,3-thiazol-4-yl]-2-fluorophenyl}-2,6-difluorobenzenesulfonamide;

N-{3-[5-(2-amino-4-pyrimidinyl)-2-(4-morpholinyl)-1,3-thiazol-4-yl]-2-fluorophenyl}-2,5-difluorobenzenesulfonamide;

N-{3-[5-(2-amino-4-pyrimidinyl)-2-(4-morpholinyl)-1,3-thiazol-4-yl]-2-chlorophenyl}-2-furansulfonamide;

N-{3-[5-(2-amino-4-pyrimidinyl)-2-(4-morpholinyl)-1,3-thiazol-4-yl]-2-chlorophenyl}-2,5-difluorobenzenesulfonamide; and N-{3-[2-(1,1-dimethylethyl)-5-(4-pyrimidinyl)-1,3-thiazol-4-yl]-2-fluorophenyl}-2,5-difluorobenzenesulfonamide; and pharmaceutically acceptable salts thereof. Particularly the free base of any of the compounds.

In another aspect of the present invention, there is provided a method of treating breast cancer, cholangiocarcinoma, colorectal cancer, melanoma, non-small cell lung cancer, ovarian cancer, or thyroid cancer, in a mammal, particularly a human, in need thereof, comprising administering to the mammal (e.g. human) a therapeutically effective amount of N-{3-[5-(2-amino-4-pyrimidinyl)-2-(1,1-dimethylethyl)-1,3-thiazol-4-yl]-2-fluorophenyl}-2,6-difluorobenzenesulfonamide;

N-{3-[2-(1,1-dimethylethyl)-5-(2-methyl-4-pyrimidinyl)-1,3-thiazol-4-yl]-2-fluorophenyl}-2,5-difluorobenzenesulfonamide; or N-{3-[5-(2-amino-4-pyrimidinyl)-2-(tetrahydro-2H-pyran-4-yl)-1,3-thiazol-4-yl]-2-fluorophenyl}-2,6-difluorobenzenesulfonamide;

or a pharmaceutically acceptable salt thereof. Particularly the free base of any of the compounds.

In another aspect, there is provided a method for treating cholangiocarcinoma, colorectal cancer, melanoma or thyroid cancer in a human in need thereof, comprising administering to the human, a therapeutically effective amount of N-{3-[5-(2-amino-4-pyrimidinyl)-2-(1,1-dimethylethyl)-1,3-thiazol-4-yl]-2-fluorophenyl}-2,6-difluorobenzenesulfonamide;

N-{3-[2-(1,1-dimethylethyl)-5-(2-methyl-4-pyrimidinyl)-1,3-thiazol-4-yl]-2-fluorophenyl}-2,5-difluorobenzenesulfonamide; or N-{3-[5-(2-amino-4-pyrimidinyl)-2-(tetrahydro-2H-pyran-4-yl)-1,3-thiazol-4-yl]-2-fluorophenyl}-2,6-difluorobenzenesulfonamide;

or a pharmaceutically acceptable salt thereof. Particularly the free base of any of the compounds.

In another aspect of the present invention, there is provided a process for preparing a compound of formula (I) or a pharmaceutically acceptable salt thereof. The process comprises reacting a compound of formula (VIII):

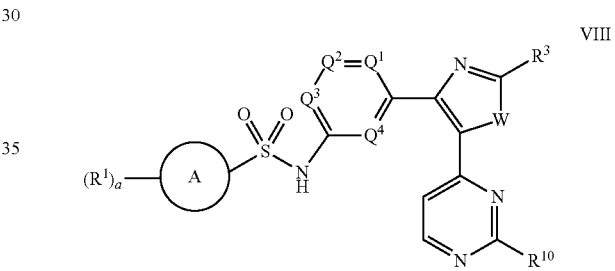

wherein $R^{10}$ is halo or thiomethyl;

with one of:

i) molecular hydrogen, or ii) an alkyl metal reagent or alkenyl metal reagent, or iii) an alcohol, or iv) a compound of formula (IX): $N(R^a)$—$R^8$, wherein $R^a$ is H or $CH_3$ and $R^8$ is as defined above;

to prepare a compound of formula (I).

In another aspect of the present invention, there is provided a process for preparing a compound of formula (I) or a pharmaceutically acceptable salt thereof. The process comprises reacting a compound of formula (XVIII):

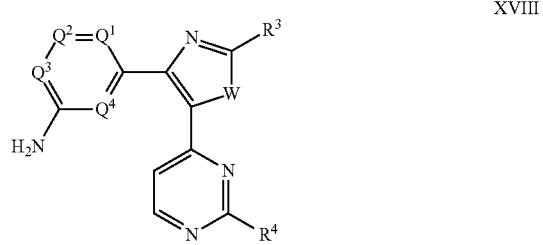

with a compound of formula (VII):

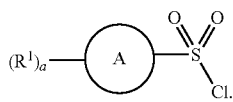

In another aspect of the present invention, there is provided a compound of formula (I), (including any particular sub-generic formula described herein) or a pharmaceutically acceptable salt thereof for use in therapy.

In another aspect, there is provided a compound of formula (I) (including any particular sub-generic formula described herein) or a pharmaceutically acceptable salt thereof for use in the treatment of a susceptible neoplasm (e.g., Barret's adenocarcinoma; billiary tract carcinomas; breast cancer; cervical cancer; cholangiocarcinoma; central nervous system tumors including primary CNS tumors such as glioblastomas, astrocytomas (e.g., glioblastoma multiforme) and ependymomas, and secondary CNS tumors (i.e., metastases to the central nervous system of tumors originating outside of the central nervous system); colorectal cancer including large intestinal colon carcinoma; gastric cancer; carcinoma of the head and neck including squamous cell carcinoma of the head and neck; hematologic cancers including leukemias and lymphomas such as acute lymphoblastic leukemia, acute myelogenous leukemia (AML), myelodysplastic syndromes, chronic myelogenous leukemia, Hodgkin's lymphoma, non-Hodgkin's lymphoma, megakaryoblastic leukemia, multiple myeloma and erythroleukemia; hepatocellular carcinoma; lung cancer including small cell lung cancer and non-small cell lung cancer; ovarian cancer; endometrial cancer; pancreatic cancer; pituitary adenoma; prostate cancer; renal cancer; sarcoma; skin cancers including melanomas; and thyroid cancers) in a mammal (e.g., human) in need thereof.

In another aspect, there is provided a compound of formula (I) (including any particular sub-generic formula described herein) or a pharmaceutically acceptable salt thereof for use in the treatment of breast cancer, cholangiocarcinoma, colorectal cancer, melanoma, non-small cell lung cancer, ovarian cancer, or thyroid cancer in a mammal (e.g., human) in need thereof.

In another aspect, there is provided a compound selected from

N-{3-[5-(2-amino-4-pyrimidinyl)-2-(1,1-dimethylethyl)-1,3-thiazol-4-yl]-2-fluorophenyl}-2,6-difluorobenzenesulfonamide;

N-{3-[2-(1,1-dimethylethyl)-5-(2-methyl-4-pyrimidinyl)-1,3-thiazol-4-yl]-2-fluorophenyl}-2,5-difluorobenzenesulfonamide;

N-{3-[5-(2-amino-4-pyrimidinyl)-2-(tetrahydro-2H-pyran-4-yl)-1,3-thiazol-4-yl]-2-fluorophenyl}-2,6-difluorobenzenesulfonamide;

N-{3-[5-(2-amino-4-pyrimidinyl)-2-(4-morpholinyl)-1,3-thiazol-4-yl]-2-fluorophenyl}-2,5-difluorobenzenesulfonamide;

N-{3-[5-(2-amino-4-pyrimidinyl)-2-(4-morpholinyl)-1,3-thiazol-4-yl]-2-chlorophenyl}-2-furansulfonamide;

N-{3-[5-(2-amino-4-pyrimidinyl)-2-(4-morpholinyl)-1,3-thiazol-4-yl]-2-chlorophenyl}-2,5-difluorobenzenesulfonamide; and N-{3-[2-(1,1-dimethylethyl)-5-(4-pyrimidinyl)-1,3-thiazol-4-yl]-2-fluorophenyl}-2,5-difluorobenzenesulfonamide;

N-{3-[5-(2-amino-4-pyrimidinyl)-2-(tetrahydro-2H-pyran-4-yl)-1,3-thiazol-4-yl]-2-chlorophenyl}-3-furansulfonamide;

N-{3-[5-(2-amino-4-pyrimidinyl)-2-(tetrahydro-2H-pyran-4-yl)-1,3-thiazol-4-yl]-2-fluorophenyl}-3-furansulfonamide; and pharmaceutically acceptable salts thereof (particularly the free base forms) for use in the treatment of a susceptible neoplasm (e.g., Barret's adenocarcinoma; billiary tract carcinomas; breast cancer; cervical cancer; cholangiocarcinoma; central nervous system tumors including primary CNS tumors such as glioblastomas, astrocytomas (e.g., glioblastoma multiforme) and ependymomas, and secondary CNS tumors (i.e., metastases to the central nervous system of tumors originating outside of the central nervous system); colorectal cancer including large intestinal colon carcinoma; gastric cancer; carcinoma of the head and neck including squamous cell carcinoma of the head and neck; hematologic cancers including leukemias and lymphomas such as acute lymphoblastic leukemia, acute myelogenous leukemia (AML), myelodysplastic syndromes, chronic myelogenous leukemia, Hodgkin's lymphoma, non-Hodgkin's lymphoma, megakaryoblastic leukemia, multiple myeloma and erythroleukemia; hepatocellular carcinoma; lung cancer including small cell lung cancer and non-small cell lung cancer; ovarian cancer; endometrial cancer; pancreatic cancer; pituitary adenoma; prostate cancer; renal cancer; sarcoma; skin cancers including melanomas; and thyroid cancers) in a mammal (e.g., human) in need thereof.

In another aspect, there is provided

N-{3-[5-(2-amino-4-pyrimidinyl)-2-(1,1-dimethylethyl)-1,3-thiazol-4-yl]-2-fluorophenyl}-2,6-difluorobenzenesulfonamide;

N-{3-[2-(1,1-dimethylethyl)-5-(2-methyl-4-pyrimidinyl)-1,3-thiazol-4-yl]-2-fluorophenyl}-2,5-difluorobenzenesulfonamide;

N-{3-[5-(2-amino-4-pyrimidinyl)-2-(tetrahydro-2H-pyran-4-yl)-1,3-thiazol-4-yl]-2-fluorophenyl}-2,6-difluorobenzenesulfonamide;

N-{3-[5-(2-amino-4-pyrimidinyl)-2-(4-morpholinyl)-1,3-thiazol-4-yl]-2-fluorophenyl}-2,5-difluorobenzenesulfonamide;

N-{3-[5-(2-amino-4-pyrimidinyl)-2-(4-morpholinyl)-1,3-thiazol-4-yl]-2-chlorophenyl}-2-furansulfonamide;

N-{3-[5-(2-amino-4-pyrimidinyl)-2-(4-morpholinyl)-1,3-thiazol-4-yl]-2-chlorophenyl}-2,5-difluorobenzenesulfonamide; or N-{3-[2-(1,1-dimethylethyl)-5-(4-pyrimidinyl)-1,3-thiazol-4-yl]-2-fluorophenyl}-2,5-difluorobenzenesulfonamide;

N-{3-[5-(2-amino-4-pyrimidinyl)-2-(tetrahydro-2H-pyran-4-yl)-1,3-thiazol-4-yl]-2-chlorophenyl}-3-furansulfonamide;

N-{3-[5-(2-amino-4-pyrimidinyl)-2-(tetrahydro-2H-pyran-4-yl)-1,3-thiazol-4-yl]-2-fluorophenyl}-3-furansulfonamide;

or a pharmaceutically acceptable salt thereof (particularly the free base of any of the compounds) for use in the treatment of breast cancer, cholangiocarcinoma, colorectal cancer, melanoma, non-small cell lung cancer, ovarian cancer, or thyroid cancer in a mammal (e.g., human) in need thereof.

In a another aspect of the present invention, there is provided the use of a compound of formula (I) (including any particular sub-generic formula described herein) or a pharmaceutically acceptable salt thereof, in the preparation of a medicament for use in the treatment of a susceptible neoplasm (e.g., Barret's adenocarcinoma; billiary tract carcinomas; breast cancer; cervical cancer; cholangiocarcinoma; central nervous system tumors including primary CNS tumors such as glioblastomas, astrocytomas (e.g., glioblastoma multiforme) and ependymomas, and secondary CNS tumors (i.e., metastases to the central nervous system of tumors originating outside of the central nervous system); colorectal cancer including large intestinal colon carcinoma; gastric cancer; carcinoma of the head and neck including squamous cell carcinoma of the head and neck; hematologic cancers including leukemias and lymphomas such as acute lymphoblastic leukemia, acute myelogenous leukemia (AML), myelodysplastic syndromes, chronic myelogenous leukemia, Hodgkin's lymphoma, non-Hodgkin's lymphoma, megakaryoblastic leukemia, multiple myeloma and erythroleukemia; hepatocellular carcinoma; lung cancer including small cell lung cancer and non-small cell lung cancer; ovarian cancer; endometrial cancer; pancreatic cancer; pituitary adenoma; prostate cancer; renal cancer; sarcoma; skin cancers including melanomas; and thyroid cancers) in a mammal (e.g., human) in need thereof.

In a another aspect of the present invention, there is provided the use of a compound of formula (I) (including any particular sub-generic formula described herein) or a pharmaceutically acceptable salt thereof, in the preparation of a medicament for use in the treatment of breast cancer, cholangiocarcinoma, colorectal cancer, melanoma, non-small cell lung cancer, ovarian cancer, or thyroid cancer in a mammal (e.g., human) in need thereof.

In a another aspect of the present invention, there is provided the use of a compound selected from
N-{3-[5-(2-amino-4-pyrimidinyl)-2-(1,1-dimethylethyl)-1,3-thiazol-4-yl]-2-fluorophenyl}-2,6-difluorobenzenesulfonamide;
N-{3-[2-(1,1-dimethylethyl)-5-(2-methyl-4-pyrimidinyl)-1,3-thiazol-4-yl]-2-fluorophenyl}-2,5-difluorobenzenesulfonamide;
N-{3-[5-(2-amino-4-pyrimidinyl)-2-(tetrahydro-2H-pyran-4-yl)-1,3-thiazol-4-yl]-2-fluorophenyl}-2,6-difluorobenzenesulfonamide;
N-{3-[5-(2-amino-4-pyrimidinyl)-2-(4-morpholinyl)-1,3-thiazol-4-yl]-2-fluorophenyl}-2,5-difluorobenzenesulfonamide;
N-{3-[5-(2-amino-4-pyrimidinyl)-2-(4-morpholinyl)-1,3-thiazol-4-yl]-2-chlorophenyl}-2-furansulfonamide;
N-{3-[5-(2-amino-4-pyrimidinyl)-2-(4-morpholinyl)-1,3-thiazol-4-yl]-2-chlorophenyl}-2,5-difluorobenzenesulfonamide; and
N-{3-[2-(1,1-dimethylethyl)-5-(4-pyrimidinyl)-1,3-thiazol-4-yl]-2-fluorophenyl}-2,5-difluorobenzenesulfonamide;
N-{3-[5-(2-amino-4-pyrimidinyl)-2-(tetrahydro-2H-pyran-4-yl)-1,3-thiazol-4-yl]-2-chlorophenyl}-3-furansulfonamide;
N-{3-[5-(2-amino-4-pyrimidinyl)-2-(tetrahydro-2H-pyran-4-yl)-1,3-thiazol-4-yl]-2-fluorophenyl}-3-furansulfonamide; and
pharmaceutically acceptable salts thereof (particularly the free base forms) for the preparation of a medicament for the treatment of a susceptible neoplasm (e.g., Barret's adenocarcinoma; billiary tract carcinomas; breast cancer; cervical cancer; cholangiocarcinoma; central nervous system tumors including primary CNS tumors such as glioblastomas, astrocytomas (e.g., glioblastoma multiforme) and ependymomas, and secondary CNS tumors (i.e., metastases to the central nervous system of tumors originating outside of the central nervous system); colorectal cancer including large intestinal colon carcinoma; gastric cancer; carcinoma of the head and neck including squamous cell carcinoma of the head and neck; hematologic cancers including leukemias and lymphomas such as acute lymphoblastic leukemia, acute myelogenous leukemia (AML), myelodysplastic syndromes, chronic myelogenous leukemia, Hodgkin's lymphoma, non-Hodgkin's lymphoma, megakaryoblastic leukemia, multiple myeloma and erythroleukemia; hepatocellular carcinoma; lung cancer including small cell lung cancer and non-small cell lung cancer; ovarian cancer; endometrial cancer; pancreatic cancer; pituitary adenoma; prostate cancer; renal cancer; sarcoma; skin cancers including melanomas; and thyroid cancers) in a mammal (e.g., human) in need thereof.

In a another aspect of the present invention, there is provided the use of a compound selected from
N-{3-[5-(2-amino-4-pyrimidinyl)-2-(1,1-dimethylethyl)-1,3-thiazol-4-yl]-2-fluorophenyl}-2,6-difluorobenzenesulfonamide;
N-{3-[2-(1,1-dimethylethyl)-5-(2-methyl-4-pyrimidinyl)-1,3-thiazol-4-yl]-2-fluorophenyl}-2,5-difluorobenzenesulfonamide;
N-{3-[5-(2-amino-4-pyrimidinyl)-2-(tetrahydro-2H-pyran-4-yl)-1,3-thiazol-4-yl]-2-fluorophenyl}-2,6-difluorobenzenesulfonamide;
N-{3-[5-(2-amino-4-pyrimidinyl)-2-(4-morpholinyl)-1,3-thiazol-4-yl]-2-fluorophenyl}-2,5-difluorobenzenesulfonamide;
N-{3-[5-(2-amino-4-pyrimidinyl)-2-(4-morpholinyl)-1,3-thiazol-4-yl]-2-chlorophenyl}-2-furansulfonamide;
N-{3-[5-(2-amino-4-pyrimidinyl)-2-(4-morpholinyl)-1,3-thiazol-4-yl]-2-chlorophenyl}-2,5-difluorobenzenesulfonamide;
N-{3-[2-(1,1-dimethylethyl)-5-(4-pyrimidinyl)-1,3-thiazol-4-yl]-2-fluorophenyl}-2,5-difluorobenzenesulfonamide;
N-{3-[5-(2-amino-4-pyrimidinyl)-2-(tetrahydro-2H-pyran-4-yl)-1,3-thiazol-4-yl]-2-chlorophenyl}-3-furansulfonamide;
N-{3-[5-(2-amino-4-pyrimidinyl)-2-(tetrahydro-2H-pyran-4-yl)-1,3-thiazol-4-yl]-2-fluorophenyl}-3-furansulfonamide; and
pharmaceutically acceptable salts thereof (particularly the free base forms) for the preparation of a medicament for the treatment of breast cancer, cholangiocarcinoma, colorectal cancer, melanoma, non-small cell lung cancer, ovarian cancer, or thyroid cancer in a mammal (e.g., human) in need thereof.

In another aspect of the present invention, there is provided a pharmaceutical composition comprising a compound of formula (I) (including any particular sub-generic formula described herein) or a pharmaceutically acceptable salt thereof for use in the treatment of a susceptible neoplasm (e.g., Barret's adenocarcinoma; billiary tract carcinomas; breast cancer; cervical cancer; cholangiocarcinoma; central nervous system tumors including primary CNS tumors such as glioblastomas, astrocytomas (e.g., glioblastoma multiforme) and ependymomas, and secondary CNS tumors (i.e., metastases to the central nervous system of tumors originating outside of the central nervous system); colorectal cancer including large intestinal colon carcinoma; gastric cancer; carcinoma of the head and neck including squamous cell carcinoma of the head and neck; hematologic cancers including leukemias and lymphomas such as acute lymphoblastic leukemia, acute myelogenous leukemia (AML), myelodysplastic syndromes, chronic myelogenous leukemia, Hodgkin's lymphoma, non-Hodgkin's lymphoma, megakaryoblastic leukemia, multiple myeloma and erythroleukemia; hepatocellular carcinoma; lung cancer including small cell lung cancer and non-small cell lung cancer; ovarian cancer; endometrial cancer; pancreatic cancer; pituitary adenoma; prostate cancer; renal cancer; sarcoma; skin cancers including melanomas; and thyroid cancers) in a mammal (e.g., human) in need thereof.

In another aspect of the present invention, there is provided a pharmaceutical composition comprising a compound of formula (I) (including any particular sub-generic formula described herein) or a pharmaceutically acceptable salt thereof for use in the treatment of breast cancer, colorectal cancer, melanoma, non-small cell lung cancer, ovarian cancer, or thyroid cancer in a mammal (e.g., human) in need thereof.

In another aspect of the present invention, there is provided a pharmaceutical composition comprising a compound selected from N-{3-[5-(2-amino-4-pyrimidinyl)-2-(1,1-dimethylethyl)-1,3-thiazol-4-yl]-2-fluorophenyl}-2,6-difluorobenzenesulfonamide;

N-{3-[2-(1,1-dimethylethyl)-5-(2-methyl-4-pyrimidinyl)-1,3-thiazol-4-yl]-2-fluorophenyl}-2,5-difluorobenzenesulfonamide;

N-{3-[5-(2-amino-4-pyrimidinyl)-2-(tetrahydro-2H-pyran-4-yl)-1,3-thiazol-4-yl]-2-fluorophenyl}-2,6-difluorobenzenesulfonamide;

N-{3-[5-(2-amino-4-pyrimidinyl)-2-(4-morpholinyl)-1,3-thiazol-4-yl]-2-fluorophenyl}-2,5-difluorobenzenesulfonamide;

N-{3-[5-(2-amino-4-pyrimidinyl)-2-(4-morpholinyl)-1,3-thiazol-4-yl]-2-chlorophenyl}-2-furansulfonamide;

N-{3-[5-(2-amino-4-pyrimidinyl)-2-(4-morpholinyl)-1,3-thiazol-4-yl]-2-chlorophenyl}-2,5-difluorobenzenesulfonamide;

N-{3-[2-(1,1-dimethylethyl)-5-(4-pyrimidinyl)-1,3-thiazol-4-yl]-2-fluorophenyl}-2,5-difluorobenzenesulfonamide;

N-{3-[5-(2-amino-4-pyrimidinyl)-2-(tetrahydro-2H-pyran-4-yl)-1,3-thiazol-4-yl]-2-chlorophenyl}-3-furansulfonamide;

N-{3-[5-(2-amino-4-pyrimidinyl)-2-(tetrahydro-2H-pyran-4-yl)-1,3-thiazol-4-yl]-2-fluorophenyl}-3-furansulfonamide; and pharmaceutically acceptable salts thereof (particularly the free base forms) for use in the treatment of a susceptible neoplasm (e.g., Barret's adenocarcinoma; billiary tract carcinomas; breast cancer; cervical cancer; cholangiocarcinoma; central nervous system tumors including primary CNS tumors such as glioblastomas, astrocytomas (e.g., glioblastoma multiforme) and ependymomas, and secondary CNS tumors (i.e., metastases to the central nervous system of tumors originating outside of the central nervous system); colorectal cancer including large intestinal colon carcinoma; gastric cancer; carcinoma of the head and neck including squamous cell carcinoma of the head and neck; hematologic cancers including leukemias and lymphomas such as acute lymphoblastic leukemia, acute myelogenous leukemia (AML), myelodysplastic syndromes, chronic myelogenous leukemia, Hodgkin's lymphoma, non-Hodgkin's lymphoma, megakaryoblastic leukemia, multiple myeloma and erythroleukemia; hepatocellular carcinoma; lung cancer including small cell lung cancer and non-small cell lung cancer; ovarian cancer; endometrial cancer; pancreatic cancer; pituitary adenoma; prostate cancer; renal cancer; sarcoma; skin cancers including melanomas; and thyroid cancers) in a mammal (e.g., human) in need thereof.

In another aspect of the present invention, there is provided a pharmaceutical composition comprising a compound selected from N-{3-[5-(2-amino-4-pyrimidinyl)-2-(1,1-dimethylethyl)-1,3-thiazol-4-yl]-2-fluorophenyl}-2,6-difluorobenzenesulfonamide;

N-{3-[2-(1,1-dimethylethyl)-5-(2-methyl-4-pyrimidinyl)-1,3-thiazol-4-yl]-2-fluorophenyl}-2,5-difluorobenzenesulfonamide;

N-{3-[5-(2-amino-4-pyrimidinyl)-2-(tetrahydro-2H-pyran-4-yl)-1,3-thiazol-4-yl]-2-fluorophenyl}-2,6-difluorobenzenesulfonamide;

N-{3-[5-(2-amino-4-pyrimidinyl)-2-(4-morpholinyl)-1,3-thiazol-4-yl]-2-fluorophenyl}-2,5-difluorobenzenesulfonamide;

N-{3-[5-(2-amino-4-pyrimidinyl)-2-(4-morpholinyl)-1,3-thiazol-4-yl]-2-chlorophenyl}-2-furansulfonamide;

N-{3-[5-(2-amino-4-pyrimidinyl)-2-(4-morpholinyl)-1,3-thiazol-4-yl]-2-chlorophenyl}-2,5-difluorobenzenesulfonamide;

N-{3-[2-(1,1-dimethylethyl)-5-(4-pyrimidinyl)-1,3-thiazol-4-yl]-2-fluorophenyl}-2,5-difluorobenzenesulfonamide;

N-{3-[5-(2-amino-4-pyrimidinyl)-2-(tetrahydro-2H-pyran-4-yl)-1,3-thiazol-4-yl]-2-chlorophenyl}-3-furansulfonamide;

N-{3-[5-(2-amino-4-pyrimidinyl)-2-(tetrahydro-2H-pyran-4-yl)-1,3-thiazol-4-yl]-2-fluorophenyl}-3-furansulfonamide; and pharmaceutically acceptable salts thereof (particularly the free base forms) for use in the treatment of breast cancer, cholangiocarcinoma, colorectal cancer, melanoma, non-small cell lung cancer, ovarian cancer, or thyroid cancer in a mammal (e.g., human) in need thereof.

These and other aspects of the invention are described further in the Detailed Description and Examples which follow.

DETAILED DESCRIPTION OF THE INVENTION

Figure 1:
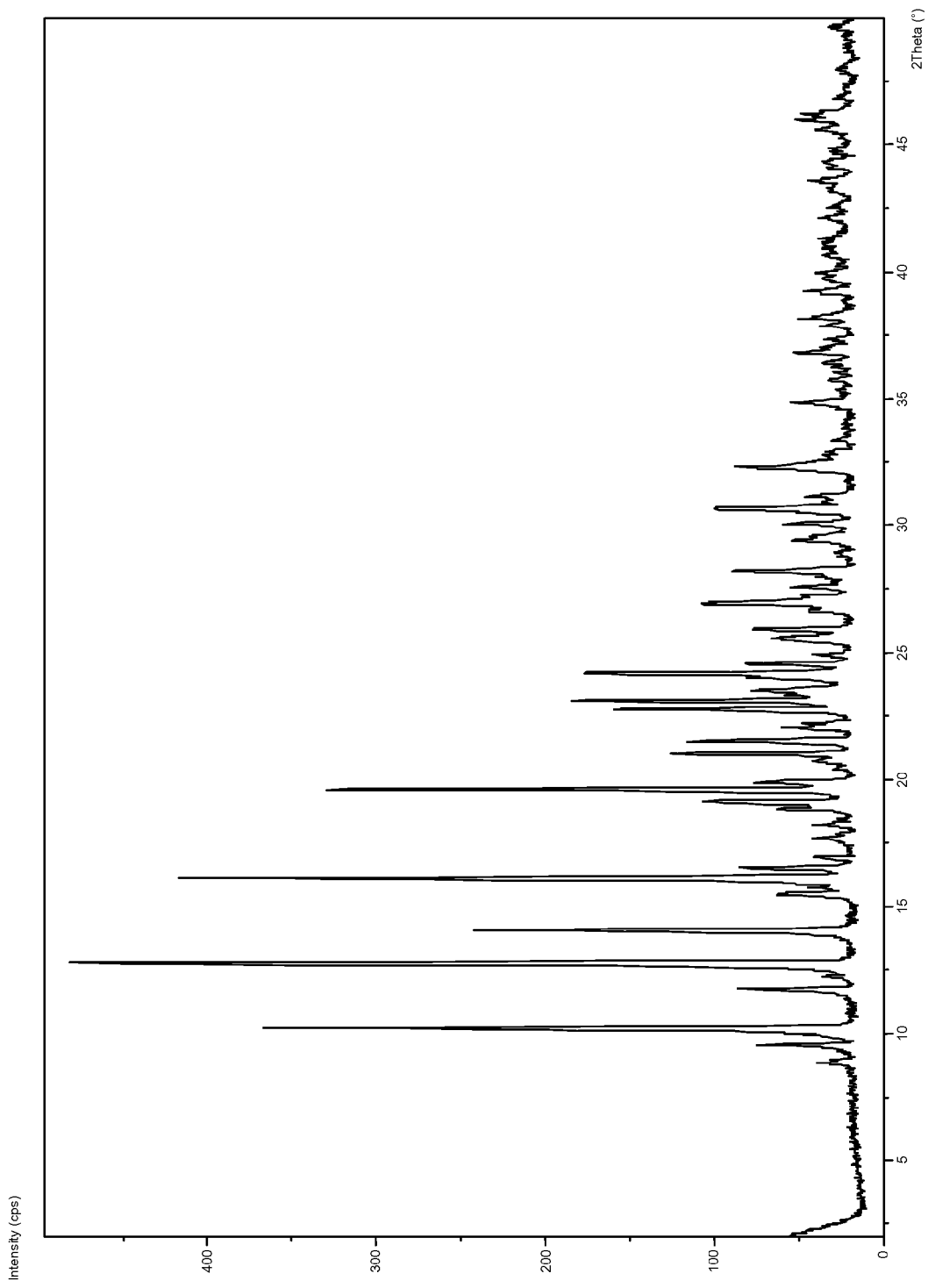
FIG. 1 is an X-Ray Powder Diffraction Pattern of a particular solid state form of N-{3-[5-(2-amino-4-pyrimidinyl)-2-(1,1-dimethylethyl)-1,3-thiazol-4-yl]-2-fluorophenyl}-2,6-difluorobenzenesulfonamide. The XRD pattern is expressed in terms of 2 theta angles and obtained with a PANalytical diffractometer equipped with a diffracted beam nickel filter using copper Kα X-radiation, according to the procedures described herein.

As used herein, the term "Raf family kinase" refers to Raf kinases including A-Raf, B-Raf and c-Raf (also known as Raf-1). Unless distinguished herein, the term refers to both wildtype and mutant variations thereof.

As used herein, "compound(s) of formula (I)" means any compound having the structural formula (I) as defined by the variable definitions provided, possible solvates, including hydrates thereof, and amorphous and crystal forms, including one or more polymorphic forms and mixtures thereof. In the case of compounds of formula (I) which possess one or more chiral centers, the compounds may be in the form of a racemic mixture, or one or more isomerically enriched or pure stereoisomers, including enantiomers and diastereomers thereof. In such embodiments, "compound(s) of formula (I)" includes the racemic form as well as the enriched or pure enantiomers and diastereomers. Enantiomerically enriched or pure compounds will be designated using conventional nomenclature, including the designations +, −, R, S, d, l, D and L, according to the predominant isomer present. Where a compound of the invention contains an alkenyl or alkenylene group, cis (E) and trans (Z) isomerism may also occur. In such embodiments, "compound(s) of formula (I)" includes the individual stereoisomers of the compound of the invention, which will be indicated using conventional, cis/trans nomenclature. It should also be understood that compounds of formula (I) may exist in tautomeric forms other than that shown in the formula and alternative tautomeric forms are also included within "compound(s) of formula (I)."

As used herein, "compound(s) of the invention" means a compound of formula (I) (as defined above) in any version, i.e., as the free base or as a pharmaceutically acceptable salt thereof. The compound as any version may be in any form, including amorphous or crystalline forms, specific polymorphic forms, solvates, including hydrates (e.g., mono-, di- and hemi-hydrates), and mixtures of various forms.

Intermediates may also be present as salts. Thus, in reference to intermediates, the phrase "compound(s) of formula (number)" means a compound having that structural formula or a pharmaceutically acceptable salt thereof.

The term "alkyl" as used herein refers to linear or branched hydrocarbon chains having from 1 to 8 carbon atoms, unless a different number of atoms is specified. Examples of "alkyl" as used herein include, but are not limited to, methyl, ethyl, n-propyl, isopropyl, n-butyl, n-pentyl, sec-butyl, isobutyl, and tert-butyl. The term "alkyl" and variations thereof (i.e., "$C_{1-4}$alkyl") is intended to independently describe each member of the genus. Similarly, the term "alkylene" refers to linear or branched divalent hydrocarbon chains containing from 1 to 8 carbon atoms, unless a different number of atoms is specified. Examples of "alkylene" as used herein include, but are not limited to, methylene, ethylene, propylene, butylene, and isobutylene. The term "alkylene" and variations thereof (i.e., "$C_{1-3}$alkylene") is intended to independently describe each member of the genus.

As used herein, the term "alkenyl" refers to linear or branched hydrocarbon chains having from 2 to 8 carbon atoms, unless a different number of atoms is specified, and at least one and up to three carbon-carbon double bonds. Examples of "alkenyl" as used herein include, but are not limited to ethenyl and propenyl. The term "alkenyl" and variations thereof (i.e., "$C_{2-4}$alkenyl") is intended to independently describe each member of the genus.

As used herein, the term "cycloalkyl" refers to a saturated monocyclic carbocyclic ring having from 3 to 8 carbon atoms, unless a different number of atoms is specified. "Cycloalkyl" includes by way of example cyclopropyl, cyclobutyl, cyclopentyl, cyclohexyl, cycloheptyl and cyclooctyl. Preferred cycloalkyl groups include substituted and unsubstituted $C_{3-6}$cycloalkyl. The term "cycloalkyl" and variations thereof (i.e., "$C_{3-6}$cycloalkyl") is intended to independently describe each member of the genus.

The terms "halo" and "halogen" are synonymous and refer to fluoro, chloro, bromo and iodo. In particular embodiments, "halo" refers to fluoro and chloro.

As used herein, "haloalkyl" refers to an alkyl, as defined above, substituted by one or more halogen atoms, fluoro, chloro, bromo or iodo. Where the haloalkyl group has less than 8 carbon atoms, the number of carbon atoms in the group is indicated as, for example, "halo$C_{1-3}$alkyl", which indicates that the haloalkyl group has 1, 2 or 3 carbon atoms. Examples of haloalkyl as used herein include, but are not limited to fluoromethyl, difluoromethyl, trifluoromethyl, fluoroethyl, trifluoroethyl, and the like. The term "haloalkyl" and variations thereof (i.e., "halo$C_{1-3}$alkyl") is intended to independently describe each member of the genus.

The term "oxo" as used herein refers to the group $=O$ attached directly to a carbon atom of a hydrocarbon ring (e.g., cycloalkyl or cycloalkenyl) or a C, N or S of a heterocyclic or heteroaryl ring to result in oxides, N-oxides, sulfones and sulfoxides.

As used herein, the terms "heterocycle" and "heterocyclic" are synonymous and refer to monocyclic saturated or unsaturated non-aromatic groups, having from 4 to 6 members (unless a different number of members is specified) and including 1, 2, or 3 heteroatoms selected from N, O and S, unless a different number of heteroatoms is specified. In all embodiments wherein the heterocycle includes 2 or more heteroatoms, the heteroatoms may be the same or different and are independently selected from N, O and S. In all embodiments wherein the compound of formula (I) includes two or more heterocyclic groups, the heterocyclic groups may be the same or different and are independently selected. Examples of particular heterocyclic groups include but are not limited to tetrahydrofuran, dihydropyran, tetrahydropyran, pyran, thietane, 1,4-dioxane, 1,3-dioxane, 1,3-dioxalane, piperidine, piperazine, pyrrolidine, morpholine, thiomorpholine, thiazolidine, oxazolidine, tetrahydrothiopyran, tetrahydrothiophene and the like. The term "heterocycle" and variations thereof (i.e., "N-heterocycle") is intended to independently describe each member of the genus.

As used herein, the term "N-heterocycle" refers to monocyclic saturated or unsaturated non-aromatic groups having from 4 to 6 members, including at least one N and optionally 1 or 2 additional heteroatoms selected from N, O and S, unless a different number of additional heteroatoms is specified. By "additional heteroatoms" is meant 1 or 2 heteroatoms in addition to the N already specified in the N-heterocycle ring. In all embodiments wherein the heterocycle includes 1 or more additional heteroatoms, the heteroatoms may be the same or different and are independently selected from N, O and S, N-heterocycles include both groups bound through the N of the N-heterocycle and groups bound through a C or S of the N-heterocycle. In all embodiments wherein the compound of formula (I) includes two or more N-heterocyclic groups, the N-heterocyclic groups may be the same or different and are independently selected.

Examples of N-heterocycles include piperidine, piperazine, pyrrolidine, morpholine, thiomorpholine and the like.

As used herein, the term "heteroaryl" refers to aromatic, monocyclic groups having 5 or 6 members (unless a different number of members is specified) including 1, 2 or 3 heteroatoms selected from N, O and S, unless a different number of heteroatoms is specified. In all embodiments wherein the heteroaryl includes 2 or more heteroatoms, the heteroatoms may be the same or different and are independently selected from N, O and S. In all embodiments wherein the compound of formula (I) includes two or more heteroaryl groups, the heteroaryl groups may be the same or different and are independently selected. Examples of particular heteroaryl groups include but are not limited to furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, and triazine. The term "heteroaryl" and variations thereof (i.e., "N-heteroaryl") is intended to independently describe each member of the genus.

As used herein, the term "N-heteroaryl" refers to aromatic, monocyclic groups having 5 or 6 members (unless a different number of members is specified) including at least one N and optionally 1 or 2 additional heteroatoms selected from N, O and S, unless a different number of heteroatoms is specified. By "additional heteroatoms" is meant 1 or 2 heteroatoms in addition to the N already specified in the N-heteroaryl ring. In all embodiments wherein the heteroaryl includes 1 or more additional heteroatoms, the heteroatoms may be the same or different and are independently selected from N, O and S. N-heteroaryls include both groups bound through the N of the N-heteroaryl and groups bound through a C or S of the N-heteroaryl. In all embodiments wherein the compound of formula (I) includes two or more N-heteroaryl groups, the N-heteroaryl groups may be the same or different and are independently selected. Examples of N-heteroaryls include pyrrole, imidazole, pyrazole, thiazole, isoxazole, pyridine, pyridazine, pyrazine, pyrimidine and triazine.

As used herein, the term "members" (and variants thereof e.g., "membered") in the context of heterocyclic and heteroaryl groups refers to the total number of ring atoms, including carbon and heteroatoms N, O and/or S. Thus, an example of a 6-membered heterocyclic ring is piperidine and an example of a 6-membered heteroaryl ring is pyridine.

As used herein, the term "optionally substituted" means unsubstituted groups or rings (e.g., cycloalkyl, heterocycle, and heteroaryl rings) and rings substituted with one or more specified substituents.

Throughout this disclosure, a list of alternatives, such as those provided above and below, is intended to particularly describe each species individually as well as sub-groups of one or more species within the list of alternatives (e.g., "or subset thereof").

The present invention provides compounds of formula (I):

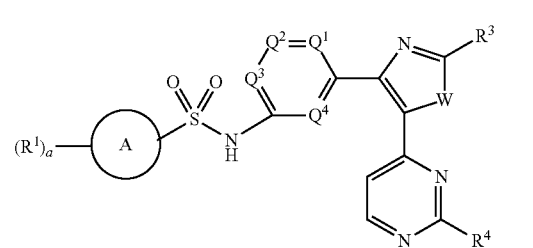

wherein:
a is 0, 1, 2 or 3;
each $R^1$ is the same or different and is independently selected from halo, alkyl, haloalkyl, —$OR^6$, —$CO_2R^6$, —$NR^6R^7$, and —CN;
Ring A is selected from $C_{3-6}$cycloalkyl, phenyl, 5-6 membered heterocycle and 5-6 membered heteroaryl, said heterocycle and said heteroaryl each having 1 or 2 heteroatoms selected from N, O and S;
each of $Q^1$, $Q^2$, $Q^3$ and $Q^4$ is CH, C—$R^2$ or N, wherein not more than one of $Q^1$, $Q^2$, $Q^3$, and $Q^4$ is N;
each $R^2$ is the same or different and is independently selected from halo, alkyl, haloalkyl, and —$OR^6$;
W is selected from —O— and —S—;
$R^3$ is selected from H, alkyl, haloalkyl-, -alkylene-OH, —$NR^6R^7$, —$C_{3-6}$cycloalkyl, -alkylene-C(O)—OH, -alkylene-$NH_2$, and Het;
 wherein said $R^3$ $C_{3-6}$cycloalkyl is optionally substituted with 1 or 2 substituents which are the same or different and are independently selected from halo, $C_{1-3}$alkyl, halo$C_{1-3}$alkyl, OH, O—$C_{1-3}$alkyl, oxo, S($C_{1-3}$alkyl), $SO_2$, $NH_2$, N(H)$C_{1-3}$alkyl and N($C_{1-3}$alkyl)$_2$;
Het is a 5-6 membered heterocycle having 1 or 2 heteroatoms selected from N, O and S and optionally substituted with 1 or 2 substituents which are the same or different and are each independently selected from halo, $C_{1-3}$alkyl, halo$C_{1-3}$alkyl, O—$C_{1-3}$alkyl, $C_{1-3}$alkylene-O—$C_{1-3}$alkyl, OH, $C_{1-3}$alkylene-OH, oxo, $SO_2(C_{1-3}$alkyl), $C_{1-3}$alkylene-$SO_2(C_{1-3}$alkyl), $NH_2$, N(H)$C_{1-3}$alkyl, N($C_{1-3}$alkyl)$_2$, CN, and —$CH_2CN$;
$R^4$ is selected from H, alkyl, haloalkyl, alkenyl, —$OR^6$, —$R^5$—$OR^6$, —$R^5$—$CO_2R^6$, —$R^5$—$SO_2R^6$, —$R^5$—Het, —$R^5$—C(O)—Het, —N(H)$R^8$, —N(CH$_3$)$R^8$, and —$R^5$—$NR^6R^7$; each $R^5$ is the same or different and is independently $C_{1-4}$alkylene;
each $R^6$ and each $R^7$ is the same or different and is independently selected from H, alkyl, haloalkyl, —C(O)-alkyl, and —C(O)-cycloalkyl;
$R^8$ is selected from H, alkyl (optionally substituted by —OH), haloalkyl, $C_{3-6}$cycloalkyl, —$R^5$—$C_{3-6}$cycloalkyl, Het$^2$, —$R^5$—Het$^2$, —$R^5$—$OR^6$, —$R^5$—O—$R^5$—$OR^6$, —$R^5$—C(O)$_2R^6$, —$R^5$—C(O)NR$^6R^7$, —$R^5$—N(H)C(O)—$R^6$, —$R^5$—N(H)C(O)—$R^5$—$OR^6$, —$R^5$—N(H)C(O)$_2$—$R^6$, —$R^5$—NR$^6R^7$, —$R^5$—S(O)$_2R^6$, —$R^5$—CN, and —$R^5$—N(H)S(O)$_2R^6$;
 wherein said $R^8$ $C_{3-6}$cycloalkyl is optionally substituted with 1 or 2 substituents which are the same or different and are independently selected from halo, $C_{1-3}$alkyl, halo$C_{1-3}$alkyl, OH, O—$C_{1-3}$alkyl, oxo, S($C_{1-3}$alkyl), $SO_2(C_{1-3}$alkyl), $NH_2$, N(H)$C_{1-3}$alkyl and N($C_{1-3}$alkyl)$_2$, and N(H)$SO_2C_{1-3}$alkyl; and
Het$^2$ is a 4-6 membered heterocycle having 1 or 2 heteroatoms selected from N, O and S and optionally substituted with 1, 2, 3, 4 or 5 $C_{1-3}$alkyl or 1 or 2 substituents which are the same or different and are each independently selected from halo, $C_{1-3}$alkyl, halo$C_{1-3}$alkyl, O—$C_{1-3}$alkyl, $C_{1-3}$alkylene-O—$C_{1-3}$alkyl, OH, $C_{1-3}$alkylene-OH, oxo, $SO_2(C_{1-3}$alkyl), $C_{1-3}$alkylene-$SO_2(C_{1-3}$alkyl), $NH_2$, $N(H)C_{1-3}$alkyl, $N(C_{1-3}$alkyl)$_2$, $N(H)SO_2C_{1-3}$alkyl, $C(O)(C_{1-3}$alkyl), $CO_2(C_{1-4}$alkyl), CN, and —$CH_2CN$;
and $R^9$ and $R^{19}$ are independently selected from H and alkyl, and pharmaceutically acceptable salts thereof.

For purposes of optimal clarity in distinguishing the cycloalkyl groups defining the variables $R^3$ and $R^8$ above, the language "$R^3$ $C_{3-6}$cycloalkyl" is used to refer to the cycloalkyl group defining the variable $R^3$ and "$R^8$ $C_{3-6}$cycloalkyl" refers to the cycloalkyl group defining the variable $R^8$.

The compounds of the invention are described in the conventional manner employing variables to represent a number of possible substituents or groups. The original, particular and preferred definitions of variables described herein apply equally to compounds of formula (I) and compounds of the invention. For brevity, the following description will generally refer to "compounds of the invention" rather than to both, as compounds of the invention encompasses all compounds of formula (I). For example, the organic chemist of ordinary skill in the art would appreciate that moieties such as N(H)$CH_2F$, —N(H)$CH_2NH_2$, —O$CH_2NH_2$, and the like, result in potentially unstable acetals, aminals or iminium ions. As such, the present invention should be understood such that the variables are defined in a manner which avoids such embodiments.

In a particular embodiment, the compounds of the invention are defined wherein a is 0, 1 or 2. In another particular embodiment, a is 1 or 2. In one particular embodiment, a is 1. In another particular embodiment, a is 2. In those embodiments wherein Ring A is phenyl, particular embodiments are defined wherein a is 1 or 2, more particularly 2. In embodiments wherein Ring A is 5-6 membered heterocycle or heteroaryl, particular embodiments are defined wherein a is 0 or 1, more particularly 0. In those embodiments wherein Ring A is cycloalkyl, particular embodiments are defined wherein a is 0.

In those embodiments of the compounds of the invention wherein a is 1, 2 or 3, each $R^1$ may be bound to Ring A through any suitable carbon or heteroatom of Ring A (to provide, for example, N-methyl, N-oxides or sulfones). In certain embodiments, wherein a is any of 1, 2 or 3, each $R^1$ is the same or different and is independently selected from halo (particularly F or Cl), alkyl, haloalkyl, and —$OR^6$, or any subset thereof. In those embodiments wherein $R^1$ is $OR^6$, where $R^6$ is H, it will be understood that when Ring A is a heterocycle or heteroaryl, the compounds of the invention include the tautomeric form wherein the heterocycle or heteroaryl Ring A is substituted by oxo. Specific examples of groups defining $R^1$ include but are not limited to F, Cl, Br, $CH_3$, $CF_3$, $CH_2CH_3$, $CH(CH_3)_2$, $CH_2CH_2CH_3$, $OCH_3$, $OCF_3$, $OCH_2CH_3$, and $OCH_2CH_2CH_3$. In one particular embodiment, each $R^1$ is the same or different and is independently selected from F, Cl, $C_{1-3}$alkyl, $CF_3$, and $OC_{1-3}$alkyl, or any subset thereof. In one particular embodiment, each $R^1$ is the same or different and is independently F, Cl, $CH_3$, $CF_3$, or $OCH_3$, or any subset thereof. In one preferred embodiment, each $R^1$ is the same or different and is independently F, Cl, or $CH_3$, or any subset thereof. In one particular preferred embodiment, each $R^1$ is the same or different and is independently F or Cl. In one particular preferred embodiment, each $R^1$ is F. In one preferred embodiment, a is 1 and $R^1$ is F. In another preferred embodiment, a is 2 and both $R^1$ are F.

in formula (I) is referred to herein as "Ring A." Ring A is selected from $C_{3-6}$cycloalkyl, phenyl, 5-6 membered heterocycle having 1 or 2 heteroatoms selected from N, O and S and 5-6 membered heteroaryl having 1 or 2 heteroatoms selected from N, O and S, or any subset thereof. Ring A may be bonded to the sulfonyl through any suitable carbon or heteroatom of Ring A. In one embodiment, Ring A is selected from phenyl, 5-6 membered heterocycle and 5-6 membered heteroaryl, or any subset thereof. In one particular embodiment, Ring A is phenyl or 5-6 membered heteroaryl having 1 or 2 heteroatoms selected from N, O and S. In one embodiment, Ring A is phenyl or 5-6 membered N-heteroaryl. The 5-6 membered N-heteroaryl may have no or 1 additional heteroatom selected from N, O and S. In one preferred embodiment, Ring A is phenyl. In another particular embodiment, Ring A is a 5-6 membered heteroaryl, particularly N-heteroaryl optionally having 1 additional heteroatom selected from N, O and S. In another preferred embodiment, Ring A is 5-membered heteroaryl, particularly a 5-membered heteroaryl having only one heteroatom which is selected from N, O and S.

Specific examples of groups defining Ring A include cyclopropyl, cyclobutyl, cyclopentyl, cyclohexyl, phenyl, tetrahydrofuranyl, tetrahydropyranyl, pyrrolidinyl, pyrrolinyl, pyrazolidinyl, pyrazolinyl, imidazolidinyl, piperidinyl, piperazinyl, morpholinyl, thiomorpholinyl, furanyl, pyranyl, thiophenyl, pyrrolyl, pyrazolyl, imidazolyl, oxazolyl, isoxazolyl, thiazolyl, isothiazolyl, pyridinyl, pyrimidinyl, and pyridizinyl. In one embodiment, Ring A is selected from these specific groups or any subset thereof. In another particular embodiment, Ring A is selected from cyclopropyl, cyclohexyl, phenyl, morpholinyl, furanyl, thiophenyl, pyrrolyl, pyrazolyl, imidazolyl, oxazolyl, isoxazolyl, thiazolyl, isothiazolyl, pyridinyl, pyrimidinyl and pyridizinyl, or any subset thereof. In one preferred embodiment, Ring A is selected from phenyl, morpholinyl, furanyl, thiophenyl, imidazolyl, thiazolyl, isothiazolyl, and pyridinyl, or any subset thereof. In one preferred embodiment, Ring A is phenyl, furanyl, thiophenyl, thiazolyl, or pyridinyl or any subset thereof. In one preferred embodiment, Ring A is phenyl, furanyl, thiazolyl or pyridinyl, or any subset thereof. In one particular preferred embodiment, Ring A is phenyl, furanyl or pyridinyl. In one preferred embodiment, Ring A is phenyl. In another preferred embodiment, Ring A is furanyl. In another preferred embodiment, Ring A is pyridinyl.

The ring defined as

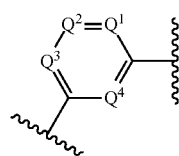

is a phenyl or pyridinyl ring wherein when the ring is a pyridinyl, the N of the pyridinyl ring may be at any of positions indicated by $Q^1$, $Q^2$, $Q^3$ and $Q^4$. In one embodiment, each of $Q^1$, $Q^2$, $Q^3$ and $Q^4$ is CH, C—$R^2$ or N, wherein not $Q^2$, more than one of $Q^1$, $Q^3$, and $Q^4$ is N and at least two of $Q^1$, $Q^2$, $Q^3$ and $Q^4$ are CH. In one embodiment, each of $Q^1$, $Q^2$, $Q^3$ and $Q^4$ is CH, C—$R^2$ or N, wherein not more than one of $Q^1$, $Q^2$, U $Q^3$, and $Q^4$ is N and not more than one of $Q^1$, $Q^2$, $Q^3$ and $Q^4$ is C—$R^2$. In one preferred embodiment, each of $Q^1$, $Q^2$, $Q^3$, and $Q^4$ is CH or C—$R^2$, and thus the ring is a phenyl ring or substituted phenyl ring. In a particular version of this embodiment, at least two of $Q^1$, $Q^2$, $Q^3$ and $Q^4$ is CH, and thus the ring is unsubstituted phenyl or phenyl substituted by 1 or two substituents $R^2$. In one embodiment, one of $Q^1$, $Q^2$, $Q^3$ and $Q^4$ is C—$R^2$ and the other three are CH. In one preferred embodiment, each of $Q^1$, $Q^2$, and $Q^3$ is CH and $Q^4$ is C—$R^2$. In another preferred embodiment, each of $Q^1$, $Q^2$, and $Q^4$ is CH and $Q^3$ is C—$R^2$.

In another embodiment, one of $Q^1$, $Q^2$, $Q^3$, and $Q^4$ is N, and thus the ring is a pyridinyl or substituted pyridinyl ring. In one version of this embodiment, at least two of $Q^1$, $Q^2$, $Q^3$ and $Q^4$ is CH. In a particular embodiment, one of $Q^1$, $Q^2$, $Q^3$, and $Q^4$ is N, and the remaining of $Q^1$, $Q^2$, $Q^3$, and $Q^4$ is CH. In one particular embodiment, $Q^3$ is N, and $Q^1$, $Q^2$, and $Q^4$ are CH. In another particular embodiment, $Q^4$ is N, and $Q^1$, $Q^2$, and $Q^3$ are CH.

Particular specific embodiments of the compounds of the invention are illustrated by formulas (I-i) and (I-ii):

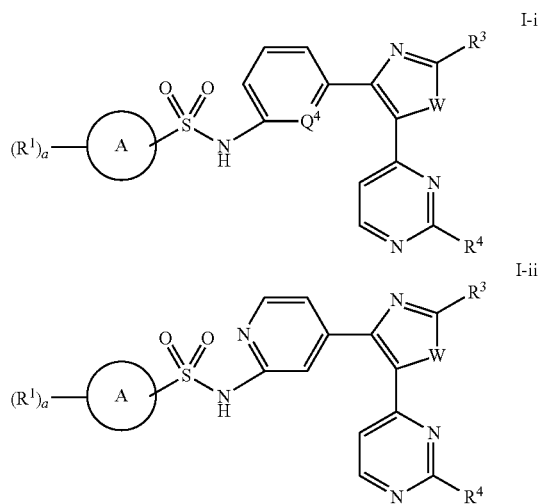

wherein $Q^4$ is CH or C—$R^2$ and all other variables are as defined herein. Thus, compounds of the invention include compounds of formula (I-i) and (I-ii) and pharmaceutically acceptable salts thereof. Other specific embodiments of the compounds of formula (I) wherein $Q^1$, $Q^2$, $Q^3$, and $Q^4$ are as described above will be readily apparent to those skilled in the art.

In one preferred embodiment, the compounds of the invention are selected from compounds of formula (I-i-a) and pharmaceutically acceptable salts thereof:

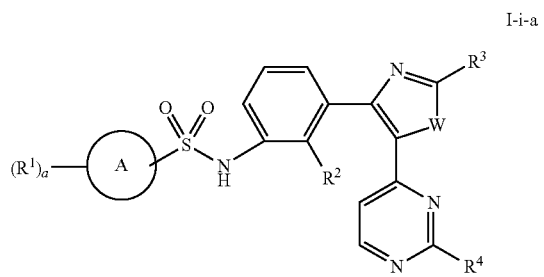

wherein all variables are as defined herein.

In those embodiments where one or more of $Q^1$, $Q^2$, $Q^3$ and $Q^4$ is C—$R^2$, each $R^2$ is the same or different and is independently halo, alkyl, haloalkyl, or —$OR^6$, or any subset thereof. In one embodiment, each $R^2$ is the same or different and is independently halo or $C_{1-3}$alkyl (i.e., any of methyl, ethyl, propyl, or isopropyl), or any subset thereof. In one embodiment, "halo" defining $R^2$ is F or Cl. In one embodiment, each $R^2$ is the same or different and is independently halo. In one particular embodiment, each $R^2$ is the same or different and is independently F or Cl. In one preferred embodiment, each $R^2$ is F.

Particular compounds of the invention are defined wherein each of $Q^1$, $Q^2$, and $Q^3$ is CH and $Q^4$ is C—F or C—Cl (illustrated generically as formula (I-i-a) above wherein $R^2$ is F or Cl). In one version of this embodiment, $Q^4$ is C—F. In another embodiment, the compounds of the invention are defined wherein each of $Q^1$, $Q^2$, and $Q^4$ is CH and $Q^3$ is C—F or C—Cl. In one version of this embodiment, $Q^3$ is C—F.

In a particular embodiment, the compounds of formula (I) are defined wherein Ring A is phenyl, $Q^1$, $Q^2$, and $Q^3$ are all CH and $Q^4$ is C—$R^2$. This embodiment is illustrated as formula (I-i-b):

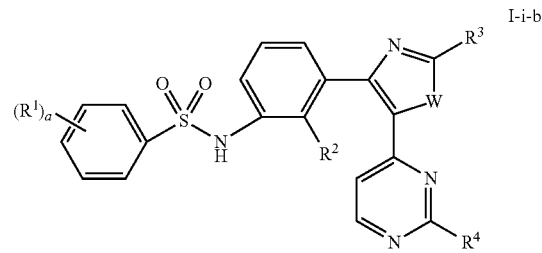

wherein all variables are as defined herein.

In one embodiment, compounds of the invention are defined wherein W is O. In one preferred embodiment the compounds of the invention are defined wherein W is S. This embodiment is illustrated by formula (I-iii):

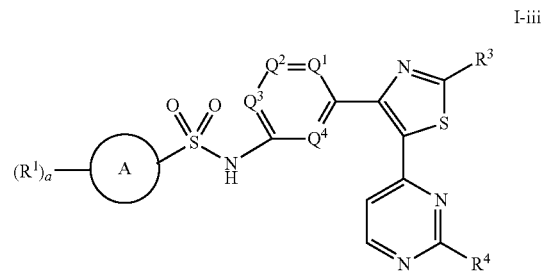

wherein all variables are as defined herein.

In one particular embodiment, W is S, each of $Q^1$, $Q^2$, and $Q^3$ is CH and $Q^4$ is CH or C—$R^2$. This embodiment is illustrated by formula (I-iii-a):

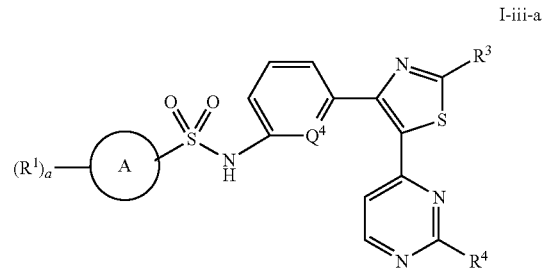

wherein $Q^4$ is CH or C—$R^2$ and all other variables are as defined herein.

In one particular preferred version of this embodiment, Ring A is phenyl. This embodiment is illustrated by formula (I-iii-b):

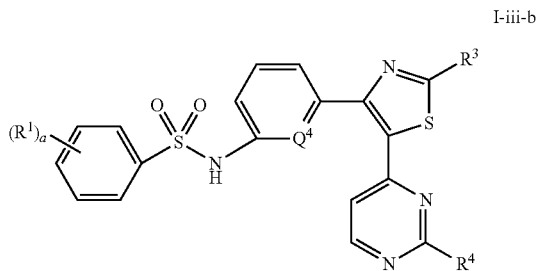

wherein $Q^4$ is CH or C—$R^2$ and all variables are as defined herein.

Other examples of embodiments of the compounds of the invention are illustrated by formulas (I-iii-c), (I-iii-d) and (I-iii-e):

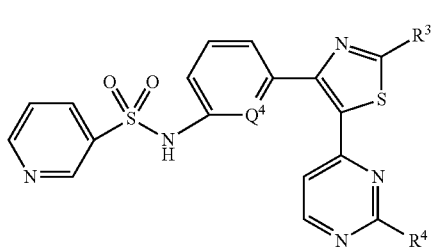

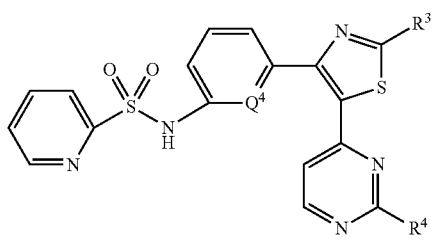

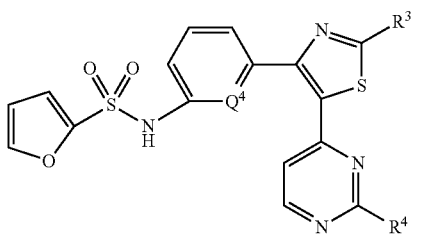

wherein $Q^4$ is CH or C—$R^2$ and all other variables are as defined herein.

In one embodiment the compounds of the invention are defined wherein, $R^3$ is alkyl, haloalkyl, unsubstituted $C_{3-6}$cycloalkyl, or Het, or any subset thereof. In one particular embodiment, $R^3$ is selected from alkyl or Het, or any subset thereof. In one particular embodiment, $R^3$ is Het, particularly Het bound through N. In one preferred embodiment, $R^3$ is alkyl. One particular embodiment of the compounds of the invention are defined wherein $R^3$ is selected from alkyl (particularly $C_{1-6}$alkyl), tetrahydrofuranyl, tetrahydropyranyl, pyrrolidinyl, pyrrolinyl, pyrazolidinyl, pyrazolinyl, imidazolinyl, imidazolidinyl, piperidinyl, piperazinyl, morpholinyl, or thiomorpholinyl, or any subset thereof. In this embodiment, the heterocyclic groups may be unsubstituted or substituted as described in the definition of "Het". In one particular embodiment, $R^3$ is selected from $C_{3-6}$alkyl (e.g., propyl, isopropyl, n-butyl, isobutyl, sec-butyl, tert-butyl (dimethylethyl), pentyl and hexyl), piperidinyl, piperazinyl, morpholinyl, and thiomorpholinyl, or any subset thereof. The piperidinyl, piperazinyl, morpholinyl, and thiomorpholinyl may be unsubstituted or substituted as described in the definition of "Het".

In one preferred embodiment, $R^3$ is alkyl, and particularly branched $C_{3-6}$alkyl (particularly isopropyl, sec-butyl, isobutyl or tert-butyl, or any subset thereof). In one specific preferred embodiment, $R^3$ is isopropyl or tert-butyl. In one specific embodiment, $R^3$ is isopropyl. In one specific embodiment, $R^3$ is tert-butyl. In one specific embodiment, $R^3$ is tetrahydropyranyl. In one specific embodiment, $R^3$ is substituted or unsubstituted morpholinyl, particularly unsubstituted morpholinyl.

Het (as employed in the definition of $R^3$) is a 5-6 membered heterocycle having 1 or 2 heteroatoms selected from N, O and S and optionally substituted with 1 or 2 substituents which are the same or different and are each independently selected from halo, $C_{1-3}$alkyl, halo$C_{1-3}$alkyl, O—$C_{1-3}$alkyl, $C_{1-3}$alkylene-O—$C_{1-3}$alkyl, OH, $C_{1-3}$alkylene-OH, oxo, $SO_2(C_{1-3}$alkyl), $C_{1-3}$alkylene-$SO_2(C_{1-3}$alkyl), $NH_2$, N(H)$C_{1-3}$alkyl, N($C_{1-3}$alkyl)$_2$, CN, and —$CH_2CN$, or any subset thereof. In one embodiment, Het in the definition of $R^3$ is a 5-6 membered N-heterocycle optionally having 1 additional heteroatom selected from N, O and S and optionally substituted as described above. In one particular embodiment, Het is a 5-6 membered N-heterocycle having no additional heteroatoms and optionally 1 substituent as described above. In one particular embodiment, Het is a 5-6 membered N-heterocycle bound through the N, optionally having 1 additional heteroatom selected from N, O and S, and optionally substituted with 1 substituent as described above. In one embodiment, Het is selected from optionally substituted tetrahydrofuranyl, tetrahydropyranyl, pyrrolidinyl, pyrrolinyl, pyrazolidinyl, pyrazolinyl, imidazolinyl, imidazolidinyl, piperidinyl, piperazinyl, morpholinyl, thiomorpholinyl, or any subset thereof, wherein the optional substituents are as recited above. In one particular embodiment, Het in the definition of $R^3$ is substituted or unsubstituted piperidinyl, piperazinyl, morpholinyl, thiomorpholinyl, or any subset thereof. In one specific embodiment, $R^3$ is tetrahydropyranyl. In one particular embodiment, $R^3$ is substituted or unsubstituted morpholinyl.

The compounds of the invention are defined wherein $R^4$ is H, alkyl, haloalkyl, alkenyl, —$OR^6$, —$R^5$—$OR^6$, —$R^5$—$CO_2R^6$, —$R^5$—$SO_2R^6$, —$R^5$—Het, —N(H)$R^8$, —N(CH$_3$)$R^8$ or —$R^5$—N$R^6R^7$, or any subset thereof. In one embodiment, $R^4$ is H, alkyl, alkenyl, —$OR^6$, —$R^5$—$OR^6$, —$R^5$—$CO_2R^6$, —$R^5$—$SO_2R^6$, —N(H)$R^8$, —N(CH$_3$)$R^8$, or —$R^5$—N$R^6R^7$, or any subset thereof. In one embodiment, $R^4$ is —$R^5$—Het, wherein $R^5$ is $C_{1-3}$alkylene and Het is a 6 membered heterocycle having 1 or 2 heteroatoms selected from N, O and S and optionally substituted with 1 or 2 substituents which are the same or different and are each independently selected from halo, $C_{1-3}$alkyl, halo$C_{1-3}$alkyl, O—$C_{1-3}$alkyl, $C_{1-3}$alkylene-O—$C_{1-3}$alkyl, OH, $C_{1-3}$alkylene-OH, oxo, $SO_2$($C_{1-3}$alkyl), $C_{1-3}$alkyleneSO$_2$($C_{1-3}$alkyl), $NH_2$, N(H)$C_{1-3}$alkyl, N($C_{1-3}$alkyl)$_2$, CN and —$CH_2$—CN, or any subset thereof. In one particular embodiment, $R^4$ is —$R^5$—Het, wherein $R^5$ is $C_{1-3}$alkylene and Het is a 6 membered N-heterocycle optionally having 1 additional heteroatom selected from N, O and S and optionally substituted with 1 or 2 substituents which are the same or different and are each independently selected from $C_{1-3}$alkyl, OH, and oxo, or any subset thereof. In one embodiment, the N-heterocycle is bound through the N. In one embodiment, $R^4$ is $—R^5—NR^6R^7$, wherein $R^5$ is $C_{1-3}$alkylene and $R^6$ and $R^7$ are each independently H or alkyl, particularly H or $C_{1-3}$alkyl.

In one embodiment, $R^4$ is H, alkyl, $N(H)R^8$ or $N(CH_3)R^8$, or any subset thereof. In one particular embodiment, $R^4$ is H, alkyl, or $N(H)R^8$, or any subset thereof.

The compounds of the invention, wherein $R^4$ is H, are illustrated by formula (I-iv):

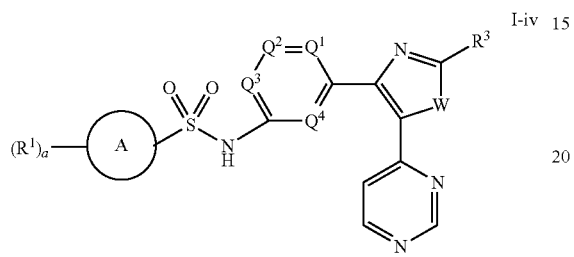

I-iv wherein all variables are as defined here.

Within this embodiment, particular embodiments of the compounds of the invention wherein $R^4$ is H, are illustrated by formulas (I-iv-a), (I-iv-b), (I-iv-c), (I-iv-d) and (I-iv-e):

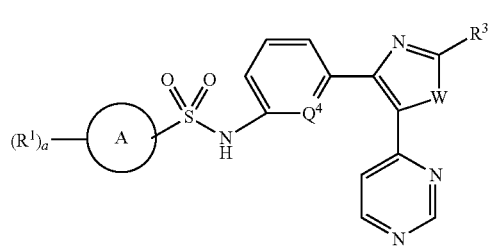

I-iv-a

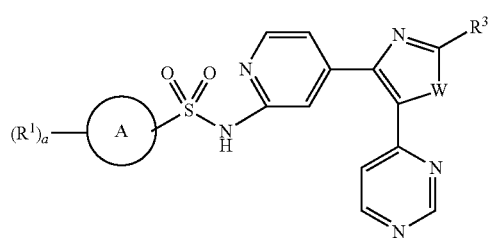

I-iv-b

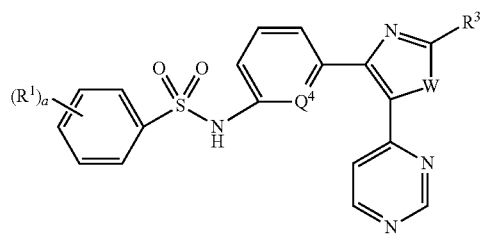

I-iv-c

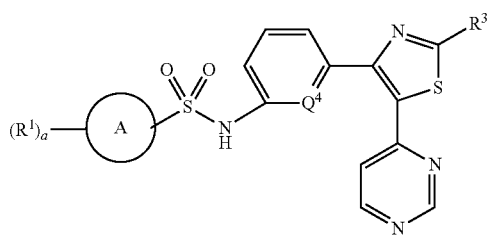

I-iv-d

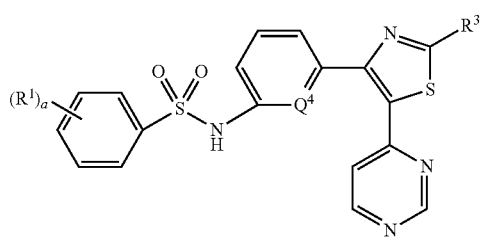

I-iv-e wherein $Q^4$ is CH or $C—R^2$ and all other variables are as defined herein.

Those skilled in the art will readily envision structural formulas illustrating compounds of the invention wherein $R^4$ is H based upon the foregoing description and examples provided.

In another particular embodiment, the compounds of the invention are defined wherein $R^4$ is alkyl. This embodiment is illustrated by formula (I-v):

I-v wherein all variables are as defined here.

Within this embodiment, particular embodiments of the compounds of the invention wherein $R^4$ is alkyl, are illustrated by formulas (I-v-a), (I-v-b), (I-v-c), (I-v-d) and (I-v-e):

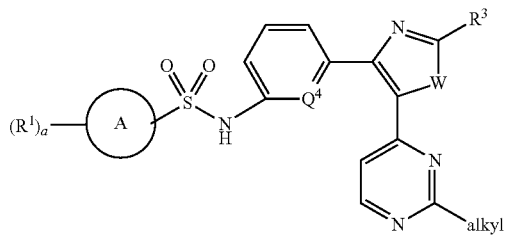

I-v-a

-continued

I-v-b
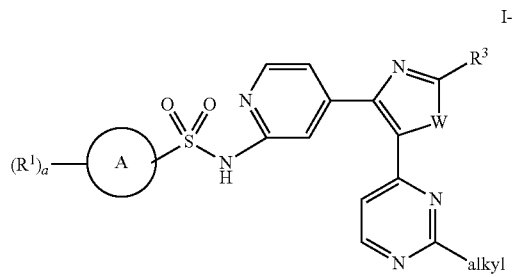

I-v-c
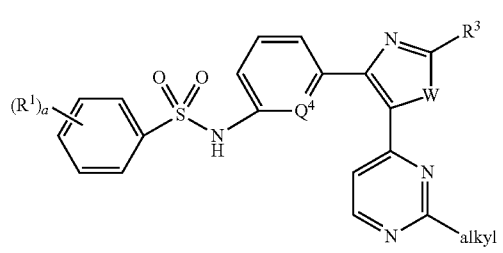

I-v-d
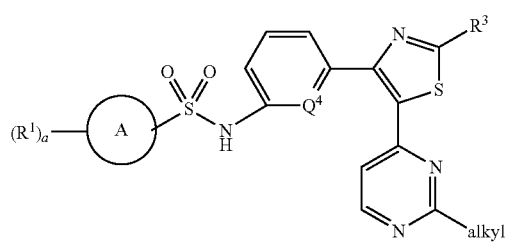

I-v-e
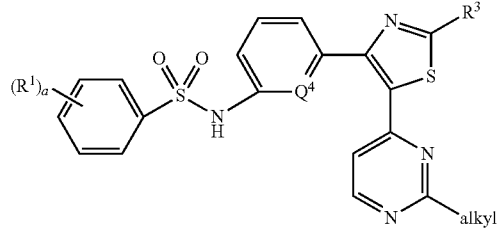

wherein $Q^4$ is CH or C—$R^2$ and all other variables are as defined herein.

Those skilled in the art will readily envision structural formulas illustrating compounds of the invention wherein $R^4$ is alkyl based upon the foregoing description and examples provided.

In one embodiment, $R^4$ is $C_{1-4}$alkyl (i.e., methyl, ethyl, propyl, isopropyl, n-butyl, sec-butyl, isobutyl or tert-butyl). In one preferred embodiment, $R^4$ is methyl.

In one particular embodiment $R^4$ is N(H)$R^8$ or N(CH$_3$)$R^8$. In one preferred embodiment, $R^4$ is N(H)$R^8$, illustrated as formula (I-vi):

I-vi
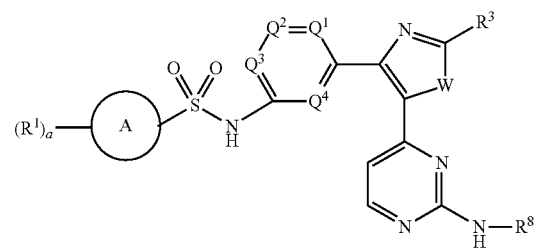

Within this embodiment, particular embodiments of the compounds of the invention wherein $R^4$ is N(H)$R^8$, are illustrated by formulas (I-vi-a), (I-vi-b), (I-vi-c), (I-vi-d), (I-vi-e), (I-vi-f), (I-vi-g), (I-vi-h), (I-vi-j), and (I-vi-k):

I-vi-a
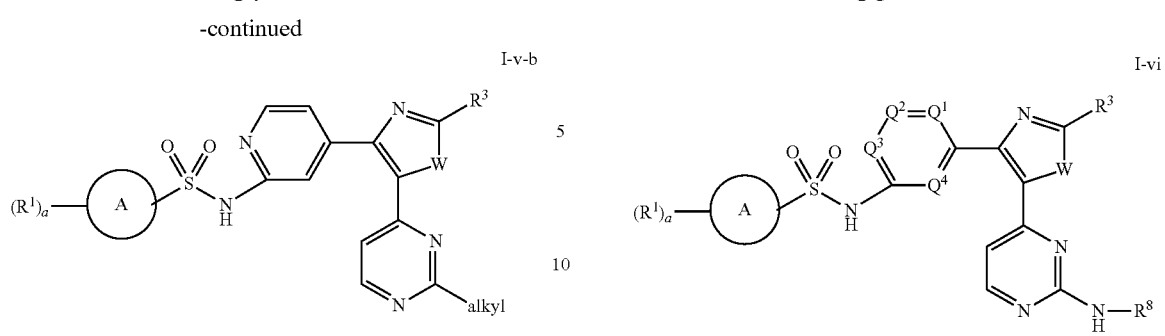

I-vi-b
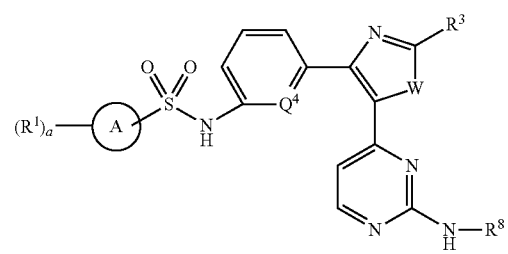

I-vi-c
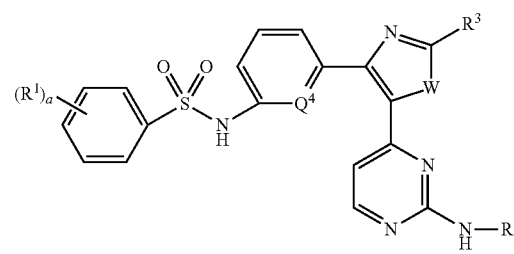

I-vi-d
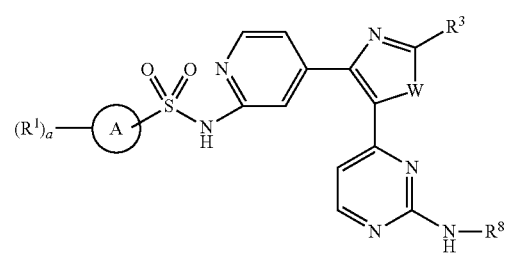

I-vi-e

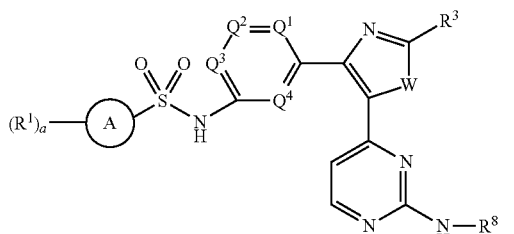

I-vi-f

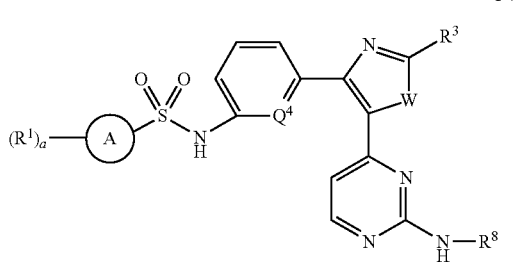

I-vi-g

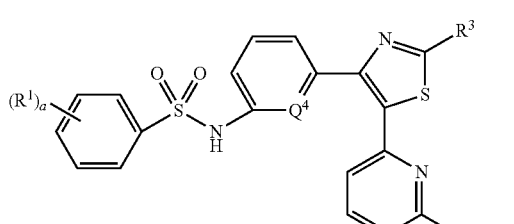

I-vi-h

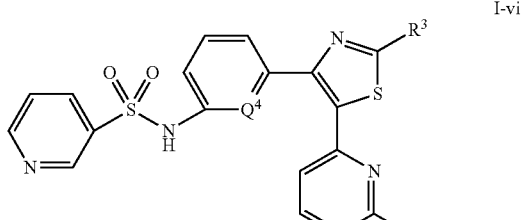

I-vi-j

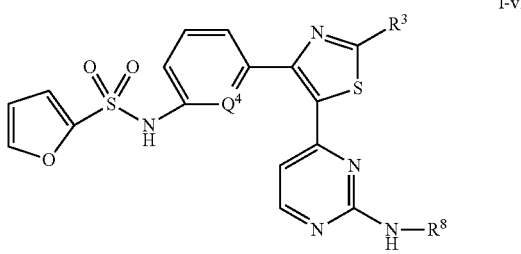

I-vi-k

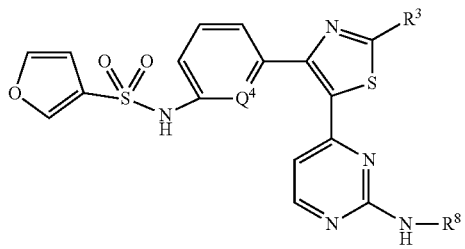

wherein in formulas (I-vi-a), (I-vi-b), (I-vi-f), (I-vi-g), (I-vi-h), (I-vi-j), and (I-vi-k), $Q^4$ is CH or C—$R^2$, and all other variables are as defined herein.

The compounds of the invention are defined wherein $R^8$ is selected from H, alkyl, haloalkyl, $C_{3-6}$cycloalkyl, —$R^5$—$C_{3-6}$cycloalkyl, $Het^2$, —$R^5$—$Het^2$, —$R^5$—$OR^6$, —$R^5$—O—$R^5$—$OR^6$, —$R^5$—C(O)$_2R^6$, —$R^5$—C(O)$NR^6R^7$, —$R^5$—N(H)C(O)—$R^6$, —$R^5$—N(H)C(O)—$R^5$—$OR^6$, —$R^5$—N(H)C(O)$_2$—$R^6$, —$R^5$—$NR^6R^7$, —$R^5$—S(O)$_2R^6$, and —$R^5$—N(H)S(O)$_2R^6$, or any subset thereof;

wherein the $R^8$ $C_{3-6}$cycloalkyl is optionally substituted with 1 or 2 substituents which are the same or different and are independently selected from halo, $C_{1-3}$alkyl, halo$C_{1-3}$alkyl, OH, O—$C_{1-3}$alkyl, oxo, S($C_{1-3}$alkyl), SO$_2$($C_{1-3}$alkyl), NH$_2$, N(H)$C_{1-3}$alkyl and N($C_{1-3}$alkyl)$_2$, and N(H)SO$_2C_{1-3}$alkyl; and $Het^2$ is a 4-6 membered heterocycle having 1 or 2 heteroatoms selected from N, O and S and optionally substituted with 1, 2, 3, 4 or 5 $C_{1-3}$alkyl or 1 or 2 substituents which are the same or different and are each independently selected from halo, $C_{1-3}$alkyl, halo$C_{1-3}$alkyl, O—$C_{1-3}$alkyl, $C_{1-3}$alkylene-O—$C_{1-3}$alkyl, OH, $C_{1-3}$alkylene-OH, oxo, SO$_2$($C_{1-3}$alkyl), $C_{1-3}$alkylene-SO$_2$($C_{1-3}$alkyl), NH$_2$, N(H)$C_{1-3}$alkyl, N($C_{1-3}$alkyl)$_2$, N(H)SO$_2C_{1-3}$alkyl, C(O)($C_{1-3}$alkyl), CO$_2$($C_{1-4}$alkyl), CN, and —CH$_2$CN;

In one embodiment, $R^8$ is selected from H, alkyl, haloalkyl, $C_{3-6}$cycloalkyl, —$R^5$—$C_{3-6}$cycloalkyl, $Het^2$, —$R^5$—$Het^2$, —$R^5$—$OR^6$, —$R^5$—O(CH$_2$)$_2$OR$^6$, —$R^5$—C(O)$NR^6R^7$, —$R^5$—N(H)C(O)—$R^6$, —$R^5$—N(H)C(O)CH$_2$OH, —$R^5$—C(O)$_2R^6$, —$R^5$—N(H)C(O)$_2$—$R^6$, —$R^5$—$NR^6R^7$, —$R^5$—S(O)$_2R^6$, and —$R^5$—N(H)S(O)$_2R^6$, or any subset thereof.

In another particular embodiment, $R^8$ is selected from H, alkyl, haloalkyl, unsubstituted cyclopropyl, optionally substituted cyclohexyl, —$R^5$—$C_{3-6}$cycloalkyl, —$R^5$—$Het^2$, —$R^5$—$OR^6$, —$R^5$—C(O)$_2R^6$, —$R^5$—C(O)$NR^6R^7$, —$R^5$—N(H)C(O)—$R^6$, —$R^5$—$NR^6R^7$, and —$R^5$—S(O)$_2R^6$, or any subset thereof. In one particular embodiment, $R^8$ is selected from H, alkyl, haloalkyl, unsubstituted cyclopropyl, optionally substituted cyclohexyl, —$R^5$—$Het^2$, —$R^5$—$OR^6$, and —$R^5$—S(O)$_2R^6$, or any subset thereof.

In one particular embodiment, the compounds of the invention are defined wherein $R^8$ is selected from H, alkyl, haloalkyl, $C_{3-6}$cycloalkyl, —$R^5$—$C_{3-6}$cycloalkyl, —$R^5$—$OR^6$, —$R^5$—O—$R^5$—$OR^6$, —$R^5$—C(O)$_2R^6$, —$R^5$—C(O)$NR^6R^7$, —$R^5$—N(H)C(O)—$R^6$, —$R^5$—N(H)C(O)—$OR^6$, —$R^5$—N(H)C(O)$_2$—$R^6$, —$R^5$—$NR^6R^7$, —$R^5$—S(O)$_2R^6$, and —$R^5$—N(H)S(O)$_2R^6$, or any subset thereof.

In one particular embodiment, $R^8$ is selected from H, alkyl, haloalkyl, $C_{3-6}$cycloalkyl, —$R^5$—$C_{3-6}$cycloalkyl, —$R^5$—$OR^6$, —$R^5$—O(CH$_2$)$_2$OR$^6$, —$R^5$—C(O)$_2R^6$, —$R^5$—C(O)$NR^6R^7$, —$R^5$—N(H)C(O)—$R^6$, —$R^5$—N(H)C(O)CH$_2$OH, —$R^5$—N(H)C(O)$_2$—$R^6$, —$R^5$—$NR^6R^7$, —$R^5$—S(O)$_2R^6$, —$R^5$—N(H)S(O)$_2R^6$, or any subset thereof.

In another embodiment, $R^8$ is selected from H, alkyl, haloalkyl, unsubstituted cyclopropyl, optionally substituted cyclohexyl, —$R^5$—$C_{3-6}$cycloalkyl, —$R^5$—$OR^6$, —$R^5$—C(O)$_2R^6$, —$R^5$—C(O)$NR^6R^7$, —$R^5$—N(H)C(O)—$R^6$, —$R^5$—$NR^6R^7$, and —$R^5$—S(O)$_2R^6$, or any subset thereof.

In one particular embodiment, $R^8$ is selected from H, alkyl, haloalkyl, unsubstituted cyclopropyl, optionally substituted cyclohexyl, —$R^5$—$OR^6$, and —$R^5$—S(O)$_2R^6$, or any subset thereof.

In one embodiment, $R^8$ $C_{3-6}$cycloalkyl is optionally substituted cyclopropyl, cyclobutyl, cyclopentyl or cyclohexyl or any subset thereof, wherein the optional substituents are as defined above. In one particular embodiment, $R^8$ $C_{3-6}$cycloalkyl is unsubstituted cyclopropyl, unsubstituted cyclobutyl or optionally substituted cyclohexyl. In one particular embodiment, $R^8$ $C_{3-6}$cycloalkyl is unsubstituted cyclopropyl, unsubstituted cyclobutyl, unsubstituted cyclohexyl or cyclohexyl substituted once by $N(H)S(O)_2CH_3$.

In another embodiment, $R^8$ is $Het^2$ or $-R^5-Het^2$, or any subset thereof. In one particular embodiment, $R^8$ is $-R^5-Het^2$, such as $CH_2-Het^2$, or $(CH_2)_2-Het^2$.

In one embodiment, $R^8$ is defined wherein $Het^2$ (including as $R^5-Het^2$) is a 5-6 membered heterocycle having 1 or 2 heteroatoms selected from N, O and S and optionally substituted with 1, 2, 3, 4 or 5 $C_{1-3}$alkyl (which are the same or different), or 1 or 2 substituents which are the same or different and are each independently selected from halo, $C_{1-3}$alkyl, halo$C_{1-3}$alkyl, $O-C_{1-3}$alkyl, $C_{1-3}$alkylene-$O-C_{1-3}$alkyl, OH, $C_{1-3}$alkylene-OH, oxo, $SO_2(C_{1-3}$alkyl), $C_{1-3}$alkylene-$SO_2(C_{1-3}$alkyl), $NH_2$, $N(H)C_{1-3}$alkyl, $N(C_{1-3}$alkyl)$_2$, $N(H)SO_2C_{1-3}$alkyl, $C(O)(C_{1-3}$alkyl), $CO_2(C_{1-4}$alkyl), CN, and $-CH_2CN$ More particularly $Het^2$ is a 5-6 membered heterocycle optionally substituted with 1, 2, 3, 4, or 5 methyl or ethyl, more particularly methyl. In another embodiment, $Het^2$ is a 5-6 membered heterocycle having 1 or 2 heteroatoms selected from N, O and S and optionally substituted with 1 or 2 substituents which are the same or different and are independently selected from halo, $C_{1-3}$alkyl, halo$C_{1-3}$alkyl, $O-C_{1-3}$alkyl, $C_{1-3}$alkylene-$O-C_{1-3}$alkyl, OH, $C_{1-3}$alkylene-OH, oxo, $SO_2(C_{1-3}$alkyl), $C_{1-3}$alkylene-$SO_2(C_{1-3}$alkyl), $NH_2$, $N(H)C_{1-3}$alkyl, $N(C_{1-3}$alkyl)$_2$, $N(H)SO_2C_{1-3}$alkyl, $C(O)(C_{1-3}$alkyl), $CO_2(C_{1-4}$alkyl), CN, and $-CH_2CN$, or any subset thereof.

In certain embodiments of the invention, the group $Het^2$ is unsubstituted. In those embodiments wherein $Het^2$ is substituted by 1 or 2 substituents as described above, a particular embodiment is defined wherein the substituent(s) is/are selected from $C_{1-3}$alkyl, halo$C_{1-3}$alkyl, $O-C_{1-3}$alkyl, $C_{1-3}$alkylene-OH, oxo, $SO_2(C_{1-3}$alkyl), $C_{1-3}$alkylene-$SO_2$ $(C_{1-3}$alkyl), $NH_2$, $N(H)C_{1-3}$alkyl, $N(C_{1-3}$alkyl)$_2$, $C(O)(C_{1-3}$alkyl), and $CH_2-CN$, or any subset thereof. In a more particular embodiment, the optional substituent(s) on $Het^2$ is/are selected from $C_{1-3}$alkyl, halo$C_{1-3}$alkyl, $O-C_{1-3}$alkyl, $C_{1-3}$alkylene-OH, oxo, $SO_2(C_{1-3}$alkyl), $C_{1-3}$alkylene-$SO_2(C_{1-3}$alkyl), $C(O)(C_{1-3}$alkyl), and $C_{1-3}$alkylene-CN, or any subset thereof. In one particular embodiment, the optional substituent(s) on $Het^2$ is/are selected from $C_{1-3}$alkyl, oxo, $SO_2(C_{1-3}$alkyl), $C_{1-3}$alkylene-$SO_2(C_{1-3}$alkyl), $NH_2$, $N(H)C_{1-3}$alkyl, $N(C_{1-3}$alkyl)$_2$, $C(O)(C_{1-3}$alkyl), and $CO_2(C_{1-4}$alkyl), or any subset thereof. In one particular embodiment, $Het^2$ is a 5-6 membered N-heterocycle optionally including 1 additional heteroatom selected from N, O and S and optionally substituted with 1 or 2 substituents as defined above.

Specific examples of groups defining $Het^2$ (including $R^5-Het^2$) within the definition of $R^8$ include but are not limited to:

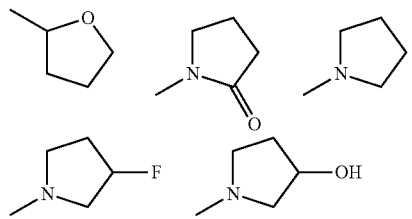

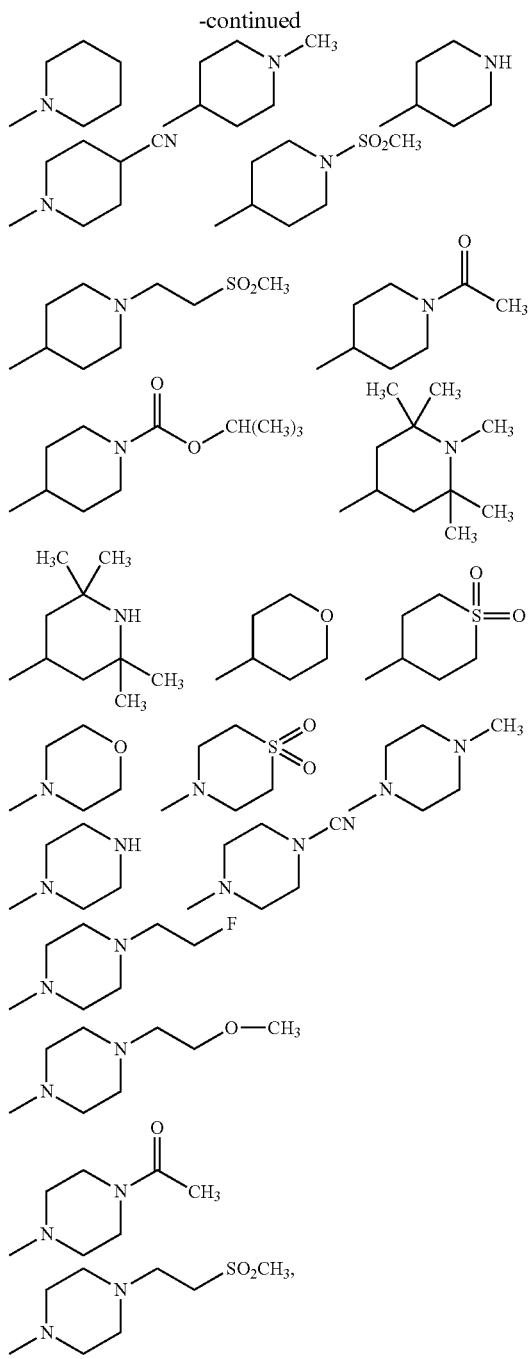

or any subset thereof. The point of attachment to the amine (NH) or the $C_{1-4}$alkylene ($R^5$), in the case of $R^5-Het^2$, is indicated by the unfilled bond.

In one preferred embodiment, the compounds of the invention are defined wherein $R^8$ is H, $C_{1-4}$alkyl or halo$C_{1-4}$alkyl. In one preferred embodiment, $R^8$ is H. In another preferred embodiment, $R^8$ is $C_{1-4}$alkyl, including each of methyl, ethyl, propyl, isopropyl, n-butyl, isobutyl, sec-butyl, and t-butyl. In one particular preferred embodiment, $R^8$ is isopropyl or isobutyl. In another preferred embodiment, $R^8$ is halo$C_{1-4}$alkyl, particularly fluoro$C_{1-4}$alkyl or chloro$C_{1-4}$alkyl, more particularly fluoro$C_{1-4}$alkyl. Particular examples of fluoro$C_{1-4}$alkyl groups include fluoroethyl, difluoroethyl, trifluoroethyl, and ethyltrifluoromethyl.

The alkylene group represented by R⁵, may be linear or branched. In one embodiment, the compounds of the invention are defined wherein R⁵ is methylene or ethylene, including —CH(CH₃)—.

In one embodiment, the compounds of the invention are defined wherein $R^6$ and $R^7$ are the same or different and are each independently selected from H, $C_{1-3}$alkyl and halo$C_{1-3}$alkyl, or any subset thereof. In one embodiment, $R^6$ and $R^7$ are the same or different and are each independently selected from H, $C_{1-3}$alkyl.

In one preferred embodiment, the compounds of the invention are compounds of formula (I-vii) or pharmaceutically acceptable salts thereof:

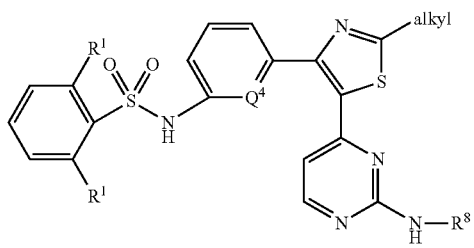

I-vii wherein $Q^4$ is CH or C—$R^2$ and all other variables are as defined herein.

In one preferred embodiment, the compounds of the invention are compounds of formula (I-viii) or pharmaceutically acceptable salts thereof:

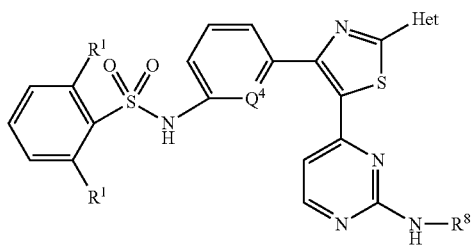

I-viii wherein $Q^4$ is CH or C—$R^2$ and all other variables are as defined herein.

In one preferred embodiment, the compounds of the invention are compounds of formula (I-ix) or pharmaceutically acceptable salts thereof:

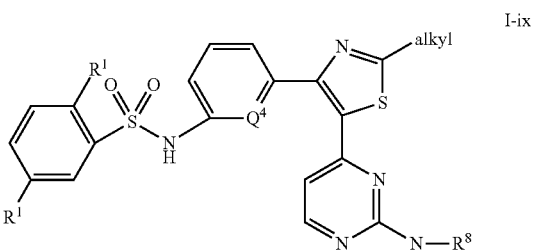

I-ix wherein $Q^4$ is CH or C—$R^2$ and all other variables are as defined herein.

In one preferred embodiment, the compounds of the invention are compounds of formula (I-x) or pharmaceutically acceptable salts thereof:

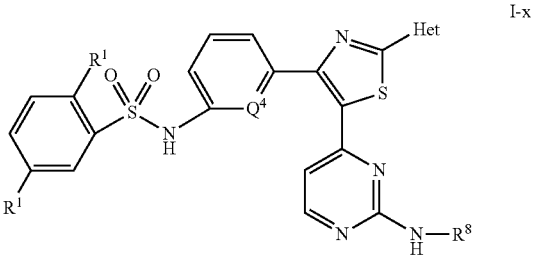

I-x wherein $Q^4$ is CH or C—$R^2$ and all other variables are as defined herein.

It is to be understood that the present invention includes all combinations and subsets of the particular and/or preferred groups defined hereinabove.

Specific examples of compounds of the present invention include those recited in the Examples which follow as well as pharmaceutically acceptable salts of compounds exemplified as the free base and other pharmaceutically acceptable salts of those compounds exemplified as salts.

Preferred compounds of formula (I) are selected from:

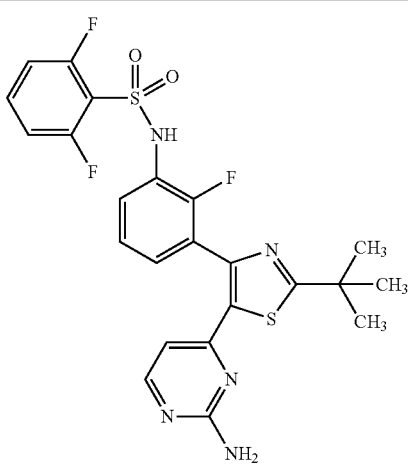 [SMILES: CC(C)(C)c1nc(-c2cccc(NS(=O)(=O)c3c(F)cccc3F)c2F)c(-c2ccnc(N)n2)s1]

N-{3-[5-(2-amino-4-pyrimidinyl)-2-(1,1-dimethylethyl)-1,3-thiazol-4-yl]-2-fluorophenyl1-2,6-difluorobenzenesulfonamide,

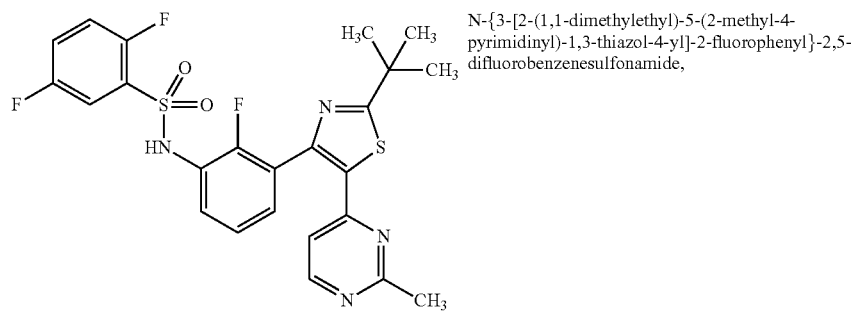 N-{3-[2-(1,1-dimethylethyl)-5-(2-methyl-4-pyrimidinyl)-1,3-thiazol-4-yl]-2-fluorophenyl}-2,5-difluorobenzenesulfonamide,

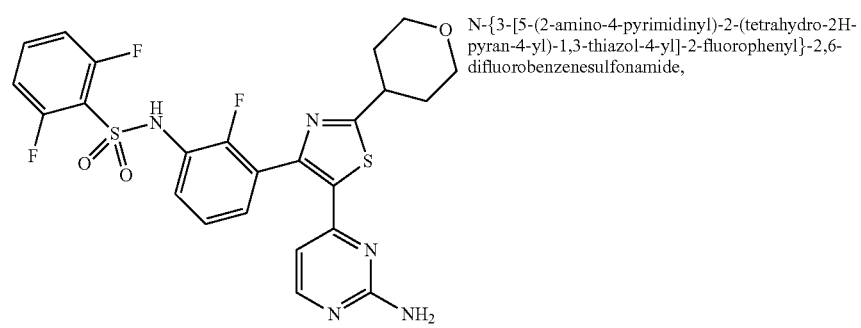 N-{3-[5-(2-amino-4-pyrimidinyl)-2-(tetrahydro-2H-pyran-4-yl)-1,3-thiazol-4-yl]-2-fluorophenyl}-2,6-difluorobenzenesulfonamide,

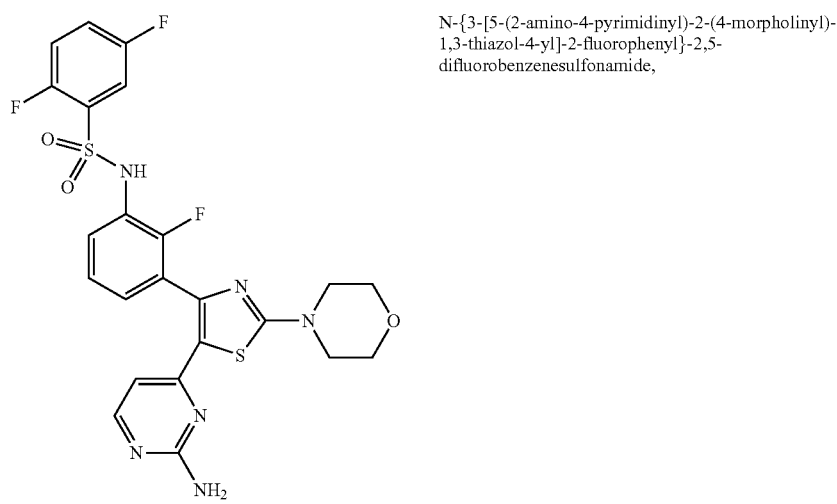 N-{3-[5-(2-amino-4-pyrimidinyl)-2-(4-morpholinyl)-1,3-thiazol-4-yl]-2-fluorophenyl}-2,5-difluorobenzenesulfonamide,

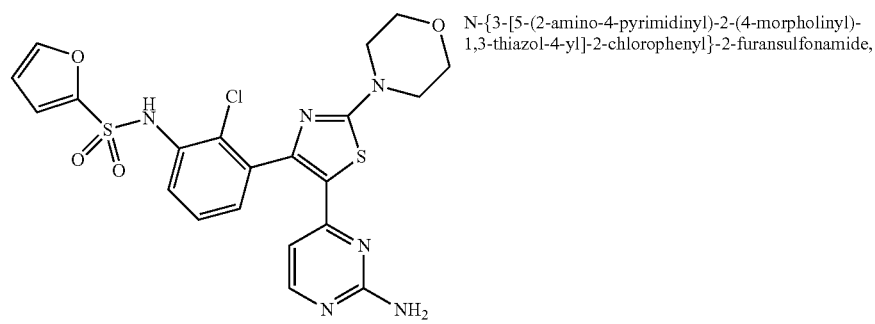 N-{3-[5-(2-amino-4-pyrimidinyl)-2-(4-morpholinyl)-1,3-thiazol-4-yl]-2-chlorophenyl}-2-furansulfonamide,

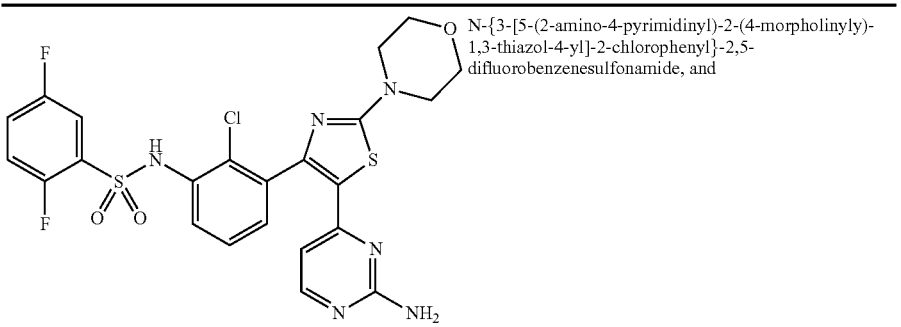

N-{3-[5-(2-amino-4-pyrimidinyl)-2-(4-morpholinyly)-1,3-thiazol-4-yl]-2-chlorophenyl}-2,5-difluorobenzenesulfonamide, and

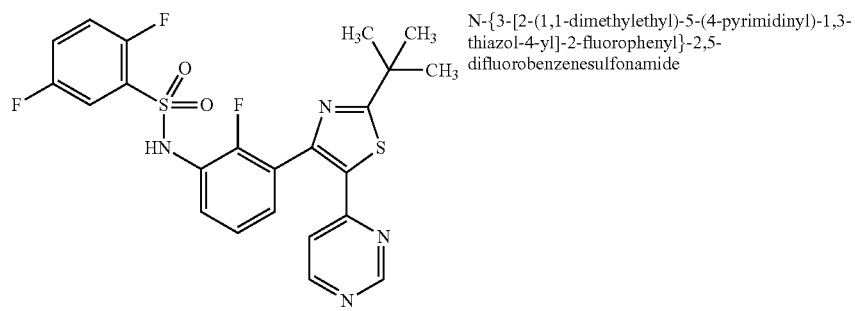

N-{3-[2-(1,1-dimethylethyl)-5-(4-pyrimidinyl)-1,3-thiazol-4-yl]-2-fluorophenyl}-2,5-difluorobenzenesulfonamide

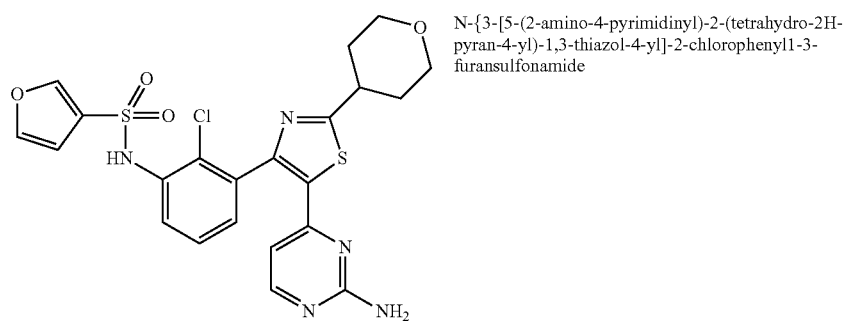

N-{3-[5-(2-amino-4-pyrimidinyl)-2-(tetrahydro-2H-pyran-4-yl)-1,3-thiazol-4-yl]-2-chlorophenyl1-3-furansulfonamide

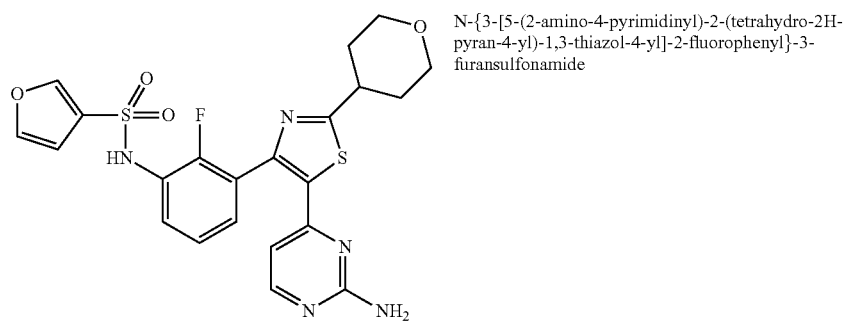

N-{3-[5-(2-amino-4-pyrimidinyl)-2-(tetrahydro-2H-pyran-4-yl)-1,3-thiazol-4-yl]-2-fluorophenyl}-3-furansulfonamide and pharmaceutically acceptable salts thereof. In one embodiment, the foregoing compounds are in the form of the free base.

In particular, preferred compounds of formula (I) include but are not limited to:

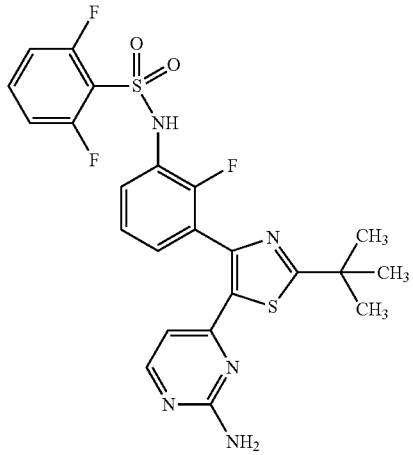 [SMILES: CC(C)(C)c1nc(-c2cccc(NS(=O)(=O)c3c(F)cccc3F)c2F)c(-c2ccnc(N)n2)s1]

N-{3-[5-(2-amino-4-pyrimidinyl)-2-(1,1-dimethylethyl)-1,3-thiazol-4-yl]-2-fluorophenyl}-2,6-difluorobenzenesulfonamide,

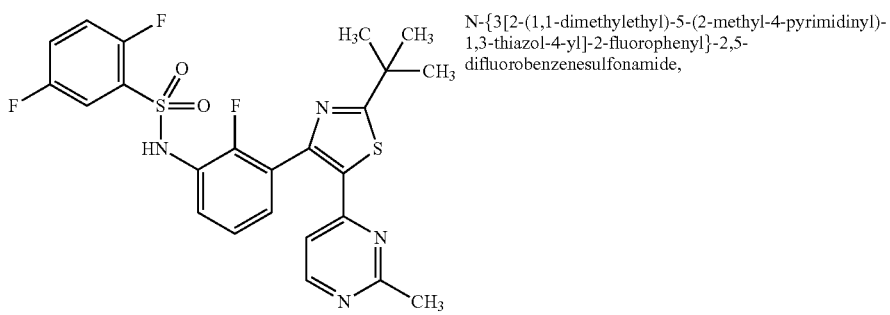

N-{3[2-(1,1-dimethylethyl)-5-(2-methyl-4-pyrimidinyl)-1,3-thiazol-4-yl]-2-fluorophenyl}-2,5-difluorobenzenesulfonamide,

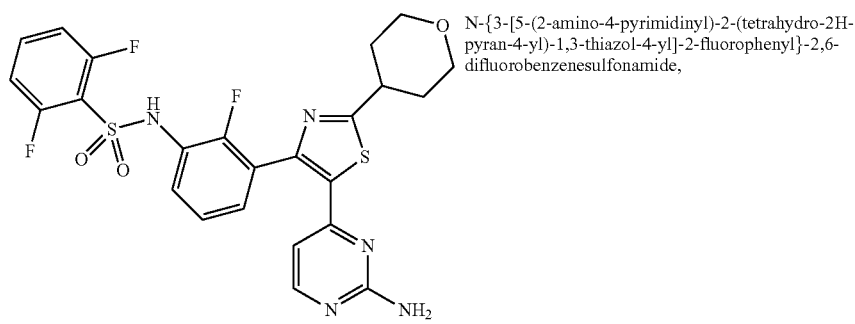

N-{3-[5-(2-amino-4-pyrimidinyl)-2-(tetrahydro-2H-pyran-4-yl)-1,3-thiazol-4-yl]-2-fluorophenyl}-2,6-difluorobenzenesulfonamide, and pharmaceutically acceptable salts thereof. In one embodiment, the foregoing compounds are in the form of the free base.

One example of a more preferred compound of formula (I) is N-{3-[5-(2-amino-4-pyrimidinyl)-2-(1,1-dimethylethyl)-1,3-thiazol-4-yl]-2-fluorophenyl}-2,6-difluorobenzenesulfonamide,

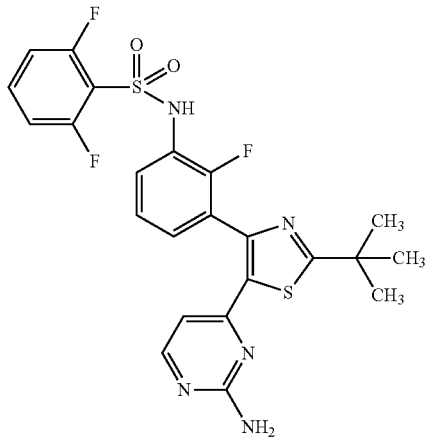 [SMILES: CC(C)(C)c1nc(-c2cccc(NS(=O)(=O)c3c(F)cccc3F)c2F)c(-c2ccnc(N)n2)s1]

and pharmaceutically acceptable salts thereof. In one embodiment, the compound is the free base. In another embodiment, the compound is a pharmaceutically acceptable salt form thereof, selected from the mesylate, sulfate, hydrochloride and sodium salt forms of the compound.

Another example of a more preferred compound of formula (I) is N-{3-[2-(1,1-dimethylethyl)-5-(2-methyl-4-pyrimidinyl)-1,3-thiazol-4-yl]-2-fluorophenyl}-2,5-difluorobenzenesulfonamide,

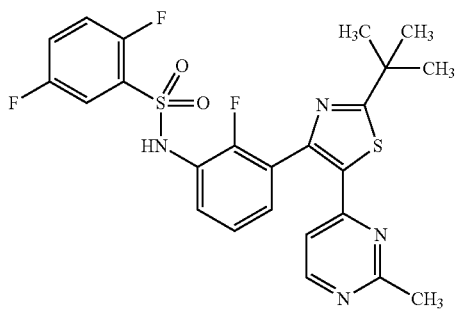 [SMILES: Cc1nccc(-c2sc(C(C)(C)C)nc2-c2cccc(NS(=O)(=O)c3cc(F)ccc3F)c2F)n1]

and pharmaceutically acceptable salts thereof. In one embodiment, the compound is the free base. In another embodiment, the compound is a pharmaceutically acceptable salt form thereof, selected from the mesylate, sulfate, hydrochloride and sodium salt forms of the compound.

Another example of a more preferred compound of formula (I) is N-{3-[5-(2-amino-4-pyrimidinyl)-2-(tetrahydro-2H-pyran-4-yl)-1,3-thiazol-4-yl]-2-fluorophenyl}-2,6-difluorobenzenesulfonamide

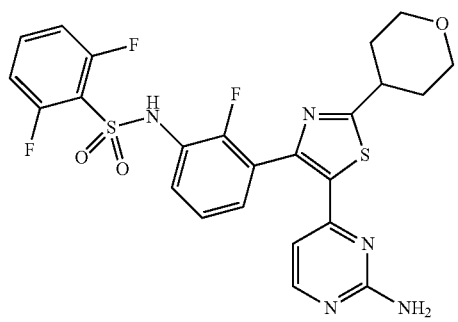 [SMILES: Nc1nccc(-c2sc(C3CCOCC3)nc2-c2cccc(NS(=O)(=O)c3c(F)cccc3F)c2F)n1]

and pharmaceutically acceptable salts thereof. In one embodiment, the compound is the free base. In another embodiment, the compound is a pharmaceutically acceptable salt form thereof, selected from the mesylate, sulfate, hydrochloride and sodium salt forms of the compound.

With regard to compounds of formula (I-iv-k) discussed above

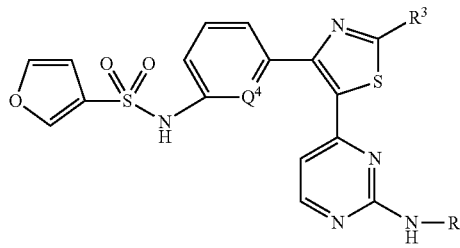

I-vi-k particularly preferred embodiments of the compounds are those of (I-iv-k1) and (I-iv-k2),

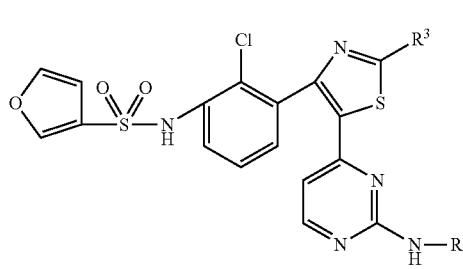

I-vi-k1

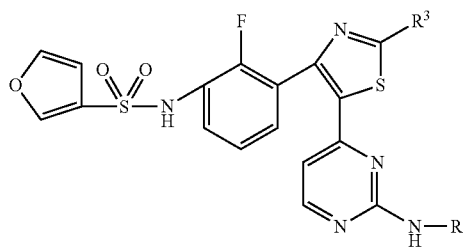

I-vi-k2

According to one embodiment of the invention, compounds of formula (I) are provided

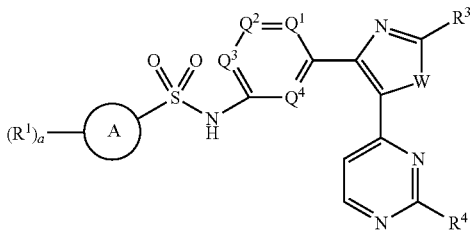

wherein:
a is 0, 1, 2 or 3;
each $R^1$ is the same or different and is independently selected from halo, alkyl, haloalkyl, —$OR^6$, —$CO_2R^6$, —$NR^6R^7$, and —CN;
Ring A is selected from $C_{3-6}$cycloalkyl, phenyl, 5-6 membered heterocycle and 5-6 membered heteroaryl, said heterocycle and said heteroaryl each having 1 or 2 heteroatoms selected from N, O and S;
each of $Q^1$, $Q^2$, $Q^3$ and $Q^4$ is CH, C—$R^2$ or N, wherein not more than one of $Q^1$, $Q^2$, $Q^3$, and $Q^4$ is N;
each $R^2$ is the same or different and is independently halo, alkyl, haloalkyl, or —$OR^6$;
W is —O— or —S—;
$R^3$ is H, alkyl, haloalkyl, alkylene-OH, $NR^6R^7$, $C_{3-6}$cycloalkyl, or Het;
  wherein said $R^3$ $C_{3-6}$cycloalkyl is optionally substituted with 1 or 2 substituents which are the same or different and are independently selected from halo, $C_{1-3}$alkyl, halo$C_{1-3}$alkyl, OH, O—$C_{1-3}$alkyl, oxo, S($C_{1-3}$alkyl), $SO_2$, $NH_2$, N(H)$C_{1-3}$alkyl and N($C_{1-3}$alkyl)$_2$;
  Het is a 5-6 membered heterocycle having 1 or 2 heteroatoms selected from N, O and S and optionally substituted with 1 or 2 substituents which are the same or different and are each independently selected from halo, $C_{1-3}$alkyl, halo$C_{1-3}$alkyl, O—$C_{1-3}$alkyl, $C_{1-3}$alkylene-O—$C_{1-3}$alkyl, OH, $C_{1-3}$alkylene-OH, oxo, $SO_2$($C_{1-3}$alkyl), $C_{1-3}$alkylene-$SO_2$($C_{1-3}$alkyl), $NH_2$, N(H)$C_{1-3}$alkyl, N($C_{1-3}$alkyl)$_2$, CN, and —$CH_2CN$;
$R^4$ is H, alkyl, haloalkyl, alkenyl, —$OR^6$, —$R^5$—$OR^6$, —$R^5$—$CO_2R^6$, —$R^5$—$SO_2R^6$, —$R^5$—Het, —N(H)$R^8$, —N($CH_3$)$R^8$, or —$R^5$—$NR^6R^7$;
each $R^5$ is the same or different and is independently $C_{1-4}$alkylene;
each $R^6$ and each $R^7$ is the same or different and is independently H, alkyl or haloalkyl; and
$R^8$ is selected from H, alkyl, haloalkyl, $C_{3-6}$cycloalkyl, —$R^5$—$C_{3-6}$cycloalkyl, $Het^2$, —$R^5$—$Het^2$, —$R^5$—$OR^6$, —$R^5$—O—$R^5$—$OR^6$, —$R^5$—$C(O)_2R^6$, —$R^5$—C(O)$NR^6R^7$, —$R^5$—N(H)C(O)—$R^6$, —$R^5$—N(H)C(O)—$R^5$—$OR^6$, —$R^5$—N(H)C(O)$_2$—$R^6$, —$R^5$—$NR^6R^7$, —$R^5$—S(O)$_2R^6$, and —$R^5$—N(H)S(O)$_2R^6$;
  wherein said $R^8$ $C_{3-6}$cycloalkyl is optionally substituted with 1 or 2 substituents which are the same or different and are independently selected from halo, halo$C_{1-3}$alkyl, OH, oxo, S($C_{1-3}$alkyl), $SO_2$, $NH_2$, N(H)$C_{1-3}$alkyl and N($C_{1-3}$alkyl)$_2$, and N(H)$SO_2C_{1-3}$alkyl; and
  $Het^2$ is a 4-6 membered heterocycle having 1 or 2 heteroatoms selected from N, O and S and optionally substituted with 1, 2, 3, 4 or 5 $C_{1-3}$alkyl or 1 or 2 substituents which are the same or different and are each independently selected from halo, $C_{1-3}$alkyl, $C_{1-3}$alkylene-O—$C_{1-3}$alkyl, OH, $C_{1-3}$alkylene-OH, oxo, $SO_2$($C_{1-3}$alkyl), $C_{1-3}$alkylene-$SO_2$($C_{1-3}$alkyl), $NH_2$, N(H)$C_{1-3}$alkyl, N($C_{1-3}$alkyl)$_2$, N(H)$SO_2C_{1-3}$alkyl, C(O)($C_{1-3}$alkyl), $CO_2$($C_{1-4}$alkyl), CN, and —$CH_2CN$;
and a pharmaceutically acceptable salts thereof.

It will be appreciated by those skilled in the art that the compounds of formula (I) may be utilized as a pharmaceutically acceptable salt version thereof. The pharmaceutically acceptable salts of the compounds of formula (I) include conventional salts formed from pharmaceutically acceptable (i.e., non-toxic) inorganic or organic acids or bases as well as quaternary ammonium salts. Representative salts include the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, ethanol amine, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate (methanesulfonate), methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate (methylbenzenesulfonate), triethiodide, trimethylammonium and valerate. Other salts, such as oxalic and trifluoroacetic, which are not themselves pharmaceutically acceptable, may be useful in the preparation of salts useful as intermediates in obtaining compounds of this invention and these form a further aspect of the invention. In one embodiment, the compound of formula (I) is in the form of the free base. In one embodiment, the compound of formula (I) is in the form of the mesylate salt. In one embodiment, the compound of formula (I) is in the form of the sulfate salt. In one embodiment, the compound of formula (I) is in the form of the hydrochloride salt. In one embodiment, the compound of formula (I) is in the form of the sodium salt. Certain salt versions of the compounds may be solvates, particularly hydrates. In one embodiment, the compound of formula (I) or a pharmaceutically acceptable salt thereof is in the form of a mono-, di-, tri- or hemi-hydrate.

Processes for preparing pharmaceutically acceptable salts of compounds such as the compounds of formula (I) are conventional in the art. See, e.g., Burger's Medicinal Chemistry And Drug Discovery 5th Edition, Vol 1: Principles And Practice. As will be apparent to those skilled in the art, in the processes described below for the preparation of compounds of formula (I), certain intermediates, may be in the form of pharmaceutically acceptable salts of the compound. Processes for preparing pharmaceutically acceptable salts of intermediates are known in the art and are analogous to the processes for preparing pharmaceutically acceptable salts of other compounds such as the compounds of formula (I).

Compounds of the invention are believed to inhibit of one or more kinases and in particular one or more Raf family kinases ("Raf inhibitor"). Compounds of the invention may also inhibit one or more other kinases, and particularly tyrosine kinases. Certain compounds of the invention may inhibit B-Raf ("B-Raf inhibitor"). It is well documented that Raf inhibitors, including B-Raf inhibitors, are believed to be useful as anticancer and antitumor agents. See, e.g., Davies (2002) supra, Garnett (2004) supra, and Zebisch (2006) supra. The anticancer and antitumor effects of these kinase inhibitors is currently believed to result from inhibition of one or more Raf family kinases, and the effect of such inhibition on cell lines whose growth and/or viability is dependent on the kinase activity of Raf family kinases.

Compounds of the invention may be Raf inhibitors and optionally also inhibit one or more ErbB family kinases (i.e., EGFR, ErbB2 and ErbB4). Certain compounds of the invention may inhibit B-Raf and also inhibit one or more ErbB family kinases (i.e., EGFR, ErbB2 and ErB4).

Some compounds of the invention may be selective inhibitors of Raf family kinases ("selective Raf inhibitor"), meaning that preferential inhibition of one or more Raf family kinases is significantly greater than that of any number of other kinases, for example by a factor of 5-fold or more.

However, the present invention is not limited to compounds which are selective inhibitors of one or more Raf family kinases rather, the present invention expressly contemplates that certain compounds of the invention may possess activity against multiple kinases, including kinases other than Raf family kinases. For example, particular compounds of the invention may possess activity against multiple other kinases, including but not limited to EGFR, ErbB2, ErbB4, IGF-1R, IR, IRR, Src, VEGFR, PDGFR, Met, Lyn, Lck, Alk5, Aurora A and B, JNK, Syk, p38, BTK, FAK, Abl, CK1. cKit, Epherin receptors (for example EphB4), FGFR, Flt, Fyn, Hck, JAK, MLK, PKCµ, Ret, Yes, and BRK, as well. Particular compounds of the invention may be deemed to be unselective or non-selective, meaning that they are not considered by one skilled in the art to be selective for any particular kinase over others.

As used herein, a Raf inhibitor is a compound that exhibits a $pIC_{50}$ of greater than about 6 against at least one Raf family kinase in the Raf inhibition enzyme assay described below and/or an $IC_{50}$ of not greater than about 5 µM potency against at least one cell line that expresses mutated B-Raf kinase (e.g., A375P, Colo205, HT-29, SK-MEL-3, SK-MEL-28) in the methylene blue and/or the CellTiter-Glo cellular proliferation assays described below. In a particular embodiment, a Raf inhibitor refers to a compound of the invention that exhibits a $pIC_{50}$ of greater than about 6.5 against at least one Raf family kinase in the Raf inhibition enzyme assay described below and an $IC_{50}$ of not greater than about 500 nM potency against at least one cell line that expresses mutated B-Raf kinase in the methylene blue and/or the CellTiter-Glo cellular proliferation assays described below.

A "B-Raf inhibitor" refers to a compound of the invention that exhibits a $pIC_{50}$ of greater than about 6.5 against B-Raf (including B-Raf mutants) in the Raf inhibition enzyme assay described below and an $IC_{50}$ of not greater than about 500 nM potency against at least one cell line that expresses mutated B-Raf kinase in the methylene blue and/or the CellTiter-Glo cellular proliferation assay described below.

The present invention provides compounds for use in medical therapy in a mammal, e.g., a human, in need thereof. The present invention provides methods for the treatment of several conditions in a mammal, in need thereof, all of which comprise the step of administering a therapeutically effective amount of a compound of the invention. All methods described herein are applicable to mammals, and particularly to humans.

As used herein, the term "treatment" or "treating" in the context of therapeutic methods, refers to alleviating the specified condition, eliminating or reducing the symptoms of the condition, slowing or eliminating the progression, invasion, or metastatic spread of the condition and preventing or delaying the reoccurrence of the condition in a previously afflicted subject. The present invention further provides use of the compounds of the invention for the preparation of a medicament for the treatment of several conditions in a mammal (e.g., human) in need thereof.

More particularly, the present invention provides compounds for use in the treatment of a condition mediated by at least one Raf family kinases (e.g., B-Raf) in a mammal in need thereof. The present invention provides a method for treating a condition mediated by at least one Raf family kinase (e.g., B-Raf) in a mammal (e.g., a human) in need thereof, which method comprises administering to the mammal a therapeutically effective amount of the compound of the invention.

In another embodiment, the invention provides compounds for use in regulating, modulating, binding or inhibiting one or more Raf family kinases (e.g., B-Raf) in a mammal. The invention also provides methods of regulating, modulating, binding, or inhibiting at least one Raf family kinase (e.g., B-Raf) by administering a therapeutically effective amount of a compound of the invention. "Regulating, modulating, binding or inhibiting at least one Raf family kinase" refers to regulating, modulating, binding or inhibiting the activity of at least one Raf family kinase, as well as regulating, modulating, binding or inhibiting overexpression of an upstream regulator of at least one Raf family kinase in order to inhibit the cellular potency of its signaling ability.

In a particular embodiment, the invention provides compounds for use in the treatment of a condition mediated by inappropriate activity of one or more Raf family kinases (e.g., B-Raf), or an upstream activator of one or more Raf family kinases in a mammal. The invention further provides methods for the treatment of a condition mediated by inappropriate activity of one or more Raf family kinases (particularly B-Raf), in a mammal in need thereof, comprising administering to the mammal, a therapeutically effective amount of a compound of the invention. In an additional aspect, the present invention provides the use of a compound of the invention for the preparation of a medicament for the treatment of a condition mediated by inappropriate activity of one or more Raf family kinases (particularly B-Raf), in a mammal. One example of a condition mediated by inappropriate activity of one or more Raf family kinases includes neoplasms.

By "inappropriate activity" is meant Raf family kinase activity that deviates from the expected activity for that kinase or for an upstream activator of that kinase in a particular mammal. The inappropriate activity of a Raf family kinase may arise from one or more of A-Raf, B-Raf or c-Raf or an upstream activator of a Raf family kinase. Inappropriate Raf family kinase activity may take the form of, for instance, an abnormal increase in activity, or an aberration in the timing and/or control of Raf family kinase activity. Such inappropriate activity may result, for example, from overexpression or mutation of the kinase, upstream activator, receptor or ligand leading to inappropriate or uncontrolled activation of the corresponding kinase or receptor. Furthermore, it is also contemplated that unwanted Raf family kinase activity may reside in an abnormal source, such as a neoplasm. Thus, the level of Raf family kinase activity does not need to be abnormal to be considered inappropriate in the case where the activity derives from an abnormal source including, but not limited to, upstream activators (e.g., activated mutant Ras GTPases) or neoplasm. In one example of inappropriate Raf family kinase activity not resulting from mutation or overexpression of a Raf family kinase, inappropriate activity of a Ras GTPase may result from mutation or overexpression of Ras GTPase, for example the G13D mutation in KRas2, and may lead to overactivation of the MAPK pathway mediated by Raf family kinase activity.

Thus, in one embodiment, the present invention provides compounds for use in the treatment of a condition which directly or indirectly results from a mutation of a Raf family kinase or overexpression of a Raf family kinase, or a mutation of an upstream activator of a Raf family kinase or overexpression of an upstream activator of a Raf family kinase in a mammal in need thereof. The present invention provides methods for the treatment of a condition which directly or indirectly results from mutation of a Raf family kinase or overexpression of a Raf family kinase, or a mutation of an upstream activator of a Raf family kinase or overexpression of an upstream activator of a Raf family kinase in a mammal in need thereof, comprising administering to the mammal, a therapeutically effective amount of a compound of the invention. In an additional aspect, the present invention provides the use of a compound of the invention for the preparation of a medicament for the treatment of a condition which directly or indirectly results from mutation of a Raf family kinase or overexpression of a Raf family kinase, or a mutation of an upstream activator of a Raf family kinase or overexpression of an upstream activator of a Raf family kinase in a mammal. Conditions which are mediated by at least one Raf family kinase, and particularly conditions mediated by inappropriate activity of one or more Raf family kinases, including those which directly or indirectly result from mutation of a Raf family kinase, overexpression of a Raf family kinase, or mutation of an upstream activator of a Raf family kinase or overexpression of an upstream activator of a Raf family kinase are known in the art and include but are not limited to neoplasms.

Compounds of the invention may also be used in the treatment of conditions attenuated by inhibition of a Raf family kinase (particularly B-Raf). Further provided are methods for treating a condition attenuated by inhibition of a Raf family kinase (particularly B-Raf) in a mammal in need thereof, comprising administering to the mammal, a therapeutically effective amount of a compound of the invention. Also provided is the use of a compound of the invention for the preparation of a medicament for the treatment of a condition attenuated by inhibition of a Raf family kinase (particularly B-Raf) in a mammal. Conditions attenuated by inhibition of a Raf family kinase (including B-Raf) include but are not limited to neoplasms.

Accordingly, compounds of the invention may be used in the treatment of a neoplasm, particularly a susceptible neoplasm (a cancer or tumor) in a mammal. The present invention also provides a method for treating a neoplasm, particularly a susceptible neoplasm in a mammal in need thereof, which method comprises administering to the mammal a therapeutically effective amount of the compound of the invention. The invention also provides the use of a compound of the invention for the preparation of a medicament for the treatment of neoplasm, particularly a susceptible neoplasm, in a mammal.

"Susceptible neoplasm" as used herein refers to neoplasms which are susceptible to treatment by a kinase inhibitor and particularly neoplasms that are susceptible to treatment by a Raf inhibitor. Neoplasms which have been associated with inappropriate activity of one or more Raf family kinases and particularly neoplasms which are exhibit mutation of a Raf family kinase, overexpression of a Raf family kinase, or mutation of an upstream activator of a Raf family kinase or overexpression of an upstream activator of a Raf family kinase, and are therefore susceptible to treatment with an Raf inhibitor are known in the art, and include both primary and metastatic tumors and cancers. See, *Catalogue of Somatic Mutations in Cancer* (COSMIC), the Wellcome Trust Sanger Institute, http://www.sanger.ac.uk/genetics/CGP/cosmic/ and those references cited in the background.

Specific examples of susceptible neoplasms within the scope of the invention include, but are not limited to:

Barret's adenocarcinoma;
billiary tract carcinomas;
breast cancer;
cervical cancer;
cholangiocarcinoma;
central nervous system tumors including primary CNS tumors such as glioblastomas, astrocytomas (including glioblastoma multiforme) and ependymomas, and secondary CNS tumors (i.e., metastases to the central nervous system of tumors originating outside of the central nervous system),
colorectal cancer, including large intestinal colon carcinoma;
gastric cancer;
carcinoma of the head and neck including squamous cell carcinoma of the head and neck;
hematologic cancers including leukemias and lymphomas such as acute lymphoblastic leukemia, acute myelogenous leukemia (AML), myelodysplastic syndromes, chronic myelogenous leukemia, Hodgkin's lymphoma, non-Hodgkin's lymphoma, megakaryoblastic leukemia, multiple myeloma and erythroleukemia;
hepatocellular carcinoma;
lung cancer including small cell lung cancer and non-small cell lung cancer;
ovarian cancer;
endometrial cancer;
pancreatic cancer;
pituitary adenoma;
prostate cancer;
renal cancer;
sarcoma;
skin cancers including melanomas; and
thyroid cancers.

The foregoing list is intended to disclose each of the recited neoplasms individually. In one particular embodiment, the susceptible neoplasm is a neoplasm which exhibits a mutation in BRaf.

Accordingly, in one embodiment, the present invention provides a method for the treatment of any of Barret's adenocarcinoma; billiary tract carcinomas; breast cancer; cervical cancer; cholangiocarcinoma; central nervous system tumors including primary CNS tumors such as glioblastomas, astrocytomas (e.g., glioblastoma multiforme) and ependymomas, and secondary CNS tumors (i.e., metastases to the central nervous system of tumors originating outside of the central nervous system); colorectal cancer including large intestinal colon carcinoma; gastric cancer; carcinoma of the head and neck including squamous cell carcinoma of the head and neck; hematologic cancers including leukemias and lymphomas such as acute lymphoblastic leukemia, acute myelogenous leukemia (AML), myelodysplastic syndromes, chronic myelogenous leukemia, Hodgkin's lymphoma, non-Hodgkin's lymphoma, megakaryoblastic leukemia, multiple myeloma and erythroleukemia; hepatocellular carcinoma; lung cancer including small cell lung cancer and non-small cell lung cancer; ovarian cancer; endometrial cancer; pancreatic cancer; pituitary adenoma; prostate cancer; renal cancer; sarcoma; skin cancers including melanomas; and thyroid cancers, or any subset thereof, in a mammal (e.g., human) in need thereof. The method comprises administering a therapeutically effective amount of a compound of the invention to the mammal (e.g., human).

In one embodiment, the present invention provides a method for treating breast cancer, cholangiocarcinoma, colorectal cancer, melanoma, non-small cell lung cancer, ovarian cancer, or thyroid cancer, or any subset thereof.

In one particular embodiment, the present invention provides a method for treating cholangiocarcinoma, colorectal cancer, melanoma, or thyroid cancer, or any subset thereof.

In one preferred embodiment, the present invention provides a method for treating colorectal cancer in a mammal (e.g., human) in need thereof. The method comprises administering to the mammal (e.g. human) a therapeutically effective amount of a compound of formula (I). In one preferred embodiment, the compound is selected from N-{3-[5-(2-amino-4-pyrimidinyl)-2-(1,1-dimethylethyl)-1,3-thiazol-4-yl]-2-fluorophenyl}-2,6-difluorobenzenesulfonamide;

N-{3-[2-(1,1-dimethylethyl)-5-(2-methyl-4-pyrimidinyl)-1,3-thiazol-4-yl]-2-fluorophenyl}-2,5-difluorobenzenesulfonamide;

N-{3-[5-(2-amino-4-pyrimidinyl)-2-(tetrahydro-2H-pyran-4-yl)-1,3-thiazol-4-yl]-2-fluorophenyl}-2,6-difluorobenzenesulfonamide;

N-{3-[5-(2-amino-4-pyrimidinyl)-2-(4-morpholinyl)-1,3-thiazol-4-yl]-2-fluorophenyl}-2,5-difluorobenzenesulfonamide;

N-{3-[5-(2-amino-4-pyrimidinyl)-2-(4-morpholinyl)-1,3-thiazol-4-yl]-2-chlorophenyl}-2-furansulfonamide;

N-{3-[5-(2-amino-4-pyrimidinyl)-2-(4-morpholinyl)-1,3-thiazol-4-yl]-2-chlorophenyl}-2,5-difluorobenzenesulfonamide; and N-{3-[2-(1,1-dimethylethyl)-5-(4-pyrimidinyl)-1,3-thiazol-4-yl]-2-fluorophenyl}-2,5-difluorobenzenesulfonamide;

and pharmaceutically acceptable salts thereof. In one particular embodiment, the method comprises administering N-{3-[5-(2-amino-4-pyrimidinyl)-2-(1,1-dimethylethyl)-1,3-thiazol-4-yl]-2-fluorophenyl}-2,6-difluorobenzenesulfonamide in the form of either a free base or a pharmaceutically acceptable salt thereof. In another particular embodiment, the method comprises administering N-{3-[2-(1,1-dimethylethyl)-5-(2-methyl-4-pyrimidinyl)-1,3-thiazol-4-yl]-2-fluorophenyl}-2,5-difluorobenzenesulfonamide in the form of either a free base or a pharmaceutically acceptable salt thereof. In another particular embodiment, the method comprises administering N-{3-[5-(2-amino-4-pyrimidinyl)-2-(tetrahydro-2H-pyran-4-yl)-1,3-thiazol-4-yl]-2-fluorophenyl}-2,6-difluorobenzenesulfonamide in the form of either a free base or a pharmaceutically acceptable salt thereof.

In one preferred embodiment, the present invention provides a method for treating melanoma in a mammal (e.g., human) in need thereof. The method comprises administering to the mammal (e.g. human) a therapeutically effective amount of a compound of formula (I). In one preferred embodiment, the compound is selected from N-{3-[5-(2-amino-4-pyrimidinyl)-2-(1,1-dimethylethyl)-1,3-thiazol-4-yl]-2-fluorophenyl}-2,6-difluorobenzenesulfonamide;

N-{3-[2-(1,1-dimethylethyl)-5-(2-methyl-4-pyrimidinyl)-1,3-thiazol-4-yl]-2-fluorophenyl}-2,5-difluorobenzenesulfonamide;

N-{3-[5-(2-amino-4-pyrimidinyl)-2-(tetrahydro-2H-pyran-4-yl)-1,3-thiazol-4-yl]-2-fluorophenyl}-2,6-difluorobenzenesulfonamide;

N-{3-[5-(2-amino-4-pyrimidinyl)-2-(4-morpholinyl)-1,3-thiazol-4-yl]-2-fluorophenyl}-2,5-difluorobenzenesulfonamide;

N-{3-[5-(2-amino-4-pyrimidinyl)-2-(4-morpholinyl)-1,3-thiazol-4-yl]-2-chlorophenyl}-2-furansulfonamide;

N-{3-[5-(2-amino-4-pyrimidinyl)-2-(4-morpholinyl)-1,3-thiazol-4-yl]-2-chlorophenyl}-2,5-difluorobenzenesulfonamide; and N-{3-[2-(1,1-dimethylethyl)-5-(4-pyrimidinyl)-1,3-thiazol-4-yl]-2-fluorophenyl}-2,5-difluorobenzenesulfonamide;

and pharmaceutically acceptable salts thereof. In one particular embodiment, the method comprises administering N-{3-[5-(2-amino-4-pyrimidinyl)-2-(1,1-dimethylethyl)-1,3-thiazol-4-yl]-2-fluorophenyl}-2,6-difluorobenzenesulfonamide in the form of either a free base or a pharmaceutically acceptable salt thereof. In another particular embodiment, the method comprises administering N-{3-[2-(1,1-dimethylethyl)-5-(2-methyl-4-pyrimidinyl)-1,3-thiazol-4-yl]-2-fluorophenyl}-2,5-difluorobenzenesulfonamide in the form of either a free base or a pharmaceutically acceptable salt thereof. In another particular embodiment, the method comprises administering N-{3-[5-(2-amino-4-pyrimidinyl)-2-(tetrahydro-2H-pyran-4-yl)-1,3-thiazol-4-yl]-2-fluorophenyl}-2,6-difluorobenzenesulfonamide in the form of either a free base or a pharmaceutically acceptable salt thereof.

In one preferred embodiment, the present invention provides a method for treating cholangiocarcinoma in a mammal (e.g., human) in need thereof. The method comprises administering to the mammal (e.g. human) a therapeutically effective amount of a compound of formula (I). In one preferred embodiment, the compound is selected from N-{3-[5-(2-amino-4-pyrimidinyl)-2-(1,1-dimethylethyl)-1,3-thiazol-4-yl]-2-fluorophenyl}-2,6-difluorobenzenesulfonamide;

N-{3-[2-(1,1-dimethylethyl)-5-(2-methyl-4-pyrimidinyl)-1,3-thiazol-4-yl]-2-fluorophenyl}-2,5-difluorobenzenesulfonamide;

N-{3-[5-(2-amino-4-pyrimidinyl)-2-(tetrahydro-2H-pyran-4-yl)-1,3-thiazol-4-yl]-2-fluorophenyl}-2,6-difluorobenzenesulfonamide;

N-{3-[5-(2-amino-4-pyrimidinyl)-2-(4-morpholinyl)-1,3-thiazol-4-yl]-2-fluorophenyl}-2,5-difluorobenzenesulfonamide;

N-{3-[5-(2-amino-4-pyrimidinyl)-2-(4-morpholinyl)-1,3-thiazol-4-yl]-2-chlorophenyl}-2-furansulfonamide;

N-{3-[5-(2-amino-4-pyrimidinyl)-2-(4-morpholinyl)-1,3-thiazol-4-yl]-2-chlorophenyl}-2,5-difluorobenzenesulfonamide; and N-{3-[2-(1,1-dimethylethyl)-5-(4-pyrimidinyl)-1,3-thiazol-4-yl]-2-fluorophenyl}-2,5-difluorobenzenesulfonamide;

and pharmaceutically acceptable salts thereof. In one particular embodiment, the method comprises administering N-{3-[5-(2-amino-4-pyrimidinyl)-2-(1,1-dimethylethyl)-1,3-thiazol-4-yl]-2-fluorophenyl}-2,6-difluorobenzenesulfonamide in the form of either a free base or a pharmaceutically acceptable salt thereof. In another particular embodiment, the method comprises administering N-{3-[2-(1,1-dimethylethyl)-5-(2-methyl-4-pyrimidinyl)-1,3-thiazol-4-yl]-2-fluorophenyl}-2,5-difluorobenzenesulfonamide in the form of either a free base or a pharmaceutically acceptable salt thereof. In another particular embodiment, the method comprises administering N-{3-[5-(2-amino-4-pyrimidinyl)-2-(tetrahydro-2H-pyran-4-yl)-1,3-thiazol-4-yl]-2-fluorophenyl}-2,6-difluorobenzenesulfonamide in the form of either a free base or a pharmaceutically acceptable salt thereof.

In one preferred embodiment, the present invention provides a method for treating thyroid cancer in a mammal (e.g., human) in need thereof. The method comprises administering to the mammal (e.g. human) a therapeutically effective amount of a compound of formula (I). In one preferred embodiment, the compound is selected from N-{3-[5-(2-amino-4-pyrimidinyl)-2-(1,1-dimethylethyl)-1,3-thiazol-4-yl]-2-fluorophenyl}-2,6-difluorobenzenesulfonamide;

N-{3-[2-(1,1-dimethylethyl)-5-(2-methyl-4-pyrimidinyl)-1,3-thiazol-4-yl]-2-fluorophenyl}-2,5-difluorobenzenesulfonamide;

N-{3-[5-(2-amino-4-pyrimidinyl)-2-(tetrahydro-2H-pyran-4-yl)-1,3-thiazol-4-yl]-2-fluorophenyl}-2,6-difluorobenzenesulfonamide;

N-{3-[5-(2-amino-4-pyrimidinyl)-2-(4-morpholinyl)-1,3-thiazol-4-yl]-2-fluorophenyl}-2,5-difluorobenzenesulfonamide;

N-{3-[5-(2-amino-4-pyrimidinyl)-2-(4-morpholinyl)-1,3-thiazol-4-yl]-2-chlorophenyl}-2-furansulfonamide;

N-{3-[5-(2-amino-4-pyrimidinyl)-2-(4-morpholinyl)-1,3-thiazol-4-yl]-2-chlorophenyl}-2,5-difluorobenzenesulfonamide; and N-{3-[2-(1,1-dimethylethyl)-5-(4-pyrimidinyl)-1,3-thiazol-4-yl]-2-fluorophenyl}-2,5-difluorobenzenesulfonamide;

and pharmaceutically acceptable salts thereof. In one particular embodiment, the method comprises administering N-{3-[5-(2-amino-4-pyrimidinyl)-2-(1,1-dimethylethyl)-1,3-thiazol-4-yl]-2-fluorophenyl}-2,6-difluorobenzenesulfonamide in the form of either a free base or a pharmaceutically acceptable salt thereof. In another particular embodiment, the method comprises administering N-{3-[2-(1,1-dimethylethyl)-5-(2-methyl-4-pyrimidinyl)-1,3-thiazol-4-yl]-2-fluorophenyl}-2,5-difluorobenzenesulfonamide in the form of either a free base or a pharmaceutically acceptable salt thereof. In another particular embodiment, the method comprises administering N-{3-[5-(2-amino-4-pyrimidinyl)-2-(tetrahydro-2H-pyran-4-yl)-1,3-thiazol-4-yl]-2-fluorophenyl}-2,6-difluorobenzenesulfonamide in the form of either a free base or a pharmaceutically acceptable salt thereof.

In one preferred embodiment, the present invention provides a method for treating breast cancer in a mammal (e.g., human) in need thereof. The method comprises administering to the mammal (e.g. human) a therapeutically effective amount of a compound of formula (I). In one preferred embodiment, the compound is selected from N-{3-[5-(2-amino-4-pyrimidinyl)-2-(1,1-dimethylethyl)-1,3-thiazol-4-yl]-2-fluorophenyl}-2,6-difluorobenzenesulfonamide;

N-{3-[2-(1,1-dimethylethyl)-5-(2-methyl-4-pyrimidinyl)-1,3-thiazol-4-yl]-2-fluorophenyl}-2,5-difluorobenzenesulfonamide;

N-{3-[5-(2-amino-4-pyrimidinyl)-2-(tetrahydro-2H-pyran-4-yl)-1,3-thiazol-4-yl]-2-fluorophenyl}-2,6-difluorobenzenesulfonamide;

N-{3-[5-(2-amino-4-pyrimidinyl)-2-(4-morpholinyl)-1,3-thiazol-4-yl]-2-fluorophenyl}-2,5-difluorobenzenesulfonamide;

N-{3-[5-(2-amino-4-pyrimidinyl)-2-(4-morpholinyl)-1,3-thiazol-4-yl]-2-chlorophenyl}-2-furansulfonamide;

N-{3-[5-(2-amino-4-pyrimidinyl)-2-(4-morpholinyl)-1,3-thiazol-4-yl]-2-chlorophenyl}-2,5-difluorobenzenesulfonamide; and N-{3-[2-(1,1-dimethylethyl)-5-(4-pyrimidinyl)-1,3-thiazol-4-yl]-2-fluorophenyl}-2,5-difluorobenzenesulfonamide;

and pharmaceutically acceptable salts thereof. In one particular embodiment, the method comprises administering N-{3-[5-(2-amino-4-pyrimidinyl)-2-(1,1-dimethylethyl)-1,3-thiazol-4-yl]-2-fluorophenyl}-2,6-difluorobenzenesulfonamide in the form of either a free base or a pharmaceutically acceptable salt thereof. In another particular embodiment, the method comprises administering N-{3-[2-(1,1-dimethylethyl)-5-(2-methyl-4-pyrimidinyl)-1,3-thiazol-4-yl]-2-fluorophenyl}-2,5-difluorobenzenesulfonamide in the form of either a free base or a pharmaceutically acceptable salt thereof. In another particular embodiment, the method comprises administering N-{3-[5-(2-amino-4-pyrimidinyl)-2-(tetrahydro-2H-pyran-4-yl)-1,3-thiazol-4-yl]-2-fluorophenyl}-2,6-difluorobenzenesulfonamide in the form of either a free base or a pharmaceutically acceptable salt thereof.

In one preferred embodiment, the present invention provides a method for treating ovarian cancer in a mammal (e.g., human) in need thereof. The method comprises administering to the mammal (e.g. human) a therapeutically effective amount of a compound of formula (I). In one preferred embodiment, the compound is selected from N-{3-[5-(2-amino-4-pyrimidinyl)-2-(1,1-dimethylethyl)-1,3-thiazol-4-yl]-2-fluorophenyl}-2,6-difluorobenzenesulfonamide;

N-{3-[2-(1,1-dimethylethyl)-5-(2-methyl-4-pyrimidinyl)-1,3-thiazol-4-yl]-2-fluorophenyl}-2,5-difluorobenzenesulfonamide;

N-{3-[5-(2-amino-4-pyrimidinyl)-2-(tetrahydro-2H-pyran-4-yl)-1,3-thiazol-4-yl]-2-fluorophenyl}-2,6-difluorobenzenesulfonamide;

N-{3-[5-(2-amino-4-pyrimidinyl)-2-(4-morpholinyl)-1,3-thiazol-4-yl]-2-fluorophenyl}-2,5-difluorobenzenesulfonamide;

N-{3-[5-(2-amino-4-pyrimidinyl)-2-(4-morpholinyl)-1,3-thiazol-4-yl]-2-chlorophenyl}-2-furansulfonamide;

N-{3-[5-(2-amino-4-pyrimidinyl)-2-(4-morpholinyl)-1,3-thiazol-4-yl]-2-chlorophenyl}-2,5-difluorobenzenesulfonamide; and N-{3-[2-(1,1-dimethylethyl)-5-(4-pyrimidinyl)-1,3-thiazol-4-yl]-2-fluorophenyl}-2,5-difluorobenzenesulfonamide;

and pharmaceutically acceptable salts thereof. In one particular embodiment, the method comprises administering N-{3-[5-(2-amino-4-pyrimidinyl)-2-(1,1-dimethylethyl)-1,3-thiazol-4-yl]-2-fluorophenyl}-2,6-difluorobenzenesulfonamide in the form of either a free base or a pharmaceutically acceptable salt thereof. In another particular embodiment, the method comprises administering N-{3-[2-(1,1-dimethylethyl)-5-(2-methyl-4-pyrimidinyl)-1,3-thiazol-4-yl]-2-fluorophenyl}-2,5-difluorobenzenesulfonamide in the form of either a free base or a pharmaceutically acceptable salt thereof. In another particular embodiment, the method comprises administering N-{3-[5-(2-amino-4-pyrimidinyl)-2-(tetrahydro-2H-pyran-4-yl)-1,3-thiazol-4-yl]-2-fluorophenyl}-2,6-difluorobenzenesulfonamide in the form of either a free base or a pharmaceutically acceptable salt thereof.

In one preferred embodiment, the present invention provides a method for treating non-small cell lung cancer in a mammal (e.g., human) in need thereof. The method comprises administering to the mammal (e.g. human) a therapeutically effective amount of a compound of formula (I). In one preferred embodiment, the compound is selected from N-{3-[5-(2-amino-4-pyrimidinyl)-2-(1,1-dimethylethyl)-1,3-thiazol-4-yl]-2-fluorophenyl}-2,6-difluorobenzenesulfonamide;

N-{3-[2-(1,1-dimethylethyl)-5-(2-methyl-4-pyrimidinyl)-1,3-thiazol-4-yl]-2-fluorophenyl}-2,5-difluorobenzenesulfonamide;

N-{3-[5-(2-amino-4-pyrimidinyl)-2-(tetrahydro-2H-pyran-4-yl)-1,3-thiazol-4-yl]-2-fluorophenyl}-2,6-difluorobenzenesulfonamide;

N-{3-[5-(2-amino-4-pyrimidinyl)-2-(4-morpholinyl)-1,3-thiazol-4-yl]-2-fluorophenyl}-2,5-difluorobenzenesulfonamide;

N-{3-[5-(2-amino-4-pyrimidinyl)-2-(4-morpholinyl)-1,3-thiazol-4-yl]-2-chlorophenyl}-2-furansulfonamide; and N-{3-[5-(2-amino-4-pyrimidinyl)-2-(4-morpholinyl)-1,3-thiazol-4-yl]-2-chlorophenyl}-2,5-difluorobenzenesulfonamide; and N-{3-[2-(1,1-dimethylethyl)-5-(4-pyrimidinyl)-1,3-thiazol-4-yl]-2-fluorophenyl}-2,5-difluorobenzenesulfonamide; and pharmaceutically acceptable salts thereof. In one particular embodiment, the method comprises administering N-{3-[5-(2-amino-4-pyrimidinyl)-2-(1,1-dimethylethyl)-1,3-thiazol-4-yl]-2-fluorophenyl}-2,6-difluorobenzenesulfonamide in the form of either a free base or a pharmaceutically acceptable salt thereof. In another particular embodiment, the method comprises administering N-{3-[2-(1,1-dimethylethyl)-5-(2-methyl-4-pyrimidinyl)-1,3-thiazol-4-yl]-2-fluorophenyl}-2,5-difluorobenzenesulfonamide in the form of either a free base or a pharmaceutically acceptable salt thereof. In another particular embodiment, the method comprises administering N-{3-[5-(2-amino-4-pyrimidinyl)-2-(tetrahydro-2H-pyran-4-yl)-1,3-thiazol-4-yl]-2-fluorophenyl}-2,6-difluorobenzenesulfonamide in the form of either a free base or a pharmaceutically acceptable salt thereof.

The present invention also provides the a compound of formula (I) for use in the treatment of Barret's adenocarcinoma; billiary tract carcinomas; breast cancer; cervical cancer; cholangiocarcinoma; central nervous system tumors including primary CNS tumors such as glioblastomas, astrocytomas (e.g., glioblastoma multiforme) and ependymomas, and secondary CNS tumors (i.e., metastases to the central nervous system of tumors originating outside of the central nervous system); colorectal cancer including large intestinal colon carcinoma; gastric cancer; carcinoma of the head and neck including squamous cell carcinoma of the head and neck; hematologic cancers including leukemias and lymphomas such as acute lymphoblastic leukemia, acute myelogenous leukemia (AML), myelodysplastic syndromes, chronic myelogenous leukemia, Hodgkin's lymphoma, non-Hodgkin's lymphoma, megakaryoblastic leukemia, multiple myeloma and erythroleukemia; hepatocellular carcinoma; lung cancer including small cell lung cancer and non-small cell lung cancer; ovarian cancer; endometrial cancer; pancreatic cancer; pituitary adenoma; prostate cancer; renal cancer; sarcoma; skin cancers including melanomas; and thyroid cancers, or any subset thereof, in a mammal (e.g., human).

The present invention further provides the use of a compound of formula (I) for the preparation of a medicament for the treatment of Barret's adenocarcinoma; billiary tract carcinomas; breast cancer; cervical cancer; cholangiocarcinoma; central nervous system tumors including primary CNS tumors such as glioblastomas, astrocytomas (e.g., glioblastoma multiforme) and ependymomas, and secondary CNS tumors (i.e., metastases to the central nervous system of tumors originating outside of the central nervous system); colorectal cancer including large intestinal colon carcinoma; gastric cancer; carcinoma of the head and neck including squamous cell carcinoma of the head and neck; hematologic cancers including leukemias and lymphomas such as acute lymphoblastic leukemia, acute myelogenous leukemia (AML), myelodysplastic syndromes, chronic myelogenous leukemia, Hodgkin's lymphoma, non-Hodgkin's lymphoma, megakaryoblastic leukemia, multiple myeloma and erythroleukemia; hepatocellular carcinoma; lung cancer including small cell lung cancer and non-small cell lung cancer; ovarian cancer; endometrial cancer; pancreatic cancer; pituitary adenoma; prostate cancer; renal cancer; sarcoma; skin cancers including melanomas; and thyroid cancers, or any subset thereof, in a mammal (e.g., human).

As is well known in the art, tumors may metastasize from a first or primary locus of tumor to one or more other body tissues or sites. In particular, metastases to the central nervous system (i.e., secondary CNS tumors), and particularly the brain (i.e., brain metastases), are well documented for tumors and cancers, such as breast, lung, melanoma, renal and colorectal. As used herein, reference to uses or methods for treatment or treatments for a "neoplasm," "tumor" or "cancer" in a subject includes use for and treatment of the primary neoplasm, tumor or cancer, and where appropriate, also the use for and treatment of metastases (i.e., metastatic tumor growth) as well.

In another embodiment, the susceptible neoplasm is colorectal cancer and the invention provides compounds for use in the treatment of colorectal cancer in a mammal (e.g., human) and the use of such compounds for the preparation of a medicament for the treatment of colorectal cancer in a mammal (e.g., human).

In another embodiment, the susceptible neoplasm is melanoma, and the invention provides compounds for use in the treatment of melanoma in a mammal (e.g., human) and the use of such compounds for the preparation of a medicament for the treatment of melanoma in a mammal (e.g., human).

In another embodiment, the susceptible neoplasm is cholangiocarcinoma, and the invention provides compounds for use in the treatment of cholangiocarcinoma in a mammal (e.g., human) and the use of such compounds for the preparation of a medicament for the treatment of cholangiocarcinoma in a mammal (e.g., human).

In another embodiment, the susceptible neoplasm is thyroid cancer, and the invention provides compounds for use in the treatment of thyroid cancer in a mammal (e.g., human) and the use of such compounds for the preparation of a medicament for the treatment of thyroid cancer in a mammal (e.g., human).

In one particular embodiment, the susceptible neoplasm is breast cancer and the invention provides compounds for use in the treatment of breast cancer in a mammal (e.g., human) and the use of such compounds for the preparation of a medicament for the treatment of breast cancer in a mammal (e.g., human).

In another embodiment, the susceptible neoplasm is ovarian cancer and the invention provides compounds for use in the treatment of ovarian cancer in a mammal (e.g., human) and the use of such compounds for the preparation of a medicament for the treatment of ovarian cancer in a mammal (e.g., human).

In another embodiment, the susceptible neoplasm is non-small cell lung cancer, and the invention provides compounds for use in the treatment of non-small cell lung cancer in a mammal (e.g., human) and the use of such compounds for the preparation of a medicament for the treatment of non-small cell lung cancer in a mammal (e.g., human).

The compounds of the invention can be used alone in the treatment of each of the foregoing conditions or can be used to provide additive or potentially synergistic effects with certain existing chemotherapies, radiation, biological or immunotherapeutics (including monoclonal antibodies) and vaccines. The compounds of the invention may be useful for restoring effectiveness of certain existing chemotherapies and radiation and or increasing sensitivity to certain existing chemotherapies and/or radiation.

In addition to the treatment of susceptible neoplasms, the compounds of the invention may also be used in the treatment of other conditions attenuated by inhibition of a Raf family kinase, such as cardio-facio cutaneous syndrome and polycystic kidney disease.

In one aspect, the present invention provides a method for treating a susceptible neoplasm in a mammal in need thereof comprising the steps of:
(a) analyzing a sample from said neoplasm to determine whether an activating mutation is present in the coding sequence for B-Raf in cells of said neoplasm;
(b) selecting a mammal having a neoplasm with an activating mutation in the coding sequence for B-Raf; and
(c) administering a therapeutically effective amount of a compound of the present invention to the mammal selected in step (b).

Figure 2:
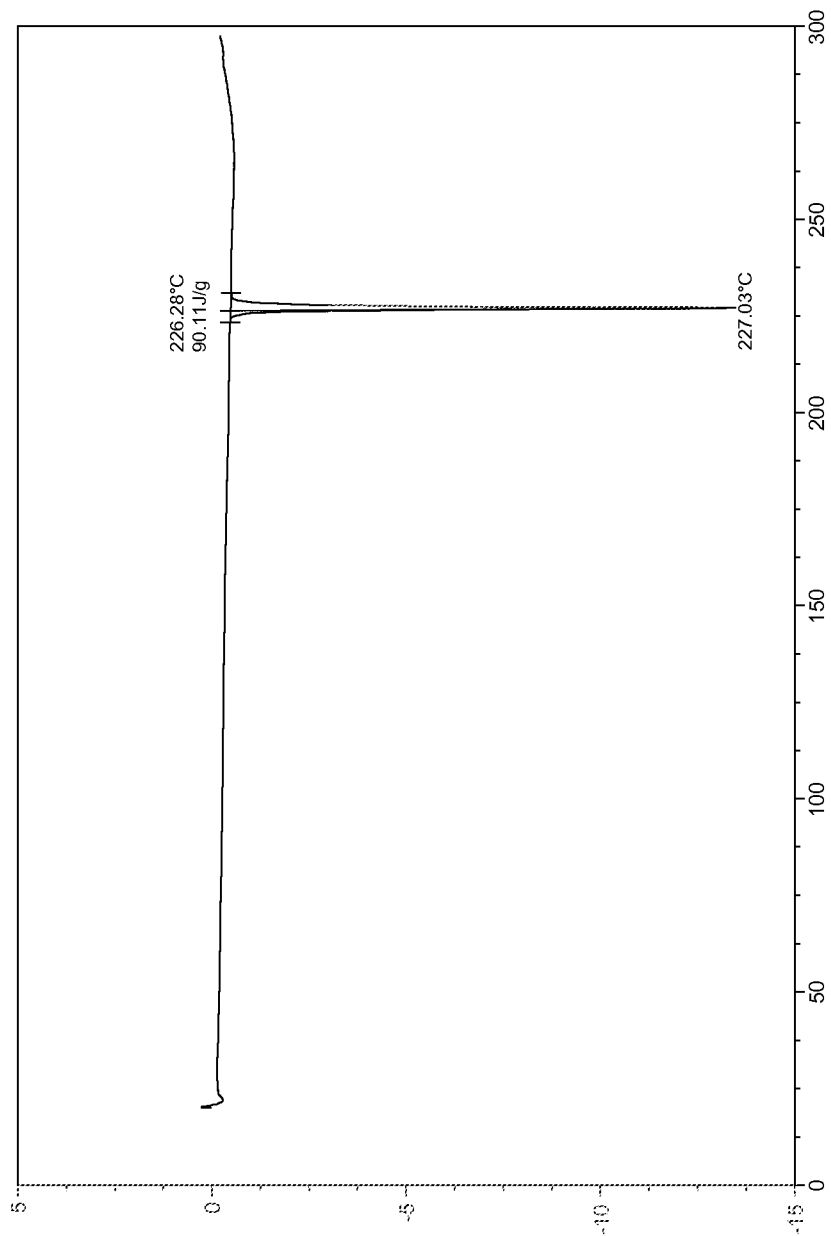
FIG. 2 is a differential scanning calorimetry (DSC) thermogram of a particular solid state form of N-{3-[5-(2-amino-4-pyrimidinyl)-2-(1,1-dimethylethyl)-1,3-thiazol-4-yl]-2-fluorophenyl}-2,6-difluorobenzenesulfonamide. The DSC was carried out on a TA Instruments DSC Q100 system at a heating rate of 10° C. per minute, using a sample size of 0.4-1.5 mg, according to the procedures described herein.
Figure 3:
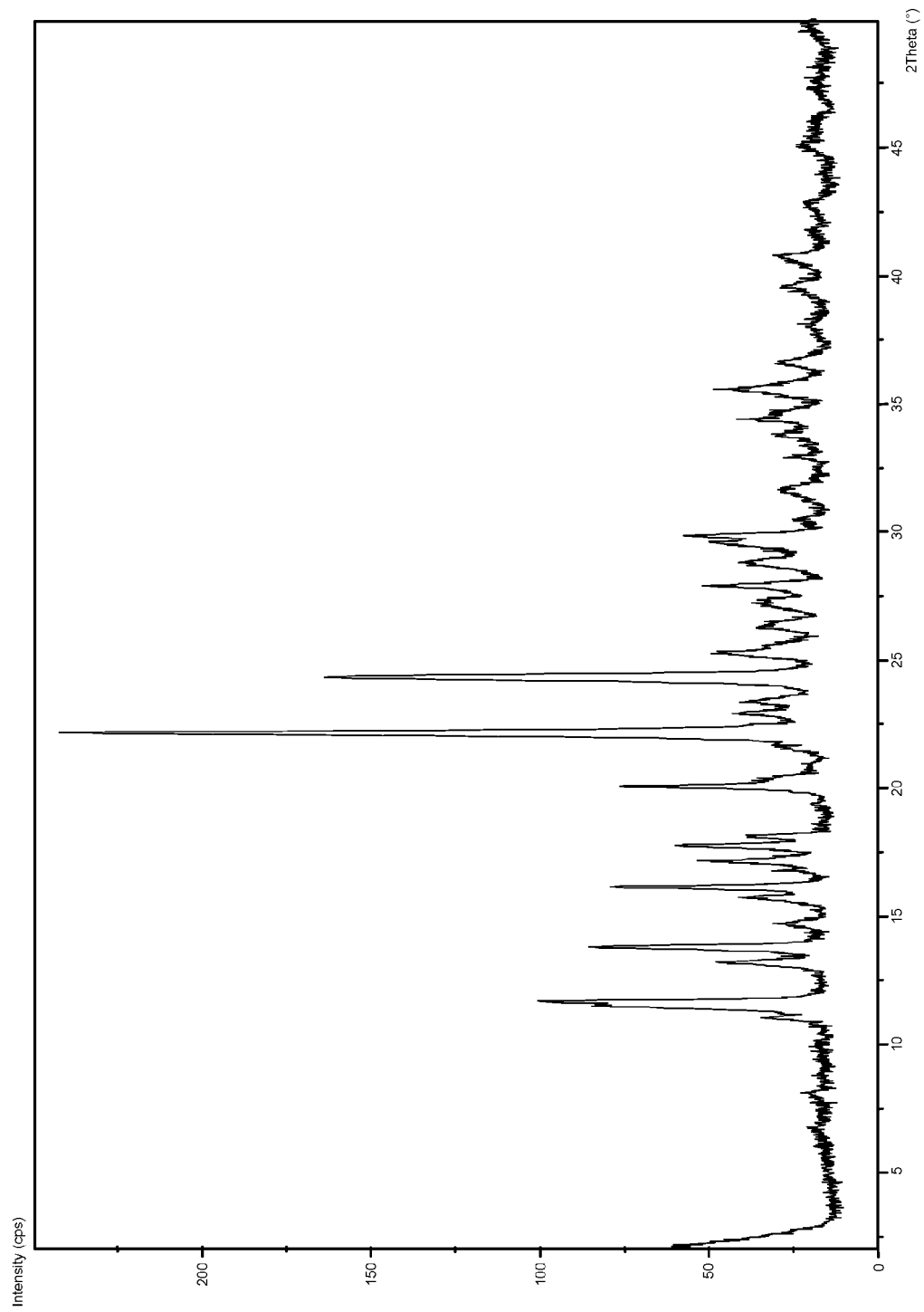
FIG. 3 is a is an X-Ray Powder Diffraction Pattern of a particular solid state form of N-{3-[5-(2-amino-4-pyrimidinyl)-2-(tetrahydro-2H-pyran-4-yl)-1,3-thiazol-4-yl]-2-fluorophenyl}-2,6-difluorobenzenesulfonamide. The XRD pattern is expressed in terms of 2 theta angles and obtained with a PANalytical diffractometer equipped with a diffracted beam nickel filter using copper Kα X-radiation, according to the procedures described herein.

In certain embodiments, the activating mutation present in the coding sequence for BRAF results in a BRAF having an amino acid substitution selected from the group consisting of R462I, I463S, G464V, G464E, G466A, G466E, G466V, G469A, G469E, D594V, F595L, G596R, L597V, L597R, T599I, V600E, V600D, V600K, V600R, T119S, and K601E. See, for example, FIG. 2 of Halilovic and Solvit (2008) *Current Opinion in Pharmacology* 8:419-26.

In one embodiment, the present invention provides a method for treating a susceptible neoplasm in a mammal in need thereof comprising the steps of:
(a) analyzing a sample from said neoplasm to determine whether a mutation encoding a V600E amino acid substitution is present in the coding sequence for B-Raf in cells of said neoplasm;
(b) selecting a mammal having a neoplasm with a mutation encoding the V600E amino acid substitution in B-Raf; and
(c) administering a therapeutically effective amount of a compound of the present invention to the mammal selected in step (b).

The V600E amino acid substitution in B-Raf is described, for example, in Kumar et al. (2004) *J Invest Dermatol.* 122 (2):342-8. This mutation commonly results from a T1799A mutation in the coding sequence for human B-Raf. Accordingly, in one embodiment of the present invention, the step of analyzing a sample from said neoplasm to determine whether a mutation encoding a V600E amino acid substitution is present in the coding sequence for B-Raf is performed by determining whether the coding sequence for B-Raf in cells of the neoplasm contains the T1799A mutation.

The neoplasm may be selected from Barret's adenocarcinoma; billiary tract carcinomas; breast cancer; cervical cancer; cholangiocarcinoma; central nervous system tumors including primary CNS tumors such as glioblastomas, astrocytomas (e.g., glioblastoma multiforme) and ependymomas, and secondary CNS tumors (i.e., metastases to the central nervous system of tumors originating outside of the central nervous system); colorectal cancer including large intestinal colon carcinoma; gastric cancer; carcinoma of the head and neck including squamous cell carcinoma of the head and neck; hematologic cancers including leukemias and lymphomas such as acute lymphoblastic leukemia, acute myelogenous leukemia (AML), myelodysplastic syndromes, chronic myelogenous leukemia, Hodgkin's lymphoma, non-Hodgkin's lymphoma, megakaryoblastic leukemia, multiple myeloma and erythroleukemia; hepatocellular carcinoma; lung cancer including small cell lung cancer and non-small cell lung cancer; ovarian cancer; endometrial cancer; pancreatic cancer; pituitary adenoma; prostate cancer; renal cancer; sarcoma; skin cancers including melanomas; and thyroid cancers.

In particular embodiments, the neoplasm is selected from breast cancer, cholangiocarcinoma, colorectal cancer, melanoma, non-small cell lung cancer, ovarian cancer, and thyroid cancer. In one preferred embodiment, the neoplasm is melanoma.

In one embodiment, the mammal is a human.

In one embodiment, the compound of the invention is, N-{3-[5-(2-amino-4-pyrimidinyl)-2-(1,1-dimethylethyl)-1,3-thiazol-4-yl]-2-fluorophenyl}-2,6-difluorobenzene-sulfonamide or a pharmaceutically acceptable salt thereof. In a particular embodiment, the compound of the invention is N-{3-[5-(2-amino-4-pyrimidinyl)-2-(1,1-dimethylethyl)-1,3-thiazol-4-yl]-2-fluorophenyl}-2,6-difluorobenzene-sulfonamide mesylate. In an alternate embodiment, the compound of the invention is N-{3-[5-(2-amino-4-pyrimidinyl)-2-(1,1-dimethylethyl)-1,3-thiazol-4-yl]-2-fluorophenyl}-2,6-difluorobenzenesulfonamide.

The sample of the neoplasm to be analyzed for the presence of B-raf activating mutations can be derived from a variety of sources including, but not limited to, single cells, a collection of cells, tissue, cell culture, bone marrow, blood, or other bodily fluids. The tissue or cell source may include a tissue biopsy sample, a cell sorted population, cell culture, or a single cell. In selecting a sample, the percentage of the sample that constitutes neoplastic cells should be considered. In some embodiments, the sample from the neoplasm is fixed using a preservative prior to analyzing for the presence of an activating mutation.

The step of analyzing a sample from the neoplasm to determine whether an activating mutation is present in the coding sequence for B-Raf in cells of said neoplasm may be performed using any method known in the art. For example, the coding sequence for B-raf in cells of the sample may be analyzed to determine if it contains a mutation which results in the expression of activated B-Raf. Methods for detecting such mutations are well known in the art. See, for example, Whitcombe et al. (1999) *Nature Biotechnology* 17:804-7, Gibson (2006) *Clinica Chimica Acta* 363: 32-47, Kim and Misra (2007) *Annual Review of Biomedical Engineering* 9:289-320, and U.S. Pat. Nos. 6,326,145 and 6,270,967). Alternatively, activating mutations in B-Raf may be identified by directly detecting the activated B-raf protein using an agent (e.g. an antibody) that selectively binds activated B-raf.

As used herein, the term "therapeutically effective amount" means an amount of a compound of the invention which is sufficient, in the subject to which it is administered, to elicit a biological or medical response of a cell culture, tissue, system, mammal (including human) that is being sought, for instance, by a researcher or clinician. The term also includes within its scope amounts effective to enhance normal physiological function. For example, a therapeutically effective amount of a compound of the invention for the treatment of a condition mediated by at least one Raf family kinase is an amount sufficient to treat the condition in the particular subject. Similarly, a therapeutically effective amount of a compound of the invention for the treatment of a susceptible neoplasm is an amount sufficient to treat the particular susceptible neoplasm in the subject. In one embodiment of the present invention, a therapeutically effective amount of a compound of the invention is an amount sufficient to regulate, modulate, bind or inhibit at least one Raf family kinase. More particularly, in such embodiment, the therapeutically effective amount of a compound of the invention is an amount sufficient to regulate, modulate, bind or inhibit B-Raf.

The precise therapeutically effective amount of the compounds of the invention will depend on a number of factors. There are variables inherent to the compounds including, but not limited to, the following: molecular weight, inhibitory activity at the target kinase, absorption, bioavailability, distribution in the body, tissue penetration, half-life, metabolism, protein binding, and excretion. These variables determine what dose of compound needs to be administered in order to inhibit the target kinase by a sufficient percentage and for a sufficient amount of time to have the desired effect on the condition being treated (e.g., neoplasm). In general, the goal will be to inhibit the target kinase by 50% or more for as long as possible. The duration of drug exposure will be limited only by the compound half-life, and side effects from treatment requiring cessation of dosing. The amount of compound administered will also depend on factors related to patients and disease including, but not limited to, the following: the age, weight, concomitant medications and medical condition of the subject being treated, the precise condition requiring treatment and its severity, the nature of the formulation, and the route of administration. Ultimately the dose will be at the discretion of the attendant physician or veterinarian. Typically, the compound of the invention will be given for treatment in the range of 0.01 to 30 mg/kg body weight of recipient (mammal) per day or per dose or per cycle of treatment and more usually in the range of 0.1 to 10 mg/kg body weight per day or per dose or per cycle of treatment. Thus, for a 70 kg adult human being treated for a condition mediated by or correlated to at least one Raf family kinase, the actual amount per day or per dose or per cycle of treatment would usually be from 1 to 2000 mg and this amount may be given in a single or multiple doses per day or per dose or per cycle of treatment. Dosing regimens may vary significantly and will be determined and altered based on clinical experience with the compound. The full spectrum of dosing regimens may be employed ranging from continuous dosing (with daily doses) to intermittent dosing. A therapeutically effective amount of a pharmaceutically acceptable salt of a compound of formula (I) may be determined as a proportion of the therapeutically effective amount of the compound of formula (I) as the free base. It is envisaged that similar dosages would be appropriate for treatment of the susceptible neoplasms described above.

While it is possible that, for use in therapy, a therapeutically effective amount of a compound of the invention may be administered as the raw chemical, it is typically presented as the active ingredient of a pharmaceutical composition or formulation. Accordingly, the invention further provides a pharmaceutical composition comprising a compound of the invention. The pharmaceutical composition may further comprise one or more pharmaceutically acceptable carriers, diluents, and/or excipients. The carrier(s), diluent(s) and/or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the invention with one or more pharmaceutically acceptable carriers, diluents and/or excipients.

Pharmaceutical formulations may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the invention (as a free-base, solvate (including hydrate) or salt, in any form), depending on the condition being treated, the route of administration, and the age, weight and condition of the patient. Preferred unit dosage formulations are those containing a daily dose, weekly dose, monthly dose, a sub-dose or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including capsules, tablets, liquid-filled capsules, disintegrating tablets, immediate, delayed and controlled release tablets, oral strips, solutions, syrups, buccal and sublingual), rectal, nasal, inhalation, topical (including transdermal), vaginal or parenteral (including subcutaneous, intramuscular, intravenous or intradermal) route. Such formulations may be prepared by any method known in the art of pharmacy, for example by bringing into association the active ingredient with the carrier(s), excipient(s) or diluent. Generally, the carrier, excipient or diluent employed in the pharmaceutical formulation is "non-toxic," meaning that it/they is/are deemed safe for consumption in the amount delivered in the pharmaceutical composition, and "inert" meaning that it/they does/do not appreciably react with or result in an undesired effect on the therapeutic activity of the active ingredient.

Pharmaceutical formulations adapted for oral administration may be presented as discrete units such as liquid-filled or solid capsules; immediate, delayed or controlled release tablets; powders or granules; solutions or suspensions in aqueous or non-aqueous liquids; edible foams or whips; oil-in-water liquid emulsions, water-in-oil liquid emulsions or oral strips, such as impregnated gel strips.

For instance, for oral administration in the form of a tablet or capsule, the active drug component can be combined with an oral pharmaceutically acceptable carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Solid capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Solutions and syrups can be prepared by dissolving the compound in a suitably flavored aqueous solution, while elixirs are prepared through the use of a pharmaceutically acceptable alcoholic vehicle. Suspensions can be formulated by dispersing the compound in a pharmaceutically acceptable vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, unit dosage formulations for oral administration can be microencapsulated. The formulation can also be prepared to prolong or sustain the release as for example by coating or embedding particulate material in polymers, wax or the like.

The compounds of the invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of the invention may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropyl-methacrylamidephenol, polyhydroxyethylaspartamidephenol, or polyethyleneoxide-polylysine substituted with palmitoyl residues. Furthermore, the compounds may be coupled to a class of biodegradable polymers useful in achieving controlled release of a drug, for example, polycentric acid, polepsilon caprolactone, polyhydroxy butyric acid, polyorthoesters, polyacetals, polydihydropyrans, polycyanoacrylates and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research* (1986) 3(6):318.

Pharmaceutical formulations adapted for topical administration may be formulated as ointments, creams, suspensions, lotions, powders, solutions, pastes, gels, sprays, aerosols or oils. For treatments of external tissues, such as skin, the formulations may be applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical formulations adapted for topical administrations to the eye include eye drops wherein the active ingredient is dissolved or suspended in a suitable carrier, especially an aqueous solvent. Pharmaceutical formulations adapted for topical administration in the mouth include lozenges, pastilles and mouth washes.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered dose pressurized aerosols, metered dose inhalers, dry powder inhalers, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation of pharmaceutically acceptable tonicity with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions may be prepared from sterile powders, granules and tablets.

It should be understood that in addition to the ingredients particularly mentioned above, the formulations may include other agents conventional in the art having regard to the type of formulation in question, for example those suitable for oral administration may include flavoring agents.

In the above-described methods of treatment and uses, a compound of the invention may be employed alone, in combination with one or more other compounds of the invention or in combination with other therapeutic methods or agents. In particular, in methods of treating a condition attenuated by inhibition of at least one Raf family kinase and in methods of treating susceptible neoplasms, combination with other chemotherapeutic, biologic, hormonal, antibody and supportive care agents is envisaged as well as combination with surgical therapy and radiotherapy. Supportive care agents include analgesics, anti-emetics and agents used to treat heamatologic side effects such as neutropenia. Analgesics are well known in the art. Anti-emetics include but are not limited to $5HT_3$ antagonists such as ondansetron, granisetron, dolasetron, palonosetron and the like; prochlorperazine; metaclopromide; diphenhydramine; promethazine; dexamethasone; lorazepam; haloperidol; dronabinol; olanzapine; and neurokinin-1 antagonists such as aprepitant, fosaprepitant and casopitant administered alone or in various combinations.

The term "chemotherapeutic" as used herein refers to any chemical agent having a therapeutic effect on the subject to which it is administered. "Chemotherapeutic" agents include but are not limited to anti-neoplastic agents. As used herein, "anti-neoplastic agents" include both cytotoxic and cytostatic agents including biological, immunological and vaccine therapies. Combination therapies according to the invention thus comprise the administration of at least one compound of the invention and the use of at least one other treatment method. In one embodiment, combination therapies according to the invention comprise the administration of at least one compound of the invention and surgical therapy. In one embodiment, combination therapies according to the invention comprise the administration of at least one compound of the invention and radiotherapy. In one embodiment, combination therapies according to the invention comprise the administration of at least one compound of the invention and at least one supportive care agent (e.g., at least one anti-emetic agent). In one embodiment, combination therapies according to the present invention comprise the administration of at least one compound of the invention and at least one other chemotherapeutic agent. In one particular embodiment, the invention comprises the administration of at least one compound of the invention and at least one anti-neoplastic agent.

As an additional aspect, the present invention provides the methods of treatment and uses as described above, which comprise administering a compound of the invention together with at least one chemotherapeutic agent. In one particular embodiment, the chemotherapeutic agent is an anti-neoplastic agent. In another embodiment, the invention provides a pharmaceutical composition as described above further comprising at least one other chemotherapeutic agent, more particularly, the chemotherapeutic agent is an anti-neoplastic agent. The invention also provides methods of treatment and uses as described above, which comprise administering a compound of the invention together with at least one supportive care agent (e.g., anti-emetic agent).

The compounds of the invention and at least one additional anti-neoplastic or supportive care therapy may be employed in combination concomitantly or sequentially in any therapeutically appropriate combination. The administration of a compound of the invention with one or more other anti-neoplastic agents may be in combination in accordance with the invention by administration concomitantly in one unitary pharmaceutical composition including both or all compounds or two or more separate pharmaceutical compositions each including one or more of the compounds. The components of the combination may be administered separately in a sequential manner wherein one active ingredient is administered first and the other(s) second or vice versa. Such sequential administration may be close in time or remote in time.

When a compound of the invention is used in combination with an anti-neoplastic and/or supportive care agent, the dose of each compound may differ from that when the compound is used alone. Appropriate doses will be readily appreciated by those skilled in the art. The appropriate dose of the compound(s) of the invention and the other therapeutically active agent(s) and the relative timings of administration will be selected in order to achieve the desired combined therapeutic effect, and are within the expertise and discretion of the attendant clinician.

Typically, any chemotherapeutic agent that has activity against a susceptible neoplasm being treated may be utilized in combination with the compounds of the invention, provided that the particular agent is clinically compatible with therapy employing a compound of the invention. Typical anti-neoplastic agents useful in the present invention include, but are not limited to: alkylating agents, anti-metabolites, antitumor antibiotics, antimitotic agents, topoisomerase I and II inhibitors, hormones and hormonal analogues; retinoids, signal transduction pathway inhibitors including inhibitors of cell growth or growth factor function, angiogenesis inhibitors, and serine/threonine or other kinase inhibitors; cyclin dependent kinase inhibitors; antisense therapies and immunotherapeutic agents, including monoclonals, vaccines or other biological agents.

Alkylating agents are non-phase specific anti-neoplastic agents and strong electrophiles. Typically, alkylating agents form covalent linkages, by alkylation, to DNA through nucleophilic moieties of the DNA molecule such as phosphate, amino, and hydroxyl groups. Such alkylation disrupts nucleic acid function leading to cell death. Alkylating agents may be employed in combination with the compounds of the invention in the compositions and methods described above. Examples of alkylating agents include but are not limited to nitrogen mustards such as cyclophosphamides, temozolamide, melphalan, and chlorambucil; oxazaphosphorines; alkyl sulfonates such as busulfan; nitrosoureas such as carmustine; triazenes such as dacarbazine; and platinum coordination complexes such as cisplatin, oxaliplatin and carboplatin.

Antimetabolite neoplastic agents are phase specific anti-neoplastic agents that act at S phase (DNA synthesis) of the cell cycle by inhibiting DNA synthesis or by inhibiting purine or pyrimidine base synthesis and thereby limiting DNA synthesis. The end result of discontinuing S phase is cell death. Antimetabolite neoplastic agents may be employed in combination with the compounds of the invention in the compositions and methods described above. Examples of antimetabolite anti-neoplastic agents include but are not limited to purine and pyrimidine analogues and anti-folate compounds, and more specifically, hydroxyurea, cytosine, arabinoside, ralitrexed, tegafur, fluorouracil (e.g., 5FU), methotrexate, cytarabine, mercaptopurine and thioguanine.

Antitumor antibiotic agents are non-phase specific agents, which bind to or intercalate with DNA. Typically, such action disrupts ordinary function of the nucleic acids, leading to cell death. Antitumor antibiotics may be employed in combination with the compounds of the invention in the compositions and methods described above. Examples of antitumor antibiotic agents include, but are not limited to, actinomycins such as dactinomycin; anthracyclines such as daunorubicin, doxorubicin, idarubicin, epirubicin and mitoxantrone; mitomycin C and bleomycins.

Antimicrotubule or antimitotic agents are phase specific agents active against the microtubules of tumor cells during M or the mitosis phase of the cell cycle. Antimitotic agents may be employed in combination with the compounds of the invention in the compositions and methods described above. Examples of antimitotic agents include, but are not limited to, diterpenoids, vinca alkaloids, polo-like kinase (Plk) inhibitors and CenpE inhibitors. Examples of diterpenoids include, but are not limited to, paclitaxel and its analog docetaxel. Examples of vinca alkaloids include, but are not limited to, vinblastine, vincristine, vindesine and vinorelbine. Plk inhibitors are discussed further below.

Topoisomerase inhibitors include inhibitors of Topoisomerase II and inhibitors of Topoisomerase I. Topoisomerase II inhibitors, such as epipodophyllotoxins, are anti-neoplastic agents derived from the mandrake plant, that typically affect cells in the S and $G_2$ phases of the cell cycle by forming a ternary complex with topoisomerase II and DNA, causing DNA strand breaks. The strand breaks accumulate and cell death follows. Examples of epipodophyllotoxins include, but are not limited to, etoposide and teniposide. Camptothecins, including camptothecin and camptothecin derivatives, are available or under development as Topoisomerase I inhibitors. Examples of camptothecins include, but are not limited to amsacrine, irinotecan, topotecan, and the various optical forms of 7-(4-methylpiperazino-methylene)-10,11-ethylenedioxy-20-camptothecin. Topoisomerase inhibitors may be employed in combination with the compounds of the invention in the compositions and methods described above.

Hormones and hormonal analogues are useful compounds for treating cancers in which there is a relationship between the hormone(s) and growth and/or lack of growth of the cancer. Antitumor hormones and hormonal analogues may be employed in combination with the compounds of the invention in the compositions and methods described above. Examples of hormones and hormonal analogues believed to be useful in the treatment of neoplasms include, but are not limited to antiestrogens, such as tamoxifen, toremifene, raloxifene, fulvestrant, iodoxyfene and droloxifene; anti-androgens; such as flutamide, nilutamide, bicalutamide and cyproterone acetate; adrenocorticosteroids such as prednisone and prednisolone; aminoglutethimide and other aromatase inhibitors such as anastrozole, letrazole, vorazole, and exemestane; progestrins such as megestrol acetate; 5α-reductase inhibitors such as finasteride and dutasteride; and gonadotropin-releasing hormones (GnRH) and analogues thereof, such as Leutinizing Hormone-releasing Hormone (LHRH) agonists and antagonists such as goserelin luprolide, leuprorelin and buserelin.

Retinoid(s) are compounds that bind to and activate at least one retinoic acid receptor selected from RARα, RARβ, and RARγ and/or compounds that bind to and activate at least one of RARα, RARβ, and RARγ and also at least one retinoic X receptor (RXR), including RXRα, RXRβ, and RXRγ. Retinoids for use in the present invention typically have affinity for RAR, and particularly for RARα and/or RARβ. However, certain synthetic retinoids, such as 9-cis-retinoic acid also have affinity for both RAR and RXR. In one embodiment, the retinoid has affinity for RARα (and RARα agonist). Examples of specific retinoids that may be used in combination with the compounds of the invention include: retinoic acid; all-trans-retinoic acid ("ATRA" also known as "tretinoin"); tamibarotene ("Am80"); 9-cis-retinoic acid ((2E,4E,6Z,8E)-3,7-Dimethyl-9-(2,6,6-trimethylcyclohex-1-enyl) nona-2,4,6,8-tetraenoic Acid) (also known as "9-cis-Tretinoin") (available from Sigma); Isotretinoin ((2Z,4E,6E,8E)-3,7-dimethyl-9-(2,6,6-trimethyl-1-cyclohexenyl)nona-2,4,6,8-tetraenoic acid) (also known as "13-cis-retinoic acid") (ACCUTANE®); Am580 (4-(5,6,7,8-tetrahydro-5,5,8,8-tetramethyl-2-naphtamido)benzoic acid), See, M. Gianni, *Blood* 1996 87(4):1520-1531; TTNPB (4-[E-2-(5,6,7,8-Tetrahydro-5,5,8,8-tetramethyl-2-naphthalenyl)-1-propenyl]benzoic acid) (also known as "Ro 13-7410") See, M. F. Boehm et al. *J. Med. Chem.* 1994 37:2930 and R. P. Bissonnette et al., *Mol. Cell. Biol.* 1995 15:5576; and BMS753 (4-[[(2,3-dihydro-1,1,3,3-tetramethyl-2-oxo-1H-inden-5-yl) carbonyl]amino]benzoic acid) See, U.S. Pat. No. 6,184,256. Other RARα agonists known the art may also be used in the present invention.

Signal transduction pathway inhibitors are those inhibitors which block or inhibit a chemical process which evokes an intracellular change. As used herein these changes include, but are not limited to, cell proliferation or differentiation or survival. Signal transduction pathway inhibitors useful in the present invention include, but are not limited to, inhibitors of receptor tyrosine kinases, non-receptor tyrosine kinases, SH2/SH3 domain blockers, serine/threonine kinases, phosphatidyl inositol-3-OH kinases, myoinositol signaling, and Ras oncogenes. Signal transduction pathway inhibitors may be employed in combination with the compounds of the invention in the compositions and methods described above.

Several protein tyrosine kinases catalyze the phosphorylation of specific tyrosine residues in various proteins involved in the regulation of cell growth. Such protein tyrosine kinases can be broadly classified as receptor or non-receptor kinases.

Receptor tyrosine kinase inhibitors which may be combined with the compounds of the invention include those involved in the regulation of cell growth, which receptor tyrosine kinases are sometimes referred to as "growth factor receptors." Examples of growth factor receptor inhibitors, include but are not limited to inhibitors of: insulin growth factor receptors (IGF-1R, IR and IRR); epidermal growth factor family receptors (EGFR, ErbB2, and ErbB4); platelet derived growth factor receptors (PDGFRs), vascular endothelial growth factor receptors (VEGFRs), tyrosine kinase with immunoglobulin-like and epidermal growth factor homology domains (TIE-2), macrophage colony stimulating factor (c-fms), c-kit, c-met, fibroblast growth factor receptors (FGFRs), hepatocyte growth factor receptors (HGFRs), Trk receptors (TrkA, TrkB, and TrkC), ephrin (Eph) receptors and the RET protooncogene.

Several inhibitors of growth factor receptors are under development and include ligand antagonists, antibodies, tyrosine kinase inhibitors, anti-sense oligonucleotides and aptamers. Any of these growth factor receptor inhibitors may be employed in combination with the compounds of the invention in any of the compositions and methods/uses described herein. Trastuzumab (Herceptin®) is an example of an anti-erbB2 antibody inhibitor of growth factor function. One example of an anti-erbB1 antibody inhibitor of growth factor function is cetuximab (Erbitux™, C225). Bevacizumab (Avastin®) is an example of a monoclonal antibody directed against VEGFR. Examples of small molecule inhibitors of epidermal growth factor receptors include but are not limited to lapatinib (Tykerb™) and erlotinib (TARCEVA®). Imatinib (GLEEVEC®) is one example of a PDGFR inhibitor. Examples of VEGFR inhibitors include pazopanib, ZD6474, AZD2171, PTK787, sunitinib and sorafenib.

In one embodiment, the invention provides methods of treatment of any of the various conditions enumerated above comprising administering a compound of the invention in combination with an EGFR or ErbB inhibitor. In one particular embodiment, the methods of the present invention comprise administering a compound of the invention in combination with lapatinib. In one particular embodiment, the methods of the present invention comprise administering a compound of the invention in combination with trastuzumab. In one particular embodiment, the methods of the present invention comprise administering a compound of the invention in combination with erlotinib. In one particular embodiment, the methods of the present invention comprise administering a compound of the invention in combination with gefitinib.

In another embodiment, the present invention provides methods of treatment of any of the various conditions enumerated above comprising administering a compound of the invention in combination with a VEGFR inhibitor. In one particular embodiment, the methods of the present invention comprise administering a compound of the invention in combination with pazopanib.

Tyrosine kinases that are not transmembrane growth factor receptor kinases are termed non-receptor, or intracellular tyrosine kinases. Inhibitors of non-receptor tyrosine kinases are sometimes referred to as "anti-metastatic agents" and are useful in the present invention. Targets or potential targets of anti-metastatic agents, include, but are not limited to, c-Src, Lck, Fyn, Yes, Jak, Abl kinase (c-Abl and Bcr-Abl), FAK (focal adhesion kinase) and Bruton's tyrosine kinase (BTK). Non-receptor kinases and agents, which inhibit non-receptor tyrosine kinase function, are described in Sinha, S. and Corey, S. J., (1999) *J. Hematother. Stem Cell Res.* 8:465-80; and Bolen, J. B. and Brugge, J. S., (1997) *Annu. Rev. of Immunol.* 15:371-404.

SH2/SH3 domain blockers are agents that disrupt SH2 or SH3 domain binding in a variety of enzymes or adaptor proteins including, but not limited to, PI3-K p85 subunit, Src family kinases, adaptor molecules (Shc, Crk, Nck, Grb2) and Ras-GAP. Examples of Src inhibitors include, but are not limited to, dasatinib and BMS-354825 (J. Med. Chem. (2004) 47:6658-6661).

Inhibitors of serine/threonine kinases may also be used in combination with the compounds of the invention in any of the compositions and methods described above. Examples of serine/threonine kinase inhibitors that may also be used in combination with a compound of the present invention include, but are not limited to, polo-like kinase inhibitors (Plk family e.g., Plk1, Plk2, and Plk3), which play critical roles in regulating processes in the cell cycle including the entry into and the exit from mitosis; MAP kinase cascade blockers, which include other Ras/Raf kinase inhibitors, mitogen or extracellular regulated kinases (MEKs), and extracellular regulated kinases (ERKs); Aurora kinase inhibitors (including inhibitors of Aurora A and Aurora B); protein kinase C (PKC) family member blockers, including inhibitors of PKC subtypes (alpha, beta, gamma, epsilon, mu, lambda, iota, zeta); inhibitors of kappa-B (IkB) kinase family (IKK-alpha, IKK-beta); PKB/Akt kinase family inhibitors; and inhibitors of TGF-beta receptor kinases. Examples of Plk inhibitors are described in PCT Publication No. WO04/014899 and WO07/03036. Other examples of serine/threonine kinase inhibitors are known in the art. In another embodiment, the present invention provides methods of treatment of any of the various conditions enumerated above comprising administering a compound of the invention in combination with a Plk inhibitor. In one particular embodiment, the methods of the present invention comprise administering a compound of the invention in combination with 5-{6-[(4-Methylpiperazin-1-yl)methyl]-1H-benzimidazol-1-yl}-3-{(1R)-1-[2-(trifluoromethyl)phenyl]ethoxy}thiophene-2-carboxamide.

Urokinase, also referred to as urokinase-type Plasminogen Activator (uPA), is a serine protease. Activation of the serine protease plasmin triggers a proteolysis cascade which is involved in thrombolysis or extracellular matrix degradation. Elevated expression of urokinase and several other components of the plasminogen activation system have been correlated with tumor malignancy including several aspects of cancer biology such as cell adhesion, migration and cellular mitotic pathways as well. Inhibitors of urokinase expression may be used in combination with the compounds of the invention in the compositions and methods described above.

Inhibitors of Ras oncogene may also be useful in combination with the compounds of the present invention. Such inhibitors include, but are not limited to, inhibitors of farnesyltransferase, geranyl-geranyl transferase, and CAAX proteases as well as antisense oligonucleotides, ribozymes and immunotherapy. Such inhibitors have been shown to block Ras activation in cells containing mutant Ras, thereby acting as antiproliferative agents.

Inhibitors of kinases involved in the IGF-1R signaling axis may also be useful in combination with the compounds of the present invention. Such inhibitors include but are not limited to inhibitors of JNK1/2/3, PI3K, AKT and MEK, and 14.3.3 signaling inhibitors. Examples of AKT inhibitors are described in PCT Publication No. WO 2007/058850, published 24 May 2007 which corresponds to PCT Application No. PCT/US2006/043513, filed 9 Nov. 2006. One particular AKT inhibitor disclosed therein is 4-(2-(4-amino-1,2,5-oxadiazol-3-yl)-1-ethyl-7-{[(3S)-3-piperidinylmethyl]oxy}-1H-imidazo[4,5-c]pyridin-4-yl)-2-methyl-3-butyn-2-ol.

Cell cycle signaling inhibitors, including inhibitors of cyclin dependent kinases (CDKs) are also useful in combination with the compounds of the invention in the compositions and methods described above. Examples of cyclin dependent kinases, including CDK2, CDK4, and CDK6 and inhibitors for the same are described in, for instance, Rosania G. R., et al., *Exp. Opin. Ther. Patents* (2000) 10:215-230.

Receptor kinase angiogenesis inhibitors may also find use in the present invention. Inhibitors of angiogenesis related to VEGFR and TIE-2 are discussed above in regard to signal transduction inhibitors (both are receptor tyrosine kinases). Other inhibitors may be used in combination with the compounds of the invention. For example, anti-VEGF antibodies, which do not recognize VEGFR (the receptor tyrosine kinase), but bind to the ligand; small molecule inhibitors of integrin (alpha$_v$ beta$_3$) that inhibit angiogenesis; endostatin and angiostatin (non-RTK) may also prove useful in combination with the compounds of the invention. One example of a VEGFR antibody is bevacizumab (AVASTIN®).

Inhibitors of phosphatidyl inositol-3-OH kinase family members including blockers of PI3-kinase, ATM, DNA-PK, and Ku may also be useful in combination with the present invention.

Also of potential use in combination with the compounds of the invention are myoinositol signaling inhibitors such as phospholipase C blockers and myoinositol analogues.

siRNA, RNAi, locked nucleic acid polynucleotides, and antisense therapies may also be used in combination with the compounds of the invention. Examples of such antisense therapies include those directed towards the targets described above such as ISIS 2503 and gene therapy approaches such as those using thymidine kinase or cytosine deaminase. Agents used in immunotherapeutic regimens may also be useful in combination with the compounds of the invention. Immunotherapeutic regimens include ex-vivo and in-vivo approaches to increasing immunogenicity of patient tumor cells such as transfection with cytokines (eg. IL-2, IL-4, GMCFS and MCFS), approaches to increase T-cell activity, approaches with transfected immune cells and approaches with anti-idiotypic antibodies. Another potentially useful immunotherapeutic regimen is monoclonal antibodies with wild-type Fc receptors that may illicit an immune response in the host (e.g., IGF-1R monoclonal antibodies).

Agents used in proapoptotic regimens (e.g., Bcl-2 antisense oligonucleotides) may also be used in combination with the compounds of the invention. Members of the Bcl-2 family of proteins block apoptosis. Upregulation of Bcl-2 has therefore been linked to chemoresistance. Studies have shown that the epidermal growth factor (EGF) stimulates anti-apoptotic members of the Bcl-2 family (i.e., mcl-1). Therefore, strategies designed to downregulate the expression of Bcl-2 in tumors have demonstrated clinical benefit and are now in Phase II/III trials, namely Genta's G3139 bcl-2 antisense oligonucleotide. Such proapoptotic strategies using the antisense oligonucleotide strategy for Bcl-2 are discussed in Water, J. S., et al., *J. Clin. Oncol.* (2000) 18:1812-1823; and Kitada, S., et al., *Antisense Res. Dev.* (1994) 4:71-79.

Compounds of the invention may be prepared using the processes described below. In all of the schemes described below, it is understood that protecting groups may be employed where necessary in accordance with general principles known to those of skill in the art, for example, see Green, T. W. and Wuts, P. G. M. (1991) *Protecting Groups in Organic Synthesis*, John Wiley & Sons. The selection of a particular protecting group and processes for installation and removal of protecting groups is within the skill of those in the art. The selection of processes for installation and removal of protecting groups as well as the reaction conditions and order of their execution shall be consistent with the preparation of compounds of the invention.

Compounds of the invention, may be conveniently prepared by the methods outlined in Scheme 1 below.

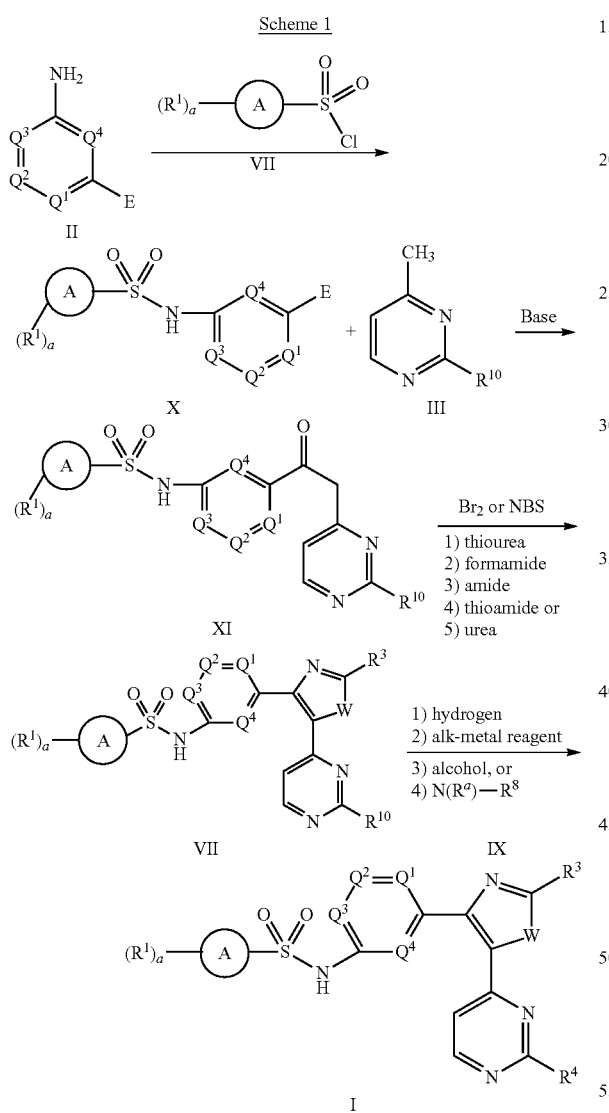

wherein:
$R^{10}$ is halo (preferably chloro) or thiomethyl;
E is a suitable carboxylic ester or carboxylic ester equivalent, particularly a methyl ester, ethyl ester, or Weinreb's amide;
$R^a$ is H or $CH_3$;
alk is alkyl or alkenyl; and
all other variables are as defined above.
In this and subsequent reaction Schemes, NBS is N-bromosuccinimide.

The process for preparing the compounds of the invention according to Scheme 1 (all formulas and all variables having been defined above) comprises the steps of:
a) reacting a compound of formula (II) with a compound of formula (VII) to prepare a compound of formula (X);
b) condensing the compound of formula (X) with a substituted pyrimidine of formula (III) to prepare a compound of formula (XI);
c) reacting the compound of formula (XI) with a suitable brominating agent, followed by reacting with one of:
  i) a thiourea,
  ii) a formamide,
  iii) an amide,
  iv) a thioamide, or
  v) a urea;
  to prepare a compound of formula (VIII);
d) reacting the compound of formula (VIII) with one of:
  i) molecular hydrogen
  ii) an alkyl metal reagent or alkenyl metal reagent
  iii) an alcohol, or
  iv) a compound of formula (IX): $N(R^a)$—$R^8$, wherein $R^a$ is H or $CH_3$, to prepare a compound of formula (I);
e) optionally converting the compound of formula (I) to a pharmaceutically acceptable salt thereof; and
f) optionally converting the compound of formula (I) or a pharmaceutically acceptable salt thereof to a different compound of formula (I) or a pharmaceutically acceptable salt thereof.

The order of the foregoing steps is not critical to the processes of the present invention and the process may be carried out using any suitable order of steps.

Compounds of formula (I) wherein $R^4$ is H may be prepared by reacting a compound of formula (VIII) with a source of molecular hydrogen in the presence of a transition metal catalyst.

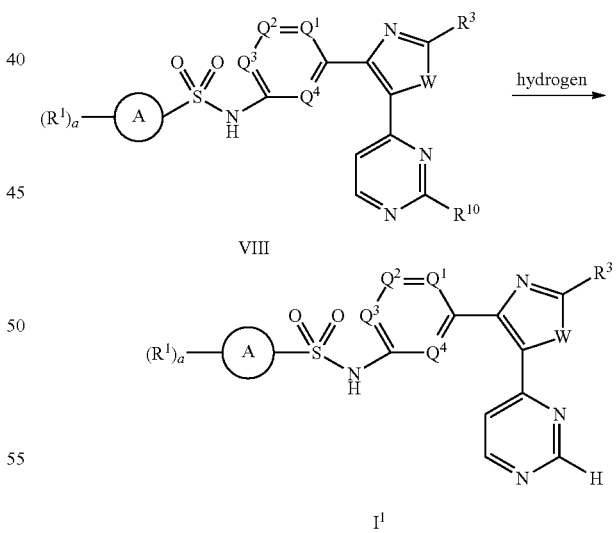

wherein all variables are as defined above.

Appropriate conditions for the reduction reaction will be apparent to those skilled in the art and include palladium hydroxide on carbon, palladium on carbon, sulfided platinum on carbon, or Raney nickel using ammonium formate or other suitable source of molecular hydrogen or alternatively under a hydrogen atmosphere. The reaction may be carried out in an inert solvent at either atmospheric or elevated pressure. The reaction may be carried out at a temperature of about 25° C. to 80° C., preferably 50-70° C. Suitable inert solvents include but are not limited to ethanol, methanol, and ethyl acetate.

Compounds of formula (I) wherein $R^4$ is alkyl, haloalkyl, alkenyl, —$R^5$—$OR^6$, $R^5$—$CO_2R^6$, —$R^5$—$SO_2R^6$, —$R^5$—Het or $R^5$—$NR^6R^7$, may be prepared by reacting a compound of formula (VIII) with an alkyl or alkenyl metal reagent such as compounds having the formula $Alk_nMX_m$ or $X_mMR^5$—$CO_2R^6$ wherein Alk is alkyl or alkenyl;
n is 1, 2, 3 or 4;
M is a transition metal such as Zn, B or Sn;
X is halo, particularly Cl or Br;
m is 0, 1 or 2; and
all other variables are as defined above.

isopropanol in the case of alkenylborates. The reaction may be carried out at a temperature of about 25° C. to 100° C.

A compound of formula ($I^2$) wherein $R^4$ is alkenyl, may be converted to a compound of formula (I) wherein $R^4$ is —$R^5$—$SO_2R^6$, —$R^5$—Het or $R^5$—$NR^6R^7$ by reaction with an appropriate nucleophile. For example a compound of formula (I) wherein $R^4$ is —$R^5$—$SO_2R^6$, or $R^5NR^6R^7$ may be prepared by reacting a compound of formula ($I^2$) wherein $R^4$ is alkenyl with a thiol or amine, respectively. Reaction conditions for such transformations are known to those skilled in the art.

Compounds of formula (I) wherein $R^4$ is —$OR^6$, are prepared by reacting a compound of formula (VIII) with a suitable alcohol.

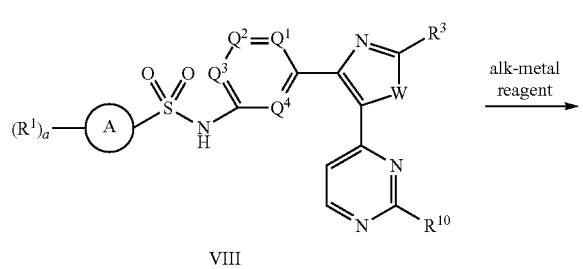

VIII

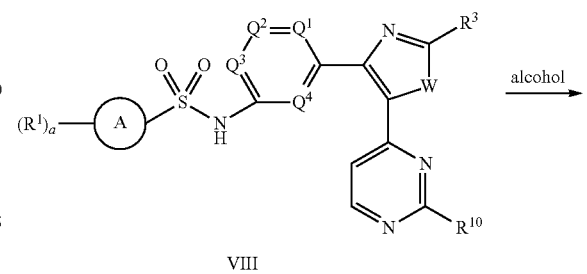

VIII

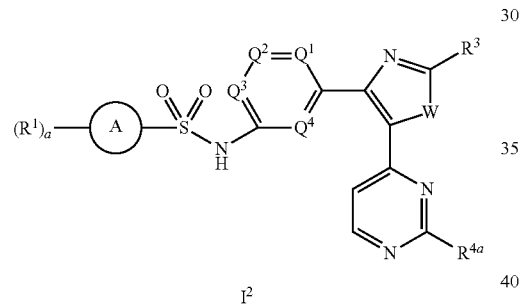

$I^2$

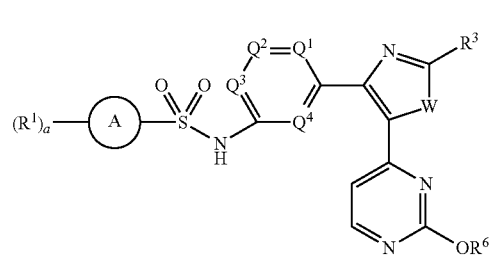

$I^3$ wherein
$R^{4a}$ is alkyl, haloalkyl, alkenyl, —$R^5$—$OR^6$, or $R^5$—$CO_2R^6$; and
all other variables are as defined above.

Specific examples of suitable alkyl or alkenyl metal reagents include but are not limited to dialkylzinc, alkylzinc halides, alkylboranes, alkenylboranes, alkenylborates and alkenylstannanes, either found commercially or which can be prepared by those of ordinary skill in the art by conventional means.

In particular, the reaction is performed in the presence of a palladium source, optionally a phosphine ligand and optionally a base in a suitable inert solvent. Examples of suitable palladium sources include but are not limited to bis(tri-t-butylphosphine)palladium (0), tris(dibenzylideneacetone)dipalladium (0), dichlorobis(triphenylphosphine)-palladium (II) or acetato(2'-di-t-butylphosphino-1,1'-biphenyl-2-yl)palladium (II). Examples of suitable phosphine ligands include but are not limited to 9,9-dimethyl-4,5-bis(diphenylphosphino)xanthene and triphenylphosphine. Examples of suitable bases include but are not limited to potassium acetate, cesium carbonate, sodium methoxide, and triethylamine. Examples of suitable inert solvents include but are not limited to THF, toluene, N,N-dimethylformamide or 1,4-dioxane, or wherein all variables are as defined above.

Specific examples of suitable alcohols include but not limited to methanol, ethanol, n-propanol or n-butanol. The reaction may optionally be carried out in the presence of a base such as, but not limited to cesium carbonate, sodium methoxide, and triethylamine. The reaction is typically carried out at a temperature of about 50-120° C., at atmospheric or elevated pressure and optionally in a microwave.

Compounds of formula (I) wherein $R^4$ is $N(H)R^8$ (i.e., compounds of formula ($I^4$)) are prepared by reacting a compound of formula (VIII) with a compound of formula (IX).

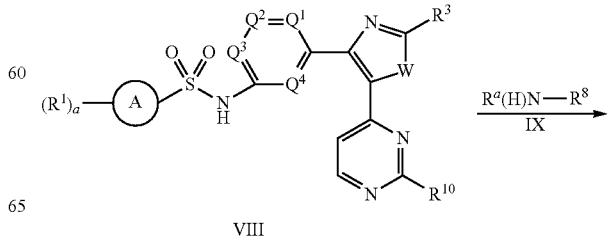

VIII

-continued

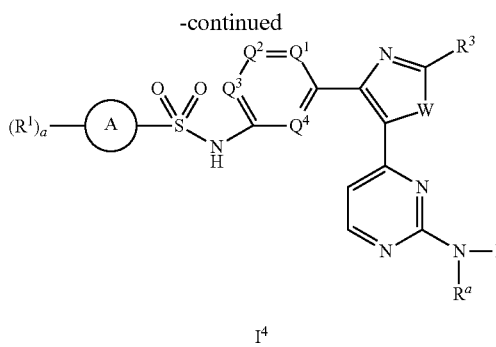

I⁴ wherein $R^a$ is H or $CH_3$ and all other variables are as defined above.

Those skilled in the art will recognize that the conditions required for the above reaction will differ depending upon the definition of $R^{10}$. When $R^{10}$ is halo (preferably chloro), the reaction is generally performed in a solvent or neat. Suitable solvents include but are not limited to isopropanol, methanol, 1,4-dioxane, ethanol, dimethylacetamide, trifluoroethanol, and N,N-dimethylformamide. The reaction is typically carried out at a temperature of from about 30 to about 120° C., or optionally in a microwave apparatus. In the embodiment where $R^4$ is $NH_2$, the reaction is carried out with a source of ammonia, for example, ammonia in methanol or preferably ammonium hydroxide. The reaction is typically carried out without the addition of other solvents and at temperatures of about 60° C. to about 120° C., in a sealed reaction vessel or optionally in a microwave apparatus. As will be apparent to those skilled in the art of organic chemistry, it may also be desirable to install appropriate protecting groups prior to reacting the compound of formula (VIII) with the compound of formula (IX). For example, in the embodiment, wherein $R^4$ is a group containing a pendant primary or secondary amine, the addition is preferably carried out when the pendant amine is protected as, for example, its corresponding t-butyl carbamate or trifluoracetamide. The choice, installation and removal of appropriate protecting groups for reactions such as this is conventional in the art. Compounds of formula (IX) are commercially available or may be synthesized using techniques conventional in the art.

When $R^{10}$ is thiomethyl, the thiomethyl may first be converted to a more suitable leaving group, for example sulfoxide, sulfone, or chloride. The thiomethyl can be converted into a sulfoxide or sulfone by oxidation with an appropriate oxidizing agent, for example oxone, sodium periodate, or meta-chloroperbenzoic acid, in an appropriate solvent, for example dichloromethane, methanol, or water. Those skilled in the art will recognize that this will produce an analogue of the compound of formula (VIII) in which $R^{10}$ is a sulfoxide or sulfone. The oxidized product can then be reacted with the compound of formula (IX) to prepare a compound of formula (I).

These reactions are generally performed in a suitable solvent, for example 2-propanol, dimethylacetamide, or dioxane, optionally with the addition of acid, for example hydrochloric acid, and at a temperature of 25-110° C., preferably 70-90° C., or in a microwave reactor at a temperature of 90-220° C., preferably 160-190° C.

Alternately, the pyrimidinyl sulfoxide or sulfone can be converted to the corresponding hydroxyl pyrimidine by reaction with an appropriate aqueous acid, for example hydrochloric acid or acetic acid, at a temperature of 25-110° C., preferably 70-90° C. The hydroxyl pyrimidine can then be converted to a chloride using an appropriate chlorinating reagent, for example phosphorous oxychloride or thionyl chloride, optionally in a solvent, for example dichloromethane, at a temperature of 25-120° C., preferably 60-80° C. Those skilled in the art will recognize that this process will produce a compound of formula (VIII) wherein $R^{10}$ is chloro, which can be reacted with a compound of formula (IX) as described above.

Compounds of formula (VIII) may be prepared by reacting a compound of formula (XI) with a suitable brominating reagent, particularly bromine or NBS, followed by reacting with one of: 1) a thiourea, 2) a formamide 3) an amide 4) a thioamide or 5) a urea depending upon whether the thiazole or oxazole and which particular substituents $R^3$, are desired.

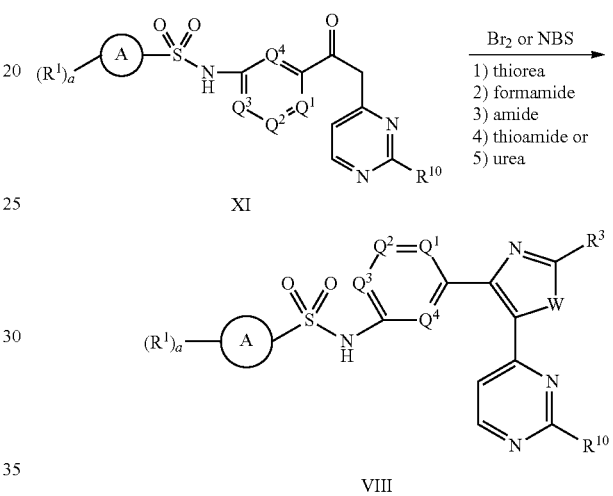

wherein all variables are as defined above.

In this and subsequent Schemes, reference to thiourea, formamide, amide, thioamide or urea in connection with this type of reaction refers to unsubstituted thiourea, formamide, amide, thioamide or urea and substituted analogs thereof. In particular, the thiourea, formamide, amide, thioamide or urea may be substituted with the desired group $R^3$. Suitably substituted analogs of thiourea, formamide, amide, thioamide or urea are commercially available or may be prepared using conventional techniques.

When an aminothiazole (i.e., the compound of formula (VIII) wherein W is S and $R^3$ is —$NR^6R^7$ or Het is desired, the reaction can be accomplished by the initial bromination of a compound of formula (XI) using an appropriate brominating reagent, for example bromine in solvent such as acetic acid or NBS.

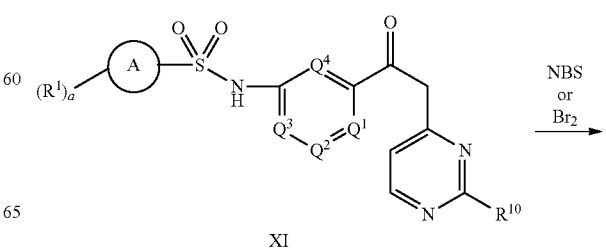

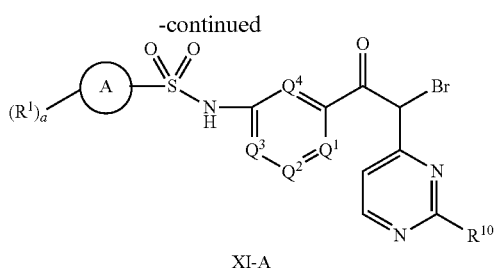

XI-A

The reaction is typically carried out in an appropriate solvent, for example dichloromethane, N,N-dimethylformamide, or N,N-dimethylacetamide, and at a temperature of 25-50° C., particularly 25° C. The brominated analog (i.e., a compound of formula (XI-A)) is then reacted with an appropriately substituted thiourea.

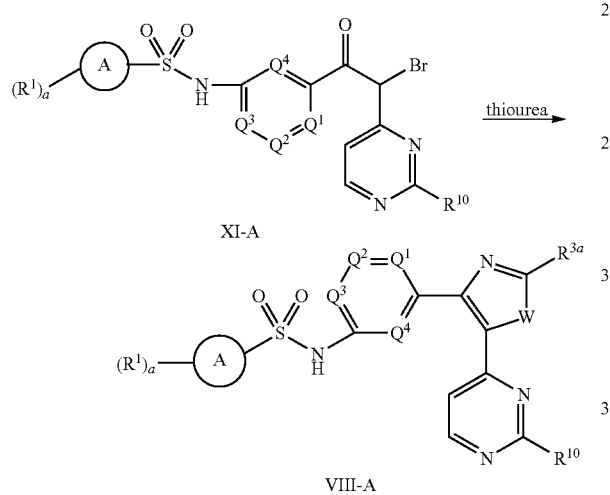

wherein W is S, $R^{3a}$ is —$NR^6R^7$ or Het and all other variables are as defined above.

The reaction is typically carried out in an appropriate solvent, for example, N,N-dimethylformamide, N,N-dimethylacetamide, dichloromethane, tetrahydrofuran, dioxane, or acetonitrile, optionally in the presence of a suitable base, for example magnesium carbonate or sodium bicarbonate, and at a temperature of 25-90° C., particularly 25-50° C. Those skilled in the art will recognize that the thiourea can be unsubstituted, thus resulting in a compound of formula (VIII) wherein $R^3$ is $NH_2$; or the thiourea may bear one or more additional substituents on one of the nitrogen atoms.

In this and subsequent reactions, a compound, such as a compound of formula (VIII), wherein $R^3$ is an amino group (i.e., —$NR^6R^7$), may be further converted to a corresponding compound wherein $R^3$ is other than amino (or substituted amino) using the techniques described herein and those conventional in the art.

For example, the aminothiazole compound of formula (VIII-A) wherein $R^3$ is an amino group, may be converted to an unsubstituted thiazole (i.e., a compound of formula (VIII) wherein $R^3$ is H) using methods familiar to those of skill in the art. For example, the thiazole may be prepared by reacting the aminothiazole with an appropriate reagent, for example t-butyl nitrite, in an appropriate solvent, for example tetrahydrofuran, and at a temperature of 35-75° C., particularly 40-60° C.

When a substituted thiazole is desired, an aminothiazole of formula (VIII) may be modified according to methods that will be familiar to those skilled in the art. For example, the aminothiazole compound of formula (VIII-A) may be converted to a compound of formula (VIII-B) by reaction with reagents capable of replacing the amino group with a halide, preferably a bromide.

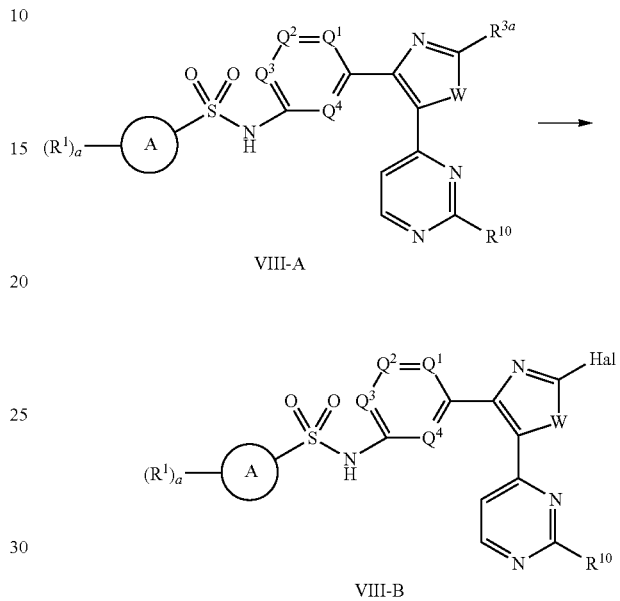

wherein Hal is halo, preferably Br; and all other variables are as defined above.

The conversion to a halo-thiazole of formula (VIII-B) may be carried out by reaction with for example, t-butyl nitrite and copper (II) bromide in a suitable solvent, such as tetrahydrofuran or acetonitrile, and at a temperature from −10° C. to 50° C., preferably 0° C. to 25° C. The halo-thiazole of formula (VIII-B), may then be reacted under a variety of conditions known to those in the art to produce different thiazole compounds of formula (VIII-C) wherein $R^3$ can be a variety of substituents consistent with the definition of $R^3$ in reference to compounds of Formula (I).

One example of such a reaction is similar to the method of J. Tsuji "Palladium Reagents and Catalysts: Innovations in Organic Synthesis", Wiley, Chichester, UK, 1995, involving reaction of the halo-thiazole of formula (VIII-B) with a reagent capable of undergoing palladium-based coupling to prepare compounds of formula (VIII-C) wherein $R^{3c}$ is alkyl, haloalkyl, or alkenyl.

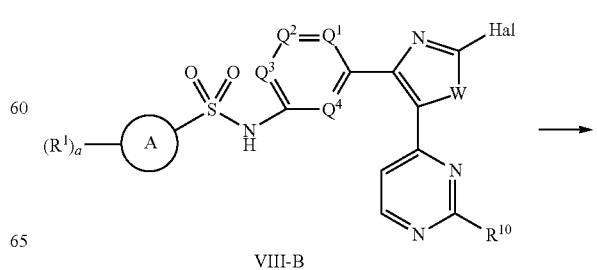

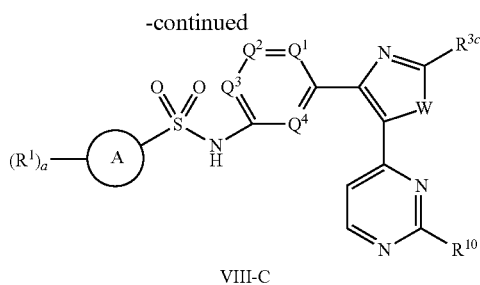

VIII-C wherein Hal is halogen;
R$^{3c}$ is alkyl, haloalkyl or alkyl-OH; and
all other variables are as defined above.

For example the halo-thiazole of formula (VIII-B) may be reacted with a boronic acid, boronate ester, alkyl tin, alkyl zinc or Grignard reagent, in an appropriate solvent, for example tetrahydrofuran, dioxane, or dimethylformamide, in the presence of a catalyst capable of inducing such a transformation, particularly a palladium catalyst, for example palladiumdicholorobistriphenylphosphine, and at a temperature of 25-150° C., preferably 25-60° C. Those skilled in the art will recognize that these coupling reactions will often require the addition of a suitable base, such as aqueous sodium carbonate, cesium carbonate, or triethylamine and/or the addition of a suitable ligand for the palladium species, for example a trialkylphosphine or a triarylphosphine, for example triphenylphosphine.

Another example of such a reaction involves the reaction of the halo-thiazole of formula (V-B) with a reagent capable of displacing the bromide, for example an amine, such as piperidine, methylamine, or methyl piperazine.

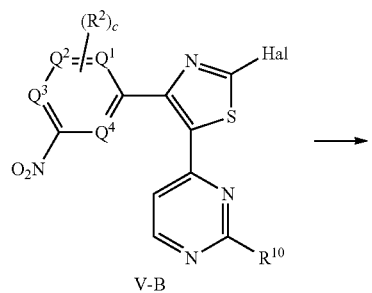

V-B

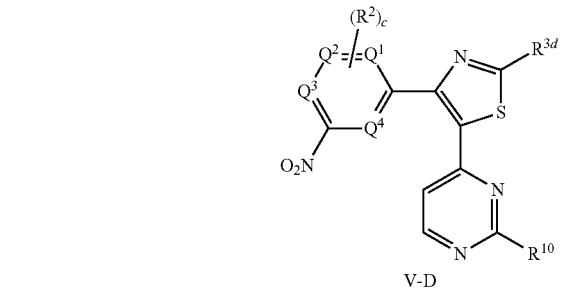

V-D wherein Hal is halogen;
R$^{3d}$ is —NR$^6$R$^7$; and
all other variables are as defined above.

In the case of reacting a halo-thiazole of formula (VIII-B) with an amine or substituted amine (e.g., dimethylamine) the reaction is generally performed by reacting the compound of formula (V-B) with the amine or substituted amine optionally in a suitable solvent, such as 2-propanol, dioxane, or dimethylformamide, at a temperature of 25° C. to 150° C., preferably 50-90° C., optionally in the presence of a suitable acid, for example hydrochloric acid.

According to another process of producing a substituted thiazole of formula (VIII), a compound of formula (XI-A) is reacted with a thioamide, for example thioacetamide, to prepare a compound of formula (VIII-D) wherein R$^{3d}$ is alkyl.

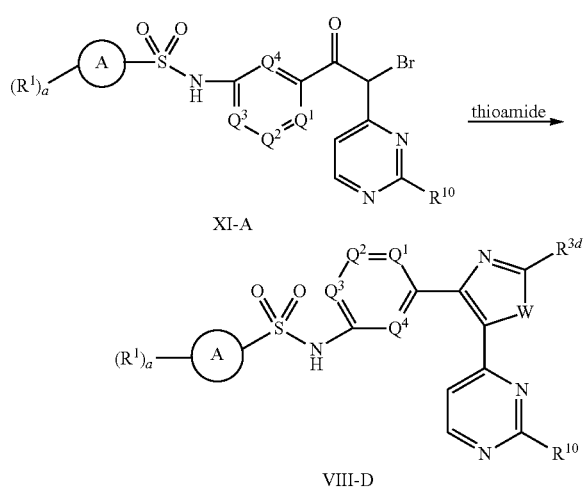

XI-A

VIII-D wherein all variables are as defined above.

Alkyl substituted thioamides for use in this process are commercially available or may be prepared using conventional techniques. Typically, the reaction is carried out in an appropriate solvent, for example, dichloromethane, tetrahydrofuran, dimethylformamide, N,N-dimethylacetamide, or acetonitrile, particularly dimethylformamide or N,N-dimethylacetamide, optionally in the presence of a suitable base, for example magnesium carbonate or sodium bicarbonate, and at a temperature of 35-100° C., preferably 50-80° C.

In the embodiment wherein an oxazole of formula (VIII) is desired wherein R$^3$ is H, the reaction can be accomplished by reacting the compound of formula (XI-A) with formamide in the presence of an acid, such as sulfuric acid, and at a temperature of 60-150° C., preferably 90-130° C.

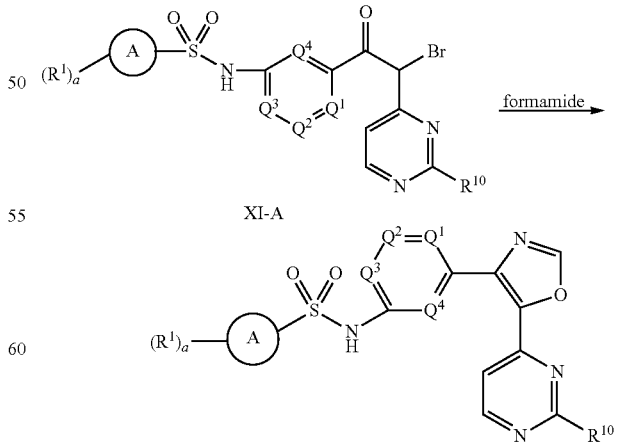

XI-A

VIII-E wherein all variables are as defined above.

A substituted oxazole of formula (VIII-F) may be prepared from the compound of formula (XI-A).

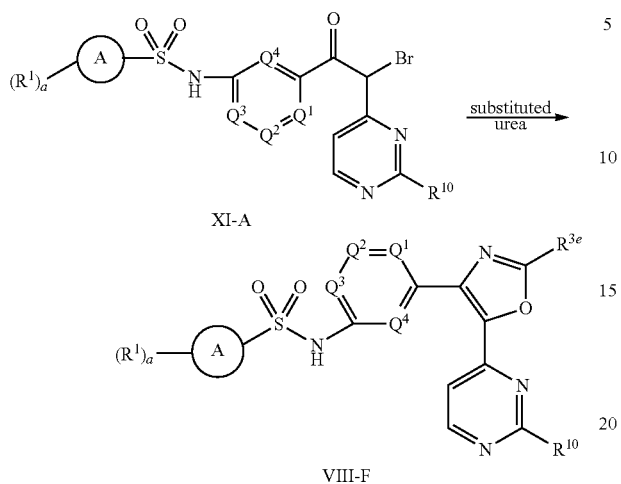

wherein $R^{3e}$ is Het or $-NR^6R^7$ and all other variables are as defined above.

The reaction may be carried out by reacting the compound of formula (XI-A) with urea or substituted urea in an appropriate solvent, for example, N,N-dimethylformamide, N,N-dimethylacetamide dichloromethane, tetrahydrofuran, dioxane, or acetonitrile, optionally in the presence of a suitable base, for example magnesium carbonate or sodium bicarbonate, and at a temperature of 25-170° C., particularly 60-150° C. or in a microwave reactor at a temperature of 100-190° C., particularly 120-160° C. Those skilled in the art will envision substituted ureas that may be employed in the foregoing method to prepare compounds of formula (VIII-F) wherein $R^{3e}$ is as defined above. One example of a substituted urea for use in this method is 1-pyrrolidinecarboxamide. Suitable substituted ureas are commercially available or can be made using techniques known to those skilled in the art.

A substituted oxazole of formula (VIII-G), may also be prepared from a compound of formula (XI-A).

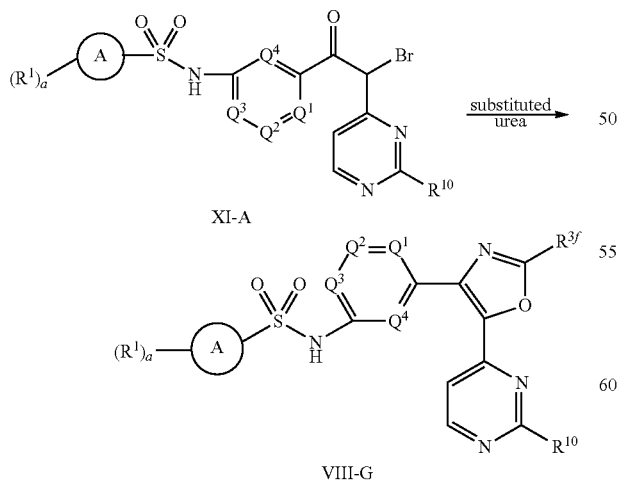

wherein $R^{3f}$ is alkyl or haloalkyl and all other variables are as defined above.

Typically, the reaction may be carried out by reacting the compound of formula (XI-A) with an amide (i.e., a compound of formula $R^{3f}$—$C(O)NH_2$), for example acetamide, in an appropriate solvent, for example, dichloromethane, tetrahydrofuran, dimethylformamide, or acetonitrile, particularly dimethylformamide or neat, optionally in the presence of a suitable base, for example magnesium carbonate or sodium bicarbonate, and at a temperature of 35-170° C., preferably 60-150° C. or in a microwave reactor at a temperature of 100-190° C., particularly 130-170° C. Suitable amides for use in this reaction will be apparent to those skilled in the art and are commercially available or may be prepared using conventional techniques.

As will be appreciated by those skilled in the art a bromo-substituted oxazole of formula (VIII-H),

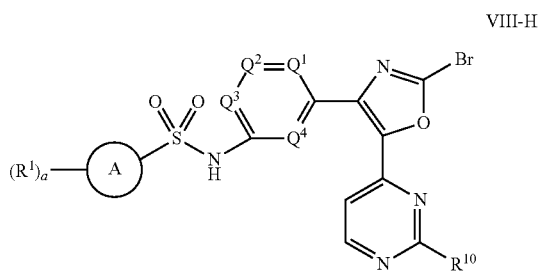

wherein all other variables are as defined above;

may also be prepared by conversion of an oxazole of formula (VIII-F) (wherein $R^3$ is an amine or substituted amino group) to the bromo analog using techniques known to those of skill in the art, including those described above.

Those of skill in the art will recognize that some of the reactions described above may be incompatible with compounds of formula (VIII) in which $R^{10}$ is chloride. In such embodiments, the foregoing reactions may be performed using compounds of formula (XI) wherein $R^{10}$ is thiomethyl, and subsequently converting the thiomethyl to a more suitable leaving group, such as a sulfoxide, sulfone or chloride using techniques conventional in the art, including those described above.

Compounds of formula (XI) may be prepared by reacting a compound of formula (X) with a substituted pyrimidine of formula (III).

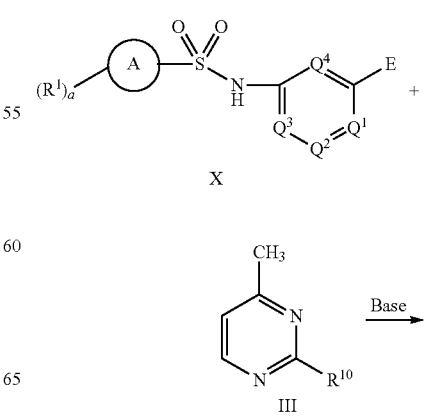

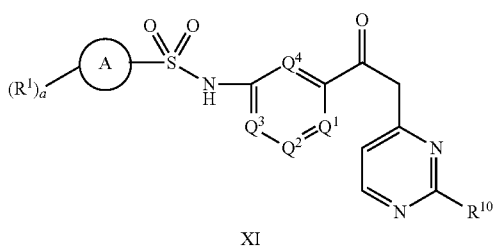

XI wherein all variables are as defined above.

The reaction is generally performed by reacting a compound of formula (X) and a compound of formula (III) in the presence of a suitable base capable of deprotonating a compound of formula (III), for example lithium hexamethyldisilazide (LiHMDS), sodium hexamethyldisilazide, or lithium diisopropylamide, particularly LiHMDS, in an appropriate solvent, such as THF, and at a temperature of about −78° C. to about 25° C., particularly about 0° C. to about 25° C.

A compound of formula (X) may be prepared by reacting the compound of formula (II) with a compound of formula (VII).

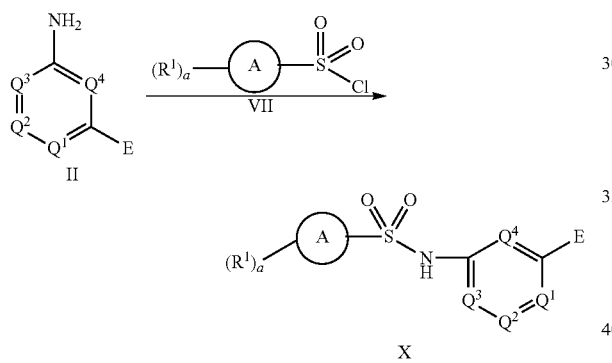

This reaction may be carried out using conditions conventional in the art for such coupling reactions, including the use of a solvent such as tetrahydrofuran, 1,4-dioxane or dichloromethane at room temperature or with heating from about 40° C. to about 100° C. Those skilled in the art will recognize that it may be desirable to carry out this reaction in the presence of a suitable base, for example pyridine or triethylamine. Compounds of formula (VII) are commercially available or may be synthesized using techniques conventional in the art.

Compounds of formula (II) wherein $Q^1$, $Q^2$, $Q^3$ and $Q^4$ are CH are commercially available. Compounds of formula (II) wherein one of $Q^1$, $Q^2$, $Q^3$ and $Q^4$ is C—$R^2$ may be prepared by reduction of the compound of formula (XIII). Appropriate conditions for the reduction reaction will be apparent to those skilled in the art and include palladium on carbon under a hydrogen atmosphere, sulfided platinum on carbon under a hydrogen atmosphere, or iron powder in acetic acid. In one embodiment, the reduction may be effected using Raney nickel under a hydrogen atmosphere. The reaction may be carried out in an inert solvent at either atmospheric or elevated pressure. Suitable inert solvents include but are not limited to ethanol, methanol, and ethyl acetate.

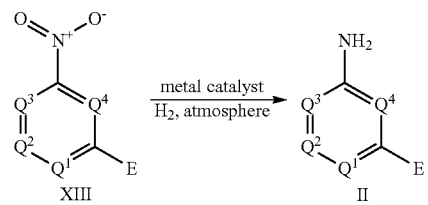

Compounds of formula (XIII) may be prepared by oxidation of the compound of formula (XX) using an appropriate oxidizing agent such as but not limited to chromium trioxide or potassium permanganate to yield compounds of formula (XXI). In one embodiment, the reaction is performed with chromium trioxide under strongly acidic conditions such as in the presence of sulfuric acid. The reaction may be carried out at a temperature of about 80° C. to 100° C. Compounds of formula (XXI) can be then converted to compounds of formula (XIII) by esterification of the acid functionality using conditions standard for such transformations, specifically in methanol in the presence of catalytic sulfuric acid.

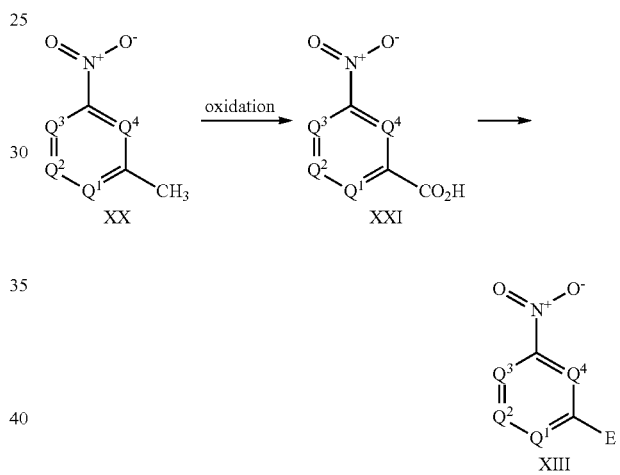

wherein all variables are as defined above.

Alternatively, compounds of formula (II) wherein one of $Q^1$, $Q^2$, $Q^3$ and $Q^4$ is C—$R^2$ may be prepared by reaction of the compound of formula (XV) with a nitrogen source such as benzophenone imine or t-butyl carbamate using conditions conventional in the art for Buchwald cross-coupling reactions. In particular, in the presence of a palladium source, optionally a phosphine ligand, and a base in a suitable inert solvent. Examples of suitable palladium sources include but are not limited to tris(dibenzylideneacetone)dipalladium (0), dichlorobis(triphenylphosphine)-palladium (II) or acetato(2′-di-t-butylphosphino-1,1-biphenyl-2-yl)palladium (II). Examples of suitable phosphine ligands include but are not limited to 9,9-dimethyl-4,5-bis(diphenylphosphino)xanthene and triphenylphosphine. Examples of suitable bases include but are not limited to potassium acetate, cesium carbonate, sodium methoxide, and triethylamine. Examples of suitable inert solvents include but are not limited to toluene, N,N-dimethylformamide or 1,4-dioxane. The reaction may be carried out at a temperature of about 80° C. to 150° C., optionally in the microwave.

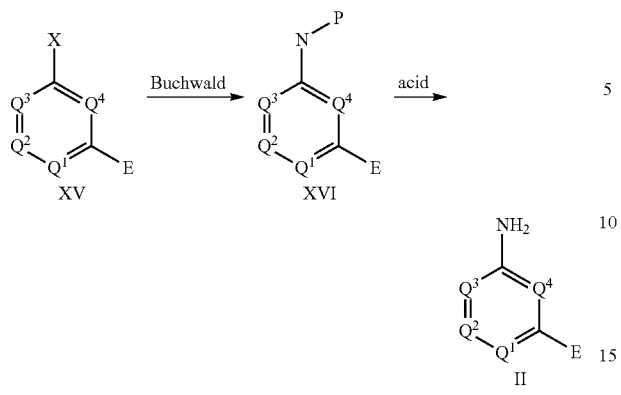

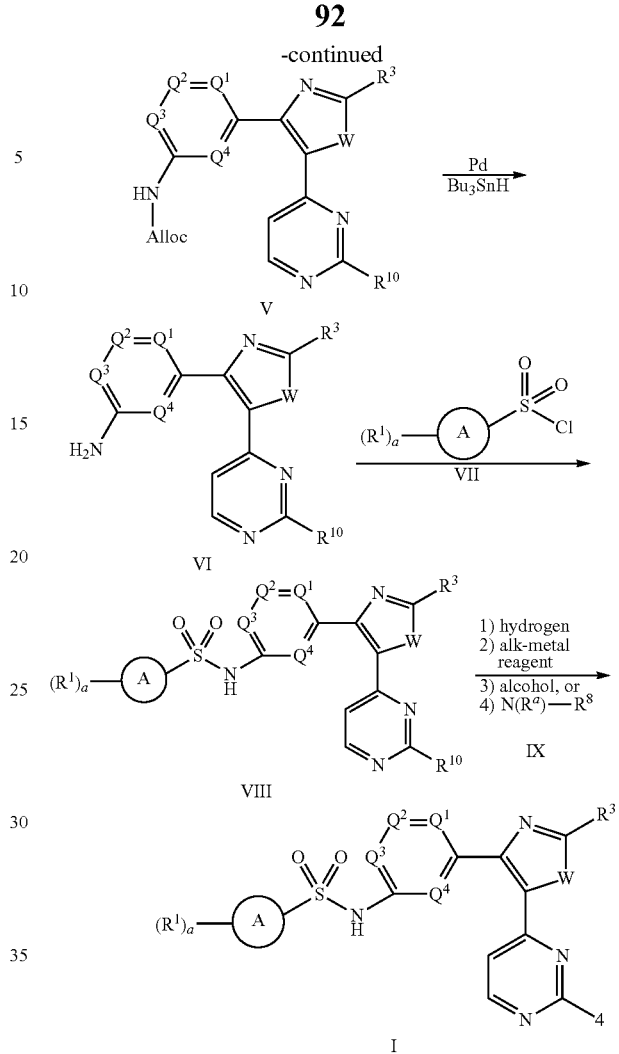

wherein X is halo, particularly Br;

P is protected nitrogen, particularly benzophenone imine or t-butyl carbamate;

and all other variables are as defined above.

Conversion of compounds of formula (XVI) to compounds of formula (II) can be achieved by reaction with a strong acid in a suitable organic solvent using conventional acidic deprotection techniques. Suitable acids used in such transformations include but are not limited to hydrochloric acid. Suitable solvents for such transformations include but are not limited to tetrahydrofuran and 1,4-dioxane. See, Kocienski, P. J. *Protecting Groups*, Georg Thieme Verlag, Stuttgart, 1994; and Greene, T. W., Wuts, P. G. M. *Protecting Groups in Organic Synthesis* (2$^{nd}$ Edition), J. Wiley and Sons, 1991.

As noted above, the order of the foregoing steps is not critical to the practice of the present invention. In another embodiment, compounds of the invention may also be prepared according to Scheme 2, which demonstrates an alternative order of the steps of Scheme 1.

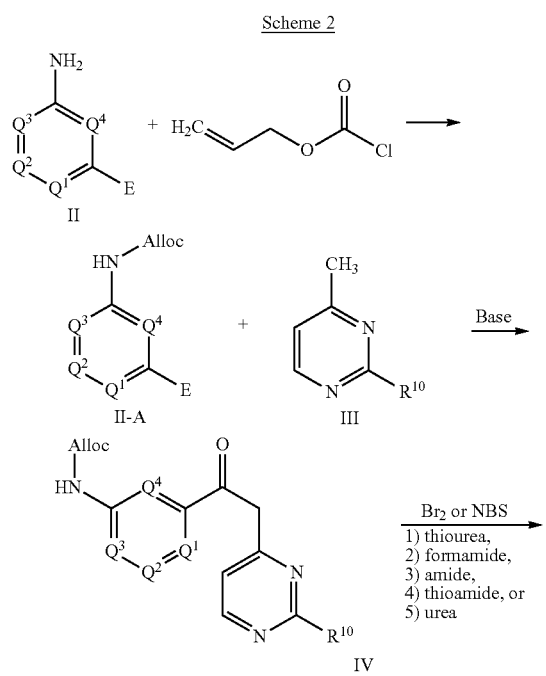

wherein:

$R^{10}$ is halo (preferably chloro) or thiomethyl;

E is a suitable carboxylic ester or ester equivalent, particularly a methyl ester, ethyl ester, or Weinreb's amide;

Alloc is allylchloroformate;

Bu$_3$SnH is tri-n-butyl tin hydride; and all other variables are as defined above.

The process according to Scheme 2 comprises the steps of:

a) installing a protecting group such as allylchloroformate, on a compound of formula (II) to prepare a compound of formula (II-A);

b) condensing the compound of formula (II-A) with a substituted pyrimidine compound of formula (III) to prepare a compound of formula (IV);

c) reacting the compound of formula (IV) with a suitable brominating agent followed by one of:
  i) a thiourea,
  ii) a formamide,
  iii) an amide,
  iv) a thioamide, or
  v) a urea;
  to prepare a compound of formula (V);

d) reacting the compound of formula (V) in the presence of a Palladium catalyst to prepare a compound of formula VI;

e) reacting a compound of formula (VI) with a compound of formula (VII) to prepare a compound of formula (VIII);

f) reacting the compound of formula (VIII) with one of:
   i) molecular hydrogen
   ii) an alkyl metal reagent or alkenyl metal reagent
   iii) an alcohol, or
   iv) a compound of formula (IX),
   to prepare a compound of formula (I);
g) optionally converting the compound of formula (I) to a pharmaceutically acceptable salt thereof; and
h) optionally converting the compound of formula (I) or a pharmaceutically acceptable salt thereof to a different compound of formula (I) or a pharmaceutically acceptable salt thereof.

The installation and removal of the Alloc protecting group may be achieved using conventional means. For example, the compound of formula (II) may be reacted with allylchloroformate using conventional acylation conditions to those skilled in the art for the installation of carbamate protecting groups. Removal of the protecting group may be achieved by reacting the compound of formula (V) with tributyltin hydride in the presence of a Pd catalyst and weak acid. In one embodiment dichlorobis(triphenylphosphine)-palladium (II) was used along with acetic acid. A variety of solvents may be used including but not limited to dichloromethane, toluene, diethyl ether, acetone and N,N-dimethylformamide. See, Kocienski, P. J. *Protecting Groups*, Georg Thieme Verlag, Stuttgart, 1994; and Greene, T. W., Wuts, P. G. M. *Protecting Groups in Organic Synthesis* ($2^{nd}$ Edition), J. Wiley and Sons, 1991.

The remaining steps of the reaction may be carried out generally in the manner described above for the analogous steps in Scheme 1.

As a further example of changing the order of the steps, compounds of the invention may also be prepared according to Scheme 3.

Scheme 3

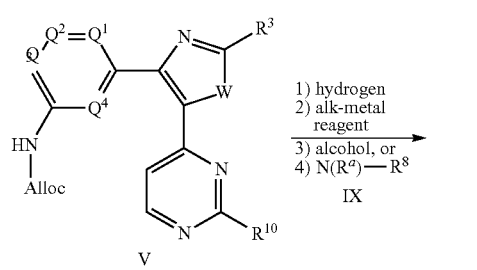

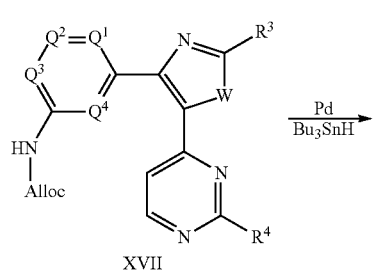

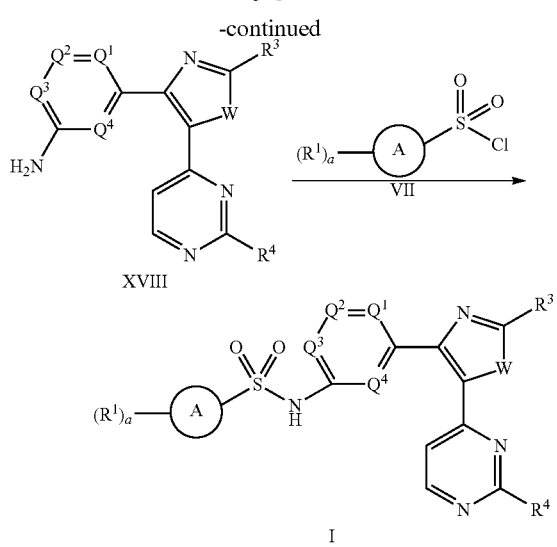

wherein $R^{10}$ is halo (preferably chloro) or thiomethyl, and all other variables are as defined above.

Generally, the process for preparing the compounds of the invention according to Scheme 3 (all formulas and all variables having been defined above) comprises the steps of:

a) reacting the compound of formula (V) with one of:
   i) molecular hydrogen
   ii) an alkyl or alkenyl metal reagent
   iii) an alcohol, or
   iv) a compound of formula (IX),
   to prepare a compound of formula (XVIII);
b) reacting the compound of formula (XVII) in the presence of a Palladium catalyst to prepare a compound of formula (XVIII);
c) reacting the compound of formula (XVIII) with a compound of formula (VII) to prepare a compound of formula (I);
d) optionally converting the compound of formula (I) to a pharmaceutically acceptable salt thereof; and
e) optionally converting the compound of formula (I) or a pharmaceutically acceptable salt thereof to a different compound of formula (I) or a pharmaceutically acceptable salt thereof.

Each of the foregoing steps may be carried out using the techniques described above for analogous reactions with different starting materials.

It will be appreciated by those skilled in the art that the optimal choice of the reaction sequence employed to prepare a particular compound of the invention may depend upon the specific compound of the invention that is desired as well as the preference and availability of starting materials.

As will be apparent to those skilled in the art, a compound of formula (I) may be converted to another compound of formula (I) using techniques well known in the art. For example, compounds of formula (I) may be modified using conventional techniques to modify or diversify the groups defined by the variable $R^3$ and thereby provide different compounds of formula (I). Specifically, a compound of formula (I-1) (wherein $R^3$ is —$NH_2$) may be converted to a compound of formula (I-2) by reductive amination of the amine with acetone and sodium cyanoborohydride.

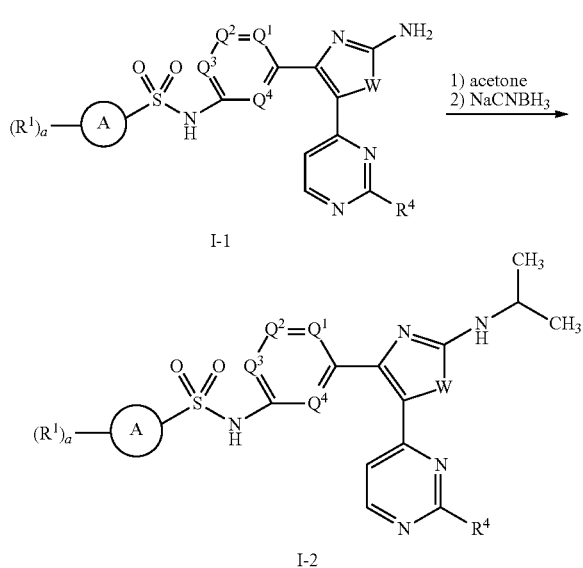

I-1

I-2 wherein all variables are as defined above.

A compound of formula (I-1) may also be converted to a compound of formula (I-3) by reacting with mesyl chloride.

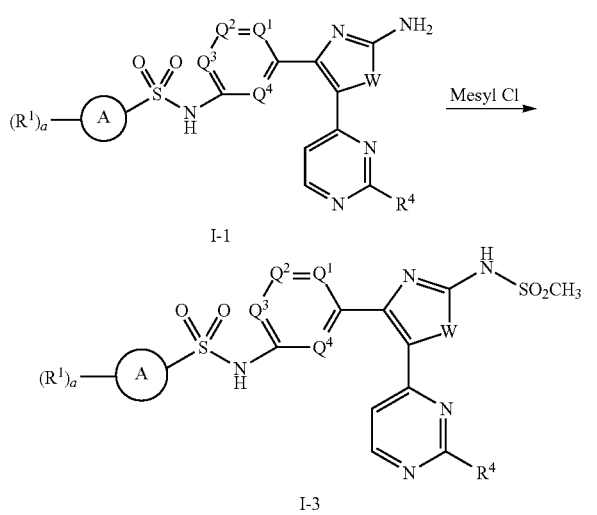

I-1

I-3 wherein all variables are as defined above.

Based upon this disclosure and the examples contained herein one skilled in the art can readily convert a compound of formula (I) or a pharmaceutically acceptable salt thereof into a different compound of formula (I), or a pharmaceutically acceptable salt thereof.

The present invention also provides radiolabeled compounds of formula (I) and biotinylated compounds of formula (I) and solid-support-bound versions thereof, i.e. a compound of formula (I) having a radiolabel or biotin bound thereto. Radiolabeled compounds of formula (I) and biotinylated compounds of formula (I) can be prepared using conventional techniques. For example, radiolabeled compounds of formula (I) can be prepared by reacting the compound of formula (I) with tritium gas in the presence of an appropriate catalyst to produce radiolabeled compounds of formula (I). In one embodiment, the compounds of formula (I) are tritiated.

The radiolabeled compounds of formula (I) and biotinylated compounds of formula (I) are useful in assays for the identification of compounds which inhibit at least one Raf family kinase, for the identification of compounds for the treatment of a condition capable of being treated with a Raf inhibitor, e.g., for the treatment of neoplasms susceptible to treatment with a Raf inhibitor. The present invention also provides an assay method for identifying such compounds, which method comprises the step of specifically binding a radiolabeled compound of the invention or a biotinylated compound of the invention to the target protein or cellular homogenate. More specifically, suitable assay methods will include competition binding assays. The radiolabeled compounds of the invention and biotinylated compounds of the invention and solid-support-bound versions thereof, can also be employed in assays according to the methods conventional in the art.

The following examples are intended for illustration only and are not intended to limit the scope of the invention in any way. The invention is defined by the claims which follow.

EXAMPLES

As used herein, the symbols and conventions used in these processes, schemes and examples are consistent with those used in the contemporary scientific literature, for example, the Journal of the American Chemical Society or the Journal of Biological Chemistry. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

| | |
|---|---|
| atm | (atmosphere); |
| g | (grams); |
| mg | (milligrams); |
| h | (hour(s)); |
| min | (minutes); |
| Hz | (Hertz); |
| MHz | (megahertz); |
| i.v. | (intravenous); |
| L | (liters); |
| mL | (milliliters); |
| μL | (microliters); |
| M | (molar); |
| mM | (millimolar); |
| mol | (moles); |
| mmol | (millimoles); |
| mp | (melting point); |
| psi | (pounds per square inch); |
| rt | (room temperature); |
| TLC | (thin layer chromatography); |
| $T_r$ | (retention time); |
| RP | (reverse phase; |
| $H_2$ | (hydrogen); |
| $N_2$ | (nitrogen) |
| Ac | (acetyl); |
| ACN | (acetonitrile); |
| $Ac_2O$ | (acetic anhydride); |
| ATP | (adenosine triphosphate); |
| BOC | (tert-butyloxycarbonyl); |
| BSA | (bovine serum albumin) |
| $CHCl_3$ | (chloroform); |
| mCPBA | (meta-chloroperbenzoic acid); |
| DCC | (dicyclohexylcarbodiimide); |
| DCE | (dichloroethane); |
| DCM | ($CH_2Cl_2$; dichloromethane); |
| DIEA | (N,N-Diisopropylethylamine); |
| DMA | (dimethyl acetamide); |
| DMAP | (4-dimethylaminopyridine); |

| | |
|---|---|
| DME | (1,2-dimethoxyethane); |
| DMEM | (Dulbecco's modified Eagle medium); |
| DMF | (N, dimethylformamide); |
| DMSO | (dimethylsulfoxide); |
| EDC | (ethylcarbodiimide hydrochloride); |
| EDTA | (ethylenediaminetetraacetic acid); |
| Et | (ethyl; —CH$_2$CH$_3$) |
| EtOH | (ethanol); |
| EtOAc | (ethyl acetate); |
| FBS | (fetal bovine serum); |
| FMOC | (9-fluorenylmethoxycarbonyl); |
| HATU | (O-(7-Azabenzotriazol-1-yl-N,N,N',N'-tetramethyluronium hexafluorophosphate); |
| HCl | (hydrochloric acid) |
| HEPES | (4-(2-hydroxyethyl)-1-piperazine ethane sulfonic acid); |
| Hex | (hexanes); |
| HOAc | (acetic acid); |
| HPLC | (high pressure liquid chromatography); |
| i-PrOH | (isopropanol); |
| K$_2$CO$_3$ | (potassium carbonate); |
| KOH | (potassuim hydroxide); |
| LiHMDS | (lithium hexamethyldisilazide); |
| LiOH | (lithium hydroxide); |
| LiOH•H$_2$O | (lithium hydroxide monohydrate); |
| Me | (methyl; —CH$_3$) |
| MeOH | (methanol); |
| MgCO$_3$ | (magnesium carbonate); |
| MgSO$_4$ | (magnesium sulfate); |
| Na$_2$CO$_3$ | (sodium carbonate); |
| NaHCO$_3$ | (sodium bicarbonate); |
| NaH | (sodium hydride) |
| Na$_2$SO$_4$ | (sodium sulfate); |
| NaHSO$_4$ | (sodium bisulfate); |
| NBS | is N-bromosuccinamide; |
| NH$_4$OH | (ammonium hydroxide); |
| Pd(PPh$_3$)$_2$Cl$_2$ | (bis(triphenylphosphine)-palladium (II) chloride); |
| PdCl$_2$(dppf) | (dichloro[1,1'bis(diphenyl-phosphino)ferrocene] palladium (II) dichloromethane adduct; |
| TBAF | (tetrabutylammonium fluoride); |
| TEA | (triethylamine); |
| TFA | (trifluoroacetic acid); |
| THF | (tetrahydrofuran); |
| TIPS | (triisopropylsilyl); |
| TMS | (trimethylsilyl); and |
| TMSE | (2-(trimethylsilyl)ethyl); and |
| TsOH | (p-Toluenesulfonic acid). |

All references to ether are to diethyl ether; brine refers to a saturated aqueous solution of NaCl. Unless otherwise indicated, all temperatures are expressed in ° C. (degrees Centigrade). All reactions are conducted under an inert atmosphere at rt unless otherwise noted.

$^1$H-NMR spectra were recorded on a Varian VXR-300, a Varian Unity-300, a Varian Unity-400 instrument, a General Electric QE-300, a Bruker 300, or a Bruker 400. Chemical shifts are expressed in parts per million (ppm, 6 units). Coupling constants are in units of hertz (Hz). Splitting patterns describe apparent multiplicities and are designated as s (singlet), d (doublet), t (triplet), q (quartet), m (multiplet), br (broad).

Low-resolution mass spectra (MS) were recorded on a Agilent LCMS, JOEL JMS-AX505HA, JOEL SX-102, a SCIEX-APIiii, a Finnegan MSQ, Waters SQD, Waters ZQ, or a Finnegan LCQ spectrometer; high resolution MS were obtained using a JOEL SX-102A spectrometer. All mass spectra were taken under electrospray ionization (ESI), chemical ionization (CI), electron impact (EI) or by fast atom bombardment (FAB) methods. All reactions were monitored by thin-layer chromatography on 0.25 mm E. Merck silica gel plates (60E-254), visualized with UV light, 5% ethanolic phosphomolybdic acid or p-anisaldehyde solution or mass spectrometry (electrospray or AP). Flash column chromatography was performed on silica gel (230-400 mesh, Merck) or using automated silica gel chromatography (Isco, Inc. Sq 16x or 100sg Combiflash). Reported HPLC retention times (RT) were obtained on a Waters 2795 instrument attached to a Waters 996 diode array detector reading 210-500 nm. The column used was a Synergi Max-RP (50×2 mm) model #00B-4337-B0, Solvent gradient was 15% MeOH:water to 100% MeOH (0.1% formic acid) over 6 min. Flow rate was 0.8 mL/min. Injection volume was 3 μL.

Intermediate 1

2-Methylpropanethioamide

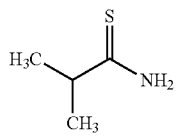

A solution of 2-methylpropanamide (6.53 g, 75.0 mmol) and 2,4-bis(4-methoxyphenyl)-1,3-dithia-2,4-diphosphetane-2,4-disulfide (15.17 g, 37.51 mmol) in THF (100 mL) was heated to reflux for 4 h. The reaction mixture was then cooled to rt and poured into saturated aqueous NaHCO$_3$ (200 mL). The mixture was extracted with ether (4×100 mL). The organic fractions were combined, dried over Na$_2$SO$_4$, filtered, and concentrated. Purification by flash column chromatography (20% EtOAc:hexanes) afforded 4.77 g (62%) of the title compound. $^1$H-NMR (400 MHz, CDCl$_3$) δ 7.63 (brs, 1H), 6.90 (brs, 1H), 2.88 (m, 1H), and 1.27 (d, 6H, J=6.8 Hz).

Intermediate 2

1-Pyrrolidinecarbothioamide

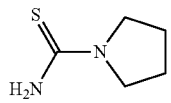

To obtain the title compound, pyrrolidine (1.5 g, 21 mmol) was placed in a round bottom flask under N$_2$ with stirring. THF (4 mL) was added followed by the drop-wise addition of 4N HCl in dioxane (5.3 mL, 21 mmol). Potassium thiocyanate (2.0 g, 21 mmol) was then added in one portion to the stirring solution of pyrrolidine hydrochloride. This mixture was then stirred at rt for 30 min followed by heating at 100° C. for 2 h. The reaction was then cooled to rt, MeOH (50 mL) was added, and solids that persisted were filtered away. Subsequent concentration of the MeOH/reaction solution yielded 3.0 g of the crude 1-pyrrolidinecarbothioamide. $^1$H-NMR (400 MHz, DMSO-d$_6$) δ 8.60 (brs, 2H), 3.07 (m, 4H), and 1.82 (m, 4H).

Intermediate 3

2,2-Dimethylpropanethioamide

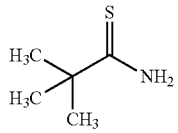

The title compound was prepared (3.2 g, 36%) from 2,2-dimethylpropanamide (7.59 g, 75.0 mmol) and 2,4-bis(4-methoxyphenyl)-1,3-dithia-2,4-diphosphetane-2,4-disulfide (15.17 g, 37.51 mmol) by a procedure analogous to Intermediate 1. $^1$H-NMR (400 MHz, CDCl$_3$) δ 7.92 (brs, 1H), 7.03 (brs, 1H), and 1.38 (s, 9H).

Intermediate 4

Tetrahydro-2H-pyran-4-carbothioamide

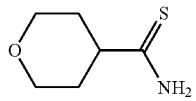

A solution of tetrahydro-2H-pyran-4-carboxamide (9.47 g, 73.3 mmol) and Lawesson's reagent (14.83 g, 36.7 mmol) in THF (98 mL) was heated to reflux for 6 h. The reaction was cooled to rt, poured into saturated aqueous NaHCO$_3$ (200 mL) and extracted with diethyl ether (4×100 mL). The combined organic extracts were dried over Na$_2$SO$_4$, filtered, and concentrated. The residual solid was triturated with 1:1 EtOAc:hexanes (100 mL) and filtered to collect the solid. The filtrate was concentrated and re-subjected to trituration and filtration using the same conditions. The combined solids were dried under vacuum to afford tetrahydro-2H-pyran-4-carbothioamide (4.91 g, 32.1 mmol, 43.8% yield) as a white solid. $^1$H NMR (400 MHz, CDCl$_3$) δ ppm 7.49 (br. s., 1H), 6.84 (br. s., 1H), 3.94-4.32 (m, 2H), 3.31-3.62 (m, 2H), 2.52-3.03 (m, 1H), 1.81-1.93 (m, 4H).

Intermediate 5

N-{3-[(Z)-2-(2-Chloro-4-pyrimidinyl)-1-hydroxyethenyl]phenyl}-2,6-difluorobenzenesulfonamide

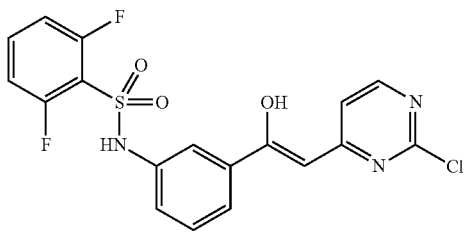 [SMILES: O=S(=O)(Nc1cccc(/C(O)=C/c2ccnc(Cl)n2)c1)c1c(F)cccc1F]

Step A: Ethyl 3-{[(2,6-difluorophenyl)sulfonyl]amino}benzoate

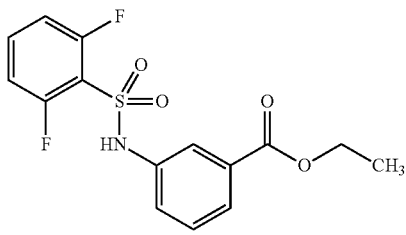 [SMILES: CCOC(=O)c1cccc(NS(=O)(=O)c2c(F)cccc2F)c1]

To a solution of ethyl-3-aminobenzoate (50 mL, 333 mmol) and 2,6-difluorobenzenesulfonyl chloride (44.2 mL, 333 mmol) in DCM (300 mL) at 0° C. was added pyridine (32.2 mL, 400 mmol). The reaction mixture was warmed to rt, stirred for 36 h, and quenched with 2 mL NH$_3$ (7 M in MeOH). The suspension washed with 10% NaHSO$_4$ and the organic extracts combined and passed through a short column of silica gel. Residual material was flushed from the column with 10% MeOH/EtOAc. The organic extracts were combined and the solvent removed under reduced pressure to provide 107.9 g (95%) of the title compound of Step A. $^1$H-NMR (400 MHz, DMSO-d6) δ ppm 11.20 (s, 1H), 7.77 (s, 1H), 7.71 (t, J=7.4 Hz, 1H), 7.63 (d, J=7.3 Hz, 1H), 7.35-7.49 (m, 2H), 7.29 (t, J=9.3 Hz, 2H), 4.28 (q, J=7.1 Hz, 2H), and 1.29 (t, J=7.1 Hz, 3H).

Step B: N-{3-[(Z)-2-(2-Chloro-4-pyrimidinyl)-1-hydroxyethenyl]phenyl}-2,6-difluorobenzenesulfonamide To a stirring solution of ethyl 3-{[(2,6-difluorophenyl)sulfonyl]amino}benzoate (47.9 g, 140 mmol) in 100 mL anhydrous THF at 0° C. was added 1M LiHMDS in THF (421 mL, 421 mmol). A solution of 2-chloro-4-methylpyrimidine (19.9 g, 154 mmol) in 100 mL of anhydrous THF was added to the reaction mixture over 30 min and warmed to rt. The reaction mixture was quenched with 50 mL of MeOH and concentrated to a black solid under vacuum. The residue was partitioned between DCM and 10% NaHSO$_4$. The aqueous and suspended solids were extracted 2× with DCM and the combined organic extracts were filtered through a pad of Celite, concentrated, and passed through a short silica gel column (elution with THF) to provide 57 g (96%) of the title compound of Step B. $^1$H-NMR (400 MHz, DMSO-d6) δ ppm 11.03-11.34 (m, 1H), 8.49-8.91 (m, 1H), 7.79 (d, J=7.4 Hz, 1H), 7.65-7.76 (m, 2H), 7.55-7.63 (m, 1H), 7.50 (t, J=7.7 Hz, 1H), 7.35-7.47 (m, 1H), 7.22-7.34 (m, 2H), 6.43 (s, 1H), and 4.60 (s, 1H); ES-LCMS m/z 423.93 (M+H).

Intermediate 6

N-{3-[5-(2-Chloro-4-pyrimidinyl)-2-(1-pyrrolidinyl)-1,3-thiazol-4-yl]phenyl}-2,6-difluorobenzenesulfonamide

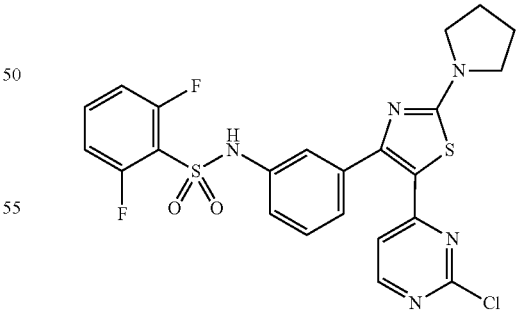

To a stirring suspension of N-{3-[(Z)-2-(2-chloro-4-pyrimidinyl)-1-hydroxyethenyl]phenyl}-2,6-difluorobenzenesulfonamide (1.0 g, 2.36 mmol, 1.0 eq) in DCM (~5 mL) was added NBS (0.44 g, 2.48 mmol, 1.05 eq). Upon formation of a red solution (~10 minutes) the reaction mixture was concentrated to a solid and taken up in dioxane (10 mL). To this solution was added MgCO$_3$ (0.38 g) followed by 1-pyrrolidinecarbothioamide (0.384 g, 2.95 mmol, 1.25 eq). After stirring 3 h, the mixture was quenched with water (50 mL) and 1N HCl (10 mL) and stirred 0.25 h. The mixture was filtered and the resultant solid triturated with EtOAc/Hexanes to give 0.52 g (41%) of the title compound. $^1$H-NMR (400 MHz, DMSO-d$_6$) δ ppm 11.11 (s, 1H), 8.14 (d, J=5.7 Hz, 1H), 7.65-7.74 (m, 1H), 7.41 (t, J=7.7 Hz, 1H), 7.18-7.29 (m, 5H), 6.44 (d, J=5.5 Hz, 1H), 3.45-3.52 (m, 4H), and 1.98-2.05 (m, 4H).

Intermediate 7

N-{3-[5-(2-Chloro-4-pyrimidinyl)-2-(1,1-dimethylethyl)-1,3-thiazol-4-yl]phenyl}-2,6-difluorobenzenesulfonamide

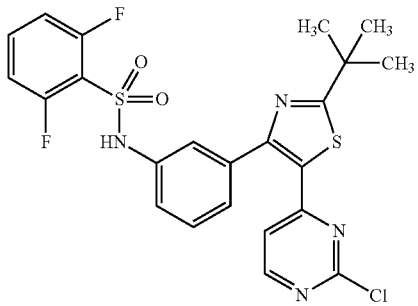 [SMILES: CC(C)(C)c1nc(-c2cccc(NS(=O)(=O)c3c(F)cccc3F)c2)c(-c2ccnc(Cl)n2)s1]

Following a procedure analogous to the procedure described in Intermediate 6, using N-{3-[(Z)-2-(2-chloro-4-pyrimidinyl)-1-hydroxyethenyl]phenyl}-2,6-difluorobenzenesulfonamide (1.00 g, 2.36 mmol) and 2,2-dimethylpropanethioamide (0.277 g, 2.36 mmol) the title compound was obtained (690 mg, 53.3% yield). MS (ESI): 521.1 [M+H]+.

Intermediate 8

N-{3-[(Z)-2-(2-Chloro-4-pyrimidinyl)-1-hydroxyethenyl]phenyl}-2,5-difluorobenzenesulfonamide

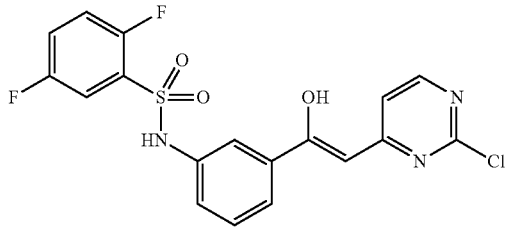 [SMILES: O=S(=O)(Nc1cccc(/C(O)=C/c2ccnc(Cl)n2)c1)c1cc(F)ccc1F]

Step A: Methyl 3-{[(2,5-difluorophenyl)sulfonyl]amino}benzoate

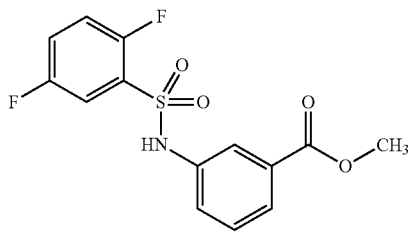 [SMILES: COC(=O)c1cccc(NS(=O)(=O)c2cc(F)ccc2F)c1]

Following a procedure analogous to the procedure described in Intermediate 5, Step A using methyl 3-aminobenzoate (16 g, 105.9 mmol) in DCM (150 mL) and 2,5-difluorobenzene-1-sulfonyl chloride (24.7 g, 116.5 mmol) the title compound was obtained (25.6 g, 73.8% yield). $^1$H NMR (400 MHz, DMSO-d6) δ ppm 11.06-11.13 (br, 1H), 7.42-7.52 (m, 2H), 7.52-7.77 (m, 4H), 7.78-7.80 (m, 1H), 3.88 (s, 3H).

Step B: N-{3-[(Z)-2-(2-Chloro-4-pyrimidinyl)-1-hydroxyethenyl]phenyl}-2,5-difluorobenzenesulfonamide Following a procedure analogous to the procedure described in Intermediate 5, Step B using methyl 3-(2,5-difluorophenylsulfonamido)benzoate (20.5 g, 62.7 mmol) and 2-chloro-4-methylpyrimidine (8.8 g, 68.9 mmol) the title compound was obtained (22.6 g, 85.3% yield). $^1$H NMR (400 MHz, CDCl$_3$) δ ppm 13.40-13.50 (br s), 10.95-11.12 (br s), 8.72-8.80 (m), 8.57-8.63 (m), 7.77-7.82 (m), 7.36-7.72 (m), 7.22-7.30 (m), 6.43 (s), 4.52 (s); m/z (ES+): 424 [M+H]+.

Intermediate 9

N-{3-[5-(2-Chloro-4-pyrimidinyl)-2-(1,1-dimethylethyl)-1,3-thiazol-4-yl]phenyl}-2,5-difluorobenzenesulfonamide

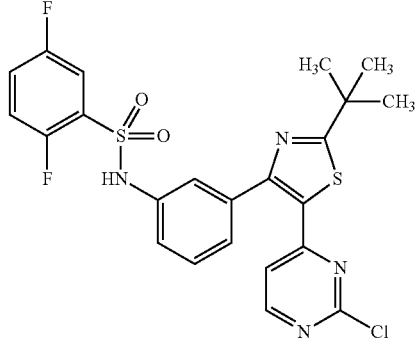 [SMILES: CC(C)(C)c1nc(-c2cccc(NS(=O)(=O)c3cc(F)ccc3F)c2)c(-c2ccnc(Cl)n2)s1]

To a solution of N-{3-[(Z)-2-(2-chloro-4-pyrimidinyl)-1-hydroxyethenyl]phenyl}-2,5-difluorobenzenesulfonamide (1.0 g, 2.4 mmol) in 25 mL DMA, NBS (0.420 g, 2.4 mmol) was added and the solution was allowed to stir 15 minutes at rt. 2,2-Dimethylpropanethioamide (0.277 g, 2.359 mmol) was then added and the reaction mixture was heated at 80° C. for 2 h. The reaction mixture was diluted with EtOAc and washed with water×3. The organic layer was dried over MgSO$_4$ and filtered. The organic solution was evaporated onto silica gel and chromatographed. 0-50% EtOAc in DCM to give the title compound (1.01 g, 81% yield). ES-LCMS m/z 521.1 (M+H).

Intermediate 10

N-{3-[5-(2-Chloro-4-pyrimidinyl)-2-(4-morpholinyl)-1,3-thiazol-4-yl]phenyl}-2,5-difluorobenzenesulfonamide

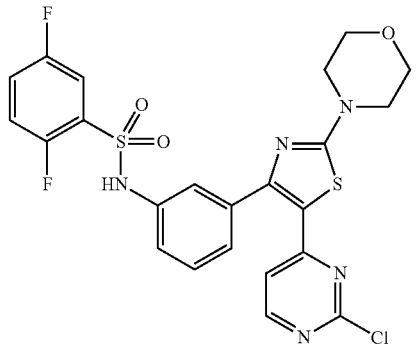 [SMILES: O=S(=O)(Nc1cccc(-c2nc(N3CCOCC3)sc2-c2ccnc(Cl)n2)c1)c1cc(F)ccc1F]

The title compound was prepared from N-{3-[(Z)-2-(2-chloro-4-pyrimidinyl)-1-hydroxyethenyl]phenyl}-2,5-difluorobenzenesulfonamide (1.5 g, 3.54 mmol), NBS (0.630 g, 3.54 mmol) and 4-morpholinecarbothioamide (0.517 g, 3.54 mmol) by a procedure analogous to Intermediate 9. The title compound was obtained as a yellow solid (1.8 g, 90% yield). ES-LCMS m/z 549.7 (M+H).

Intermediate 11

2-Propen-1-yl {3-[(2-chloro-4-pyrimidinyl)acetyl]phenyl}carbamate

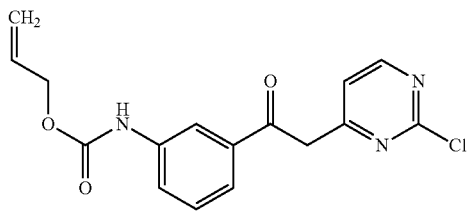 [SMILES: C=CCOC(=O)Nc1cccc(C(=O)Cc2ccnc(Cl)n2)c1]

Step A: Ethyl 3-{[(2-propen-1-yloxy)carbonyl]amino}benzoate

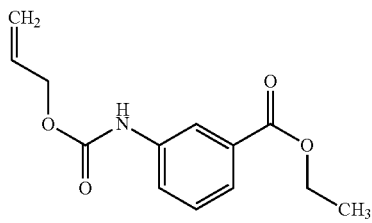 [SMILES: C=CCOC(=O)Nc1cccc(C(=O)OCC)c1]

A solution of ethyl-3-aminobenzoate (25.0 g, 151.33 mmol) in DCM (500 mL) was cooled to 0° C. 2,6-Lutidine (19.46 g, 181.60 mmol) was added to the solution followed by addition of 2-propen-1-yl chloridocarbonate (20.07 g, 166.46 mmol). Following addition, the reaction was removed from ice bath and stirred at rt for 30 min. The reaction was quenched with saturated NaHCO$_3$ and the layers were separated. The mixture was extracted with DCM×3, and the combined organics were washed with 10% HCl/H$_2$O×3, dried over MgSO$_4$ and the solvent was removed to give the title compound of Step A (38.80 g, 80% yield). $^1$H-NMR (400 MHz, DMSO-d$_6$) δ 9.96 (s, 1H), 8.15 (s, 1H), 7.66-7.72 (m, 1H), 7.59 (d, J=7.7 Hz, 1H), 7.43 (t, J=7.9 Hz, 1H), 5.94-6.04 (m, 1H), 5.37 (dd, J=17.4 and 1.7 Hz, 1H), 5.24 (dd, J=10.6 and 1.5 Hz, 1H), 4.63 (d, J=5.5 Hz, 2H), 4.31 (q, J=7.3 Hz, 2H), and 1.31 (t, J=7.1 Hz, 3H); ES-LCMS m/z 250 (M+H).

Step B: 2-Propen-1-yl {3-[(2-chloro-4-pyrimidinyl)acetyl]phenyl}carbamate

Ethyl 3-{[(2-propen-1-yloxy)carbonyl]amino}benzoate (20.0 g, 80.24 mmol) was dissolved in 1 M LiHMDS in THF (260 mL) and cooled to 0° C. A solution containing 2-chloro-4-methylpyrimidine (10.32 g, 80.24 mmol) in 20 mL dry THF was added to the reaction mixture. The reaction was stirred at 0° C. for 2 h, quenched with MeOH (100 mL), dried directly onto silica, and purified via flash chromatography EtOAc/CH$_2$Cl$_2$ 0-100% gradient run over 60 min. The desired fractions were combined and the solvent was removed to give the title compound (13.6 g, 51% yield); ES-LCMS m/z 332 (M+H).

Intermediate 12

2-Propen-1-yl {3-[5-(2-chloro-4-pyrimidinyl)-2-(1-methylethyl)-1,3-thiazol-4-yl]phenyl}carbamate

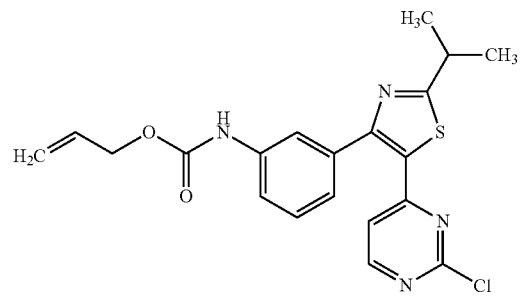 [SMILES: C=CCOC(=O)Nc1cccc(-c2nc(C(C)C)sc2-c2ccnc(Cl)n2)c1]

Following a procedure analogous to the procedure described in Intermediate 6, using 2-propen-1-yl {3-[(2-chloro-4-pyrimidinyl)acetyl]phenyl}carbamate (10.0 g, 30.14 mmol), and 2-methylpropanethioamide (3.73 g, 36.17 mmol), prepared by a procedure analogous to Intermediate 1, 5.74 g of the title compound was obtained. MS (ESI): 415 [M+H]$^+$.

Intermediate 13

3-[5-(2-chloro-4-pyrimidinyl)-2-(1-methylethyl)-1,3-thiazol-4-yl]aniline

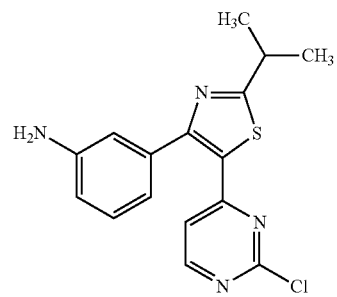 [SMILES: CC(C)c1nc(-c2cccc(N)c2)c(-c2ccnc(Cl)n2)s1]

To a solution containing 2-propen-1-yl {3-[5-(2-chloro-4-pyrimidinyl)-2-(1-methylethyl)-1,3-thiazol-4-yl]phenyl}carbamate (5.3 g, 12.77 mmol) and DCM (225 mL) was added tri-n-butyltin hydride (5.95 g, 20.43 mmol), followed by trans-dichlorobis(triphenylphosphine)palladium (II) (0.53 g, 0.64 mmol) and HOAc (1.84 g, 30.65 mmol). At the conclusion of the reaction, silica was added and the volatiles removed under reduced pressure. The residue was purified by flash column chromatography with (84% DCM, 15% MeOH, and 1% NH$_4$OH): DCM 0% to 100% to afford 3.4 g of the title compound. $^1$H-NMR (400 MHz, DMSO-d$_6$) δ 8.57 (d, J=5.1 Hz, 1H), 7.16 (d, J=5.1 Hz, 1H), 7.10 (t, J=7.7 Hz, 1H), 6.72-6.75 (m, 1H), 6.64-6.69 (m, 1H), 6.60-6.63 (m, 1H), 5.28 (s, 2H), 3.27-3.40 (m, 1H), and 1.38 (d, J=7.0 Hz, 6H). MS (ESI): 331 [M+H]$^+$.

Intermediate 14

N-{3-[5-(2-Chloro-4-pyrimidinyl)-2-(1-methyl-ethyl)-1,3-thiazol-4-yl]phenyl}-2,6-difluorobenzene-sulfonamide

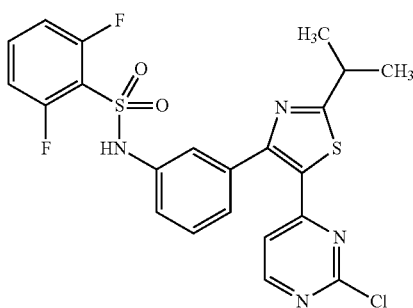 [SMILES: CC(C)c1nc(-c2cccc(NS(=O)(=O)c3c(F)cccc3F)c2)c(-c2ccnc(Cl)n2)s1]

To a solution of 3-[5-(2-chloro-4-pyrimidinyl)-2-(1-methylethyl)-1,3-thiazol-4-yl]phenyl amine (1.0 g, 3.0 mmol), and pyridine (360 µL, 4.5 mmol) in DCM (50 mL) was added a solution of 2,6-difluorobenzenesulfonyl chloride (620 µL, 4.5 mmol) in DCM (25 mL).

The reaction was stirred for 48 h at rt. The reaction mixture was concentrated, adsorbed onto silica gel, and purified via flash chromatography with 0-50% EtOAc/DCM to give 1.39 g (91% yield) of the title compound as a white powder. ES-LCMS m/z 507 (M+H).

Intermediate 15

N-{3-[(2-Chloro-4-pyrimidinyl)acetyl]-2-fluorophenyl}-2,6-difluorobenzenesulfonamide

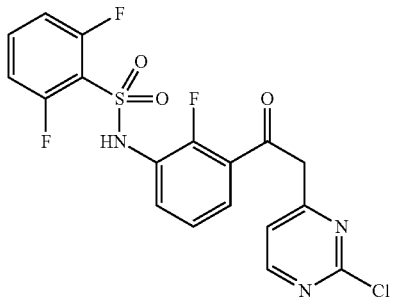 [SMILES: O=C(Cc1ccnc(Cl)n1)c1cccc(NS(=O)(=O)c2c(F)cccc2F)c1F]

Step A: Methyl 3-bromo-2-fluorobenzoate

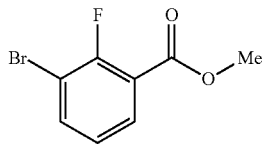 [SMILES: COC(=O)c1cccc(Br)c1F]

To a 100 mL round bottom flask was added 3-bromo-2-fluorobenzoic acid (10.4 g, 47.5 mmol), MeOH (100 mL, 2472 mmol) and sulfuric acid (6 mL, 113 mmol). The reaction mixture was refluxed for 1 hr. After cooling to rt, the MeOH was removed under reduced pressure and the acidic residue was poured into cold water and EtOAc, the layers were separated and the aqueous layer was extracted with EtOAc. The organic layers were combined, washed with brine, dried over NaSO$_4$ and concentrated under reduced pressure to afford 10.02 g of methyl 3-bromo-2-fluorobenzoate. $^1$H-NMR (400 MHz, DMSO-d$_6$) δ 7.95 (ddd, J=8.1, 6.4, and 1.7 Hz, 1H), 7.82-7.87 (m, 1H), 7.26 (t, J=7.9 Hz, 1H), and 3.86 (s, 3H).

Step B: Methyl 3-amino-2-fluorobenzoate

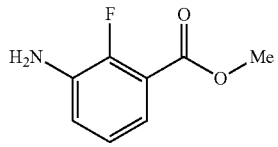 [SMILES: COC(=O)c1cccc(N)c1F]

In a 500 mL flask was placed 1,1-dimethylethyl carbamate (6.03 g, 51.5 mmol), methyl 3-bromo-2-fluorobenzoate (10 g, 42.9 mmol), Pd$_2$(dba)$_3$.CHCl$_3$ (0.89 g, 0.86 mmol), xantphos (1.49 g, 2.57 mmol) and cesium carbonate (16.8 g, 51.5 mmol). The flask was sealed with a rubber septum, placed under high vacuum, and toluene (200 mL) was added. Three cycles of high vacuum/N$_2$ were performed and the reaction mixture was stirred at 90° C. overnight. The reaction was filtered through a pad of celite with EtOAc washing and concentrated. To the residue was added DCM (200 mL) followed by TFA (50 mL, 649 mmol), and the mixture was stirred at rt for 1 h. The volatiles were removed under reduced pressure and the residue was taken up in EtOAc and washed with saturated NaHCO$_3$ and brine. The organic layer was dried over NaSO$_4$, stripped onto silica and column chromatographed on silica with 5% to 50% EtOAc:Hexane to give 5.53 g (76%) of the title compound of Step B. $^1$H-NMR (400 MHz, DMSO-d$_6$) δ 6.92-7.01 (m, 3H), 5.37 (s, 2H), and 3.81 (s, 3H). MS (ESI): 170 [M+H]$^+$.

Step C: Methyl 3-{[(2,6-difluorophenyl)sulfonyl]amino}-2-fluorobenzoate

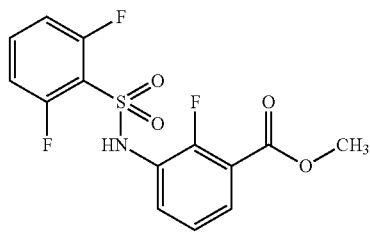 [SMILES: COC(=O)c1cccc(NS(=O)(=O)c2c(F)cccc2F)c1F]

In a 500 mL flask was placed methyl 3-amino-2-fluorobenzoate (5.5 g, 32.5 mmol) and DCM (100 mL), and pyridine (2.9 mL, 35.8 mmol) was added. 2,6-Difluorobenzenesulfonyl chloride (7.6 g, 35.8 mmol) in DCM (50 mL) was added dropwise via addition funnel and the reaction mixture was allowed to stir at rt overnight. The reaction mixture was stripped onto silica and column chromatographed on silica with 5% to 100% EtOAc:Hexane to give 9.75 g (87%) of the title compound of Step C. $^1$H-NMR (400 MHz, DMSO-d$_6$) δ 10.98 (s, 1H), 7.64-7.82 (m, 3H), 7.46-7.61 (m, 1H), 7.29 (t, J=8.8 Hz, 2H), and 3.81 (s, 3H). MS (ESI): 346 [M+H]$^+$.

Step D: N-{3-[(2-Chloro-4-pyrimidinyl)acetyl]-2-fluorophenyl}-2,6-difluorobenzenesulfonamide In a 1000 mL flask was placed methyl 3-{[(2,6-difluorophenyl)sulfonyl]amino}-2-fluorobenzoate (9.64 g, 27.9 mmol) and THF (200 mL) was added. The flask was placed in an ice/water bath and LiHMDS (90 mL, 90 mmol) was added. 2-Chloro-4-methylpyrimidine (4.5 g, 35.0 mmol) in THF (60 mL) was added dropwise via addition funnel. After the addition was complete, the reaction was allowed to warm to 20° C. over 1 h. The THF volume was reduced to half under reduced pressure and then treated with 6 N HCl. EtOAc was added and the layers were separated. The aqueous layer was extracted twice with EtOAc and the combined organic layer was washed once with brine, dried over $NaSO_4$, and concentrated. The residue was triturated with EtOAc/ether to afford 8.71 g (71%) of the title compound of Step D. MS (ESI): 442 $[M+H]^+$.

Alternative method of preparing methyl 3-amino-2-fluorobenzoate (Step B of intermediate 15, above)

Step A: 2-fluoro-3-nitrobenzoic acid

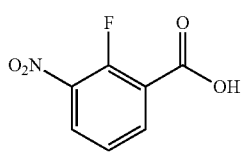 [SMILES: O=C(O)c1cccc([N+](=O)[O-])c1F]

Concentrated sulfuric acid (195 ml) was added carefully with stirring to a solution of 2-fluoro-3-nitrotoluene (100 g, 645 mmol) in acetic acid (1000 ml). The mixture was warmed up to 95° C. and the solution of chromium trioxide (226 g, 2.25 mol) in water (200 ml) was added dropwise with stirring over 2 h. After addition the mixture was heated with stirring for another 3 h, allowed to cool down to room temperature and poured into water (3 L). The mixture was extracted with ethyl acetate (3×1 L), the combined organic layers were dried over $Na_2SO_4$ and concentrated under reduced pressure to afford a light green solid, which was washed with dichloromethane (3×300 ml) and dried under vacuum to afford the title compound was obtained as a light yellow solid (75 g, 62.8%). $^1$H NMR (300 MHz, DMSO) δ ppm 8.27 (m, 1H), 8.15 (m, 1H), 7.48 (m, 1H).

Step B: methyl 2-fluoro-3-nitrobenzoate

2-Fluoro-3-nitrobenzoic acid (75 g) was dissolved in 300 ml of methanol, and then 20 ml of concentrated $H_2SO_4$ was added. The mixture was stirred at 70° C. overnight and cooled to rt, the resulting solid was filtered and washed with water (3×200 ml), to the filtered was added water (400 ml), the resulting precipitate was filtered and washed with water (2×100 ml) to afford another batch of product. The solid were combined and dried under vacuum to afford the title compound was obtained as a light yellow solid (78 g, 96%).

Step C: methyl 3-amino-2-fluorobenzoate

To a solution of methyl 2-fluoro-3-nitrobenzoate (78 g) in THF (400 ml) and methanol (100 ml) was added Raney Ni (40 g), the mixture was heated to 70° C., and then 25 ml of hydrazine hydrate ($N_2H_4H_2O$, 85%) was added dropwise. The reaction was monitored by TLC, when the starting material was totally consumed the addition of hydrazine was stop. The mixture was cooled to rt and filtered, the filtrate was concentrated under vacuum to leave a brown oil, which was purified by chromatography ($SiO_2$, 300-400 mesh, PE:EtOAc=11:2) to afford the title compound was obtained as a yellow oil (45 g, 68%). $^1$H NMR (300 MHz, DMSO) δ ppm 6.96 (m, 3H), 5.36 (s, 2H), 3.81 (s, 3H).

Intermediate 16

N-{3-[5-(2-Chloro-4-pyrimidinyl)-2-(tetrahydro-2H-pyran-4-yl)-1,3-thiazol-4-yl]-2-fluorophenyl}-2,6-difluorobenzenesulfonamide

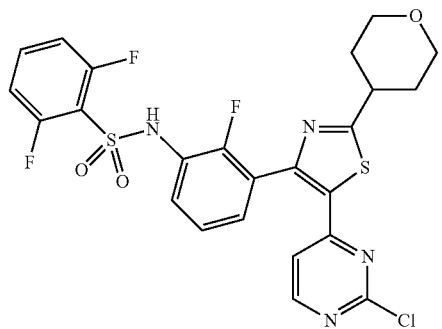 [SMILES: O=S(=O)(Nc1cccc(-c2nc(C3CCOCC3)sc2-c2ccnc(Cl)n2)c1F)c1c(F)cccc1F]

To a solution of N-{3-[(2-chloro-4-pyrimidinyl)acetyl]-2-fluorophenyl}-2,6-difluorobenzenesulfonamide (5.00 g, 11.3 mmol) in DMA (47.2 mL) was added NBS (2.115 g, 11.88 mmol). The reaction stirred 30 min at rt and then tetrahydro-2H-pyran-4-carbothioamide (2.137 g, 14.71 mmol) was added. The reaction stirred 16 h at rt. The reaction mixture was poured into water (500 mL), causing precipitation of a solid. The solid was collected by vacuum filtration, re-dissolved in EtOAc (200 mL), and concentrated onto silica gel. Purification by ISCO chromatography (20 to 100% EtOAc: hexanes) afforded the title compound (3.58 g, 5.87 mmol, 51.9% yield) as a light orange solid. $^1$H NMR (400 MHz, DMSO-$d_6$) δ ppm 10.93 (s, 1H), 8.55 (d, J=5.3 Hz, 1H), 7.58-7.79 (m, 1H), 7.38-7.52 (m, 2H), 7.33 (t, J=7.9 Hz, 1H), 7.24 (t, J=9.1 Hz, 2H), 6.87 (d, J=5.1 Hz, 1H), 3.84-4.00 (m, 2H), 3.41-3.54 (m, 2H), 3.31-3.39 (m, 1H), 1.92-2.13 (m, 2H), 1.66-1.91 (m, 2H); m/z (ESI): 567.03 [M+H]⁺.

Intermediate 17

N-{3-[5-(2-Chloro-4-pyrimidinyl)-2-(1-methylethyl)-1,3-thiazol-4-yl]-2-fluorophenyl}-2,6-difluorobenzenesulfonamide

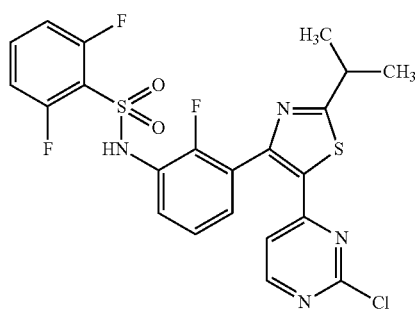 [SMILES: CC(C)c1nc(-c2cccc(NS(=O)(=O)c3c(F)cccc3F)c2F)c(-c2ccnc(Cl)n2)s1]

In a 250 mL flask was placed N-{3-[(2-chloro-4-pyrimidinyl)acetyl]-2-fluorophenyl}-2,6-difluorobenzenesulfonamide (4 g, 9.05 mmol) and DMF (60 mL) was added. NBS (1.62 g, 9.10 mmol) was added and, after stirring at rt for 40 min, 2-methylpropanethioamide (1.4 g, 13.6 mmol), prepared by a procedure analogous to Intermediate 1, was added. After 4 h at rt, the reaction mixture was poured into 800 mL of EtOAc and washed 4 times with 250 mL of H₂O, washed once with 200 mL of brine, and dried over NaSO₄. Silica gel was added and the volatiles were removed under reduced pressure. Column chromatography with 10% to 60% EtOAc:Hexane gave 2.15 g (45%) of the title compound. ¹H-NMR (400 MHz, DMSO-d₆) δ 11.43 (s, 1H), 9.06 (d, J=5.3 Hz, 1H), 8.12-8.30 (m, 1H), 7.93-8.06 (m, 2H), 7.84 (t, J=7.9 Hz, 1H), 7.75 (t, J=9.2 Hz, 2H), 7.37 (d, J=5.3 Hz, 1H), 3.77-3.93 (m, 1H), and 1.89 (d, J=6.8 Hz, 6H). MS (ESI): 524 [M]⁺.

Intermediate 18

N-{3-[5-(2-Chloro-4-pyrimidinyl)-2-(1,1-dimethylethyl)-1,3-thiazol-4-yl]-2-fluorophenyl}-2,6-difluorobenzenesulfonamide

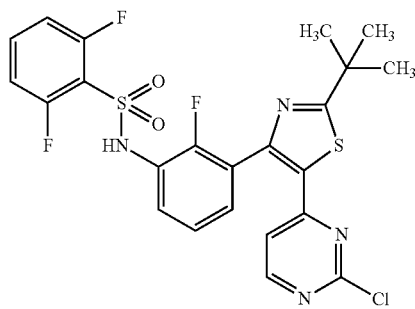 [SMILES: CC(C)(C)c1nc(-c2cccc(NS(=O)(=O)c3c(F)cccc3F)c2F)c(-c2ccnc(Cl)n2)s1]

To a solution of N-{3-[(2-chloro-4-pyrimidinyl)acetyl]-2-fluorophenyl}-2,6-difluorobenzenesulfonamide (2.0 g, 4.53 mmol) in 40 mL DMA, 1.0 eq. NBS (0.806 g, 4.53 mmol) was added and the solution was allowed to stir 15 min at rt. 2,2-dimethylpropanethioamide (0.531 g, 4.53 mmol) was then added at rt. The reaction was heated to 60° C. for 2 hours. The reaction was not complete by LC-MS. The reaction mixture was then heated to 80° C. for an additional hour. The reaction mixture was diluted with water and extracted×2 with EtOAc. The combined EtOAc washings were washed with water×3 to remove DMA, dried over MgSO₄, filtered and concentrated onto silica gel. The crude material was chromatographed in 10-80% EtOAc in Hexanes to give the desired product, 1.6 g (64%). MS (ESI): 539.1 [M+H]⁺.

Intermediate 19

N-(3-(2-(2-Chloropyrimidin-4-yl)acetyl)-2-fluorophenyl)-2,5-difluorobenzenesulfonamide

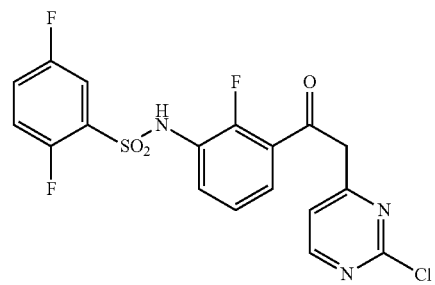 [SMILES: O=C(Cc1ccnc(Cl)n1)c1cccc(NS(=O)(=O)c2cc(F)ccc2F)c1F]

Step A: Methyl 3-(2,5-difluorophenylsulfonamido)-2-fluorobenzoate

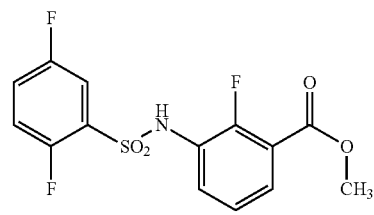 [SMILES: COC(=O)c1cccc(NS(=O)(=O)c2cc(F)ccc2F)c1F]

To a solution of methyl 3-amino-2-fluorobenzoate (21.8 g, 129 mmol) in DCM (300 mL) were added pyridine (30.6 g, 387.6 mmol) and a catalytic amount of DMAP. The mixture was cooled to 0° C. 2,5-Difluorobenzene-1-sulfonyl chloride (28.8 g, 136 mmol) in DCM (20 mL) was added dropwise to the mixture. The reaction was stirred at rt overnight. The reaction mixture was washed with water (300 mL), and extracted with DCM (2×200 mL). The organic layer was washed with brine, dried over anhydrous NaSO₄, filtered and concentrated under reduced pressure to give the crude product, which was washed with petroleum ether to afford the title compound of Step A. (16 g, 35.9%). ¹H NMR (400 MHz, DMSO-d6) δ ppm 10.71-10.91 (br, 1H), 7.65-7.73 (m, 1H), 7.48-7.62 (m, 4H), 7.20-7.28 (m, 1H), 3.77 (s, 3H).

Step B: N-(3-(2-(2-Chloropyrimidin-4-yl)acetyl)-2-fluorophenyl)-2,5-difluorobenzenesulfonamide To a solution of methyl 3-(2,5-difluorophenylsulfonamido)-2-fluorobenzoate (44 g, 128 mmol (from a compilation of batches prepared as described above) in dry THF (500 mL) at −10° C., LiHMDS (1M in THF, 448 mmol, 448 mL) was added dropwise and the solution was allowed to stir for 1 h at 0° C. A solution of 2-chloro-4-methylpyrimidine (19.4 g, 154 mmol) in THF (50 mL) was then added dropwise to the solution of ester and base at 0° C. over 20 min. The solution was allowed to stir 1 h at rt. TLC showed the reaction was complete. The reaction was quenched by addition of the saturated aqueous NH$_4$Cl (300 mL) at 0° C. The reaction mixture was extracted with EtOAc (500 mL×3). The combined organic layers were washed with water and brine successively, dried over Na$_2$SO$_4$, filtered and concentrated under reduced pressure to give the crude product, which was purified by flash column on silica gel, eluting with DCM. This solution was evaporated to obtain a solid. The orange solid was triturated with a small amount of EtOAc and filtered, rinsing with diethyl ether to give the title compound (18.6 g, 33.2% yield). $^1$H NMR (400 MHz, CDCl$_3$) δ ppm 13.70-13.74 (br, 1H), 8.59 (d, J=5.29 Hz, 0.3H), 8.42 (d, J=5.51 Hz, 1H), 7.75-7.79 (m, 0.3H), 7.51-7.66 (m, 3.6H), 7.12-7.28 (m, 6.6H), 6.91 (d, J=5.51 Hz, 1H), 6.03 (s, 1H), 4.37 (s, 0.6H). MS (ES+): 442 [M+H]$^+$ Intermediate 20

2-Propen-1-yl {3-[(2-chloro-4-pyrimidinyl)acetyl]-2-fluorophenyl}carbamate

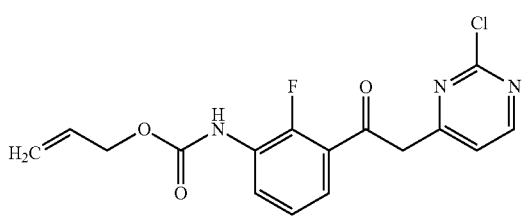 [SMILES: C=CCOC(=O)Nc1cccc(C(=O)Cc2ccnc(Cl)n2)c1F]

Step A: Methyl 3-(allyloxycarbonylamino)-2-fluorobenzoate

To a solution of methyl 3-amino-2-fluorobenzoate (200.0 g, 1183 mmol, 1 eq) in THF (500 mL), saturated NaHCO$_3$ (1600 mL) was added. Then 2-propen-1-yl chloridocarbonate (170.0 g, 1420 mmol, 1.2 eq) was added dropwise at 0° C. The mixture was stirred at rt for 2 h. The solution was extracted with EtOAc (1 L×3). The combined organic layers were washed with water and brine successively, dried over Na$_2$SO$_4$, filtered and concentrated under reduced pressure to give the crude product (260 g, 86.9% yield), which was used in the next step directly. $^1$H NMR (400 MHz, DMSO-d$_6$) δ ppm 9.66 (s, 1H), 7.96 (t, J=7.6 Hz, 1H), 7.64 (t, J=6.4 Hz, 1H), 7.33 (t, J=8.0 Hz, 1H), 6.07-6.00 (m, 1H), 5.43 (dd, J=1.6, 17.6 Hz, 1H), 5.30 (dd, J=1.2, 10.4 Hz, 1H) 4.67 (d, J=5.6 Hz, 2H), 3.91 (s, 3H).

Step B: 2-Propen-1-yl {3-[(2-chloro-4-pyrimidinyl)acetyl]-2-fluorophenyl}carbamate To a solution of methyl 3-(allyloxycarbonylamino)-2-fluorobenzoate (86.7 g, 342 mmol, 1 eq) in dry THF (500 mL) at −10° C., LiHMDS (1M in THF, 1198 mmol, 1198 mL, 3.5 eq) was added dropwise and the solution was allowed to stir for 1 h at 0° C. A solution of pyrimidine chloride (48.0 g, 376 mmol, 1.2 eq) in THF (200 mL) was then added dropwise to the solution of ester and base at 0° C. over 20 min. The solution was allowed to stir 1 h at rt. TLC showed the reaction was complete. The reaction was quenched by addition of the saturated aqueous NH$_4$Cl (800 mL) at 0° C. The reaction mixture was extracted with EtOAc (1 L×3). The combined organic layers were washed with water and brine successively, dried over Na$_2$SO$_4$, filtered and concentrated under reduced pressure to give the crude product, which was purified by flash column on silica gel, rinsing with DCM. This solution was concentrated to obtain a solid. The orange solid was triturated with a small amount of EtOAc and filtered, rinsing with diethyl ether to give the product (240.1 g, 67.0%, three batches combined). $^1$H NMR (400 MHz, DMSO-d$_6$) δ ppm 13.70 (s, 1H), 8.52 (dd, J=0.8, 4.8 Hz, 0.3H), 8.34 (dd, J=0.8, 5.2 Hz, 1H), 8.27 (s, 0.4H), 8.10 (s, 1H), 7.47 (t, J=8.0 Hz, 1.4H), 7.22-7.12 (m, 1.8H), 6.96 (s, 1.4H), 6.85 (d, J=4.2 Hz, 1H), 6.07 (s, 1H), 5.97-5.86 (m, 1.4H), 5.32 (d, J=15.6 Hz, 1.4H), 5.24 (d, J=6.4 Hz, 1.4H), 4.64 (d, J=6.0 Hz, 2.8H), 4.38 (d, J=2.8 Hz, 0.8H).

Intermediate 21

2-Propen-1-yl {3-[5-(2-chloro-4-pyrimidinyl)-2-(1-methylethyl)-1,3-thiazol-4-yl]-2-fluorophenyl}carbamate

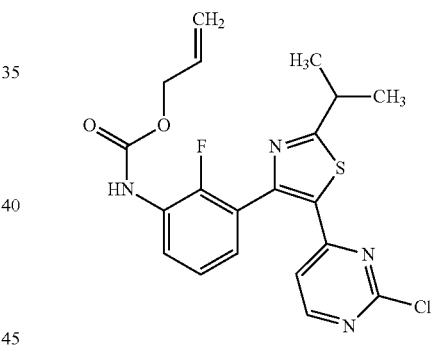

2-Propen-1-yl {3-[(2-chloro-4-pyrimidinyl)acetyl]-2-fluorophenyl}carbamate (10 g, 28.6 mmol) and N,N-dimethylacetamide (50 mL) were combined and treated with recrystallized NBS (5.11 g, 28.7 mmol). The reaction mixture was stirred at rt for 15 min then added 2-methylpropanethioamide (3.54 g, 34.3 mmol). The reaction mixture was heated to 55° C. for 30 min then poured into 500 mL of water. The water was decanted off and dissolved solid residue in EtOAc. The residue was added to the EtOAc solution, concentrated and purified on silica gel [100% DCM to 60% (3:1 DCM:EtOAc)]. The combined clean fractions were diluted with water and extracted three times with EtOAc. The combined EtOAc layers were dried over Na$_2$SO$_4$, filtered, concentrated and put on vacuum pump overnight. The combined unclean fractions from the first column and the residue from the water extractions were concentrated onto silica gel. The residue was purified by silica gel chromatography eluting with 100% DCM to 60% (3:1 DCM:EtOAc). The combined clean fractions from both chromatography and initial workup were triturated in diethyl ether and filtered to obtain a beige solid (2.1 g). The diethyl ether filtrate was concentrated and triturated with EtOH and filtered to obtain a yellow solid (1.3 g). The EtOH filtrate was concentrated and triturated again in diethyl ether and filtered to obtain a light yellow solid (1.0 g). The three batches afforded 4.4 g of the title compound (35% yield). $^1$H NMR (400 MHz, DMSO-d$_6$) δ ppm 9.50 (s, 1H) 8.57 (d, J=5.4 Hz, 1H) 7.72-7.87 (m, 1H) 7.20-7.36 (m, 2H) 7.00 (d, J=5.3 Hz, 1H) 5.80-6.03 (m, 1H) 5.31 (dd, J=17.3, 1.1 Hz, 1H) 5.18 (dd, J=10.5, 0.9 Hz, 1H) 4.56 (d, J=5.3 Hz, 2H) 3.20-3.49 (m, 1H) 1.35 (d, J=6.9 Hz, 6H).

Intermediate 22

3-(5-(2-Chloropyrimidin-4-yl)-2-isopropylthiazol-4-yl)-2-fluoroaniline

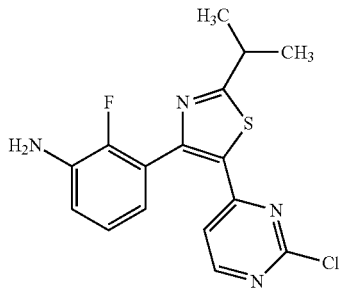 [SMILES: CC(C)c1nc(-c2cccc(N)c2F)c(-c2ccnc(Cl)n2)s1]

To a solution of 2-propen-1-yl {3-[5-(2-chloro-4-pyrimidinyl)-2-(1-methylethyl)-1,3-thiazol-4-yl]-2-fluorophenyl}carbamate (15 g, 34.7 mmol) in DCM (500 mL), HOAc (5 g, 83.3 mmol), Pd(PPh$_3$)$_2$Cl$_2$ (0.5 g, 0.69 mmol) were added. Then tri-n-butyl tin hydride (15 g, 52 mmol) was added dropwise to the mixture at 0° C. The mixture was stirred at rt for 30 min. The reaction was quenched by adding saturated NaHCO$_3$ (200 mL) slowly. The two layers were separated. The aqueous layer was extracted with DCM (1 L×2). The combined organic layers were washed with water and brine successively, dried over Na$_2$SO$_4$, filtered and concentrated under reduced pressure to give the crude product, which was washed with petroleum ether (200 mL) to afford the title compound. (10.5 g, 87.6% yield). $^1$H NMR (400 MHz, DMSO-d6) δ ppm 8.58 (d, J=5.2 Hz, 1H), 7.01-6.96 (m, 2H), 6.89-6.85 (m, 1H), 6.63-6.59 (m, 1H), 5.29 (br. s., 2H), 3.38-3.30 (m, 1H), 1.37 (d, J=6.8 Hz, 6H).

Intermediate 23

2-Propen-1-yl {3-[5-(2-chloro-4-pyrimidinyl)-2-(1,1-dimethylethyl)-1,3-thiazol-4-yl]-2-fluorophenyl}carbamate

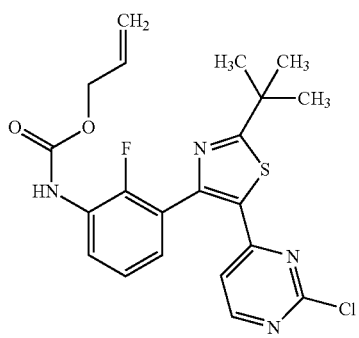 [SMILES: C=CCOC(=O)Nc1cccc(-c2nc(C(C)(C)C)sc2-c2ccnc(Cl)n2)c1F]

To a solution of 2-propen-1-yl {3-[(2-chloro-4-pyrimidinyl)acetyl]-2-fluorophenyl}carbamate (30 g, 85.9 mmol) (Intermediate 20) in DMA (300 mL), NBS (15.3 g, 85.9 mmol) was added. The reaction mixture was stirred at rt for 1 h. Then 2,2-dimethylpropanethioamide (11.0 g, 94.5 mmol) was added at 0° C. The mixture was stirred at rt for 2 h. The mixture was poured into water and extracted with EtOAc (200 mL×3). The combined organic layers were washed with water and brine successively, dried over Na$_2$SO$_4$, filtered and concentrated under reduced pressure to give the crude product, which was purified by column chromatography on silica gel (DCM:petroleum ether 2:1) to afford the title compound. (11 g, 35.4% yield). $^1$H NMR (400 MHz, CDCl$_3$) δ ppm 8.29 (d, J=5.27 Hz, 1H), 8.12-8.19 (m, 1H), 7.12-7.25 (m, 2H), 6.80-6.88 (m, 2H), 5.85-5.98 (m, 1H), 5.20-5.37 (m, 2H), 4.61-4.67 (m, 2H). MS (ES+): 447 [M+H]$^+$.

Intermediate 24

3-[5-(2-Chloro-4-pyrimidinyl)-2-(1,1-dimethylethyl)-1,3-thiazol-4-yl]-2-fluoroaniline

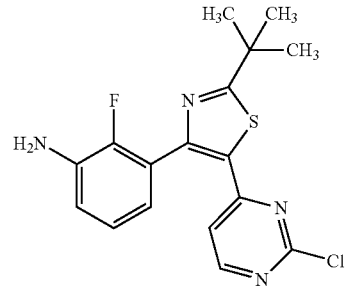 [SMILES: CC(C)(C)c1nc(-c2cccc(N)c2F)c(-c2ccnc(Cl)n2)s1]

In a round bottom flask 2-propen-1-yl {3-[5-(2-chloro-4-pyrimidinyl)-2-(1,1-dimethylethyl)-1,3-thiazol-4-yl]-2-fluorophenyl}carbamate (800 mg, 1.79 mmol) was dissolved in DCM (30 mL) and water (0.5 ml). Tri-n-butyltin hydride (0.480 mL, 1.79 mmol) was added followed by tetrakis(triphenylphosphine)palladium (0) (103 mg, 0.090 mmol). This mixture was stirred 3 h at rt. By TLC all starting material is consumed. The reaction was concentrated to dryness. The crude was then dissolved into a small amount of DCM and injected onto a 25 g silica gel column. The column was eluted with EtOAc and hexanes. The title compound was obtained (0.594 g, 1.47 mmol, 82% yield). $^1$H NMR (400 MHz, DMSO-d$_6$) δ ppm 8.62 (d, J=5.3 Hz, 1H), 6.96-7.08 (m, 2H), 6.91 (t, J=8.2 Hz, 1H), 6.64 (t, J=6.7 Hz, 1H), 5.33 (s, 2H), 1.44 (s, 9H).

Intermediate 25

N-{3-[5-(2-chloro-4-pyrimidinyl)-2-(1,1-dimethylethyl)-1,3-thiazol-4-yl]-2-fluorophenyl}-2,5-difluorobenzenesulfonamide

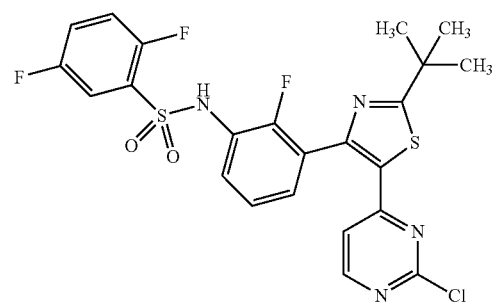 [SMILES: CC(C)(C)c1nc(-c2cccc(NS(=O)(=O)c3cc(F)ccc3F)c2F)c(-c2ccnc(Cl)n2)s1]

To a solution of 3-[5-(2-chloro-4-pyrimidinyl)-2-(1,1-dimethylethyl)-1,3-thiazol-4-yl]-2-fluoroaniline (30 g, 82.8 mmol) in DCM (250 mL) was added pyridine (19.6 g, 248 mmol). The mixture was cooled to 0° C. 2,5-Difluorobenzene-1-sulfonyl chloride (17.6 g, 82.8 mmol) in DCM (20 mL) was added dropwise to the mixture. The reaction was stirred at rt overnight. Then the reaction was washed with water (300 mL), and extracted with DCM (2×400 mL). The organic layer was washed with brine, dried over anhydrous NaSO$_4$, filtrated and concentrated under reduced pressure to give the crude product, which was purified by column chromatography on silica gel (petroleum ether:EtOAc:DCM 20:1:5) to afford the title compound (20.4 g, 45.8% yield). $^1$H NMR (400 MHz, CDCl$_3$) δ ppm 8.26 (d, J=5.3 Hz, 1H), 7.60-7.66 (m, 1H), 7.51-7.60 (m, 1H), 7.30-7.36 (m, 1H), 7.17-7.30 (m, 3H), 7.07-7.17 (m, 1H), 6.68 (d, J=5.3 Hz, 1H), 1.45 (s, 9H). MS (ES+): 539 [M+H]$^+$.

Intermediate 26

2-Propen-1-yl {3-[5-(2-chloro-4-pyrimidinyl)-2-(4-morpholinyl)-1,3-thiazol-4-yl]-2-fluorophenyl}carbamate

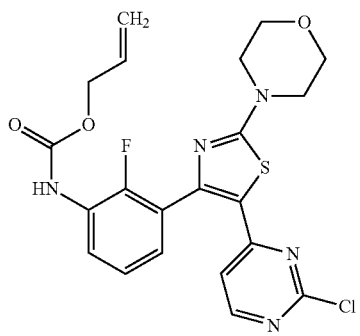 [SMILES: C=CCOC(=O)Nc1cccc(-c2nc(N3CCOCC3)sc2-c2ccnc(Cl)n2)c1F]

To a solution of 2-propen-1-yl {3-[(2-chloro-4-pyrimidinyl)acetyl]-2-fluorophenyl}carbamate (20 g, 57 mmol) (Intermediate 20) in DMA (300 mL), NBS (10.2 g, 57 mmol) was added. The reaction mixture was stirred at rt for 1 h. Then morpholine-4-carbothioamide (9.2 g, 63 mmol) was added at 0° C. The mixture was stirred at rt for 2 h. The mixture was poured into water and extracted with EtOAc (1 L×3). The combined organic layers were washed with water and brine successively, dried over Na$_2$SO$_4$, filtered and concentrated under reduced pressure to give the crude product, which was purified by column chromatography on silica gel (DCM: petroleum ether 2:1) to afford the title compound (20 g, 83.5% yield). $^1$H NMR (400 MHz, CDCl$_3$) δ ppm 8.20-8.27 (m, 1H), 8.19 (d, J=5.5 Hz, 1H), 7.20-7.26 (m, 1H), 7.08-7.12 (m, 1H), 6.92-6.98 (br, 1H), 6.62 (d, J=5.5 Hz, 1H), 5.90-6.03 (m, 1H), 5.25-5.41 (m, 2H), 5.65-5.70 (m, 2H), 3.57-3.63 (m, 4H), 3.77-3.86 (m, 4H). m/z (ES+): 476 [M+H]$^+$ Intermediate 27

3-(5-(2-Chloropyrimidin-4-yl)-2-morpholinothiazol-4-yl)-2-fluoroaniline

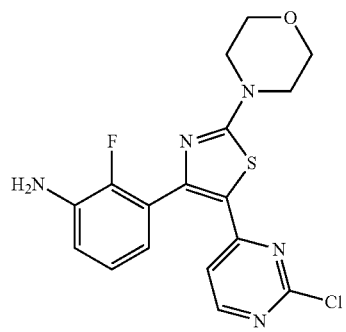 [SMILES: Nc1cccc(-c2nc(N3CCOCC3)sc2-c2ccnc(Cl)n2)c1F]

To a solution of 2-propen-1-yl {3-[5-(2-chloro-4-pyrimidinyl)-2-(4-morpholinyl)-1,3-thiazol-4-yl]-2-fluorophenyl}carbamate (57 g, 120 mmol) (prepared by a process analogous to that described for Intermediate 26) in DCM (500 mL), HOAc (17.3 g, 288 mmol), Pd(PPh$_3$)$_2$Cl$_2$ (1.68 g, 2.4 mmol) were added. Then tri-n-butyltin hydride (38.4 g, 132 mmol) was added dropwise to the mixture at 0° C. The mixture was stirred at rt for 30 min. The reaction was quenched by adding saturated NaHCO$_3$ (300 mL) slowly. The two layers were separated. The aqueous layer was extracted with DCM (1 L×2). The combined organic layers were washed with water and brine successively, dried over Na$_2$SO$_4$, filtered and concentrated under reduced pressure to give the crude product, which was washed with petroleum ether (500 mL) to afford the title compound (43 g, 91.6% yield). $^1$H NMR (400 MHz, CDCl$_3$) δ ppm 8.15 (d, J=5.5 Hz, 1H), 6.95-7.07 (m, 1H), 6.83-6.92 (m, 1H), 6.74-6.80 (m, 1H), 6.70 (d, J=5.5 Hz, 1H), 3.57-3.63 (m, 4H), 3.75-3.88 (m, 4H).

Intermediate 28

N-{3-[5-(2-Chloro-4-pyrimidinyl)-2-(4-morpholinyl)-1,3-thiazol-4-yl]-2-fluorophenyl}-2,6-difluorobenzenesulfonamide

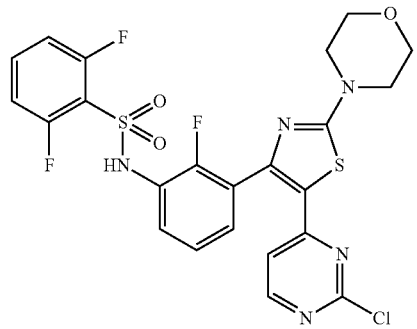 [SMILES: O=S(=O)(Nc1cccc(-c2nc(N3CCOCC3)sc2-c2ccnc(Cl)n2)c1F)c1c(F)cccc1F]

To a solution of 3-(5-(2-chloropyrimidin-4-yl)-2-morpholinothiazol-4-yl)-2-fluoroaniline (35 g, 89.5 mmol) in pyridine (400 mL), 2,6-difluorobenzene-1-sulfonyl chloride (20.9 g, 98.5 mmol) was added dropwise. The reaction was stirred at rt for 2 h. Then the reaction was washed with water (400 mL), and extracted with DCM (2×400 mL). The organic layer was washed with water, brine, dried over anhydrous NaSO$_4$, filtrated and concentrated under reduced pressure to give the crude product, which was purified by column chromatography on silica gel (petroleum ether:DCM 1:2) to afford the title compound (18.5 g, 36.4% yield). $^1$H NMR (400 MHz, CDCl$_3$) δ ppm 8.03 (d, J=5.3 Hz, 1H), 7.65-7.70 (m, 1H), 7.40-7.50 (m, 1H), 7.25-7.30 (br, 1H), 7.18-7.23 (m, 2H), 6.88-6.98 (m, 2H), 6.38 (d, J=5.3 Hz, 1H), 3.72-3.80 (m, 4H), 3.50-3.58 (m, 4H); m/z (ES+): 568 [M+H]$^+$.

Intermediate 29

N-{3-[5-(2-Chloro-4-pyrimidinyl)-2-(4-morpholinyl)-1,3-thiazol-4-yl]-2-fluorophenyl}-2,5-difluorobenzenesulfonamide

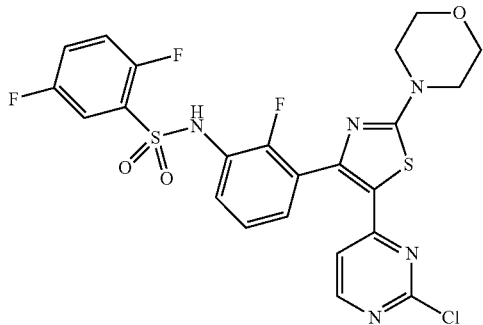 [SMILES: O=S(=O)(Nc1cccc(-c2nc(N3CCOCC3)sc2-c2ccnc(Cl)n2)c1F)c1cc(F)ccc1F]

To a solution of 3-(5-(2-chloropyrimidin-4-yl)-2-morpholinothiazol-4-yl)-2-fluoroaniline (35 g, 89.5 mmol) (Intermediate 27) in pyridine (400 mL), 2,5-difluorobenzene-1-sulfonyl chloride (20.9 g, 98.5 mmol) was added dropwise. The reaction was stirred at rt for 2 h. Then the reaction was washed with water (400 mL), and extracted with DCM (2×400 mL). The organic layer was washed with water, brine, dried over anhydrous NaSO$_4$, filtrated and concentrated under reduced pressure to give the crude product, which was purified by column chromatography on silica gel (petroleum ether:DCM 1:2) to afford the title compound (22.7 g, 44.6% yield). $^1$H NMR (400 MHz, DMSO-d6) δ ppm 10.75-10.83 (br, 1H), 8.32 (d, J=5.3 Hz, 1H), 7.28-7.60 (m, 6H), 6.48 (d, J=5.3 Hz, 1H), 3.65-3.80 (m, 4H), 3.50-3.65 (m, 4H); m/z (ES+): 568 [M+H]$^+$.

Intermediate 30

2-Propen-1-yl {3-[5-(2-chloro-4-pyrimidinyl)-2-(tetrahydro-2H-pyran-4-yl)-1,3-thiazol-4-yl]-2-fluorophenyl}carbamate

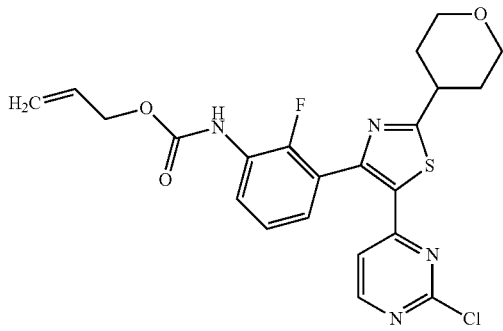 [SMILES: C=CCOC(=O)Nc1cccc(-c2nc(C3CCOCC3)sc2-c2ccnc(Cl)n2)c1F]

To a solution of 2-propen-1-yl {3-[(2-chloro-4-pyrimidinyl)acetyl]-2-fluorophenyl}carbamate (85 g, 243 mmol) in DMA (700 mL), NBS (43.2 g, 243 mmol) was added at 0° C. The reaction mixture was stirred at rt for 1 h. Then tetrahydro-2H-pyran-4-carbothioamide (42.3 g, 291.6 mmol) was added at rt. The mixture was stirred at 60° C. for 1.5 h. The mixture was poured into water and extracted with EtOAc (400 mL×3). The combined organic layers were washed with water and brine successively, dried over Na$_2$SO$_4$, filtered and concentrated under reduced pressure to give the crude product, which was purified by column chromatography on silica gel (DCM:petroleum ether 2:1) to afford the title compound. (40 g, 35% yield). $^1$H NMR (400 MHz, DMSO-d6) δ ppm 9.48-9.54 (br, 1H), 8.58 (d, J=5.3 Hz, 1H), 7.76-7.83 (m, 1H), 7.23-7.32 (m, 2H), 7.02 (d, J=5.3 Hz, 1H), 5.87-5.98 (m, 1H), 5.27-5.36 (m, 1H), 5.16-5.21 (m, 1H), 4.54-4.60 (m, 2H), 3.87-3.94 (m, 2H), 3.41-3.50 (m, 2H), 3.27-3.37 (m, 1H), 1.97-2.04 (m, 2H), 1.69-1.82 (m, 2H).

Intermediate 31

3-[5-(2-Chloro-4-pyrimidinyl)-2-(tetrahydro-2H-pyran-4-yl)-1,3-thiazol-4-yl]-2-fluoroaniline

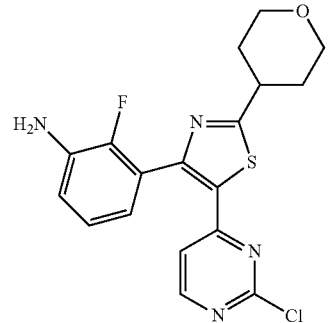 [SMILES: Nc1cccc(-c2nc(C3CCOCC3)sc2-c2ccnc(Cl)n2)c1F]

To a solution of 2-propen-1-yl {3-[5-(2-chloro-4-pyrimidinyl)-2-(tetrahydro-2H-pyran-4-yl)-1,3-thiazol-4-yl]-2-fluorophenyl}carbamate (28 g, 59 mmol) in DCM (300 mL), HOAc (8.5 g, 141.6 mmol), Pd(PPh$_3$)$_2$Cl$_2$ (0.827 g, 1.18 mmol) were added. Then tri-n-butyl tin hydride (27 g, 88.5 mmol) was added dropwise to the mixture at 0° C. The mixture was stirred at rt for 30 min. The reaction was quenched by added the saturated NaHCO$_3$ (200 mL) slowly. The two layers were separated. The aqueous layer was extracted with DCM (300 mL×2). The combined organic layers were washed with water and brine successively, dried over Na$_2$SO$_4$, filtered and concentrated under reduced pressure to give the crude product, which was washed with petroleum ether (200 mL) to afford the title compound, which was used to the next step directly. (22.5 g, 97.8% yield). $^1$H NMR (400 MHz, CDCl$_3$) δ ppm 8.35 (d, J=5.3 Hz, 1H), 7.01-7.08 (m, 1H), 6.98 (d, J=5.3 Hz, 1H), 6.85-6.92 (m, 1H), 6.79-6.85 (m, 1H), 4.05-4.12 (m, 2H), 3.79-3.86 (br, 2H), 3.51-3.59 (m, 2H), 3.23-3.34 (m, 1H), 2.07-2.15 (m, 2H), 1.89-2.01 (m, 2H).

Intermediate 32

N-{3-[5-(2-Chloro-4-pyrimidinyl)-2-(tetrahydro-2H-pyran-4-yl)-1,3-thiazol-4-yl]-2-fluorophenyl}-2,5-difluorobenzenesulfonamide

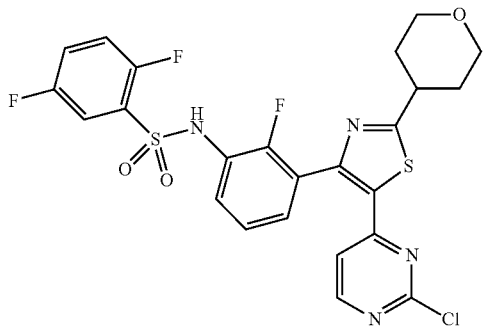 [SMILES: O=S(=O)(Nc1cccc(-c2nc(C3CCOCC3)sc2-c2ccnc(Cl)n2)c1F)c1cc(F)ccc1F]

To a solution of 3-[5-(2-chloro-4-pyrimidinyl)-2-(tetrahydro-2H-pyran-4-yl)-1,3-thiazol-4-yl]-2-fluoroaniline (1.24 g, 3.17 mmol) in DCM (31.7 mL) was added pyridine (0.269 mL, 3.33 mmol) and 2,5-difluorobenzenesulfonyl chloride (0.448 mL, 3.33 mmol). The reaction was stirred 18 h at rt. The reaction mixture was concentrated onto silica gel. Purification by chromatography (5 to 100% EtOAc:DCM) afforded the title compound (1.21 g, 2.13 mmol, 67.3% yield) as an off-white solid. $^1$H NMR (400 MHz, DMSO-$d_6$) δ ppm 10.79 (s, 1H), 8.57 (d, J=5.5 Hz, 1H), 7.37-7.67 (m, 5H), 7.32 (t, J=7.9 Hz, 1H), 6.90 (d, J=5.3 Hz, 1H), 3.93 (dd, J=11.4, 2.0 Hz, 2H), 3.39-3.58 (m, 2H), 3.26-3.40 (m, 1H), 1.98-2.09 (m, 2H), 1.63-1.86 (m, 2H). MS (ESI): 567.06 [M+H]$^+$.

Intermediate 33

N-{5-[(2-Chloro-4-pyrimidinyl)acetyl]-2-fluorophenyl}-2,6-difluorobenzenesulfonamide

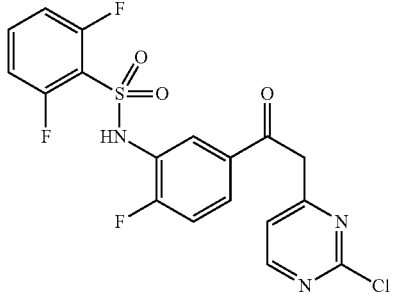 [SMILES: O=C(Cc1ccnc(Cl)n1)c1ccc(F)c(NS(=O)(=O)c2c(F)cccc2F)c1]

Step A: Ethyl 3-{[(2,6-difluorophenyl)sulfonyl]amino}-4-fluorobenzoate

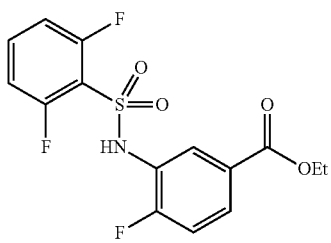 [SMILES: CCOC(=O)c1ccc(F)c(NS(=O)(=O)c2c(F)cccc2F)c1]

To a solution of ethyl 3-amino-4-fluorobenzoate (5.47 g, 30 mmol) and pyridine (2.55 mL, 33 mmol) in DCM (150 mL) was added 2,6-difluorobenzenesulfonyl chloride (4.45 mL, 33 mmol). The reaction was stirred overnight at rt. After 16 h, the reaction mixture was concentrated, triturated with ether, and dried in vacuo to generate 7.87 g (66% yield) of the product of Step A as a white powder. MS (ESI): 360 (M+H).

Step B: N-{5-[(2-Chloro-4-pyrimidinyl)acetyl]-2-fluorophenyl}-2,6-difluorobenzenesulfonamide To a solution of ethyl 3-{[(2,6-difluorophenyl)sulfonyl]amino}-4-fluorobenzoate (5.0 g, 13.9 mmol) in THF (100 mL) was added 1.0 M LiHMDS in THF (34.8 mL, 34.8 mmol). A solution of 2-chloro-4-methylpyrimidine (2.7 g, 20.9 mmol) in THF (100 mL) was added dropwise over 30 min, and the reaction was stirred overnight at rt. The reaction was quenched with 10 mL of MeOH and concentrated, and the residue was partitioned between EtOAc and saturated aqueous NaHCO$_3$. The aqueous layer was extracted with 2×50 mL EtOAc, and the combined organic layers were passed through a pad of silica gel, concentrated, and adsorbed onto silica gel. The crude product was purified via flash chromatography with 0-100% EtOAc/DCM to generate 3.07 g (50% yield) of the title compound as a white powder. MS (ESI): 443 (M+H).

Intermediate 34

N-{5-[5-(2-Chloro-4-pyrimidinyl)-2-(1-methylethyl)-1,3-thiazol-4-yl]-2-fluorophenyl}-2,6-difluorobenzenesulfonamide

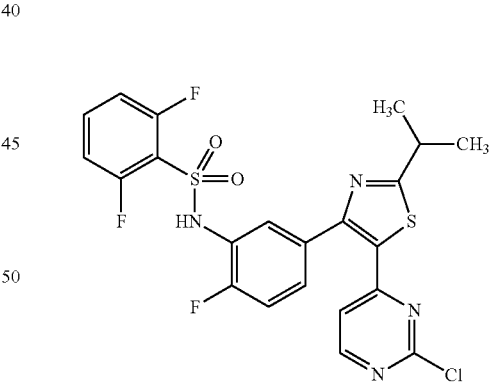

To a solution of N-{5-[(2-chloro-4-pyrimidinyl)acetyl]-2-fluorophenyl}-2,6-difluorobenzenesulfonamide (1.0 g, 2.3 mmol) in DMF (10 mL) was added NBS (0.49 g, 2.8 mmol). After stirring for 45 min at rt, 2-methylpropanethioamide (0.35 g, 3.4 mmol), was added and the reaction was stirred at rt. After 4 h, the reaction mixture was partitioned between ether and saturated aqueous NaHCO$_3$. The organic layer was washed with brine, dried over anhydrous NaSCO$_4$, filtered, and concentrated to generate 0.49 g (41% yield) as a yellow powder. MS (ESI) 525 (M+H).

Intermediate 35

N-{5-[(2-Chloro-4-pyrimidinyl)acetyl]-2-fluorophenyl}-2,5-difluorobenzenesulfonamide

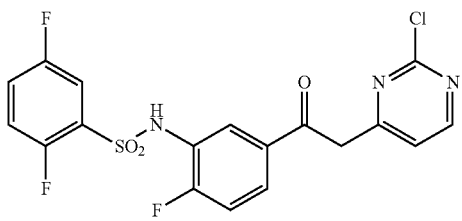 [SMILES: O=C(Cc1ccnc(Cl)n1)c1ccc(F)c(NS(=O)(=O)c2cc(F)ccc2F)c1]

Step A: Methyl 3-(2,5-difluorophenylsulfonamido)-4-fluorobenzoate

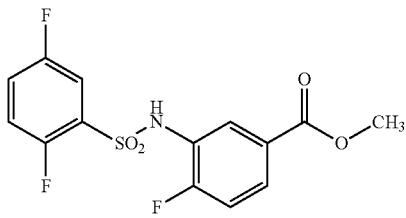 [SMILES: COC(=O)c1ccc(F)c(NS(=O)(=O)c2cc(F)ccc2F)c1]

To a solution of methyl 3-amino-4-fluorobenzoate (25 g, 149 mmol) in DCM (150 mL) were added pyridine (35.3 g, 446 mmol) and a catalytic amount of DMAP (1.8 g, 14.9 mmol). The mixture was cooled to 0° C. 2,5-Difluorobenzene-1-sulfonyl chloride (34.7 g, 212 mmol) in DCM (20 mL) was added dropwise to the mixture. The reaction was stirred at rt overnight. Then the reaction was washed with water (300 mL), and extracted with DCM (2×400 mL). The organic layer was washed with brine, dried over anhydrous $NaSO_4$, filtrated and concentrated under reduced pressure to give the crude product, which was washed with petroleum ether to afford the title compound of Step A (48.2 g, 94.5% yield). $^1$H NMR (400 MHz, $CDCl_3$) δ ppm 8.12-8.18 (m, 1H), 7.73-7.80 (m, 1H), 7.47-7.53 (m, 1H), 7.10-7.25 (m, 1H), 7.00-7.07 (m, 1H), 3.86 (s, 3H).

Step B: N-(5-(2-(2-Chloropyrimidin-4-yl)acetyl)-2-fluorophenyl)-2,5-difluorobenzenesulfonamide To a solution of methyl 3-(2,5-difluorophenylsulfonamido)-4-fluorobenzoate (40 g, 116 mmol) in dry THF (500 mL) at −10° C., LiHMDS (1M in THF, 406 mmol, 406 mL) was added dropwise and the solution was allowed to stir for 1 h at 0° C. A solution of 2-chloro-4-methylpyrimidine (17.8 g, 139 mmol) in THF (50 mL) was then added dropwise to the solution of ester and base at 0° C. over 20 min. The solution was allowed to stir 1 h at rt. TLC showed the reaction was complete. The reaction was quenched by addition of the saturated aqueous $NH_4Cl$ (300 mL) at 0° C. The reaction mixture was extracted with EtOAc (500 mL×3). The combined organic layers were washed with water and brine successively, dried over $Na_2SO_4$, filtered and concentrated under reduced pressure to give the crude product, which was purified by flash column on silica gel, eluting with DCM. This solution was evaporated to obtain a solid. The orange solid was triturated with a small amount of EtOAc and filtered, rinsing with diethyl ether to give the title compound of Step B (31 g, 60.8% yield). $^1$H NMR (400 MHz, $CDCl_3$) δ ppm 13.72-13.77 (br, 1H), 8.57-8.61 (m, 0.4H), 8.38-8.42 (m, 1H), 8.13-8.19 (m, 0.4H), 7.97-8.02 (m, 1H), 7.78-7.82 (m, 0.4H), 7.57-7.63 (m, 1H), 7.52-7.57 (1.4H), 7.02-7.30 (m, 4.2H), 6.91-6.93 (m, 1H), 5.93 (s, 1H), 4.40 (s, 1H). MS (ES+): 442 [M+H]$^+$.

Intermediate 36

N-{5-[5-(2-Chloro-4-pyrimidinyl)-2-(tetrahydro-2H-pyran-4-yl)-1,3-thiazol-4-yl]-2-fluorophenyl}-2,5-difluorobenzenesulfonamide

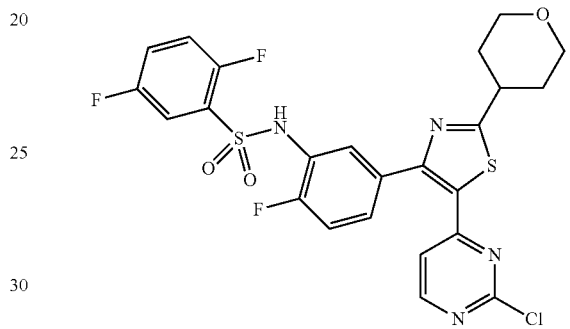

To a solution of N-{5-[(2-chloro-4-pyrimidinyl)acetyl]-2-fluorophenyl}-2,5-difluorobenzenesulfonamide (0.910 g, 2.06 mmol) (prepared in a manner analogous to Intermediate 35) in DMA (8.24 mL) was added NBS (0.385 g, 2.16 mmol). The reaction stirred 30 min at rt and then tetrahydro-2H-pyran-4-carbothioamide (0.389 g, 2.68 mmol) was added. The reaction stirred 16 h at rt. The reaction mixture was poured into water (150 mL), causing precipitation of a solid. The solid was collected by vacuum filtration, redissolved in EtOAc (50 mL), and concentrated onto silica gel. Purification by chromatography (20 to 100% EtOAc:hexanes) afforded the title compound (690 mg, 1.21 mmol, 58.5% yield) as a yellow solid. $^1$H NMR (400 MHz, DMSO-$d_6$) δ ppm 10.86 (s, 1H), 8.58 (d, J=5.3 Hz, 1H), 7.45-7.69 (m, 4H), 7.42 (dd, J=7.5, 2.0 Hz, 1H), 7.32 (dd, J=10.1, 8.8 Hz, 1H), 7.14 (d, J=5.3 Hz, 1H), 3.95 (dd, J=11.7, 2.0 Hz, 2H), 3.40-3.56 (m, 2H), 3.25-3.41 (m, 1H), 2.02 (dd, J=12.9, 1.6 Hz, 2H), 1.65-1.86 (m, 2H). MS (ESI): 567.09 [M+H]$^+$.

Intermediate 37

2-Propen-1-yl {5-[(2-chloro-4-pyrimidinyl)acetyl]-2-fluorophenyl}carbamate

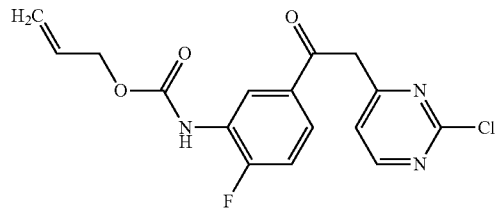 [SMILES: C=CCOC(=O)Nc1cc(C(=O)Cc2ccnc(Cl)n2)ccc1F]

123

Step A: Methyl 4-fluoro-3-{[(2-propen-1-yloxy)carbonyl]amino}benzoate

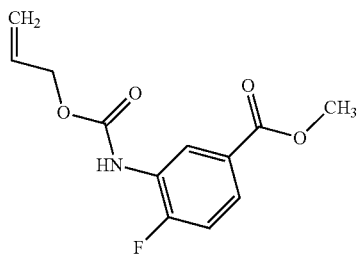 [SMILES: C=CCOC(=O)Nc1cc(C(=O)OC)ccc1F]

To a solution of methyl 3-amino-4-fluorobenzoate (109 g, 644 mmol) in THF (2000 mL), saturated NaHCO$_3$ (68 g, 805 mmol) was added. Then 2-propen-1-yl chloridocarbonate (93 g, 773 mmol) was added dropwise at 0° C. The mixture was stirred at rt for 2 h. The solution was extracted with EtOAc (500 mL×3). The combined organic layers were washed with water and brine successively, dried over Na$_2$SO$_4$, filtered and concentrated under reduced pressure to give the crude product (160 g, 98%), which was used in the next step directly. $^1$H NMR (400 MHz, CDCl$_3$) δ ppm 8.72-8.81 (m, 1H), 7.71-7.79 (m, 1H), 7.09-7.16 (m, 1H), 6.87-6.94 (br, 1H), 5.91-6.03 (m, 1H), 5.41 (d, J=17.1 Hz, 1H), 5.28 (d, J=10.5, 1H), 4.70 (d, J=10.5 Hz, 1H), 4.70 (d, J=5.5 Hz, 2H), 3.90 (s, 3H).

Step B: 2-Propen-1-yl {5-[(2-chloro-4-pyrimidinyl)acetyl]-2-fluorophenyl}carbamate To a solution of methyl 4-fluoro-3-{[(2-propen-1-yloxy)carbonyl]amino}benzoate (60 g, 237 mmol) in dry THF (500 mL) at −10° C., LiHMDS (1M in THF, 735 mmol, 735 mL) was added dropwise and the solution was allowed to stir for 1 h at 0° C. A solution of 2-chloro-4-methylpyrimidine (30.5 g, 237 mmol) in THF (50 mL) was then added dropwise to the solution of ester and base at 0° C. over 20 min. The solution was allowed to stir 1 h at rt. TLC showed the reaction was complete. The reaction was quenched by addition of the saturated aqueous NH$_4$Cl (200 mL) at 0° C. The reaction mixture was extracted with EtOAc (500 mL×3). The combined organic layers were washed with water and brine successively, dried over Na$_2$SO$_4$, filtered and concentrated under reduced pressure to give the crude product, which was purified by flash column on silica gel, eluting with DCM. This solution was evaporated to obtain a solid. The orange solid was triturated with a small amount of EtOAc and filtered, rinsing with diethyl ether to give the title compound (69.8 g, 81.6% yield). $^1$H NMR (400 MHz, CDCl$_3$) δ ppm 13.66 (br, 0.55H), 8.79-8.83 (m, 0.36H), 8.53-8.61 (m, 0.91H), 8.33-8.37 (m, 0.59H), 7.65-7.72 (m, 0.40H), 7.50-7.57 (m, 0.59H), 7.26-7.30 (m, 0.35H), 7.08-7.19 (m, 1H), 6.92-7.12 (br, 1H), 6.87-6.92 (m, 0.64H), 5.90-6.21 (m, 1.5H), 5.39 (d, J=18.1 Hz, 1H), 5.29 (d, J=10.4 Hz, 1H), 4.70 (d, J=5.5 Hz, 2H), 4.44 (s, 1H).

124

Intermediate 38

2-Propen-1-yl {5-[5-(2-chloro-4-pyrimidinyl)-2-(1,1-dimethylethyl)-1,3-thiazol-4-yl]-2-fluorophenyl}carbamate

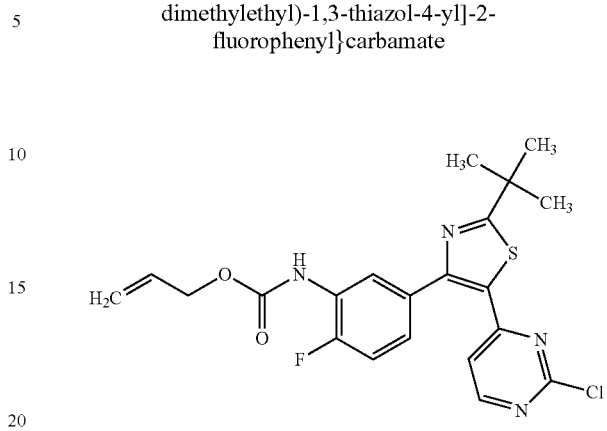

To a solution of 2-propen-1-yl {5-[(2-chloro-4-pyrimidinyl)acetyl]-2-fluorophenyl}carbamate (35 g, 100.3 mmol in DMA, 500 mL), NBS (17.8 g, 100.3 mmol) was added. The reaction mixture was stirred at rt for 1 h. Then 2,2-dimethylpropanethioamide (13 g, 111 mmol) was added at 0° C. The mixture was stirred at 80° C. for 2 h. The mixture was poured into water and extracted with EtOAc (1 L×3). The combined organic layers were washed with water and brine successively, dried over Na$_2$SO$_4$, filtered and concentrated under reduced pressure to give the crude product, which was purified by column chromatography on silica gel (DCM:petroleum ether 2:1) to afford the title compound (36 g, 80.5% yield). $^1$H NMR (400 MHz, CDCl$_3$) δ ppm 8.24-8.31 (m, 2H), 7.09-7.18 (m, 2H), 7.01 (d, J=5.5 Hz, 1H), 6.92-6.98 (br, 1H), 5.87-5.97 (m, 1H), 5.31-5.37 (m, 1H), 5.24-5.28 (m, 1H), 4.61-4.65 (m, 2H), 1.46 (s, 9H).

Intermediate 39

5-[5-(2-Chloro-4-pyrimidinyl)-2-(1,1-dimethylethyl)-1,3-thiazol-4-yl]-2-fluoroaniline

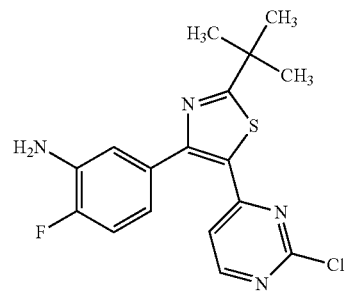 [SMILES: CC(C)(C)c1nc(-c2ccc(F)c(N)c2)c(-c2ccnc(Cl)n2)s1]

To a solution of 2-propen-1-yl {5-[5-(2-chloro-4-pyrimidinyl)-2-(1,1-dimethylethyl)-1,3-thiazol-4-yl]-2-fluorophenyl}carbamate (35 g, 78.4 mmol) in DCM (400 mL), HOAc (11.3 g, 188 mmol), Pd(PPh$_3$)$_2$Cl$_2$ (1.1 g, 1.57 mmol) were added. Then tri-n-butyl tin hydride (34.2 g, 117 mmol) was added dropwise to the mixture at 0° C. The mixture was stirred at rt for 30 min. The reaction was quenched by added the saturated NaHCO$_3$ (400 mL) slowly. The two layers were separated. The aqueous layer was extracted with DCM (500 mL×2). The combined organic layers were washed with water and brine successively, dried over Na$_2$SO$_4$, filtered and concentrated under reduced pressure to give the crude product, which was washed with petroleum ether (200 mL) to afford the title compound (18.3 g, 64.4% yield). $^1$H NMR (400 MHz, CDCl$_3$) δ ppm 8.31 (d, J=5.5 Hz, 1H), 6.96-7.03 (m, 3H), 6.78-6.83 (m, 1H), 2.30-2.60 (br, 2H), 1.48 (s, 9H).

Intermediate 40

N-{5-[5-(2-Chloro-4-pyrimidinyl)-2-(1,1-dimethylethyl)-1,3-thiazol-4-yl]-2-fluorophenyl}-2,6-difluorobenzenesulfonamide

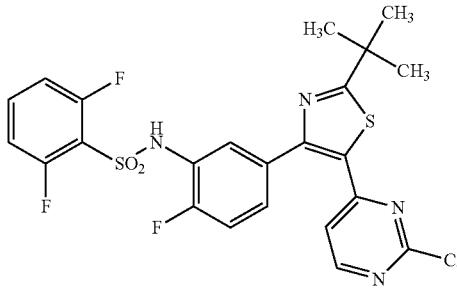

To a solution of 5-[5-(2-chloro-4-pyrimidinyl)-2-(1,1-dimethylethyl)-1,3-thiazol-4-yl]-2-fluoroaniline (13 g, 36 mmol) in DCM (100 mL) was added pyridine (8.5 g, 107 mmol). The mixture was cooled to 0° C. 2,6-Difluorobenzene-1-sulfonyl chloride (9.1 g, 43 mmol) in DCM (20 mL) was added dropwise to the mixture. The reaction was stirred at rt over night. Then the reaction was washed with water (100 mL), and extracted with DCM (2×200 mL). The organic layer was washed with brine, dried over anhydrous NaSO$_4$, filtrated and concentrated under reduced pressure to give the crude product, which was purified by column chromatography on silica gel (petroleum ether:DCM 1:2) to afford the title compound (12 g, 62.2% yield, two batches combined). $^1$H NMR (400 MHz, DMSO-d6) δ ppm 10.95-11.05 (br, 1H), 8.54 (d, J=5.2 Hz, 1H), 7.67-7.79 (m, 1H), 7.45-7.50 (m, 2H), 7.22-7.37 (m, 3H), 7.10 (d, J=5.2 Hz, 1H), 1.42 (s, 9H). MS (ES+): 539 [M+H]$^+$.

Intermediate 41

2-Propen-1-yl {5-[5-(2-chloro-4-pyrimidinyl)-2-(1-methylethyl)-1,3-thiazol-4-yl]-2-fluorophenyl}carbamate

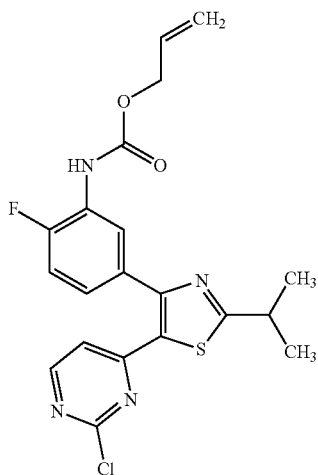 [SMILES: C=CCOC(=O)Nc1cc(-c2nc(C(C)C)sc2-c2ccnc(Cl)n2)ccc1F]

In a procedure analogous to Intermediate 6, 1.5 g (43% yield) of 2-propen-1-yl {5-[5-(2-chloro-4-pyrimidinyl)-2-(1-methylethyl)-1,3-thiazol-4-yl]-2-fluorophenyl}carbamate was prepared from 2-propen-1-yl {5-[5-(2-chloro-4-pyrimidinyl)acetyl]-2-fluorophenyl}carbamate (2.8 g, 8 mmol) (Intermediate 37). MS (ESI): 432.82 (M+H)$^+$.

Intermediate 42

5-[5-(2-Chloro-4-pyrimidinyl)-2-(1-methylethyl)-1,3-thiazol-4-yl]-2-fluoroaniline

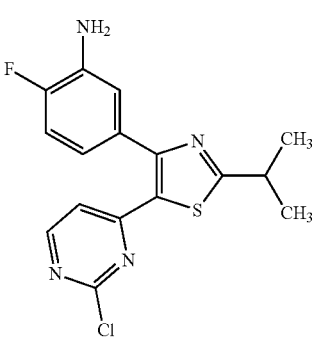 [SMILES: CC(C)c1nc(-c2ccc(F)c(N)c2)c(-c2ccnc(Cl)n2)s1]

In a procedure analogous to Intermediate 13, 1.1 g (92% yield) of the title compound was prepared from 2-propen-1-yl {5-[5-(2-chloro-4-pyrimidinyl)-2-(1-methylethyl)-1,3-thiazol-4-yl]-2-fluorophenyl}carbamate (1.5 g, 3.5 mmol) (Intermediate 41). MS (ES+) MS: 349.27 (M+H)$^+$.

Intermediate 43

N-{5-[5-(2-Chloro-4-pyrimidinyl)-2-(1-methylethyl)-1,3-thiazol-4-yl]-2-fluorophenyl}-2,5-difluorobenzenesulfonamide

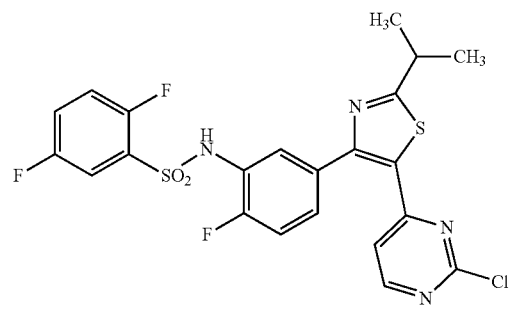 [SMILES: CC(C)c1nc(-c2ccc(F)c(NS(=O)(=O)c3cc(F)ccc3F)c2)c(-c2ccnc(Cl)n2)s1]

In a procedure analogous to Intermediate 14 using 5-[5-(2-chloro-4-pyrimidinyl)-2-(1-methylethyl)-1,3-thiazol-4-yl]-2-fluoroaniline (23 g, 66.1 mmol) and 2,5-difluorobenzene-1-sulfonyl chloride (15.4 g, 72.7 mmol) the title compound was obtained (19.6 g, 62.2% yield). $^1$H NMR (400 MHz, CDCl$_3$) δ ppm 8.32 (d, J=5.3 Hz, 1H), 7.62 (dd, J=2.2, 7.7 Hz, 1H), 7.44-7.49 (m, 1H), 7.34-7.37 (br, 1H), 7.14-7.34 (m, 3H), 7.08 (dd, J=8.4, 9.7 Hz, 1H), 6.92 (d, J=5.3 Hz, 1H), 3.32 (m, 1H), 1.44 (d, J=6.8 Hz, 6H). MS (ES+): 525 [M+H]$^+$.

Intermediate 44

N-{2-Chloro-3-[(E)-2-(2-chloro-4-pyrimidinyl)-1-hydroxyethenyl]phenyl}-2,6-difluorobenzene-sulfonamide

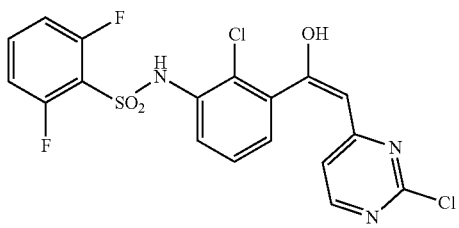 [SMILES: O=S(=O)(Nc1cccc(/C(O)=C\c2ccnc(Cl)n2)c1Cl)c1c(F)cccc1F]

Step A: Methyl 2-chloro-3-nitrobenzoate

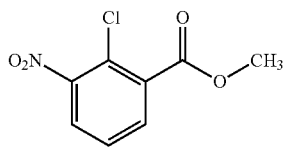

To a suspension of 2-chloro-3-nitrobenzoic acid (100 g, 495 mmol) in MeOH (600 mL) was added TsOH (20 g, 10%). Then the mixture was heated at reflux overnight. The solvent was removed. The residue was diluted with EtOAc (1 L). Then the pH was adjusted to around 9 by progressively adding saturated NaHCO$_3$. The organic layer was separated. The aqueous layer was extracted with EtOAc (1 L×3). The combined organic layers were washed with water and brine successively, dried over Na$_2$SO$_4$, filtered and concentrated under reduced pressure to give the title compound (96 g, 90.6% yield). $^1$H NMR (400 MHz, CDCl$_3$) δ ppm 7.90 (dd, J=1.8 Hz, 7.9 Hz, 1H), 7.81 (dd, J=1.5 Hz, 7.7 Hz, 1H), 7.45 (dd, J=7.7 Hz, 7.9 Hz, 1H), 3.94 (s, 1H).

Step B: Methyl 3-amino-2-chlorobenzoate

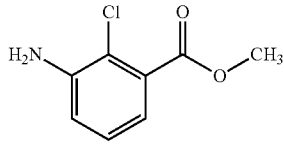

To a solution of methyl 2-chloro-3-nitrobenzoate (25 g, 116 mmol) in MeOH (150 mL) was added Raney Ni (3 g). The mixture was stirred under H$_2$ atmosphere (50 psi at 25° C.) for 3.5 h. The catalyst was filtered, and the filtrate was concentrated under the reduced pressure to dryness to give the crude product, which was purified by recrystallization in EtOAc to afford the title compound (69 g, 83.5% yield, four batches combined). $^1$H NMR (400 MHz, CDCl$_3$) δ ppm 6.70-7.25 (m, 3H), 4.40-4.50 (br, 2H), 3.87 (s, 3H).

Step C: Methyl 2-chloro-3-(2,6-difluorophenylsulfonamido)benzoate

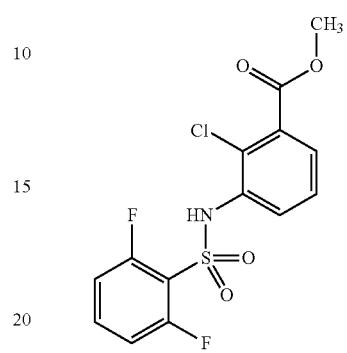

Following a procedure analogous to Intermediate 5, Step A using methyl 3-amino-2-chlorobenzoate (39 g, 211 mmol) in DCM (200 mL) was added pyridine (51 g, 633 mmol) and 2,6-difluorobenzene-1-sulfonyl chloride (49.1 g, 232 mmol) the title compound was obtained (62 g, 81.6% yield). $^1$H NMR (400 MHz, CDCl$_3$) δ ppm 7.87 (dd, J=1.8 Hz, 8.38 Hz, 1H), 7.72-7.79 (br, 1H), 7.56 (dd, J=1.8 Hz, 7.94 Hz, 1H), 7.45-7.53 (m, 1H), 7.28 (dd, J=7.9 Hz, 8.4 Hz, 1H), 6.95-7.01 (m, 2H), 3.89 (s, 3H).

Step D: N-{2-chloro-3-[(E)-2-(2-chloro-4-pyrimidinyl)-1-hydroxyethenyl]phenyl}-2,6-difluorobenzene-sulfonamide Following a procedure analogous to Intermediate 5, Step B using methyl 2-chloro-3-(2,6-difluorophenylsulfonamido)benzoate (31 g, 85.9 mmol) and 2-chloro-4-methylpyrimidine (12.2 g, 94.5 mmol) the title compound was obtained (33 g, 73.5% yield). $^1$H NMR (400 MHz, CDCl$_3$) δ ppm 13.47-13.52 (br, 0.96H), 8.50-8.56 (m, 0.13H), 8.38 (d, J=5.3 Hz, 1H), 7.78-7.82 (m, 0.15H), 7.62-7.73 (m, 2H), 7.40-7.50 (m, 1.18H), 7.17-7.30 (m, 1.77H), 6.90-6.97 (m, 2.29H), 6.83 (d, J=5.3 Hz, 1H), 5.65 (s, 1H), 4.28 (s, 0.26H). MS (ES+): 458 [M+H]$^+$.

Intermediate 45

N-{2-Chloro-3-[(E)-2-(2-chloro-4-pyrimidinyl)-1-hydroxyethenyl]phenyl}-2,5-difluorobenzene-sulfonamide

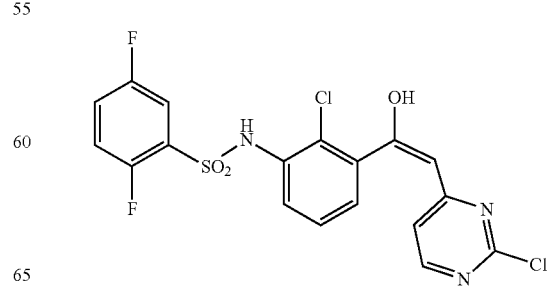

To a solution of methyl 3-amino-2-chlorobenzoate (16.3 g, 88 mmol) in pyridine (150 mL) was added 2,5-difluorobenzenesulfonyl chloride (13.0 ml, 97 mmol) dropwise. The solution was stirred at rt overnight. The crude reaction mixture was concentrated by about half, and ~200 mL of water was added. A red oil precipitated from the mixture. The oil was separated, and crystallized upon standing. The crystals were collected by vacuum filtration, washed with ether, and dried in vacuo to generate 16.8 g (46.4 mmol, 52.8% yield) as a white powder. LC/MS indicates that the product is a ~2:1 mixture of the desired product and the bis-sulfonamide. The white powder was dissolved in THF (100 mL), and a 1 M solution of LiHMDS in THF (100 mL, 100 mmol) was added. A solution of 2-chloro-4-methylpyrimidine (8.0 g, 62.2 mmol) in THF (10 mL) was added dropwise over 15 minutes. The solution was stirred at 20° C. for an additional 20 minutes, and then the reaction was quenched with MeOH (5 mL). The solvent was removed with a rotary evaporator, and the residue was partitioned between EtOAc and water. The aqueous layer was acidified to pH<9 with saturated aqueous ammonium chloride, and extracted with EtOAc. The combined organic layers were dried over anhydrous NaSO₄, filtered, and concentrated to ~50 mL. The brown solution was passed through a pad of silica gel (eluting with EtOAc) and concentrated to generate the title compound (6.78 g, 14.8 mmol, 16.8% yield) as a yellow powder. MS (ESI): 458.0 [M+H]+.

Example 1

2,6-Difluoro-N-{3-[2-(1-methylethyl)-5-(2-{[2-(methylsulfonyl)ethyl]amino}-4-pyrimidinyl)-1,3-thiazol-4-yl]phenyl}benzenesulfonamide

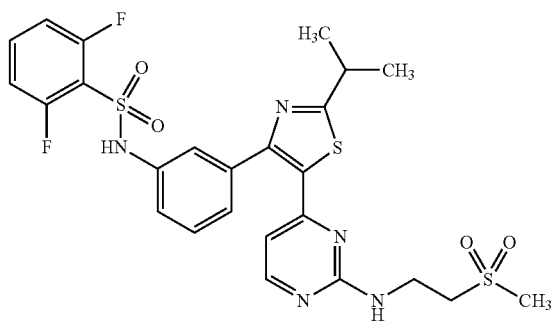

A neat mixture of N-{3-[5-(2-chloro-4-pyrimidinyl)-2-(1-methylethyl)-1,3-thiazol-4-yl]phenyl}-2,6-difluorobenzenesulfonamide (0.15 g, 0.30 mmol) and 2-aminoethyl-methylsulfone (0.20 g, 1.62 mmol) was heated at 60° C. overnight. The reaction mixture was diluted with 1M HCl and extracted with DCM twice. The organic layer was dried over MgSO₄ and evaporated onto silica gel. Purification by ISCO chromatography (0 to 40% 1:9 MeOH:EtOAC in DCM) afforded the title compound (74 mg, 40.0% yield) as a white solid. ¹H NMR (400 MHz, DMSO-d6) δ ppm 11.04 (s, 1H), 8.06 (d, J=5.1 Hz, 1H), 7.65-7.75 (m, 1H), 7.46 (t, J=5.7 Hz, 1H), 7.35 (t, J=7.9 Hz, 1H), 7.16-7.30 (m, 5H), 6.09 (br. s., 1H), 3.60- 3.73 (m, 2H), 3.34-3.38 (m, 2H), 3.25-3.30 (m, 1H), 3.02 (s, 3H), 1.36 (d, J=6.9 Hz, 6H). MS (ESI): 594.2 [M+H]+.

Example 2

N-{3-[2-(1,1-Dimethylethyl)-5-(2-{[2-(methylsulfonyl)ethyl]amino}-4-pyrimidinyl)-1,3-thiazol-4-yl]phenyl}-2,6-difluorobenzenesulfonamide

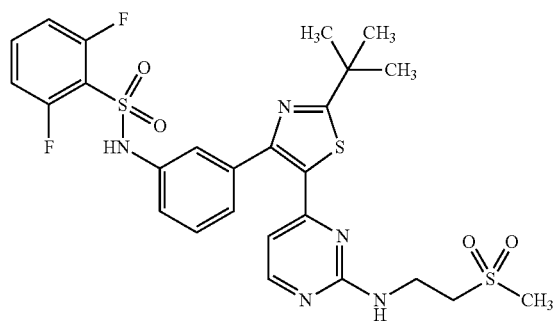 [SMILES: CC(C)(C)c1nc(-c2cccc(NS(=O)(=O)c3c(F)cccc3F)c2)c(-c2ccnc(NCCS(C)(=O)=O)n2)s1]

Following a procedure analogous to that described in Example 1 using N-{3-[5-(2-chloro-4-pyrimidinyl)-2-(1,1-dimethylethyl)-1,3-thiazol-4-yl]phenyl}-2,6-difluorobenzenesulfonamide (0.08 g, 0.15 mmol), 42 mg (43% yield) of the title compound was obtained. ¹H NMR (400 MHz, DMSO-d6) δ ppm 11.05 (s, 1H), 8.06 (d, J=5.1 Hz, 1H), 7.65-7.77 (m, 1H), 7.45 (t, J=5.7 Hz, 1H), 7.35 (t, J=7.9 Hz, 1H), 7.16-7.31 (m, 5H), 6.06-6.20 (m, 1H), 3.59-3.74 (m, 2H), 3.33-3.40 (m, 2H), 3.02 (s, 3H), 1.42 (s, 9H). MS (ESI): 608.2 [M+H]+.

Example 3

N-[3-(2-(1,1-Dimethylethyl)-5-{2-[(2-methylpropyl)amino]-4-pyrimidinyl}-1,3-thiazol-4-yl)phenyl]-2,5-difluorobenzenesulfonamide

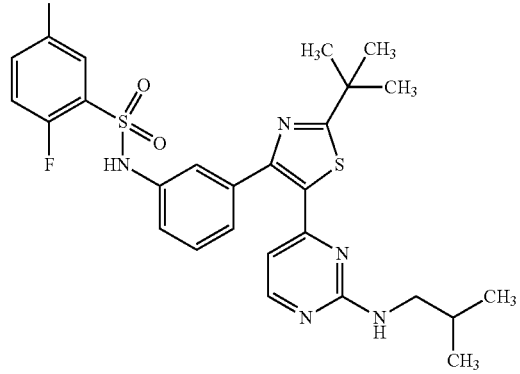

A suspension of N-{3-[5-(2-chloro-4-pyrimidinyl)-2-(1,1-dimethylethyl)-1,3-thiazol-4-yl]phenyl}-2,5-difluorobenzenesulfonamide (150 mg, 0.288 mmol) and isobutylamine (1 mL, 10.06 mmol) was stirred at rt overnight. The reaction mixture was diluted with DCM and washed with dilute aqueous HCl. The DCM extract was dried over MgSO₄, filtered, evaporated onto silica gel and chromatographed (0-20% MeOH in DCM). The title compound was obtained as a yellow solid (75 mg, 44% yield). $^1$H NMR (400 MHz, DMSO-d6) δ ppm 10.87 (s, 1H), 7.96 (d, J=5.2 Hz, 1H), 7.40-7.62 (m, 3H), 7.23-7.33 (m, 2H), 7.20 (s, 1H), 7.14 (d, J=7.7 Hz, 2H), 6.00 (br. s., 1H), 2.85-3.11 (m, 2H), 1.67-1.87 (m, 1H), 1.36 (s, 9H), 0.82 (d, J=6.4 Hz, 6H). MS (ESI): 558.0 [M+H]$^+$.

Example 4

N-{5-[5-(2-{[2-(Ethyloxy)ethyl]amino}-4-pyrimidinyl)-2-(1-methylethyl)-1,3-thiazol-4-yl]-2-fluorophenyl}-2,6-difluorobenzenesulfonamide

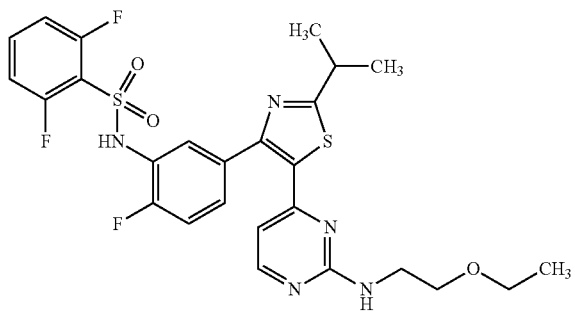 [SMILES: CCOCCNc1nccc(-c2sc(C(C)C)nc2-c2ccc(F)c(NS(=O)(=O)c3c(F)cccc3F)c2)n1]

Following a procedure analogous to the procedure described in Example 1 using N-{5-[5-(2-chloro-4-pyrimidinyl)-2-(1-methylethyl)-1,3-thiazol-4-yl]-2-fluorophenyl}-2,6-difluorobenzenesulfonamide (0.150 g, 0.286 mmol) and 2-ethoxyethylamine (0.5 mL, 4.77 mmol), the title compound was obtained (64 mg, 36% yield). $^1$H NMR (400 MHz, DMSO-d6) δ ppm 10.92 (s, 1H), 8.08 (d, J=5.1 Hz, 1H), 7.66-7.77 (m, 1H), 7.36-7.46 (m, 2H), 7.20-7.32 (m, 4H), 6.19 (s, 1H), 3.35-3.51 (m, 6H), 3.24-3.30 (m, 1H), 1.36 (d, J=6.9 Hz, 6H), 1.10 (q, J=6.7 Hz, 3H). MS (ESI): 578.2 [M+H]$^+$.

Example 5

2,6-Difluoro-N-[2-fluoro-5-(2-(1-methylethyl)-5-{2-[(tetrahydro-2-furanylmethyl)amino]-4-pyrimidinyl}-1,3-thiazol-4-yl)phenyl]benzenesulfonamide

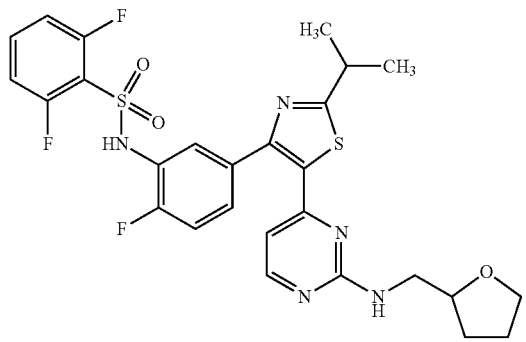 [SMILES: CC(C)c1nc(-c2ccc(F)c(NS(=O)(=O)c3c(F)cccc3F)c2)c(-c2ccnc(NCC3CCCO3)n2)s1]

Following a procedure analogous to the procedure described in Example 1 using N-{5-[5-(2-chloro-4-pyrimidinyl)-2-(1-methylethyl)-1,3-thiazol-4-yl]-2-fluorophenyl}-2, 6-difluorobenzenesulfonamide (0.150 g, 0.286 mmol) and tetrahydrofufurylamine (0.5 mL, 4.84 mmol), the title compound was obtained as a white solid (71 mg, 41% yield). $^1$H NMR (400 MHz, DMSO-d6) δ ppm 10.93 (s, 1H), 8.08 (d, J=5.1 Hz, 1H), 7.67-7.76 (m, 1H), 7.43 (dd, J=7.6, 2.2 Hz, 1H), 7.37-7.41 (m, 1H), 7.23-7.32 (m, 4H), 6.19 (br. s., 1H), 3.93-4.01 (m, 1H), 3.72-3.80 (m, 1H), 3.57-3.65 (m, 1H), 3.35-3.41 (m, 1H), 3.26-3.32 (m, 2H), 1.74-1.93 (m, 3H), 1.51-1.62 (m, 1H), 1.36 (d, J=6.9 Hz, 6H). MS (ESI): 590.2 [M+H]$^+$.

Example 6

N-{5-[5-{2-[(Cyclopropylmethyl)amino]-4-pyrimidinyl}-2-(1-methylethyl)-1,3-thiazol-4-yl]-2-fluorophenyl}-2,6-difluorobenzenesulfonamide

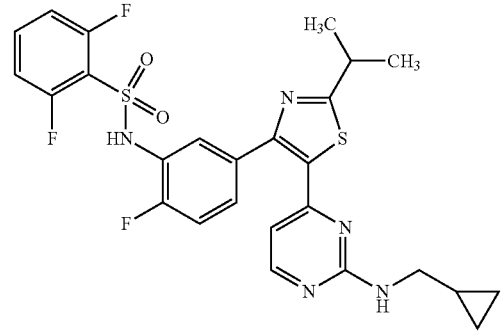 [SMILES: CC(C)c1nc(-c2ccc(F)c(NS(=O)(=O)c3c(F)cccc3F)c2)c(-c2ccnc(NCC3CC3)n2)s1]

Following a procedure analogous to the procedure described in Example 1 using N-{5-[5-(2-chloro-4-pyrimidinyl)-2-(1-methylethyl)-1,3-thiazol-4-yl]-2-fluorophenyl}-2, 6-difluorobenzenesulfonamide (60 mg, 0.11 mmol) and 1-cyclopropylmethanamine (0.1 mL, approx. 1.4 mmol) the title compound was obtained as an off-white solid (25 mg, 39% yield). $^1$H NMR (400 MHz, DMSO-d$_6$) δ ppm 10.90 (s, 1H), 8.05 (d, J=5.1 Hz, 1H), 7.59-7.79 (m, 1H), 7.33-7.44 (m, 3H), 7.20-7.29 (m, 3H), 6.15 (br. s., 1H), 3.00-3.15 (m, 2H), 2.42-2.45 (m, 1H), 1.34 (d, J=7.0 Hz, 6H), 0.94-1.06 (m, 1H), 0.34-0.42 (m, 2H), 0.16-0.22 (m, 2H). MS (ESI): 560.1 [M+H]$^+$.

Example 7

2,6-Difluoro-N-{2-fluoro-5-[2-(1-methylethyl)-5-(2-{[3-(4-morpholinyl)propyl]amino}-4-pyrimidinyl)-1,3-thiazol-4-yl]phenyl}benzenesulfonamide

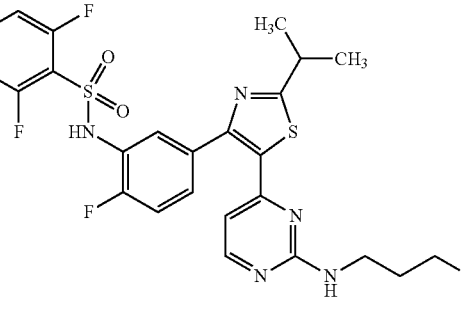

Following a procedure analogous to the procedure described in Example 1 using N-{5-[5-(2-chloro-4-pyrimidinyl)-2-(1-methylethyl)-1,3-thiazol-4-yl]-2-fluorophenyl}-2,6-difluorobenzenesulfonamide (80 mg, 0.15 mmol) and 3-(4-morpholinyl)-1-propanamine (0.10 mL, approx. 6.9 mmol) the title compound was obtained as a white solid (85 mg, 89% yield). $^1$H NMR (400 MHz, DMSO-d$_6$) δ ppm 8.01 (d, J=5.1 Hz, 1H), 7.52-7.67 (m, 1H), 7.36 (dd, J=7.6, 1.6 Hz, 1H), 7.21-7.32 (m, 2H), 7.07-7.21 (m, 3H), 6.14 (br. s., 1H), 3.57 (br. s., 4H), 3.20-3.36 (m, 8H), 2.36-2.41 (m, 1H), 1.65 (br. s., 2H), 1.31 (d, J=6.8 Hz, 6H). MS (ESI): 633.5 [M+H]$^+$.

Example 8

2,6-Difluoro-N-{2-fluoro-5-[2-(1-methylethyl)-5-(2-{[2-(methylsulfonyl)ethyl]amino}-4-pyrimidinyl)-1,3-thiazol-4-yl]phenyl}benzenesulfonamide

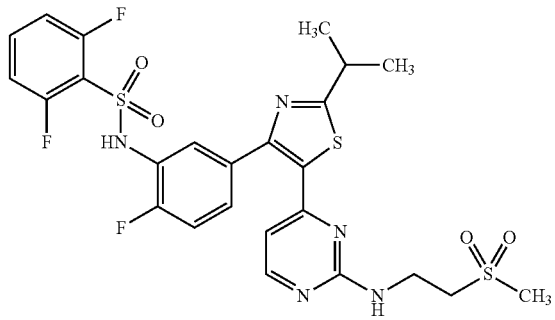 [SMILES: CC(C)c1nc(-c2ccc(F)c(NS(=O)(=O)c3c(F)cccc3F)c2)c(-c2ccnc(NCCS(C)(=O)=O)n2)s1]

Following a procedure analogous to the procedure described in Example 1 using N-{5-[5-(2-chloro-4-pyrimidinyl)-2-(1-methylethyl)-1,3-thiazol-4-yl]-2-fluorophenyl}-2,6-difluorobenzenesulfonamide (3.0 g, 5.71 mmol) and 2-aminoethyl-methyl-sulfone (2.82 g, 22.86 mmol), the title compound was obtained as a white solid (1.9 g, 53% yield). $^1$H NMR (400 MHz, DMSO-d6) δ ppm 10.93 (s, 1H), 8.14 (d, J=5.0 Hz, 1H), 7.67-7.77 (m, 1H), 7.48 (t, J=5.5 Hz, 1H), 7.38-7.46 (m, 2H), 7.28 (q, J=9.2 Hz, 3H), 6.22-6.31 (m, 1H), 3.62-3.73 (m, 2H), 3.34-3.40 (m, 2H), 3.25-3.30 (m, 1H), 3.02 (s, 3H), 1.36 (d, J=6.9 Hz, 6H). MS (ESI): 612.2 [M+H]$^+$.

Example 9

N-{5-[5-[2-(Ethylamino)-4-pyrimidinyl]-2-(1-methylethyl)-1,3-thiazol-4-yl]-2-fluorophenyl}-2,6-difluorobenzenesulfonamide

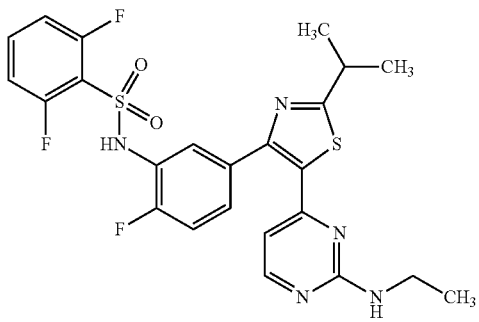 [SMILES: CCNc1nccc(-c2sc(C(C)C)nc2-c2ccc(F)c(NS(=O)(=O)c3c(F)cccc3F)c2)n1]

Following a procedure analogous to the procedure described in Example 1 using N-{5-[5-(2-chloro-4-pyrimidinyl)-2-(1-methylethyl)-1,3-thiazol-4-yl]-2-fluorophenyl}-2,6-difluorobenzenesulfonamide (0.150 g, 0.286 mmol) and ethyl amine 2.0 M in THF (2 mL, 4.00 mmol), the title compound was obtained as an off-white solid (74 mg, 49% yield). $^1$H NMR (400 MHz, DMSO-d6) δ ppm 10.92 (s, 1H), 8.07 (d, J=5.0 Hz, 1H), 7.65-7.80 (m, 1H), 7.44 (dd, J=7.5, 1.8 Hz, 1H), 7.36-7.42 (m, 1H), 7.21-7.33 (m, 4H), 6.17 (br. s., 1H), 3.16-3.31 (m, 3H), 1.36 (d, J=6.9 Hz, 6H), 1.10 (t, J=7.1 Hz, 3H). MS (ESI): 534.2 [M+H]$^+$.

Example 10

N-{5-[2-(1,1-Dimethylethyl)-5-(2-{[2-(methylsulfonyl)ethyl]amino}-4-pyrimidinyl)-1,3-thiazol-4-yl]-2-fluorophenyl}-2,6-difluorobenzenesulfonamide

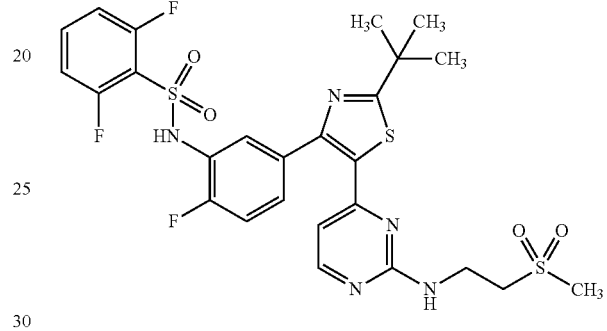

Following a procedure analogous to the procedure described in Example 1 using N-{5-[5-(2-chloro-4-pyrimidinyl)-2-(1,1-dimethylethyl)-1,3-thiazol-4-yl]-2-fluorophenyl}-2,6-difluorobenzenesulfonamide (0.149 g, 0.276 mmol) and 2-aminoethyl-methyl-sulfone (0.3 g, 2.4 mmol), the title compound was obtained as a white solid (75 mg, 43% yield). $^1$H NMR (400 MHz, DMSO-d6) δ ppm 10.95 (s, 1H), 8.14 (d, J=5.0 Hz, 1H), 7.65-7.79 (m, 1H), 7.36-7.53 (m, 3H), 7.22-7.34 (m, 3H), 6.28 (br. s., 1H), 3.60-3.75 (m, 2H), 3.35-3.40 (m, 2H), 3.02 (s, 3H), 1.42 (s, 9H). MS (ESI): 626.2 [M+H]$^+$.

Example 11

2,6-Difluoro-N-{2-fluoro-3-[2-(1-methylethyl)-5-(2-{[2-(methylsulfonyl)ethyl]amino}-4-pyrimidinyl)-1,3-thiazol-4-yl]phenyl}benzenesulfonamide

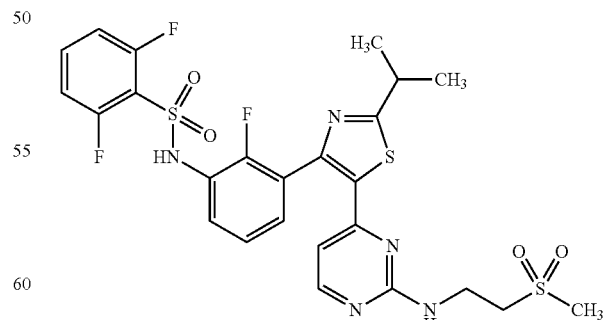

Following a procedure analogous to the procedure described in Example 1 using N-{3-[5-(2-chloro-4-pyrimidinyl)-2-(1-methylethyl)-1,3-thiazol-4-yl]-2-fluorophenyl}-2,6-difluorobenzenesulfonamide (0.100 g, 0.190 mmol) and 2-aminoethyl-methyl-sulfone (0.100 g, 0.812 mmol), the title compound was obtained as an off-white solid (53 mg, 43% yield). $^1$H NMR (400 MHz, DMSO-d6) δ ppm 10.87 (s, 1H), 8.09 (d, J=5.1 Hz, 1H), 7.62-7.74 (m, 1H), 7.39-7.49 (m, 2H), 7.33-7.39 (m, 1H), 7.20-7.32 (m, 3H), 5.89-6.05 (m, 1H), 3.63 (br. s., 2H), 3.34-3.39 (m, 2H), 3.25-3.31 (m, 1H), 2.99-3.04 (m, 3H), 1.35 (d, J=6.9 Hz, 6H). MS (ESI): 613.2 [M+H]$^+$.

Example 12

N-{3-[2-(1,1-Dimethylethyl)-5-(2-{[3-(methylsulfonyl)propyl]amino}-4-pyrimidinyl)-1,3-thiazol-4-yl]-2-fluorophenyl}-2,6-difluorobenzenesulfonamide

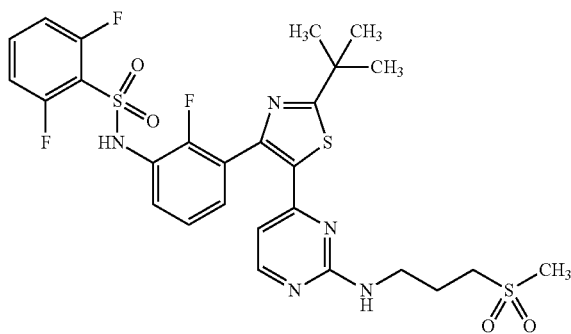 [SMILES: CC(C)(C)c1nc(-c2cccc(NS(=O)(=O)c3c(F)cccc3F)c2F)c(-c2ccnc(NCCCS(C)(=O)=O)n2)s1]

Step A: N-{3-[2-(1,1-Dimethylethyl)-5-(2-{[3-(methylthio)propyl]amino}-4-pyrimidinyl)-1,3-thiazol-4-yl]-2-fluorophenyl}-2,6-difluorobenzenesulfonamide

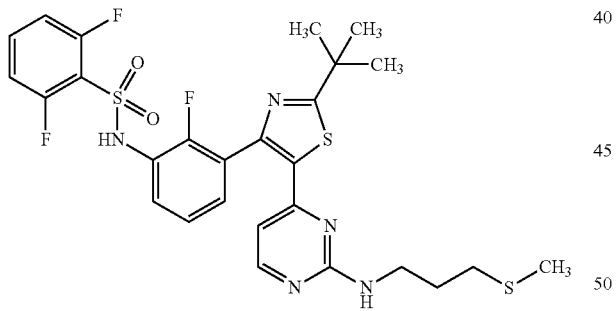

Following a procedure analogous to the procedure described in Example 1 using N-{3-[5-(2-chloro-4-pyrimidinyl)-2-(1,1-dimethylethyl)-1,3-thiazol-4-yl]-2-fluorophenyl}-2,6-difluorobenzenesulfonamide (110 mg, 0.204 mmol) and [3-(methylthio)propyl]amine (200 mg, 1.90 mmol) the title compound of Step A was obtained (124 mg, 90% yield). MS (ESI): 608.1 [M+H]$^+$.

Step B: N-{3-[2-(1,1-Dimethylethyl)-5-(2-{[3-(methylsulfonyl)propyl]amino}-4-pyrimidinyl)-1,3-thiazol-4-yl]-2-fluorophenyl}-2,6-difluorobenzenesulfonamide To a solution of oxone (376 mg, 0.612 mmol) in water (5 mL) at 0° C., a solution of N-{3-[2-(1,1-dimethylethyl)-5-(2-{[3-(methylthio)propyl]amino}-4-pyrimidinyl)-1,3-thiazol-4-yl]-2-fluorophenyl}-2,6-difluorobenzenesulfonamide (124 mg, 0.204 mmol) in 90% EtOH (10 mL) was added dropwise. The solution was allowed to stir at rt for 1 hr. The reaction mixture was diluted with EtOAc and washed with water. The organic layer was dried over MgSO$_4$, filtered, evaporated onto silica gel and chromatographed (0-40% 1:9 MeOH:EtOAc in DCM). The title compound was obtained as a white solid (30 mg, 22% yield). $^1$H NMR (400 MHz, DMSO-d6) δ ppm 10.88 (s, 1H), 8.04 (d, J=5.2 Hz, 1H), 7.58-7.77 (m, 2H), 7.32-7.51 (m, 2H), 7.13-7.34 (m, 3H), 5.87-6.07 (m, 1H), 3.19-3.30 (m, 2H), 3.08-3.18 (m, 2H), 2.97 (s, 3H), 1.82-2.01 (m, 2H), 1.40 (s, 9H). MS (ESI): 640.2 [M+H]$^+$.

Example 13

N-[3-(2-(1,1-Dimethylethyl)-5-{2-[(1,1-dioxidotetrahydro-2H-thiopyran-4-yl)-amino]-4-pyrimidinyl}-1,3-thiazol-4-yl)-2-fluorophenyl]-2,6-difluorobenzenesulfonamide

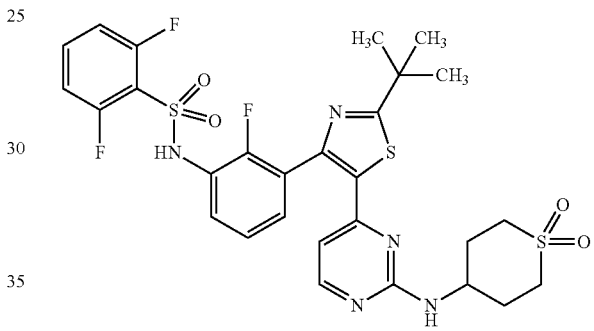

Step A: N-(3-{2-(1,1-Dimethylethyl)-5-[2-(tetrahydro-2H-thiopyran-4-ylamino)-4-pyrimidinyl]-1,3-thiazol-4-yl}-2-fluorophenyl)-2,6-difluorobenzenesulfonamide

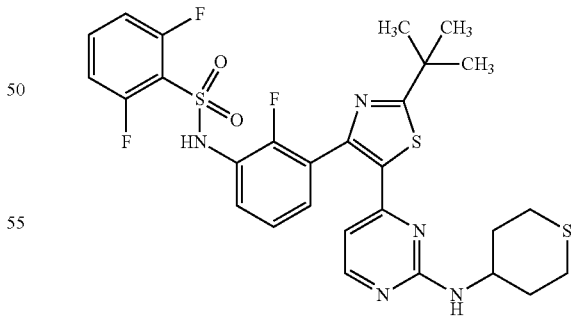

Following a procedure analogous to the procedure described in Example 1 using N-{3-[5-(2-chloro-4-pyrimidinyl)-2-(1,1-dimethylethyl)-1,3-thiazol-4-yl]-2-fluorophenyl}-2,6-difluorobenzenesulfonamide (100 mg, 0.186 mmol) and tetrahydro-2H-thiopyran-4-amine (100 mg, 0.853 mmol) the title compound was obtained as a crude yellow foam and used directly in the next step. MS (ESI): 620.2 [M+H]$^+$.

Step B: N-[3-(2-(1,1-Dimethylethyl)-5-{2-[(1,1-dioxidotetrahydro-2H-thiopyran-4-yl)amino]-4-pyrimidinyl}-1,3-thiazol-4-yl)-2-fluorophenyl]-2,6-difluorobenzenesulfonamide Following a procedure analogous to the procedure described in Example 12, Step B using crude N-(3-{2-(1,1-dimethylethyl)-5-[2-(tetrahydro-2H-thiopyran-4-ylamino)-4-pyrimidinyl]-1,3-thiazol-4-yl}-2-fluorophenyl)-2,6-difluorobenzenesulfonamide and oxone (342 mg, 0.557 mmol), the title compound was obtained as an off-white solid (30 mg, 24% yield over 2 steps). $^1$H NMR (400 MHz, DMSO-d6) δ ppm 10.88 (s, 1H), 8.08 (d, J=5.1 Hz, 1H), 7.60-7.75 (m, 1H), 7.48 (d, J=7.4 Hz, 1H), 7.32-7.44 (m, 2H), 7.28 (t, J=7.9 Hz, 1H), 7.23 (t, J=9.1 Hz, 2H), 6.01 (br. s., 1H), 3.07-3.24 (m, 4H), 1.91-2.19 (m, 5H), 1.41 (s, 9H). MS (ESI): 652.1 [M+H]$^+$.

Example 14

2,6-Difluoro-N-{2-fluoro-3-[5-(2-{[2-(methylsulfonyl)ethyl]amino}-4-pyrimidinyl)-2-(4-morpholinyl)-1,3-thiazol-4-yl]phenyl}benzenesulfonamide

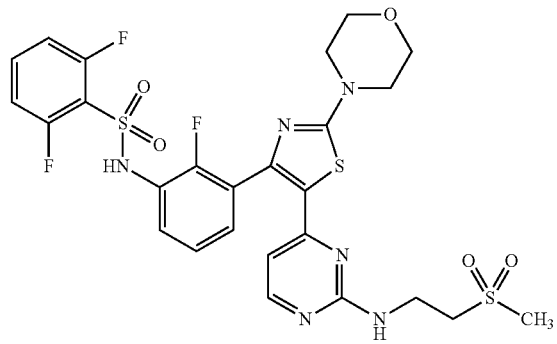 [SMILES: CS(=O)(=O)CCNc1nccc(-c2sc(N3CCOCC3)nc2-c2cccc(NS(=O)(=O)c3c(F)cccc3F)c2F)n1]

Following a procedure analogous to the procedure described in Example 1 using N-{3-[5-(2-chloro-4-pyrimidinyl)-2-(4-morpholinyl)-1,3-thiazol-4-yl]-2-fluorophenyl}-2,6-difluorobenzenesulfonamide (0.101 g, 0.178 mmol) and 2-aminoethyl-methyl-sulfone (0.30 g, 2.436 mmol) the title compound was obtained as a yellow solid (72 mg, 61% yield). $^1$H NMR (400 MHz, DMSO-d6) δ ppm 10.87 (s, 1H), 7.93 (d, J=5.3 Hz, 1H), 7.62-7.75 (m, 1H), 7.36-7.51 (m, 1H), 7.17-7.36 (m, 5H), 5.72 (d, J=5.3 Hz, 1H), 3.71 (t, J=4.6 Hz, 4H), 3.59-3.68 (m, 2H), 3.46 (t, J=4.6 Hz, 4H), 3.34 (s, 2H), 3.02 (s, 3H). MS (ESI): 655.2 [M+H]$^+$.

Example 15

2,6-Difluoro-N-{2-fluoro-3-[5-(2-{[3-(methylsulfonyl)propyl]amino}-4-pyrimidinyl)-2-(4-morpholinyl)-1,3-thiazol-4-yl]phenyl}benzenesulfonamide

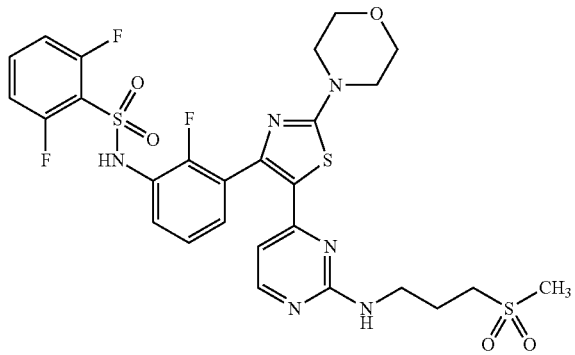 [SMILES: CS(=O)(=O)CCCNc1nccc(-c2sc(N3CCOCC3)nc2-c2cccc(NS(=O)(=O)c3c(F)cccc3F)c2F)n1]

Step A: 2,6-Difluoro-N-{2-fluoro-3-[5-(2-{[3-(methylthio)propyl]amino}-4-pyrimidinyl)-2-(4-morpholinyl)-1,3-thiazol-4-yl]phenyl}benzenesulfonamide

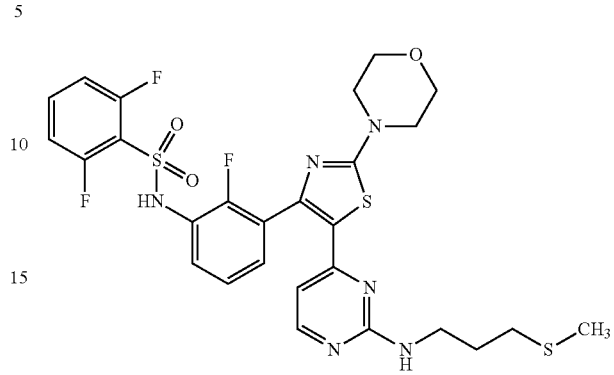

Following a procedure analogous to the procedure described in Example 1 using N-{3-[5-(2-chloro-4-pyrimidinyl)-2-(4-morpholinyl)-1,3-thiazol-4-yl]-2-fluorophenyl}-2,6-difluorobenzenesulfonamide (150 mg, 0.264 mmol) and 3-(methylthio)-1-propanamine (300 mg, 2.85 mmol), the title compound was obtained as a crude yellow foam and used directly in the next step. MS (ESI): 637.2 [M+H]$^+$.

Step B: 2,6-Difluoro-N-{2-fluoro-3-[5-(2-{[3-(methylsulfonyl)propyl]amino}-4-pyrimidinyl)-2-(4-morpholinyl)-1,3-thiazol-4-yl]phenyl}benzenesulfonamide Following a procedure analogous to the procedure described in Example 12, Step B using crude 2,6-difluoro-N-{2-fluoro-3-[5-(2-{[3-(methylthio)propyl]amino}-4-pyrimidinyl)-2-(4-morpholinyl)-1,3-thiazol-4-yl]phenyl}benzenesulfonamide and oxone (527 mg, 0.857 mmol) the title compound was obtained as a white solid (83 mg, 46% yield over 2 steps). $^1$H NMR (400 MHz, DMSO-d6) δ ppm 10.87 (s, 1H), 7.88 (d, J=5.4 Hz, 1H), 7.59-7.76 (m, 1H), 7.42 (td, J=7.3, 2.3 Hz, 1H), 7.16-7.33 (m, 5H), 5.67 (br. s., 1H), 3.63-3.77 (m, 4H), 3.39-3.51 (m, 4H), 3.22-3.31 (m, 2H), 3.08-3.19 (m, 2H), 2.96 (s, 3H), 1.82-2.00 (m, 2H). MS (ESI): 669.2 [M+H]$^+$.

Example 16

N-(5-{2-(1,1-Dimethylethyl)-5-[2-({trans-4-[(methylsulfonyl)amino]cyclohexyl}amino)-4-pyrimidinyl]-1,3-thiazol-4-yl}-2-fluorophenyl)-2,6-difluorobenzenesulfonamide

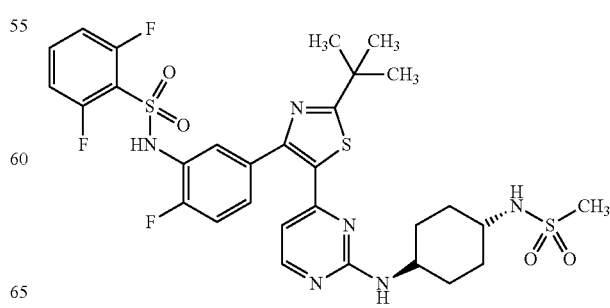

Step A: 1,1-Dimethylethyl {4-[(methylsulfonyl)amino]cyclohexyl}carbamate

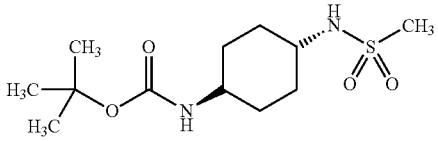

The trans-N-boc-1,4-cyclohexanediamine (1.00 g, 4.67 mmol) was dissolved in DCM (50 mL). Next, TEA was added (1.301 mL, 9.33 mmol), followed by methanesulfonyl chloride (0.397 mL, 5.13 mmol). The reaction was allowed to stir at rt for 22 h. The reaction mixture was partitioned between DCM (100 mL) and water (25 mL). The phases were separated and the aqueous phase was extracted with DCM (50 mL). Combined organic layer was dried over MgSO$_4$ for 20 h overnight. Filtered and evaporated to dryness to give the title compound of Step A as a solid (0.924 g). $^1$H NMR (400 MHz, DMSO-d$_6$) δ ppm 3.32 (s, 8H), 2.89 (s, 3H), 1.83-1.91 (m, 1H), 1.70-1.78 (m, 1H), 1.37 (s, 9H).

Step B: N-(4-Aminocyclohexyl)methanesulfonamide

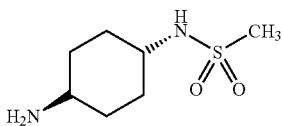

1,1-Dimethylethyl {4-[(methylsulfonyl)amino]cyclohexyl}carbamate (0.922 g, 3.15 mmol) was dissolved in DCM (50 mL). TFA was added (2.429 mL, 31.5 mmol) and the reaction allowed to stir at rt for 1 h. Evaporated off the volatiles and added DCM (50 mL) followed by evaporation of volatiles. The DCM addition/evaporation was repeated several times to give a maroon semi-solid. The residual semi-solid was treated with diethyl ether (10 mL) after which the suspension was sonicated and triturated, then filtered. Solids were triturated with more diethyl ether (10 mL). The product was suction dried to give title compound of Step B as a light pink solid (0.938 g). $^1$H NMR (400 MHz, DMSO-d$_6$) δ ppm 7.80 (br. s., 2H), 7.07 (d, J=7.2 Hz, 1H), 3.33 (s, 2H), 3.01-3.14 (m, 1H), 2.78-3.01 (m, 2H), 1.80-2.02 (m, 4H), 1.17-1.47 (m, 4H).

Step C: N-(5-{2-(1,1-Dimethylethyl)-5-[2-({trans-4-[(methylsulfonyl)amino]cyclohexyl}amino)-4-pyrimidinyl]-1,3-thiazol-4-yl}-2-fluorophenyl)-2,6-difluorobenzenesulfonamide N-{5-[5-(2-Chloro-4-pyrimidinyl)-2-(1,1-dimethylethyl)-1,3-thiazol-4-yl]-2-fluorophenyl}-2,6-difluorobenzenesulfonamide (50 mg, 0.093 mmol) and N-(4-aminocyclohexyl)-methanesulfonamide (19.62 mg, 0.102 mmol) were dissolved in n-butanol (1 mL) and TEA (0.052 mL, 0.371 mmol) was added. The reaction was stirred in a closed vessel at 90° C. for 18 h. The reaction mixture was cooled to rt and solvent was removed. The residue was purified via Gilson Acidic HPLC (10 to 90% gradient, Acetonitrile/H2O+TFA; C18 column). Desired fractions were combined and solvent removed to give the title compound as a white solid (0.006 g).

$^1$H NMR (400 MHz, DMSO-d$_6$) δ ppm 10.95 (s, 1H), 8.09 (d, J=5.0 Hz, 1H), 7.67-7.78 (m, 1H), 7.41 (d, J=3.5 Hz, 1H), 7.28 (q, J=8.7 Hz, 2H), 7.00 (dt, J=2.6, 1.3 Hz, 1H), 6.10-6.28 (m, 1H), 3.56-3.70 (m, 1H), 3.41-3.52 (m, 1H), 3.09 (td, J=4.2, 1.7 Hz, 1H), 2.92 (s, 3H), 1.83-1.98 (m, 4H), 1.21-1.50 (m, 13H). MS (ESI): 695 [M+H]$^+$.

Example 17

2,6-Difluoro-N-{3-[5-[2-({trans-4-[(methylsulfonyl)amino]cyclohexyl}amino)-4-pyrimidinyl]-2-(1-pyrrolidinyl)-1,3-thiazol-4-yl]phenyl}benzenesulfonamide

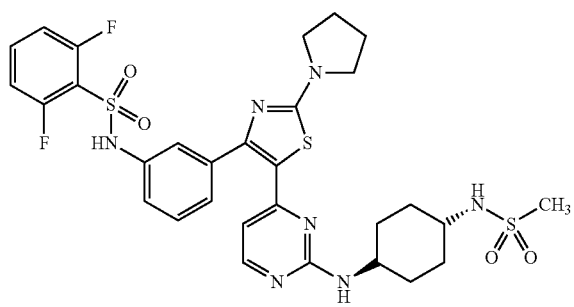

N-{3-[5-(2-Chloro-4-pyrimidinyl)-2-(1-pyrrolidinyl)-1,3-thiazol-4-yl]phenyl}-2,6-difluorobenzenesulfonamide was dissolved in n-butanol and N-(4-aminocyclohexyl)methanesulfonamide (27.0 mg, 0.140 mmol) was added at rt followed by TEA (52.2 μl, 0.375 mmol). The reaction was heated to 60° C. for 12 h. Purified via Gilson Acidic HPLC (10 to 90% gradient, Acetonitrile/H2O+TFA; C18 column). Desired fractions were combined and washed with NaHCO$_3$, dried over MgSO$_4$ and solvent removed to give the title compound as a yellow solid (0.010 g). $^1$H NMR (400 MHz, DMSO-d$_6$) δ ppm 7.73 (d, J=5.1 Hz, 1H), 7.38-7.55 (m, 1H), 7.11-7.31 (m, 2H), 6.93-7.10 (m, 3H), 6.72-6.88 (m, 1H), 6.42-6.48 (m, 1H), 6.28-6.35 (m, 1H), 5.79-5.88 (m, 1H), 3.52-3.63 (m, 1H), 3.29-3.45 (m, 6H), 3.05-3.16 (m, 1H), 2.91 (s, 3H), 1.77-2.02 (m, 6H), 1.19-1.42 (m, 4H). MS (ESI): 690 [M+H]$^+$.

Example 18

N-{2-Chloro-3-[5-{2-[(2-methylpropyl)amino]-4-pyrimidinyl}-2-(tetrahydro-2H-pyran-4-yl)-1,3-thiazol-4-yl]phenyl}-2,6-difluorobenzenesulfonamide

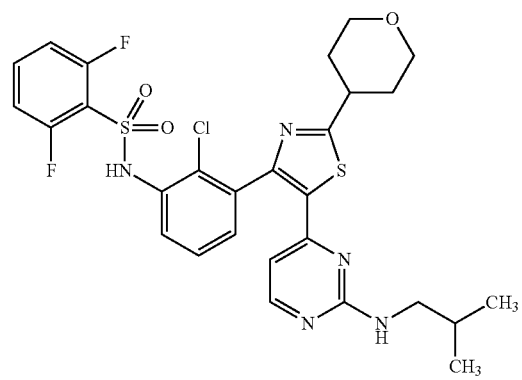 [SMILES: CC(C)CNc1nccc(-c2sc(C3CCOCC3)nc2-c2cccc(NS(=O)(=O)c3c(F)cccc3F)c2Cl)n1]

Step A: N-{2-Chloro-3-[5-(2-chloro-4-pyrimidinyl)-2-(tetrahydro-2H-pyran-4-yl)-1,3-thiazol-4-yl]phenyl}-2,6-difluorobenzenesulfonamide

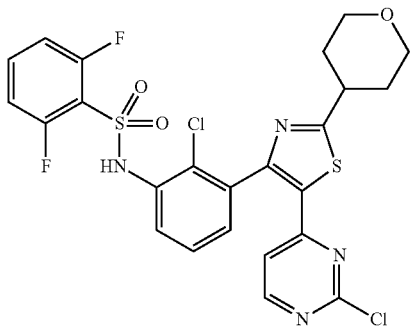

Recrystallized NBS (1.56 g, 8.8 mmol) was added to a suspension of N-{2-chloro-3-[(E)-2-(2-chloro-4-pyrimidinyl)-1-hydroxyethenyl]phenyl}-2,6-difluorobenzenesulfonamide (4.02 g, 8.80 mmol) in DMA (15 mL) in an ice-bath. The reaction was immediately removed from the ice bath and allowed to warm to rt over 0.5 h. Tetrahydro-2H-pyran-4-carbothioamide (1.27 g, 8.80 mmol) was added and the reaction warmed in an oil bath (rt to 65° C.). The reaction was diluted with water (100 mL) which caused the precipitation of a yellow solid. The solid was then dissolved by the addition of EtOAc (100 mL) and the phases separated. The aqueous phase was extracted with EtOAc (50 mL). The combined organic phase was filtered through Whatman 1 PS (phase separating) paper and concentrated under vacuum to a crude orange residue. The residue was purified by silica gel chromatography eluting with 0-100% EtOAc/hexanes to give the title compound of Step A as a bright yellow solid (2.56 g; 50.1% yield). $^1$H NMR (400 MHz, DMSO-d6) δ ppm 10.88 (s, 1H), 8.55 (d, J=5.4 Hz, 1H), 7.62-7.74 (m, 1H), 7.48-7.57 (m, 2H), 7.42-7.47 (m, 1H), 7.22 (t, J=9.1 Hz, 2H), 6.54 (d, J=5.3 Hz, 1H), 3.92 (d, J=11.0 Hz, 2H), 3.41-3.51 (m, 2H), 2.03 (br. s., 2H), 1.69-1.83 (m, J=12.1, 12.1, 11.9, 4.2 Hz, 2H).

Step B: 2,6-Difluoro-N-{2-fluoro-3-[5-{2-[(2-methylpropyl)amino]-4-pyrimidinyl}-2-(tetrahydro-2H-pyran-4-yl)-1,3-thiazol-4-yl]phenyl}benzenesulfonamide N-{2-chloro-3-[5-(2-chloro-4-pyrimidinyl)-2-(tetrahydro-2H-pyran-4-yl)-1,3-thiazol-4-yl]phenyl}-2,6-difluorobenzenesulfonamide (0.15 g, 0.26 mmol) and isobutylamine (0.15 g, 2.01 mmol) were combined in i-PrOH (3 mL) in a sealed vessel and heated at 80° C. for 16 h. The reaction was concentrated to a yellow solid that was dissolved in DCM and delivered on the top of a pre-pack (5 g) SiO$_2$ cartridge. The residue was purified by silica gel chromatography eluting with 0-100% DCM:MeOH:NH$_4$OH/84:15:1 in DCM. The resulting crude yellow product was dissolved with DCM (10 mL) and the addition of hexanes precipitated the title compound as a yellow solid, which was collected and air-dried (0.100 g, 58.4% yield). $^1$H NMR (400 MHz, DMSO-d6) δ ppm 10.82 (s, 1H), 8.01 (d, J=5.1 Hz, 1H), 7.62-7.73 (m, 1H), 7.50 (s, 1H), 7.45 (t, J=7.8 Hz, 1H), 7.35 (d, J=6.6 Hz, 2H), 7.21 (t, J=9.0 Hz, 2H), 5.66 (br. s., 1H), 3.91 (ddd, J=9.6, 2.0, 1.8 Hz, 2H), 3.41-3.50 (m, 2H), 3.22-3.31 (m, 1H), 2.97-3.09 (m, 2H), 1.98 (dd, J=12.8, 1.9 Hz, 2H), 1.84 (dt, J=13.5, 6.8 Hz, 1H), 1.65-1.78 (m, 2H), 0.87 (d, J=6.7 Hz, 6H). MS (ESI) 620.2 [M+H]$^+$.

Example 19

N-{2-Chloro-3-(2-(1,1-dimethylethyl)-5-{2-[(2-methylpropyl)amino]-4-pyrimidinyl}-1,3-thiazol-4-yl)phenyl}-2,6-difluorobenzenesulfonamide

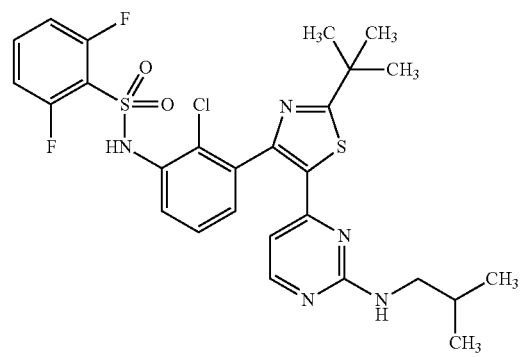 [SMILES: CC(C)CNc1nccc(-c2sc(C(C)(C)C)nc2-c2cccc(NS(=O)(=O)c3c(F)cccc3F)c2Cl)n1]

Step A: N-{2-Chloro-3-[5-(2-chloro-4-pyrimidinyl)-2-(1,1-dimethylethyl)-1,3-thiazol-4-yl]phenyl}-2,6-difluorobenzenesulfonamide

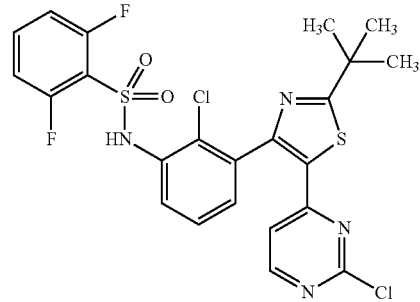 [SMILES: CC(C)(C)c1nc(-c2cccc(NS(=O)(=O)c3c(F)cccc3F)c2Cl)c(-c2ccnc(Cl)n2)s1]

Following a procedure analogous to the procedure described in Example 18, Step A using N-{2-chloro-3-[(E)-2-(2-chloro-4-pyrimidinyl)-1-hydroxyethenyl]phenyl}-2,6-difluorobenzenesulfonamide (4.03 g, 8.80 mmol) and 2,2-dimethylpropanethioamide (1.03 g, 8.80 mmol), the title compound was obtained as a bright yellow solid (2.25 g; 43.7% yield). $^1$H NMR (400 MHz, DMSO-d6) δ ppm 10.87 (s, 1H), 8.54 (d, J=5.3 Hz, 1H), 7.63-7.73 (m, 1H), 7.42-7.57 (m, 3H), 7.22 (t, J=9.2 Hz, 2H), 6.53 (d, J=5.3 Hz, 1H), 1.42 (s, 9H).

Step B: N-[2-Chloro-3-(2-(1,1-dimethylethyl)-5-{2-[(2-methylpropyl)amino]-4-pyrimidinyl}-1,3-thiazol-4-yl)phenyl]-2,6-difluorobenzenesulfonamide Following a procedure analogous to the procedure described in Example 18, Step B using N-{2-chloro-3-[5-(2-chloro-4-pyrimidinyl)-2-(1,1-dimethylethyl)-1,3-thiazol-4-yl]phenyl}-2,6-difluorobenzenesulfonamide (0.15 g, 0.28 mmol) and isobutylamine (0.15 g, 2.01 mmol), the title compound was obtained as a yellow solid (0.078 g, 45.4% yield).

¹H NMR (400 MHz, DMSO-d6) δ ppm 10.81 (s, 1H), 8.01 (d, J=5.1 Hz, 1H), 7.62-7.71 (m, 1H), 7.49-7.53 (m, 1H), 7.45 (t, J=7.7 Hz, 1H), 7.29-7.39 (m, 2H), 7.21 (t, J=9.1 Hz, 2H), 5.65 (d, 1H), 3.03 (br. s., 2H), 1.84 (dt, J=13.4, 6.7 Hz, 1H), 1.40 (s, 9H), 0.88 (d, J=6.6 Hz, 6H). MS (ESI) 592.2 [M+H]⁺.

Example 20

N-{2-Chloro-3-[5-{2-[(2-methylpropyl)amino]-4-pyrimidinyl}-2-(4-morpholinyl)-1,3-thiazol-4-yl]phenyl}-2,6-difluorobenzenesulfonamide

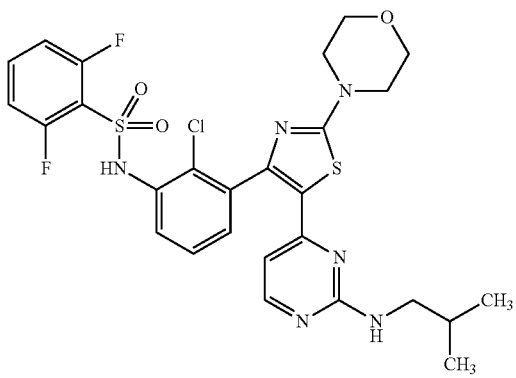 [SMILES: CC(C)CNc1nccc(-c2sc(N3CCOCC3)nc2-c2cccc(NS(=O)(=O)c3c(F)cccc3F)c2Cl)n1]

Step A: N-{2-Chloro-3-[5-(2-chloro-4-pyrimidinyl)-2-(4-morpholinyl)-1,3-thiazol-4-yl]phenyl}-2,6-difluorobenzenesulfonamide

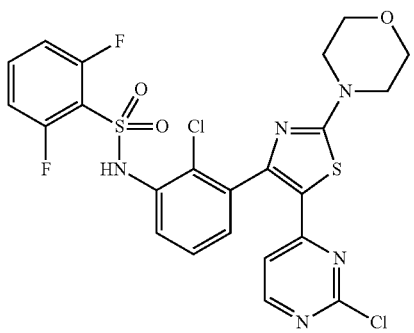 [SMILES: O=S(=O)(Nc1cccc(-c2nc(N3CCOCC3)sc2-c2ccnc(Cl)n2)c1Cl)c1c(F)cccc1F]

Following a procedure analogous to the procedure described in Example 18, Step A using N-{2-chloro-3-[(E)-2-(2-chloro-4-pyrimidinyl)-1-hydroxyethenyl]phenyl}-2,6-difluorobenzenesulfonamide (4.05 g, 8.83 mmol) and 4-morpholinecarbothioamide (1.29 g, 8.83 mmol), the title compound was obtained as a bright yellow solid (2.61 g; 48% yield). ¹H NMR (400 MHz, DMSO-d6) d ppm 10.87 (s, 1H), 8.29 (d, J=5.5 Hz, 1H), 7.64-7.74 (m, 1H), 7.46-7.56 (m, 2H), 7.39 (dd, J=7.1, 1.7 Hz, 1H), 7.23 (t, J=9.1 Hz, 2H), 6.19 (d, J=5.5 Hz, 1H), 3.71 (t, J=4.6 Hz, 4H), 3.54 (t, J=4.3 Hz, 4H).

Step B: N-{2-Chloro-3-[5-{2-[(2-methylpropyl)amino]-4-pyrimidinyl}-2-(4-morpholinyl)-1,3-thiazol-4-yl]phenyl}-2,6-difluorobenzenesulfonamide Following a procedure analogous to the procedure described in Example 18, Step B using N-{2-Chloro-3-[5-(2-chloro-4-pyrimidinyl)-2-(4-morpholinyl)-1,3-thiazol-4-yl]phenyl}-2,6-difluorobenzenesulfonamide (0.16 g, 0.27 mmol) and isobutylamine (0.15 g, 2.01 mmol), the title compound was obtained as a pale yellow solid (0.026 g; 14.1% yield). ¹H NMR (400 MHz, DMSO-d6) δ ppm 10.79 (s, 1H), 7.84 (d, J=5.3 Hz, 1H), 7.60-7.72 (m, 1H), 7.46-7.51 (m, 1H), 7.43 (t, J=7.6 Hz, 1H), 7.30 (d, J=6.9 Hz, 1H), 7.21 (t, J=9.1 Hz, 2H), 7.12 (d, J=0.5 Hz, 1H), 5.42 (d, J=4.9 Hz, 1H), 3.70 (t, J=4.6 Hz, 4H), 3.44 (t, J=4.6 Hz, 4H), 3.02 (t, J=6.2 Hz, 2H), 0.87 (d, J=6.7 Hz, 9H). MS (ESI) 621.2 [M+H]⁺.

Example 21

N-{3-[5-(2-Amino-4-pyrimidinyl)-2-(4-morpholinyl)-1,3-thiazol-4-yl]-2-chlorophenyl}-2,6-difluorobenzenesulfonamide

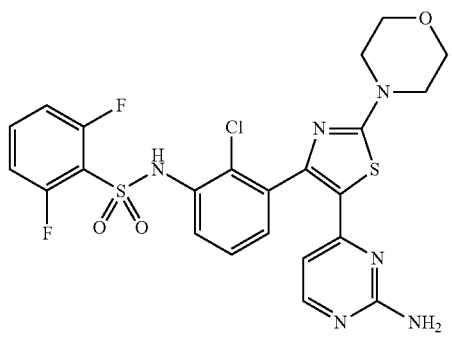 [SMILES: Nc1nccc(-c2sc(N3CCOCC3)nc2-c2cccc(NS(=O)(=O)c3c(F)cccc3F)c2Cl)n1]

In a pressure vessel was placed N-{2-Chloro-3-[5-(2-chloro-4-pyrimidinyl)-2-(4-morpholinyl)-1,3-thiazol-4-yl]phenyl}-2,6-difluorobenzenesulfonamide (300 mg, 0.513 mmol) and NH₄OH (2 mL) and 1,4-dioxane (2 mL) were added. The vessel was sealed and heated at 100° C. for 18 h. The reaction mixture was cooled, concentrated onto silica and the residue was column chromatographed to give the title compound (0.10 g, 35% yield). ¹H NMR (400 MHz, DMSO-d₆) d ppm 10.81 (br. s., 1H), 7.81 (d, J=5.3 Hz, 1H), 7.62-7.73 (m, 1H), 7.39-7.52 (m, 2H), 7.28-7.34 (m, 1H), 7.21 (t, J=9.1 Hz, 2H), 6.55 (s, 2H), 5.44 (d, J=5.3 Hz, 1H), 3.70 (t, J=4.7 Hz, 4H), 3.44 (t, J=4.6 Hz, 4H). MS (ES+): 566 [M+H]⁺.

Example 22

N-{2-Chloro-3-[5-{2-[(2-methylpropyl)amino]-4-pyrimidinyl}-2-(4-morpholinyl)-1,3-thiazol-4-yl]phenyl}-2,5-difluorobenzenesulfonamide

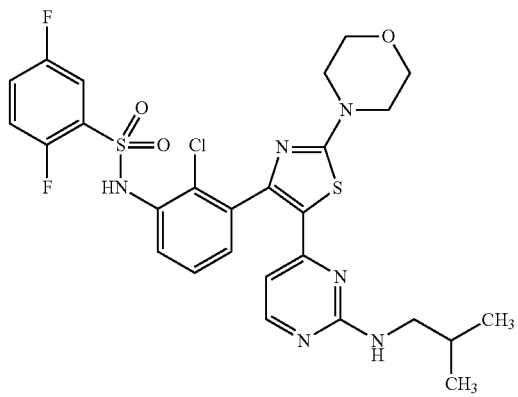 [SMILES: CC(C)CNc1nccc(-c2sc(N3CCOCC3)nc2-c2cccc(NS(=O)(=O)c3cc(F)ccc3F)c2Cl)n1]

Step A: N-{2-Chloro-3-[5-(2-chloro-4-pyrimidinyl)-2-(4-morpholinyl)-1,3-thiazol-4-yl]phenyl}-2,5-difluorobenzenesulfonamide

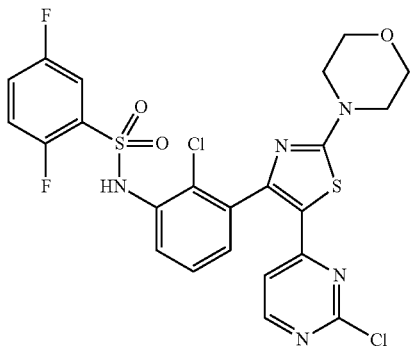 [SMILES: O=S(=O)(Nc1cccc(-c2nc(N3CCOCC3)sc2-c2ccnc(Cl)n2)c1Cl)c1cc(F)ccc1F]

Following a procedure analogous to the procedure described in Example 18, Step A using NBS (0.41 g, 2.29 mmol), N-{2-chloro-3-[(E)-2-(2-chloro-4-pyrimidinyl)-1-hydroxyethenyl]phenyl}-2,5-difluorobenzenesulfonamide (1.0 g, 2.18 mmol) and 4-morpholinecarbothioamide (0.35 g, 2.40 mmol) the title compound was obtained as a yellow solid (1.27 g; 95% yield). $^1$H NMR (400 MHz, DMSO-d6) δ ppm 10.74 (s, 1H), 8.31 (d, J=5.5 Hz, 1H), 7.28-7.75 (m, 8H), 6.20 (d, J=5.5 Hz, 1H), 3.71 (t, J=4.7 Hz, 4H), 3.54 (t, J=4.6 Hz, 4H).

Step B: N-{2-Chloro-3-[5-{2-[(2-methylpropyl)amino]-4-pyrimidinyl}-2-(4-morpholinyl)-1,3-thiazol-4-yl]phenyl}-2,5-difluorobenzenesulfonamide Following a procedure analogous to the procedure described in Example 18, Step B using N-{2-chloro-3-[5-(2-chloro-4-pyrimidinyl)-2-(4-morpholinyl)-1,3-thiazol-4-yl]phenyl}-2,5-difluorobenzenesulfonamide (0.15 g, 0.26 mmol) and isobutylamine (0.19 g, 2.57 mmol) the title compound was obtained as a yellow solid (0.132 g, 79% yield). $^1$H NMR (400 MHz, DMSO-d6) δ ppm 10.70 (br. s., 1H), 7.84 (d, J=4.9 Hz, 1H), 7.38-7.62 (m, 6H), 7.29 (d, J=7.1 Hz, 1H), 5.42 (d, J=4.9 Hz, 1H), 3.70 (br. s., 4H), 3.44 (br. s., 4H), 3.02 (d, J=5.8 Hz, 2H), 1.83 (ddd, J=12.8, 6.7, 6.5 Hz, 1H), 0.87 (d, J=6.5 Hz, 6H). m/z (ESI) 621.2 [M+H]$^+$.

Example 23

N-[2-Chloro-3-(2-(1,1-dimethylethyl)-5-{2-[(2-methylpropyl)amino]-4-pyrimidinyl}-1,3-thiazol-4-yl)phenyl]-2,5-difluorobenzenesulfonamide

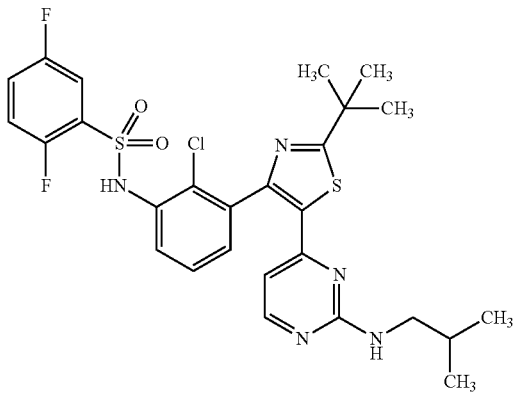 [SMILES: CC(C)CNc1nccc(-c2sc(C(C)(C)C)nc2-c2cccc(NS(=O)(=O)c3cc(F)ccc3F)c2Cl)n1]

Step A: N-{2-Chloro-3-[5-(2-chloro-4-pyrimidinyl)-2-(1,1-dimethylethyl)-1,3-thiazol-4-yl]phenyl}-2,5-difluorobenzenesulfonamide

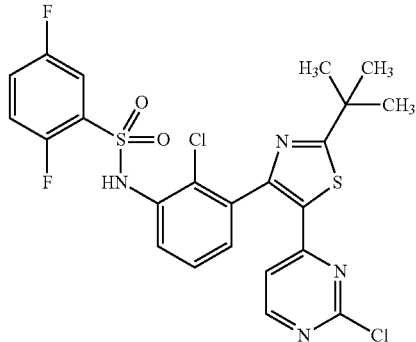 [SMILES: CC(C)(C)c1nc(-c2cccc(NS(=O)(=O)c3cc(F)ccc3F)c2Cl)c(-c2ccnc(Cl)n2)s1]

To a solution of N-{2-chloro-3-[(E)-2-(2-chloro-4-pyrimidinyl)-1-hydroxyethenyl]phenyl}-2,5-difluorobenzenesulfonamide (3.0 g, 6.55 mmol) in DMA (25 mL) was added NBS (1.165 g, 6.55 mmol). After stirring for 1 h at rt, 2,2-dimethylpropanethioamide (0.767 g, 6.55 mmol) was added and the reaction mixture was stirred at 80° C. for 2 h. The reaction mixture was diluted with EtOAc (100 mL) and extracted five times with water. The organic layer was dried over anhydrous NaSO$_4$, adsorbed onto silica gel, and purified via column chromatography, eluting with 0-50% EtOAc/DCM. The desired fractions were combined and concentrated to generate 1.31 g (2.36 mmol, 36.0% yield) of the title compound as a yellow powder. $^1$H NMR (400 MHz, DMSO-d$_6$): δ 10.74 (s, 1H), 8.56 (d, J=5.4 Hz, 1H), 7.41-7.58 (m, 6H), 6.57 (d, J=5.4 Hz, 1H), 1.42 (s, 9H). MS (ESI): 555.0 [M+H]+.

Step B: N-[2-Chloro-3-(2-(1,1-dimethylethyl)-5-{2-[(2-methylpropyl)amino]-4-pyrimidinyl}-1,3-thiazol-4-yl)phenyl]-2,5-difluorobenzenesulfonamide Following a procedure analogous to the procedure described in Example 18, Step B using N-{2-chloro-3-[5-(2-chloro-4-pyrimidinyl)-2-(1,1-dimethylethyl)-1,3-thiazol-4-yl]phenyl}-2,5-difluorobenzenesulfonamide (0.10 g; 0.18 mmol) and isobutylamine (0.13 g; 1.81 mmol) the title compound was obtained as a yellow solid (0.050 g, 44.6% yield). $^1$H NMR (400 MHz, DMSO-d6) δ ppm 10.70 (br. s., 1H), 8.00 (d, J=5.1 Hz, 1H), 7.40-7.60 (m, 5H), 7.28-7.37 (m, 2H), 5.65 (d, 1H), 3.01 (br. s., 2H), 1.76-1.89 (m, J=13.3, 6.7, 6.7, 6.7, 6.7 Hz, 1H), 1.39 (s, 9H), 0.87 (d, J=6.7 Hz, 6H). MS (ESI) 592.2 [M+H]$^+$.

Example 24

N-{3-[5-(2-Amino-4-pyrimidinyl)-2-(4-morpholinyl)-1,3-thiazol-4-yl]-2-chlorophenyl}-2-furansulfonamide

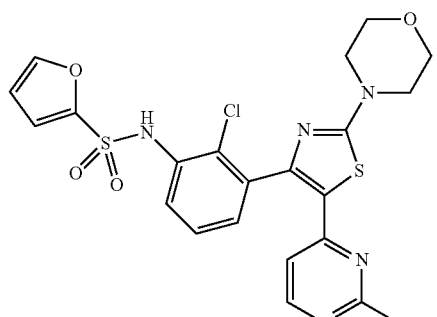

Step A: Methyl 2-chloro-3-{[(2-propen-1-yloxy)carbonyl]amino}benzoate

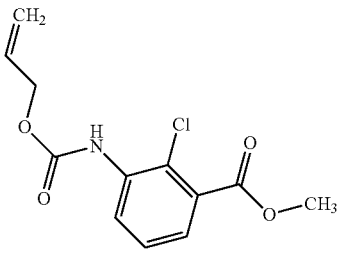 [SMILES: C=CCOC(=O)Nc1cccc(C(=O)OC)c1Cl]

To a solution of methyl 3-amino-2-chlorobenzoate (29 g, 0.162 mol) in THF (50 mL) and saturated NaHCO$_3$ (200 mL) was added 2-propen-1-yl chloridocarbonate (24 g, 0.194 mol) dropwise at 0° C. The reaction mixture was allowed to warm to rt for 2 h. The reaction was extracted with EtOAc (2×200 mL). The organic layer was dried over Na$_2$SO$_4$, and the solvent was removed to give the crude product of Step A, which was directly used to the next step. (42 g, 96.3% yield). $^1$H NMR (400 MHz, CDCl$_3$) δ ppm 8.30-8.37 (m, 1H), 7.47-7.51 (m, 1H), 7.35-7.43 (br, 1H), 7.28-7.33 (m, 1H), 5.90-6.06 (m, 1H), 5.25-5.41 (m, 2H), 4.68-4.70 (m, 2H), 3.91 (s, 3H).

Step B: 2-Propen-1-yl {2-chloro-3-[(E)-2-(2-chloro-4-pyrimidinyl)-1-hydroxyethenyl]phenyl}carbamate

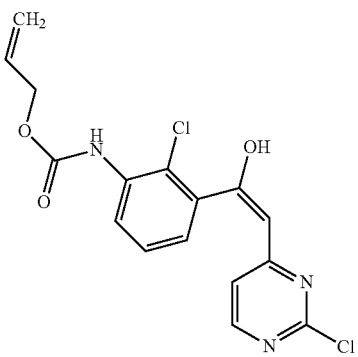 [SMILES: C=CCOC(=O)Nc1cccc(/C(O)=C\c2ccnc(Cl)n2)c1Cl]

Following a procedure analogous to the procedure described in Intermediate 5, Step B using methyl 2-chloro-3-{[(2-propen-1-yloxy)carbonyl]amino}benzoate (30 g, 0.11 mol) and 2-chloro-4-methylpyrimidine (15.8 g, 0.12 mol) the title compound of Step B was prepared (29 g, 79.6% yield). $^1$H NMR (400 MHz, CDCl$_3$) δ ppm 13.52-13.58 (br, 0.9H), 8.41-8.42 (m, 1H), 8.22-8.27 (m, 1H), 7.28-7.35 (m, 2.2H), 7.21-7.24 (m, 1.2H), 6.85-6.88 (m, 1H), 5.91-6.02 (m, 1H), 5.73 (s, 1H), 5.23-5.40 (m, 2H), 4.66-4.70 (m, 2H).

Step C: 2-Propen-1-yl {2-chloro-3-[5-(2-chloro-4-pyrimidinyl)-2-(4-morpholinyl)-1,3-thiazol-4-yl]phenyl}carbamate

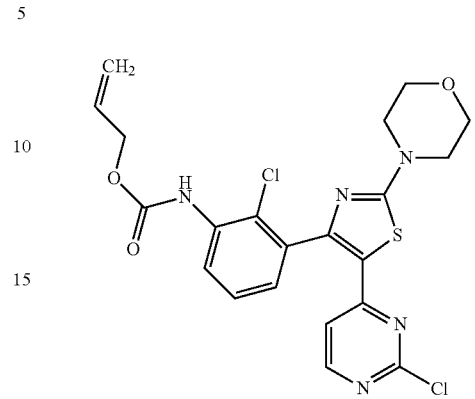

Following a procedure analogous to the procedure described in Example 18, Step A using 2-propen-1-yl {2-chloro-3-[(2-chloro-4-pyrimidinyl)acetyl]phenyl}carbamate (3.00 g, 8.19 mmol), NBS (1.531 g, 8.60 mmol) and 4-morpholinecarbothioamide (1.677 g, 11.47 mmol) the title compound of Step C was obtained as an orange solid (4.03 g, 7.86 mmol, 96% yield). $^1$H NMR (400 MHz, DMSO-d$_6$) δ ppm 9.29 (s, 1H), 8.33 (d, J=5.5 Hz, 1H), 7.67-7.84 (m, 1H), 7.48 (t, J=7.8 Hz, 1H), 7.29 (dd, J=7.7, 1.5 Hz, 1H), 6.41 (d, J=5.5 Hz, 1H), 5.83-6.08 (m, 1H), 5.36 (dd, J=17.2, 1.5 Hz, 1H), 5.23 (dd, J=10.4, 1.5 Hz, 1H), 4.62 (d, J=5.3 Hz, 2H), 3.73 (t, J=4.8 Hz, 4H), 3.57 (t, J=4.8 Hz, 4H). MS (ESI): 491.98 [M+H]$^+$.

Step D: {2-Chloro-3-[5-(2-chloro-4-pyrimidinyl)-2-(4-morpholinyl)-1,3-thiazol-4-yl]phenyl}amine

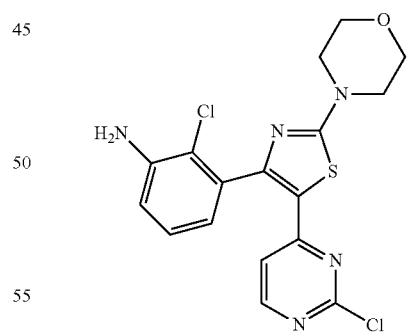

Following a procedure analogous to the procedure described in Intermediate 13 using 2-propen-1-yl {2-chloro-3-[5-(2-chloro-4-pyrimidinyl)-2-(4-morpholinyl)-1,3-thiazol-4-yl]phenyl}carbamate (2.50 g, 5.08 mmol) the title compound of Step D was obtained as a yellow solid (2.08 g, 4.99 mmol, 98% yield). MS (ESI): 407.97 [M+H]$^+$.

Step E: N-{2-Chloro-3-[5-(2-chloro-4-pyrimidinyl)-2-(4-morpholinyl)-1,3-thiazol-4-yl]phenyl}-2-furansulfonamide

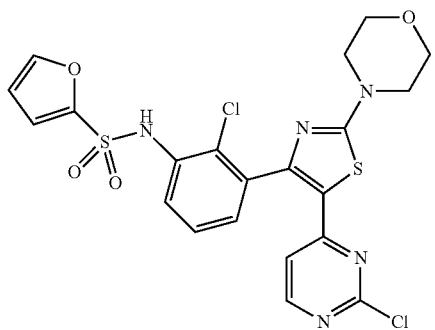 [SMILES: O=S(=O)(Nc1cccc(-c2nc(N3CCOCC3)sc2-c2ccnc(Cl)n2)c1Cl)c1ccco1]

Following a procedure analogous to the procedure described in Intermediate 14 using {2-chloro-3-[5-(2-chloro-4-pyrimidinyl)-2-(4-morpholinyl)-1,3-thiazol-4-yl]phenyl}amine (1.03 g, 2.52 mmol) and 2-furansulfonyl chloride (0.588 g, 3.53 mmol) the title compound of Step E was obtained as an off-white solid (430 mg, 0.735 mmol, 29.1% yield). $^1$H NMR (400 MHz, DMSO-$d_6$) δ ppm 10.53 (s, 1H), 8.38 (d, J=5.5 Hz, 1H), 7.91 (d, J=0.9 Hz, 1H), 7.43-7.58 (m, 2H), 7.31-7.43 (m, 1H), 7.08 (d, J=3.5 Hz, 1H), 6.55 (dd, J=3.5, 1.8 Hz, 1H), 6.18 (d, J=5.5 Hz, 1H), 3.71 (t, J=4.8 Hz, 4H), 3.55 (t, J=4.7 Hz, 4H). MS (ESI): 537.96 [M+H]$^+$.

Step F: N-{3-[5-(2-Amino-4-pyrimidinyl)-2-(4-morpholinyl)-1,3-thiazol-4-yl]-2-chlorophenyl}-2-furansulfonamide Following a procedure analogous to the procedure described in Example 21 using N-{2-chloro-3-[5-(2-chloro-4-pyrimidinyl)-2-(4-morpholinyl)-1,3-thiazol-4-yl]phenyl}-2-furansulfonamide (0.100 g, 0.186 mmol) and ammonium hydroxide (1.21 mL, 9.29 mmol) heated to 120° C. for 20 min in a microwave reactor the title compound was obtained as a white solid (54 mg, 0.104 mmol, 56.0% yield). $^1$H NMR (400 MHz, DMSO-$d_6$) δ ppm 10.47 (s, 1H), 7.90 (d, J=5.5 Hz, 2H), 7.43 (d, J=3.8 Hz, 2H), 7.30 (d, J=3.3 Hz, 1H), 7.03 (d, J=3.3 Hz, 1H), 6.43-6.62 (m, 3H), 5.47 (d, J=5.3 Hz, 1H), 3.71 (t, J=4.7 Hz, 4H), 3.45 (t, J=4.7 Hz, 4H). MS (ESI): 519.00 [M+H]$^+$.

Example 25

N-{2-Chloro-3-[5-(2-methyl-4-pyrimidinyl)-2-(tetrahydro-2H-pyran-4-yl)-1,3-thiazol-4-yl]phenyl}-2,6-difluorobenzenesulfonamide trifluoroacetate

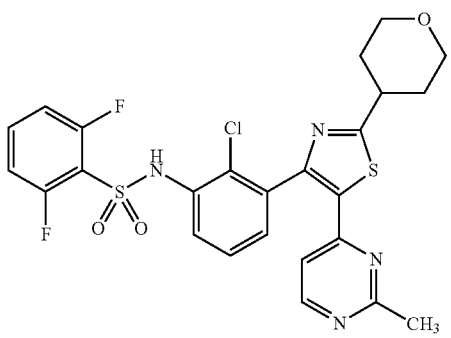

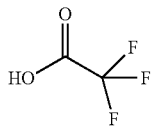

A solution of N-{2-chloro-3-[5-(2-chloro-4-pyrimidinyl)-2-(tetrahydro-2H-pyran-4-yl)-1,3-thiazol-4-yl]phenyl}-2,6-difluorobenzenesulfonamide (0.16 g; 0.27 mmol) in 1,4-dioxane (4 mL) with PdCl$_2$(dppf) (0.055 g, 0.075 mmol) was degassed for 5 min. To this mixture was added 2.0 M dimethylzinc in toluene (0.4 mL, 0.80 mmol). The reaction mixture was heated to 80° C. After 2 h, the reaction was quenched slowly with MeOH (25 mL). The reaction was further diluted with DCM (50 mL), filtered through a nylon membrane and evaporated to a crude yellow residue. Purification was accomplished with a C-18 reverse phase column running a gradient of 10-90% MeCN/H$_2$O (+0.1% TFA) over 14 min to afford the title compound as an ivory solid (0.051 g; 27.1% yield). $^1$H NMR (400 MHz, DMSO-d6) δ ppm 10.84 (s, 1H), 8.45 (d, J=5.4 Hz, 1H), 7.61-7.73 (m, 1H), 7.51-7.55 (m, 1H), 7.48 (t, J=7.7 Hz, 1H), 7.41 (dd, J=7.3, 1.9 Hz, 1H), 7.21 (t, J=9.1 Hz, 2H), 6.35 (d, J=5.4 Hz, 1H), 3.92 (ddd, J=9.6, 2.0, 1.8 Hz, 2H), 3.46 (td, J=11.5, 1.9 Hz, 2H), 3.25-3.35 (m, 1H), 2.58 (s, 3H), 2.01 (dd, J=12.7, 2.0 Hz, 2H), 1.68-1.81 (m, 2H). MS (ESI) 563.1 [M+H]$^+$.

Example 26

N-{2-Chloro-3-[5-(4-pyrimidinyl)-2-(tetrahydro-2H-pyran-4-yl)-1,3-thiazol-4-yl]phenyl}-2,6-difluorobenzenesulfonamide

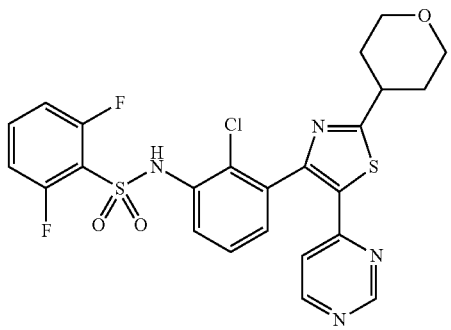

To a solution of N-{2-chloro-3-[5-(2-chloro-4-pyrimidinyl)-2-(tetrahydro-2H-pyran-4-yl)-1,3-thiazol-4-yl]phenyl}-2,6-difluorobenzenesulfonamide (0.15 g, 0.26 mmol) and ammonium formate (0.17 g, 2.6 mmol) in EtOAc (7 mL) and MeOH (7 mL) was added 20% palladium hydroxide on carbon (0.17 g, 0.24 mmol). The reaction mixture was heated to 60° C. for 2 h. The palladium was filtered off using a nylon membrane. The filtrate was concentrated under vacuum to a crude yellow solid. The residue was purified by silica gel chromatography eluting 0-100% EtOAC/hexanes. The resulting solid was dissolved in DCM (5 mL) and hexanes added to afford the title compound as a pale yellow solid (58 mg, 38.3% yield). $^1$H NMR (400 MHz, DMSO-d6) δ ppm 10.85 (s, 1H), 9.11 (d, J=1.3 Hz, 1H), 8.57 (d, J=5.4 Hz, 1H), 7.60-7.73 (m, 1H), 7.52-7.55 (m, 1H), 7.49 (t, J=7.7 Hz, 1H), 7.41-7.45 (m, 1H), 7.20 (t, J=9.1 Hz, 2H), 6.56 (dd, J=5.4, 1.3 Hz, 1H), 3.92 (ddd, J=9.6, 2.0, 1.9 Hz, 2H), 3.46 (td, J=11.6, 1.9 Hz, 2H), 2.00 (dd, J=12.8, 1.9 Hz, 2H), 1.68-1.80 (m, 2H), *Note: The methine (—H) peak of the THP (tetrahydro-2H-pyran-4-yl) group is submerged under the water peak at 3.33 ppm causing broadening. MS (ESI) 549.1 [M+H]+.

Example 27

N-{2-Chloro-3-[2-(4-morpholinyl)-5-(4-pyrimidinyl)-1,3-thiazol-4-yl]phenyl}-2,6-difluorobenzenesulfonamide

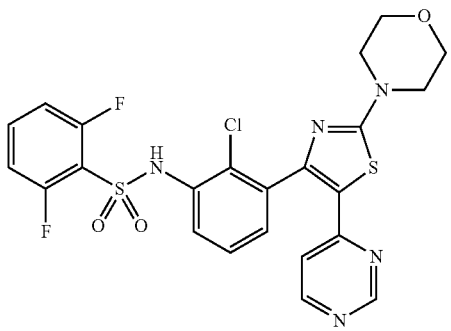 [SMILES: O=S(=O)(Nc1cccc(-c2nc(N3CCOCC3)sc2-c2ccncn2)c1Cl)c1c(F)cccc1F]

To a solution of N-{2-chloro-3-[5-(2-chloro-4-pyrimidinyl)-2-(4-morpholinyl)-1,3-thiazol-4-yl]phenyl}-2,6-difluorobenzenesulfonamide (0.15 g, 0.26 mmol) and ammonium formate (0.16 g, 2.6 mmol) in EtOAc (7 mL) and MeOH (7 mL) was added 20% palladium hydroxide on carbon (0.16 g, 0.23 mmol). The reaction mixture was heated to 60° C. for 2 h. The palladium was filtered off using a nylon membrane. The filtrate was concentrated under vacuum to a crude yellow solid. The residue was purified by silica gel chromatography eluting 10-100% EtOAc/hexanes to afford the title compound as a bright yellow solid (0.045 g; 29.7% yield). $^1$H NMR (400 MHz, DMSO-d6) δ ppm 10.85 (s, 1H), 8.96 (d, J=1.3 Hz, 1H), 8.36 (d, J=5.6 Hz, 1H), 7.62-7.75 (m, 1H), 7.44-7.55 (m, 2H), 7.38 (d, J=6.1 Hz, 1H), 7.22 (t, J=9.1 Hz, 2H), 6.25 (dd, J=5.6, 1.3 Hz, 1H), 3.66-3.76 (m, 4H), 3.46-3.54 (m, 4H). MS (ESI) 550.1 [M+H]+.

Example 28

N-{2-Chloro-3-[5-(2-methyl-4-pyrimidinyl)-2-(4-morpholinyl)-1,3-thiazol-4-yl]phenyl}-2,5-difluorobenzenesulfonamide

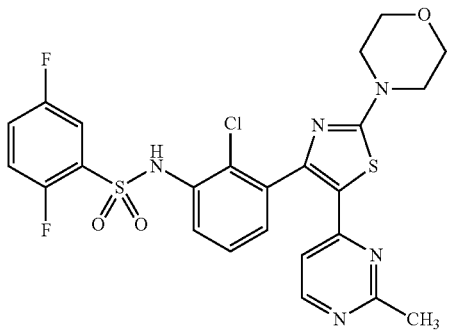 [SMILES: Cc1nccc(-c2sc(N3CCOCC3)nc2-c2cccc(NS(=O)(=O)c3cc(F)ccc3F)c2Cl)n1]

A solution of N-{2-chloro-3-[5-(2-chloro-4-pyrimidinyl)-2-(4-morpholinyl)-1,3-thiazol-4-yl]phenyl}-2,5-difluorobenzenesulfonamide (0.15 g, 0.26 mmol) in 1,4-dioxane (3 mL) with PdCl$_2$(dppf) (0.047 g, 0.064 mmol) was degassed for 5 min. To this mixture was added 2.0 M dimethylzinc in toluene (0.39 mL, 0.77 mmol). The reaction mixture was heated to 80° C. After 2 h, the reaction was quenched slowly with MeOH (15 mL) and then was further diluted with DCM (50 mL), filtered through a nylon membrane and evaporated to a crude yellow residue. The residue was purified by silica gel chromatography eluting 0-100% EtOAC/hexanes, followed by 10% EtOH/EtOAc. The resulting solid was dissolved in DCM (10 mL) and hexanes (20 mL) added to afford the title compound as a yellow solid (0.02 g; 13.1% yield). $^1$H NMR (400 MHz, DMSO-d6) δ ppm 10.72 (s, 1H), 8.26 (d, J=5.6 Hz, 1H), 7.51-7.60 (m, 2H), 7.40-7.50 (m, 3H), 7.32-7.39 (m, 1H), 6.07 (d, J=5.5 Hz, 1H), 3.71 (t, J=4.8 Hz, 4H), 3.48-3.53 (m, 4H) *Note: The 2-Me group is submerged under the water peak at 2.5 ppm. MS (ESI) 564.1 [M+H]+.

Example 29

2,4-Difluoro-N-{2-fluoro-5-[2-(1-methylethyl)-5-(2-{[2-(methylsulfonyl)ethyl]amino}-4-pyrimidinyl)-1,3-thiazol-4-yl]phenyl}benzenesulfonamide

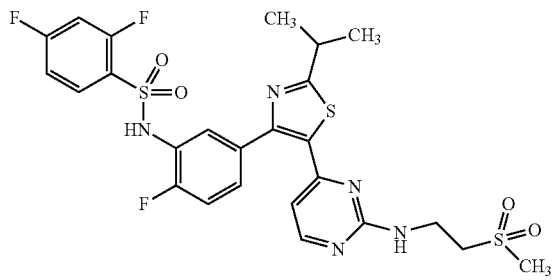 [SMILES: CC(C)c1nc(-c2ccc(F)c(NS(=O)(=O)c3ccc(F)cc3F)c2)c(-c2ccnc(NCCS(C)(=O)=O)n2)s1]

Step A: N-{5-[5-(2-Chloro-4-pyrimidinyl)-2-(1-methylethyl)-1,3-thiazol-4-yl]-2-fluorophenyl}-2,4-difluorobenzenesulfonamide

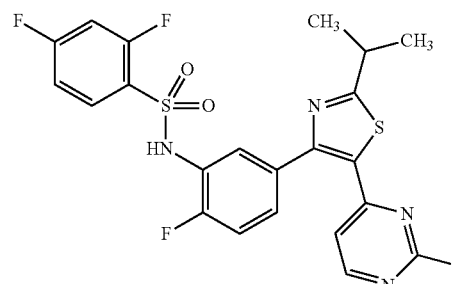

To a solution of 5-[5-(2-chloro-4-pyrimidinyl)-2-(1-methylethyl)-1,3-thiazol-4-yl]-2-fluoroaniline (12 g, 34.4 mmol) in DCM (100 mL) was added pyridine (8.2 g, 103 mmol). The mixture was cooled to 0° C. 2,4-Difluorobenzene-1-sulfonyl chloride (7.32 g, 34.4 mmol) in DCM (30 mL) was added dropwise to the mixture. The reaction was stirred at rt for 4 h.

Then the reaction was washed with water (200 mL), and extracted with DCM (2×200 mL). The organic layer was washed with brine, dried over anhydrous NaSO₄, filtrated and concentrated under reduced pressure to give the crude product, which was purified by column chromatography on silica gel (petroleum ether:DCM 1:1) to afford the title compound (9.0 g, 49.8% yield). $^1$H NMR (400 MHz, DMSO-d6) δ ppm 10.63-10.70 (br, 1H), 8.55 (d, J=5.3 Hz, 1H), 7.71-7.82 (m, 1H), 7.50-7.57 (m, 1H), 7.41-7.48 (m, 1H), 7.34-7.40 (m, 1H), 7.24-7.32 (m, 1H), 7.15-7.23 (m, 1H), 7.08 (d, J=5.3, 1H), 3.27-3.37 (m, 1H), 1.36 (d, J=6.8 Hz, 6H). MS (ES+): 525 [M+H]⁺.

Step B: 2,4-Difluoro-N-{2-fluoro-5-[2-(1-methylethyl)-5-(2-{[2-(methylsulfonyl)ethyl]amino}-4-pyrimidinyl)-1,3-thiazol-4-yl]phenyl}benzenesulfonamide

[2-(Methylsulfonyl)ethyl]amine (352 mg, 2.86 mmol) and N-{5-[5-(2-chloro-4-pyrimidinyl)-2-(1-methylethyl)-1,3-thiazol-4-yl]-2-fluorophenyl}-2,4-difluorobenzenesulfonamide (150 mg, 0.286 mmol) were combined and heated to 55° C. overnight. Isopropanol (1 mL) was added to the reaction mixture and stirred an additional 30 min. The reaction mixture was cooled to rt and partitioned between DCM and 10% aqueous HCl. The organic layer was separated and dried over MgSO₄, filtered, and concentrated over silica gel. The crude product was chromatographed on silica gel eluting with 100% DCM to 6:4 [DCM:(9:1 EtOAc:MeOH)]. The clean fractions were combined and concentrated to obtain the title compound as a white foam (82.1 mg; 45% yield). $^1$H NMR (400 MHz, DMSO-d₆) δ ppm 10.65 (s, 1H) 8.14 (d, J=4.2 Hz, 1H) 7.72 (q, J=7.6 Hz, 1H) 7.54 (t, J=9.7 Hz, 1H) 7.47 (br. s., 1H) 7.30-7.42 (m, 2H) 7.11-7.30 (m, 2H) 6.23 (d, J=1.2 Hz, 1H) 3.64 (d, J=0.9 Hz, 2H) 3.20-3.40 (m, 2H range includes water peak) 2.99 (s, 3H) 1.33 (d, J=6.7 Hz, 6H). MS (ESI): 612.2 [M+H]⁺.

Example 30

N-{3-[2-(1-Methylethyl)-5-(2-{[2-(methylsulfonyl)ethyl]amino}-4-pyrimidinyl)-1,3-thiazol-4-yl]phenyl}-2-furansulfonamide

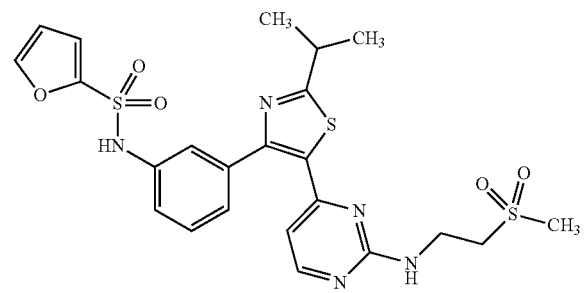 [SMILES: CC(C)c1nc(-c2cccc(NS(=O)(=O)c3ccco3)c2)c(-c2ccnc(NCCS(C)(=O)=O)n2)s1]

Step A: N-{3-[5-(2-Chloro-4-pyrimidinyl)-2-(1-methylethyl)-1,3-thiazol-4-yl]phenyl}-2-furansulfonamide

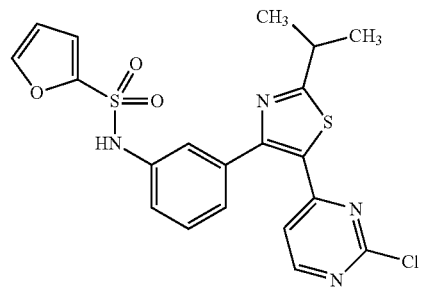 [SMILES: CC(C)c1nc(-c2cccc(NS(=O)(=O)c3ccco3)c2)c(-c2ccnc(Cl)n2)s1]

Following a procedure analogous to the procedure described in Intermediate 14 using 3-[5-(2-chloro-4-pyrimidinyl)-2-(1-methylethyl)-1,3-thiazol-4-yl]aniline (3 g, 9.1 mmol) and furan-2-sulfonyl chloride (1.81 g, 10.9 mmol) the title compound was obtained (2.0 g, 48.9% yield). $^1$H NMR (400 MHz, DMSO-d6) δ ppm 10.74-10.87 (br, 1H), 8.53 (d, J=5.3 Hz, 1H), 7.91-7.93 (m, 1H), 7.33-7.38 (m, 1H), 7.21-7.28 (m, 3H), 7.10-7.13 (m, 1H), 6.98 (d, J=5.3 Hz, 1H), 6.57-6.60 (m, 1H), 3.23-3.35 (m, 1H), 1.36 (d, J=6.8 Hz, 6H). MS (ES+): 661 [M+H]⁺.

Step B: N-{3-[2-(1-Methylethyl)-5-(2-{[2-(methylsulfonyl)ethyl]amino}-4-pyrimidinyl)-1,3-thiazol-4-yl]phenyl}-2-furansulfonamide

[2-(Methylsulfonyl)ethyl]amine (267 mg, 2.169 mmol) and N-{3-[5-(2-chloro-4-pyrimidinyl)-2-(1-methylethyl)-1,3-thiazol-4-yl]phenyl}-2-furansulfonamide (100 mg, 0.217 mmol) were combined and heated to 56° C. overnight. The reaction mixture was cooled to rt and diluted with DCM and 10% aqueous HCl. The layers were separated and the water layer was extracted twice more with DCM. The combined organic layers were dried over MgSO₄, filtered and concentrated to yield an oil. The oil was chromatographed on silica gel eluting with 100% DCM to 4:6 [DCM:(9:1 EtOAc:MeOH)]. The clean fractions were combined and concentrated to yield an oil. Diethyl ether was added to the oil and concentrated to obtain the title compound as a light brown solid (25.1 mg, 20% yield). $^1$H NMR (400 MHz, DMSO-d₆ heated to 60° C.) δ ppm 10.53-10.65 (m, 1H) 8.06-8.16 (m, 1H) 7.88 (s, 1H) 7.30-7.42 (m, 1H) 7.16-7.30 (m, 4H) 7.05 (d, J=3.6 Hz, 1H) 6.53-6.65 (m, 1H) 6.14-6.27 (m, 1H) 3.59-3.74 (m, 2H) 3.24-3.43 (m, 3H) 2.97 (br. s., 3H) 1.36 (dd, J=6.6, 2.7 Hz, 6H). MS (ESI): 548.0[M+H]⁺.

Example 31

N-{3-[2-(1-Methylethyl)-5-(2-{[2-(methylsulfonyl)ethyl]amino}-4-pyrimidinyl)-1,3-thiazol-4-yl]phenyl}-2-thiophenesulfonamide

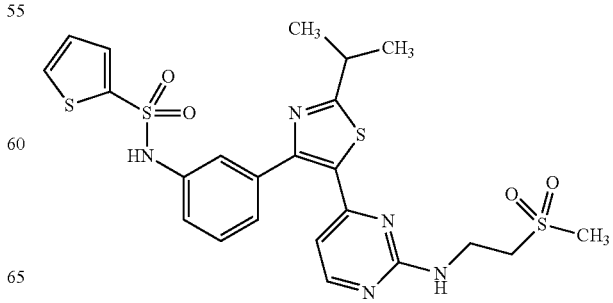

Step A: N-{3-[5-(2-Chloro-4-pyrimidinyl)-2-(1-methylethyl)-1,3-thiazol-4-yl]phenyl}-2-thiophenesulfonamide

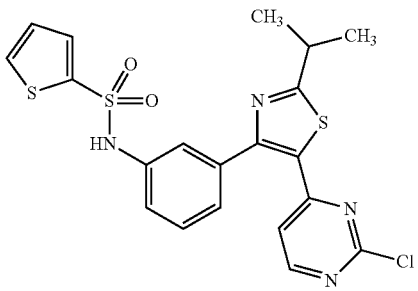 [SMILES: CC(C)c1nc(-c2cccc(NS(=O)(=O)c3cccs3)c2)c(-c2ccnc(Cl)n2)s1]

Following a procedure analogous to the procedure described in Intermediate 14, using 3-[5-(2-chloro-4-pyrimidinyl)-2-(1-methylethyl)-1,3-thiazol-4-yl]aniline (600 mg, 1.8 mmol) and thiophene-2-sulfonyl chloride (331 mg, 1.1 mmol) the title compound was obtained (760 mg, 87.8% yield). $^1$H NMR (400 MHz, CDCl$_3$) δ ppm 8.27 (d, J=5.3 Hz, 1H), 7.51-7.57 (m, 2H), 7.29-7.38 (m, 2H), 7.20-7.27 (m, 2H), 7.13-7.17 (br, 1H), 6.98-7.03 (m, 1H), 6.88 (d, J=5.3 Hz, 1H), 3.27-3.37 (m, 1H), 1.43 (d, J=7.1 Hz, 6H). MS (ES+): 477 [M+H]$^+$.

Step B: N-{3-[2-(1-Methylethyl)-5-(2-{[2-(methylsulfonyl)ethyl]amino}-4-pyrimidinyl)-1,3-thiazol-4-yl]phenyl}-2-thiophenesulfonamide Following a procedure analogous to the procedure described in Example 1 using 2-aminoethyl-methyl-sulfone (258 mg, 2.096 mmol) and N-{3-[5-(2-chloro-4-pyrimidinyl)-2-(1-methylethyl)-1,3-thiazol-4-yl]phenyl}-2-thiophenesulfonamide (100 mg, 0.210 mmol) the title compound was obtained as a light yellow solid (20 mg, 17% yield). $^1$H NMR (400 MHz, DMSO-d$_6$) δ ppm 10.49 (s, 1H) 8.07 (d, J=4.9 Hz, 1H) 7.82-7.92 (m, 1H) 7.46-7.52 (m, 1H) 7.37-7.46 (m, 1H) 7.28-7.36 (m, 1H) 7.12-7.25 (m, 3H) 7.04-7.12 (m, 1H) 6.04-6.14 (m, 1H) 3.55-3.69 (m, 2H) 3.30-3.37 (m, 3H) 2.97 (s, 3H) 1.32 (d, J=6.8 Hz, 6H). MS (ESI): 564.1[M+H]$^+$.

Example 32

2,6-Difluoro-N-{3-[5-(2-{[2-(methylsulfonyl)ethyl]amino}-4-pyrimidinyl)-2-(1-pyrrolidinyl)-1,3-thiazol-4-yl]phenyl}benzenesulfonamide

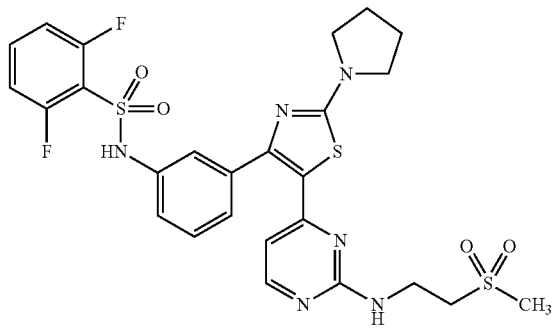 [SMILES: CS(=O)(=O)CCNc1nccc(-c2sc(N3CCCC3)nc2-c2cccc(NS(=O)(=O)c3c(F)cccc3F)c2)n1]

Following a procedure analogous to the procedure described in Example 1 using 2-aminoethyl-methyl-sulfone (923 mg, 7.49 mmol) and N-{3-[5-(2-chloro-4-pyrimidinyl)-2-(1-pyrrolidinyl)-1,3-thiazol-4-yl]phenyl}-2,6-difluorobenzenesulfonamide (400 mg, 0.749 mmol) the title compound was obtained as a white solid (27 mg, 4% yield). $^1$H NMR (400 MHz, DMSO-d$_6$) δ ppm 10.87-11.12 (m, 1H) 7.75 (d, J=5.4 Hz, 1H) 7.55-7.72 (m, 1H) 7.24-7.38 (m, 1H) 7.10-7.25 (m, 4H) 7.08 (d, J=7.8 Hz, 1H) 5.57-5.85 (m, 1H) 3.54-3.70 (m, 2H) 3.29-3.43 (m, 7H) 2.88-3.05 (m, 4H) 1.86-2.04 (m, 3H). MS (ESI): 621.1 [M+H]$^+$.

Example 33

N-{3-[2-(1-Methylethyl)-5-(2-{[2-(methylsulfonyl)ethyl]amino}-4-pyrimidinyl)-1,3-thiazol-4-yl]phenyl}-3-pyridinesulfonamide

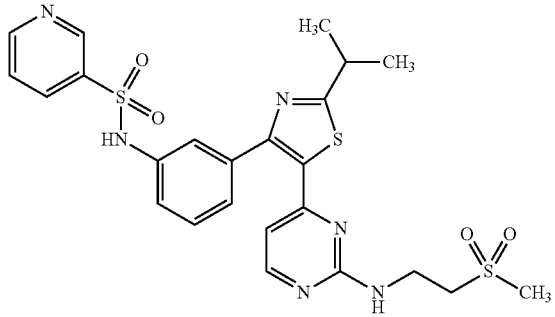 [SMILES: CC(C)c1nc(-c2cccc(NS(=O)(=O)c3cccnc3)c2)c(-c2ccnc(NCCS(C)(=O)=O)n2)s1]

Step A: N-{3-[5-(2-Chloro-4-pyrimidinyl)-2-(1-methylethyl)-1,3-thiazol-4-yl]phenyl}-3-pyridinesulfonamide

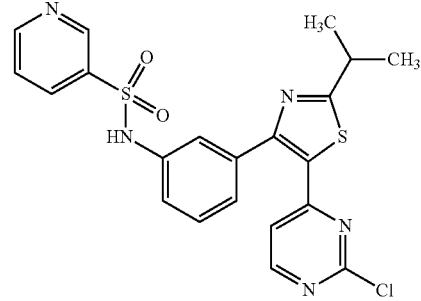 [SMILES: CC(C)c1nc(-c2cccc(NS(=O)(=O)c3cccnc3)c2)c(-c2ccnc(Cl)n2)s1]

Following a procedure analogous to the procedure described in Intermediate 14 using 3-[5-(2-Chloro-4-pyrimidinyl)-2-(1-methylethyl)-1,3-thiazol-4-yl]aniline (3 g, 9.1 mmol) and pyridine-3-sulfonyl chloride (1.93 g, 10.9 mmol) the title compound was obtained (3.1 g, 72% yield). $^1$H NMR (400 MHz, DMSO-d6) δ ppm 10.57-10.63 (br, 1H), 8.84 (d, J=2.2 Hz, 1H), 8.74-8.78 (m, 1H), 8.50 (d, J=5.3 Hz, 1H), 8.07-8.12 (m, 1H), 7.55-7.59 (m, 1H), 7.31-7.37 (m, 1H), 7.17-7.28 (m, 3H), 6.92 (d, J=5.3 Hz, 1H), 3.24-3.34 (m, 1H), 1.34 (d, J=6.8 Hz, 6H). MS (ES+): 472 [M+H]$^+$.

Step B: N-{3-[2-(1-Methylethyl)-5-(2-{[2-(methylsulfonyl)ethyl]amino}-4-pyrimidinyl)-1,3-thiazol-4-yl]phenyl}-3-pyridinesulfonamide Following a procedure analogous to the procedure described in Example 1 using 2-aminoethyl-methyl-sulfone (391 mg, 3.18 mmol) and N-{3-[5-(2-chloro-4-pyrimidinyl)-2-(1-methylethyl)-1,3-thiazol-4-yl]phenyl}-3-pyridinesulfonamide (150 mg, 0.318 mmol) the title compound was obtained as a white foam (72 mg, 41% yield). $^1$H NMR (400 MHz, DMSO-d$_6$) δ ppm 10.60 (s, 1H) 8.84 (d, J=1.8 Hz, 1H) 8.76 (dd, J=4.8, 1.3 Hz, 1H) 8.02-8.13 (m, 2H) 7.58 (dd, J=7.9, 4.8 Hz, 1H) 7.46 (t, J=5.3 Hz, 1H) 7.32 (t, J=8.2 Hz, 1H) 7.12-7.27 (m, 3H) 5.98-6.16 (m, 1H) 3.64 (dd, J=2.4, 1.3 Hz, 2H) 3.31-3.37 (m, 2H) 3.16-3.29 (m, 1H) 2.99 (s, 3H) 1.33 (d, J=6.9 Hz, 6H). MS (ESI): 559.0 [M+H]$^+$.

Example 34

N-{2-Fluoro-5-[2-(1-methylethyl)-5-(2-{[2-(methylsulfonyl)ethyl]amino}-4-pyrimidinyl)-1,3-thiazol-4-yl]phenyl}-2-furansulfonamide trifluoroacetic acid salt

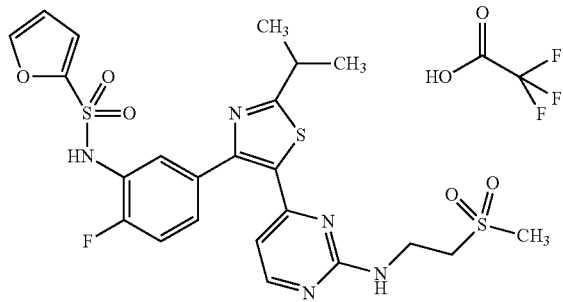 [SMILES: CC(C)c1nc(-c2ccc(F)c(NS(=O)(=O)c3ccco3)c2)c(-c2ccnc(NCCS(C)(=O)=O)n2)s1 ; O=C(O)C(F)(F)F]

Step A: N-{5-[5-(2-Chloro-4-pyrimidinyl)-2-(1-methylethyl)-1,3-thiazol-4-yl]-2-fluorophenyl}-2-furansulfonamide

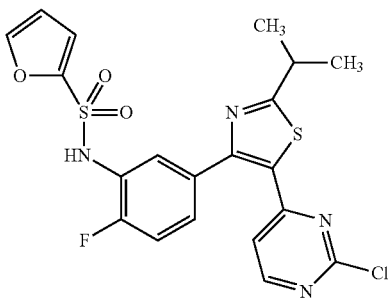 [SMILES: CC(C)c1nc(-c2ccc(F)c(NS(=O)(=O)c3ccco3)c2)c(-c2ccnc(Cl)n2)s1]

The 5-[5-(2-chloro-4-pyrimidinyl)-2-(1-methylethyl)-1,3-thiazol-4-yl]-2-fluorophenyl}amine (524 mg, 1.50 mmol) was dissolved in DCM (20 mL) and treated with pyridine (0.243 mL, 3.00 mmol). After 5 min, 2-furansulfonyl chloride (250 mg, 1.501 mmol) was added at rt overnight. The reaction mixture was diluted with 2N aqueous HCl and extracted with DCM. The DCM layer was washed with brine and dried over NaSO$_4$, filtered, added silica gel and concentrated. The crude product was chromatographed on silica gel eluting with 1:1 hexane:(6:4:0.5 Hexane:DCM:EtOAc). The title compound was obtained (88 mg, 12% yield). MS (ESI): 479.1[M+H]$^+$.

Step B: N-{2-Fluoro-5-[2-(1-methylethyl)-5-(2-{[2-(methylsulfonyl)ethyl]amino}-4-pyrimidinyl)-1,3-thiazol-4-yl]phenyl}-2-furansulfonamide trifluoroacetic acid salt Following a procedure analogous to the procedure described in Example 1 using N-{5-[5-(2-chloro-4-pyrimidinyl)-2-(1-methylethyl)-1,3-thiazol-4-yl]-2-fluorophenyl}-2-furansulfonamide (85 mg, 0.177 mmol) and 2-aminoethyl-methyl-sulfone (250 mg, 2.03 mmol) the title compound was obtained as a white foam (35 mg, 29% yield) after purification by Gilson Acidic HPLC (10 to 90% gradient, Acetonitrile/H2O+TFA; C18 column). $^1$H NMR (400 MHz, DMSO-d$_6$) δ ppm 10.59 (s, 1H), 8.14 (d, J=4.9 Hz, 1H), 7.83-8.01 (m, 1H), 7.41-7.47 (m, 1H), 7.35-7.41 (m, 1H), 7.33 (dd, J=7.5, 1.9 Hz, 1H), 7.26 (t, J=9.3 Hz, 1H), 6.97 (d, J=3.5 Hz, 1H), 6.57 (dd, J=3.4, 1.7 Hz, 1H), 6.25 (d, J=4.5 Hz, 1H), 3.60-3.74 (m, 2H), 3.15-3.40 (m, 3H), 2.97 (s, 3H), 1.32 (d, J=6.9 Hz, 6H). MS (ESI) free base: 567.2 [M+H]$^+$.

Example 35

1-Methyl-N-{3-[2-(1-methylethyl)-5-(2-{[2-(methylsulfonyl)ethyl]amino}-4-pyrimidinyl)-1,3-thiazol-4-yl]phenyl}-1H-pyrazole-4-sulfonamide trifluoroacetic acid salt

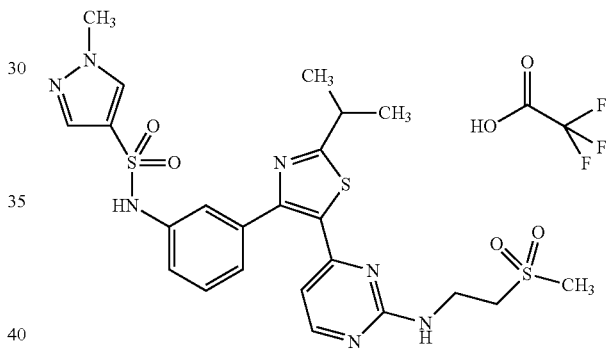

Step A: N-{3-[5-(2-Chloro-4-pyrimidinyl)-2-(1-methylethyl)-1,3-thiazol-4-yl]phenyl}-1-methyl-1H-pyrazole-4-sulfonamide

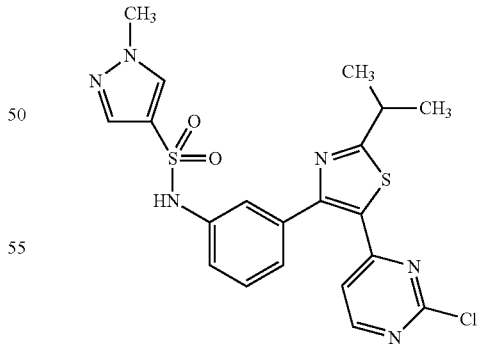

Following a procedure analogous to the procedure described in Intermediate 14 using 3-[5-(2-chloro-4-pyrimidinyl)-2-(1-methylethyl)-1,3-thiazol-4-yl]aniline (600 mg, 1.8 mmol) and 1-methyl-1H-pyrazole-4-sulfonyl chloride (0.49 g, 2.7 mmol) the title compound was obtained (500 mg, 58.6% yield). $^1$H NMR (400 MHz, CDCl$_3$) δ ppm 8.31 (d, J=5.3 Hz, 1H), 7.72 (d, J=0.9 Hz, 1H), 7.65 (d, J=0.9 Hz, 1H), 7.32-7.37 (m, 1H), 7.21-7.30 (m, 2H), 6.94 (S, 1H), 6.92 (d, J=5.3 Hz, 1H), 3.86 (S, 3H), 3.31-3.41 (m, 1H), 1.44 (d, J=6.8, 6H). MS (ES+): 475 [M+H]+.

Step B: 1-Methyl-N-{3-[2-(1-methylethyl)-5-(2-{[2-(methylsulfonyl)ethyl]amino}-4-pyrimidinyl)-1,3-thiazol-4-yl]phenyl}-1H-pyrazole-4-sulfonamide trifluoroacetic acid salt Following a procedure analogous to the procedure described in Example 1 using N-{3-[5-(2-chloro-4-pyrimidinyl)-2-(1-methylethyl)-1,3-thiazol-4-yl]phenyl}-1-methyl-1H-pyrazole-4-sulfonamide (100 mg, 0.211 mmol) and 2-aminoethyl-methyl-sulfone (259 mg, 2.105 mmol) the title compound was obtained (75 mg, 50% yield) as a yellow foam after purification by Gilson Acidic HPLC (10 to 90% gradient, Acetonitrile/H2O+TFA; C18 column). 1H NMR (400 MHz, DMSO-d6) δ ppm 10.21 (s, 1H), 8.18 (s, 1H), 8.07 (d, J=5.0 Hz, 1H), 7.62 (s, 1H), 7.45 (br. s., 1H), 7.31 (t, J=7.9 Hz, 1H), 7.16-7.24 (m, 2H), 7.14 (d, J=7.6 Hz, 1H), 6.15 (d, J=4.6 Hz, 1H), 3.77 (s, 3H), 3.51-3.69 (m, 2H), 3.17-3.36 (m, 3H), 2.97 (s, 3H), 1.32 (d, J=6.9, 6H). MS (ESI) free base: 562.1 [M+H]+.

Example 36

N-{2-Fluoro-5-[2-(1-methylethyl)-5-(2-{[3-(methylsulfonyl)propyl]amino}-4-pyrimidinyl)-1,3-thiazol-4-yl]phenyl}-1-methyl-1H-imidazole-4-sulfonamide

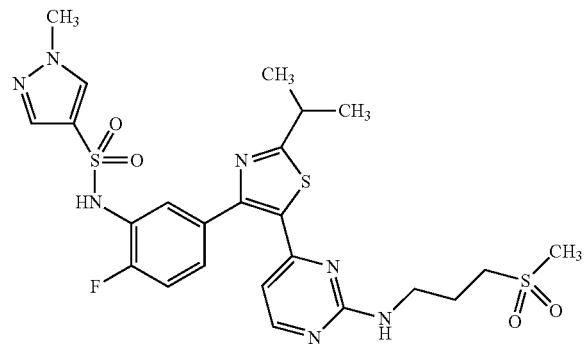 [SMILES: CC(C)c1nc(-c2ccc(F)c(NS(=O)(=O)c3cnn(C)c3)c2)c(-c2ccnc(NCCCS(C)(=O)=O)n2)s1]

Step A: N-{5-[5-(2-Chloro-4-pyrimidinyl)-2-(1-methylethyl)-1,3-thiazol-4-yl]-2-fluorophenyl}-1-methyl-1H-imidazole-4-sulfonamide

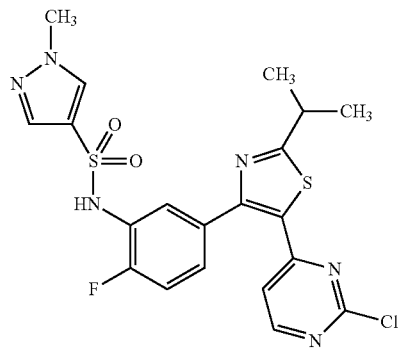 [SMILES: CC(C)c1nc(-c2ccc(F)c(NS(=O)(=O)c3cnn(C)c3)c2)c(-c2ccnc(Cl)n2)s1]

{5-[5-(2-chloro-4-pyrimidinyl)-2-(1-methylethyl)-1,3-thiazol-4-yl]-2-fluorophenyl}amine (160 mg, 0.459 mmol) was dissolved in DMF (3 mL) and added pyridine (0.074 mL; 0.917 mmol). The reaction was stirred 5 min and added 1-methylimidazole-4-sulfonyl chloride (83 mg, 0.459 mmol). The reaction mixture was heated at 45° C. for two days. The reaction mixture was cooled to rt, added silica gel, and concentrated. The crude product was chromatographed on silica gel eluting with 100% DCM to 100% EtOAc to obtained the title compound as a white solid (150 mg, 66% yield). 1H NMR (400 MHz, DMSO-d6) δ ppm 10.12 (br. s., 1H), 8.49 (d, J=5.4 Hz, 1H), 7.52-7.83 (m, 2H), 7.51 (d, J=1.8 Hz, 1H), 7.28-7.43 (m, 1H), 7.25 (t, J=9.3 Hz, 1H), 7.05 (d, J=5.3 Hz, 1H), 3.58 (s, 3H), 3.00-3.23 (m, 1H), 1.35 (d, J=6.9 Hz, 6H).

Step B: N-{2-Fluoro-5-[2-(1-methylethyl)-5-(2-{[3-(methylthio)propyl]amino}-4-pyrimidinyl)-1,3-thiazol-4-yl]phenyl}-1-methyl-1H-imidazole-4-sulfonamide

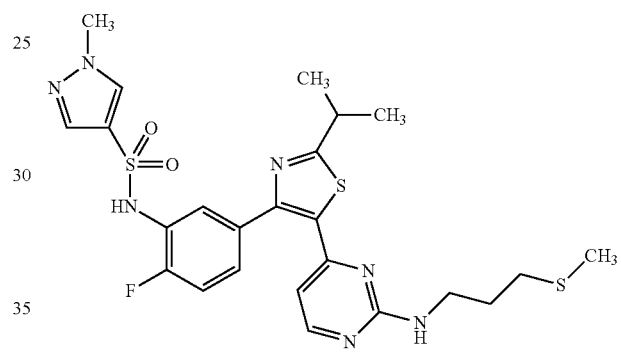

Following a procedure analogous to the procedure described in Example 1 using N-{5-[5-(2-chloro-4-pyrimidinyl)-2-(1-methylethyl)-1,3-thiazol-4-yl]-2-fluorophenyl}-1-methyl-1H-imidazole-4-sulfonamide (75 mg, 0.152 mmol) and [3-(methylthio)propyl]amine (86 mg, 0.817 mmol) the title compound of Step B was obtained as a golden oil (76 mg, 89% yield). MS (ESI): 561.4 [M+H]+.

Step C: N-{2-Fluoro-5-[2-(1-methylethyl)-5-(2-{[3-(methylsulfonyl)propyl]amino}-4-pyrimidinyl)-1,3-thiazol-4-yl]phenyl}-1-methyl-1H-imidazole-4-sulfonamide Following a procedure analogous to the procedure described in Example 12, Step B using oxone (208 mg, 0.34 mmoles) and N-{2-Fluoro-5-[2-(1-methylethyl)-5-(2-{[3-(methylthio)propyl]amino}-4-pyrimidinyl)-1,3-thiazol-4-yl]phenyl}-1-methyl-1H-imidazole-4-sulfonamide [76 mg, 0.135 mmoles (obtained from a compilation of multiple batches prepared in a manner analogous to Step B)] the title compound was obtained as a white solid (40 mg; 50% yield). 1H NMR (400 MHz, DMSO-d6) δ ppm 10.07 (s, 1H), 8.06 (d, J=5.2 Hz, 1H), 7.66 (d, J=6.3 Hz, 2H), 7.39-7.55 (m, 1H), 7.37 (t, J=5.6 Hz, 1H), 7.11-7.31 (m, 2H), 6.06-6.22 (m, 1H), 3.57 (s, 3H), 3.30-3.39 (m, 2H), 3.20-3.26 (m, 1H), 3.04-3.16

(m, 2H), 2.92 (s, 3H), 1.85-1.97 (m, 2H), 1.32 (d, J=6.9 Hz, 6H). MS (ESI): 593.9 [M+H]+.

Example 37

N-{3-[2-(1-Methylethyl)-5-(2-{[2-(methylsulfonyl)ethyl]amino}-4-pyrimidinyl)-1,3-thiazol-4-yl]phenyl}-4-morpholinesulfonamide trifluoroacetic acid salt

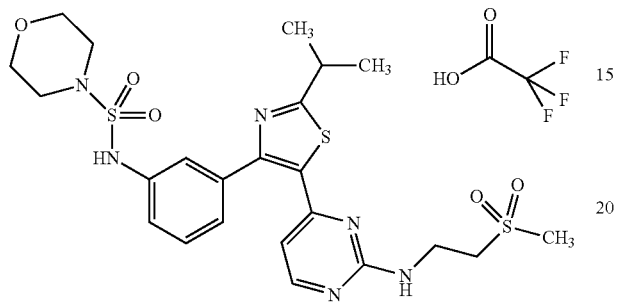

Step A: N-{3-[5-(2-Chloro-4-pyrimidinyl)-2-(1-methylethyl)-1,3-thiazol-4-yl]phenyl}-4-morpholinesulfonamide

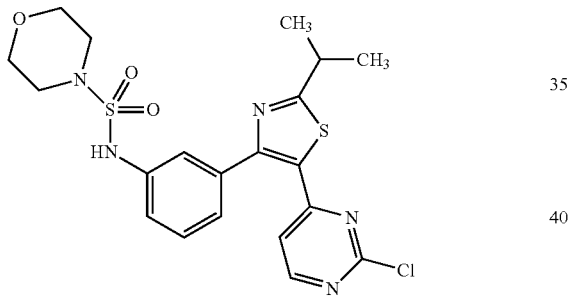

To a solution of 3-[5-(2-chloro-4-pyrimidinyl)-2-(1-methylethyl)-1,3-thiazol-4-yl]aniline (1.5 g, 4.5 mmol) in pyridine (15 mL) was added morpholine-4-sulfonyl chloride (1.26 g, 6.8 mmol). The reaction was stirred at rt for 12 h. Then the reaction was washed with water (50 mL), and extracted with DCM (2×50 mL). The organic layer was washed with brine, dried over anhydrous NaSO4, filtrated and concentrated under reduced pressure to give the crude product, which was purified by column chromatography on silica gel (DCM:EtOAc 60:1) to afford the title compound of Step A (297 mg, 13.8% yield). $^1$H NMR (400 MHz, CDCl$_3$) δ ppm 8.30 (d, J=5.3 Hz, 1H), 7.27-7.36 (m, 2H), 7.21-7.26 (m, 2H), 6.98 (d, J=5.3 Hz, 1H), 3.58-3.64 (m, 4H), 3.22-3.33 (m, 1H), 3.14-3.21 (m, 4H), 1.40 (d, J=7.0 Hz, 6H). MS (ES+): 480 [M+H]+.

Step B: N-{3-[2-(1-Methylethyl)-5-(2-{[2-(methylsulfonyl)ethyl]amino}-4-pyrimidinyl)-1,3-thiazol-4-yl]phenyl}-4-morpholinesulfonamide trifluoroacetic acid salt Following a procedure analogous to the procedure described in Example 1 using N-{3-[5-(2-chloro-4-pyrimidinyl)-2-(1-methylethyl)-1,3-thiazol-4-yl]phenyl}-4-morpholinesulfonamide (92 mg, 0.192 mmol) and 2-aminoethyl-methyl-sulfone (189 mg, 1.533 mmol) the title compound was obtained (79 mg, 61% yield) as a light yellow solid after purification by Gilson Acidic HPLC (10 to 90% gradient, Acetonitrile/H$_2$O+TFA; C18 column). $^1$H NMR (400 MHz, DMSO-d$_6$) δ ppm 10.09 (s, 1H), 8.12 (d, J=4.9 Hz, 1H), 7.46 (br. s., 1H), 7.35 (t, J=7.9 Hz, 1H), 7.30 (s, 1H), 7.25 (d, J=8.2 Hz, 1H), 7.19 (d, J=7.6 Hz, 1H), 6.28 (d, J=4.8 Hz, 1H), 3.63 (d, J=6.0 Hz, 2H), 3.41-3.53 (m, 4H), 3.21-3.40 (m, 3H), 2.99-3.05 (m, 4H), 2.98 (s, 3H), 1.33 (d, J=6.9 Hz, 6H). MS (ESI) free base: 566.2 [M+H]+.

Example 38

5-Fluoro-N-[3-(2-(1-methylethyl)-5-{2-[(2-methylpropyl)amino]-4-pyrimidinyl}-1,3-thiazol-4-yl)phenyl]-2-(methyloxy)benzenesulfonamide

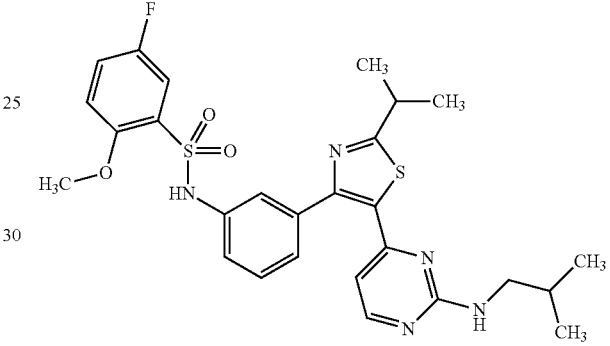

Step A: N-{3-[5-(2-Chloro-4-pyrimidinyl)-2-(1-methylethyl)-1,3-thiazol-4-yl]phenyl}-5-fluoro-2-(methyloxy)benzenesulfonamide

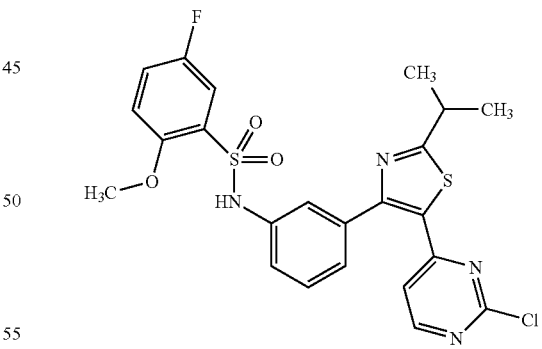

Following a procedure analogous to the procedure described in Intermediate 14 using 3-[5-(2-chloro-4-pyrimidinyl)-2-(1-methylethyl)-1,3-thiazol-4-yl]aniline (309 mg, 0.934 mmol) and 5-fluoro-2-(methyloxy)benzenesulfonyl chloride (210 mg, 0.934 mmol) the title compound of Step A was obtained as a white solid. (381 mg, 79% yield). $^1$H NMR (400 MHz, DMSO-d$_6$) δ ppm 10.34 (s, 1H), 8.42 (d, J=5.3 Hz, 1H), 7.39-7.54 (m, 2H), 7.23-7.37 (m, 1H), 7.09-7.23 (m, 4H), 6.87 (d, J=5.3 Hz, 1H), 3.79 (s, 3H), 3.29-3.38 (m, 1H), 1.33 (d, J=6.9 Hz, 6H).

Step B: 5-Fluoro-N-[3-(2-(1-methylethyl)-5-{2-[(2-methylpropyl)amino]-4-pyrimidinyl}-1,3-thiazol-4-yl)phenyl]-2-(methyloxy)benzenesulfonamide Following a procedure analogous to the procedure described in Example 18, Step B using N-{3-[5-(2-Chloro-4-pyrimidinyl)-2-(1-methylethyl)-1,3-thiazol-4-yl]phenyl}-5-fluoro-2-(methyloxy)benzenesulfonamide (89 mg, 0.171 mmol) and isobutylamine (0.172 mL, 1.715 mmol) the title compound was obtained as a yellow foam (58 mg, 61% yield). $^1$H NMR (400 MHz, DMSO-d$_6$) δ ppm 10.27 (s, 1H), 7.92 (d, J=5.1 Hz, 1H), 7.36-7.52 (m, 2H), 7.29 (t, J=5.9 Hz, 1H), 7.09-7.26 (m, 4H), 7.06 (d, J=7.5 Hz, 1H), 5.92 (dd, J=6.6, 0.9 Hz, 1H), 3.79 (s, 3H), 3.15-3.27 (m, 1H), 2.99 (d, J=0.9 Hz, 2H), 1.71-1.87 (m, 1H), 1.31 (d, J=6.9 Hz, 6H), 0.82 (d, J=6.7 Hz, 6H). MS (ESI): 556.0 [M+H]$^+$.

Example 39

N-[2-Fluoro-3-(2-(1-methylethyl)-5-{2-[(2-methylpropyl)amino]-4-pyrimidinyl}-1,3-thiazol-4-yl)phenyl]-2-methylbenzenesulfonamide

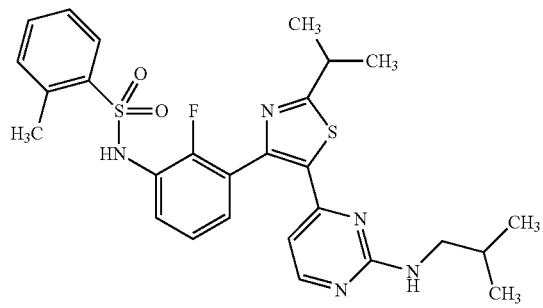 [SMILES: Cc1ccccc1S(=O)(=O)Nc1cccc(-c2nc(C(C)C)sc2-c2ccnc(NCC(C)C)n2)c1F]

Step A: N-{3-[5-(2-Chloro-4-pyrimidinyl)-2-(1-methylethyl)-1,3-thiazol-4-yl]-2-fluorophenyl}-2-methylbenzenesulfonamide

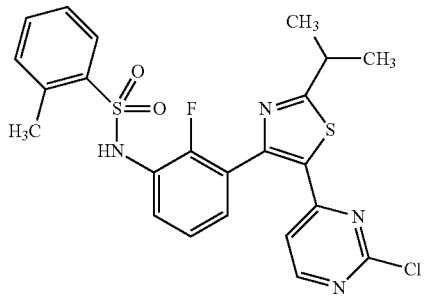 [SMILES: Cc1ccccc1S(=O)(=O)Nc1cccc(-c2nc(C(C)C)sc2-c2ccnc(Cl)n2)c1F]

Following a procedure analogous to the procedure described in Intermediate 14 using 3-(5-(2-chloropyrimidin-4-yl)-2-isopropylthiazol-4-yl)-2-fluoroaniline (350 mg, 1.003 mmol) and 2-methylbenzenesulfonyl chloride (0.145 mL, 1.00 mmol) the title compound of Step A was obtained as a yellow solid (140 mg, 28% yield). $^1$H NMR (400 MHz, DMSO-d$_6$) δ ppm 10.37 (s, 1H), 8.35-8.65 (m, 1H), 7.70 (d, J=7.8 Hz, 1H), 7.11-7.50 (m, 6H), 6.73 (d, J=5.2 Hz, 1H), 3.35-3.41 (m, 1H), 2.54 (s, 3H), 1.34 (d, J=6.9 Hz, 6H).

Step B: N-[2-Fluoro-3-(2-(1-methylethyl)-5-{2-[(2-methylpropyl)amino]-4-pyrimidinyl}-1,3-thiazol-4-yl)phenyl]-2-methylbenzenesulfonamide Following a procedure analogous to the procedure described in Example 18, Step B using N-{3-[5-(2-chloro-4-pyrimidinyl)-2-(1-methylethyl)-1,3-thiazol-4-yl]-2-fluorophenyl}-2-methylbenzenesulfonamide (70 mg, 0.139 mmol) and isobutylamine (0.140 mL, 1.39 mmol) the title compound was obtained as a light yellow solid (45 mg, 60% yield). $^1$H NMR (400 MHz, DMSO-d$_6$) δ ppm 10.37 (s, 1H), 8.01 (d, J=5.1 Hz, 1H), 7.67-7.85 (m, 1H), 7.41-7.59 (m, 1H), 7.28-7.42 (m, 4H), 7.15-7.28 (m, 2H), 5.64-5.89 (m, 1H), 3.23-3.30 (m, 1H), 2.88-3.13 (m, 2H), 2.57 (s, 3H), 1.72-1.91 (m, 1H), 1.34 (d, J=6.8 Hz, 6H), 0.86 (d, J=6.1 Hz, 6H). MS (ESI): 540.0 [M+H]$^+$.

Example 40

N-{2-Fluoro-3-[2-(1-methylethyl)-5-(2-{[1-(methylsulfonyl)-4-piperidinyl]amino}-4-pyrimidinyl)-1,3-thiazol-4-yl]phenyl}-1,3-thiazole-2-sulfonamide

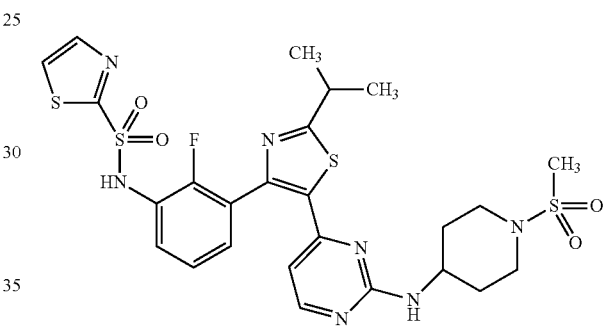

Step A: N-{3-[5-(2-Chloro-4-pyrimidinyl)-2-(1-methylethyl)-1,3-thiazol-4-yl]-2-fluorophenyl}-1,3-thiazole-2-sulfonamide

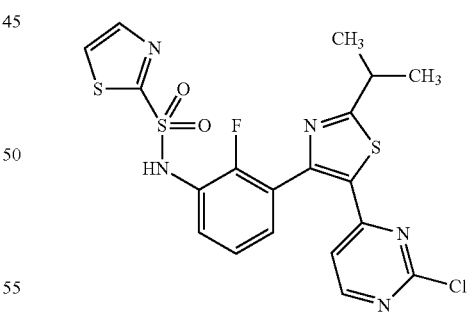

Following a procedure analogous to the procedure described in Intermediate 14 using 3-(5-(2-chloropyrimidin-4-yl)-2-isopropylthiazol-4-yl)-2-fluoroaniline (2.5 g, 7.2 mmol) and thiazole-2-sulfonyl chloride (1.45 g, 7.88 mmol) the title compound of Step A was obtained (1.05 g, 30.0% yield). $^1$H NMR (400 MHz, DMSO-d6) δ ppm 11.01 (br. s., 2H), 8.58 (d, J=5.2 Hz, 1H), 8.09 (d, J=3.2 Hz, 1H), 8.01 (d, J=2.8 Hz, 1H), 7.49-7.40 (m, 1H), 7.31-7.25 (m, 1H), 6.88 (d, J=5.6 Hz, 1H), 3.35-3.30 (m, 1H), 1.36 (d, J=6.8 Hz, 6H). MS (ES+): 496 [M+H]$^+$.

Step B: N-{2-Fluoro-3-[2-(1-methylethyl)-5-(2-{[1-(methylsulfonyl)-4-piperidinyl]amino}-4-pyrimidinyl)-1,3-thiazol-4-yl]phenyl}-1,3-thiazole-2-sulfonamide Following a procedure analogous to the procedure described in Example 1 using N-{3-[5-(2-chloro-4-pyrimidinyl)-2-(1-methylethyl)-1,3-thiazol-4-yl]-2-fluorophenyl}-1,3-thiazole-2-sulfonamide (70 mg, 0.141 mmol) and 1-(methylsulfonyl)-4-piperidinamine (126 mg, 0.706 mmol) the title compound was obtained as an off-white solid (43 mg, 48% yield). $^1$H NMR (400 MHz, DMSO-d$_6$) δ ppm 10.96 (d, J=1.6 Hz, 1H), 8.08 (d, J=4.3 Hz, 1H), 7.71-8.02 (m, 2H), 7.39-7.49 (m, 1H), 7.25 (d, J=7.7 Hz, 1H), 6.95-7.23 (m, 2H), 5.90-6.23 (m, 1H), 3.64-3.94 (m, 1H), 3.37-3.64 (m, 3H), 3.24 (br. s., 0H), 2.65-2.93 (m, 5H), 1.79-2.00 (m, 2H), 1.39-1.59 (m, 2H), 1.24-1.40 (m, 6H). MS (ESI): 638.1 [M+H]$^+$.

Example 41

N-{2-Fluoro-3-[5-(2-{[1-(methylsulfonyl)-4-piperidinyl]amino}-4-pyrimidinyl)-2-(4-morpholinyl)-1,3-thiazol-4-yl]phenyl}-2-furansulfonamide

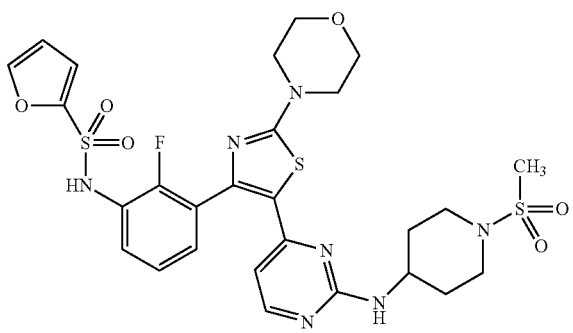 [SMILES: CS(=O)(=O)N1CCC(Nc2nccc(-c3sc(N4CCOCC4)nc3-c3cccc(NS(=O)(=O)c4ccco4)c3F)n2)CC1]

Step A: N-{3-[5-(2-Chloro-4-pyrimidinyl)-2-(4-morpholinyl)-1,3-thiazol-4-yl]-2-fluorophenyl}-2-furansulfonamide

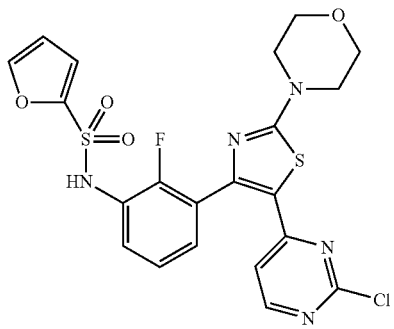 [SMILES: O=S(=O)(Nc1cccc(-c2nc(N3CCOCC3)sc2-c2ccnc(Cl)n2)c1F)c1ccco1]

Following a procedure analogous to the procedure described in Intermediate 14 using 3-(5-(2-chloropyrimidin-4-yl)-2-morpholinothiazol-4-yl)-2-fluoroaniline (3.0 g, 7.6 mmol) and furan-2-sulfonyl chloride (1.4 g, 8.4 mmol) the title compound of Step A was obtained (2.5 g, 63% yield). $^1$H NMR (400 MHz, DMSO-d6) δ ppm 8.07 (d, J=5.5 Hz, 1H), 7.59-7.66 (m, 1H), 7.42-7.75 (br, 1H), 7.13-7.20 (m, 2H), 7.02 (d, J=5.5 Hz, 1H), 6.93-6.98 (m, 1H), 6.37-6.42 (m, 2H), 3.50-3.57 (m, 4H), 3.72-3.78 (m, 4H). MS (ES+): 522 [M+H]$^+$.

Step B: N-{2-Fluoro-3-[5-(2-{[1-(methylsulfonyl)-4-piperidinyl]amino}-4-pyrimidinyl)-2-(4-morpholinyl)-1,3-thiazol-4-yl]phenyl}-2-furansulfonamide Following a procedure analogous to the procedure described in Example 1 using N-{3-[5-(2-chloro-4-pyrimidinyl)-2-(4-morpholinyl)-1,3-thiazol-4-yl]-2-fluorophenyl}-2-furansulfonamide (91.2 mg, 0.175 mmol) and 1-(methylsulfonyl)-4-piperidinamine (249 mg, 1.398 mmol) the title compound was obtained as a yellow solid (55 mg, 48% yield). $^1$H NMR (400 MHz, DMSO-d$_6$) δ ppm 10.57 (s, 1H), 7.82-8.02 (m, 2H), 7.34 (td, J=7.3, 1.8 Hz, 1H), 7.17-7.29 (m, 2H), 6.95-7.15 (m, 2H), 6.54 (dd, J=3.2, 1.7 Hz, 1H), 5.71 (s, 2H), 3.67 (t, J=4.6 Hz, 4H), 3.36-3.55 (m, 6H), 2.64-2.95 (m, 5H), 1.86 (d, J=10.3 Hz, 2H), 1.48 (d, J=10.4 Hz 2H). MS (ESI): 664.2 [M+H]$^+$.

Example 42

N-[2-Fluoro-3-(2-(1-methylethyl)-5-{2-[(2-methylpropyl)amino]-4-pyrimidinyl}-1,3-thiazol-4-yl)phenyl]-3-pyridinesulfonamide

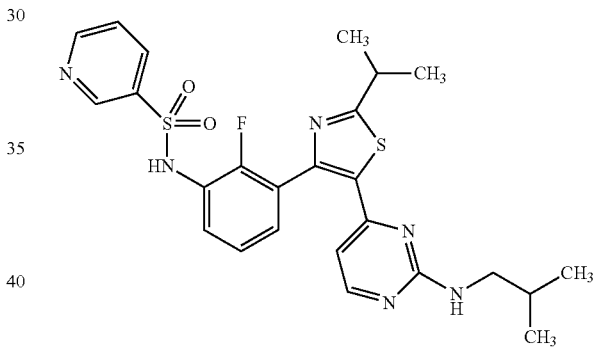

Step A: N-{3-[5-(2-Chloro-4-pyrimidinyl)-2-(1-methylethyl)-1,3-thiazol-4-yl]-2-fluorophenyl}-3-pyridinesulfonamide

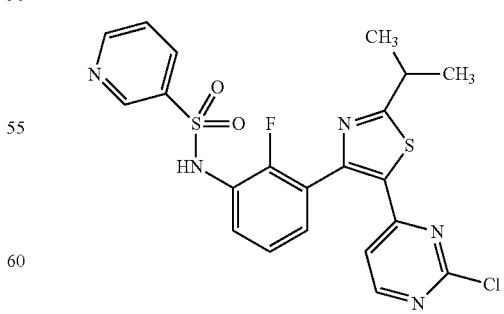

Following a procedure analogous to the procedure described in Intermediate 14 using 3-(5-(2-chloropyrimidin-4-yl)-2-isopropylthiazol-4-yl)-2-fluoroaniline (3 g, 8.6 mmol) and pyridine-3-sulfonyl chloride (1.68 g, 9.5 mmol)

the title compound of Step A was obtained (2.1 g, 75.3% yield). ¹H NMR (400 MHz, CDCl₃) δ ppm 8.97-9.01 (br, 1H), 8.76-8.79 (m, 1H), 8.35 (d, J=5.3 Hz, 1H), 8.08-8.12 (m, 1H), 7.68-7.74 (m, 1H), 7.40-7.44 (m, 1H), 7.22-7.34 (m, 3H), 6.69 (d, J=5.3 Hz, 1H), 3.29-3.38 (m, 1H), 1.44 (d, J=6.8 Hz, 6H). MS (ES+): 490 [M+H]⁺.

Step B: N-[2-Fluoro-3-(2-(1-methylethyl)-5-{2-[(2-methylpropyl)amino]-4-pyrimidinyl}-1,3-thiazol-4-yl)phenyl]-3-pyridinesulfonamide Following a procedure analogous to the procedure described in Example 18, Step B using N-{3-[5-(2-chloro-4-pyrimidinyl)-2-(1-methylethyl)-1,3-thiazol-4-yl]-2-fluorophenyl}-3-pyridinesulfonamide (150 mg, 0.306 mmol) and isobutylamine (0.307 mL, 3.06 mmol). the title compound was obtained as a white solid (105 mg, 65% yield). ¹H NMR (400 MHz, DMSO-d₆) δ ppm 10.53 (s, 1H), 8.83 (d, J=2.2 Hz, 1H), 8.73 (dd, J=4.8, 1.0 Hz, 1H), 8.03-8.13 (m, 1H), 7.99 (d, J=5.1 Hz, 1H), 7.53 (dd, J=8.1, 4.9 Hz, 1H), 7.31-7.41 (m, 1H), 7.09-7.33 (m, 3H), 5.67-5.93 (m, 1H), 3.14-3.25 (m, 1H), 2.84-3.09 (m, 2H), 1.69-1.87 (m, 1H), 1.30 (d, J=6.9 Hz, 6H), 0.81 (d, J=5.3 Hz, 6H). MS (ESI): 527.2 [M+H]⁺.

Example 43

N-{2-fluoro-3-[5-{2-[(2-methylpropyl)amino]-4-pyrimidinyl}-2-(4-morpholinyl)-1,3-thiazol-4-yl]phenyl}-2-furansulfonamide

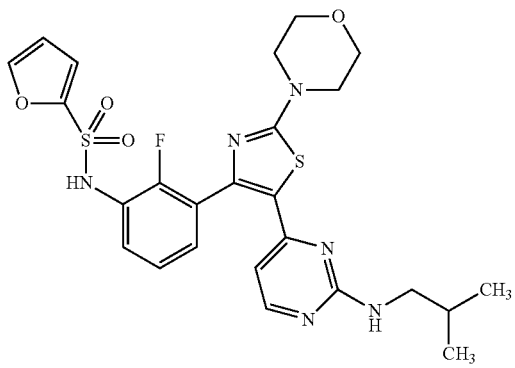 [SMILES: CC(C)CNc1nccc(-c2sc(N3CCOCC3)nc2-c2cccc(NS(=O)(=O)c3ccco3)c2F)n1]

Following a procedure analogous to the procedure described in Example 18, Step B using N-{3-[5-(2-chloro-4-pyrimidinyl)-2-(4-morpholinyl)-1,3-thiazol-4-yl]-2-fluorophenyl}-2-furansulfonamide (150 mg, 0.287 mmol) and isobutylamine (0.288 mL, 2.87 mmol) the title compound was obtained as a light yellow solid (88 mg, 55% yield). ¹H NMR (400 MHz, DMSO-d₆) δ ppm 10.56 (s, 1H), 7.77-7.91 (m, 2H), 7.30-7.41 (m, 1H), 7.16-7.32 (m, 2H), 7.10 (d, J=1.1 Hz, 1H), 7.03 (d, J=3.4 Hz, 1H), 6.54 (dd, J=3.3, 1.7 Hz, 1H), 3.66 (t, J=4.6 Hz, 4H), 3.41 (t, J=4.5 Hz, 4H), 2.97 (br. s., 2H), 1.78 (dt, J=13.4, 6.7 Hz, 1H), 0.73-0.87 (m, 7H). MS (ESI): 559.0 [M+H]⁺.

Example 44

2,6-Difluoro-N-[3-(2-(1-methylethyl)-5-{2-[(2-methylpropyl)amino]-4-pyrimidinyl}-1,3-thiazol-4-yl)-2-(methyloxy)phenyl]benzenesulfonamide

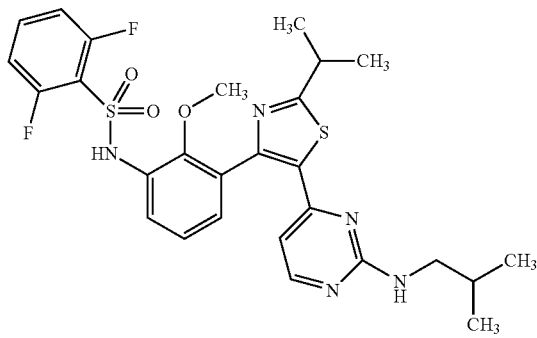 [SMILES: COc1c(NS(=O)(=O)c2c(F)cccc2F)cccc1-c1nc(C(C)C)sc1-c1ccnc(NCC(C)C)n1]

Step A: Methyl 2-hydroxy-3-nitrobenzoate

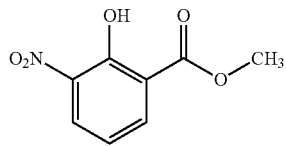

To a solution of 2-hydroxy-3-nitrobenzoic acid (25 g, 136 mmol) in DMF (125 mL) was added K₂CO₃ (37.8 g, 273 mmol). Then dimethyl sulfate (48.2 g, 382 mmol) was added dropwise to the mixture at rt. The mixture was stirred at rt overnight. Then the reaction was quenched by the addition of the saturated aqueous NH₄Cl (800 mL) at 0° C. The reaction mixture was extracted with EtOAc (500 mL×2). The combined organic layers were washed with water successively, dried over Na₂SO₄, filtered and concentrated under reduced pressure to give the title compound of Step A (26.8 g, 99.6% yield). ¹H NMR (400 MHz, CDCl₃) δ ppm 8.10-8.18 (m, 2H), 7.97-8.03 (br, 1H), 6.95-7.03 (m, 1H), 4.00 (s, 3H).

Step B: Methyl 2-methoxy-3-nitrobenzoate

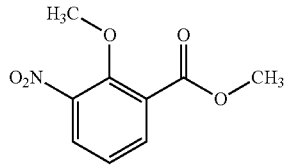

To a solution of methyl 2-hydroxy-3-nitrobenzoate (26.8 g, 136 mmol) in DMF (200 mL) was added K₂CO₃ (61 g, 440 mmol). Then iodomethane (62 g, 436 mmol) was added dropwise to the mixture at rt. The mixture was stirred at 45° C. for 5 h. Then the mixture was cooled to rt and water was added. The reaction mixture was extracted with EtOAc (500 mL×2). The combined organic layers were washed with water successively, dried over Na₂SO₄, filtered and concentrated under reduced pressure to give the title compound of Step B (28.4 g, 98.8% yield). ¹H NMR (400 MHz, DMSO-d6) δ ppm 8.10 (dd, J=1.8 Hz, 8.4 Hz, 1H), 8.00 (dd, J=1.3 Hz, 8.2 Hz, 1H), 7.40 (dd, J=8.2 Hz, 8.4 Hz, 1H), 3.87 (s, 3H), 3.85 (s, 3H).

Step C: Methyl 3-amino-2-methoxybenzoate

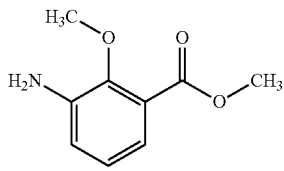

To a solution of methyl 2-methoxy-3-nitrobenzoate (28.4 g, 134 mmol) in MeOH (150 mL) was added Raney Ni (3 g). The mixture was stirred under $H_2$ atmosphere (50 psi/25° C.) for 3.5 h. The catalyst was filtered, and the filtrate was concentrated under the reduced pressure to dryness to give the crude product, which was purified by recrystallization in EtOAc to afford the title compound of Step C, methyl 3-amino-2-methoxybenzoate (23.5 g, 96.4% yield). $^1$H NMR (400 MHz, DMSO-d6) δ ppm 6.80-6.93 (m, 3H), 5.10-5.25 (br, 2H), 3.78 (s, 3H), 3.67 (s, 3H).

Step D: Methyl 2-(methyloxy)-3-{[(2-propen-1-yloxy)carbonyl]amino}benzoate

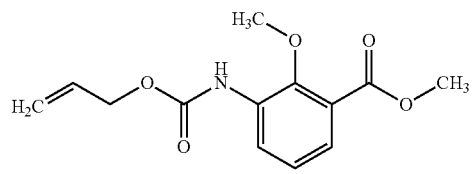 [SMILES: C=CCOC(=O)Nc1cccc(C(=O)OC)c1OC]

To a solution of methyl 3-amino-2-methoxybenzoate (94 g, 580 mmol) (from composite batches prepared as described above) in THF (1800 mL), saturated $NaHCO_3$ (60.9 g, 725 mmol) was added. Then 2-propen-1-yl chloridocarbonate (83.7 g, 696 mmol) was added dropwise at 0° C. The mixture was stirred at rt for 2 h. The solution was extracted with EtOAc (700 mL×3). The combined organic layers were washed with water and brine successively, dried over $Na_2SO_4$, filtered and concentrated under reduced pressure to give the title compound of Step D (123 g, 80% yield), which was used in the next step directly. $^1$H NMR (400 MHz, CDCl$_3$) δ ppm 8.25-8.35 (m, 1H), 7.49-7.53 (m, 1H), 7.36-7.42 (br, 1H), 7.10-7.18 (m, 1H), 5.91-6.07 (m, 1H), 5.75-5.90 (m, 2H), 4.63-4.70 (m, 2H), 3.92 (s, 3H), 3.86 (s, 3H).

Step E: 2-Propen-1-yl [3-[(2-chloro-4-pyrimidinyl)acetyl]-2-(methyloxy)phenyl]carbamate

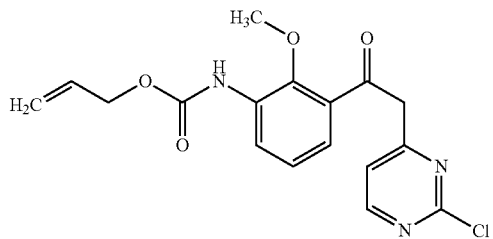 [SMILES: C=CCOC(=O)Nc1cccc(C(=O)Cc2ccnc(Cl)n2)c1OC]

To a solution of methyl 2-(methyloxy)-3-{[(2-propen-1-yloxy)carbonyl]amino}benzoate (123 g, 464 mmol), in dry THF (800 mL) at −10° C., LiHMDS (1M in THF, 1440 mmol, 1440 mL) was added dropwise and the solution was allowed to stir for 1 h at 0° C. A solution of 2-chloro-4-methylpyrimidine (72 g, 560 mmol) in THF (150 mL) was then added dropwise to the solution of ester and base at 0° C. over 20 min. The solution was allowed to stir 1 h at rt. TLC showed the reaction was complete. The reaction was quenched by addition of the saturated aqueous $NH_4Cl$ (800 mL) at 0° C. The reaction mixture was extracted with EtOAc (1 L×3). The combined organic layers were washed with water and brine successively, dried over $Na_2SO_4$, filtered and concentrated under reduced pressure to give the crude product, which was purified by flash column on silica gel, eluting with DCM. This solution was evaporated to obtain a solid. The orange solid was triturated with a small amount of EtOAc and filtered, rinsing with diethyl ether to give the title compound of Step E (109.9 g, 67.8% yield). $^1$H NMR (400 MHz, CDCl$_3$) δ ppm 13.64-13.68 (br, 1H), 8.38 (d, J=5.3 Hz, 1H), 8.15-8.21 (m, 1H), 7.31-7.39 (m, 2H), 7.15-7.18 (m, 1H), 6.87 (d, J=5.3 Hz, 1H), 6.19 (s, 1H), 5.92-6.15 (m, 1H), 5.23-5.40 (m, 2H), 4.66-4.70 (m, 2H), 3.76 (s, 3H).

Step F: 2-Propen-1-yl [3-[5-(2-chloro-4-pyrimidinyl)-2-(1-methylethyl)-1,3-thiazol-4-yl]-2-(methyloxy)phenyl]carbamate

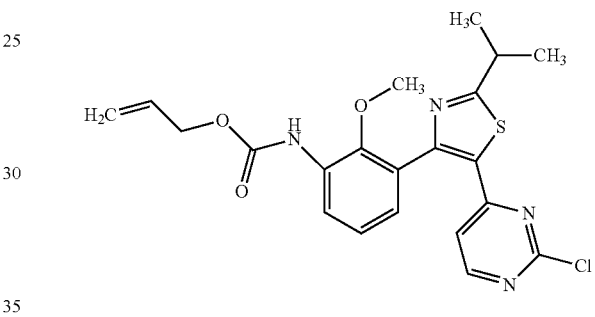

To a solution of 2-propen-1-yl [3-[(2-chloro-4-pyrimidinyl)acetyl]-2-(methyloxy)phenyl]carbamate (15.4 g, 42 mmol) in DCM (150 mL), NBS (7.6 g, 42 mmol) was added and the solution was allowed to stir at rt for 30 min. The reaction mixture was then concentrated in vacuo and the resulting oil was diluted with DMSO (150 mL) and 2-methylpropanethioamide (6.6 g 63.8 mmol) was added at once. The reaction was complete after stirring 1 h at rt. The reaction mixture was diluted with EtOAc and organic layer was washed with water and brine successively, dried over $Na_2SO_4$, filtered and concentrated under reduced pressure to give the crude product, which was purified by column chromatography on silica gel (DCM:petroleum ether 2:1) to afford the title compound of Step F (12.1 g, 63.8% yield) which was used directly in the next step.

Step G: 3-[5-(2-Chloro-4-pyrimidinyl)-2-(1-methylethyl)-1,3-thiazol-4-yl]-2-(methyloxy)aniline

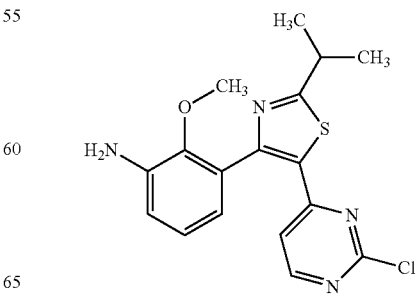

To the solution of 2-propen-1-yl [3-[5-(2-chloro-4-pyrimidinyl)-2-(1-methylethyl)-1,3-thiazol-4-yl]-2-(methyloxy)phenyl]carbamate (12.1 g, 22.5 mmol) in DCM (200 mL), acetic acid (3.8 mL, 66.6 mmol), Pd(PPh₃)₂Cl₂ (0.45 g, 0.56 mmol) were added. Then tri-n-butyl tin hydride (8.5 mL, 33 mmol) was added dropwise to the mixture at 0° C. The mixture was stirred at rt for 30 min. The reaction was quenched by added the saturated NaHCO₃ (200 mL) slowly. The two layers were separated. The aqueous layer was extracted with DCM (200 mL×2). The combined organic layers were washed with water and brine successively, dried over Na₂SO₄, filtered and concentrated under reduced pressure to give the crude product, which was washed with petroleum ether (500 mL) to afford the title compound of Step G (10 g, 60.8% yield), which was used directly in the next step.

Step H: N-[3-[5-(2-Chloro-4-pyrimidinyl)-2-(1-methylethyl)-1,3-thiazol-4-yl]-2-(methyloxy)phenyl]-2,6-difluorobenzenesulfonamide

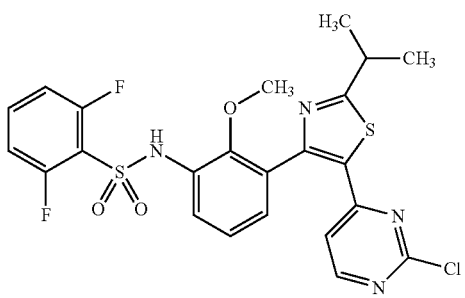 [SMILES: COc1c(NS(=O)(=O)c2c(F)cccc2F)cccc1-c1nc(C(C)C)sc1-c1ccnc(Cl)n1]

To a solution of 3-[5-(2-chloro-4-pyrimidinyl)-2-(1-methylethyl)-1,3-thiazol-4-yl]-2-(methyloxy)aniline (10 g, 28 mmol), in DCM (100 mL) was added pyridine (6.6 g, 83.7 mmol) and the mixture was cooled to 0° C. 2,6-Difluorobenzene-1-sulfonyl chloride (5.9 g, 27.9 mmol) in DCM (100 mL) was added dropwise to the mixture. The reaction was stirred at rt for 4 h. Then the reaction was washed with water (200 mL), and extracted with DCM (2×200 mL). The organic layer was washed with brine, dried over anhydrous NaSO₄, filtrated and concentrated under reduced pressure to give the crude product, which was purified by column chromatography on silica gel (petroleum ether:DCM 1:1) to afford the title compound of Step H (8.7 g, 58.2% yield). ¹H NMR (400 MHz, CDCl₃) δ ppm 8.21 (d, J=5.6 Hz, 1H), 7.70-7.75 (m, 1H), 7.63-7.67 (br, 1H), 7.46-7.55 (m, 1H), 7.15-7.19 (m, 2H), 6.95-7.03 (m, 2H), 6.58 (d, J=5.6 Hz, 1H), 3.35-3.40 (m, 4H), 1.44 (d, J=6.4 Hz, 6H). m/z (ES+): 537 [M+H]⁺.

Step I: 2,6-Difluoro-N-[3-(2-(1-methylethyl)-5-{2-[(2-methylpropyl)amino]-4-pyrimidinyl}-1,3-thiazol-4-yl)-2-(methyloxy)phenyl]benzenesulfonamide Following a procedure analogous to the procedure described in Example 1 using N-[3-[5-(2-chloro-4-pyrimidinyl)-2-(1-methylethyl)-1,3-thiazol-4-yl]-2-(methyloxy)phenyl]-2,6-difluorobenzenesulfonamide (150 mg, 0.279 mmol) and isobutylamine (0.140 mL, 1.397 mmol) the title compound was obtained as an off-white foam (86.3 mg, 27% yield). ¹H NMR (400 MHz, DMSO-d₆) δ ppm 10.37 (s, 1H), 7.94 (d, J=4.9 Hz, 1H), 7.54-7.73 (m, 1H), 7.37 (d, J=7.3 Hz, 1H), 7.15-7.32 (m, 3H), 6.99-7.17 (m, 2H), 5.74 (dd, J=2.2, 1.1 Hz, 1H), 3.24-3.28 (m, 1H), 3.12 (s, 3H), 3.01 (br. s., 2H), 1.81 (dt, J=13.3, 6.6 Hz, 1H), 1.31 (d, J=6.8 Hz, 6H), 0.85 (d, J=6.6 Hz, 6H). MS (ESI): 574.2 [M+H]⁺.

Example 45

N-{2-Fluoro-3-[5-{2-[(2-methylpropyl)amino]-4-pyrimidinyl}-2-(4-morpholinyl)-1,3-thiazol-4-yl]phenyl}-3-pyridinesulfonamide

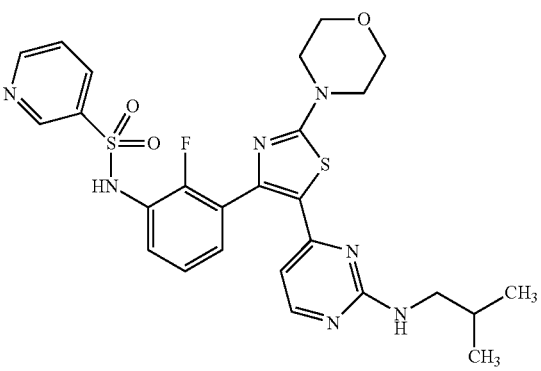 [SMILES: CC(C)CNc1nccc(-c2sc(N3CCOCC3)nc2-c2cccc(NS(=O)(=O)c3cccnc3)c2F)n1]

Step A: N-{3-[5-(2-Chloro-4-pyrimidinyl)-2-(4-morpholinyl)-1,3-thiazol-4-yl]-2-fluorophenyl}-3-pyridinesulfonamide

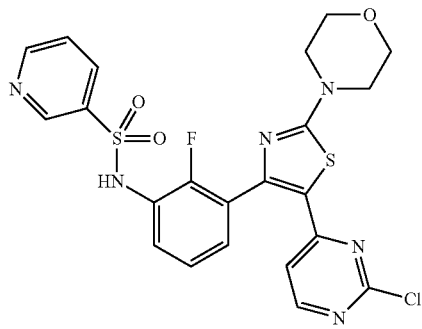 [SMILES: O=S(=O)(Nc1cccc(-c2nc(N3CCOCC3)sc2-c2ccnc(Cl)n2)c1F)c1cccnc1]

Following a procedure analogous to the procedure described in Intermediate 14, using 3-(5-(2-chloropyrimidin-4-yl)-2-morpholinothiazol-4-yl)-2-fluoroaniline (3 g, 7.7 mmol) and pyridine-3-sulfonyl chloride (1.49 g, 8.4 mmol) the title compound of Step A was obtained (2.9 g, 71.5% yield). ¹H NMR (400 MHz, DMSO-d6) δ ppm 10.55-10.60 (br, 1H), 8.82-8.86 (m, 1H), 8.72-8.76 (m, 1H), 8.30 (d, J=5.3 Hz, 1H), 8.07-8.13 (m, 1H), 7.51-7.52 (m, 1H), 7.39-7.47 (m, 1H), 7.27-7.40 (m, 2H), 6.47 (d, J=5.3 Hz, 1H), 3.47-3.57 (m, 4H), 3.67-3.75 (m, 4H). MS (ES+): 533 [M+H]⁺.

Step B: N-{2-Fluoro-3-[5-{2-[(2-methylpropyl)amino]-4-pyrimidinyl}-2-(4-morpholinyl)-1,3-thiazol-4-yl]phenyl}-3-pyridinesulfonamide Following a procedure analogous to the procedure described in Example 18, Step B, using N-{3-[5-(2-chloro-4-pyrimidinyl)-2-(4-morpholinyl)-1,3-thiazol-4-yl]-2-fluorophenyl}-3-pyridinesulfonamide (155 mg, 0.291 mmol) and isobutylamine (0.292 mL, 2.91 mmol) the title compound was obtained as a yellow foam (83 mg, 50% yield). $^1$H NMR (400 MHz, DMSO-d$_6$) δ ppm 10.53 (s, 1H), 8.83 (d, J=2.3 Hz, 1H), 8.73 (dd, 1H), 8.03-8.13 (m, 1H), 7.83 (d, J=5.2 Hz, 1H), 7.53 (dd, J=8.1, 4.9 Hz, 1H), 7.31-7.44 (m, 1H), 7.17-7.34 (m, 2H), 7.09 (d, J=1.4 Hz, 1H), 5.39-5.65 (m, 1H), 3.66 (t, J=4.6 Hz, 4H), 3.36-3.49 (m, 4H), 2.82-3.14 (m, 2H), 1.77 (dt, J=13.3, 6.7 Hz, 1H), 0.82 (d, J=6.6 Hz, 6H). MS (ESI): 570.1 [M+H]$^+$.

Example 46

N-[5-(2-(1,1-Dimethylethyl)-5-{2-[(2-methylpropyl)amino]-4-pyrimidinyl}-1,3-thiazol-4-yl)-2-fluorophenyl]-2,6-difluorobenzenesulfonamide

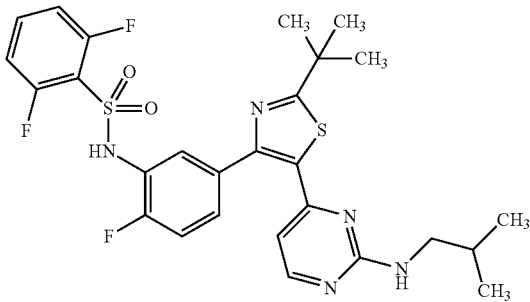 [SMILES: CC(C)CNc1nccc(-c2sc(C(C)(C)C)nc2-c2ccc(F)c(NS(=O)(=O)c3c(F)cccc3F)c2)n1]

Following a procedure analogous to the procedure described in Example 18, Step B using N-{5-[5-(2-chloro-4-pyrimidinyl)-2-(1,1-dimethylethyl)-1,3-thiazol-4-yl]-2-fluorophenyl}-2,6-difluorobenzenesulfonamide (200 mg, 0.371 mmol) and isobutylamine (0.372 mL, 3.71 mmol) the title compound was obtained as an off-white foam (90 mg, 42% yield). $^1$H NMR (400 MHz, DMSO-d$_6$) δ ppm 10.88 (s, 1H), 8.03 (d, J=5.1 Hz, 1H), 7.61-7.78 (m, 1H), 7.26-7.42 (m, 3H), 7.14-7.27 (m, 3H), 6.04-6.22 (m, 1H), 2.89-3.07 (m, 2H), 1.72-1.85 (m, 1H), 1.37 (s, 9H), 0.82 (d, J=6.4 Hz, 6H). MS (ESI): 576.2 [M+H]$^+$.

Example 47

2,6-Difluoro-N-{2-(methyloxy)-3-[5-{2-[(2-methylpropyl)amino]-4-pyrimidinyl}-2-(4-morpholinyl)-1,3-thiazol-4-yl]phenyl}benzenesulfonamide

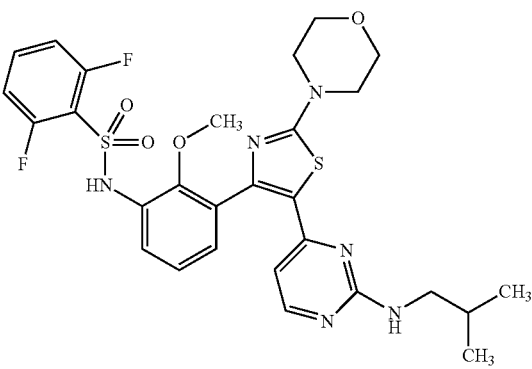 [SMILES: COc1c(NS(=O)(=O)c2c(F)cccc2F)cccc1-c1nc(N2CCOCC2)sc1-c1ccnc(NCC(C)C)n1]

Step A: 2-Propen-1-yl [3-[5-(2-chloro-4-pyrimidinyl)-2-(4-morpholinyl)-1,3-thiazol-4-yl]-2-(methyloxy)phenyl]carbamate

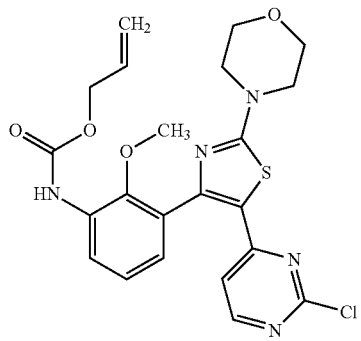 [SMILES: C=CCOC(=O)Nc1cccc(-c2nc(N3CCOCC3)sc2-c2ccnc(Cl)n2)c1OC]

To a solution of 2-propen-1-yl [3-[(2-chloro-4-pyrimidinyl)acetyl]-2-(methyloxy)phenyl]carbamate (30 g, 82.9 mmol) in DCM (300 mL), NBS (14.8 g, 82.9 mmol) was added and the solution was allowed to stir at rt for 30 min. The reaction mixture was then concentrated on the rotovap and the resulting oil was diluted with DMSO (240 mL) and 4-morpholinecarbothioamide (14.8 g 101 mmol) was added at once. The reaction was complete after stirring 1 h at rt. The combined organic layers were washed with water and brine successively, dried over Na$_2$SO$_4$, filtered and concentrated under reduced pressure to give the crude product which was purified by column chromatography on silica gel (DCM:petroleum ether 2:1) to afford the product of Step A (40 g, 98.8% yield) which was used directly in the next step.

Step B: 3-[5-(2-Chloro-4-pyrimidinyl)-2-(4-morpholinyl)-1,3-thiazol-4-yl]-2-(methyloxy)aniline

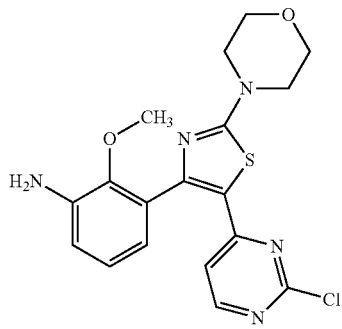 [SMILES: COc1c(N)cccc1-c1nc(N2CCOCC2)sc1-c1ccnc(Cl)n1]

To a solution of 2-propen-1-yl [3-[5-(2-chloro-4-pyrimidinyl)-2-(4-morpholinyl)-1,3-thiazol-4-yl]-2-(methyloxy)phenyl]carbamate (40 g, 99 mmol) in DCM (500 mL), acetic acid (11.3 mL, 197 mmol) and Pd(PPh$_3$)$_2$Cl$_2$ (1.3 g, 1.64 mmol) were added. Then tri-n-butyl tin hydride (37.3 mL, 145 mmol) was added dropwise to the mixture at 0° C. The mixture was stirred at rt for 30 min. The reaction was quenched by slow addition of saturated NaHCO$_3$ (200 mL). The two layers were separated. The aqueous layer was extracted with DCM (400 mL×2). The combined organic layers were washed with water and brine successively, dried over Na$_2$SO$_4$, filtered and concentrated under reduced pressure to give the crude product, which was washed with petroleum ether (500 mL) to afford the title compound of Step B (26.1 g, 79.1% yield). $^1$H NMR (400 MHz, CDCl$_3$) δ ppm 8.10 (d, J=5.5 Hz, 1H), 7.01 (dd, J=7.5 Hz, 8.1 Hz, 1H), 6.83 (dd, J=1.5 Hz, 8.2 Hz, 1H), 6.68 (dd, J=1.5 Hz, 7.5 Hz, 1H), 6.61 (d, J=5.5 Hz, 1H), 3.86-3.95 (br, 2H), 3.78-3.82 (m, 4H), 3.58-3.63 (m, 4H), 3.56 (s, 3H).

Step C: N-[3-[5-(2-Chloro-4-pyrimidinyl)-2-(4-morpholinyl)-1,3-thiazol-4-yl]-2-(methyloxy)phenyl]-2,6-difluorobenzenesulfonamide

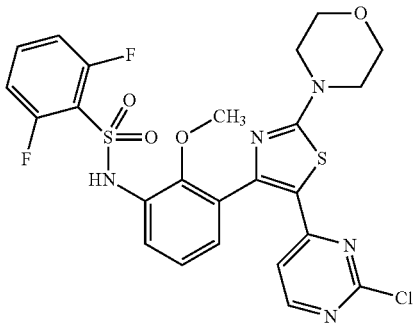 [SMILES: COc1c(NS(=O)(=O)c2c(F)cccc2F)cccc1-c1nc(N2CCOCC2)sc1-c1ccnc(Cl)n1]

Following a procedure analogous to the procedure described in Intermediate 14 using 3-(5-(2-chloropyrimidin-4-yl)-2-morpholinothiazol-4-yl)-2-methoxyaniline (26.1 g, 64.7 mmol) and 2,6-difluorobenzene-1-sulfonyl chloride (13.8 g, 64.7 mmol) the title compound of Step C was obtained (10.2 g, 27.2% yield). $^1$H NMR (400 MHz, DMSO-d6) δ ppm 8.23 (d, J=5.5 Hz, 1H), 7.62-7.71 (m, 1H), 7.38-7.45 (m, 1H), 7.15-7.30 (m, 4H), 6.40 (d, J=5.5 Hz, 1H), 3.67-3.78 (m, 4H), 3.50-3.61 (m, 4H), 3.18 (s, 3H). MS (ES+): 580 [M+H]$^+$.

Step D: 2,6-Difluoro-N-{2-(methyloxy)-3-[5-{2-[(2-methylpropyl)amino]-4-pyrimidinyl}-2-(4-morpholinyl)-1,3-thiazol-4-yl]phenyl}benzenesulfonamide Following a procedure analogous to the procedure described in Example 18, Step B using N-[3-[5-(2-chloro-4-pyrimidinyl)-2-(4-morpholinyl)-1,3-thiazol-4-yl]-2-(methyloxy)phenyl]-2,6-difluorobenzenesulfonamide (150 mg, 0.259 mmol) and isobutylamine (0.259 mL, 2.59 mmol) the title compound was obtained as a yellow solid (17.8 mg, 11% yield). $^1$H NMR (400 MHz, DMSO-d$_6$) δ ppm 10.31 (s, 1H), 7.78 (d, J=5.3 Hz, 1H), 7.59-7.70 (m, 1H), 7.33 (dd, J=7.9, 1.5 Hz, 1H), 7.20 (t, J=9.1 Hz, 2H), 6.97-7.15 (m, 3H), 5.53 (d, J=5.3 Hz, 1H), 3.66 (t, J=4.7 Hz, 4H), 3.40 (t, J=4.6 Hz, 4H), 3.20 (s, 3H), 2.99 (t, J=6.3 Hz, 2H), 1.64-1.85 (m, 1H), 0.83 (d, J=6.6 Hz, 6H). MS (ESI): 617.2 [M+H]$^+$.

Example 48

N-{3-[5-(2-Amino-4-pyrimidinyl)-2-(4-morpholinyl)-1,3-thiazol-4-yl]-2-fluorophenyl}cyclohexanesulfonamide

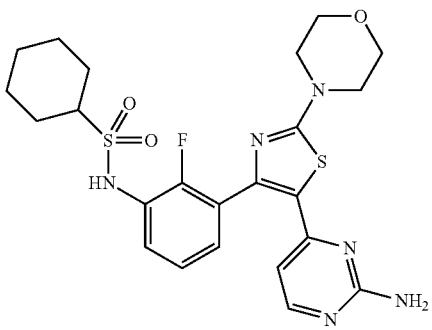 [SMILES: Nc1nccc(-c2sc(N3CCOCC3)nc2-c2cccc(NS(=O)(=O)C3CCCCC3)c2F)n1]

Step A: N-{3-[5-(2-Chloro-4-pyrimidinyl)-2-(4-morpholinyl)-1,3-thiazol-4-yl]-2-fluorophenyl}cyclohexanesulfonamide

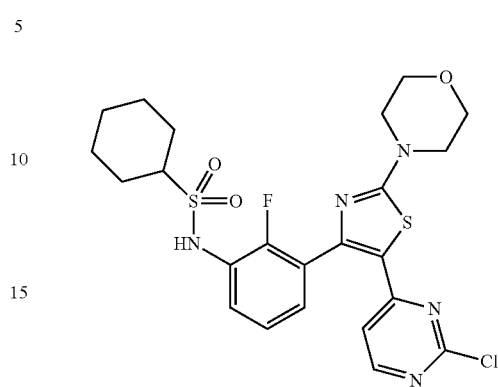

3-(5-(2-Chloropyrimidin-4-yl)-2-morpholinothiazol-4-yl)-2-fluoroaniline (200 mg, 0.510 mmol) was suspended in pyridine (2 mL) and after 5 min, cyclohexanesulfonyl chloride (0.148 mL 1.021 mmol) was added. The mixture was stirred overnight. Additional cyclohexanesulfonyl chloride (0.100 mL 0.69 mmol) was added and stirred overnight. Silica gel was added the reaction mixture and concentrated. The crude product was chromatographed on silica gel eluting with DCM and 9:1 (EtOAc:MeOH). The product was chromatographed again with 9:1 hexane:EtOAc increasing to 1:1 gradient. The clean fractions were concentrated to yield the title compound of Step A (102 mg, 37% yield). A second reaction was run (46 mg, 17% yield) same scale and combined to yield the title compound of Step A (148 mg). $^1$H NMR (400 MHz, DMSO-d$_6$) δ ppm 9.70 (s, 1H) 8.34 (d, J=5.5 Hz, 1H) 7.55 (td, J=7.6, 2.0 Hz, 2H) 7.14-7.38 (m, 3H) 6.65 (d, J=5.5 Hz, 1H) 3.68 (t, J=4.7 Hz, 4H) 3.52 (t, J=4.6 Hz, 4H) 2.79-3.04 (m, 1H) 2.01 (d, J=11.4 Hz, 2H) 1.69 (d, J=13.0 Hz, 3H) 1.47-1.63 (m, 2H) 1.26-1.42 (m, 3H) 0.84 (t, J=7.4 Hz, 1H).

Step B: N-{3-[5-(2-Amino-4-pyrimidinyl)-2-(4-morpholinyl)-1,3-thiazol-4-yl]-2-fluorophenyl}cyclohexanesulfonamide N-[3-(5-(2-Chloro-4-pyrimidinyl)-2-{ethyl[2-(methyloxy)ethyl]amino}-1,3-thiazol-4-yl)-2-fluorophenyl]cyclohexanesulfonamide (148 mg, 0.275 mmol) was suspended in NH$_4$OH (4 mL) and heated in microwave reactor at 120° C. for 48 min. The reaction was diluted with water and neutralized with 5% aqueous HCl and solid formed. A solid was diluted with DCM and water. The organic layer was dried over Na$_2$SO$_4$, filtered, added silica gel and concentrated. The crude product was chromatographed on silica gel eluting with 100% DCM to 1:1 [DCM:(9:1 EtOAC:MeOH)]. The clean fractions were combined and concentrated. The product was triturated in diethyl ether and filtered to obtain the title compound as a yellow powder (58 mg, 41% yield). $^1$H NMR (400 MHz, DMSO-d$_6$) δ ppm 9.67 (s, 1H), 7.87 (d, J=5.3 Hz, 1H), 7.43-7.62 (m, 1H), 7.09-7.41 (m, 2H), 6.35-6.74 (m, 2H), 5.80 (d, J=5.3 Hz, 1H), 3.68 (t, J=4.6 Hz, 4H), 3.43 (t, J=4.6

Hz, 4H), 2.81-3.02 (m, 1H), 1.69 (d, J=12.5 Hz, 2H), 1.51 (br. s., 1H), 1.33 (qd, J=12.1, 2.2 Hz, 2H), 0.89-1.22 (m, 5H). MS (ESI): 518.9 [M+H]+.

Example 49

N-{3-[5-(2-Amino-4-pyrimidinyl)-2-(4-morpholinyl)-1,3-thiazol-4-yl]-2-fluorophenyl}-1-piperidinesulfonamide

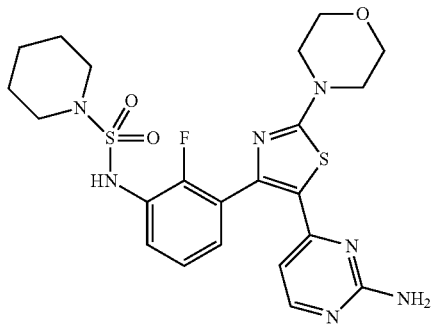 [SMILES: Nc1nccc(-c2sc(N3CCOCC3)nc2-c2cccc(NS(=O)(=O)N3CCCCC3)c2F)n1]

Step A: N-{3-[5-(2-Chloro-4-pyrimidinyl)-2-(4-morpholinyl)-1,3-thiazol-4-yl]-2-fluorophenyl}-1-piperidinesulfonamide

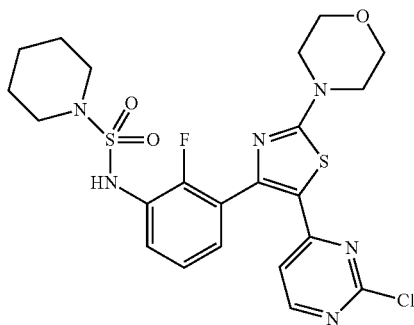 [SMILES: O=S(=O)(Nc1cccc(-c2nc(N3CCOCC3)sc2-c2ccnc(Cl)n2)c1F)N1CCCCC1]

Following a procedure analogous to the procedure described in Intermediate 14 using 3-(5-(2-chloropyrimidin-4-yl)-2-morpholinothiazol-4-yl)-2-fluoroaniline (200 mg, 0.510 mmol) and 1-piperidinosulfonyl chloride (0.201 mL, 1.531 mmol) the title compound of Step A was obtained as a yellow foam (193 mg, 41% and 29% yield, repeated twice). $^1$H NMR (400 MHz, DMSO-d$_6$) δ ppm 9.72 (s, 1H), 8.15-8.44 (m, 1H), 7.45-7.67 (m, 1H), 7.22-7.42 (m, 2H), 6.61 (d, J=5.4 Hz, 1H), 3.68 (t, J=4.7 Hz, 4H), 3.52 (t, J=4.7 Hz, 4H), 3.03 (t, J=5.0 Hz, 4H), 1.24-1.66 (m, 6H).

Step B: N-{3-[5-(2-Amino-4-pyrimidinyl)-2-(4-morpholinyl)-1,3-thiazol-4-yl]-2-fluorophenyl}-1-piperidinesulfonamide Following a procedure analogous to the procedure described in Example 21 using N-{3-[5-(2-chloro-4-pyrimidinyl)-2-(4-morpholinyl)-1,3-thiazol-4-yl]-2-fluorophenyl}-1-piperidinesulfonamide (190 mg, 0.352 mmol) and NH$_4$OH (4 mL) in a microwave reactor for 75 min at 120° C., the title compound was obtained an off-white solid (75 mg, 41% yield). $^1$H NMR (400 MHz, DMSO-d$_6$) δ ppm 9.69 (s, 1H) 7.83 (d, J=5.3 Hz, 1H) 7.51 (td, J=7.4, 2.2 Hz, 1H) 7.05-7.38 (m, 2H) 6.54 (s, 2H) 5.79 (d, J=5.3 Hz, 1H) 3.68 (t, J=4.7 Hz, 4H) 3.43 (t, J=4.6 Hz, 4H), 3.01 (t, J=5.0 Hz, 4H) 1.33-1.52 (m, 6H). MS (ESI): 520.0 [M+H]+.

Example 50

N-{3-[5-(2-Amino-4-pyrimidinyl)-2-(4-morpholinyl)-1,3-thiazol-4-yl]-2-fluorophenyl}-4-morpholinesulfonamide

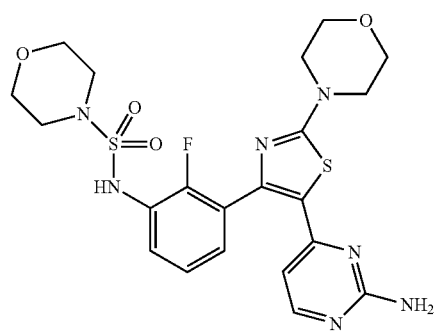 [SMILES: Nc1nccc(-c2sc(N3CCOCC3)nc2-c2cccc(NS(=O)(=O)N3CCOCC3)c2F)n1]

Step A: N-{3-[5-(2-Chloro-4-pyrimidinyl)-2-(4-morpholinyl)-1,3-thiazol-4-yl]-2-fluorophenyl}-4-morpholinesulfonamide

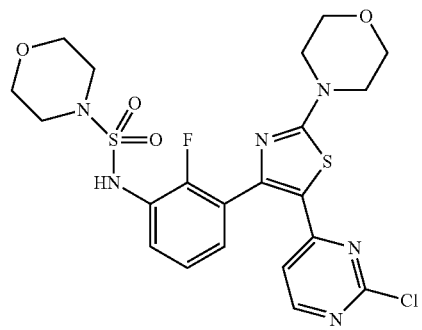 [SMILES: O=S(=O)(Nc1cccc(-c2nc(N3CCOCC3)sc2-c2ccnc(Cl)n2)c1F)N1CCOCC1]

Following a procedure analogous to the procedure described in Intermediate 14 using 3-(5-(2-chloropyrimidin-4-yl)-2-morpholinothiazol-4-yl)-2-fluoroaniline (150 mg, 0.383 mmol) and 4-morpholinesulfonyl chloride (142 mg, 0.766 mmol) the title compound of Step A was obtained as a yellow foam (96 mg, 46% yield). $^1$H NMR (400 MHz, DMSO-d$_6$) δ ppm 9.78-10.01 (m, 1H), 8.34 (d, J=5.5 Hz, 1H), 7.58 (td, J=7.4, 2.4 Hz, 1H), 7.17-7.41 (m, 2H), 6.57-6.68 (m, 1H), 3.68 (t, J=4.7 Hz, 4H), 3.42-3.63 (m, 8H), 2.91-3.11 (m, 4H).

Step B: N-{3-[5-(2-Amino-4-pyrimidinyl)-2-(4-morpholinyl)-1,3-thiazol-4-yl]-2-fluorophenyl}-4-morpholinesulfonamide Following a procedure analogous to the procedure described in Example 21 using N-{3-[5-(2-chloro-4-pyrimidinyl)-2-(4-morpholinyl)-1,3-thiazol-4-yl]-2-fluorophenyl}-4-morpholinesulfonamide (96 mg, 0.177 mmol) in NH₄OH (4 mL), heated in a microwave reactor for 40 min at 120° C. the title compound was obtained as a yellow solid (20 mg, 22% yield). ¹H NMR (400 MHz, DMSO-d₆) δ ppm 9.86 (s, 1H), 7.87 (d, J=5.3 Hz, 1H), 7.54 (td, J=6.8, 3.5 Hz, 1H), 7.19-7.31 (m, 2H), 6.54 (s, 2H), 5.80 (d, J=5.3 Hz, 1H), 3.68 (t, J=4.4 Hz, 4H), 3.48-3.55 (m, 4H), 3.43 (t, J=4.4 Hz, 4H), 2.96-3.03 (m, 4H). MS (ESI): 521.8 [M+H]⁺.

Example 51

N-{3-[5-(2-Amino-4-pyrimidinyl)-2-(4-morpholinyl)-1,3-thiazol-4-yl]-2-fluorophenyl}cyclopropanesulfonamide

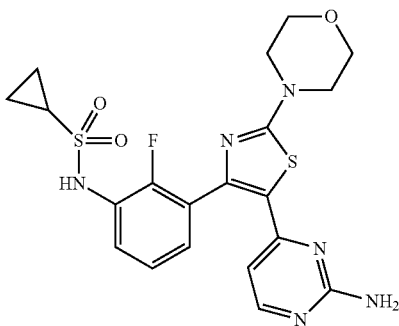 [SMILES: Nc1nccc(-c2sc(N3CCOCC3)nc2-c2cccc(NS(=O)(=O)C3CC3)c2F)n1]

Step A: N-{3-[5-(2-Chloro-4-pyrimidinyl)-2-(4-morpholinyl)-1,3-thiazol-4-yl]-2-fluorophenyl}cyclopropanesulfonamide

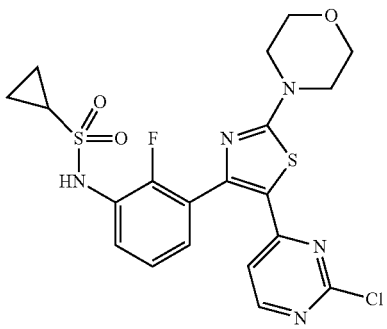 [SMILES: O=S(=O)(Nc1cccc(-c2nc(N3CCOCC3)sc2-c2ccnc(Cl)n2)c1F)C1CC1]

Following a procedure analogous to the procedure described in Intermediate 14 using 3-(5-(2-chloropyrimidin-4-yl)-2-morpholinothiazol-4-yl)-2-fluoroaniline (150 mg, 0.383 mmol) and cyclopropanesulfonyl chloride (0.039 mL, 0.383 mmol) the title compound of Step A was obtained as a yellow solid (125 mg, 66% yield). ¹H NMR (400 MHz, DMSO-d₆) δ ppm 9.71 (s, 1H), 8.27-8.39 (m, 1H), 7.54 (td, J=7.6, 1.7 Hz, 1H), 7.22-7.42 (m, 2H), 6.62-6.72 (m, 1H), 5.30 (s, 1H), 3.68 (t, J=4.7 Hz, 4H), 3.52 (t, J=4.6 Hz, 4H), 2.59-2.70 (m, 1H), 0.75-0.93 (m, 3H).

Step B: N-{3-[5-(2-Amino-4-pyrimidinyl)-2-(4-morpholinyl)-1,3-thiazol-4-yl]-2-fluorophenyl}cyclopropanesulfonamide A suspension of N-{3-[5-(2-chloro-4-pyrimidinyl)-2-(4-morpholinyl)-1,3-thiazol-4-yl]-2-fluorophenyl}cyclopropanesulfonamide (125 mg, 0.252 mmol) and 7M ammonia in MeOH (7 mL, 0.49 mmol) was heated in a sealed tube to 80° C. for 2 days. The reaction was diluted with DCM and added silica gel and concentrated. The crude product was chromatographed on silica gel eluting with 100% DCM to 1:1 [DCM:(9:1 EtOAc:MeOH)]. The clean fractions were concentrated to yield the crude product as a yellow solid (62 mg). The crude product was repurified by reverse phase HPLC (a gradient of acetonitrile:water with 0.1% TFA in both). The combined clean fractions were concentrated then partitioned between DCM and saturated NaHCO₃. The DCM layer was separated and dried over Na₂SO₄. The title compound was obtained as a yellow solid (26 mg, 21% yield). ¹H NMR (400 MHz, DMSO-d₆) δ ppm 9.67 (s, 1H), 7.86 (d, J=5.4 Hz, 1H), 7.49 (td, J=7.4, 2.2 Hz, 1H), 7.11-7.38 (m, 2H), 6.53 (s, 2H), 5.84 (d, J=5.3 Hz, 1H), 3.68 (t, J=4.7 Hz, 4H), 3.43 (t, J=4.7 Hz, 4H), 2.53-2.68 (m, 1H), 0.74-0.92 (m, 4H). MS (ESI): 477.0 [M+H]⁺.

Example 52

N-{3-[2-(1-Methylethyl)-5-(2-{[2-(methylsulfonyl)ethyl]amino}-4-pyrimidinyl)-1,3-thiazol-4-yl]phenyl}cyclopropanesulfonamide

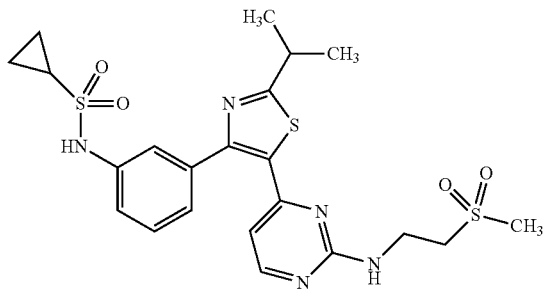 [SMILES: CC(C)c1nc(-c2cccc(NS(=O)(=O)C3CC3)c2)c(-c2ccnc(NCCS(C)(=O)=O)n2)s1]

Step A: N-{3-[5-(2-Chloro-4-pyrimidinyl)-2-(1-methylethyl)-1,3-thiazol-4-yl]phenyl}cyclopropanesulfonamide

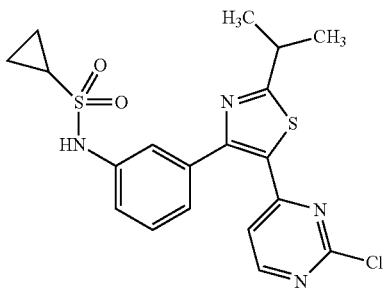 [SMILES: CC(C)c1nc(-c2cccc(NS(=O)(=O)C3CC3)c2)c(-c2ccnc(Cl)n2)s1]

Following a procedure analogous to the procedure described in Intermediate 14 using 3-[5-(2-chloro-4-pyrimidinyl)-2-(1-methylethyl)-1,3-thiazol-4-yl]aniline (1.0 g, 3.03 mmol) and cyclopropanesulfonyl chloride (465 mg, 3.32 mmol) the title compound of Step A was obtained (1.24 g, 94.4% yield). ¹H NMR (400 MHz, CDCl₃) δ ppm 8.30 (d, J=5.3 Hz, 1H), 7.36-7.42 (m, 2H), 7.29-7.36 (m, 2H), 7.01 (d, J=5.3 Hz, 1H), 6.91-6.93 (br, 1H), 3.29-3.40 (m, 1H), 2.46-

2.53 (m, 1H), 1.44 (d, J=7.0 Hz, 6H), 1.12-1.18 (m, 2H), 0.93-1.01 (m, 2H). MS (ES+): 435 [M+H]⁺.

Step B: N-{3-[2-(1-Methylethyl)-5-(2-{[2-(methylsulfonyl)ethyl]amino}-4-pyrimidinyl)-1,3-thiazol-4-yl]phenyl}cyclopropanesulfonamide Following a procedure analogous to the procedure described in Example 1 using 2-aminoethyl-methyl-sulfone (396 mg, 3.22 mmol) and N-{3-[5-(2-chloro-4-pyrimidinyl)-2-(1-methylethyl)-1,3-thiazol-4-yl]phenyl}cyclopropanesulfonamide (140 mg, 0.322 mmol) the title compound was obtained as a white solid (41 mg, 23% yield). ¹H NMR (400 MHz, DMSO-d₆) δ ppm 9.84 (s, 1H), 8.17 (d, J=4.0 Hz, 1H), 7.48 (br. s., 1H), 7.37 (s, 2H), 7.33 (s, 1H), 7.27 (d, J=7.5 Hz, 1H), 6.34 (d, J=3.5 Hz, 1H), 3.67 (d, J=5.5 Hz, 2H), 3.35-3.44 (m, 2H), 3.25-3.30 (m, 1H), 3.02 (s, 3H), 2.54-2.64 (m, 1H), 1.37 (d, J=6.8 Hz, 6H), 0.92 (d, J=6.2 Hz, 4H). MS (ESI): 522.2 [M+H]⁺.

Example 53

N-{3-[5-(2-Amino-4-pyrimidinyl)-2-(1,1-dimethylethyl)-1,3-thiazol-4-yl]-2-fluorophenyl}-5-fluoro-2-methylbenzenesulfonamide

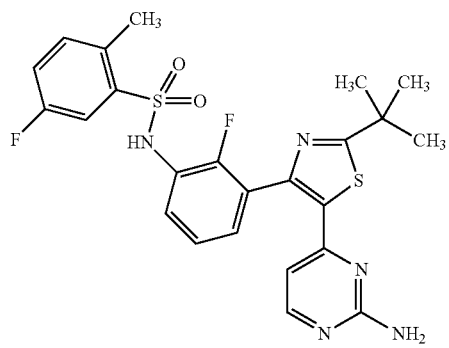 [SMILES: Cc1ccc(F)cc1S(=O)(=O)Nc1cccc(-c2nc(C(C)(C)C)sc2-c2ccnc(N)n2)c1F]

Step A: 4-[4-(3-Amino-2-fluorophenyl)-2-(1,1-dimethylethyl)-1,3-thiazol-5-yl]-2-pyrimidinamine

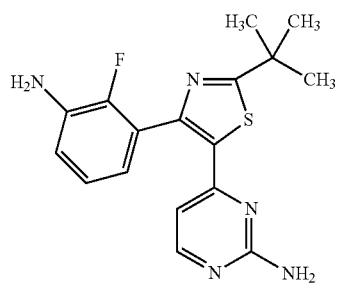 [SMILES: CC(C)(C)c1nc(-c2cccc(N)c2F)c(-c2ccnc(N)n2)s1]

In a microwave reaction vessel 3-[5-(2-chloro-4-pyrimidinyl)-2-(1,1-dimethylethyl)-1,3-thiazol-4-yl]-2-fluoroaniline (590 mg, 1.626 mmol) was combined with NH₄OH 28-30% (15 mL, 385 mmol) and 1,4-dioxane (4 mL). The mixture was heated in the microwave for 40 min at 130° C. The crude product was then diluted with water (100 mL) followed by extraction with EtOAc (100 mL). The EtOAc layer was washed with brine then dried over Na₂SO₄. The organics were then filtered and concentrated to dryness. The crude material was dissolved in DCM (2 mL), injected onto the top of a silica gel column then purified using EtOAc and hexanes. Desired fractions were concentrated to dryness to yield the title compound of Step A as a beige powder (490 mg, 1.355 mmol, 83% yield). ¹H NMR (400 MHz, DMSO-d₆) δ ppm 8.06 (d, J=5.1 Hz, 1H), 6.97 (t, J=7.8 Hz, 1H), 6.86 (t, J=8.2 Hz, 1H), 6.71 (s, 2H), 6.58 (t, J=6.2 Hz, 1H), 6.15 (d, J=5.1 Hz, 1H), 5.26 (s, 2H), 1.42 (s, 9H).

Step B: N-{3-[5-(2-Amino-4-pyrimidinyl)-2-(1,1-dimethylethyl)-1,3-thiazol-4-yl]-2-fluorophenyl}-5-fluoro-2-methylbenzenesulfonamide Following a procedure analogous to the procedure described in Intermediate 14 using 4-[4-(3-amino-2-fluorophenyl)-2-(1,1-dimethylethyl)-1,3-thiazol-5-yl]-2-pyrimidinamine (0.082 g, 0.239 mmol) and 2-methyl 5-fluorobenzenesulfonyl chloride (0.055 g, 0.263 mmol) the title compound was obtained (57 mg, 0.11 mmol, 46% yield). ¹H NMR (400 MHz, DMSO-d₆) δ ppm 10.48 (s, 1H), 7.91 (d, J=5.3 Hz, 1H), 7.44 (dd, J=8.8, 2.6 Hz, 1H), 7.29-7.42 (m, 3H) 7.16-7.29 (m, 2H), 6.71 (s, 2H), 5.73 (d, J=5.1 Hz, 1H), 2.49 (s, 3H), 1.35 (s, 9H). MS (ES+): 516 [M+H]+.

Example 54

N-{3-[5-(2-Amino-4-pyrimidinyl)-2-(1,1-dimethylethyl)-1,3-thiazol-4-yl]-2-fluorophenyl}-2-fluorobenzenesulfonamide

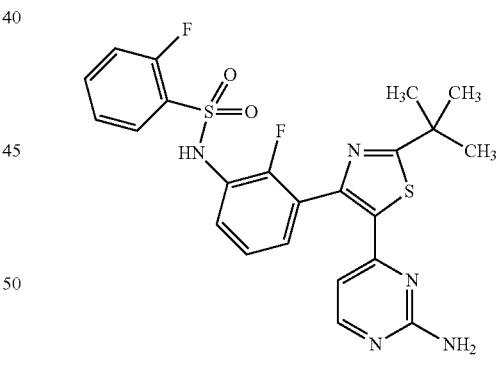

Following a procedure analogous to the procedure described in Intermediate 14 using 4-[4-(3-amino-2-fluorophenyl)-2-(1,1-dimethylethyl)-1,3-thiazol-5-yl]-2-pyrimidinamine (0.082 g, 0.239 mmol) and 2-fluorobenzenesulfonyl chloride (0.051 g, 0.263 mmol) the title compound, N-{3-[5-(2-amino-4-pyrimidinyl)-2-(1,1-dimethylethyl)-1,3-thiazol-4-yl]-2-fluorophenyl}-2-fluorobenzenesulfonamide was obtained (66 mg, 0.125 mmol, 52.4% yield). ¹H NMR (400 MHz, DMSO-d₆) δ ppm 10.57 (s, 1H), 7.98 (d, J=5.3 Hz, 1H), 7.63-7.74 (m, 2H), 7.36-7.46 (m, 2H), 7.32 (t, J=7.4 Hz, 2H), 7.20-7.29 (m, 1H), 6.75 (s, 2H), 5.79 (d, J=5.1 Hz, 1H), 1.40 (s, 9H). MS (ES+): 502 [M+H]+.

Example 55

N-{2-fluoro-5-[2-(1-methylethyl)-5-(2-{[2-(methyl-sulfonyl)ethyl]amino}-4-pyrimidinyl)-1,3-thiazol-4-yl]phenyl}cyclopropanesulfonamide

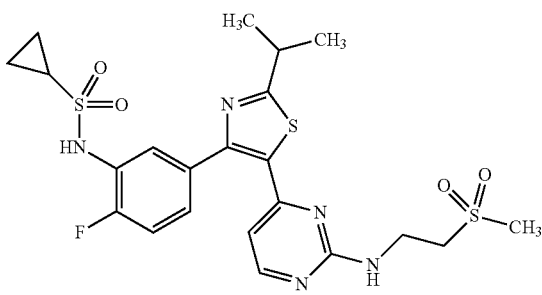 [SMILES: CC(C)c1nc(-c2ccc(F)c(NS(=O)(=O)C3CC3)c2)c(-c2ccnc(NCCS(C)(=O)=O)n2)s1]

Step A: N-{3-[5-(2-Chloro-4-pyrimidinyl)-2-(1-methylethyl)-1,3-thiazol-4-yl]phenyl}cyclopropanesulfonamide

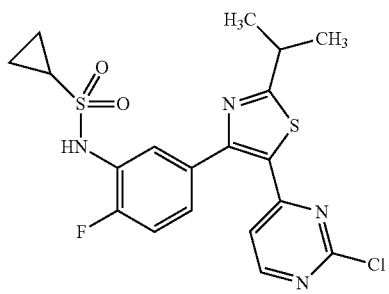 [SMILES: CC(C)c1nc(-c2ccc(F)c(NS(=O)(=O)C3CC3)c2)c(-c2ccnc(Cl)n2)s1]

Following a procedure analogous to the procedure described in Intermediate 14 using {5-[5-(2-chloro-4-pyrimidinyl)-2-(1-methylethyl)-1,3-thiazol-4-yl]-2-fluorophenyl}amine (283 mg, 0.811 mmol) and cyclopropanesulfonyl chloride (114 mg, 0.811 mmol) the title compound was obtained as a white solid (247 mg, 67% yield). MS (ESI): 453.3 [M+H]+.

Step B: N-{2-Fluoro-5-[2-(1-methylethyl)-5-(2-{[2-(methylsulfonyl)ethyl]amino}-4-pyrimidinyl)-1,3-thiazol-4-yl]phenyl}cyclopropanesulfonamide Following a procedure analogous to the procedure described in Example 1 using N-{5-[5-(2-chloro-4-pyrimidinyl)-2-(1-methylethyl)-1,3-thiazol-4-yl]-2-fluorophenyl}cyclopropanesulfonamide (80 mg, 0.177 mmol) and 2-aminoethyl-methyl-sulfone (174 mg, 1.413 mmol) the title compound was obtained as a white solid (49 mg, 51% yield). $^1$H NMR (400 MHz, DMSO-d$_6$) δ ppm 9.70 (s, 1H), 8.13 (d, J=4.8 Hz, 1H), 7.50 (dd, J=7.6, 1.6 Hz, 1H), 7.44 (t, J=4.9 Hz, 1H), 7.25-7.41 (m, 2H), 6.33 (d, J=4.5 Hz, 1H), 3.62 (d, J=5.5 Hz, 2H), 3.32 (br. s., 2H), 3.22-3.27 (m, 1H), 2.97 (s, 3H), 2.52-2.68 (m, 1H), 1.33 (d, J=6.9 Hz, 6H), 0.71-0.96 (m, 4H). MS (ESI): 540.1 [M+H]$^+$.

Example 56

N-{3-[5-(2-Amino-4-pyrimidinyl)-2-(4-morpholinyl)-1,3-thiazol-4-yl]-2-fluorophenyl}-2,5-difluorobenzenesulfonamide

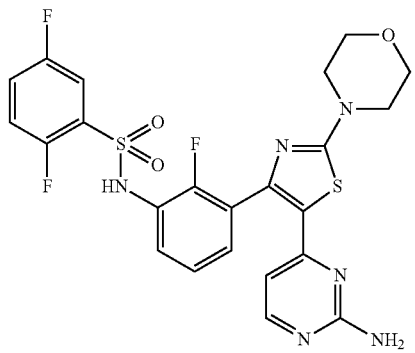

A suspension of N-{3-[5-(2-chloro-4-pyrimidinyl)-2-(4-morpholinyl)-1,3-thiazol-4-yl]-2-fluorophenyl}-2,5-difluorobenzenesulfonamide (200 mg, 0.352 mmol) and ammonia in MeOH 7M (7 ml, 49.0 mmol) was heated in a sealed tube at 80° C. for 48 h. The reaction mixture was evaporated onto silica gel and chromatographed, 0-50% 1:9 acetone:CHCl$_3$ in EtOAc. The resulting solid was triturated in MeOH to give the title compound (54 mg, 27% yield). $^1$H NMR (400 MHz, DMSO-d6) δ ppm 10.70 (br. s., 1H), 7.78 (d, J=5.3 Hz, 1H), 7.40-7.59 (m, 3H), 7.37 (td, J=7.4, 2.0 Hz, 1H), 7.14-7.31 (m, 2H), 6.52 (s, 2H), 5.58 (d, J=5.2 Hz, 1H), 3.66 (t, J=4.6 Hz, 4H), 3.40 (t, J=4.6 Hz, 4H). MS (ESI): 549.1 [M+H]$^+$.

Example 57

N-{3-[5-(2-Amino-4-pyrimidinyl)-2-(1,1-dimethylethyl)-1,3-thiazol-4-yl]-2-fluorophenyl}-2,5-difluorobenzenesulfonamide

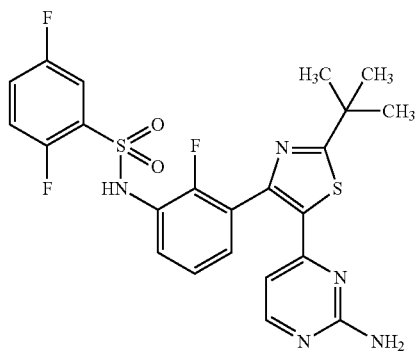 [SMILES: CC(C)(C)c1nc(-c2cccc(NS(=O)(=O)c3cc(F)ccc3F)c2F)c(-c2ccnc(N)n2)s1]

Following a procedure analogous to the procedure described in Example 51, Step B using N-{3-[5-(2-chloro-4-pyrimidinyl)-2-(1,1-dimethylethyl)-1,3-thiazol-4-yl]-2-fluorophenyl}-2,5-difluorobenzenesulfonamide (200 mg, 0.371 mmol) and ammonia in MeOH 7M (6 ml, 42.0 mmol) and heating to 80° C. overnight, the title compound was obtained as an off-white solid (158 mg, 78% yield). ¹H NMR (400 MHz, DMSO-d6) δ ppm 10.70 (s, 1H), 7.93 (d, J=5.1 Hz, 1H), 7.40-7.56 (m, 3H), 7.35-7.41 (m, 1H), 7.28-7.35 (m, 1H), 7.20-7.28 (m, 1H), 6.71 (s, 2H), 5.79 (d, J=5.1 Hz, 1H), 1.35 (s, 9H). MS (ESI): 520.2 [M+H]⁺.

Example 58a

N-{3-[5-(2-Amino-4-pyrimidinyl)-2-(1,1-dimethylethyl)-1,3-thiazol-4-yl]-2-fluorophenyl}-2,6-difluorobenzenesulfonamide

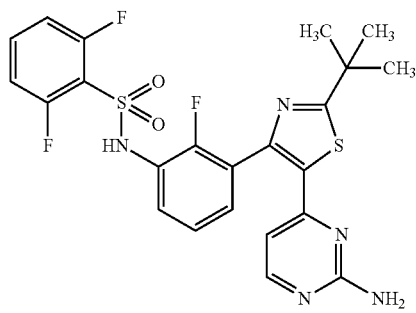 [SMILES: CC(C)(C)c1nc(-c2cccc(NS(=O)(=O)c3c(F)cccc3F)c2F)c(-c2ccnc(N)n2)s1]

Following a procedure analogous to the procedure described in Example 51, Step B using N-{3-[5-(2-chloro-4-pyrimidinyl)-2-(1,1-dimethylethyl)-1,3-thiazol-4-yl]-2-fluorophenyl}-2,6-difluorobenzenesulfonamide (196 mg, 0.364 mmol) and ammonia in methanol 7M (8 ml, 56.0 mmol) and heating to 90° C. for 24 h, the title compound, N-{3-[5-(2-amino-4-pyrimidinyl)-2-(1,1-dimethylethyl)-1,3-thiazol-4-yl]-2-fluorophenyl}-2,6-difluorobenzenesulfonamide was obtained (94 mg, 47% yield). ¹H NMR (400 MHz, DMSO-d6) δ ppm 10.83 (s, 1H), 7.93 (d, J=5.2 Hz, 1H), 7.55-7.70 (m, 1H), 7.35-7.43 (m, 1H), 7.31 (t, J=6.3 Hz, 1H), 7.14-7.27 (m, 3H), 6.70 (s, 2H), 5.79 (d, J=5.13 Hz, 1H), 1.35 (s, 9H). MS (ESI): 519.9 [M+H]⁺.

Example 58b

N-{3-[5-(2-Amino-4-pyrimidinyl)-2-(1,1-dimethylethyl)-1,3-thiazol-4-yl]-2-fluorophenyl}-2,6-difluorobenzenesulfonamide 19.6 mg of N-{3-[5-(2-Amino-4-pyrimidinyl)-2-(1,1-dimethylethyl)-1,3-thiazol-4-yl]-2-fluorophenyl}-2,6-difluorobenzenesulfonamide (may be prepared in accordance with example 58a) was combined with 500 μL of ethyl acetate in a 2-mL vial at room temperature. The slurry was temperature-cycled between 0-40° C. for 48 hrs. The resulting slurry was allowed to cool to room temperature and the solids were collected by vacuum filtration. The solids were analyzed by Raman, PXRD, DSC/TGA analyses, which indicated a crystal form different from the crystal form resulting from Example 58a, above.

Example 58c

N-{3-[5-(2-amino-4-pyrimidinyl)-2-(1,1-dimethylethyl)-1,3-thiazol-4-yl]-2-fluorophenyl}-2,6-difluorobenzenesulfonamide

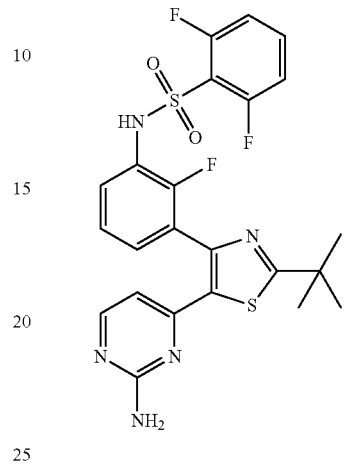

Step A: methyl 3-{[(2,6-difluorophenyl)sulfonyl]amino}-2-fluorobenzoate

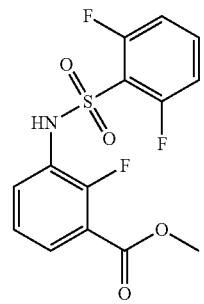 [SMILES: COC(=O)c1cccc(NS(=O)(=O)c2c(F)cccc2F)c1F]

Methyl 3-amino-2-fluorobenzoate (50 g, 1 eq) was charged to reactor followed by dichloromethane (250 mL, 5 vol). The contents were stirred and cooled to ~15° C. and pyridine (26.2 mL, 1.1 eq) was added. After addition of the pyridine, the reactor contents were adjusted to ~15° C. and the addition of 2,6-difluorobenzenesulfonyl chloride (39.7 mL, 1.0 eq) was started via addition funnel. The temperature during addition was kept <25° C. After complete addition, the reactor contents were warmed to 20-25° C. and held overnight. Ethyl acetate (150 mL) was added and dichloromethane was removed by distillation. Once distillation was complete, the reaction mixture was then diluted once more with ethyl acetate (5 vol) and concentrated. The reaction mixture was diluted with ethyl acetate (10 vol) and water (4 vol) and the contents heated to 50-55° C. with stirring until all solids dissolve. The layers were settled and separated. The organic layer was diluted with water (4 vol) and the contents heated to 50-55° for 20-30 min. The layers were settled and then separated and the ethyl acetate layer was evaporated under reduced pressure to ~3 volumes. Ethyl Acetate (5 vol.) was added and again evaporated under reduced pressure to ~3 volumes. Cyclohexane (9 vol) was then added to the reactor and the contents were heated to reflux for 30 min then cooled to 0° C. The solids were filtered and rinsed with cyclohexane (2×100 mL). The solids were air dried overnight to obtain methyl 3-{[(2,6-difluorophenyl)sulfonyl]amino}-2-fluorobenzoate (94.1 g, 91%).

Step B: N-{3-[(2-chloro-4-pyrimidinyl)acetyl]-2-fluorophenyl}-2,6-difluorobenzenesulfonamide

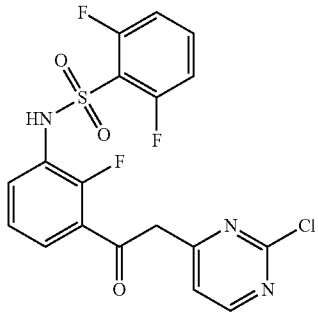 [SMILES: O=C(Cc1ccnc(Cl)n1)c1cccc(NS(=O)(=O)c2c(F)cccc2F)c1F]

Methyl 3-{[(2,6-difluorophenyl)sulfonyl]amino}-2-fluorobenzoate (490 g, 1 equiv.), prepared generally in accordance with Step A, above, was dissolved in THF (2.45 L, 5 vols) and stirred and cooled to 0-3° C. 1M lithium bis(trimethylsilyl)amide in THF (5.25 L, 3.7 equiv.) solution was charged to the reaction mixture followed addition of 2-chloro-4-methylpyrimidine (238 g, 1.3 equiv.) in THF (2.45 L, 5 vols). The reaction was then stirred for 1 hr. The reaction was quenched with 4.5M HCl (3.92 L, 8 vols). The aqueous layer (bottom layer) was removed and discarded. The organic layer was concentrated under reduced pressure to ~2 L. IPAC (isopropyl acetate) (2.45 L) was added to the reaction mixture which was then concentrated to ~2 L. IPAC (0.5 L) and MTBE (2.45 L) was added and stirred overnight under N₂. The solids were filtered. The solids and mother filtrate added back together and stirred for several hours. The solids were filtered and washed with MTBE (~5 vol). The solids were placed in vacuum oven at 50° C. overnight. The solids were dried in vacuum oven at 30° C. over weekend to obtain N-{3-[(2-chloro-4-pyrimidinyl)acetyl]-2-fluorophenyl}-2,6-difluorobenzenesulfonamide (479 g, 72%).

Step C: N-{3-[5-(2-chloro-4-pyrimidinyl)-2-(1,1-dimethylethyl)-1,3-thiazol-4-yl]-2-fluorophenyl}-2,6-difluorobenzenesulfonamide

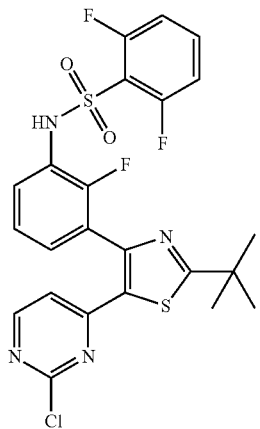 [SMILES: CC(C)(C)c1nc(-c2cccc(NS(=O)(=O)c3c(F)cccc3F)c2F)c(-c2ccnc(Cl)n2)s1]

To a reactor vessel was charged N-{3-[(2-chloro-4-pyrimidinyl)acetyl]-2-fluorophenyl}-2,6-difluorobenzenesulfonamide (30 g, 1 eq) followed by dichloromethane (300 mL). The reaction slurry was cooled to ~10° C. and N-bromosuccinimide ("NBS") (12.09 g, 1 eq) was added in 3 approximately equal portions, stirring for 10-15 minutes between each addition. After the final addition of NBS, the reaction mixture was warmed to ~20° C. and stirred for 45 min. Water (5 vol) was then added to the reaction vessel and the mixture was stirred and then the layers separated. Water (5 vol) was again added to the dichloromethane layer and the mixture was stirred and the layers separated. The dichloromethane layers were concentrated to ~120 mL. Ethyl acetate (7 vol) was added to the reaction mixture and concentrated to ~120 mL. Dimethylacetamide (270 mL) was then added to the reaction mixture and cooled to ~10° C. 2,2-Dimethylpropanethioamide (1.3 g, 0.5 eq) in 2 equal portions was added to the reactor contents with stirring for ~5 minutes between additions. The reaction was warmed to 20-25° C. After 45 min, the vessel contents were heated to 75° C. and held for 1.75 hours. The reaction mixture was then cooled to 5° C. and water (270 ml) was slowly charged keeping the temperature below 30° C. Ethyl acetate (4 vol) was then charged and the mixture was stirred and layers separated. Ethyl acetate (7 vol) was again charged to the aqueous layer and the contents were stirred and separated. Ethyl acetate (7 vol) was charged again to the aqueous layer and the contents were stirred and separated. The organic layers were combined and washed with water (4 vol) 4 times and stirred overnight at 20-25° C. The organic layers were then concentrated under heat and vacuum to 120 mL. The vessel contents were then heated to 50° C. and heptanes (120 mL) were added slowly. After addition of heptanes, the vessel contents were heated to reflux then cooled to 0° C. and held for ~2 hrs. The solids were filtered and rinsed with heptanes (2×2 vol). The solid product was then dried under vacuum at 30° C. to obtain N-{3-[5-(2-chloro-4-pyrimidinyl)-2-(1,1-dimethylethyl)-1,3-thiazol-4-yl]-2-fluorophenyl}-2,6-difluorobenzenesulfonamide (28.8 g, 80%).

Step D: N-{3-[5-(2-amino-4-pyrimidinyl)-2-(1,1-dimethylethyl)-1,3-thiazol-4-yl]-2-fluorophenyl}-2,6-difluorobenzenesulfonamide In 1 gal pressure reactor, a mixture of N-{3-[5-(2-chloro-4-pyrimidinyl)-2-(1,1-dimethylethyl)-1,3-thiazol-4-yl]-2-fluorophenyl}-2,6-difluorobenzenesulfonamide (120 g) prepared in accordance with Step C, above, and ammonium hydroxide (28-30%, 2.4 L, 20 vol) was heated in the sealed pressure reactor to 98-103° C. and stirred at this temperature for 2 hours. The reaction was cooled slowly to room temperature (20° C.) and stirred overnight. The solids were filtered and washed with minimum amount of the mother liquor and dried under vacuum. The solids were added to a mixture of EtOAc (15 vol)/water (2 vol) and heated to complete dissolution at 60-70° C. and the aqueous layer was removed and discarded. The EtOAC layer was charged with water (1 vol) and neutralized with aq. HCl to ~pH 5.4-5.5. and added water (1 vol). The aqueous layer was removed and discarded at 60-70° C. The organic layer was washed with water (1 vol) at 60-70° C. and the aqueous layer was removed and discarded. The organic layer was filtered at 60° C. and concentrated to 3 volumes. EtOAc (6 vol) was charged into the mixture and heated and stirred at 72° C. for 10 min, then cooled to 20° C. and stirred overnight. EtOAc was removed via vacuum distillation to concentrate the reaction mixture to ~3 volumes. The reaction mixture was maintained at ~65-70° C. for ~30 mins. Product crystals having the same crystal form as those prepared in Example 58b (and preparable by the procedure of Example 58b), above, in heptanes slurry were charged. Heptane (9 vol) was slowly added at 65-70° C. The slurry was stirred at 65-70° C. for 2-3 hours and then cooled slowly to 0-5° C. The product was filtered, washed with EtOAc/heptane (3/1 v/v, 4 vol) and dried at 45° C. under vacuum to obtain N-{3-[5-(2-amino-4-pyrimidinyl)-2-(1,1-dimethylethyl)-1,3-thiazol-4-yl]-2-fluorophenyl}-2,6-difluorobenzenesulfonamide (102.3 g, 88%).

Example 58d

N-{3-[5-(2-amino-4-pyrimidinyl)-2-(1,1-dimethylethyl)-1,3-thiazol-4-yl]-2-fluorophenyl}-2,6-difluorobenzenesulfonamide methanesulfonate

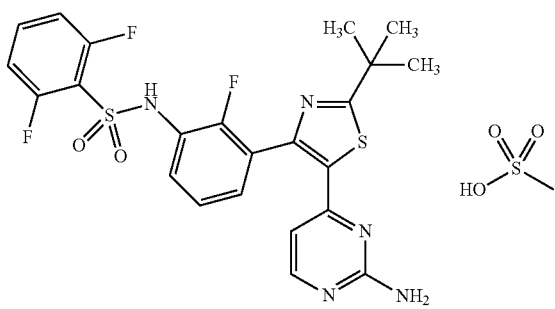

To a solution of N-{3-[5-(2-amino-4-pyrimidinyl)-2-(1,1-dimethylethyl)-1,3-thiazol-4-yl]-2-fluorophenyl}-2,6-difluorobenzenesulfonamide (204 mg, 0.393 mmol) in isopropanol (2 mL), methanesulfonic acid (0.131 mL, 0.393 mmol) was added and the solution was allowed to stir at room temperature for 3 hours. A white precipitate formed and the slurry was filtered and rinsed with diethyl ether to give the title product as a white crystalline solid (210 mg, 83% yield). $^1$H NMR (400 MHz, DMSO-d6) δ ppm 10.85 (s, 1H) 7.92-8.05 (m, 1H) 7.56-7.72 (m, 1H) 6.91-7.50 (m, 7H) 5.83-5.98 (m, 1H) 2.18-2.32 (m, 3H) 1.36 (s, 9H). MS (ESI): 520.0 [M+H]$^+$.

Example 58e

N-{3-[5-(2-amino-4-pyrimidinyl)-2-(1,1-dimethylethyl)-1,3-thiazol-4-yl]-2-fluorophenyl}-2,6-difluorobenzenesulfonamide methanesulfonate N-{3-[5-(2-amino-4-pyrimidinyl)-2-(1,1-dimethylethyl)-1,3-thiazol-4-yl]-2-fluorophenyl}-2,6-difluorobenzenesulfonamide (as may be prepared according to example 58a) (2.37 g, 4.56 mmol) was combined with pre-filtered acetonitrile (5.25 vol, 12.4 mL). A pre-filtered solution of mesic acid (1.1 eq., 5.02 mmol, 0.48 g) in H$_2$O (0.75 eq., 1.78 mL) was added at 20° C. The temperature of the resulting mixture was raised to 50-60° C. while maintaining a low agitation speed. Once the mixture temperature reached to 50-60° C., a seed slurry of N-{3-[5-(2-amino-4-pyrimidinyl)-2-(1,1-dimethylethyl)-1,3-thiazol-4-yl]-2-fluorophenyl}-2,6-difluorobenzenesulfonamide methanesulfonate (1.0% w/w slurried in 0.2 vol of pre-filtered acetonitrile) was added, and the mixture was aged while agitating at a speed fast enough to keep solids from settling at 50-60° C. for 2 hr. The mixture was then cooled to 0-5° C. at 0.25° C./min and held at 0-5° C. for at 6 hr. The mixture was filtered and the wet cake was washed twice with pre-filtered acetonitrile. The first wash consisted of 14.2 ml (6 vol) pre-filtered acetonitrile and the second wash consisted of 9.5 ml (4 vol) pre-filtered acetonitrile. The wet solid was dried at 50° C. under vacuum, yielding 2.39 g (85.1% yield) of product.

Example 59

N-{3-[5-(2-Amino-4-pyrimidinyl)-2-(4-morpholinyl)-1,3-thiazol-4-yl]-2-fluorophenyl}-2,6-difluorobenzenesulfonamide

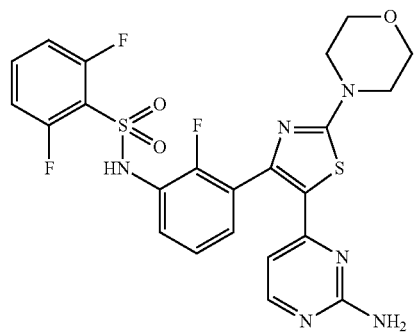 [SMILES: Nc1nccc(-c2sc(N3CCOCC3)nc2-c2cccc(NS(=O)(=O)c3c(F)cccc3F)c2F)n1]

Following a procedure analogous to the procedure described in Example 51, Step B using N-{3-[5-(2-chloro-4-pyrimidinyl)-2-(4-morpholinyl)-1,3-thiazol-4-yl]-2-fluorophenyl}-2,6-difluorobenzenesulfonamide (250 mg, 0.440 mmol) and ammonia in MeOH 7M (7 ml, 49.0 mmol) the title compound was obtained as a yellow solid (187 mg, 72% yield). $^1$H NMR (400 MHz, DMSO-d6) δ ppm 10.82 (br. s., 1H), 7.78 (d, J=5.3 Hz, 1H), 7.55-7.71 (m, 1H), 7.31-7.43 (m, 1H), 7.10-7.30 (m, 4H), 6.52 (s, 2H), 5.59 (d, J=5.2 Hz, 1H), 3.66 (t, J=4.3 Hz, 4H), 3.40 (d, J=4.5 Hz, 4H). MS (ESI): 549.1 [M+H]$^+$.

Example 60

N-{3-[5-(2-Amino-4-pyrimidinyl)-2-(1-methylethyl)-1,3-thiazol-4-yl]-2-fluorophenyl}-2,6-difluorobenzenesulfonamide

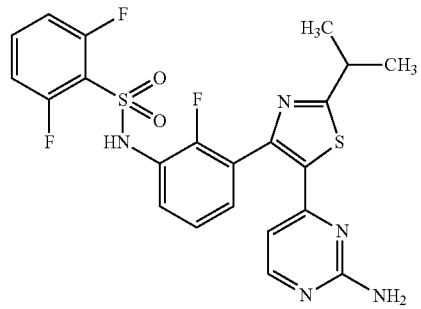 [SMILES: CC(C)c1nc(-c2cccc(NS(=O)(=O)c3c(F)cccc3F)c2F)c(-c2ccnc(N)n2)s1]

Following a procedure analogous to the procedure described in Example 51, Step B using N-{3-[5-(2-chloro-4-pyrimidinyl)-2-(1-methylethyl)-1,3-thiazol-4-yl]-2-fluorophenyl}-2,6-difluorobenzenesulfonamide (200 mg, 0.381 mmol) and ammonia in MeOH 7M (6 ml, 42.0 mmol) and heating to 45° C. overnight, the title compound was obtained as a light yellow solid (128 mg, 63% yield). $^1$H NMR (400

MHz, DMSO-d6) δ ppm 10.84 (s, 1H), 7.93 (d, J=5.2 Hz, 1H), 7.55-7.70 (m, 1H), 7.34-7.43 (m, 1H), 7.30 (t, J=6.3 Hz, 1H), 7.13-7.27 (m, 3H), 6.71 (s, 2H), 5.79 (d, J=5.1 Hz, 1H), 3.17-3.27 (m, 1H), 1.30 (d, J=6.9 Hz, 6H). MS (ESI): 506.1 [M+H]+.

Example 61

N-{3-[5-(2-Amino-4-pyrimidinyl)-2-(4-morpholinyl)-1,3-thiazol-4-yl]-2-fluorophenyl}-3-pyridinesulfonamide

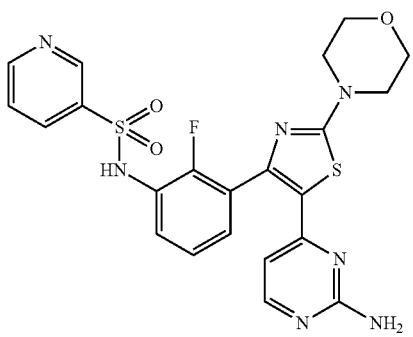 [SMILES: Nc1nccc(-c2sc(N3CCOCC3)nc2-c2cccc(NS(=O)(=O)c3cccnc3)c2F)n1]

Step A: N-{3-[5-(2-Chloro-4-pyrimidinyl)-2-(4-morpholinyl)-1,3-thiazol-4-yl]-2-fluorophenyl}-3-pyridinesulfonamide

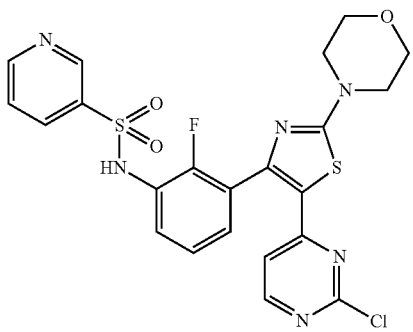 [SMILES: O=S(=O)(Nc1cccc(-c2nc(N3CCOCC3)sc2-c2ccnc(Cl)n2)c1F)c1cccnc1]

To a solution of 3-(5-(2-chloropyrimidin-4-yl)-2-morpholinothiazol-4-yl)-2-fluoroaniline (3 g, 7.7 mmol) in pyridine (15 mL) was added pyridine-3-sulfonyl chloride (1.49 g, 8.4 mmol) dropwise to the mixture. The reaction was stirred at rt overnight. The reaction was washed with water (100 mL), and extracted with DCM (2×100 mL). The organic layer was washed with brine, dried over anhydrous Na2SO4, filtered and concentrated under reduced pressure to give the crude product, which was purified by column chromatography on silica gel (petroleum ether:EtOAc 5:1) to afford the title compound of Step A (2.9 g, 71.5% yield). 1H NMR (400 MHz, DMSO-d6) δ ppm 10.55-10.60 (br, 1H), 8.82-8.86 (m, 1H), 8.72-8.76 (m, 1H), 8.30 (d, J=5.3 Hz, 1H), 8.07-8.13 (m, 1H), 7.51-7.52 (m, 1H), 7.39-7.47 (m, 1H), 7.27-7.40 (m, 2H), 6.47 (d, J=5.3 Hz, 1H) 3.47-3.57 (m, 4H), 3.67-3.75 (m, 4H). MS (ES+): 533 [M+H]+.

Step B: N-{3-[5-(2-Amino-4-pyrimidinyl)-2-(4-morpholinyl)-1,3-thiazol-4-yl]-2-fluorophenyl}-3-pyridinesulfonamide A suspension of N-{3-[5-(2-chloro-4-pyrimidinyl)-2-(4-morpholinyl)-1,3-thiazol-4-yl]-2-fluorophenyl}-3-pyridinesulfonamide (195 mg, 0.366 mmol) and ammonia in i-PrOH 2M (8 mL, 16.0 mmol) was heated in a sealed tube at 100° C. overnight. The reaction mixture was evaporated onto silica gel and chromatographed (10-100% 1:9 MeOH:EtOAc in DCM). The title compound was obtained as a yellow solid after trituration in diethyl ether (88 mg, 45% yield). 1H NMR (400 MHz, DMSO-d6) δ ppm 10.56 (s, 1H), 8.84 (d, J=1.7 Hz, 1H), 8.75 (dd, J=4.7, 1.0 Hz, 1H), 7.99-8.15 (m, 1H), 7.82 (d, J=5.3 Hz, 1H), 7.55 (dd, J=7.9, 5.0 Hz, 1H), 7.33-7.46 (m, 1H), 7.24 (d, J=6.3 Hz, 2H), 6.55 (br. s., 2H), 5.56 (d, J=5.2 Hz, 1H), 3.59-3.72 (m, 4H), 3.34-3.49 (m, 4H). MS (ESI): 514.1 [M+H]+.

Example 62

N-{3-[5-(2-Amino-4-pyrimidinyl)-2-(4-morpholinyl)-1,3-thiazol-4-yl]-2-fluorophenyl}-2-furansulfonamide

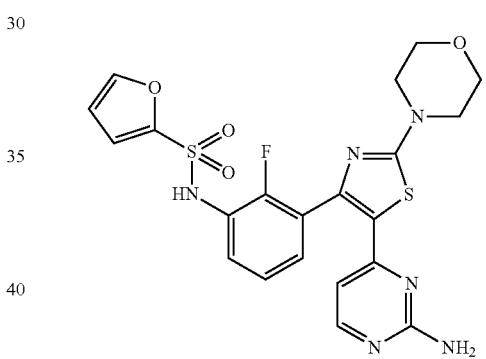

Step A: N-{3-[5-(2-Chloro-4-pyrimidinyl)-2-(4-morpholinyl)-1,3-thiazol-4-yl]-2-fluorophenyl}-2-furansulfonamide


To a solution of 3-(5-(2-chloropyrimidin-4-yl)-2-morpholinothiazol-4-yl)-2-fluoroaniline (3 g, 7.6 mmol) in DCM (50 mL) was added pyridine (10 mL). The mixture was cooled to 0° C. Furan-2-sulfonyl chloride (1.4 g, 8.4 mmol) in DCM (5 mL) was added dropwise to the mixture. The reaction was stirred at rt overnight. Then the reaction was washed with water (100 mL), and extracted with DCM (2×100 mL). The organic layer was washed with brine, dried over anhydrous Na$_2$SO$_4$, filtrated and concentrated under reduced pressure to give the crude product, which was purified by column chromatography on silica gel (petroleum ether:EtOAc 4:1) to afford the title compound of Step A (2.5 g, 63% yield). $^1$H NMR (400 MHz, DMSO-d6) δ ppm 8.07 (d, J=5.5 Hz, 1H), 7.59-7.66 (m, 1H), 7.42-7.75 (br, 1H), 7.13-7.20 (m, 2H), 7.02 (d, J=5.5 Hz, 1H), 6.93-6.98 (m, 1H), 6.37-6.42 (m, 2H), 3.50-3.57 (m, 4H), 3.72-3.78 (m, 4H). MS (ES+): 522 [M+H]$^+$.

Step B: N-{3-[5-(2-Amino-4-pyrimidinyl)-2-(4-morpholinyl)-1,3-thiazol-4-yl]-2-fluorophenyl}-2-furansulfonamide A suspension of N-{3-[5-(2-chloro-4-pyrimidinyl)-2-(4-morpholinyl)-1,3-thiazol-4-yl]-2-fluorophenyl}-2-furansulfonamide (150 mg, 0.287 mmol) and NH$_4$OH (5 mL, 128 mmol) was heated in a microwave reactor at 120° C. for 40 min. LC-MS looks good for desired product. The reaction mixture was neutralized with 5N HCl and extracted with DCM×2. The crude mixture was evaporated onto silica gel and chromatographed (10-50% 1:9 MeOH:EtOAc in DCM). The title compound was obtained as a yellow solid after trituration in MeOH (102 mg, 68% yield). $^1$H NMR (400 MHz, DMSO-d6) δ ppm 10.57 (s, 1H), 7.78-7.94 (m, 2H), 7.34 (td, J=7.4, 2.0 Hz, 1H), 7.14-7.30 (m, 2H), 7.03 (d, J=3.5 Hz, 1H), 6.44-6.61 (m, 3H), 5.64 (d, J=5.3 Hz, 1H), 3.67 (t, J=4.7 Hz, 4H), 3.41 (t, J=4.6 Hz, 4H). MS (ESI): 502.2 [M−H]$^−$.

Example 63

N-{3-[5-(2-Amino-4-pyrimidinyl)-2-(1,1-dimethylethyl)-1,3-thiazol-4-yl]-2-fluorophenyl}cyclohexanesulfonamide

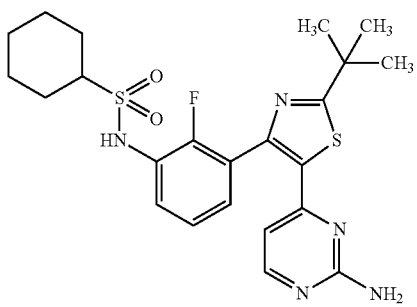 [SMILES: CC(C)(C)c1nc(-c2cccc(NS(=O)(=O)C3CCCCC3)c2F)c(-c2ccnc(N)n2)s1]

Step A: 2-Propen-1-yl {3-[5-(2-amino-4-pyrimidinyl)-2-(1,1-dimethylethyl)-1,3-thiazol-4-yl]-2-fluorophenyl}carbamate

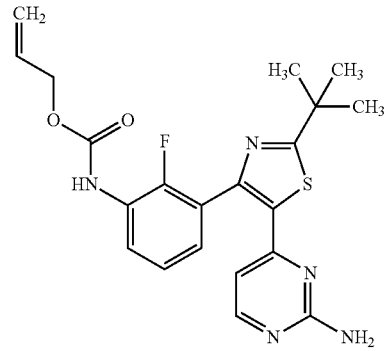 [SMILES: C=CCOC(=O)Nc1cccc(-c2nc(C(C)(C)C)sc2-c2ccnc(N)n2)c1F]

A solution of 2-propen-1-yl {3-[5-(2-chloro-4-pyrimidinyl)-2-(1,1-dimethylethyl)-1,3-thiazol-4-yl]-2-fluorophenyl}carbamate (535 mg, 1.197 mmol) and ammonia in MeOH 7N (6 ml, 42.0 mmol) was heated to 80° C. for 24 h. The crude reaction mixture was evaporated onto silica gel and chromatographed, (0-15% MeOH in DCM). The title compound was obtained as a yellow foam (233 mg, 41% yield). MS (ESI): 428.1 [M+H]$^+$.

Step B: 4-[4-(3-Amino-2-fluorophenyl)-2-(1,1-dimethylethyl)-1,3-thiazol-5-yl]-2-pyrimidinamine

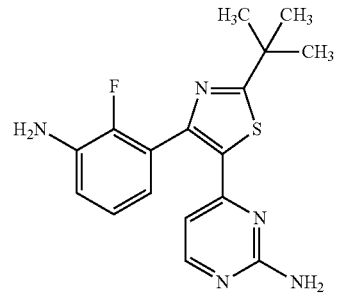 [SMILES: CC(C)(C)c1nc(-c2cccc(N)c2F)c(-c2ccnc(N)n2)s1]

A solution of 2-propen-1-yl {3-[5-(2-amino-4-pyrimidinyl)-2-(1,1-dimethylethyl)-1,3-thiazol-4-yl]-2-fluorophenyl}carbamate (220 mg, 0.515 mmol) in TBAF (1 mL, 1.0 mmol) in 1M THF was heated in a microwave reactor at 130° C. for 10 min. The crude reaction mixture was evaporated onto silica gel and chromatographed (1:9:90 NH$_4$OH:MeOH:DCM in DCM 10-80%). The title compound was obtained as a white solid (100 mg, 56% yield). MS (ESI): 344.1 [M+H]$^+$.

Step C: N-{3-[5-(2-Amino-4-pyrimidinyl)-2-(1,1-dimethylethyl)-1,3-thiazol-4-yl]-2-fluorophenyl}cyclohexanesulfonamide To a solution of 4-[4-(3-amino-2-fluorophenyl)-2-(1,1-dimethylethyl)-1,3-thiazol-5-yl]-2-pyrimidinamine (100 mg, 0.291 mmol) in DCM (2 ml), pyridine (0.4 mL, 4.95 mmol) was added followed by cyclohexylsulfonyl chloride (0.042 mL, 0.291 mmol). The solution was allowed to stir at rt for 24 h at rt. The solvent was removed and the concentrated residue was allowed to sit at rt overnight. The residue was then evaporated onto silica gel and chromatographed (1:9 MeOH:EtOAc in DCM). The title compound was obtained after trituration in diethyl ether (50 mg, 33% yield). $^1$H NMR (400 MHz, DMSO-d6) δ ppm 9.65 (s, 1H), 8.02 (d, J=5.1 Hz, 1H), 7.52 (t, J=7.7 Hz, 1H), 7.33 (t, J=6.4 Hz, 1H), 7.26 (t, J=7.9

Hz, 1H), 6.72 (s, 2H), 6.01 (d, J=5.1 Hz, 1H), 2.79-2.92 (m, 1H), 1.92-2.05 (m, 2H), 1.68 (d, J=12.6 Hz, 2H), 1.47-1.57 (m, 1H), 1.38 (s, 9H), 1.22-1.36 (m, 2H), 1.07-1.24 (m, 3H). MS (ESI): 490.2 [M+H]$^+$.

Example 64

N-{3-[5-(2-Amino-4-pyrimidinyl)-2-(tetrahydro-2H-pyran-4-yl)-1,3-thiazol-4-yl]-2-fluorophenyl}-2,6-difluorobenzenesulfonamide

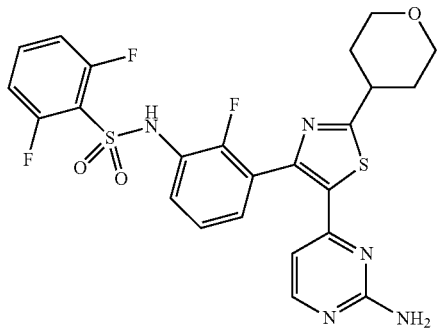 [SMILES: Nc1nccc(-c2sc(C3CCOCC3)nc2-c2cccc(NS(=O)(=O)c3c(F)cccc3F)c2F)n1]

A suspension of N-{3-[5-(2-chloro-4-pyrimidinyl)-2-(tetrahydro-2H-pyran-4-yl)-1,3-thiazol-4-yl]-2-fluorophenyl}-2,6-difluorobenzenesulfonamide (20.7 g, 36.5 mmol) and ammonia hydroxide (500 mL) was heated in a steel reactor to 100° C. After 3 h, the reaction cooled and checked by HPLC. The reaction mixture was concentrated. The reaction mixture wad diluted with CH$_2$Cl$_2$ (300 mL) and water (300 mL) then acidified with 6 N HCl to pH=1. The mixture was extracted with 1% MeOH in CH$_2$Cl$_2$ (4×). The CH$_2$Cl$_2$ layer were dried over Na$_2$SO$_4$ and filtered and concentrated to 400 mL. Ethanol (400 mL) was added to the reaction mixture and concentrated to dryness. Ethanol (400 mL) was added again to the reaction mixture and concentrated to dryness. Ethanol (500 mL) was added to the reaction mixture and refluxed. After 4 h, the reaction mixture was cooled to 0° C., filtered, and wash with EtOH. The product was dried under vacuum at 60° C. for 2 days. Title compound was obtained as an off-white solid (17 g, 85% yield). $^1$H NMR (400 MHz, DMSO-d$_6$) δ ppm 10.90 (br. s., 1H), 7.98 (d, J=5.3 Hz, 1H), 7.56-7.84 (m, 1H), 6.93-7.54 (m, 5H), 6.77 (br. s., 2H), 5.85 (d, J=4.6 Hz, 1H), 3.92 (d, J=9.9 Hz, 2H), 3.46 (t, J=11.2 Hz, 2H), 3.20-3.32 (m, 1H), 1.90-2.06 (m, 2H), 1.57-1.81 (m, 2H). MS (ESI): 548.10 [M+H]$^+$.

Example 65

N-{3-[2-(1,1-Dimethylethyl)-5-(2-methyl-4-pyrimidinyl)-1,3-thiazol-4-yl]-2-fluorophenyl}-2,5-difluorobenzenesulfonamide

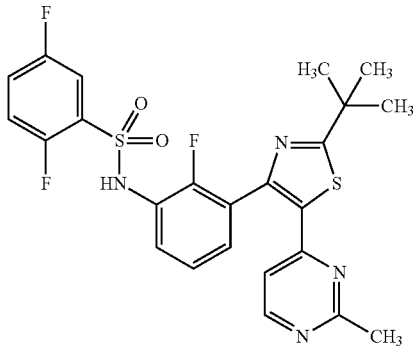 [SMILES: Cc1nccc(-c2sc(C(C)(C)C)nc2-c2cccc(NS(=O)(=O)c3cc(F)ccc3F)c2F)n1]

To a suspension of N-{3-[5-(2-chloro-4-pyrimidinyl)-2-(1,1-dimethylethyl)-1,3-thiazol-4-yl]-2-fluorophenyl}-2,5-difluorobenzenesulfonamide (200 mg, 0.371 mmol) and tetrakis(triphenylphosphine)palladium (8.6 mg, 7.4 µmol) in THF (5 mL) was added a 2 M solution of methylzinc chloride in THF (0.371 mL, 0.742 mmol). The suspension was stirred for 16 h at 60° C. The reaction mixture was partitioned between water and EtOAc, and the aqueous layer was extracted with EtOAc. The combined organic layers were dried over anhydrous Na$_2$SO$_4$, filtered, concentrated, and purified via column chromatography, eluting with 0-100% EtOAc/DCM. The desired fractions were combined and concentrated to generate 90 mg (0.174 mmol, 46.8% yield) of the title compound as a white powder. $^1$H NMR (400 MHz, DMSO-d$_6$): δ 10.75 (s, 1H), 8.47 (d, J=5.3 Hz, 1H), 7.52-7.58 (m, 1H), 7.40-7.50 (m, 4H), 7.29 (t, J=7.8 Hz, 1H), 6.64 (d, J=5.3 Hz, 1H), 2.58 (s, 3H), 1.42 (s, 9H). MS (ESI): 520.0 [M+H]$^+$.

Example 65

Alternative

N-{3-[2-(1,1-Dimethylethyl)-5-(2-methyl-4-pyrimidinyl)-1,3-thiazol-4-yl]-2-fluorophenyl}-2,5-difluorobenzenesulfonamide

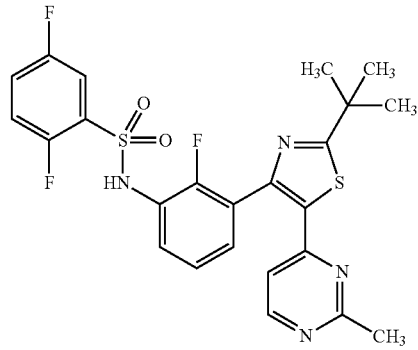 [SMILES: Cc1nccc(-c2sc(C(C)(C)C)nc2-c2cccc(NS(=O)(=O)c3cc(F)ccc3F)c2F)n1]

To a suspension of N-{3-[5-(2-chloro-4-pyrimidinyl)-2-(1,1-dimethylethyl)-1,3-thiazol-4-yl]-2-fluorophenyl}-2,5-difluorobenzenesulfonamide (21.54 g, 40 mmol) in 1,4-dioxane (300 mL) was bubble with argon for 10 min. The reaction mixture was treated with 2N dimethylzinc in toluene (40 mL, 80 mmol) under argon. The reaction mixture was treated with PdCl$_2$(dppf)CH$_2$Cl$_2$ adduct (0.326 g, 0.400 mmol) and heated to 80° C. After 2 h, the reaction was check by HPLC. The reaction was cooled to room temperature and slowly added MeOH until reaction was quenched. After quenched, the reaction mixture was diluted with NaHCO$_3$ (sat'd) (200 mL) and extracted with EtOAc (3×, 200 mL). The EtOAc layers were stirred with activated carbon (darco G-60, 100 mesh, powder) for 1 h. The reaction mixture was filtered through pad of SiO$_2$ (3"×3") and washed with EtOAc. The reaction mixture was concentrated. IPA (350 mL) was to the reaction mixture and heated to reflux. After 2 h, the reaction mixture was cooled to room temperature and filtered and washed with IPA and water (200 mL). The product was dried under vacuum at 60° C. for 2 days. Title compound was obtained as an off-white solid (17.5 g, 80% yield). $^1$H NMR (400 MHz, DMSO-d$_6$): δ 10.75 (s, 1H), 8.47 (d, J=5.3 Hz, 1H), 7.52-7.58

(m, 1H), 7.40-7.50 (m, 4H), 7.29 (t, J=7.8 Hz, 1H), 6.64 (d, J=5.3 Hz, 1H), 2.58 (s, 3H), 1.42 (s, 9H). MS (ESI): 519 [M+H]⁺.

Example 66

N-{3-[2-(1,1-Dimethylethyl)-5-(4-pyrimidinyl)-1,3-thiazol-4-yl]-2-fluorophenyl}-2,5-difluorobenzenesulfonamide

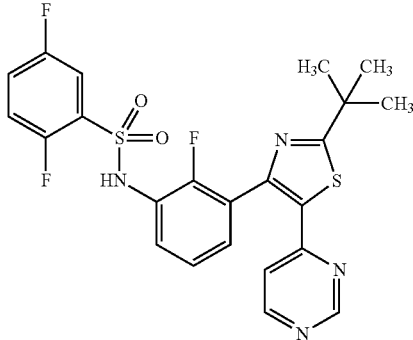 [SMILES: CC(C)(C)c1nc(-c2cccc(NS(=O)(=O)c3cc(F)ccc3F)c2F)c(-c2ccncn2)s1]

To a solution of N-{3-[5-(2-chloro-4-pyrimidinyl)-2-(1,1-dimethylethyl)-1,3-thiazol-4-yl]-2-fluorophenyl}-2,5-difluorobenzenesulfonamide (100 mg, 0.186 mmol) and TEA (52 µL, 0.371 mmol) in EtOH (5 mL) and MeOH (1 mL) was added 10% (w/w) palladium on carbon (50 mg, 0.048 mmol). The suspension was transferred to a hydrogenation bottle, and installed in a Fisher-Porter hydrogenation apparatus. The bottle was charged with H₂ (50 psi) and stirred at rt for 72 h. The reaction mixture was filtered through Celite and concentrated to generate 90 mg (0.178 mmol, 96%) of the title compound as a white powder. ¹H NMR (400 MHz, DMSO-d₆): δ 10.75 (s, 1H), 9.10 (s, 1H), 8.60 (d, J=5.3 Hz, 1H), 7.53-7.57 (m, 1H), 7.40-7.50 (m, 4H), 7.30 (t, J=7.6 Hz, 1H), 6.89 (d, J=5.3 Hz, 1H), 1.43 (s, 9H). MS (ESI): 504.6 [M+H]+.

Example 67

2,5-Difluoro-N-{2-fluoro-3-[5-{2-[(2-methylpropyl)amino]-4-pyrimidinyl}-2-(tetrahydro-2H-pyran-4-yl)-1,3-thiazol-4-yl]phenyl}benzenesulfonamide

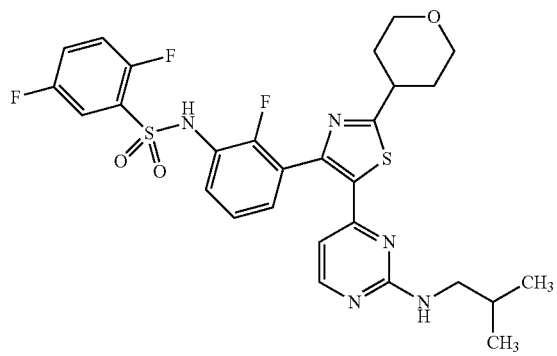 [SMILES: CC(C)CNc1nccc(-c2sc(C3CCOCC3)nc2-c2cccc(NS(=O)(=O)c3cc(F)ccc3F)c2F)n1]

Following a procedure analogous to the procedure described in Example 18, Step B using N-{3-[5-(2-chloro-4-pyrimidinyl)-2-(tetrahydro-2H-pyran-4-yl)-1,3-thiazol-4-yl]-2-fluorophenyl}-2,5-difluorobenzenesulfonamide (0.150 g, 0.265 mmol) and isobutylamine (1.052 mL, 10.58 mmol) the title compound was obtained as an off-white solid (108 mg, 0.166 mmol, 62.9% yield). ¹H NMR (400 MHz, DMSO-d₆) δ ppm 10.77 (s, 1H), 8.02 (d, J=5.1 Hz, 1H), 7.44-7.64 (m, 3H), 7.31-7.44 (m, 3H), 7.27 (t, J=7.8 Hz, 1H), 5.68-6.07 (m, 1H), 3.83-3.96 (m, 2H), 3.38-3.55 (m, 2H), 3.21-3.32 (m, 1H), 2.87-3.18 (m, 2H), 1.92-2.06 (m, 2H), 1.61-1.92 (m, 3H), 0.74-0.99 (m, 6H). MS (ESI): 604.20 [M+H]⁺.

Example 68

N-{5-[5-(2-Amino-4-pyrimidinyl)-2-(tetrahydro-2H-pyran-4-yl)-1,3-thiazol-4-yl]-2-fluorophenyl}-2,5-difluorobenzenesulfonamide

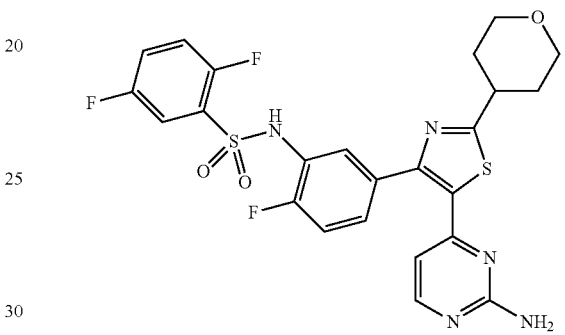

Following a procedure analogous to the procedure described in Example 51, Step B using N-{5-[5-(2-chloro-4-pyrimidinyl)-2-(tetrahydro-2H-pyran-4-yl)-1,3-thiazol-4-yl]-2-fluorophenyl}-2,5-difluorobenzenesulfonamide (0.120 g, 0.212 mmol) and ammonia (7 N solution in MeOH, 4.54 mL, 31.7 mmol) the title compound was obtained as a white solid (71 mg, 0.13 mmol, 60% yield). ¹H NMR (400 MHz, DMSO-d₆) δ ppm 10.80 (s, 1H), 8.06 (d, J=5.1 Hz, 1H), 7.45-7.71 (m, 3H), 7.34-7.45 (m, 2H), 7.23-7.34 (m, 1H), 6.80 (s, 2H), 6.19 (d, J=5.1 Hz, 1H), 3.88-4.03 (m, 2H), 3.40-3.56 (m, 2H), 3.21-3.31 (m, 1H), 1.92-2.07 (m, 2H), 1.63-1.82 (m, 2H). MS (ESI): 548.11 [M+H]⁺.

Example 69

2,5-Difluoro-N-{2-fluoro-5-[5-{2-[(2-methylpropyl)amino]-4-pyrimidinyl}-2-(tetrahydro-2H-pyran-4-yl)-1,3-thiazol-4-yl]phenyl}benzenesulfonamide

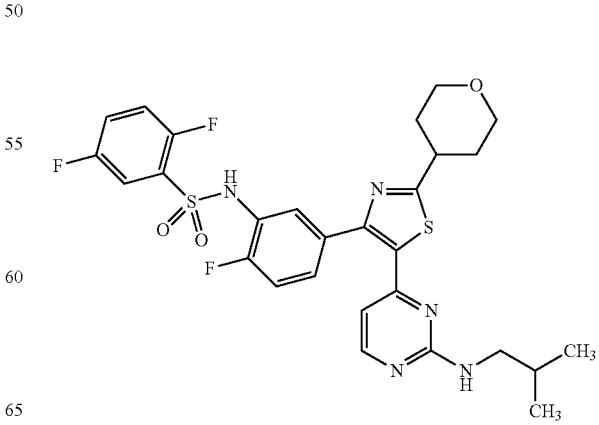

Following a procedure analogous to the procedure described in Example 18, Step B using N-{5-[5-(2-chloro-4-pyrimidinyl)-2-(tetrahydro-2H-pyran-4-yl)-1,3-thiazol-4-yl]-2-fluorophenyl}-2,5-difluorobenzenesulfonamide (120 mg, 0.212 mmol) and isobutylamine (1.1 mL, 11 mmol) the title compound was obtained as a light orange solid (94 mg, 0.16 mmol, 74% yield). $^1$H NMR (400 MHz, DMSO-$d_6$) δ ppm 10.81 (br. s., 1H), 7.83-8.30 (m, 1H), 7.43-7.71 (m, 3H), 7.30-7.43 (m, 3H), 7.15-7.30 (m, 1H), 5.97-6.36 (m, 1H), 3.73-4.07 (m, 2H), 3.47 (t, J=11.0 Hz, 2H), 3.20-3.31 (m, 1H), 2.94-3.16 (m, 2H), 1.93-2.08 (m, 2H), 1.61-1.89 (m, 3H), 0.75-0.93 (m, 6H). MS (ESI): 604.19 [M+H]$^+$.

Example 70

2,5-Difluoro-N-{2-fluoro-5-[5-(2-{[1-(methylsulfonyl)-4-piperidinyl]amino}-4-pyrimidinyl)-2-(tetrahydro-2H-pyran-4-yl)-1,3-thiazol-4-yl]phenyl}benzenesulfonamide

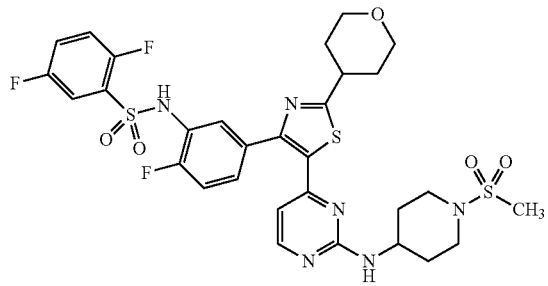 [SMILES: CS(=O)(=O)N1CCC(Nc2nccc(-c3sc(C4CCOCC4)nc3-c3ccc(F)c(NS(=O)(=O)c4cc(F)ccc4F)c3)n2)CC1]

Following a procedure analogous to the procedure described in Example 1 using N-{5-[5-(2-chloro-4-pyrimidinyl)-2-(tetrahydro-2H-pyran-4-yl)-1,3-thiazol-4-yl]-2-fluorophenyl}-2,5-difluorobenzenesulfonamide (120 mg, 0.212 mmol) and 1-(methylsulfonyl)-4-piperidinamine (377 mg, 2.12 mmol) in THF (1 mL) the title compound was obtained as a light yellow solid (89 mg, 0.12 mmol, 59% yield). $^1$H NMR (400 MHz, DMSO-$d_6$) δ ppm 10.83 (s, 1H), 8.14 (d, J=4.9 Hz, 1H), 7.46-7.73 (m, 3H), 7.34-7.45 (m, 3H), 7.22-7.34 (m, 1H), 5.99-6.51 (m, 1H), 3.95 (dd, J=11.4, 2.0 Hz, 2H), 3.41-3.58 (m, 4H), 3.18-3.33 (m, 1H), 2.69-2.93 (m, 5H), 1.81-2.06 (m, 5H), 1.66-1.81 (m, 2H), 1.42-1.65 (m, 2H). MS (ESI): 709.18 [M+H]$^+$.

Example 71

N-{3-[5-(2-Amino-4-pyrimidinyl)-2-(tetrahydro-3-furanyl)-1,3-thiazol-4-yl]-2-fluorophenyl}-2,6-difluorobenzenesulfonamide

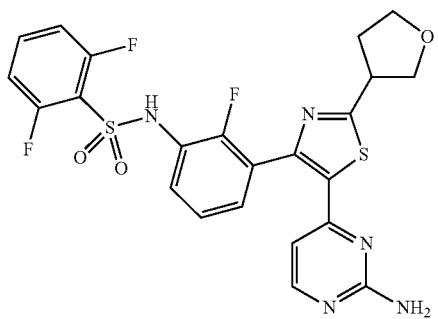 [SMILES: Nc1nccc(-c2sc(C3CCOC3)nc2-c2cccc(NS(=O)(=O)c3c(F)cccc3F)c2F)n1]

Step A: Methyl tetrahydro-3-furancarboxylate

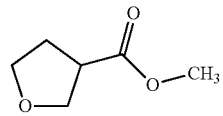

To a solution of tetrahydro-3-furancarboxylic acid (10.00 g, 86.0 mmol) in MeOH (172 mL) was added sulfuric acid (13.8 mL, 258 mmol). The reaction was heated to reflux for 18 h. The reaction was then cooled to rt and concentrated. The residue was partitioned between water (500 mL) and DCM (200 mL). The phases were separated and the aqueous fraction was extracted with DCM (200 mL). The combined organic fractions were washed with saturated aqueous NaHCO$_3$ (200 mL) and brine (200 mL), dried over Na$_2$SO$_4$, filtered, and concentrated to afford methyl tetrahydro-3-furancarboxylate (10.1 g, 78 mmol, 90% yield) as a pale yellow oil. $^1$H NMR (400 MHz, CDCl$_3$) δ ppm 3.99 (t, J=8.4 Hz, 1H), 3.86-3.95 (m, 2H), 3.76-3.86 (m, 1H), 3.71 (s, 3H), 3.01-3.18 (m, 1H), 2.03-2.32 (m, 2H).

Step B: Tetrahydro-3-furancarboxamide

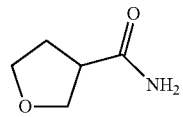

A solution of methyl tetrahydro-3-furancarboxylate (10.1 g, 78 mmol) in ammonia (7 N solution in MeOH, 55.5 mL, 388 mmol) was heated to 80° C. for 72 h. The reaction mixture was then concentrated and dried for 16 h under high vacuum to afford tetrahydro-3-furancarboxamide (7.73 g, 67.1 mmol, 86% yield) as an off-white solid. $^1$H NMR (400 MHz, CDCl$_3$) δ ppm 5.12-6.10 (m, 2H), 3.86-4.05 (m, 3H), 3.74-3.86 (m, 1H), 2.84-3.04 (m, J=7.1, 6.8, 6.6, 6.6 Hz, 1H), 2.00-2.31 (m, 2H).

Step C: Tetrahydro-3-furancarbothioamide

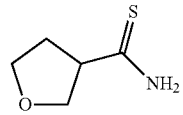

A solution of tetrahydro-3-furancarboxamide (7.73 g, 67.1 mmol) and Lawesson's reagent (13.6 g, 33.6 mmol) in THF (90 mL) was heated to reflux for 16 h. The reaction was cooled to rt, poured into saturated aqueous NaHCO$_3$ (250 mL) and extracted with diethyl ether (4×100 mL). The combined organic extracts were dried over Na$_2$SO$_4$, filtered, and concentrated. Purification by chromatography (20 to 100% EtOAc:hexanes) afforded tetrahydro-3-furancarbothioamide (3.78 g, 28.8 mmol, 42.9% yield) as a white solid. $^1$H NMR (400 MHz, CDCl$_3$) δ ppm 7.35 (br. s., 2H), 3.95-4.30 (m, 2H), 3.70-3.94 (m, 2H), 3.40-3.69 (m, 1H), 2.28-2.52 (m, 1H), 2.14-2.28 (m, 1H).

Step D: N-{3-[5-(2-Chloro-4-pyrimidinyl)-2-(tetrahydro-3-furanyl)-1,3-thiazol-4-yl]-2-fluorophenyl}-2,6-difluorobenzenesulfonamide

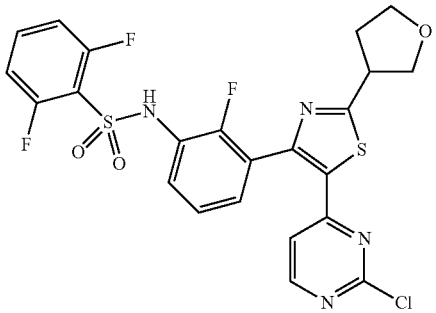 [SMILES: O=S(=O)(Nc1cccc(-c2nc(C3CCOC3)sc2-c2ccnc(Cl)n2)c1F)c1c(F)cccc1F]

Following a procedure analogous to the procedure described in Example 18, Step A using N-{3-[(2-chloro-4-pyrimidinyl)acetyl]-2-fluorophenyl}-2,6-difluorobenzenesulfonamide (1.00 g, 2.26 mmol), NBS (0.423 g, 2.38 mmol) and tetrahydro-3-furancarbothioamide (0.386 g, 2.94 mmol) the title compound of Step D was obtained as an orange solid (890 mg, 1.42 mmol, 62.6% yield). $^1$H NMR (400 MHz, DMSO-$d_6$) δ ppm 10.94 (s, 1H), 8.56 (d, J=5.5 Hz, 1H), 7.59-7.83 (m, 1H), 7.40-7.55 (m, 2H), 7.33 (t, J=7.8 Hz, 1H), 7.24 (t, J=9.1 Hz, 2H), 6.87 (d, J=5.3 Hz, 1H), 3.98-4.09 (m, 1H), 3.71-3.99 (m, 4H), 2.35-2.48 (m, 1H), 2.09-2.28 (m, 1H). MS (ESI) 553.03 [M+H]$^+$.

Step E: N-{3-[5-(2-Amino-4-pyrimidinyl)-2-(tetrahydro-3-furanyl)-1,3-thiazol-4-yl]-2-fluorophenyl}-2,6-difluorobenzenesulfonamide Following a procedure analogous to the procedure described in Example 51, Step B using N-{3-[5-(2-chloro-4-pyrimidinyl)-2-(tetrahydro-3-furanyl)-1,3-thiazol-4-yl]-2-fluorophenyl}-2,6-difluorobenzenesulfonamide (0.100 g, 0.181 mmol) and ammonia (7 N solution in MeOH, 3.88 mL, 27.1 mmol) the title compound was obtained as a light yellow solid (53 mg, 0.099 mmol, 55% yield). $^1$H NMR (400 MHz, DMSO-$d_6$) δ ppm 10.90 (s, 1H), 7.99 (d, J=5.1 Hz, 1H), 7.62-7.79 (m, 1H), 7.40-7.49 (m, 1H), 7.36 (t, J=6.1 Hz, 1H), 7.17-7.33 (m, 3H), 6.78 (br. s., 2H), 5.84 (d, J=5.1 Hz, 1H), 3.96-4.09 (m, 1H), 3.73-3.95 (m, 4H), 2.34-2.47 (m, 1H), 2.05-2.22 (m, 1H). MS (ESI) 534.10 [M+H]$^+$.

Example 72

N-{3-[5-(2-Amino-4-pyrimidinyl)-2-cyclobutyl-1,3-thiazol-4-yl]-2-chlorophenyl}-2,6-difluorobenzenesulfonamide

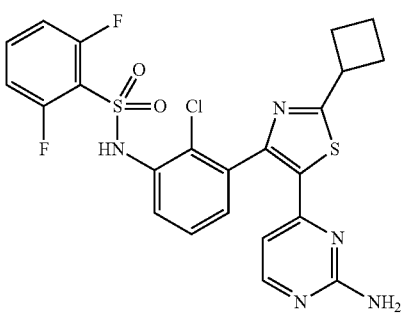 [SMILES: Nc1nccc(-c2sc(C3CCC3)nc2-c2cccc(NS(=O)(=O)c3c(F)cccc3F)c2Cl)n1]

Step A: N-{2-Chloro-3-[5-(2-chloro-4-pyrimidinyl)-2-cyclobutyl-1,3-thiazol-4-yl]phenyl}-2,6-difluorobenzenesulfonamide

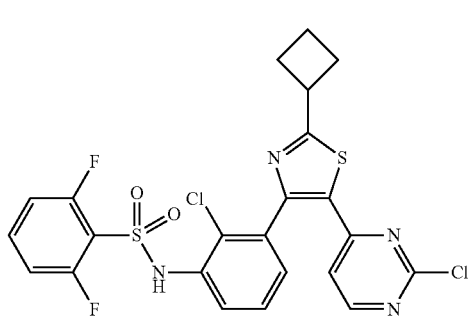 [SMILES: O=S(=O)(Nc1cccc(-c2nc(C3CCC3)sc2-c2ccnc(Cl)n2)c1Cl)c1c(F)cccc1F]

Following a procedure analogous to the procedure described in Example 18, Step A using N-{2-chloro-3-[(E)-2-(2-chloro-4-pyrimidinyl)-1-hydroxyethenyl]phenyl}-2,6-difluorobenzenesulfonamide (1.2 g, 2.5 mmol), NBS (0.45 g, 2.5 mmol) and cyclobutanecarbothioamide (0.29 g, 2.5 mmol) the title compound was obtained as a white solid (0.75 g, 1.6 mmol, 54% yield). $^1$H NMR (400 MHz, DMSO-$d_6$) δ ppm 10.92-10.69 (m, 1H), 8.32-8.85 (m, 1H), 7.83-7.57 (m, 1H), 7.59-7.31 (m, 3H), 7.33-7.07 (m, 2H), 6.49 (d, J=5.3 Hz, 1H), 3.89 (quin, J=8.5 Hz, 1H), 2.67-2.14 (m, 4H), 2.14-1.79 (m, 2H). MS (ESI): 553 [M+H]$^+$.

Step B: N-{3-[5-(2-Amino-4-pyrimidinyl)-2-cyclobutyl-1,3-thiazol-4-yl]-2-chlorophenyl}-2,6-difluorobenzenesulfonamide Following a procedure analogous to the procedure described in Example 51, Step B using N-{2-chloro-3-[5-(2-chloro-4-pyrimidinyl)-2-cyclobutyl-1,3-thiazol-4-yl]phenyl}-2,6-difluorobenzenesulfonamide (0.20 g, 0.36 mmol) and 7N ammonia in MeOH (10 ml, 70 mmol) the title compound was obtained (0.030 g, 0.056 mmol, 15%). $^1$H NMR (400 MHz, DMSO-$d_6$) δ ppm 10.80 (s, 1H), 7.95 (d, J=5.1 Hz, 1H), 7.64 (dd, J=14.3, 2.0 Hz, 1H), 7.55-7.38 (m, 2H), 7.34 (d, J=7.0 Hz, 1H), 7.18 (t, J=9.1 Hz, 2H), 6.72 (br, 2H), 5.61 (d, J=5.1 Hz, 1H), 3.83 (quin, J=8.4 Hz, 1H), 3.45-3.19 (m, 1H), 2.38 (q, J=8.5 Hz, 1H), 2.24 (quin, J=9.1 Hz, 1H), 2.10-1.92 (m, 1H), 1.86 (q, J=9.4 Hz, 1H), 1.06 (t, J=7.0 Hz, 1H). MS (ESI): 534 [M+H]$^+$.

Example 73

2,5-Difluoro-N-{2-fluoro-5-[5-[2-(methylamino)-4-pyrimidinyl]-2-(1-methylethyl)-1,3-thiazol-4-yl]phenyl}benzenesulfonamide

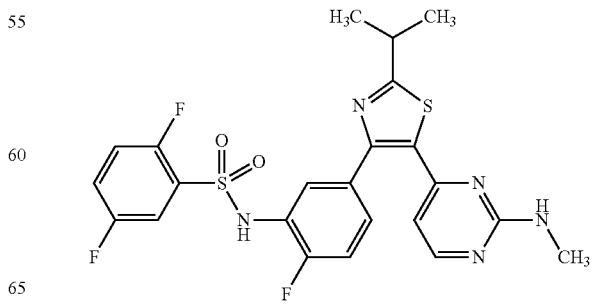

Following a procedure analogous to the procedure described in Example 1 using N-{5-[5-(2-chloro-4-pyrimidinyl)-2-(1-methylethyl)-1,3-thiazol-4-yl]-2-fluorophenyl}-2,5-difluorobenzenesulfonamide (0.10 g, 0.190 mmol) and methylamine in THF (1.0 mL, 2.0 mmol) the title compound was obtained (0.082 g, 0.16 mmol, 83% yield). $^1$H NMR (400 MHz, DMSO-d$_6$) δ 10.75 (1H, s), 8.08-8.00 (m, 1H), 7.59-7.40 (m, 3H), 7.39-7.30 (m, 2H), 7.27-7.11 (m, 2H), 6.16 (br. s., 1H), 3.30-3.21 (m, 1H), 2.71 (br, 3H), 1.31 (d, J=7.0 Hz, 6H). MS (ESI): 520 [M+H]$^+$.

Example 74

2,5-Difluoro-N-[2-fluoro-5-(2-(1-methylethyl)-5-{2-[(2,2,6,6-tetramethyl-4-piperidinyl)amino]-4-pyrimidinyl}-1,3-thiazol-4-yl)phenyl]benzenesulfonamide

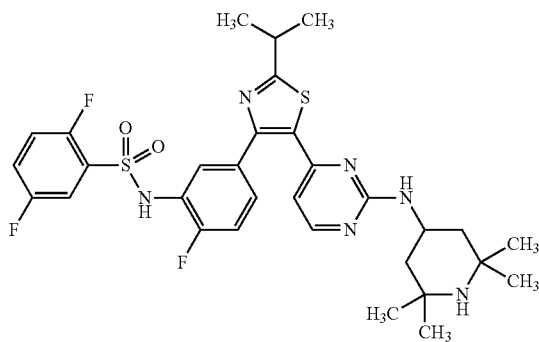 [SMILES: CC(C)c1nc(-c2ccc(F)c(NS(=O)(=O)c3cc(F)ccc3F)c2)c(-c2ccnc(NC3CC(C)(C)NC(C)(C)C3)n2)s1]

Following a procedure analogous to the procedure described in Example 1 using N-{5-[5-(2-chloro-4-pyrimidinyl)-2-(1-methylethyl)-1,3-thiazol-4-yl]-2-fluorophenyl}-2,5-difluorobenzenesulfonamide (0.10 g, 0.19 mmol) and 2,2,6,6-tetramethyl-4-piperidinamine (0.30 g, 1.9 mmol) the title compound was obtained (0.035 g, 0.054 mmol, 29% yield). $^1$H NMR (400 MHz, DMSO-d$_6$) δ ppm 10.88 (s, 1H), 8.95-8.72 (m, 1H), 8.20 (d, J=4.9 Hz, 1H), 7.95-7.72 (m, 1H), 7.72-7.20 (m, 6H), 6.43-6.20 (m, 1H), 2.05 (d, J=12.8 Hz, 2H), 1.75-1.27 (m, 22H). MS (ESI): 645 [M+H]$^+$.

Example 75

2,5-Difluoro-N-{2-fluoro-5-[2-(1-methylethyl)-5-(2-{[1-(methylsulfonyl)-4-piperidinyl]amino}-4-pyrimidinyl)-1,3-thiazol-4-yl]phenyl}benzenesulfonamide

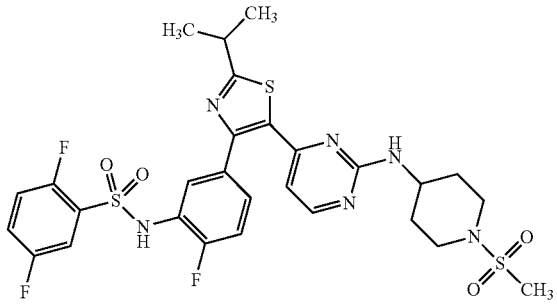 [SMILES: CC(C)c1nc(-c2ccc(F)c(NS(=O)(=O)c3cc(F)ccc3F)c2)c(-c2ccnc(NC3CCN(S(C)(=O)=O)CC3)n2)s1]

Following a procedure analogous to the procedure described in Example 1 using N-{5-[5-(2-chloro-4-pyrimidinyl)-2-(1-methylethyl)-1,3-thiazol-4-yl]-2-fluorophenyl}-2,5-difluorobenzenesulfonamide (0.30 g, 0.57 mmol), 1-(methylsulfonyl)-4-piperidinamine (0.3 g, 1.7 mmol) and THF (1 mL) the title compound was obtained (0.32 g, 0.48 mmol, 84% yield). $^1$H NMR (400 MHz, DMSO-d$_6$) δ ppm 10.82 (s, 1H), 8.13 (d, J=5.0 Hz, 1H), 7.71-7.44 (m, 3H), 7.45-7.32 (m, 3H), 7.29 (t, J=9.2 Hz, 1H), 6.30 (m, 1H), 3.50 (m, 2H), 3.30-3.24 (m, 1H), 2.86 (s, 3H), 2.83-2.64 (m, 2H), 1.90 (m, 2H), 1.67-1.44 (m, 2H), 1.36 (d, J=6.8 Hz, 6H). MS (ESI): 667 [M+H]$^+$.

Example 76

2,5-Difluoro-N-(2-fluoro-5-{2-(1-methylethyl)-5-[2-(tetrahydro-2H-pyran-4-ylamino)-4-pyrimidinyl]-1,3-thiazol-4-yl}phenyl)benzenesulfonamide

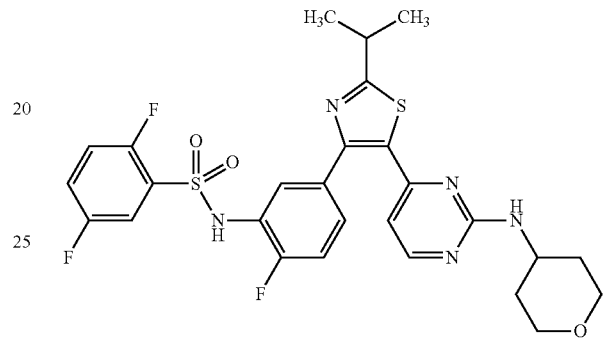

Following a procedure analogous to the procedure described in Example 1 using N-{5-[5-(2-chloro-4-pyrimidinyl)-2-(1-methylethyl)-1,3-thiazol-4-yl]-2-fluorophenyl}-2,5-difluorobenzenesulfonamide (0.10 g, 0.19 mmol) and tetrahydro-2H-pyran-4-amine (0.19 g, 1.90 mmol) in THF (1 mL) the title compound was obtained as an off-white solid (0.094 g, 0.16 mmol, 84% yield). $^1$H NMR (400 MHz, DMSO-d$_6$) δ ppm 8.02 (d, J=5.2 Hz, 1H), 7.75-7.65 (m, 1H), 7.55-7.38 (m, 1H), 7.38-7.28 (m, 1H), 7.28-7.11 (m, 3H), 7.11-6.88 (m, 2H), 6.22 (d, J=5.2 Hz, 1H), 5.06 (d, J=7.8 Hz, 1H), 4.02-3.92 (m, 4H), 3.56-3.46 (m, 2H), 3.29 (quin, J=6.9 Hz, 1H), 2.00 (d, J=13.2 Hz, 2H), 1.41 (d, J=7.0 Hz, 6H). MS (ESI): 590 [M+H]$^+$.

Example 77

N-{5-[5-{2-[(1-Acetyl-4-piperidinyl)amino]-4-pyrimidinyl}-2-(1-methylethyl)-1,3-thiazol-4-yl]-2-fluorophenyl}-2,5-difluorobenzenesulfonamide

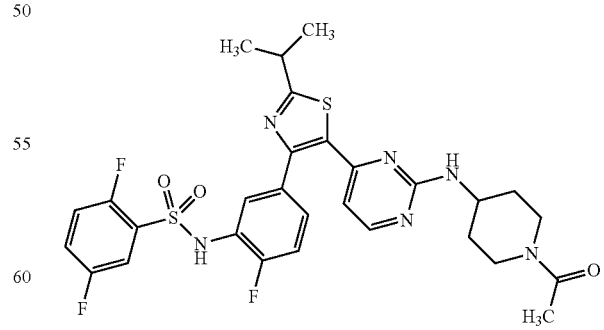

Following a procedure analogous to the procedure described in Example 1 using N-{5-[5-(2-chloro-4-pyrimidinyl)-2-(1-methylethyl)-1,3-thiazol-4-yl]-2-fluorophenyl}-2,5-difluorobenzenesulfonamide (0.10 g, 0.19 mmol) and 1-acetyl-4-piperidinamine (0.27 g, 1.9 mmol) in THF (1 mL) the title compound was obtained as an off-white solid (0.075 g, 0.12 mmol, 62% yield). $^1$H NMR (400 MHz, DMSO-$d_6$) δ ppm 10.82 (s, 1H), 8.12 (d, J=5.0 Hz, 1H), 7.68-7.43 (m, 3H), 7.44-7.17 (m, 5H), 4.33-4.18 (m, 1H), 3.83-3.73 (m, 1H), 3.44-3.20 (m, 2H), 2.66-2.32 (m, 4H), 1.99 (s, 3H), 1.36 (d, J=6.8 Hz, 6H), 1.35-1.10 (m, 2H). MS (ESI): 631 [M+H]$^+$.

Example 78

N-{3-[2-(1,1-Dimethylethyl)-5-(2-{[1-(methylsulfonyl)-4-piperidinyl]amino}-4-pyrimidinyl)-1,3-thiazol-4-yl]-2-fluorophenyl}-2,6-difluorobenzenesulfonamide

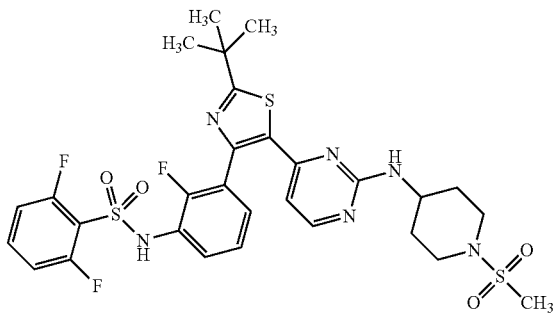 [SMILES: CC(C)(C)c1nc(-c2cccc(NS(=O)(=O)c3c(F)cccc3F)c2F)c(-c2ccnc(NC3CCN(S(C)(=O)=O)CC3)n2)s1]

Following a procedure analogous to the procedure described in Example 1 using N-{3-[5-(2-chloro-4-pyrimidinyl)-2-(1,1-dimethylethyl)-1,3-thiazol-4-yl]-2-fluorophenyl}-2,6-difluorobenzenesulfonamide (0.10 g, 0.19 mmol) and 1-(methylsulfonyl)-4-piperidinamine (0.30 g, 1.7 mmol) in 2,2,2-trifluoroethanol (2 mL) the title compound was obtained (0.026 g, 0.038 mmol, 20% yield). $^1$H NMR (400 MHz, DMSO-$d_6$) δ ppm 10.84 (s, 1H), 8.03 (br. s., 1H), 7.72-7.54 (m, 1H), 7.47-7.06 (m, 7H), 3.53-3.38 (m, 2H), 2.83 (s, 3H), 2.83-2.72 (m, 3H), 1.91-1.73 (m, 2H), 1.58-1.32 (m, 2H), 1.36 (s, 9H). MS (ESI): 681 [M+H]$^+$.

Example 79

2,6-Difluoro-N-{2-fluoro-3-[5-(2-{[1-(methylsulfonyl)-4-piperidinyl]amino}-4-pyrimidinyl)-2-(4-morpholinyl)-1,3-thiazol-4-yl]phenyl}benzenesulfonamide

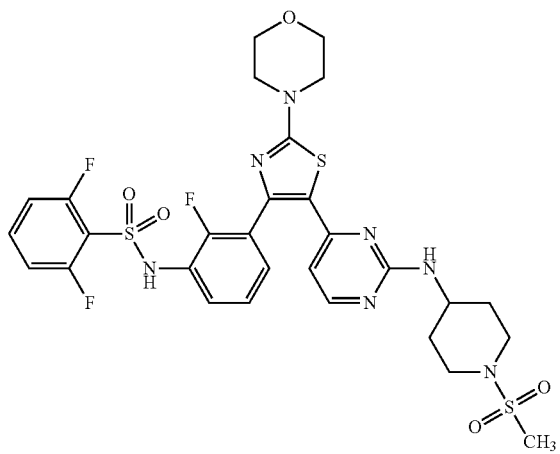 [SMILES: CS(=O)(=O)N1CCC(Nc2nccc(-c3sc(N4CCOCC4)nc3-c3cccc(NS(=O)(=O)c4c(F)cccc4F)c3F)n2)CC1]

Following a procedure analogous to the procedure described in Example 1 using N-{3-[5-(2-chloro-4-pyrimidinyl)-2-(4-morpholinyl)-1,3-thiazol-4-yl]-2-fluorophenyl}-2,6-difluorobenzenesulfonamide (0.107 g, 0.188 mmol) and 1-(methylsulfonyl)-4-piperidinamine (0.3 g, 1.68 mmol) in 2,2,2-trifluoroethanol (2 mL) the title compound was obtained (0.020 g, 0.028 mmol, 15% yield). $^1$H NMR (400 MHz, DMSO-$d_6$) δ ppm 10.83 (s, 1H), 7.85 (d, J=5.1 Hz, 2H), 7.70-7.57 (m, 2H), 7.42-7.33 (m, 2H), 7.30-7.03 (m, 4H), 5.47-5.86 (m, 1H) 3.72-3.31 (m, 11H), 2.91-2.73 (m, 5H), 1.92-1.77 (m, 2H), 1.58-1.40 (m, 2H). MS (ESI): 710 [M+H]$^+$.

Example 80

N-{5-[2-Cyclobutyl-5-(2-{[1-(methylsulfonyl)-4-piperidinyl]amino}-4-pyrimidinyl)-1,3-thiazol-4-yl]-2-fluorophenyl}-2,5-difluorobenzenesulfonamide

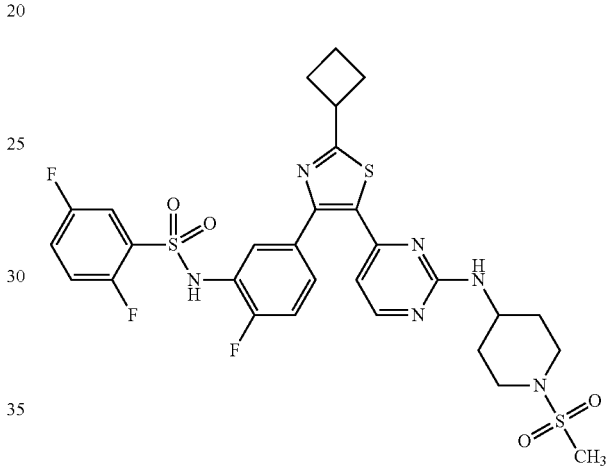

Step A: N-{5-[5-(2-Chloro-4-pyrimidinyl)-2-cyclobutyl-1,3-thiazol-4-yl]-2-fluorophenyl}-2,5-difluorobenzenesulfonamide

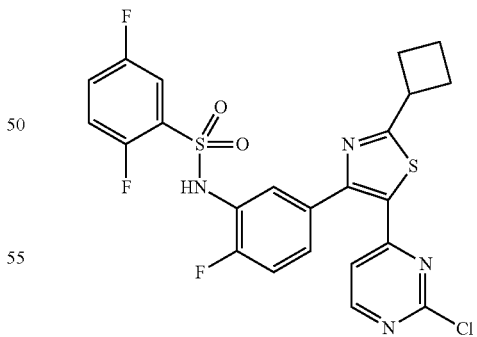

Following a procedure analogous to the procedure described in Example 18, Step A using N-{5-[(2-chloro-4-pyrimidinyl)acetyl]-2-fluorophenyl}-2,5-difluorobenzenesulfonamide (1.34 g, 3.03 mmol), NBS (0.540 g, 3.03 mmol), cyclobutanecarbothioamide (0.349 g, 3.03 mmol) the title compound of Step A was obtained (0.5 g, 0.931 mmol, 30.7% yield). $^1$H NMR (400 MHz, DMSO-$d_6$) δ ppm 10.74 (s, 1H), 8.52 (d, J=5.3 Hz, 1H), 7.58-7.33 (m, 6H), 7.28 (t, J=7.9 Hz, 1H), 6.83 (d, J=5.3 Hz, 1H), 3.89 (quin, J=8.6 Hz, 1H), 2.43-2.19 (m, 4H), 2.08-1.92 (m, 1H), 1.92-1.78 (m, 1H). MS (ESI): 537 [M+H]+.

Step B: N-{5-[2-Cyclobutyl-5-(2-{[1-(methylsulfonyl)-4-piperidinyl]amino}-4-pyrimidinyl)-1,3-thiazol-4-yl]-2-fluorophenyl}-2,5-difluorobenzenesulfonamide Following a procedure analogous to the procedure described in Example 1 using N-{5-[5-(2-chloro-4-pyrimidinyl)-2-cyclobutyl-1,3-thiazol-4-yl]-2-fluorophenyl}-2,5-difluorobenzenesulfonamide (0.10 g, 0.19 mmol) was added 1-(methylsulfonyl)-4-piperidinamine (0.33 g, 1.9 mmol) and THF (2 mL) the title compound was obtained (0.12 g, 0.18 mmol, 98% yield). ¹H NMR (400 MHz, DMSO-d₆) δ ppm 10.77 (s, 1H), 8.08 (d, J=5.1 Hz, 1H), 7.64-7.19 (m, 7H), 6.34-6.01 (m, 1H), 3.83 (quin, J=8.5 Hz, 1H), 3.72-3.40 (m, 2H), 2.91-2.64 (m, 5H), 2.43-2.15 (m, 6H), 2.08-1.77 (m, 3H), 1.63-1.33 (m, 2H). MS (ESI): 679 [M+H]+.

Example 81

N-{3-[2-Cyclobutyl-5-(2-{[1-(methylsulfonyl)-4-piperidinyl]amino}-4-pyrimidinyl)-1,3-thiazol-4-yl]-2-fluorophenyl}-2,5-difluorobenzenesulfonamide

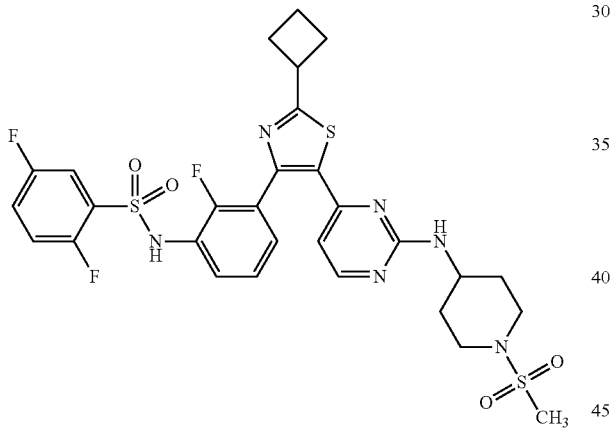

Step A: N-{3-[5-(2-Chloro-4-pyrimidinyl)-2-cyclobutyl-1,3-thiazol-4-yl]-2-fluorophenyl}-2,5-difluorobenzenesulfonamide

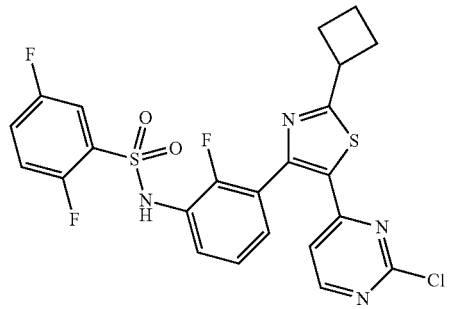 [SMILES: O=S(=O)(Nc1cccc(-c2nc(C3CCC3)sc2-c2ccnc(Cl)n2)c1F)c1cc(F)ccc1F]

Following a procedure analogous to the procedure described in Example 18, Step A using N-(3-(2-(2-chloropyrimidin-4-yl)acetyl)-2-fluorophenyl)-2,5-difluorobenzenesulfonamide (1.1 g, 2.5 mmol), NBS (0.44 g, 2.5 mmol) cyclobutanecarbothioamide (0.29 g, 2.5 mmol) the title compound of Step A was obtained (0.30 g, 0.56 mmol, 22% yield). ¹H NMR (400 MHz, DMSO-d₆) δ ppm 10.80 (s, 1H), 8.52 (d, J=5.3 Hz, 1H), 7.63-7.22 (m, 6H), 7.07 (d, J=5.3 Hz, 1H), 3.89 (quin, J=8.5 Hz, 1H), 2.44-2.34 (m, 2H), 2.34-2.19 (m, 2H) 2.13-1.94 (m, 1H), 1.94-1.80 (m, 1H). MS (ESI): 537 [M+H]+.

Step B: N-{3-[2-Cyclobutyl-5-(2-{[1-(methylsulfonyl)-4-piperidinyl]amino}-4-pyrimidinyl)-1,3-thiazol-4-yl]-2-fluorophenyl}-2,5-difluorobenzenesulfonamide Following a procedure analogous to the procedure described in Example 1 using N-{3-[5-(2-chloro-4-pyrimidinyl)-2-cyclobutyl-1,3-thiazol-4-yl]-2-fluorophenyl}-2,5-difluorobenzenesulfonamide (0.10 g, 0.19 mmol) and 1-(methylsulfonyl)-4-piperidinamine (0.33 g, 1.9 mmol) in THF (2 mL) the title compound was obtained (0.075 g, 0.11 mmol, 59% yield). ¹H NMR (400 MHz, DMSO-d₆) δ ppm 10.72 (s, 1H), 8.08-7.97 (m, 1H), 7.59-7.18 (m, 7H), 6.17-5.73 (m, 1H), 3.84 (quin, J=8.4 Hz, 1H), 3.60-3.39 (m, 2H), 2.93-2.62 (m, 7H), 2.43-2.12 (m, 4H), 2.10-1.68 (m, 3H), 1.64-1.29 (m, 2H), m/z (ESI): 679 [M+H]+.

Example 82

2,5-Difluoro-N-{2-fluoro-3-[5-(2-{[1-(methylsulfonyl)-4-piperidinyl]amino}-4-pyrimidinyl)-2-(4-morpholinyl)-1,3-thiazol-4-yl]phenyl}benzenesulfonamide

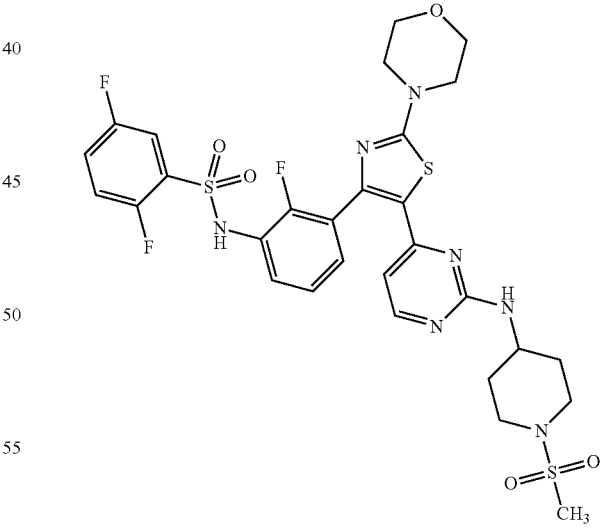

Following a procedure analogous to the procedure described in Example 1 using N-{3-[5-(2-chloro-4-pyrimidinyl)-2-(4-morpholinyl)-1,3-thiazol-4-yl]-2-fluorophenyl}-2,5-difluorobenzenesulfonamide (0.2 g, 0.352 mmol) and 1-(methylsulfonyl)-4-piperidinamine (0.314 g, 1.76 mmol) in THF (1 mL) the title compound was obtained as a white solid (0.14 g, 0.197 mmol, 56.0% yield). ¹H NMR (400 MHz, DMSO-d₆) δ ppm 10.75 (s, 1H), 7.90 (d, J=5.2 Hz, 1H), 7.68-7.71 (m, 1H), 7.45-7.63 (m, 3H), 7.36-7.45 (m, 1H), 7.21-7.35 (m, 2H), 7.05-7.20 (m, 1H), 3.38-3.78 (m, 5H), 3.32 (s, 3H), 2.56-3.18 (m, 4H), 1.38-2.43 (m, 8H). MS (ESI): 710 [M+H]⁺.

Example 83

2,5-Difluoro-N-{2-fluoro-3-[5-{2-[(1-methylethyl)amino]-4-pyrimidinyl}-2-(4-morpholinyl)-1,3-thiazol-4-yl]phenyl}benzenesulfonamide

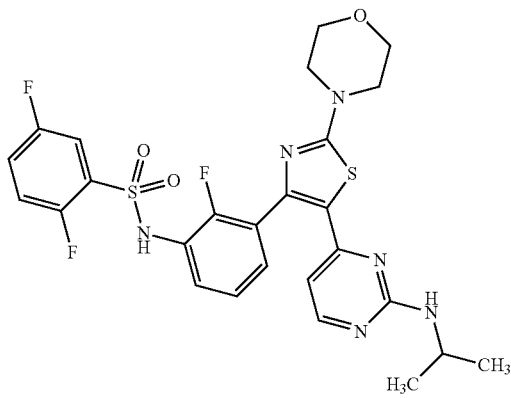 [SMILES: CC(C)Nc1nccc(-c2sc(N3CCOCC3)nc2-c2cccc(NS(=O)(=O)c3cc(F)ccc3F)c2F)n1]

Following a procedure analogous to the procedure described in Example 18, Step B using N-{3-[5-(2-chloro-4-pyrimidinyl)-2-(4-morpholinyl)-1,3-thiazol-4-yl]-2-fluorophenyl}-2,5-difluorobenzenesulfonamide (0.20 g, 0.35 mmol) and isopropylamine (2 mL) the title compound was obtained as a yellow solid (0.15 g, 0.25 mmol, 72% yield). ¹H NMR (400 MHz, DMSO-d₆) δ ppm 14.28 (br. s., 1H), 8.35 (d, J=7.2 Hz, 1H), 7.84 (s, 1H) 7.67-7.51 (m, 2H), 7.47 (d, J=6.8 Hz, 1H), 7.33-7.07 (m, 3H), 5.90 (d, J=6.6 Hz, 1H), 4.08 (dq, J=13.3, 6.7 Hz, 1H), 3.88-3.73 (m, 4H), 3.71-3.52 (m, 4H), 1.27 (d, J=6.4 Hz, 6H). MS (ESI): 591 [M+H]⁺.

Example 84

N-{5-[5-(2-Amino-4-pyrimidinyl)-2-(1-methylethyl)-1,3-thiazol-4-yl]-2-fluorophenyl}-3-fluorobenzenesulfonamide

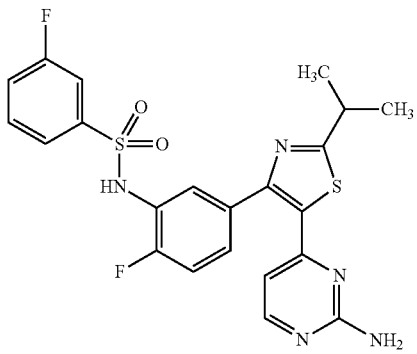 [SMILES: CC(C)c1nc(-c2ccc(F)c(NS(=O)(=O)c3cccc(F)c3)c2)c(-c2ccnc(N)n2)s1]

Step A: N-{5-[5-(2-Chloro-4-pyrimidinyl)-2-(1-methylethyl)-1,3-thiazol-4-yl]-2-fluorophenyl}-3-fluorobenzenesulfonamide

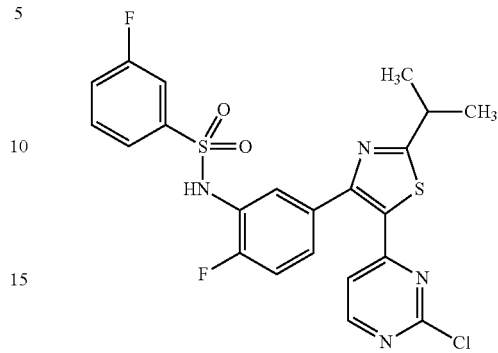

Following a procedure analogous to the procedure described in Intermediate 14 using 5-[5-(2-chloro-4-pyrimidinyl)-2-(1-methylethyl)-1,3-thiazol-4-yl]-2-fluoroaniline (12 g, 34.5 mmol) and 3-fluorobenzenesulfonyl chloride (8.72 g, 44.8 mmol) the title compound of Step A was obtained (9.3 g, 53.4%). ¹H NMR (400 MHz, CDCl₃) δ ppm 8.35 (d, J=5.3 Hz, 1H), 7.65-7.73 (m, 1H), 7.52-7.60 (m, 1H), 7.41-7.50 (m, 2H), 7.20-7.37 (m, 1H), 7.04-7.12 (m, 1H), 6.83-7.00 (m, 2H), 3.30-3.40 (m, 1H), 1.46 (d, J=6.8 Hz, 6H). MS (ES+): 507 [M+H]⁺.

Step B: N-{5-[5-(2-Amino-4-pyrimidinyl)-2-(1-methylethyl)-1,3-thiazol-4-yl]-2-fluorophenyl}-3-fluorobenzenesulfonamide Following a procedure analogous to the procedure described in Example 51, Step B using N-{5-[5-(2-chloro-4-pyrimidinyl)-2-(1-methylethyl)-1,3-thiazol-4-yl]-2-fluorophenyl}-3-fluorobenzenesulfonamide (100 mg, 0.20 mmol) and 7 N ammonia in MeOH (2 mL) the title compound was obtained as a white powder (46 mg, 0.09 mmol, 47.2% yield). ¹H NMR (400 MHz, DMSO-d₆) ppm δ 10.48 (s, 1H), 8.07 (d, J=5.1 Hz, 1H), 7.62 (t, J=6.8 Hz, 1H), 7.50-7.55 (m, 3H), 7.34-7.39 (m, 2H), 7.26 (t, J=10.4 Hz, 1H), 6.78 (s, 2H), 6.17 (d, J=5.1 Hz, 1H), 3.25-3.30 (m, 1H), 1.36 (d, J=6.8 Hz, 6H). MS (ESI): 487.8 [M+H]⁺.

Example 85

N-{4-[4-(3-{[(3-Fluorophenyl)sulfonyl]amino}phenyl)-2-(1-methylethyl)-1,3-thiazol-5-yl]-2-pyrimidinyl}glycine

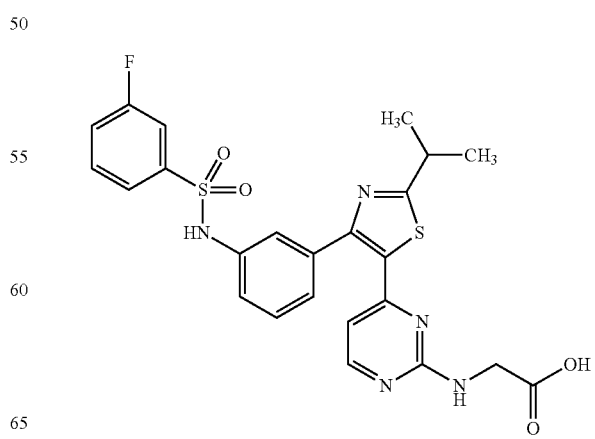

Step A: N-{3-[5-(2-Chloro-4-pyrimidinyl)-2-(1-methylethyl)-1,3-thiazol-4-yl]phenyl}-3-fluorobenzenesulfonamide

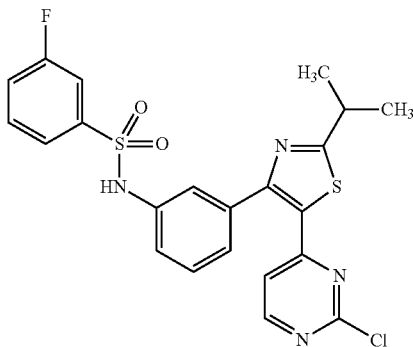 [SMILES: CC(C)c1nc(-c2cccc(NS(=O)(=O)c3cccc(F)c3)c2)c(-c2ccnc(Cl)n2)s1]

Following a procedure analogous to the procedure described in Intermediate 14 using 3-[5-(2-chloro-4-pyrimidinyl)-2-(1-methylethyl)-1,3-thiazol-4-yl]aniline (1.0 g, 3.0 mmol) and 3-fluorobenzenesulfonyl chloride (0.60 mL, 4.5 mmol) the title compound of Step A was obtained (1.46 g, 2.99 mmol, 100% yield). $^1$H NMR (400 MHz, DMSO-$d_6$): δ 10.56 (s, 1H), 8.51 (d, J=5.2 Hz, 1H), 7.48-7.65 (m, 4H), 7.37 (t, J=7.7 Hz, 1H), 7.20-7.28 (m, 3H), 6.97 (d, J=5.1 Hz, 1H), 3.30-3.37 (m, 1H), 1.38 (d, J=7.0 Hz, 6H). MS (ESI): 489.1 [M+H]$^+$.

Step B: N-{4-[4-(3-{[(3-Fluorophenyl)sulfonyl]amino}phenyl)-2-(1-methylethyl)-1,3-thiazol-5-yl]-2-pyrimidinyl}glycine To a solution of N-{3-[5-(2-chloro-4-pyrimidinyl)-2-(1-methylethyl)-1,3-thiazol-4-yl]phenyl}-3-fluorobenzenesulfonamide (100 mg, 0.20 mmol) in 1-butanol (5 mL) was added glycine (153 mg, 2.0 mmol) and K$_2$CO$_3$ (566 mg, 4.0 mmol). The reaction was stirred at 60° C. for 16 h, then partitioned between water and EtOAc. The pH of the aqueous layer was adjusted to below 4 with 1 N HCl, and the aqueous layer was extracted with EtOAc. This organic layer was dried over anhydrous Na$_2$SO$_4$, filtered, and concentrated to generate the title compound as a white powder (24 mg, 0.05 mmol, 22.8% yield). $^1$H NMR (400 MHz, DMSO-$d_6$): δ 8.04 (d, J=4.5 Hz, 1H), 7.46-7.64 (m, 5H), 7.33 (t, J=8.1 Hz, 1H), 7.18-7.24 (m, 3H), 6.07 (s, 1H), 3.89 (s, 2H), 3.25-3.29 (m, 1H), 1.36 (d, J=6.7 Hz, 6H). MS (ESI): 528.1 [M+H]$^+$.

Example 86

3-Fluoro-N-{3-[5-[2-(methylamino)-4-pyrimidinyl]-2-(1-methylethyl)-1,3-thiazol-4-yl]phenyl}benzenesulfonamide

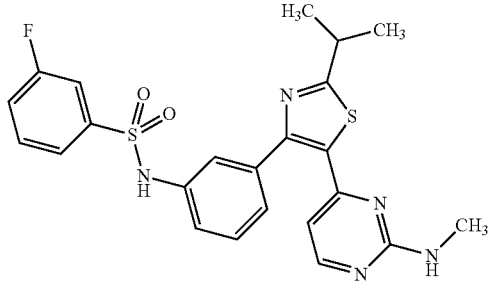 [SMILES: CNc1nccc(-c2sc(C(C)C)nc2-c2cccc(NS(=O)(=O)c3cccc(F)c3)c2)n1]

Following a procedure analogous to the procedure described in Example 1 using N-{3-[5-(2-chloro-4-pyrimidinyl)-2-(1-methylethyl)-1,3-thiazol-4-yl]phenyl}-3-fluorobenzenesulfonamide (100 mg, 0.20 mmol), methylamine (2.0 M in THF, 2.0 mL, 4.0 mmol) and K$_2$CO$_3$ (283 mg, 2.0 mmol) in 1-butanol (5 mL) the title compound was obtained as a white powder (100 mg, 0.21 mmol, 100% yield). $^1$H NMR (400 MHz, DMSO-$d_6$): δ 10.51 (s, 1H), 8.02 (d, J=5.1 Hz, 1H), 7.57-7.65 (m, 2H), 7.48-7.53 (m, 2H), 7.33 (t, J=7.8 Hz, 1H), 7.19-7.22 (m, 4H), 6.04 (s, 1H), 3.23-3.30 (m, 1H), 2.76 (s, 3H), 1.36 (d, J=6.7 Hz, 6H); m/z (ESI): 485.3 [M+H]$^+$.

Example 87

N$^2$-{4-[4-(3-{[(3-Fluorophenyl)sulfonyl]amino}phenyl)-2-(1-methylethyl)-1,3-thiazol-5-yl]-2-pyrimidinyl}glycinamide

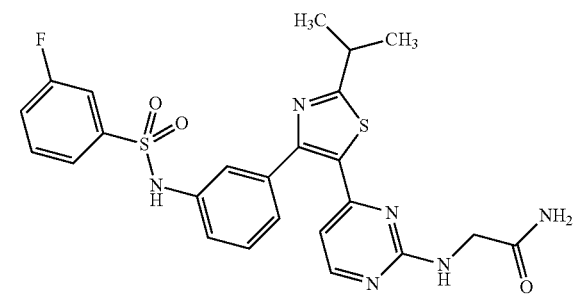 [SMILES: CC(C)c1nc(-c2cccc(NS(=O)(=O)c3cccc(F)c3)c2)c(-c2ccnc(NCC(N)=O)n2)s1]

Following a procedure analogous to the procedure described in Example 86, Step B using N-{3-[5-(2-chloro-4-pyrimidinyl)-2-(1-methylethyl)-1,3-thiazol-4-yl]phenyl}-3-fluorobenzenesulfonamide (100 mg, 0.20 mmol) and glycinamide hydrochloride (225 mg, 2.0 mmol) and K$_2$CO$_3$ (566 mg, 4.0 mmol) in 1-butanol (5 mL) the title compound was obtained as a white powder (29 mg, 27.6% yield). $^1$H NMR (400 MHz, DMSO-$d_6$): δ 10.51 (s, 1H), 8.02 (d, J=5.1 Hz, 1H), 7.57-7.65 (m, 2H), 7.48-7.53 (m, 2H), 7.33 (t, J=7.8 Hz, 1H), 7.19-7.22 (m, 4H), 6.04 (s, 1H), 3.23-3.30 (m, 1H), 2.76 (s, 3H), 1.36 (d, J=6.7 Hz, 6H). MS (ESI): 527.1 [M+H]$^+$.

Example 88

N-{3-[5-(2-{[3-(Dimethylamino)propyl]amino}-4-pyrimidinyl)-2-(1-methylethyl)-1,3-thiazol-4-yl]phenyl}-3-fluorobenzenesulfonamide

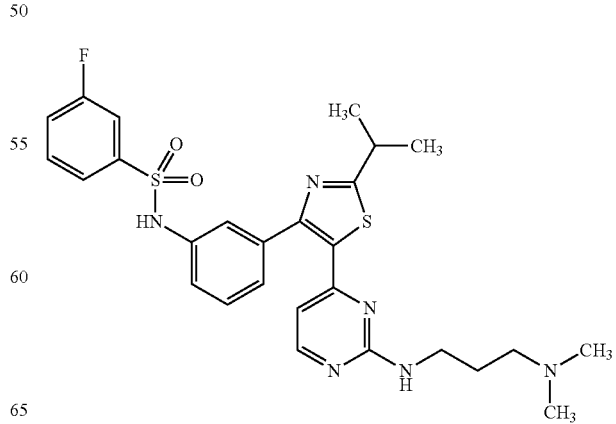

Following a procedure analogous to the procedure described in Example 1 using N-{3-[5-(2-chloro-4-pyrimidinyl)-2-(1-methylethyl)-1,3-thiazol-4-yl]phenyl}-3-fluorobenzenesulfonamide (100 mg, 0.20 mmol), N,N-dimethyl-1.3-propanediamine (260 μL, 2.0 mmol) and K$_2$CO$_3$ (283 mg, 2.0 mmol) in 1-butanol (5 mL) the title compound was obtained as a white powder (84 mg, 0.15 mmol, 75.8% yield). $^1$H NMR (400 MHz, DMSO-d$_6$): δ 8.01 (d, J=5.1 Hz, 1H), 7.45-7.63 (m, 4H), 7.28-7.32 (m, 2H), 7.15-7.20 (m, 3H), 6.04 (s, 1H), 3.24-3.31 (m, 3H), 2.31 (t, J=7.1 Hz, 2H), 2.17 (s, 6H), 1.66 (t, J=7.0 Hz, 2H), 1.35 (d, J=6.8 Hz, 6H). MS (ESI): 555.3 [M+H]+.

Example 89

N-{3-[5-[2-(Cyclopropylamino)-4-pyrimidinyl]-2-(1-methylethyl)-1,3-thiazol-4-yl]phenyl}-3-fluorobenzenesulfonamide

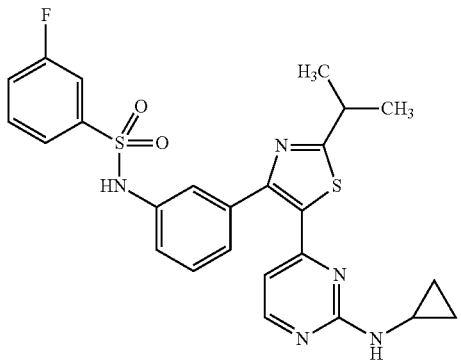 [SMILES: CC(C)c1nc(-c2cccc(NS(=O)(=O)c3cccc(F)c3)c2)c(-c2ccnc(NC3CC3)n2)s1]

Following a procedure analogous to the procedure described in Example 1 using N-{3-[5-(2-chloro-4-pyrimidinyl)-2-(1-methylethyl)-1,3-thiazol-4-yl]phenyl}-3-fluorobenzenesulfonamide (100 mg, 0.20 mmol) and cyclopropylamine (141 μL, 2.0 mmol) and K$_2$CO$_3$ (283 mg, 2.0 mmol) in 1-butanol (5 mL) the title compound was obtained as a white powder (43 mg, 0.08 mmol, 42.2% yield). $^1$H NMR (400 MHz, DMSO-d$_6$): δ 10.51 (s, 1H), 8.05 (d, J=5.0 Hz, 1H), 7.48-7.65 (m, 5H), 7.33 (t, J=7.4 Hz, 1H), 7.19-7.23 (m, 3H), 6.09 (d, J=4.7 Hz, 1H), 3.25-3.30 (m, 1H), 2.67 (bs, 1H), 1.35 (d, J=7.0 Hz, 6H), 0.63 (d, J=4.7 Hz, 2H), 0.46 (bs, 2H). MS (ESI): 510.4 [M+H]+.

Example 90

N-{3-[5-(2-Amino-4-pyrimidinyl)-2-(1-methylethyl)-1,3-thiazol-4-yl]phenyl}-2,6-difluorobenzenesulfonamide

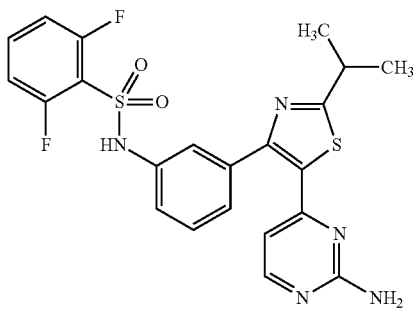 [SMILES: CC(C)c1nc(-c2cccc(NS(=O)(=O)c3c(F)cccc3F)c2)c(-c2ccnc(N)n2)s1]

Following a procedure analogous to the procedure described in Example 51, Step B using N-{3-[5-(2-chloro-4-pyrimidinyl)-2-(1-methylethyl)-1,3-thiazol-4-yl]phenyl}-2,6-difluorobenzenesulfonamide (200 mg, 0.39 mmol) in 7 N ammonia in MeOH (2 mL) the title compound was obtained as a white powder (0.16 g, 0.328 mmol, 84.2% yield). $^1$H NMR (400 MHz, DMSO-d$_6$): δ 11.03 (s, 1H), 7.95 (d, J=5.1 Hz, 1H), 7.68-7.72 (m, 1H), 7.35 (t, J=7.7 Hz, 1H), 7.18-7.28 (m, 5H), 6.76 (s, 2H), 6.00 (d, J=5.1 Hz, 1H), 3.25-3.31 (m, 1H), 1.36 (d, J=7.0 Hz, 6H). MS (ESI): 488.1 [M+H]+.

Example 91

2,6-Difluoro-N-{2-fluoro-3-[5-{2-[(2-methylpropyl)amino]-4-pyrimidinyl}-2-(4-morpholinyl)-1,3-thiazol-4-yl]phenyl}benzenesulfonamide

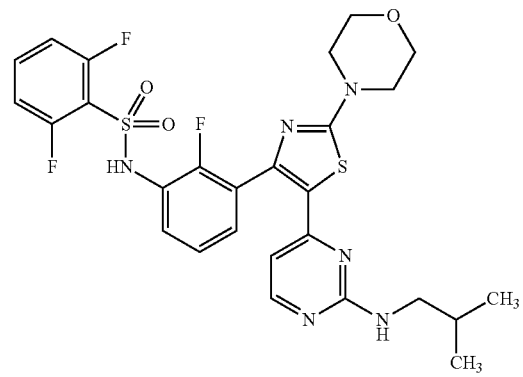 [SMILES: CC(C)CNc1nccc(-c2sc(N3CCOCC3)nc2-c2cccc(NS(=O)(=O)c3c(F)cccc3F)c2F)n1]

Following a procedure analogous to the procedure described in Example 18, Step B using N-{3-[5-(2-chloro-4-pyrimidinyl)-2-(4-morpholinyl)-1,3-thiazol-4-yl]-2-fluorophenyl}-2,6-difluorobenzenesulfonamide (100 mg, 0.176 mmol) and isobutylamine (2 mL) the title compound was obtained as a yellow powder (90 mg, 0.149 mmol, 85% yield). $^1$H NMR (400 MHz, DMSO-d$_6$): δ 10.87 (s, 1H), 7.86 (d, J=5.3 Hz, 1H), 7.67 (t, J=6.1 Hz, 1H), 7.42 (t, J=7.6 Hz, 1H), 7.21-7.31 (m, 4H), 7.14 (bs, 1H), 5.62 (bs, 1H), 3.71 (t, J=4.7 Hz, 4H), 3.45 (t, J=4.8 Hz, 4H), 3.02 (bs, 2H), 1.78-1.86 (m, 1H), 0.87 (d, J=6.6 Hz, 6H). MS (ESI): 603 [M–H]–.

Example 92

N-[3-(2-(1,1-Dimethylethyl)-5-{2-[(2-methylpropyl)amino]-4-pyrimidinyl}-1,3-thiazol-4-yl)-2-fluorophenyl]-2,5-difluorobenzenesulfonamide

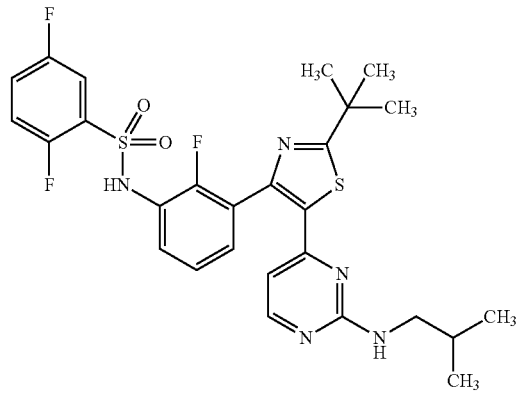 [SMILES: CC(C)CNc1nccc(-c2sc(C(C)(C)C)nc2-c2cccc(NS(=O)(=O)c3cc(F)ccc3F)c2F)n1]

Following a procedure analogous to the procedure described in Example 18, Step B using N-{3-[5-(2-chloro-4-pyrimidinyl)-2-(1,1-dimethylethyl)-1,3-thiazol-4-yl]-2-fluorophenyl}-2,5-difluorobenzenesulfonamide (100 mg, 0.186 mmol) and isobutylamine (2 mL) the title compound was obtained as a white powder (52 mg, 48.7% yield). $^1$H NMR (400 MHz, DMSO-d$_6$): δ 10.76 (s, 1H), 8.04 (d, J=5.2 Hz, 1H), 7.35-7.57 (m, 6H), 7.28 (t, J=7.8 Hz, 1H), 5.84 (bs, 1H), 2.95 (bs, 2H), 1.80 (bs, 1H), 1.40 (s, 9H), 0.86 (d, J=5.5 Hz, 6H). MS (ESI): 574 [M−H]−.

Example 93

N-{5-[5-{2-[(2,2-Difluoroethyl)amino]-4-pyrimidinyl}-2-(1-methylethyl)-1,3-thiazol-4-yl]-2-fluorophenyl}-2,6-difluorobenzenesulfonamide

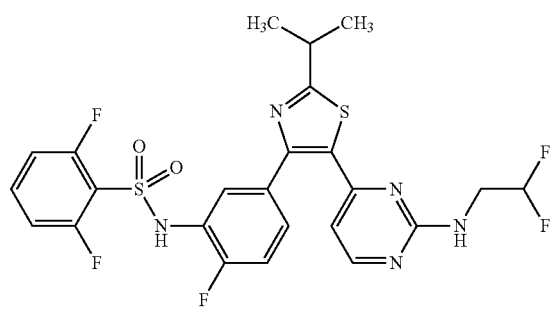 [SMILES: CC(C)c1nc(-c2ccc(F)c(NS(=O)(=O)c3c(F)cccc3F)c2)c(-c2ccnc(NCC(F)F)n2)s1]

Following a procedure analogous to the procedure described in Example 18, Step B using N-{5-[5-(2-chloro-4-pyrimidinyl)-2-(1-methylethyl)-1,3-thiazol-4-yl]-2-fluorophenyl}-2,6-difluorobenzenesulfonamide (100 mg, 0.190 mmol) and 2,2-difluoroethylamine (300 µL, 3.92 mmol) the title compound was obtained as a white powder (57 mg, 0.100 mmol, 52.5% yield). $^1$H NMR (400 MHz, DMSO-d$_6$): δ 10.94 (s, 1H), 8.15 (d, J=5.1 Hz, 1H), 7.65-7.75 (m, 2H), 7.38-7.44 (m, 2H), 7.27 (q, J=7.5 Hz, 3H), 6.30 (bs, 1H), 3.63 (bs, 2H), 3.27-3.31 (m, 1H), 1.36 (d, J=7.0 Hz, 6H). MS (ESI): 569.9 [M+H]+.

Example 94

N-[3-(2-(1,1-Dimethylethyl)-5-{2-[(2,2,2-trifluoroethyl)amino]-4-pyrimidinyl}-1,3-thiazol-4-yl)-2-fluorophenyl]-2,5-difluorobenzenesulfonamide

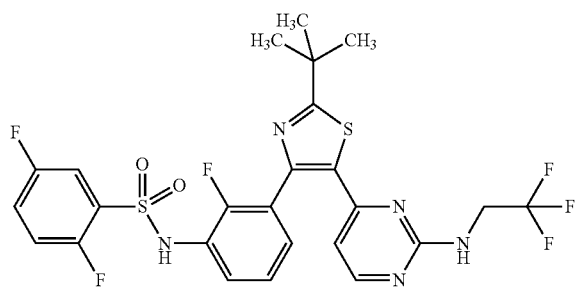 [SMILES: CC(C)(C)c1nc(-c2cccc(NS(=O)(=O)c3cc(F)ccc3F)c2F)c(-c2ccnc(NCC(F)(F)F)n2)s1]

Following a procedure analogous to the procedure described in Example 18, Step B using N-{3-[5-(2-chloro-4-pyrimidinyl)-2-(1,1-dimethylethyl)-1,3-thiazol-4-yl]-2-fluorophenyl}-2,5-difluorobenzenesulfonamide (100 mg, 0.190 mmol) and 2,2,2-trifluoroethylamine (0.5 ml, 0.190 mmol) the title compound, was obtained as a white powder (70 mg, 0.116 mmol, 62.7% yield). $^1$H NMR (400 MHz, DMSO-d$_6$): δ 10.78 (s, 1H), 8.49 (d, J=5.2 Hz, 1H), 7.37-7.51 (m, 4H), 7.21-7.29 (m, 2H), 6.72 (d, J=5.2 Hz, 1H), 4.85 (q, J=8.9 Hz, 2H), 1.42 (s, 9H). MS (ESI): 602.9 [M+H]+.

Example 95

2,6-Difluoro-N-{2-fluoro-5-[2-(1-methylethyl)-5-(2-{[3-(2-oxo-1-pyrrolidinyl)propyl]amino}-4-pyrimidinyl)-1,3-thiazol-4-yl]phenyl}benzenesulfonamide

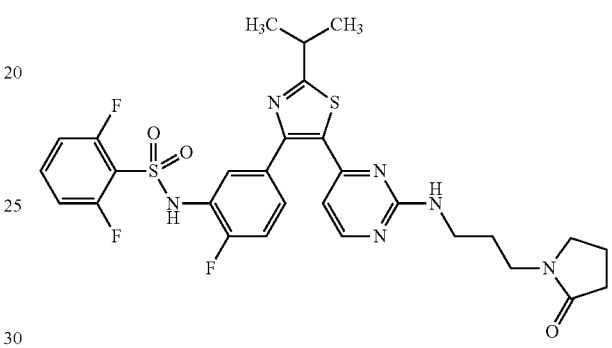

Following a procedure analogous to the procedure described in Example 1 using N-{5-[5-(2-chloro-4-pyrimidinyl)-2-(1-methylethyl)-1,3-thiazol-4-yl]-2-fluorophenyl}-2,6-difluorobenzenesulfonamide (0.15 g, 0.29 mmol) and 1-(3-aminopropyl)-2-pyrrolidinone (0.60 ml, 4.3 mmol) the title compound was obtained (0.070 g, 37% yield); $^1$H NMR (400 MHz, DMSO-d$_6$) δ ppm 10.92 (s, 1H), 8.08 (d, J=5.0 Hz, 1H), 7.65-7.79 (m, 1H), 7.35-7.49 (m, 2H), 7.19-7.34 (m, 4H), 6.11-6.26 (m, 1H), 3.22 (t, J=6.8 Hz, 4H), 2.21 (t, J=8.1 Hz, 2H), 1.91 (quin, J=7.6 Hz, 2H), 1.63-1.74 (m, 2H), 1.36 (d, J=6.9 Hz, 6H). MS (ES+): 631 [M+H]+.

Example 96

N-{3-[2-(1,1-Dimethylethyl)-5-(2-{[3-(2-oxo-1-pyrrolidinyl)propyl]amino}-4-pyrimidinyl)-1,3-thiazol-4-yl]-2-fluorophenyl}-2,5-difluorobenzenesulfonamide

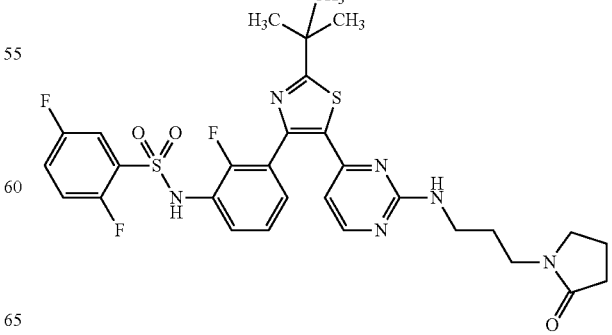

Following a procedure analogous to the procedure described in Example 1 using N-{3-[5-(2-chloro-4-pyrimidinyl)-2-(1,1-dimethylethyl)-1,3-thiazol-4-yl]-2-fluorophenyl}-2,5-difluorobenzenesulfonamide (0.20 g, 0.37 mmol) and 1-(3-aminopropyl)-2-pyrrolidinone (0.52 ml, 3.7 mmol) the title compound was obtained (0.20 g, 80% yield). $^1$H NMR (400 MHz, DMSO-d$_6$) δ ppm 10.75 (s, 1H), 8.03 (d, J=5.1 Hz, 1H), 7.15-7.64 (m, 7H), 5.81-5.98 (m, 1H), 3.21 (t, J=6.6 Hz, 2H), 3.07-3.16 (m, 2H), 2.21 (t, J=8.0 Hz, 2H), 1.92 (quin, J=7.4 Hz, 2H), 1.66 (br. s., 2H), 1.40 (s, 9H). MS (ES+): 645 [M+H]$^+$.

Example 97

N-{3-[2-(1,1-Dimethylethyl)-5-(2-{[2-(2-oxo-1-pyrrolidinyl)ethyl]amino}-4-pyrimidinyl)-1,3-thiazol-4-yl]-2-fluorophenyl}-2,5-difluorobenzenesulfonamide

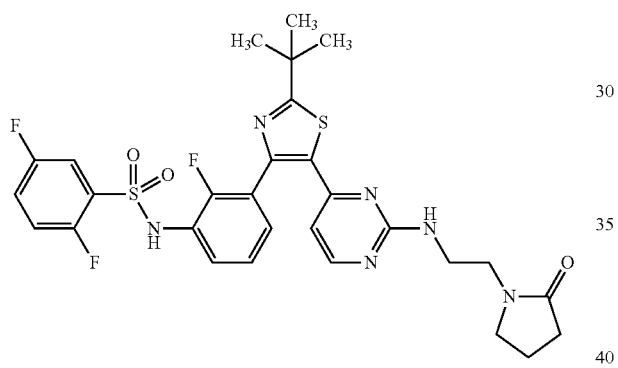

A mixture of N-{3-[5-(2-chloro-4-pyrimidinyl)-2-(1,1-dimethylethyl)-1,3-thiazol-4-yl]-2-fluorophenyl}-2,5-difluorobenzenesulfonamide (0.15 g, 0.28 mmol), 1-(2-aminoethyl)-2-pyrrolidinone (0.18 g, 0.83 mmol) and DIEA (0.10 ml, 0.56 mmol) in MeOH (0.5 ml) was heated at 50° C. for 2 h. LCMS analysis indicated that the reaction was proceeding very slowly, another equivalent amine and DIEA was added and the reaction was heated overnight. LCMS analysis indicated the reaction had still not progressed sufficiently so the reaction was heated overnight again. LCMS analysis indicated the reaction had progressed sufficiently so the reaction mixture was concentrated onto silica gel and purified by flash chromatography to afford a colourless foam. The product was dissolved in DCM and washed with HCl (10% Aq.) to remove some residual DIEA and the organics were dried over MgSO$_4$, filtered and the filtrate was concentrated in vacuo to afford the title compound (0.12 g, 67% yield); $^1$H NMR (400 MHz, DMSO-d$_6$) δ ppm 10.77 (s, 1H), 8.07 (d, J=5.1 Hz, 1H), 7.22-7.65 (m, 7H), 3.21-3.45 (m, 6H), 2.11-2.22 (m, 2H), 1.82-1.93 (m, 2H), 1.41 (s, 9H). MS (ES+): 631 [M+H]$^+$.

Example 98

N-[2-({4-[4-(3-{[(2,5-Difluorophenyl)sulfonyl]amino}-2-fluorophenyl)-2-(1,1-dimethylethyl)-1,3-thiazol-5-yl]-2-pyrimidinyl}amino)ethyl]-2-hydroxyacetamide

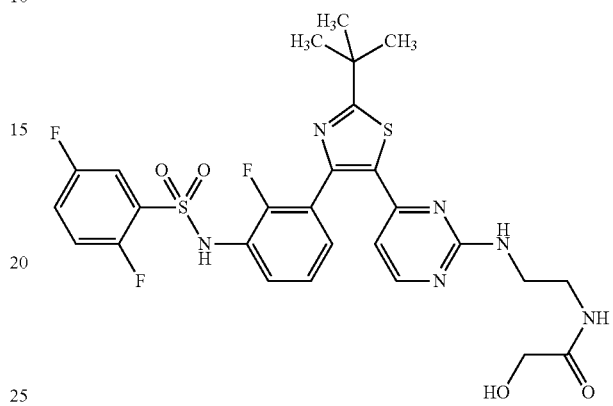

Step A: 1,1-Dimethylethyl [2-({4-[4-(3-{[(2,5-difluorophenyl)sulfonyl]amino}-2-fluorophenyl)-2-(1,1-dimethylethyl)-1,3-thiazol-5-yl]-2-pyrimidinyl}amino)ethyl]carbamate

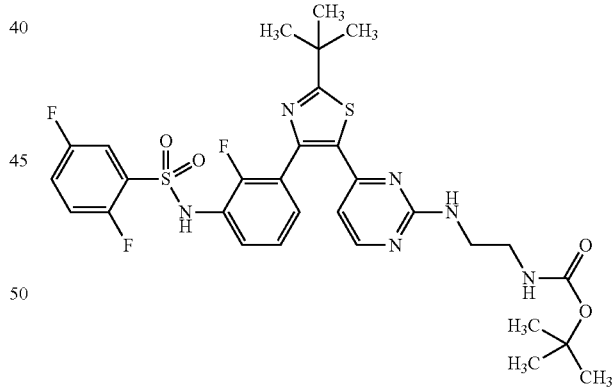

Following a procedure analogous to the procedure described in Example 1 using N-{3-[5-(2-chloro-4-pyrimidinyl)-2-(1,1-dimethylethyl)-1,3-thiazol-4-yl]-2-fluorophenyl}-2,5-difluorobenzenesulfonamide (0.30 g, 0.56 mmol), 1,1-dimethylethyl (2-aminoethyl)carbamate (0.089 g, 0.56 mmol) the title compound of Step A was obtained (0.34 g, 88% yield). $^1$H NMR (400 MHz, DMSO-d6) δ ppm 10.75 (s, 1H), 8.03 (d, J=5.1 Hz, 1H), 7.13-7.67 (m, 7H), 6.85 (br. s., 1H), 5.80-6.02 (m, 1H), 3.16-3.28 (m, 2H), 2.99-3.13 (m, 2H), 1.40 (s, 9H), 1.37 (s, 9H); m/z (ES+): 663 [M+H]+.

Step B: N-{3-[5-{2-[(2-Aminoethyl)amino]-4-pyrimidinyl}-2-(1,1-dimethylethyl)-1,3-thiazol-4-yl]-2-fluorophenyl}-2,5-difluorobenzenesulfonamide

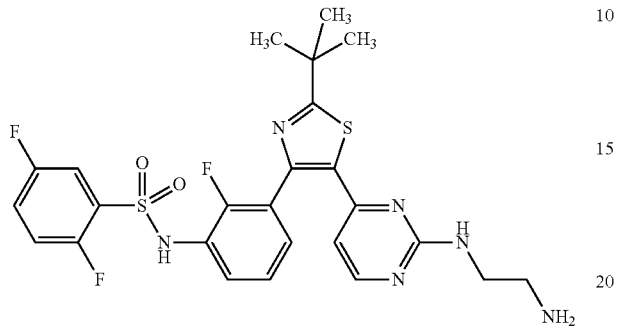

A 4 N solution of HCl in 1,4-dioxane (1.7 ml, 7.1 mmol) was added to a stirring solution of 1,1-dimethylethyl [2-({4-[4-(3-{[(2,5-difluorophenyl)sulfonyl]amino}-2-fluorophenyl)-2-(1,1-dimethylethyl)-1,3-thiazol-5-yl]-2-pyrimidinyl}amino)ethyl]carbamate (0.31 g, 0.47 mmol) (composite batches prepared as described in the previous step) in DCM (10 ml) at rt. MeOH (1 ml) was added to aid in solubility. The reaction was allowed to stir at rt for 3 h. The volatiles were removed and the residue was dried in vacuo to afford the title compound of Step B (0.31 g, quantitative yield) as a hydrochloride salt that was used without further purification; 1H NMR (400 MHz, DMSO-d6) δ ppm 10.77 (s, 1H), 7.93-8.18 (m, 4H), 7.20-7.69 (m, 7H), 3.37-3.53 (m, 2H), 2.96 (d, J=5.1 Hz, 2H), 1.41 (s, 9H). MS (ES+): 563 [M+H]+.

Step C: N-[2-({4-[4-(3-{[(2,5-Difluorophenyl)sulfonyl]amino}-2-fluorophenyl)-2-(1,1-dimethylethyl)-1,3-thiazol-5-yl]-2-pyrimidinyl}amino)ethyl]-2-hydroxyacetamide A mixture of glycolic acid (0.040 g, 0.50 mmol), HATU (0.19 g, 0.50 mmol) and DIEA (0.09 ml, 0.50 mmol) in DMF (1 mL) was added to a stirring solution of N-{3-[5-{2-[(2-aminoethyl)amino]-4-pyrimidinyl}-2-(1,1-dimethylethyl)-1,3-thiazol-4-yl]-2-fluorophenyl}-2,5-difluorobenzenesulfonamide (0.15 g, 0.25 mmol) and DIEA (0.09 ml, 0.50 mmol) in DMF (1 mL). The reaction was stirred for 1 h. LCMS analysis indicated approximately 50% conversion to product. An additional 2.0 equivalents of activated glycolic acid was added and the reaction was allowed to stir for an additional 1 h. LCMS analysis indicated the starting material was still not completely consumed so an additional 2.0 equivalents of activated glycolic acid was added and the reaction was stirred for an addition 1 h. The reaction was diluted with EtOAc, washed with water (×5) and a saturated aqueous brine solution (×2). The organic layer was dried over MgSO4, filtered and the filtrate was concentrated onto silica gel and purified by flash chromatography to afford the title compound (0.072 g, 44% yield). 1H NMR (400 MHz, DMSO-d6) δ ppm 10.75 (br. s., 1H), 8.04 (d, J=5.1 Hz, 1H), 7.77-7.98 (m, 1H), 7.15-7.65 (m, 7H), 5.81-6.01 (m, 1H), 5.49 (t, J=5.2 Hz, 1H), 3.80 (d, J=5.3 Hz, 2H), 3.29 (br. s., 2H), 1.40 (s, 9H). MS (ES+): 621 [M+H]+.

Example 99

N-(3-{5-(2-Amino-4-pyrimidinyl)-2-[4-(methylsulfonyl)-1-piperazinyl]-1,3-thiazol-4-yl}-2-fluorophenyl)-2,5-difluorobenzenesulfonamide

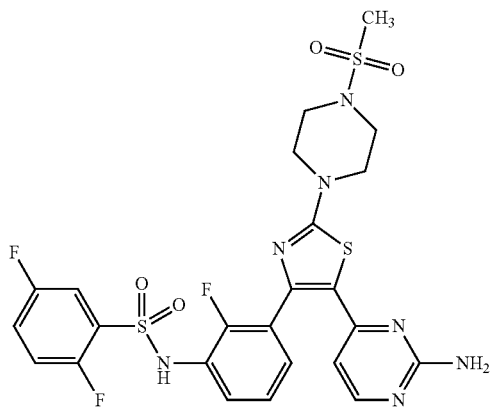 [SMILES: CS(=O)(=O)N1CCN(c2nc(-c3cccc(NS(=O)(=O)c4cc(F)ccc4F)c3F)c(-c3ccnc(N)n3)s2)CC1]

Step A: 1,1-Dimethylethyl 4-(aminocarbonothioyl)-1-piperazinecarboxylate

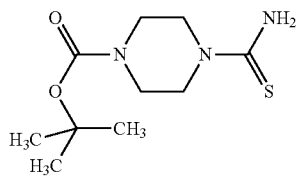

1,1-Dimethylethyl 1-piperazinecarboxylate (24 g, 129 mmol) in THF (1 L) was treated with 4 N HCl in dioxane (32.2 mL, 129 mmol)), and thiocyanate (12.52 g, 129 mmol) dissolved in minimal amount of water was added. After stirring at rt overnight, the volatiles were removed under reduced pressure. The residue was taken up in MeOH and filtered to remove inorganic salts and the solvent removed in vacuo and the cycle was repeated 3 more times. Then twice taken up in DCM and filtered and concentrated to give the title compound of Step A (29 g, 92% yield). 1H NMR (400 MHz, DMSO-d6) δ ppm 8.74 (br. s., 2H), 3.50 (br. s., 4H), 3.07 (t, J=5.0 Hz, 4H), 1.40 (s, 9H).

Step B: 1,1-Dimethylethyl 4-[5-(2-chloro-4-pyrimidinyl)-4-(3-{[(2,5-difluorophenyl)sulfonyl]amino}-2-fluorophenyl)-1,3-thiazol-2-yl]-1-piperazinecarboxylate

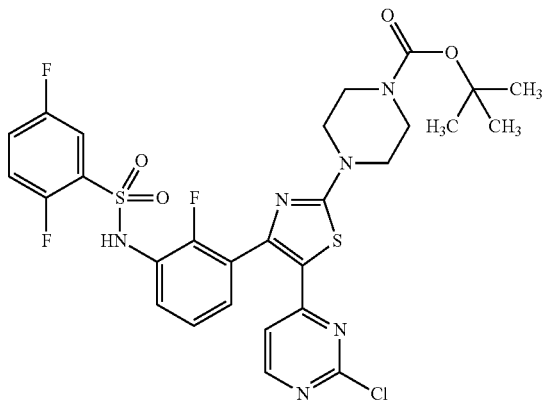 [SMILES: CC(C)(C)OC(=O)N1CCN(c2nc(-c3cccc(NS(=O)(=O)c4cc(F)ccc4F)c3F)c(-c3ccnc(Cl)n3)s2)CC1]

NBS (0.21 g, 1.2 mmol) was added to a stirring solution of N-(3-(2-(2-chloropyrimidin-4-yl)acetyl)-2-fluorophenyl)-2,5-difluorobenzenesulfonamide (0.50 g, 1.13 mmol) in DMA (5.5 ml) at rt. The reaction was allowed to stir for 15 min, then 1,1-dimethylethyl 4-(aminocarbonothioyl)-1-piperazinecarboxylate (0.55 g, 2.26 mmol) was added and the reaction was allowed to stir for 1 h. LCMS analysis indicated the reaction had progressed sufficiently, the reaction was poured into water and the bright yellow precipitate was collected by filtration. The filter cake was dissolved in DCM, dried over MgSO$_4$, filtered and the filtrate was concentrated onto silica gel. Purification by flash chromatography afforded the title compound of Step B (0.36 g, 45% yield) as a yellow solid. $^1$H NMR (400 MHz, DMSO-d$_6$) δ ppm 10.79 (s, 1H), 8.32 (d, J=5.5 Hz, 1H), 7.25-7.64 (m, 6H), 6.47 (d, J=5.5 Hz, 1H), 3.53-3.58 (m, 4H), 3.43-3.51 (m, 4H), 1.42 (s, 9H).

Step C: N-{3-[5-(2-Chloro-4-pyrimidinyl)-2-(1-piperazinyl)-1,3-thiazol-4-yl]-2-fluorophenyl}-2,5-difluorobenzenesulfonamide

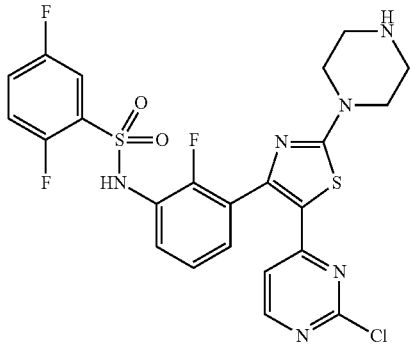 [SMILES: O=S(=O)(Nc1cccc(-c2nc(N3CCNCC3)sc2-c2ccnc(Cl)n2)c1F)c1cc(F)ccc1F]

A 4 N solution of HCl in 1,4-dioxane (1.1 ml, 4.3 mmol) was added to a stirring solution of 1,1-dimethylethyl 4-[5-(2-chloro-4-pyrimidinyl)-4-(3-{[(2,5-difluorophenyl)sulfonyl]amino}-2-fluorophenyl)-1,3-thiazol-2-yl]-1-piperazinecarboxylate (0.36 g, 0.54 mmol) in DCM (8 mL) and MeOH (1 mL) at rt. The reaction was allowed to stir overnight. LCMS analysis indicated complete consumption of the starting material. The volatiles were removed in vacuo to afford the HCl salt of the desired product of Step C (0.40 g, 100% yield) which was carried forward without further purification. MS (ES+): 568 [M+H]$^+$.

Step D: N-(3-{5-(2-Chloro-4-pyrimidinyl)-2-[4-(methylsulfonyl)-1-piperazinyl]-1,3-thiazol-4-yl}-2-fluorophenyl)-2,5-difluorobenzenesulfonamide

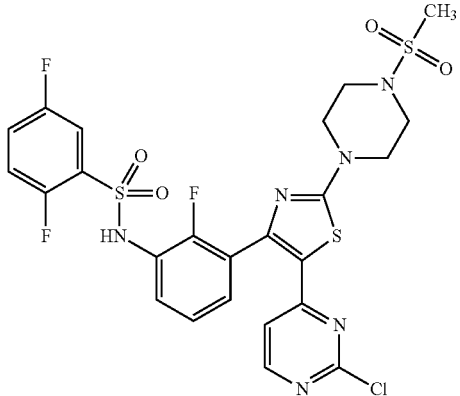 [SMILES: CS(=O)(=O)N1CCN(c2nc(-c3cccc(NS(=O)(=O)c4cc(F)ccc4F)c3F)c(-c3ccnc(Cl)n3)s2)CC1]

Methanesulfonyl chloride (0.05 mL, 0.7 mmol) was added to a stirring solution of N-{3-[5-(2-chloro-4-pyrimidinyl)-2-(1-piperazinyl)-1,3-thiazol-4-yl]-2-fluorophenyl}-2,5-difluorobenzenesulfonamide (0.40 g, 0.66 mmol) and TEA (0.32 mL, 2.3 mmol) in DCM (10 mL) at rt. LCMS analysis indicated clean conversion to product. The reaction was quenched with water and the whole was extracted with DCM. The combined organic extracts were dried over MgSO$_4$, filtered, and the filtrate was concentrated onto silica gel. Purification by flash chromatography afforded the title compound of Step D (0.14 g, 30% yield). $^1$H NMR (400 MHz, DMSO-d$_6$) δ ppm 10.80 (s, 1H), 8.34 (d, J=5.5 Hz, 1H), 7.25-7.63 (m, 5H), 6.50 (d, J=5.3 Hz, 1H), 3.69 (br. s., 4H), 3.27 (br. s., 4H), 2.93 (s, 3H).

Step E: N-(3-{5-(2-Amino-4-pyrimidinyl)-2-[4-(methylsulfonyl)-1-piperazinyl]-1,3-thiazol-4-yl}-2-fluorophenyl)-2,5-difluorobenzenesulfonamide A solution of N-(3-{5-(2-chloro-4-pyrimidinyl)-2-[4-(methylsulfonyl)-1-piperazinyl]-1,3-thiazol-4-yl}-2-fluorophenyl)-2,5-difluorobenzenesulfonamide (0.14 g, 0.22 mmol) in NH$_4$OH (2.5 mL, 65 mmol) was sealed in a microwave vial and irradiated at 140° C. for 12 min. LCMS analysis indicates complete conversion to product. The reaction mixture was transferred to a round bottom flask with DCM and MeOH. A precipitate formed while attempting to remove the volatiles in vacuo and it was collected by vacuum filtration.

The pale yellow solid was dried in vacuo to afford the title compound (0.14 g, 100% yield). $^1$H NMR (400 MHz, DMSO-d$_6$) δ ppm 10.76 (br. s., 1H), 7.84 (d, J=5.3 Hz, 1H), 7.46-7.61 (m, 3H), 7.38-7.46 (m, 1H), 7.22-7.34 (m, 2H), 6.59 (br. s., 2H), 5.64 (d, J=5.1 Hz, 1H), 3.60 (br. s., 4H), 3.26 (br. s., 4H), 2.92 (s, 3H). MS (ES+): 626 [M+H]$^+$.

Example 100

N-(3-{5-(2-Amino-4-pyrimidinyl)-2-[4-(methylsulfonyl)-1-piperazinyl]-1,3-thiazol-4-yl}-2-fluorophenyl)-2,6-difluorobenzenesulfonamide

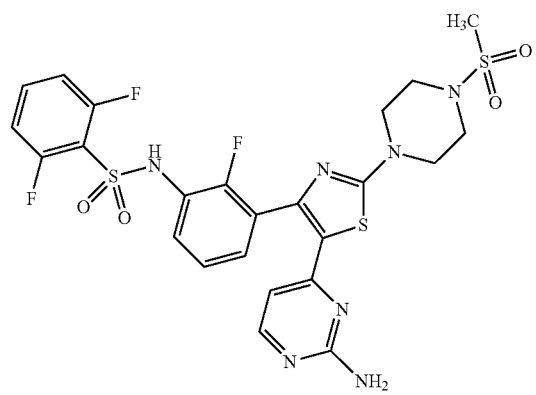 [SMILES: CS(=O)(=O)N1CCN(c2nc(-c3cccc(NS(=O)(=O)c4c(F)cccc4F)c3F)c(-c3ccnc(N)n3)s2)CC1]

Step A: 1,1-Dimethylethyl 4-[5-(2-chloro-4-pyrimidinyl)-4-(3-{[(2,6-difluorophenyl)sulfonyl]amino}-2-fluorophenyl)-1,3-thiazol-2-yl]-1-piperazinecarboxylate

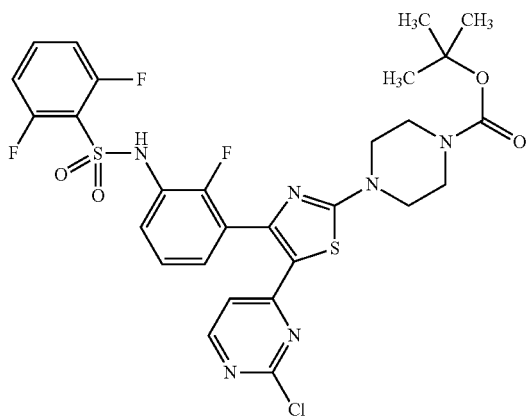 [SMILES: CC(C)(C)OC(=O)N1CCN(c2nc(-c3cccc(NS(=O)(=O)c4c(F)cccc4F)c3F)c(-c3ccnc(Cl)n3)s2)CC1]

Following a procedure analogous to Intermediate 6 using N-{3-[(2-chloro-4-pyrimidinyl)acetyl]-2-fluorophenyl}-2,6-difluorobenzenesulfonamide (2.00 g, 4.53 mmol), NBS (0.85 g, 4.75 mmol) and 1,1-dimethylethyl 4-(aminocarbonothioyl)-1-piperazinecarboxylate (2.22 g, 9.05 mmol) the title compound of Step A was obtained (1.16 g, 38% yield). $^1$H NMR (400 MHz, DMSO-d6) δ ppm 10.93 (s, 1H), 8.30 (d, J=5.49 Hz, 1H), 7.62-7.76 (m, 1H), 7.46 (td, J=7.46, 1.28 Hz, 1H), 7.38 (t, J=6.09 Hz, 1H), 7.32 (t, J=7.78 Hz, 1H), 7.25 (t, J=9.11 Hz, 2H), 6.46 (d, J=5.40 Hz, 1H), 3.56 (br. s., 4H), 3.47 (br. s., 4H), 1.42 (s, 9H). m/z (ES+): 668 [M+H]$^+$.

Step B: N-{3-[5-(2-Chloro-4-pyrimidinyl)-2-(1-piperazinyl)-1,3-thiazol-4-yl]-2-fluorophenyl}-2,6-difluorobenzenesulfonamide

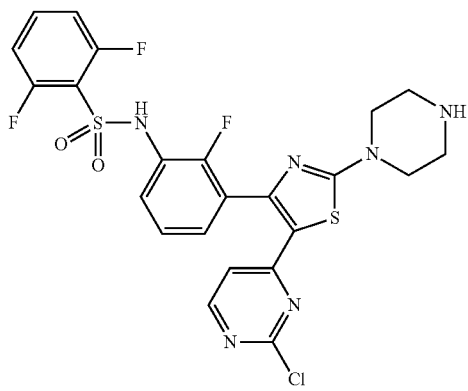 [SMILES: O=S(=O)(Nc1cccc(-c2nc(N3CCNCC3)sc2-c2ccnc(Cl)n2)c1F)c1c(F)cccc1F]

To 1,1-dimethylethyl 4-[5-(2-chloro-4-pyrimidinyl)-4-(3-{[(2,6-difluorophenyl)sulfonyl]amino}-2-fluorophenyl)-1,3-thiazol-2-yl]-1-piperazinecarboxylate (1.13 g, 1.694 mmol) in DCM (20 mL) was treated with TFA (20 mL) at rt for 30 min. The reaction mixture was concentrated and the residue was triturated with DCM and hexane to give (1.10 g, 95% yield) of the title compound of Step B. $^1$H NMR (400 MHz, DMSO-d$_6$) d ppm 10.95 (br. s., 1H), 9.04 (br. s., 1H), 8.34 (d, J=5.5 Hz, 1H), 7.63-7.76 (m, 1H), 7.42-7.49 (m, 1H), 7.38 (t, J=6.1 Hz, 1H), 7.30-7.36 (m, 1H), 7.26 (t, J=9.2 Hz, 2H), 6.52 (d, J=5.4 Hz, 1H), 3.77 (d, J=4.8 Hz, 4H), 3.27 (br. s., 4H). m/z (ES+): 568 [M+H]$^+$.

Step C: N-(3-{5-(2-Chloro-4-pyrimidinyl)-2-[4-(methylsulfonyl)-1-piperazinyl]-1,3-thiazol-4-yl}-2-fluorophenyl)-2,6-difluorobenzenesulfonamide

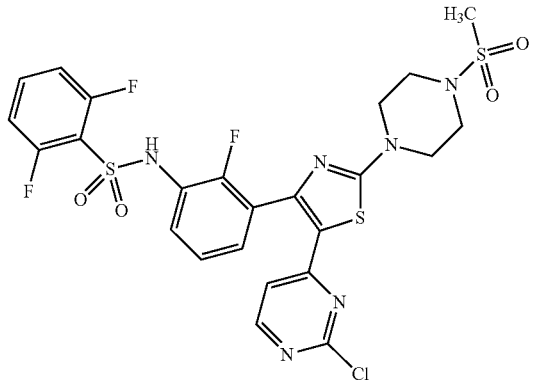 [SMILES: CS(=O)(=O)N1CCN(c2nc(-c3cccc(NS(=O)(=O)c4c(F)cccc4F)c3F)c(-c3ccnc(Cl)n3)s2)CC1]

N-{3-[5-(2-Chloro-4-pyrimidinyl)-2-(1-piperazinyl)-1,3-thiazol-4-yl]-2-fluorophenyl}-2,6-difluorobenzenesulfonamide (0.50 g, 0.734 mmol) in DCM (10 mL) was treated with methanesulfonyl chloride (0.074 mL, 0.954 mmol) and stirred at rt for 3 h. Silica was added and concentrated. The residue was column chromatographed with EtOAc/DCM to give title compound of Step C (0.38 g, 96% yield). $^1$H NMR (400 MHz, DMSO-d$_6$) δ ppm 10.93 (s, 1H), 8.32 (d, J=5.5 Hz, 1H), 7.64-7.74 (m, 1H), 7.42-7.50 (m, 1H), 7.39 (t, J=6.1 Hz, 1H), 7.29-7.35 (m, 1H), 7.25 (t, J=9.1 Hz, 2H), 6.49 (d, J=5.4 Hz, 1H), 3.63-3.76 (m, 4H), 3.27 (t, J=4.7 Hz, 4H), 2.93 (s, 3H). m/z (ES+): 646 [M+H]$^+$.

Step D: N-(3-{5-(2-Amino-4-pyrimidinyl)-2-[4-(methylsulfonyl)-1-piperazinyl]-1,3-thiazol-4-yl}-2-fluorophenyl)-2,6-difluorobenzenesulfonamide Following a procedure analogous to Example 51, Step B using N-(3-{5-(2-chloro-4-pyrimidinyl)-2-[4-(methylsulfonyl)-1-piperazinyl]-1,3-thiazol-4-yl}-2-fluorophenyl)-2,6-difluorobenzenesulfonamide (0.140 g, 0.217 mmol) and 7M ammonia in MeOH (25 mL) the title compound was obtained (0.041 g, 30% yield). $^1$H NMR (400 MHz, DMSO-d$_6$) δ ppm 10.88 (br. s., 1H), 7.84 (d, J=5.3 Hz, 1H), 7.63-7.73 (m, 1H), 7.37-7.48 (m, 1H), 7.17-7.34 (m, 4H), 6.58 (br. s., 2H), 5.65 (d, J=5.2 Hz, 1H), 3.60 (br. s., 4H), 3.26 (br. s., 4H), 2.92 (s, 3H). m/z (ES+): 626 [M+H]$^+$.

Example 101

N-(3-{5-(2-Amino-4-pyrimidinyl)-2-[1-(methylsulfonyl)-4-piperidinyl]-1,3-thiazol-4-yl}-2-fluorophenyl)-2,5-difluorobenzenesulfonamide

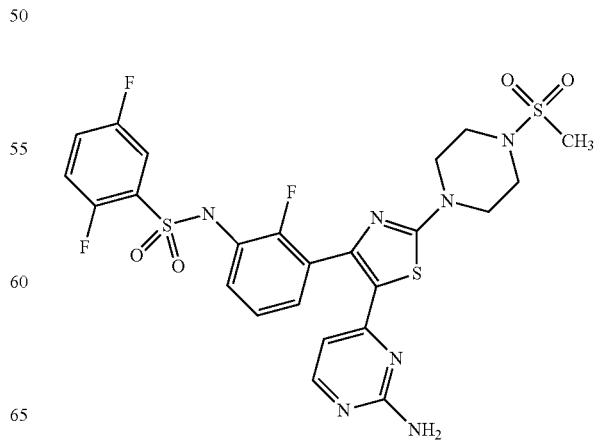

Step A: 1,1-Dimethylethyl 4-[5-(2-chloro-4-pyrimidinyl)-4-(3-{[(2,5-difluorophenyl)sulfonyl]amino}-2-fluorophenyl)-1,3-thiazol-2-yl]-1-piperidinecarboxylate

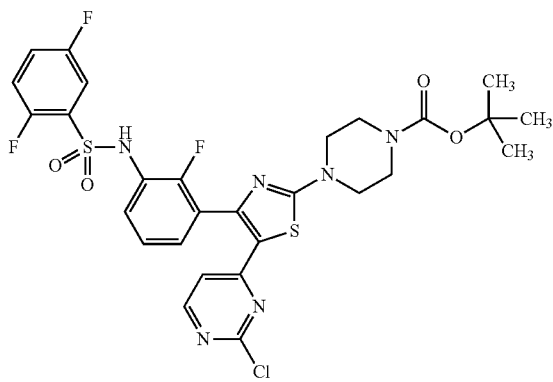 [SMILES: CC(C)(C)OC(=O)N1CCN(c2nc(-c3cccc(NS(=O)(=O)c4cc(F)ccc4F)c3F)c(-c3ccnc(Cl)n3)s2)CC1]

Following a procedure analogous to Intermediate 6 using N-(3-(2-(2-chloropyrimidin-4-yl)acetyl)-2-fluorophenyl)-2,5-difluorobenzenesulfonamide (4.80 g, 10.86 mmol) and 1,1-dimethylethyl 4-(aminocarbonothioyl)-1-piperidinecarboxylate (3.19 g, 13.04 mmol) the title compound of Step A was obtained (4.31 g, 60% yield). $^1$H NMR (400 MHz, DMSO-$d_6$) δ ppm 10.78 (s, 1H), 8.57 (d, J=5.3 Hz, 1H), 7.36-7.68 (m, 5H), 7.32 (t, J=7.8 Hz, 1H), 6.90 (d, J=5.3 Hz, 1H), 4.01 (d, J=11.4 Hz, 2H), 3.20-3.34 (m, 1H), 2.92 (d, J=12.6 Hz, 2H), 2.07 (d, J=11.3 Hz, 2H), 1.52-1.70 (m, 2H), 1.40 (s, 9H). m/z (ES+): 667 [M+H]$^+$.

Step B: N-{3-[5-(2-Chloro-4-pyrimidinyl)-2-(4-piperidinyl)-1,3-thiazol-4-yl]-2-fluorophenyl}-2,5-difluorobenzenesulfonamide

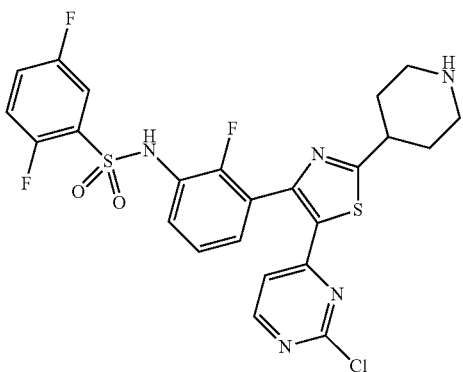 [SMILES: O=S(=O)(Nc1cccc(-c2nc(C3CCNCC3)sc2-c2ccnc(Cl)n2)c1F)c1cc(F)ccc1F]

Following a procedure analogous to Example 100, Step B using 1,1-dimethylethyl 4-[5-(2-chloro-4-pyrimidinyl)-4-(3-{[(2,5-difluorophenyl)sulfonyl]amino}-2-fluorophenyl)-1,3-thiazol-2-yl]-1-piperidinecarboxylate (2.00 g, 3.00 mmol) the title compound of Step B was obtained (1.80 g, 88% yield). $^1$H NMR (400 MHz, DMSO-$d_6$) δ ppm 10.81 (s, 1H), 8.86 (d, J=9.6 Hz, 1H), 8.48-8.66 (m, 2H), 7.38-7.65 (m, 5H), 7.33 (t, J=7.8 Hz, 1H), 6.92 (d, J=5.2 Hz, 1H), 3.32-3.54 (m, 2H), 2.97-3.15 (m, 2H), 2.26 (d, J=12.2 Hz, 2H), 1.80-1.97 (m, 2H). m/z (ES+): 567 [M+H]$^+$.

Step C: N-(3-{5-(2-Amino-4-pyrimidinyl)-2-[1-(methylsulfonyl)-4-piperidinyl]-1,3-thiazol-4-yl}-2-fluorophenyl)-2,5-difluorobenzenesulfonamide To N-{3-[5-(2-chloro-4-pyrimidinyl)-2-(4-piperidinyl)-1,3-thiazol-4-yl]-2-fluorophenyl}-2,5-difluorobenzenesulfonamide (0.30 g, 0.441 mmol) in DCM (5 mL) was added methanesulfonyl chloride (0.038 mL, 0.485 mmol) at rt and stirred for 3 h. The reaction mixture was concentrated with silica and was chromatographed to give the sulfonamide compound (0.17 g, 0.261 mmol), which was treated with NH$_4$OH (6 mL, 154 mmol) and microwave irradiated at 130° C. for 30 min. The reaction was concentrated onto silica and column chromatographed to give the title compound (0.12 g, 71%). $^1$H NMR (400 MHz, DMSO-$d_6$) δ ppm 10.77 (s, 1H), 7.99 (d, J=5.1 Hz, 1H), 7.20-7.62 (m, 6H), 6.78 (s, 2H), 5.85 (d, J=5.1 Hz, 1H), 3.63 (d, J=12.1 Hz, 2H), 3.10-3.23 (m, 1H), 2.84-2.96 (m, 5H), 2.18 (d, J=11.1 Hz, 2H), 1.66-1.82 (m, 2H). m/z (ES+): 625 [M+H]$^+$.

Example 102

N-{3-[5-(2-Amino-4-pyrimidinyl)-2-(1,1-dioxido-4-thiomorpholinyl)-1,3-thiazol-4-yl]-2-fluorophenyl}-2,6-difluorobenzenesulfonamide

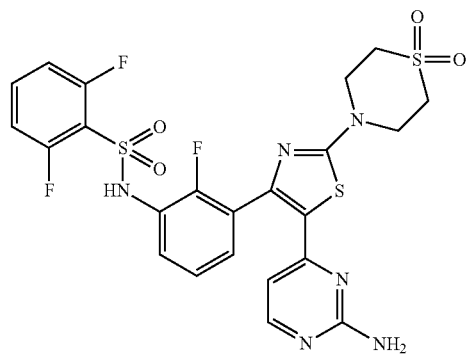 [SMILES: Nc1nccc(-c2sc(N3CCS(=O)(=O)CC3)nc2-c2cccc(NS(=O)(=O)c3c(F)cccc3F)c2F)n1]

Step A: N-{3-[5-(2-Chloro-4-pyrimidinyl)-2-(1,1-dioxido-4-thiomorpholinyl)-1,3-thiazol-4-yl]-2-fluorophenyl}-2,6-difluorobenzenesulfonamide

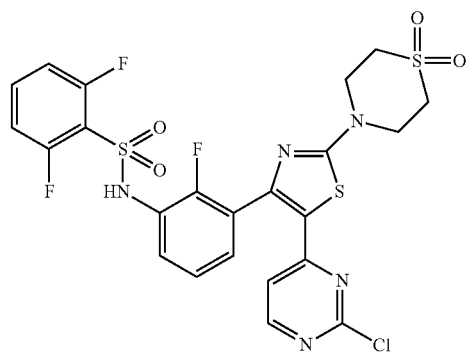 [SMILES: O=S1(=O)CCN(c2nc(-c3cccc(NS(=O)(=O)c4c(F)cccc4F)c3F)c(-c3ccnc(Cl)n3)s2)CC1]

Following a procedure analogous to Intermediate 6 using N-{3-[(2-chloro-4-pyrimidinyl)acetyl]-2-fluorophenyl}-2,6-difluorobenzenesulfonamide (1.5 g, 3.40 mmol), NBS (0.60 g, 3.40 mmol) and 4-thiomorpholinecarbothioamide 1,1-dioxide (0.80 g, 4.12 mmol) the title compound of Step A was obtained (1.88 g, 90% yield). $^1$H NMR (400 MHz, DMSO-d$_6$) δ ppm 10.94 (br. s., 1H), 8.34 (d, J=5.1 Hz, 1H), 7.59-7.78 (m, 1H), 7.37-7.52 (m, 2H), 7.32 (t, J=7.7 Hz, 1H), 7.25 (t, J=9.1 Hz, 2H), 6.55 (d, J=4.9 Hz, 1H), 4.04 (br. s., 4H), 3.32 (br. s., 4H). m/z (ES+): 617 [M+H]$^+$.

Step B: N-{3-[5-(2-Amino-4-pyrimidinyl)-2-(1,1-dioxido-4-thiomorpholinyl)-1,3-thiazol-4-yl]-2-fluorophenyl}-2,6-difluorobenzenesulfonamide Following a procedure analogous to Example 51, Step B using N-{3-[5-(2-chloro-4-pyrimidinyl)-2-(1,1-dioxido-4-thiomorpholinyl)-1,3-thiazol-4-yl]-2-fluorophenyl}-2,6-difluorobenzenesulfonamide (0.30 g, 0.487 mmol) and 7 M ammonia (20 mL) the title compound was obtained (0.11 g, 38% yield). $^1$H NMR (400 MHz, DMSO-d$_6$) δ ppm 10.88 (br. s., 1H), 7.85 (d, J=5.3 Hz, 1H), 7.63-7.75 (m, 1H), 7.42 (td, J=7.5, 1.7 Hz, 1H), 7.19-7.36 (m, 4H), 6.60 (br. s., 2H), 5.68 (d, J=5.1 Hz, 1H), 3.97 (br. s., 4H), 3.29 (br. s., 4H). m/z (ES+): 597 [M+H]$^+$.

Example 103

N-(3-{5-(2-Amino-4-pyrimidinyl)-2-[(2R,6S)-2,6-dimethyl-4-morpholinyl]-1,3-thiazol-4-yl}-2-fluorophenyl)-2,5-difluorobenzenesulfonamide

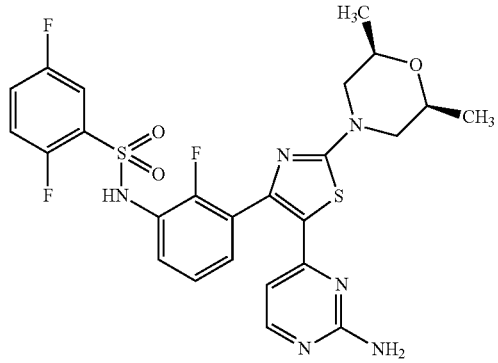 [SMILES: C[C@@H]1CN(c2nc(-c3cccc(NS(=O)(=O)c4cc(F)ccc4F)c3F)c(-c3ccnc(N)n3)s2)C[C@H](C)O1]

Step A: N-(3-{5-(2-Chloro-4-pyrimidinyl)-2-[(2R,6S)-2,6-dimethyl-4-morpholinyl]-1,3-thiazol-4-yl}-2-fluorophenyl)-2,5-difluorobenzenesulfonamide

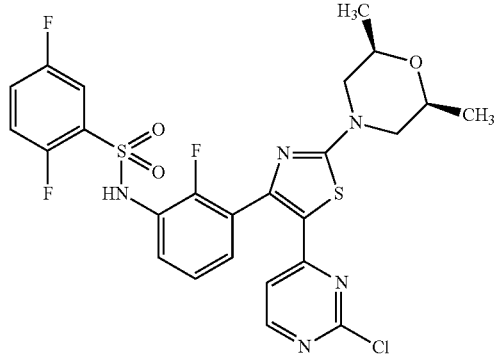 [SMILES: C[C@@H]1CN(c2nc(-c3cccc(NS(=O)(=O)c4cc(F)ccc4F)c3F)c(-c3ccnc(Cl)n3)s2)C[C@H](C)O1]

To N-(3-(2-(2-chloropyrimidin-4-yl)acetyl)-2-fluorophenyl)-2,5-difluorobenzenesulfonamide (1.5 g, 3.40 mmol) was added DMA (10 mL) and NBS (0.61 g, 3427 mmol). After stirring at rt for 10 min, (2R,6S)-2,6-dimethyl-4-morpholinecarbothioamide (0.800 g, 4.59 mmol) was added and stirring continued for 2 h. Water was added and the solid was collected by filtration and dried over two days to afford the title compound of Step A (1.80 g, 89% yield). $^1$H NMR (400 MHz, DMSO-d$_6$) δ ppm 10.80 (s, 1H), 8.31 (d, J=5.4 Hz, 1H), 7.49-7.63 (m, 3H), 7.45 (t, J=7.6 Hz, 2H), 7.39 (t, J=6.4 Hz, 1H), 7.31 (t, J=7.8 Hz, 1H), 6.46 (d, J=5.3 Hz, 1H), 3.88 (d, J=11.4 Hz, 1H), 3.66 (br. s., 1H), 2.94 (s, 2H), 2.78 (s, 2H), 1.14 (d, J=6.0 Hz, 6H). m/z (ES+): 597 [M+H]$^+$.

Step B: N-(3-{5-(2-Amino-4-pyrimidinyl)-2-[(2R,6S)-2,6-dimethyl-4-morpholinyl]-1,3-thiazol-4-yl}-2-fluorophenyl)-2,5-difluorobenzenesulfonamide In a pressure vessel was placed N-(3-{5-(2-chloro-4-pyrimidinyl)-2-[(2R,6S)-2,6-dimethyl-4-morpholinyl]-1,3-thiazol-4-yl}-2-fluorophenyl)-2,5-difluorobenzenesulfonamide (0.30 g, 0.503 mmol) and NH$_4$OH (3 mL, 77 mmol) and 1,4-dioxane (3 mL) were added. The vessel was sealed and heated at 100° C. for 18 h. The reaction was cooled, concentrated onto silica and the residue was column chromatographed to give the title compound was obtained (0.22 g, 75% yield). $^1$H NMR (400 MHz, DMSO-d$_6$) δ ppm 10.77 (br. s., 1H), 7.82 (d, J=5.3 Hz, 1H), 7.46-7.65 (m, 3H), 7.37-7.46 (m, 1H), 7.27 (t, J=6.7 Hz, 2H), 6.54 (br. s., 2H), 5.62 (d, J=5.3 Hz, 1H), 3.77 (d, J=12.2 Hz, 2H), 3.60-3.73 (m, 2H), 2.73 (t, J=11.6 Hz, 2H), 1.14 (d, J=6.0 Hz, 6H). m/z (ES+): 577 [M+H]$^+$.

Example 104

N-{3-[5-(2-Amino-4-pyrimidinyl)-2-cyclohexyl-1,3-thiazol-4-yl]-2-fluorophenyl}-2,6-difluorobenzenesulfonamide

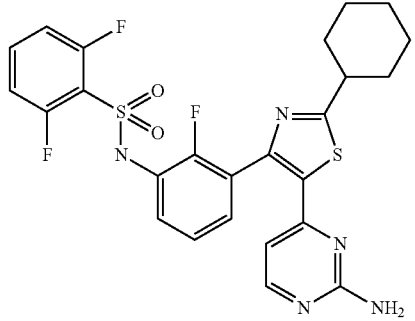 [SMILES: Nc1nccc(-c2sc(C3CCCCC3)nc2-c2cccc(NS(=O)(=O)c3c(F)cccc3F)c2F)n1]

Step A: Cyclohexanecarbothioamide

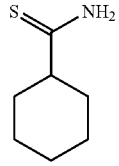

Cyclohexanecarboxamide (1 g, 7.86 mmol) and Lawesson's Reagent (2 g, 4.94 mmol) in THF (50 mL) was heated at 70° C. for 3 h. Silica was added and the volatiles were removed under reduced pressure. The residue was column chromatographed with EtOAc/DCM to afford cyclohexanecarbothioamide (0.557 g, 49% yield). $^1$H NMR (400 MHz, CDCl$_3$) δ ppm 7.67 (br. s., 1H), 6.91 (br. s., 1H), 2.56 (tt, J=11.8, 3.3 Hz, 1H), 1.90-2.02 (m, 2H), 1.78-1.90 (m, 2H), 1.71 (d, J=12.0 Hz, 1H), 1.51 (qd, J=12.3, 2.8 Hz, 2H), 1.16-1.40 (m, 3H), e/z (ES+): 144 [M+H]$^+$.

Step B: N-{3-[5-(2-Chloro-4-pyrimidinyl)-2-cyclohexyl-1,3-thiazol-4-yl]-2-fluorophenyl}-2,6-difluorobenzenesulfonamide

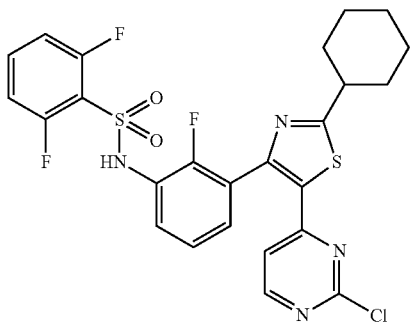 [SMILES: O=S(=O)(Nc1cccc(-c2nc(C3CCCCC3)sc2-c2ccnc(Cl)n2)c1F)c1c(F)cccc1F]

Following a procedure analogous to Intermediate 6 using N-{3-[(2-chloro-4-pyrimidinyl)acetyl]-2-fluorophenyl}-2,6-difluorobenzenesulfonamide (0.45 g, 1.019 mmol) and cyclohexanecarbothioamide (0.18 mg, 1.23 mmol) the title compound of Step B was obtained (0.38 g, 66% yield). $^1$H NMR (400 MHz, DMSO-$d_6$) δ ppm 10.92 (s, 1H), 8.54 (d, J=5.3 Hz, 1H), 7.61-7.75 (m, 1H), 7.39-7.50 (m, 2H), 7.32 (t, J=7.9 Hz, 1H), 7.24 (t, J=9.1 Hz, 2H), 6.86 (d, J=5.3 Hz, 1H), 2.96-3.12 (m, 1H), 2.09 (d, J=10.6 Hz, 2H), 1.78 (dd, J=9.7, 3.2 Hz, 2H), 1.68 (d, J=12.5 Hz, 1H), 1.47-1.61 (m, 2H), 1.33-1.45 (m, 2H), 1.21-1.32 (m, 1H). m/z (ES+): 566 [M+H]$^+$.

Step C: N-{3-[5-(2-Amino-4-pyrimidinyl)-2-cyclohexyl-1,3-thiazol-4-yl]-2-fluorophenyl}-2,6-difluorobenzenesulfonamide Following a procedure analogous to Example 21 using N-{3-[5-(2-chloro-4-pyrimidinyl)-2-cyclohexyl-1,3-thiazol-4-yl]-2-fluorophenyl}-2,6-difluorobenzenesulfonamide (0.10 g, 0.177 mmol) and NH$_4$OH (3 mL) the title compound was obtained (0.055 g, 57% yield). $^1$H NMR (400 MHz, DMSO-$d_6$) δ ppm 10.88 (br. s., 1H), 7.97 (br. s., 1H), 7.68 (br. s., 1H), 7.09-7.57 (m, 5H), 6.75 (br. s., 2H), 5.84 (br. s., 1H), 2.98 (d, J=0.5 Hz, 1H), 2.06 (br. s., 2H), 1.59-1.91 (m, 3H), 1.06-1.59 (m, 5H). m/z (ES+): 546 [M+H]$^+$.

Example 105

N-{3-[5-(2-Amino-4-pyrimidinyl)-2-(4-morpholinyl)-1,3-thiazol-4-yl]-2,4-difluorophenyl}-2,5-difluorobenzenesulfonamide

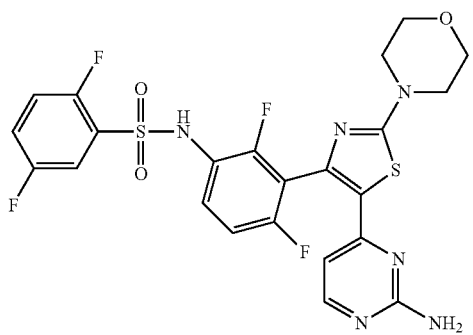 [SMILES: Nc1nccc(-c2sc(N3CCOCC3)nc2-c2c(F)ccc(NS(=O)(=O)c3cc(F)ccc3F)c2F)n1]

Step A: Methyl 2,6-difluorobenzoate

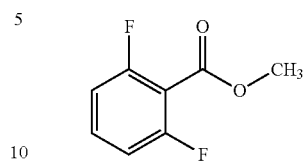

To a suspension of carboxylic acid (50 g, 316 mmol) in MeOH (800 mL) was added TsOH (6 g, 10%), the mixture was heated to reflux overnight. TLC shows reaction complete. The solvent was removed under reduced pressure. The residue was dissolved in EtOAc and washed by saturated NaHCO$_3$ and brine successively. The organic layer was separated, dried over Na$_2$SO$_4$ and concentrated under reduced pressure to give methyl 2,6-difluorobenzoate (41 g, 75.9% yield). $^1$H NMR (400 MHz, CDCl$_3$) δ ppm 7.37-7.46 (m, 1H), 6.91-6.98 (m, 2H), 3.95 (s, 3H).

Step B: Methyl 2,6-difluoro-3-nitrobenzoate

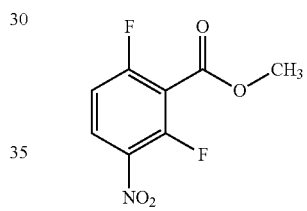

Fuming nitric acid (11 g, 174 mmol) was added to a solution of methyl 2,6-difluorobenzoate (25 g, 145 mmol) in concentrated sulfuric acid (50 mL) at 0° C., and the reaction was stirred for 30 min at 0° C. The reaction mixture was poured over ice-water. The precipitate was filtered off by suction to give the desired product of Step B (25.1 g, 80.6%). $^1$H NMR (400 MHz, CDCl$_3$) δ ppm 8.13-8.20 (m, 1H), 7.02-7.10 (m, 1H), 3.93 (s, 3H).

Step C: Methyl 3-amino-2,6-difluorobenzoate

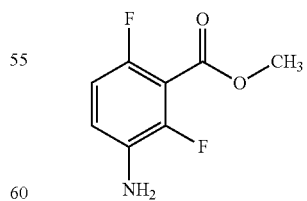

To a solution of methyl 2,6-difluoro-3-nitrobenzoate (25 g, 115 mmol) in MeOH (150 mL) was added 5% palladium on carbon (2.5 g). The mixture was stirred under H$_2$ atmosphere (50 psi/25° C.) for 12 h. The catalyst was filtered, and the filtrate was concentrated under the reduced pressure to dryness to give the product of Step C (20 g, 93.0%). ¹H NMR (400 MHz, DMSO-d6) δ ppm 6.95-7.10 (m, 2H), 3.86 (s, 3H)

Step D: Methyl 2,6-difluoro-3-{[(2-propen-1-yloxy)carbonyl]amino}benzoate

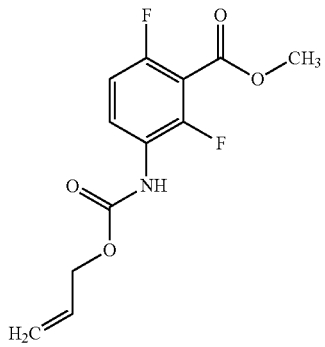 [SMILES: C=CCOC(=O)Nc1ccc(F)c(C(=O)OC)c1F]

To a solution of methyl 3-amino-2,6-difluorobenzoate (75 g, 401 mmol) in THF (300 mL), saturated NaHCO₃ (1400 mL) was added. Then 2-propen-1-yl chloridocarbonate (67.0 g, 561 mmol) was added dropwise at 0° C. The mixture was stirred at rt for 2 h. The solution was extracted with EtOAc (500 mL×3). The combined organic layers were washed with water and brine successively, dried over Na₂SO₄, filtered and concentrated under reduced pressure to give the title compound of Step D (92.5 g, 85.6% yield), which was used to the next step directly. ¹H NMR (400 MHz, CDCl₃) δ ppm 8.05-8.20 (br, 1H), 6.88-6.95 (m, 1H), 5.86-6.01 (m, 1H), 5.21-5.40 (m, 2H), 4.54-4.69 (m, 2H), 3.92 (s, 3H).

Step E: 2-Propen-1-yl {3-[(2-chloro-4-pyrimidinyl)acetyl]-2,4-difluorophenyl}carbamate

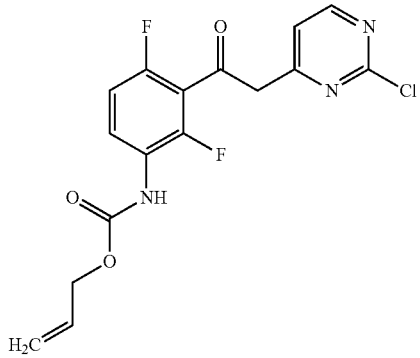 [SMILES: C=CCOC(=O)Nc1ccc(F)c(C(=O)Cc2ccnc(Cl)n2)c1F]

Following a procedure analogous to the procedure described in Intermediate 11 using methyl 2,6-difluoro-3-{[(2-propen-1-yloxy)carbonyl]amino}benzoate (80 g, 295 mmol) and 2-chloro-4-methylpyrimidine (41.6 g, 324 mmol) the title compound of Step E was obtained (65 g, 60.2% yield). ¹H NMR (400 MHz, DMSO-d6) δ ppm 9.49-9.60 (m, 1H), 8.72-8.77 (m, 0.3H), 8.58-8.64 (m, 0.6H), 7.57-7.83 (m, 2H), 7.15-7.25 (m, 1H), 5.89-6.01 (m, 1H), 5.75-5.82 (m, 0.6H), 5.20-5.40 (m, 2H), 4.55-4.62 (m, 2H), m/z (ES+): 368 [M+H]⁺.

Step F: 2-Propen-1-yl {3-[5-(2-chloro-4-pyrimidinyl)-2-(4-morpholinyl)-1,3-thiazol-4-yl]-2,4-difluorophenyl}carbamate

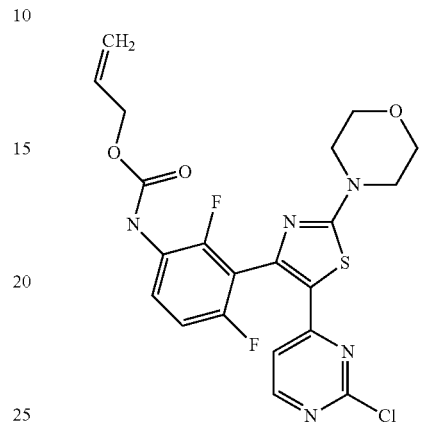

Following a procedure analogous to the procedure described in Intermediate 6 using 2-propen-1-yl {3-[(2-chloro-4-pyrimidinyl)acetyl]-2,4-difluorophenyl}carbamate (4.0 g, 10.88 mmol), NBS (2.033 g, 11.42 mmol) and 4-morpholinecarbothioamide (1.749 g, 11.97 mmol) the title compound of Step F was obtained as a yellow solid (5.11 g, 95% yield). ¹H NMR (400 MHz, DMSO-d6) δ ppm 9.56 (br. s., 1H), 8.41-8.51 (m, 1H), 7.83 (d, J=5.9 Hz, 1H), 7.27 (t, J=8.7 Hz, 1H), 6.76 (d, J=5.3 Hz, 1H), 5.88-6.03 (m, 1H), 5.34 (d, J=17.2 Hz, 1H), 5.22 (d, J=10.1 Hz, 1H), 4.61 (d, J=5.1 Hz, 2H), 3.70-3.76 (m, 4H), 3.57 (d, J=4.4 Hz, 4H). MS (ESI): 493 [M+H]⁺.

Step G: 3-[5-(2-Chloro-4-pyrimidinyl)-2-(4-morpholinyl)-1,3-thiazol-4-yl]-2,4-difluoroaniline

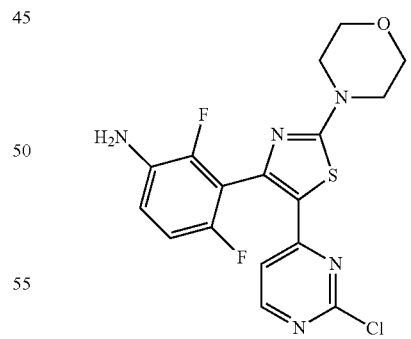

Following a procedure analogous to the procedure described in Intermediate 13 using 2-propen-1-yl {3-[5-(2-chloro-4-pyrimidinyl)-2-(4-morpholinyl)-1,3-thiazol-4-yl]-2,4-difluorophenyl}carbamate (5.11 g, 10.35 mmol) the title compound of Step G was obtained as a light yellow solid (2.71 g 64% yield). ¹H NMR (400 MHz, DMSO-d6) δ ppm 8.44 (d, J=5.5 Hz, 1H), 6.90-7.00 (m, 2H), 6.73 (d, J=5.5 Hz, 1H), 5.23 (s, 2H), 3.71-3.76 (m, 4H), 3.54-3.60 (m, 4H). MS (ESI): 409 [M+H]⁺.

Step H: N-{3-[5-(2-Chloro-4-pyrimidinyl)-2-(4-morpholinyl)-1,3-thiazol-4-yl]-2,4-difluorophenyl}-2,5-difluorobenzenesulfonamide

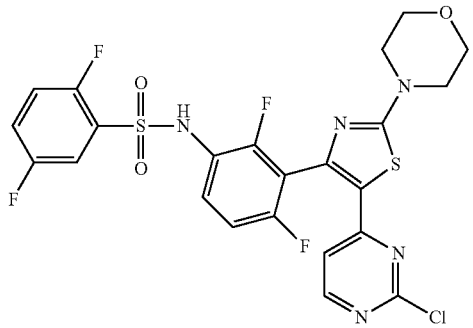 [SMILES: O=S(=O)(Nc1ccc(F)c(-c2nc(N3CCOCC3)sc2-c2ccnc(Cl)n2)c1F)c1cc(F)ccc1F]

Following a procedure analogous to the procedure described in Intermediate 14 using 3-[5-(2-chloro-4-pyrimidinyl)-2-(4-morpholinyl)-1,3-thiazol-4-yl]-2,4-difluoroaniline (900 mg, 2.196 mmol) and 2,5-difluorobenzenesulfonyl chloride (0.355 mL, 2.64 mmol) the title compound of Step H was obtained as a light yellow solid (774 mg, 60% yield). $^1$H NMR (400 MHz, DMSO-d6) δ ppm 8.41 (d, J=5.5 Hz, 1H), 7.48-7.57 (m, 4H), 7.29 (t, J=8.8 Hz, 1H), 6.57 (d, J=5.5 Hz, 1H), 3.70-3.74 (m, 4H), 3.52-3.55 (m, 4H). MS (ESI): 585 [M+H]$^+$.

Step I: N-{3-[5-(2-Amino-4-pyrimidinyl)-2-(4-morpholinyl)-1,3-thiazol-4-yl]-2,4-difluorophenyl}-2,5-difluorobenzenesulfonamide Following a procedure analogous to the procedure described in Example 21 using N-{3-[5-(2-chloro-4-pyrimidinyl)-2-(4-morpholinyl)-1,3-thiazol-4-yl]-2,4-difluorophenyl}-2,5-difluorobenzenesulfonamide (150 mg, 0.256 mmol) and NH$_4$OH (2.5 mL, 17.97 mmol) heated in a microwave reactor at 130° C. for 30 min the title compound was obtained as a light yellow solid (127 mg, 83% yield). $^1$H NMR (400 MHz, DMSO-d6) δ ppm 10.74 (br. s., 1H), 7.90 (d, J=5.3 Hz, 1H), 7.46-7.58 (m, 4H), 7.25 (t, J=8.8 Hz, 1H), 6.62 (br. s., 2H), 5.61 (d, J=5.1 Hz, 1H), 3.69-3.74 (m, 4H), 3.42-3.47 (m, 4H). MS (ESI): 566 [M+H]$^+$.

Example 106

N-{3-[5-(2-Amino-4-pyrimidinyl)-2-(4-morpholinyl)-1,3-thiazol-4-yl]-2,4-difluorophenyl}-2,6-difluorobenzenesulfonamide

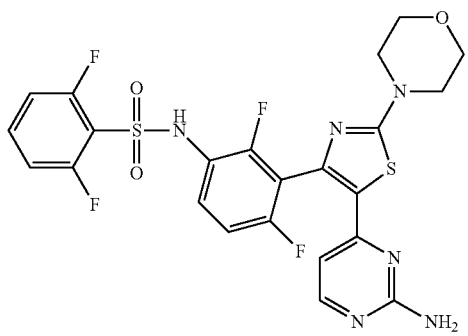 [SMILES: Nc1nccc(-c2sc(N3CCOCC3)nc2-c2c(F)ccc(NS(=O)(=O)c3c(F)cccc3F)c2F)n1]

Step A: N-{3-[5-(2-Chloro-4-pyrimidinyl)-2-(4-morpholinyl)-1,3-thiazol-4-yl]-2,4-difluorophenyl}-2,6-difluorobenzenesulfonamide

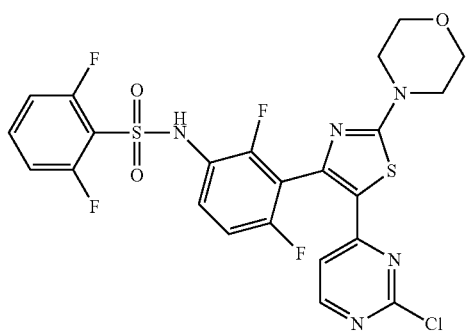 [SMILES: O=S(=O)(Nc1ccc(F)c(-c2nc(N3CCOCC3)sc2-c2ccnc(Cl)n2)c1F)c1c(F)cccc1F]

Following a procedure analogous to the procedure described in Intermediate 14 using 3-[5-(2-chloro-4-pyrimidinyl)-2-(4-morpholinyl)-1,3-thiazol-4-yl]-2,4-difluoroaniline (900 mg, 2.196 mmol) and 2,6-difluorobenzenesulfonyl chloride (0.357 mL, 2.64 mmol) the title compound of Step A was obtained as a light yellow solid (857 mg, 66% yield). $^1$H NMR (400 MHz, DMSO-d6) δ ppm 10.89 (s, 1H), 8.40 (d, J=5.5 Hz, 1H), 7.64-7.72 (m, 1H), 7.49-7.56 (m, 1H), 7.21-7.32 (m, 3H), 6.55 (d, J=5.3 Hz, 1H), 3.70-3.74 (m, 4H), 3.52-3.55 (m, 4H). MS (ESI): 585 [M+H]$^+$.

Step B: N-{3-[5-(2-Amino-4-pyrimidinyl)-2-(4-morpholinyl)-1,3-thiazol-4-yl]-2,4-difluorophenyl}-2,6-difluorobenzenesulfonamide Following a procedure analogous to the procedure described in Example 21 using N-{3-[5-(2-chloro-4-pyrimidinyl)-2-(4-morpholinyl)-1,3-thiazol-4-yl]-2,4-difluorophenyl}-2,6-difluorobenzenesulfonamide (150 mg, 0.256 mmol) and NH$_4$OH (2.5 mL, 17.97 mmol) heated in the microwave at 130° C. for 15 min the title compound was obtained as a light yellow solid (124 mg, 81%). $^1$H NMR (400 MHz, DMSO-d6) δ ppm 10.85 (br. s., 1H), 7.90 (d, J=5.3 Hz, 1H), 7.60-7.74 (m, 1H), 7.49 (td, J=8.7, 6.1 Hz, 1H), 7.16-7.34 (m, 3H), 6.62 (s, 2H), 5.63 (d, J=5.3 Hz, 1H), 3.67-3.74 (m, 4H), 3.40-3.48 (m, 4H). MS (ESI): 566 [M+H]$^+$.

Example 107

N-{3-[5-(2-amino-4-pyrimidinyl)-2-(1,1-dimethylethyl)-1,3-thiazol-4-yl]-2,4-difluorophenyl}-2,6-difluorobenzenesulfonamide

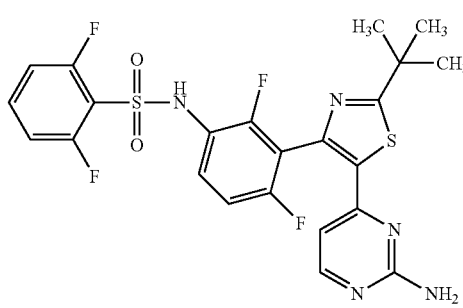

Step A: 2-Propen-1-yl {3-[5-(2-chloro-4-pyrimidinyl)-2-(1,1-dimethylethyl)-1,3-thiazol-4-yl]-2,4-difluorophenyl}carbamate

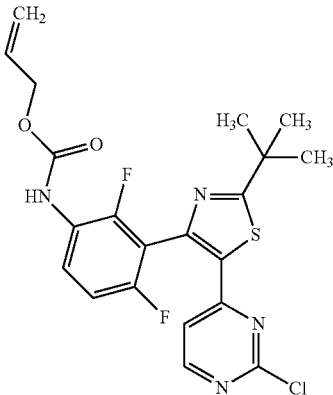 [SMILES: C=CCOC(=O)Nc1ccc(F)c(-c2nc(C(C)(C)C)sc2-c2ccnc(Cl)n2)c1F]

Following a procedure analogous to the procedure described in Intermediate 6 using 2-propen-1-yl {3-[(2-chloro-4-pyrimidinyl)acetyl]-2,4-difluorophenyl}carbamate (10 g, 27.2 mmol) NBS (5.08 g, 28.6 mmol) and 2,2-dimethylpropanethioamide (3.51 g, 29.9 mmol) the title compound of Step A was obtained (2.15 g, 17% yield). $^1$H NMR (400 MHz, DMSO-d6) δ ppm 9.55 (br. s., 1H), 8.67 (d, J=5.3 Hz, 1H), 7.83 (d, J=6.0 Hz, 1H), 7.27 (t, J=8.9 Hz, 1H), 7.16 (d, J=5.3 Hz, 1H), 5.89-6.01 (m, 1H), 5.34 (d, J=17.2 Hz, 1H), 5.22 (d, J=10.4 Hz, 1H), 4.60 (d, J=5.3 Hz, 2H), 1.45 (s, 9H); MS (ESI): 464 [M+H]$^+$.

Step B: {3-[5-(2-Chloro-4-pyrimidinyl)-2-(1,1-dimethylethyl)-1,3-thiazol-4-yl]-2,4-difluorophenyl}amine

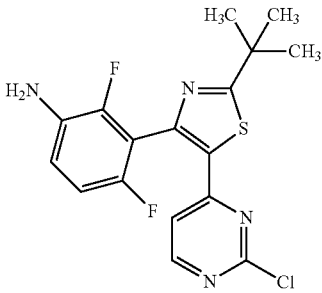 [SMILES: CC(C)(C)c1nc(-c2c(F)ccc(N)c2F)c(-c2ccnc(Cl)n2)s1]

Following a procedure analogous to the procedure described in Intermediate 13 using 2-propen-1-yl {3-[5-(2-chloro-4-pyrimidinyl)-2-(1,1-dimethylethyl)-1,3-thiazol-4-yl]-2,4-difluorophenyl}carbamate (2.962 g, 6.37 mmol) (from composite batches prepared as described above) the title compound of Step B was obtained (1.96 g, 81% yield). $^1$H NMR (400 MHz, DMSO-d6) δ ppm 8.67 (d, J=5.3 Hz, 1H), 7.09 (d, J=5.3 Hz, 1H), 6.88-7.02 (m, 2H), 5.23 (s, 2H), 1.45 (s, 9H); MS (ESI): 380 [M+H]$^+$.

Step C: N-{3-[5-(2-Chloro-4-pyrimidinyl)-2-(1,1-dimethylethyl)-1,3-thiazol-4-yl]-2,4-difluorophenyl}-2,6-difluorobenzenesulfonamide

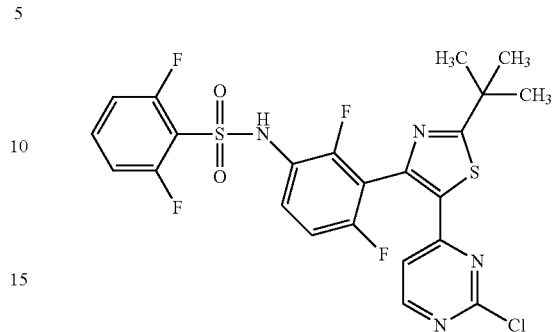

Following a procedure analogous to the procedure described in Intermediate 14 using {3-[5-(2-chloro-4-pyrimidinyl)-2-(1,1-dimethylethyl)-1,3-thiazol-4-yl]-2,4-difluorophenyl}amine (500 mg, 1.313 mmol) and 2,6-difluorobenzenesulfonyl chloride (0.214 mL, 1.575 mmol) the title compound of Step C was obtained as a light yellow solid (653 mg, 89% yield). $^1$H NMR (400 MHz, DMSO-d6) δ ppm 10.88 (s, 1H), 8.63 (d, J=5.3 Hz, 1H), 7.63-7.74 (m, 1H), 7.52 (td, J=8.7, 6.0 Hz, 1H), 7.17-7.35 (m, 3H), 6.99 (d, J=5.3 Hz, 1H), 1.42 (s, 9H). MS (ESI): 556 [M+H]$^+$.

Step D: N-{3-[5-(2-Amino-4-pyrimidinyl)-2-(1,1-dimethylethyl)-1,3-thiazol-4-yl]-2,4-difluorophenyl}-2,6-difluorobenzenesulfonamide Following a procedure analogous to the procedure described in Example 21 using N-{3-[5-(2-chloro-4-pyrimidinyl)-2-(1,1-dimethylethyl)-1,3-thiazol-4-yl]-2,4-difluorophenyl}-2,6-difluorobenzenesulfonamide (150 mg, 0.269 mmol) and NH$_4$OH (2.5 mL, 17.97 mmol) heated in the microwave at 130° C. for 15 min the title compound was obtained as a light yellow solid (135 mg, 89% yield). $^1$H NMR (400 MHz, DMSO-d6) δ ppm 10.86 (s, 1H), 8.05 (d, J=5.1 Hz, 1H), 7.62-7.73 (m, 1H), 7.44-7.59 (m, 1H), 7.17-7.34 (m, 3H), 6.79 (br. s., 2H), 5.83 (d, J=5.1 Hz, 1H), 1.39 (s, 9H). MS (ESI): 537 [M+H]$^+$.

Example 108

N-{3-[5-(2-Amino-4-pyrimidinyl)-2-(4-morpholinyl)-1,3-thiazol-4-yl]-4-fluorophenyl}-2,6-difluorobenzenesulfonamide

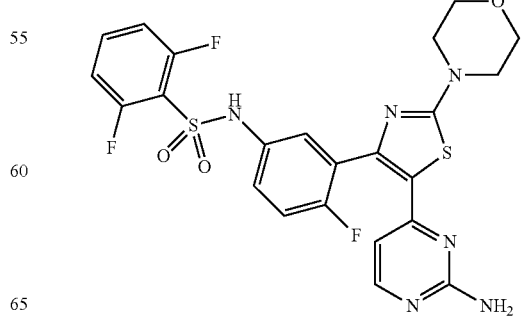

Step A: Methyl 5-amino-2-fluorobenzoate

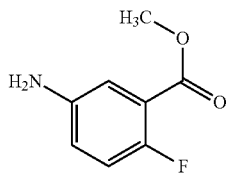

To a solution of 5-amino-2-fluorobenzoic acid (89.6 g, 577 mmol) in MeOH (1000 mL) was added sulfurous dichloride (82.4 g, 692 mmol) dropwise at 0° C. Then the mixture was heated to reflux for overnight. The solvent was removed. The residue was diluted with EtOAc (1 L). Then the pH was adjusted to around 9 by progressively adding saturated NaHCO₃. The organic layer was separated. The aqueous layer was extracted with EtOAc (500 L×3). The combined organic layers were washed with water and brine successively, dried over Na₂SO₄, filtered and concentrated under reduced pressure to give the title compound of step A (79.8 g, 81.8% yield). ¹H NMR (400 MHz, CDCl₃) δ ppm 7.16-7.20 (m, 1H), 6.90-6.98 (m, 1H), 6.75-6.82 (m, 1H), 3.89 (s, 3H), 3.51-3.70 (br, 2H).

Step B: Methyl 5-{[(2,6-difluorophenyl)sulfonyl]amino}-2-fluorobenzoate

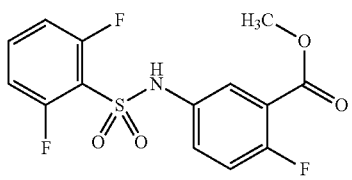 [SMILES: COC(=O)c1cc(NS(=O)(=O)c2c(F)cccc2F)ccc1F]

Following a procedure analogous to the procedure described in Example 5, Step A using methyl 5-amino-2-fluorobenzoate (10 g, 59.2 mmol) and 2,6-difluorobenzene-1-sulfonyl chloride (13.2 g, 62.2 mmol) the title compound of Step B was obtained (21 g, 100% yield). ¹H NMR (400 MHz, CDCl₃) δ ppm 7.58-7.60 (m, 1H), 7.38-7.48 (m, 2H), 7.10-7.15 (br, 1H), 6.89-6.97 (m, 2H), 6.97-7.06 (m, 1H), 3.85 (s, 3H).

Step C: N-{3-[5-(2-Chloro-4-pyrimidinyl)-2-(4-morpholinyl)-1,3-thiazol-4-yl]-4-fluorophenyl}-2,6-difluorobenzenesulfonamide

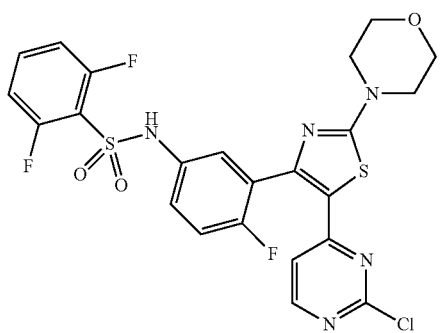 [SMILES: O=S(=O)(Nc1ccc(F)c(-c2nc(N3CCOCC3)sc2-c2ccnc(Cl)n2)c1)c1c(F)cccc1F]

To a solution of methyl 5-{[(2,6-difluorophenyl)sulfonyl]amino}-2-fluorobenzoate (21 g, 60.8 mmol) in dry THF (250 mL) at –10° C., LIHMDS (1M in THF, 213 mmol, 213 mL) was added dropwise and the solution was allowed to stir for 1 h at 0° C. A solution of pyrimidine chloride (9.3 g, 73 mmol) in THF (50 mL) was then added dropwise to the solution of ester and base at 0° C. over 20 min. The solution was allowed to stir 1 h at rt. TLC showed the reaction was complete. The reaction was quenched by addition of the saturated aqueous NH₄Cl (200 mL) at 0° C. The reaction mixture was extracted with EtOAc (100 mL×3). The combined organic layers were washed with water and brine successively, dried over Na₂SO₄, filtered and concentrated under reduced pressure to give the crude product, which was purified by flush column on silica gel, rinsing with DCM. This solution was concentrated to obtain a solid. The orange solid was triturated with a small amount of EtOAc and filtered, rinsing with diethyl ether to give N-(3-(2-(2-chloropyrimidin-4-yl)acetyl)-4-fluorophenyl)-2,6-difluorobenzenesulfonamide (13 g, 50.5%). N-(3-(2-(2-chloropyrimidin-4-yl)acetyl)-4-fluorophenyl)-2,6-difluorobenzenesulfonamide (13 g) was diluted in DMA (150 mL). NBS (5.5 g, 30.7 mmol) was added and the reaction mixture was stirred at rt for 1 h. Then 2-methylpropanethioamide (4.8 g, 33.8 mmol) was added at 0° C. The mixture was stirred at rt for 2 h. The mixture was poured into water and extracted with EtOAc (500 mL×3). The combined organic layers were washed with water and brine successively, dried over Na₂SO₄, filtered and concentrated under reduced pressure to give the crude product, which was purified by column chromatography on silica gel (DCM:petroleum ether 2:1) to afford the title compound of Step C (7.5 g, 22% yield over 2 steps). ¹H NMR (400 MHz, CDCl₃) δ ppm 8.11 (d, J=5.5 Hz, 1H), 7.48-7.56 (m, 1H), 7.40-7.48 (br, 1H), 7.26-7.38 (m, 2H), 7.07-7.14 (m, 1H), 6.92-7.04 (m, 2H), 6.51 (d, J=5.5 Hz, 1H), 3.80-3.88 (m, 4H), 3.58-3.65 (m, 4H). m/z (ES+): 468 [M+H]⁺.

Step D: N-{3-[5-(2-Amino-4-pyrimidinyl)-2-(4-morpholinyl)-1,3-thiazol-4-yl]-4-fluorophenyl}-2,6-difluorobenzenesulfonamide Following a procedure analogous to the procedure described in Example 21 using N-{3-[5-(2-chloro-4-pyrimidinyl)-2-(4-morpholinyl)-1,3-thiazol-4-yl]-4-fluorophenyl}-2,6-difluorobenzenesulfonamide (150 mg, 0.264 mmol) and NH₄OH (3 mL) heated at 120° C. in a microwave reactor for 15 min, the title compound was obtained as a yellow solid (67 mg, 0.122 mmol, 46.2% yield). ¹H NMR (400 MHz, DMSO-d6) δ ppm 10.99 (s, 1H), 7.78 (d, J=5.3 Hz, 1H), 7.59-7.75 (m, 1H), 7.18-7.30 (m, 4H), 7.15 (d, J=5.8 Hz, 1H), 6.57 (s, 2H), 5.59 (d, J=5.2 Hz, 1H), 3.64-3.77 (m, 4H), 3.40-3.47 (m, 4H). m/z (ES+): 549 [M+H]+.

Example 109

N-{3-[5-(2-Chloro-4-pyrimidinyl)-2-(1,1-dimethylethyl)-1,3-thiazol-4-yl]-4-fluorophenyl}-2,6-difluorobenzenesulfonamide

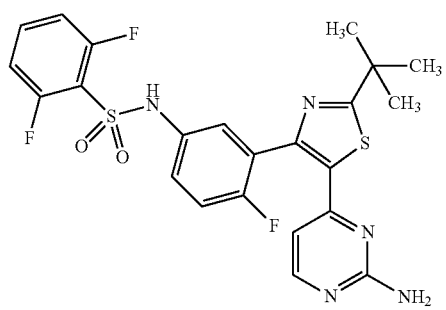 [SMILES: CC(C)(C)c1nc(-c2cc(NS(=O)(=O)c3c(F)cccc3F)ccc2F)c(-c2ccnc(N)n2)s1]

Step A: Methyl 2-fluoro-5-{[(2-propen-1-yloxy)carbonyl]amino}benzoate

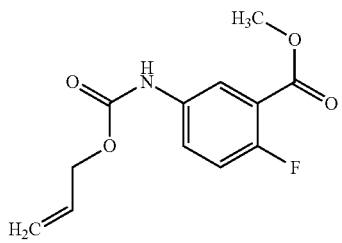 [SMILES: C=CCOC(=O)Nc1ccc(F)c(C(=O)OC)c1]

To a solution of methyl 5-amino-2-fluorobenzoate (67 g, 396 mmol) in THF (400 mL), saturated NaHCO₃ (1200 mL) was added. Then 2-propen-1-yl chloridocarbonate (57 g, 476 mmol), was added dropwise at 0° C. The mixture was stirred at rt for 2 h. The solution was extracted with EtOAc (500 mL×3). The combined organic layers were washed with water and brine successively, dried over Na₂SO₄, filtered and concentrated under reduced pressure to give the title compound of Step A (102 g, 100% yield), which was used to the next step directly. ¹H NMR (400 MHz, CD₃Cl) δ ppm 7.75-7.78 (m, 1H), 7.57-7.67 (m, 1H), 6.98-7.07 (m, 1H), 6.67-6.70 (m, 5.83-5.97), 5.83-5.97 (m, 1H), 5.17-7.35 (m, 2H), 4.60-4.65 (m, 2H), 3.85 (s, 1H).

Step B: 2-Propen-1-yl {3-[(2-chloro-4-pyrimidinyl)acetyl]-4-fluorophenyl}carbamate

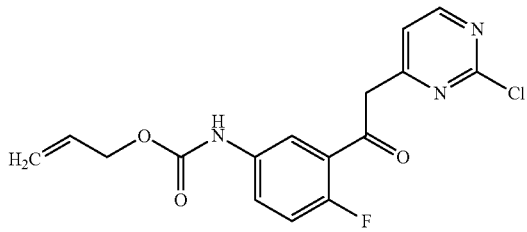 [SMILES: C=CCOC(=O)Nc1ccc(F)c(C(=O)Cc2ccnc(Cl)n2)c1]

Using multiple interations of a procedure analogous to the procedure described in Intermediate 11 using methyl 2-fluoro-5-{[(2-propen-1-yloxy)carbonyl]amino}benzoate (104 g, 411 mmol) and 2-chloro-4-methylpyrimidine (59 g, 493 mmol), the title compound of Step B was obtained (100 g, 69.9% yield). ¹H NMR (400 MHz, CDCl₃) δ ppm 13.67-13.75 (br, 1H), 8.50-8.53 (m, 0.3H), 8.31-8.38 (m, 1H), 7.50-7.82 (m, 2.6H), 6.56-7.20 (m, 3.5H), 6.20-6.25 (m, 1H), 5.82-6.01 (1.3H), 5.20-5.40 (m, 2.6H), 4.50-4.61 (m, 2.6H), 4.31-4.41 (m, 0.9H).

Step C: 2-Propen-1-yl {3-[5-(2-chloro-4-pyrimidinyl)-2-(1,1-dimethylethyl)-1,3-thiazol-4-yl]-4-fluorophenyl}carbamate

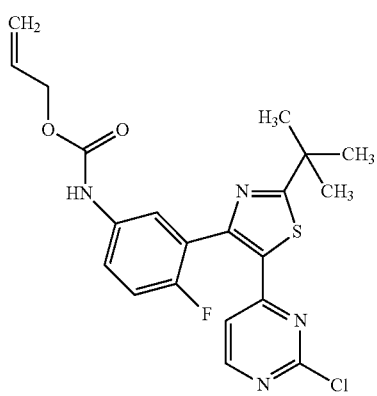 [SMILES: C=CCOC(=O)Nc1ccc(F)c(-c2nc(C(C)(C)C)sc2-c2ccnc(Cl)n2)c1]

Following a procedure analogous to the procedure described in Intermediate 6 using 2-propen-1-yl {3-[(2-chloro-4-pyrimidinyl)acetyl]-4-fluorophenyl}carbamate (20 g, 57.3 mmol), NBS (10.2 g, 57.3 mmol) and 2-methylpropanethioamide (7.4 g, 63 mmol) the title compound of Step C was obtained (11 g, 44.9% yield). ¹H NMR (400 MHz, DMSO-d6) δ ppm 9.90-9.98 (br, 1H), 8.61 (d, J=5.3 Hz, 1H), 7.65-7.72 (m, 1H), 7.49-7.54 (m, 1H), 7.21-7.30 (m, 1H), 7.10 (d, J=5.3 Hz, 1H), 5.90-6.05 (m, 1H), 5.20-5.40 (m, 2H), 4.58-4.63 (m, 2H), 1.47 (s, 9H).

Step D: 3-[5-(2-Chloro-4-pyrimidinyl)-2-(1,1-dimethylethyl)-1,3-thiazol-4-yl]-4-fluoroaniline

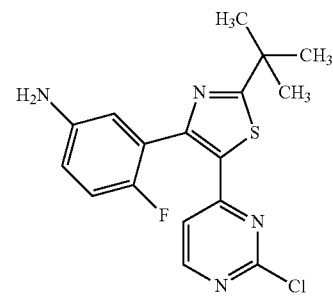 [SMILES: CC(C)(C)c1nc(-c2cc(N)ccc2F)c(-c2ccnc(Cl)n2)s1]

To a solution of 2-propen-1-yl {3-[5-(2-chloro-4-pyrimidinyl)-2-(1,1-dimethylethyl)-1,3-thiazol-4-yl]-4-fluorophenyl}carbamate (11 g, 24.6 mmol) in DCM (200 mL), HOAc (3.6 g, 59.2 mmol), Pd(PPh₃)₂Cl₂ (345 mg, 0.5 mmol) were added. Then tri-n-butyl tin hydride (8.6 g, 29.6 mmol) was added dropwise to the mixture at 0° C. The mixture was stirred at rt for 30 min. The reaction was quenched by adding saturated NaHCO₃ (100 mL) slowly. The two layers were separated. The aqueous layer was extracted with DCM (100 mL×2). The combined organic layers were washed with water and brine successively, dried over Na₂SO₄, filtered and concentrated under reduced pressure and washed with petroleum ether (200 mL) to afford the crude product, 3-[5-(2-chloro-4-pyrimidinyl)-2-(1,1-dimethylethyl)-1,3-thiazol-4-yl]-4-fluoroaniline (7.62 g, 85.3% yield), 7.4 g of which was used directly in the next step.

Step E: N-{3-[5-(2-Chloro-4-pyrimidinyl)-2-(1,1-dimethylethyl)-1,3-thiazol-4-yl]-4-fluorophenyl}-2,6-difluorobenzenesulfonamide

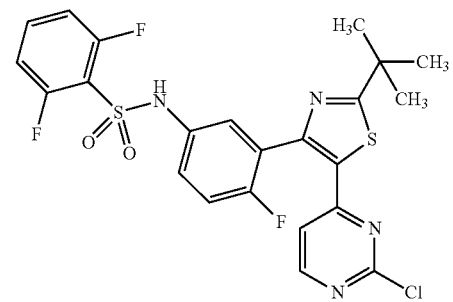 [SMILES: CC(C)(C)c1nc(-c2cc(NS(=O)(=O)c3c(F)cccc3F)ccc2F)c(-c2ccnc(Cl)n2)s1]

To a solution of 3-[5-(2-chloro-4-pyrimidinyl)-2-(1,1-dimethylethyl)-1,3-thiazol-4-yl]-4-fluoroaniline (7.4 g, 20.4 mmol) in DCM (200 mL) was added pyridine (4.85 g, 61.3 mmol) and cooled to 0° C. 2,6-Difluorobenzene-1-sulfonyl chloride (4.76 g, 22.5 mmol) in DCM (10 mL) was added dropwise to the mixture. The reaction was stirred at rt overnight. Then the reaction was washed with water (200 mL), and extracted with DCM (2×100 mL). The organic layer was washed with brine, dried over anhydrous $Na_2SO_4$, filtrated and concentrated under reduced pressure to give the crude product, which was purified by column chromatography on silica gel (petroleum ether:EtOAc 5:1) to afford the title compound of Step E (2.3 g, 7.2% yield). $^1$H NMR (400 MHz, DMSO-d6) δ ppm 8.56 (d, J=5.3 Hz, 1H), 7.62-7.75 (m, 1H), 7.20-7.32 (m, 5H), 6.92 (d, J=5.3 Hz, 1H), 1.40 (s, 9H). m/z (ES+): 539 [M+H]$^+$.

Step F: N-{3-[5-(2-Chloro-4-pyrimidinyl)-2-(1,1-dimethylethyl)-1,3-thiazol-4-yl]-4-fluorophenyl}-2,6-difluorobenzenesulfonamide Following a procedure analogous to the procedure described in Example 21 using N-{3-[5-(2-chloro-4-pyrimidinyl)-2-(1,1-dimethylethyl)-1,3-thiazol-4-yl]-4-fluorophenyl}-2,6-difluorobenzenesulfonamide (150 mg, 0.278 mmol) and NH$_4$OH (3 mL) heated in a microwave reactor at 120° C. for 20 min the title compound was obtained as an off-white solid (135 mg, 0.260 mmol, 93% yield). $^1$H NMR (400 MHz, DMSO-d6) δ ppm 11.01 (br. s., 1H), 7.93 (d, J=5.1 Hz, 1H), 7.54-7.76 (m, 1H), 7.10-7.30 (m, 5H), 6.71 (s, 2H), 5.81 (d, J=5.0 Hz, 1H), 1.36 (s, 9H). m/z (ES+): 520 [M+H]+.

Example 110

N-{3-[5-(2-Amino-4-pyrimidinyl)-2-(1-pyrrolidinyl)-1,3-oxazol-4-yl]phenyl}-2,6-difluorobenzenesulfonamide

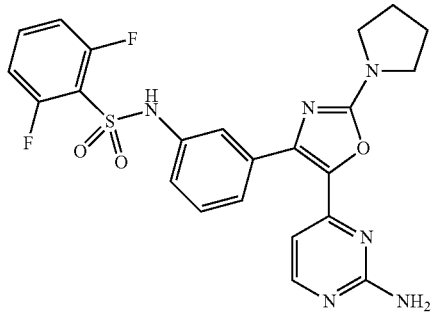 [SMILES: Nc1nccc(-c2oc(N3CCCC3)nc2-c2cccc(NS(=O)(=O)c3c(F)cccc3F)c2)n1]

Step A: N-{3-[5-(2-Chloro-4-pyrimidinyl)-2-(1-pyrrolidinyl)-1,3-oxazol-4-yl]phenyl}-2,6-difluorobenzenesulfonamide

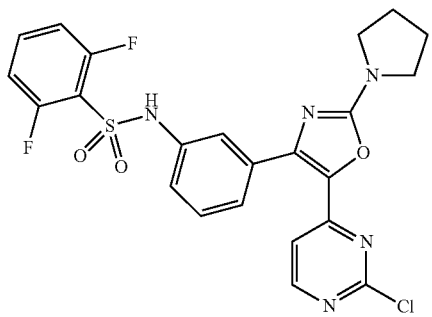 [SMILES: O=S(=O)(Nc1cccc(-c2nc(N3CCCC3)oc2-c2ccnc(Cl)n2)c1)c1c(F)cccc1F]

Following a procedure analogous to the procedure described in Intermediate 6 using N-{3-[(Z)-2-(2-chloro-4-pyrimidinyl)-1-hydroxyethenyl]phenyl}-2,6-difluorobenzenesulfonamide (2.0 g, 4.72 mmol, NBS (0.924 g, 5.19 mmol) and 1-pyrrolidinecarboxamide (1.077 g, 9.44 mmol) heated to 90° C. for 24 h the title compound of Step A was obtained as an orange solid (0.980 g). MS-ESI m/z 518 (M+H).

Step B: N-{3-[5-(2-amino-4-pyrimidinyl)-2-(1-pyrrolidinyl)-1,3-oxazol-4-yl]phenyl}-2,6-difluorobenzenesulfonamide Following a procedure analogous to the procedure described in Example 21 using -{3-[5-(2-chloro-4-pyrimidinyl)-2-(1-pyrrolidinyl)-1,3-oxazol-4-yl]phenyl}-2,6-difluorobenzenesulfonamide (0.100 g, 0.193 mmol) and NH$_4$OH (2 mL) heated in a microwave reactor at 120° C. for 10 min the title compound was obtained as a yellow solid (0.010 g). $^1$H NMR (400 MHz, DMSO-d$_6$) δ ppm 10.92 (s, 1H), 8.14 (d, J=5.2 Hz, 1H), 7.86-8.02 (m, 2H), 7.59-7.70 (m, 1H), 7.31 (t, J=7.6 Hz, 1H), 7.10-7.26 (m, 3H), 6.50-6.60 (m, 3H), 3.50 (t, J=6.4 Hz, 4H), 1.88-1.99 (m, 4H). MS-ESI m/z 499 (M+H)

Example 111

2,6-Difluoro-N-{3-[5-{2-[(2-methylpropyl)amino]-4-pyrimidinyl}-2-(1-pyrrolidinyl)-1,3-oxazol-4-yl]phenyl}benzenesulfonamide

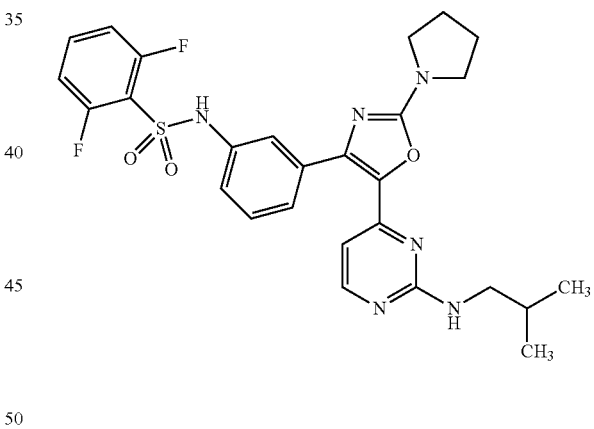

To a 8 mL vial N-{3-[5-(2-chloro-4-pyrimidinyl)-2-(1-pyrrolidinyl)-1,3-oxazol-4-yl]phenyl}-2,6-difluorobenzenesulfonamide (0.100 g, 0.193 mmol) was taken up in isobutylamine (2 mL) to give a yellow solution. Vial was capped and heated to 45° C. for 2 h. The solvent was removed and residue was purified via Gilson Acidic HPLC (10 to 90% gradient, Acetonitrile/H$_2$O+TFA; C18 column). Desired fractions were diluted with EtOAc and washed with saturated aq. NaHCO$_3$, dried over Na$_2$SO$_4$ and solvent removed to give title compound as a yellow solid (0.074 g). $^1$H NMR (400 MHz, DMSO-d$_6$) δ ppm 10.93 (s, 1H), 8.18 (d, J=5.1 Hz, 1H), 7.81 (br. s., 1H), 7.59-7.73 (m, 2H), 7.24 (t, J=9.1 Hz, 3H), 7.14 (d, J=7.9 Hz, 1H), 6.97 (t, J=5.7 Hz, 1H), 6.57 (d, J=1.6

Hz, 1H), 3.52 (t, J=6.3 Hz, 4H), 2.76-2.90 (m, 1H), 1.92-2.01 (m, 4H), 0.55-0.94 (m, 6H). MS-ESI m/z 555 (M+H).

Example 112

N-{3-[5-(2-Amino-4-pyrimidinyl)-2-(dimethylamino)-1,3-thiazol-4-yl]phenyl}-2,6-difluorobenzenesulfonamide

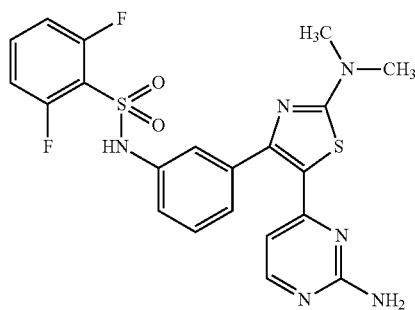 [SMILES: CN(C)c1nc(-c2cccc(NS(=O)(=O)c3c(F)cccc3F)c2)c(-c2ccnc(N)n2)s1]

Step A: N-{3-[5-(2-Chloro-4-pyrimidinyl)-2-(dimethylamino)-1,3-thiazol-4-yl]phenyl}-2,6-difluorobenzenesulfonamide

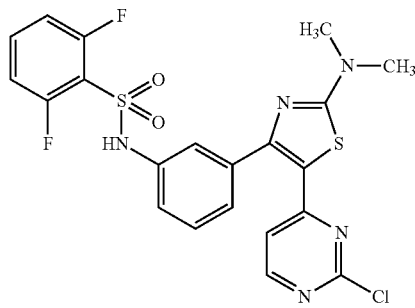 [SMILES: CN(C)c1nc(-c2cccc(NS(=O)(=O)c3c(F)cccc3F)c2)c(-c2ccnc(Cl)n2)s1]

To N-{3-[(Z)-2-(2-chloro-4-pyrimidinyl)-1-hydroxyethenyl]phenyl}-2,6-difluorobenzenesulfonamide (2.0 g, 4.72 mmol) in 25 mL DMA was added NBS (0.88 g, 4.95 mmol). The mixture stirred at rt for 30 min. N,N-Dimethylthiourea (0.6 g, 5.66 mmol) was added and the mixture heated to 40° C. overnight. The mixture was poured into 300 mL ice water and the crude product was collected by filtration. The crude product was then purified by flash chromatography to give the title compound of Step A (0.6 g, 1.18 mmol, 25% yield). $^1$H NMR (400 MHz, DMSO-d6) δ ppm 11.09 (s, 1H), 8.14 (d, J=5.5 Hz, 1H), 7.68 (s, 2H), 7.37 (d, J=7.9 Hz, 1H), 7.22 (ddd, J=17.3, 8.5, 8.2 Hz, 5H), 6.47 (d, J=5.5 Hz, 1H), 3.12 (s, 6H).

Step B: N-{3-[5-(2-Amino-4-pyrimidinyl)-2-(dimethylamino)-1,3-thiazol-4-yl]phenyl}-2,6-difluorobenzenesulfonamide N-{3-[5-(2-Chloro-4-pyrimidinyl)-2-(dimethylamino)-1,3-thiazol-4-yl]phenyl}-2,6-difluorobenzenesulfonamide (0.1 g, 0.2 mmol) was taken up in 2 mL 30% NH$_4$OH (aq) and heated to 140° C. for 20 min in a microwave reactor. The solvent was removed under reduced pressure and the residue taken up in EtOAc and washed with 2 mL of 0.1 N HCl (aq). The organic layer was dried over Na$_2$SO$_4$ and evaporated onto silica gel. Purification by flash chromatography (0 to 40% EtOAC/DCM) afforded the title compound (30 mg, 0.061 mmol, 31% yield) as a yellow solid. $^1$H NMR (400 MHz, DMSO-d6) δ ppm 10.98 (s, 1H), 7.59-7.70 (m, 2H), 7.26-7.35 (m, 1H), 7.15-7.25 (m, 4H), 7.09 (d, J=7.5 Hz, 1H), 6.48 (s, 2H), 5.68 (d, J=5.3 Hz, 1H), 3.03 (s, 6H)). MS (ESI): 489 [M+H]$^+$.

Example 113

N-[3-(2-(Dimethylamino)-5-{2-[(2-methylpropyl)amino]-4-pyrimidinyl}-1,3-thiazol-4-yl)phenyl]-2,6-difluorobenzenesulfonamide

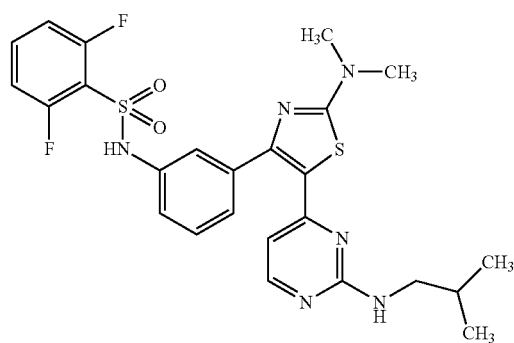 [SMILES: CC(C)CNc1nccc(-c2sc(N(C)C)nc2-c2cccc(NS(=O)(=O)c3c(F)cccc3F)c2)n1]

N-{3-[5-(2-Chloro-4-pyrimidinyl)-2-(dimethylamino)-1,3-thiazol-4-yl]phenyl}-2,6-difluorobenzenesulfonamide (0.1 g, 0.2 mmol) was taken up in 2 mL isobutylamine and heated to 35° C. overnight. The solvent was removed under reduce pressure and the residue taken up in EtOAc and washed with 2 mL of 0.1 N HCl (aq). The organic layer was dried over Na$_2$SO$_4$ and evaporated to afforded the title compound (36 mg, 0.066 mmol, 33.6% yield) as a yellow solid. $^1$H NMR (400 MHz, DMSO-d6) δ ppm 11.01 (s, 1H), 7.74 (d, J=5.3 Hz, 1H), 7.67 (ddd, J=14.6, 8.4, 6.1 Hz, 1H), 7.28-7.35 (m, 1H), 7.18-7.28 (m, 4H), 7.12 (d, J=7.7 Hz, 1H), 7.07 (t, J=5.5 Hz, 1H), 5.68 (s, 1H), 3.06 (s, 6H), 3.02 (t, J=6.3 Hz, 2H), 1.82 (dt, J=13.4, 6.7 Hz, 1H), 0.86 (d, J=6.8 Hz, 6H). MS (ESI): 545 [M+H]$^+$.

Example 114

N-{3-[5-(2-Amino-4-pyrimidinyl)-1,3-thiazol-4-yl]phenyl}-2,6-difluorobenzenesulfonamide

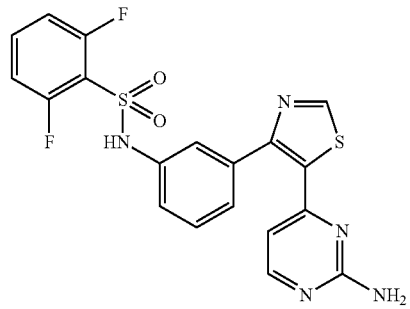 [SMILES: Nc1nccc(-c2scnc2-c2cccc(NS(=O)(=O)c3c(F)cccc3F)c2)n1]

Step A: N-{3-[2-Amino-5-(2-chloro-4-pyrimidinyl)-1,3-thiazol-4-yl]phenyl}-2,6-difluorobenzenesulfonamide

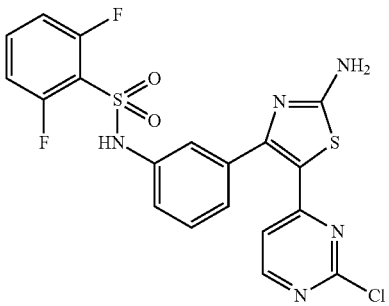 [SMILES: Nc1nc(-c2cccc(NS(=O)(=O)c3c(F)cccc3F)c2)c(-c2ccnc(Cl)n2)s1]

To N-{3-[(Z)-2-(2-chloro-4-pyrimidinyl)-1-hydroxyethenyl]phenyl}-2,6-difluorobenzenesulfonamide (2.0 g, 4.72 mmol) in 40 mL of DMA was added NBS (0.88 g, 4.95 mmol). The mixture stirred at room temperature for 30 min. Thiourea (0.36 g, 4.72 mmol) as added and the mixture heated to 80° C. for 1 h. The mixture was poured into 300 mL of ice water and the product was collected by filtration. The crude product was then purified by flash chromatography to give the title compound of Step A (1.61 g, 3.35 mmol, 67.5% yield). $^1$H NMR (400 MHz, DMSO-d6) δ ppm 11.05 (s, 1H), 8.16 (d, J=5.5 Hz, 1H), 7.94 (s, 2H), 7.64-7.75 (m, 1H), 7.37 (d, J=7.8 Hz, 1H), 7.16-7.29 (m, 5H), 6.52 (d, J=5.6 Hz, 1H).

Step B: N-{3-[5-(2-Chloro-4-pyrimidinyl)-1,3-thiazol-4-yl]phenyl}-2,6-difluorobenzenesulfonamide

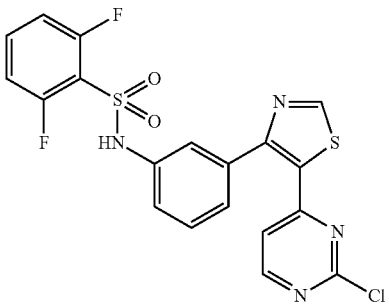 [SMILES: O=S(=O)(Nc1cccc(-c2ncsc2-c2ccnc(Cl)n2)c1)c1c(F)cccc1F]

To N-{3-[2-amino-5-(2-chloro-4-pyrimidinyl)-1,3-thiazol-4-yl]phenyl}-2,6-difluorobenzene sulfonamide (0.8 g, 1.67 mmol) in 10 mL THF was added t-butylnitrite (0.4 mL, 4 mmol) by syringe. The mixture stirred at rt for 1 h. More t-butylnitrite (0.2 mL, 2 mmol) was added and the mixture heated to 80° C. for 1 h. The mixture was cooled, diluted with 100 mL EtOAc, washed with 20 mL water, filtered through Whatman 1 PS (phase separating) paper and concentrated under vacuum. The crude product was then purified by flash chromatography to give the title compound of Step B (0.53 g, 1.14 mmol, 65% yield). $^1$H NMR (400 MHz, DMSO-d6) δ ppm 11.07 (s, 1H), 9.37 (s, 1H), 8.55 (d, J=5.3 Hz, 1H), 7.65-7.75 (m, 1H), 7.40 (t, J=8.0 Hz, 1H), 7.23-7.32 (m, 5H), 7.03 (d, J=5.3 Hz, 1H).

Step C: N-{3-[5-(2-Amino-4-pyrimidinyl)-1,3-thiazol-4-yl]phenyl}-2,6-difluorobenzenesulfonamide N-{3-[5-(2-Chloro-4-pyrimidinyl)-1,3-thiazol-4-yl]phenyl}-2,6-difluorobenzenesulfonamide (0.1 g, 0.2 mmol) was taken up in 2 mL NH$_4$OH and heated to 140° C. for 20 min in a microwave reactor. The solvent was removed under reduced pressure and the residue was taken up in EtOAc and washed with 2 mL of 0.1 N HCl (aq). The organic layer was dried over Na$_2$SO$_4$ and evaporated onto silica gel. Purification by ISCO chromatography (0 to 50% EtOAC in DCM) afforded the title compound (62 mg, 0.139 mmol, 64.7% yield) as a yellow solid. $^1$H NMR (400 MHz, DMSO-d6) δ ppm 11.00 (s, 1H), 9.16 (s, 1H), 7.94 (d, J=5.1 Hz, 1H), 7.59-7.69 (m, 1H), 7.32 (t, J=7.9 Hz, 1H), 7.16-7.27 (m, 5H), 6.78 (s, 2H), 5.99 (d, J=5.3 Hz, 1H). MS (ESI): 446 [M+H]$^+$.

Example 115

2,6-Difluoro-N-[3-(5-{2-[(2-methylpropyl)amino]-4-pyrimidinyl}-1,3-thiazol-4-yl)phenyl]benzenesulfonamide

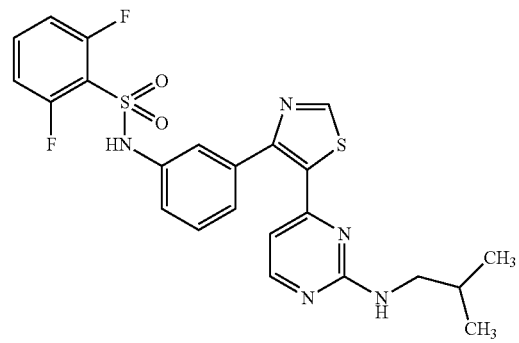 [SMILES: CC(C)CNc1nccc(-c2scnc2-c2cccc(NS(=O)(=O)c3c(F)cccc3F)c2)n1]

N-{3-[5-(2-Chloro-4-pyrimidinyl)-1,3-thiazol-4-yl]phenyl}-2,6-difluorobenzenesulfonamide (0.1 g, 0.2 mmol) was taken up in 2 mL isobutylamine and heated to 35° C. overnight. The solvent was removed in vacuo and the residue taken up in EtOAc and washed with 2 mL of 0.1 N HCl (aq). The organic layer was dried over Na$_2$SO$_4$ and evaporated to afford the title compound (65 mg, 0.130 mmol), 60.2% yield) as a yellow solid. $^1$H NMR (400 MHz, DMSO-d6) δ ppm 11.00 (s, 1H), 9.15 (s, 1H), 7.98 (d, J=5.1 Hz, 1H), 7.60-7.69 (m, 1H), 7.37 (t, J=5.9 Hz, 1H), 7.31 (t, J=7.9 Hz, 1H), 7.26 (s, 1H), 7.15-7.24 (m, 4H), 5.93-6.05 (m, 1H), 2.95-3.06 (m, 2H), 0.82 (d, J=6.6 Hz, 6H). MS (ESI): 501 [M+H]$^+$.

Example 116

N-{3-[5-(2-Amino-4-pyrimidinyl)-2-(1,1-dimethylethyl)-1,3-thiazol-4-yl]phenyl}-2,5-difluorobenzenesulfonamide

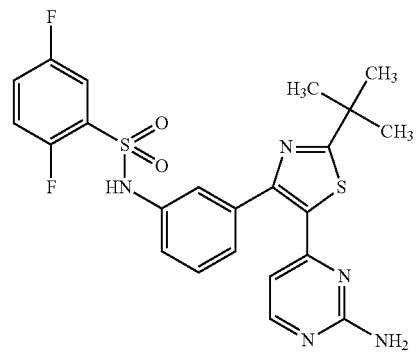 [SMILES: CC(C)(C)c1nc(-c2cccc(NS(=O)(=O)c3cc(F)ccc3F)c2)c(-c2ccnc(N)n2)s1]

A suspension of N-{3-[5-(2-chloro-4-pyrimidinyl)-2-(1,1-dimethylethyl)-1,3-thiazol-4-yl]phenyl}-2,5-difluorobenzenesulfonamide (150 mg, 0.288 mmol) and 2M ammonia in isopropanol (8.0 mL, 16.0 mmol) was heated in a sealed tube at 100° C. overnight. The reaction mixture was evaporated onto silica gel and chromatographed (10-100% 1:9 MeOH: EtOAc in DCM). The title compound was recovered as a beige solid (38 mg, 25% yield). $^1$H NMR (400 MHz, DMSO-d6) δ ppm 10.89 (s, 1H), 7.95 (d, J=5.1 Hz, 1H), 7.41-7.68 (m, 3H), 7.31 (t, J=7.9 Hz, 1H), 7.23 (s, 1H), 7.17 (d, J=7.9 Hz, 2H), 6.74 (s, 2H), 6.01 (d, J=5.1 Hz, 1H), 1.38 (s, 9H). MS (ESI): 502.1 [M+H]$^+$.

Examples 117-217

The following compounds were prepared using method analogous to those described above.

| Ex | Structure | m/z [M + H]$^+$ | $^1$H NMR |
|---|---|---|---|
| 117 | 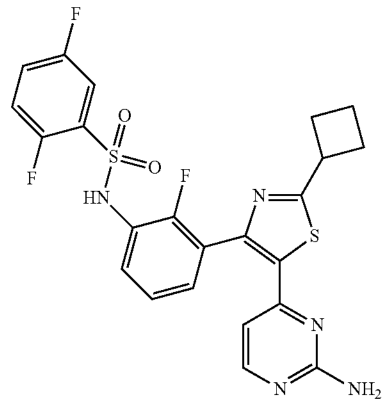 [SMILES: Nc1nccc(-c2sc(C3CCC3)nc2-c2cccc(NS(=O)(=O)c3cc(F)ccc3F)c2F)n1] | 518 [ES+] | $^1$H NMR (400 MHz, CDCl$_3$) δ ppm 7.95 (d, J = 5.2 Hz, 1 H) 7.47-7.66 (m, 2 H) 7.04-7.44 (m, 5 H) 6.06 (d, J = 5.2 Hz, 1 H) 4.92-5.08 (m, 2 H) 3.82 (quin, J = 8.4 Hz, 1 H) 2.25-2.55 (m, 4 H) 1.87-2.16 (m, 2 H) |
| 118 | 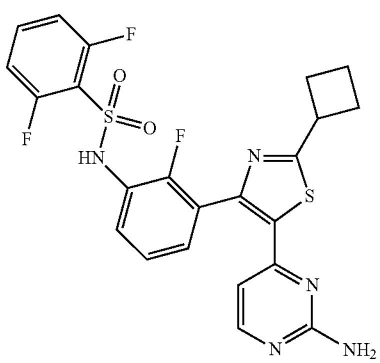 [SMILES: Nc1nccc(-c2sc(C3CCC3)nc2-c2cccc(NS(=O)(=O)c3c(F)cccc3F)c2F)n1] | 518 [ES+] | $^1$H NMR (400 MHz, CDCl$_3$) δ ppm 7.95 (d, J = 5.3 Hz, 1 H) 7.70 (t, J = 7.2 Hz, 1 H) 7.37-7.51 (m, 2 H) 7.27 (t, J = 7.1 Hz, 1 H) 7.18 (t, J = 8.0 Hz, 1 H) 6.94 (t, J = 8.9 Hz, 2 H) 6.09 (d, J = 5.1 Hz, 1 H) 4.99 (br. s., 2 H) 3.82 (quin, J = 8.6 Hz, 1 H) 2.26-2.55 (m, 1 H) 1.86-2.14 (m, 2H) |
| 119 | 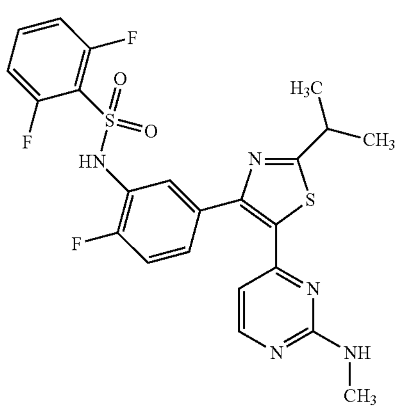 [SMILES: CNc1nccc(-c2sc(C(C)C)nc2-c2ccc(F)c(NS(=O)(=O)c3c(F)cccc3F)c2)n1] | 520 [ES+] | $^1$H NMR (400 MHz, DMSO-d$_6$) δ ppm 10.87 (s, 1 H) 8.04 (d, J = 4.4 Hz, 1 H) 7.61-7.74 (m, 1 H) 7.29-7.47 (m, 2 H) 7.10-7.30 (m, 4 H) 7.16 (br. s., 1 H) 3.17-3.28 (m, 1 H) 2.69 (br. s., 3 H) 1.32 (d, J = 6.8 Hz, 6 H) |

-continued

| Ex | Structure | m/z [M + H]⁺ | ¹H NMR |
|---|---|---|---|
| 120 | 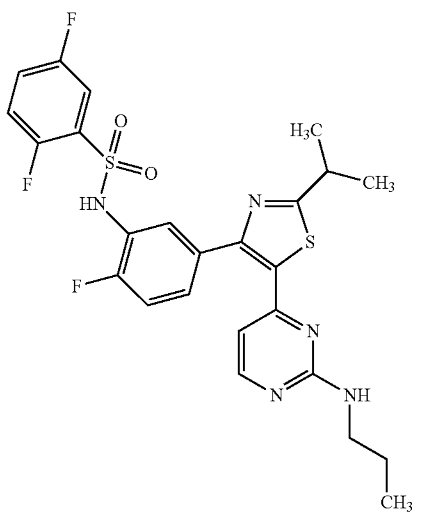 [SMILES: CCCNc1nccc(-c2sc(C(C)C)nc2-c2ccc(F)c(NS(=O)(=O)c3cc(F)ccc3F)c2)n1] | 548 [ES+] | ¹H NMR (400 MHz, DMSO-d₆) δ ppm 10.78 (s, 1 H) 8.07 (d, J = 5.3 Hz, 1 H) 7.71 (br. s., 1 H) 7.42-7.62 (m, 3 H) 7.32-7.42 (m, 2 H) 7.25 (t, J = 9.2 Hz, 1 H) 6.25 (br. s., 1 H) 3.27 (quin, J = 6.9 Hz, 1 H) 3.16 (br. s., 2 H) 1.38-1.58 (m, 2 H) 1.32 (d, J = 7.0 Hz, 6 H) 0.83 (t, J = 7.2 Hz, 3 H) |
| 121 | 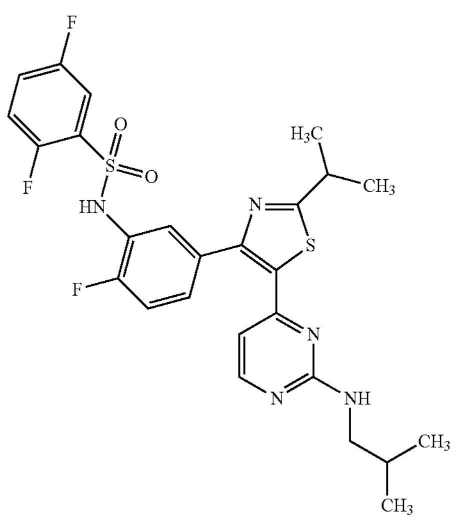 [SMILES: CC(C)CNc1nccc(-c2sc(C(C)C)nc2-c2ccc(F)c(NS(=O)(=O)c3cc(F)ccc3F)c2)n1] | 562 [ES+] | ¹H NMR (400 MHz, DMSO-d₆) δ ppm 10.78 (s, 1 H) 8.07 (d, J = 4.4 Hz, 1 H) 7.76 (br. s., 1 H) 7.42-7.62 (m, 3 H) 7.32-7.42 (m, 2 H) 7.25 (t, J = 9.2 Hz, 1H) 6.26 (br. s., 1 H) 3.27 (quin, J = 6.9 Hz, 1H) 3.02 (br. s., 2 H) 1.79 (br. s., 1 H) 1.32 (d, J = 6.8 Hz, 6 H) 0.83 (d, 6 H) |
| 122 | 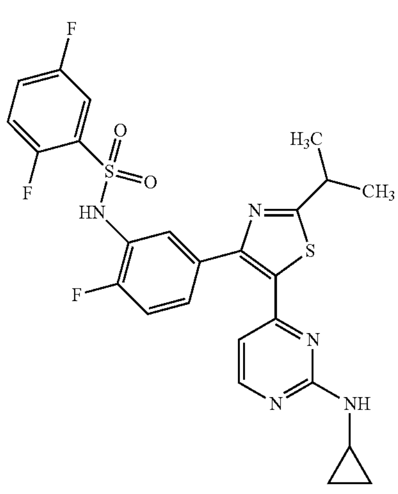 [SMILES: CC(C)c1nc(-c2ccc(F)c(NS(=O)(=O)c3cc(F)ccc3F)c2)c(-c2ccnc(NC3CC3)n2)s1] | 546 [ES+] | ¹H NMR (400 MHz, DMSO-d₆) δ ppm 10.74 (s, 1 H) 8.08 (d, J = 4.8 Hz, 1 H) 7.40-7.62 (m, 5 H) 7.36 (d, J = 7.0 Hz, 2 H) 7.23 (t, J = 9.6 Hz, 1 H) 6.21 (d, J = 4.8 Hz, 1 H) 3.18-3.27 (m, 1 H) 2.62 (br. s., 1 H) 1.32 (d, J = 6.8 Hz, 6 H) 0.58 (d, J = 5.3 Hz, 2 H) 0.42 (br. s., 2 H) |

| Ex | Structure | m/z [M + H]+ | 1H NMR |
|---|---|---|---|
| 123 | 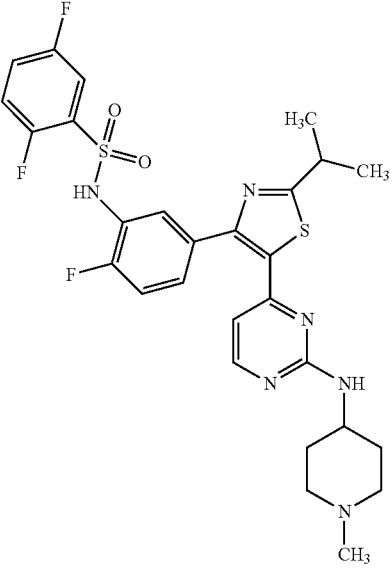 [SMILES: CC(C)c1nc(-c2ccc(F)c(NS(=O)(=O)c3cc(F)ccc3F)c2)c(-c2ccnc(NC3CCN(C)CC3)n2)s1] | 603 [ES+] | 1H NMR (400 MHz, DMSO-d6) δ ppm 8.09 (s, 1 H) 7.96 (d, J = 4.9 Hz, 2 H) 7.16-7.37 (m, 4H) 6.96 (dd, J = 10.1, 9.0 Hz, 1 H) 6.77 (br. s., 1 H) 6.17 (br. s., 1 H) 3.04-3.26 (m, 4 H) 2.67 (br. s., 2 H) 2.53 (br. s., 4 H) 1.81-1.99 (m, 2 H) 1.61 (br. s., 2 H) 1.30 (d, J = 6.8 Hz, 6 H) |
| 124 | 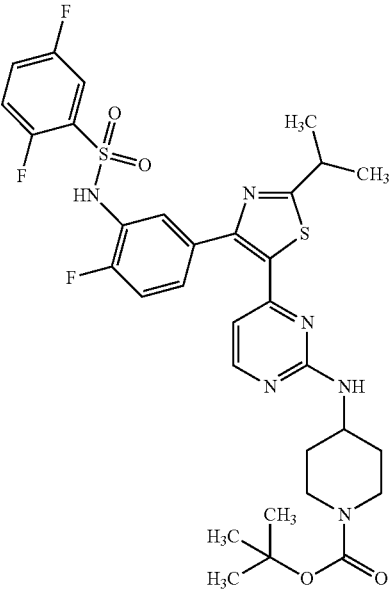 [SMILES: CC(C)c1nc(-c2ccc(F)c(NS(=O)(=O)c3cc(F)ccc3F)c2)c(-c2ccnc(NC3CCN(C(=O)OC(C)(C)C)CC3)n2)s1] | 689 [ES+] | 1H NMR (400 MHz, CDCl3) δ ppm 8.01 (d, J = 5.1 Hz, 1 H) 7.68 (d, J = 7.0 Hz, 1 H) 7.45 (td, J = 4.8, 2.7 Hz, 1 H) 7.31 (td, J = 5.4, 2.4 Hz, 1 H) 7.10-7.28 (m, 3 H) 7.03 (t, J = 9.2 Hz, 1 H) 6.21 (d, J = 5.3 Hz, 1 H) 5.08 (d, J = 7.7 Hz, 1 H) 3.83-4.15 (m, 3 H) 3.29 (quin, J = 6.9 Hz, 1 H) 2.84-3.01 (m, 2 H) 2.00 (d, J = 10.3 Hz, 2 H) 1.56 (br. s., 2 H) 1.44 (s, 9 H) 1.41 (d, J = 7.0 Hz, 6 H) |

-continued
| Ex | Structure | m/z [M+H]+ | 1H NMR |
|---|---|---|---|
| 125 | 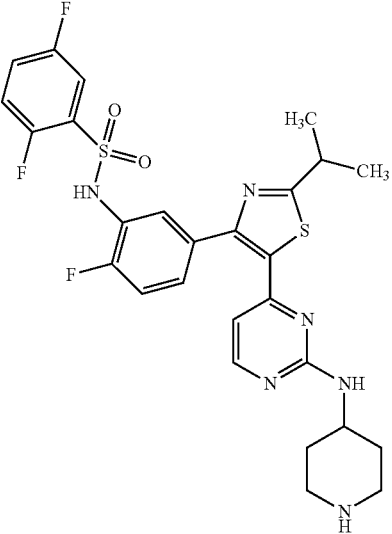 [SMILES: CC(C)c1nc(-c2ccc(F)c(NS(=O)(=O)c3cc(F)ccc3F)c2)c(-c2ccnc(NC3CCNCC3)n2)s1] | 589 [ES+] | 1H NMR (400 MHz, DMSO-d6) δ ppm 8.23 (br. s., 1 H) 7.92 (d, J = 4.4 Hz, 1 H) 7.34 (d, J = 7.1 Hz, 1H) 7.22-7.30 (m, 1 H) 7.19 (dd, J = 8.6, 1.6 Hz, 1 H) 7.11 (t, J = 5.8 Hz, 2 H) 6.89 (dd, J = 11.1, 8.3 Hz, 1 H) 6.58 (br. s., 1 H) 6.17 (br. s., 1 H) 3.82 (br. s., 1 H) 3.14-3.25 (m, 2 H) 2.92 (dd, J = 11.5, 10.8 Hz, 2 H) 1.95 (d, J = 11.5 Hz, 2 H) 1.49-1.71 (m, 2 H) 1.30 (d, J = 7.0 Hz, 6 H) |
| 126 | 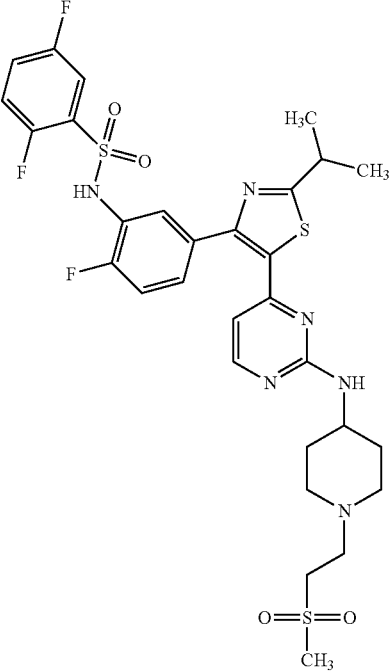 [SMILES: CC(C)c1nc(-c2ccc(F)c(NS(=O)(=O)c3cc(F)ccc3F)c2)c(-c2ccnc(NC3CCN(CCS(C)(=O)=O)CC3)n2)s1] | 695 [ES+] | 1H NMR (400 MHz, DMSO-d6) δ ppm 8.04 (d, J = 5.1 Hz, 1 H) 7.37-7.63 (m, 4 H) 7.14-7.47 (m, 4 H) 6.05-6.26 (m, 1 H) 3.33 (q, J = 7.1 Hz, 2 H) 3.14-3.25 (m, 1 H) 2.99 (s, 3 H) 2.93 (s, 2 H) 2.62-2.77 (m, 2 H) 2.05 (br. s., 2 H) 1.78 (br. s., 2 H) 1.31 (d, J = 6.8 Hz, 6 H) 1.04 (t, J = 7.0 Hz, 2 H) |

| Ex | Structure | m/z [M + H]+ | 1H NMR |
|---|---|---|---|
| 127 | 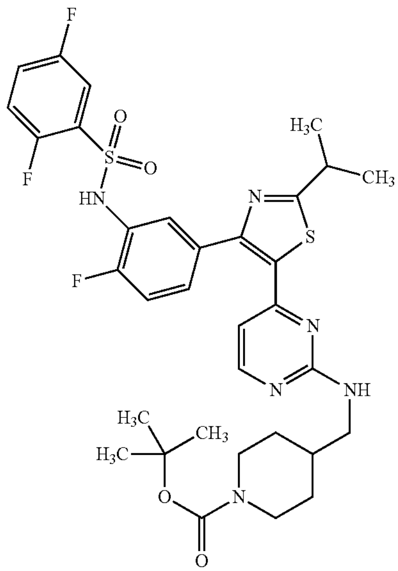 [SMILES: CC(C)c1nc(-c2ccc(F)c(NS(=O)(=O)c3cc(F)ccc3F)c2)c(-c2ccnc(NCC3CCN(C(=O)OC(C)(C)C)CC3)n2)s1] | 703 [ES+] | 1H NMR (400 MHz, CDCl3) δ ppm 8.00 (br. s., 1 H) 7.67 (d, J = 5.9 Hz, 1 H) 7.46 (t, J = 7.5 Hz, 1 H) 7.32 (dd, J = 5.2, 3.2 Hz, 1 H) 7.10-7.28 (m, J = 9.0, 9.0, 4.8, 4.6 Hz, 1 H) 7.02 (t, J = 9.2 Hz, 1 H) 6.20 (d, J = 5.3 Hz, 1 H) 5.35 (br. s., 1 H) 4.11 (br. s., 2 H) 3.24-3.39 (m, 3 H) 2.69 (br. s., 2 H) 1.74 (d, J = 10.8 Hz, 3 H) 1.38-1.48 (m, 15 H) 1.05-1.28 (m, 2 H) |
| 128 | 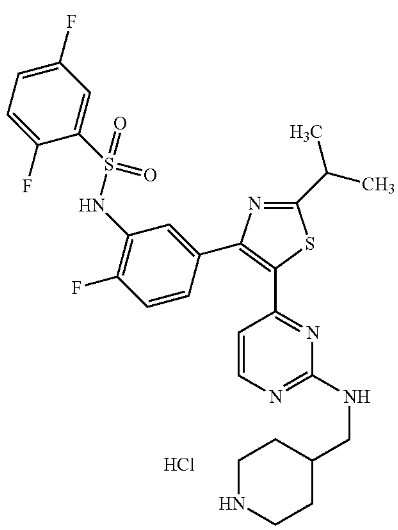 [SMILES: CC(C)c1nc(-c2ccc(F)c(NS(=O)(=O)c3cc(F)ccc3F)c2)c(-c2ccnc(NCC3CCNCC3)n2)s1 ; Cl] | 603 [ES+] | 1H NMR (400 MHz, DMSO-d6) δ ppm 10.83 (s, 1 H) 8.11 (d, J = 5.2 Hz, 1 H) 7.44-7.68 (m, 4 H) 7.35-7.44 (m, 2 H) 7.31 (dd, J = 9.6, 8.8 Hz, 1 H) 3.19-3.36 (m, 2 H) 2.82 (br. s., 3 H) 1.80 (br. s., 3 H) 1.36 (d, J = 7.0 Hz, 6 H) 1.24-1.34 (m, 1 H) |

-continued

| Ex | Structure | m/z [M+H]+ | 1H NMR |
|---|---|---|---|
| 129 | 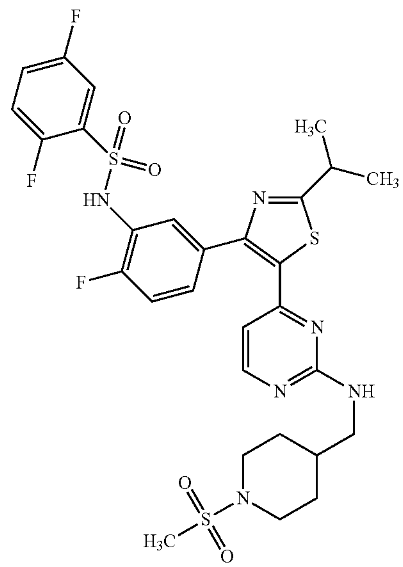 [SMILES: CC(C)c1nc(-c2ccc(F)c(NS(=O)(=O)c3cc(F)ccc3F)c2)c(-c2ccnc(NCC3CCN(S(C)(=O)=O)CC3)n2)s1] | 681 [ES+] | 1H NMR (400 MHz, DMSO-d6) δ ppm 10.81 (s, 1 H) 8.10 (d, J = 5.0 Hz, 1 H) 7.34-7.68 (m, 6 H) 7.28 (t, J = 9.4 Hz, 1 H) 6.85-6.97 (m, 1 H) 3.43-3.63 (m, 2 H) 3.24-3.31 (m, 1 H) 3.03-3.23 (m, 2 H) 2.82 (s, 4 H) 2.63 (t, J = 11.8 Hz, 2 H) 1.69 (d, J = 12.0 Hz, 2 H) 1.37 (d, J = 1.6 Hz, 6 H) 1.03-1.30 (m, 2 H) |
| 130 | 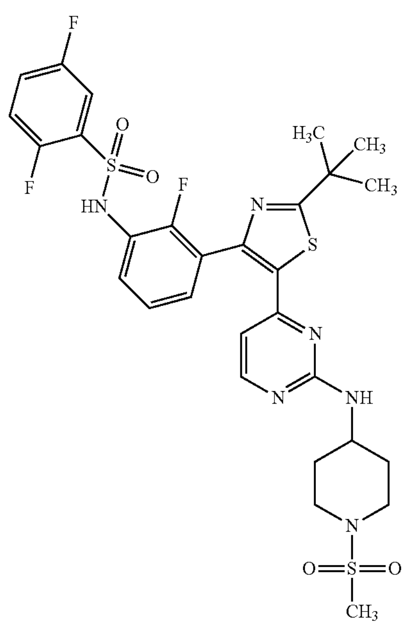 [SMILES: CC(C)(C)c1nc(-c2cccc(NS(=O)(=O)c3cc(F)ccc3F)c2F)c(-c2ccnc(NC3CCN(S(C)(=O)=O)CC3)n2)s1] | 681 [ES+] | 1H NMR (400 MHz, DMSO-d6) δ ppm 10.76 (s, 1 H) 8.07 (br. s., 1 H) 7.21-7.62 (m, 7 H) 5.69-6.27 (m, 1 H) 3.64-3.98 (m, 1 H) 3.42-3.64 (m, 2 H) 2.87 (s, 3 H) 2.59-2.87 (m, 2 H) 1.66-2.04 (m, 2 H) 1.40 (s, 9 H) 1.30-1.65 (m, 2 H) |

| Ex | Structure | m/z [M + H]+ | ¹H NMR |
|---|---|---|---|
| 131 | 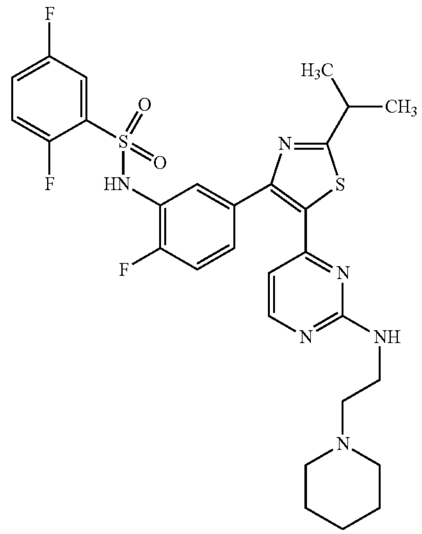 [SMILES: CC(C)c1nc(-c2ccc(F)c(NS(=O)(=O)c3cc(F)ccc3F)c2)c(-c2ccnc(NCCN3CCCCC3)n2)s1] | 617 [ES+] | ¹H NMR (400 MHz, DMSO-d₆) δ ppm 7.96 (d, J = 4.8 Hz, 1 H) 7.04-7.39 (m, 6 H) 6.97 (t, J = 9.4 Hz, 1 H) 6.77 (br. s., 1 H) 6.18 (br. s., 1 H) 3.04-3.67 (m, 3 H) 2.52-2.93 (m, 4 H) 2.16-2.39 (m, 2 H) 1.36-1.68 (m, 6 H) 1.30 (d, 6 H) |
| 132 | 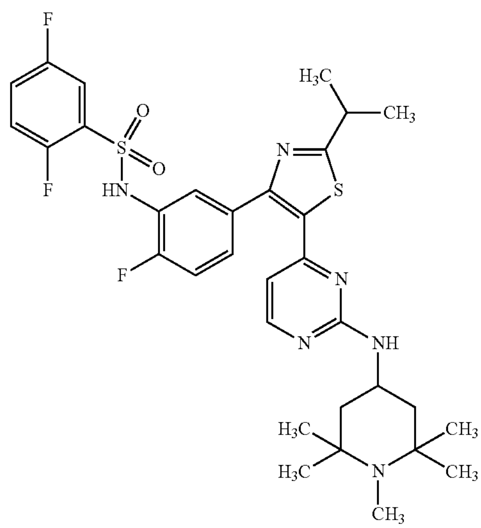 [SMILES: CC(C)c1nc(-c2ccc(F)c(NS(=O)(=O)c3cc(F)ccc3F)c2)c(-c2ccnc(NC3CC(C)(C)N(C)C(C)(C)C3)n2)s1] | 659 [ES+] | ¹H NMR (400 MHz, DMSO-d₆) δ ppm 7.85 (br. s., 1 H) 7.17-7.34 (m, 1 H) 7.10 (dd, J = 7.1, 4.8 Hz, 2 H) 6.94-7.05 (m, 1 H) 6.88 (dd, J = 10.9, 8.7 Hz, 1 H) 6.48-6.64 (m, 1 H) 6.01-6.14 (m, 2 H) 4.02 (br. s., 1 H) 3.01-3.23 (m, 1 H) 2.06-2.21 (m, 5 H) 1.69-1.84 (m, 1 H) 1.65 (dd, J = 12.0, 2.8 Hz, 2 H) 1.28 (d, J = 6.8 Hz, 4 H) 1.18 (t, J = 12.2 Hz, 2 H) 0.96-1.10 (m, 14 H) 0.92 (s, 6 H) |
| 133 | 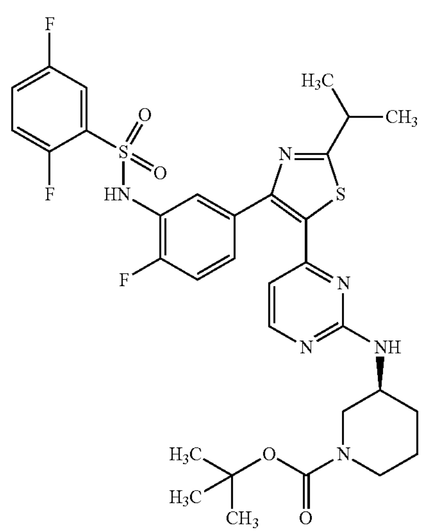 [SMILES: CC(C)c1nc(-c2ccc(F)c(NS(=O)(=O)c3cc(F)ccc3F)c2)c(-c2ccnc(N[C@H]3CCCN(C(=O)OC(C)(C)C)C3)n2)s1] | 689 [ES+] | ¹H NMR (400 MHz, DMSO-d₆) δ ppm 10.75 (s, 1 H) 7.96-8.14 (m, 2 H) 7.92 (s, 1 H) 7.40-7.61 (m, 2 H) 7.17-7.40 (m, 2 H) 6.16 (br. s., 1 H) 3.33-4.18 (m, 3 H) 2.53-3.16 (m, 2 H) 1.75 (s, 4 H) 1.08-1.42 (m, 17 H) |

| Ex | Structure | m/z [M+H]+ | 1H NMR |
|---|---|---|---|
| 134 | 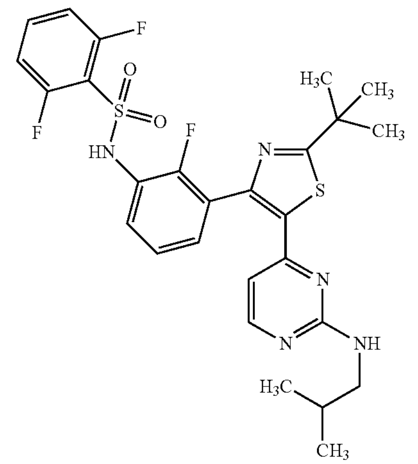 [SMILES: CC(C)CNc1nccc(-c2sc(C(C)(C)C)nc2-c2cccc(NS(=O)(=O)c3c(F)cccc3F)c2F)n1] | 576 [ES+] | 1H NMR (400 MHz, DMSO-d6) δ ppm 10.82 (s, 1 H) 7.97 (d, J = 5.1 Hz, 1 H) 7.56-7.68 (m, 1 H) 7.38 (t, J = 7.0 Hz, 1 H) 7.11-7.33 (m, 5 H) 5.65-6.02 (m, 1 H) 2.72-3.16 (m, 2 H) 1.62-1.92 (m, 1 H) 1.36 (s, 9 H) 0.82 (d, J = 6.4 Hz, 6 H) |
| 135 | 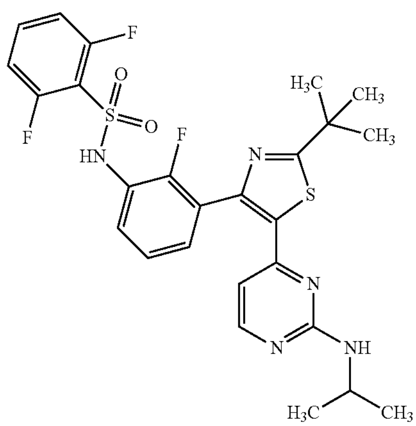 [SMILES: CC(C)Nc1nccc(-c2sc(C(C)(C)C)nc2-c2cccc(NS(=O)(=O)c3c(F)cccc3F)c2F)n1] | 563 [ES+] | 1H NMR (400 MHz, CDCl3) δ ppm 7.42-8.64 (m, 5 H) 7.10-7.42 (m, 2 H) 6.84-7.11 (m, 2 H) 6.24 (br. s., 1 H) 4.07 (br. s., 1 H) 3.43 (d, J = 6.2 Hz, 1 H) 1.44 (br. s., 9 H) 1.26 (d, J = 4.8 Hz, 6 H) |
| 136 | 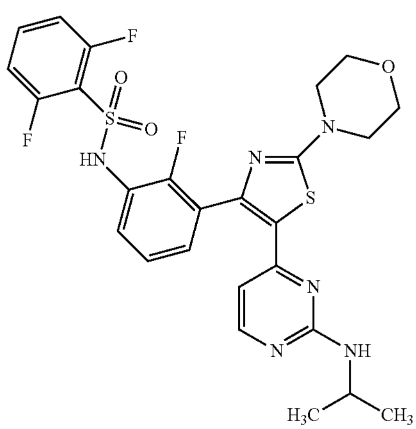 [SMILES: CC(C)Nc1nccc(-c2sc(N3CCOCC3)nc2-c2cccc(NS(=O)(=O)c3c(F)cccc3F)c2F)n1] | 591 [ES+] | 1H NMR (400 MHz, CDCl3) δ ppm 8.32 (d, J = 7.4 Hz, 1 H) 7.95 (br. s., 1 H) 7.68 (dt, J = 10.0, 3.6 Hz, 1 H) 7.54 (dd, J = 14.2, 2.4 Hz, 1 H) 7.44 (d, J = 7.0 Hz, 1 H) 7.17-7.22 (m, 2 H) 6.91-7.05 (m, 2 H) 5.89 (d, J = 6.2 Hz, 1 H) 4.08 (quin, J = 6.6 Hz, 1 H) 3.79 (t, J = 4.7 Hz, 5 H) 3.62 (t, J = 4.5 Hz, 4 H) 1.27 (d, J = 6.4 Hz, 6 H) |

-continued

| Ex | Structure | m/z [M + H]+ | 1H NMR |
|---|---|---|---|
| 137 | 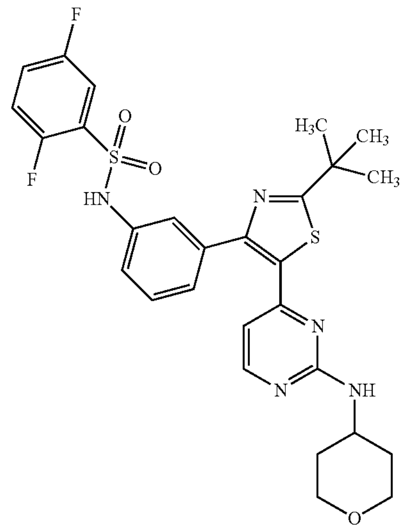 [SMILES: CC(C)(C)c1nc(-c2cccc(NS(=O)(=O)c3cc(F)ccc3F)c2)c(-c2ccnc(NC3CCOCC3)n2)s1] | 586 [ES+] | 1H NMR (400 MHz, DMSO-d6) δ ppm 10.90 (s, 1 H) 8.02 (br. s., 1 H) 7.36-7.67 (m, 4 H) 7.29 (t, J = 7.9 Hz, 1 H) 7.05-7.24 (m, 2 H) 5.82-6.41 (m, 1 H) 3.62-3.96 (m, 2 H) 3.09-3.41 (m, 3 H) 1.59-1.85 (m, 2 H) 1.39-1.56 (m, 1 H) 1.37 (s, 9 H) |
| 138 | 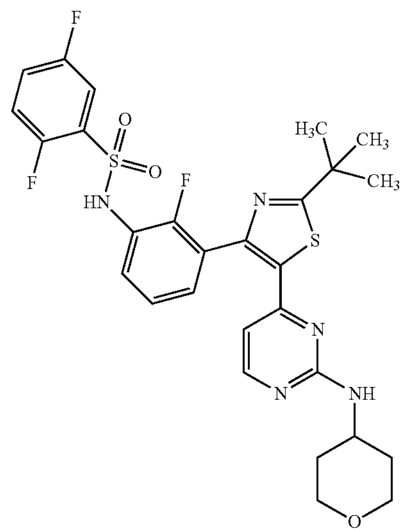 [SMILES: CC(C)(C)c1nc(-c2cccc(NS(=O)(=O)c3cc(F)ccc3F)c2F)c(-c2ccnc(NC3CCOCC3)n2)s1] | 604 [ES+] | 1H NMR (400 MHz, DMSO-d6) δ ppm 10.74 (s, 1 H) 8.07 (br. s., 1 H) 7.29-7.74 (m, 6 H) 7.24 (t, J = 7.8 Hz, 1 H) 5.67-6.36 (m, 1 H) 3.66-3.92 (m, 2 H) 3.10-3.37 (m, 3 H) 1.68 (br. s., 2 H) 1.38-1.54 (m, 2 H) 1.36 (s, 9 H) |
| 139 | 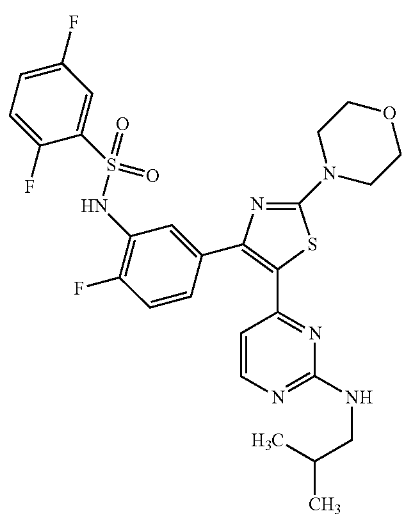 [SMILES: CC(C)CNc1nccc(-c2sc(N3CCOCC3)nc2-c2ccc(F)c(NS(=O)(=O)c3cc(F)ccc3F)c2)n1] | 605 [ES+] | 1H NMR (400 MHz, DMSO-d6) δ ppm 10.84 (br. s., 1 H) 8.24 (br. s., 1 H) 7.63-8.01 (m, 4 H) 7.43-7.63 (m, 2 H) 7.14-7.43 (m, 2 H) 6.07 (br. s., 1 H) 3.58-3.77 (m, 4 H) 3.39-3.56 (m, 2 H) 2.98-3.19 (m, 1 H) 2.33-2.50 (m, 4 H) 1.71-1.91 (m, 1 H) 0.87 (d, J = 6.6 Hz, 6 H) |

-continued
| Ex | Structure | m/z [M + H]+ | 1H NMR |
|---|---|---|---|
| 140 | 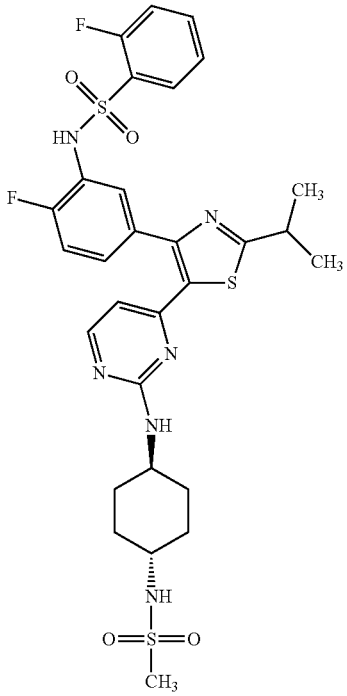 [SMILES: CC(C)c1nc(-c2ccc(F)c(NS(=O)(=O)c3ccccc3F)c2)c(-c2ccnc(N[C@H]3CC[C@H](NS(C)(=O)=O)CC3)n2)s1] | 663 | 1H NMR (400 MHz, DMSO-d6) δ ppm 10.50 (s, 1 H), 8.11 (d, J = 5.0 Hz, 1 H), 7.58-7.67 (m, 1 H), 7.47-7.57 (m, 2 H), 7.22-7.42 (m, 3 H), 7.01 (d, J = 6.9 Hz, 1 H), 6.11-6.27 (m, 1 H), 3.53-4.01 (m, 4 H), 3.26-3.35 (m, 1 H), 3.09 (dt, J = 3.3, 1.6 Hz, 1 H), 2.92 (s, 3 H), 1.92 (d, J = 10.6 Hz, 4 H), 1.19-1.42 (m, 8 H). |
| 141 | 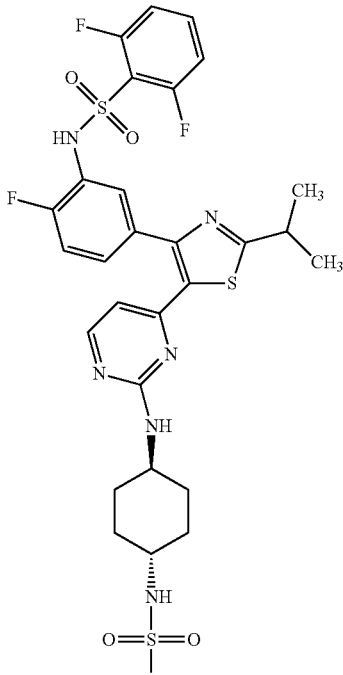 | 681 | 1H NMR (400 MHz, DMSO-d6) δ ppm 10.94 (br. s., 1 H), 8.04-8.13 (m, 1 H), 7.64-7.77 (m, 1 H), 7.16-7.51 (m, 4 H), 7.02 (td, J = 2.8, 0.7 Hz, 1 H), 6.07-6.33 (m, 1 H), 3.60-4.11 (m, 6 H), 3.26-3.39 (m, 1 H), 3.03-3.17 (m, 1 H), 2.92 (br. s., 3 H), 1.76-2.09 (m, 3 H), 1.13-1.48 (m, 8 H). |

-continued

| Ex | Structure | m/z [M + H]+ | 1H NMR |
|---|---|---|---|
| 142 | 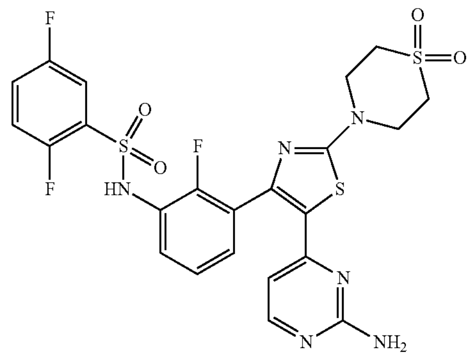 [SMILES: Nc1nccc(-c2sc(N3CCS(=O)(=O)CC3)nc2-c2cccc(NS(=O)(=O)c3cc(F)ccc3F)c2F)n1] | 597 | 1H NMR (400 MHz, DMSO-d6) δ ppm 10.76 (br. s., 1 H), 7.86 (d, J = 5.4 Hz, 1 H), 7.54-7.62 (m, 1 H), 7.46-7.54 (m, 2 H), 7.42 (t, J = 7.4 Hz, 1 H), 7.33 (t, J = 6.2 Hz, 1 H), 7.24-7.30 (m, 1 H), 6.60 (s, 2 H), 5.68 (d, J = 5.3 Hz, 1 H), 3.97 (br. s., 4 H), 3.29 (br. s., 4 H) |
| 143 | 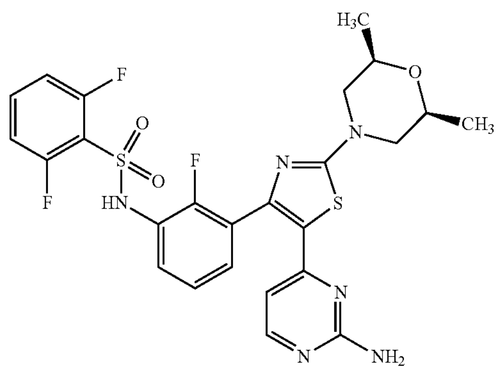 | Chiral 577 | 1H NMR (400 MHz, DMSO-d6) δ ppm 10.88 (br. s., 1 H), 7.82 (d, J = 5.4 Hz, 1 H), 7.61-7.75 (m, 1 H), 7.42 (td, J = 7.0, 2.9 Hz, 1 H), 7.16-7.34 (m, 4 H), 6.54 (br. s., 2 H), 5.63 (d, J = 5.3 Hz, 1 H), 3.77 (d, J = 12.1 Hz, 2 H), 3.61-3.72 (m, 2 H), 2.73 (t, J = 11.6 Hz, 2 H), 1.14 (d, J = 6.1 Hz, 6 H) |
| 144 | 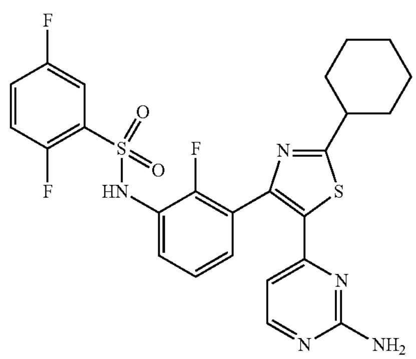 [SMILES: Nc1nccc(-c2sc(C3CCCCC3)nc2-c2cccc(NS(=O)(=O)c3cc(F)ccc3F)c2F)n1] | 546 | 1H NMR (400 MHz, DMSO-d6) δ ppm 10.76 (s, 1 H), 7.97 (d, J = 5.1 Hz, 1 H), 7.45-7.64 (m, 3 H), 7.32-7.45 (m, 2 H), 7.20-7.33 (m, 1 H), 6.76 (s, 2 H), 5.84 (d, J = 5.1 Hz, 1 H), 2.98 (tt, J = 11.0, 3.4 Hz, 1 H), 2.07 (d, J = 10.8 Hz, 2 H), 1.72-1.84 (m, 2 H), 1.67 (d, J = 12.5 Hz, 1 H), 1.32-1.56 (m, 5 H) |
| 145 | 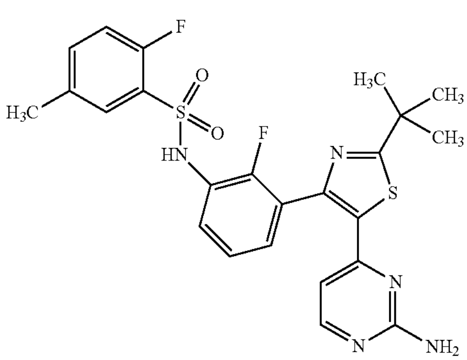 [SMILES: Cc1ccc(F)c(S(=O)(=O)Nc2cccc(-c3nc(C(C)(C)C)sc3-c3ccnc(N)n3)c2F)c1] | 516 | 1H NMR (400 MHz, DMSO-d6) δ ppm 10.51 (1 H, s) 7.96 (1 H, d, J = 5.13 Hz) 7.52 (1 H, d, J = 6.41 Hz) 7.44-7.50 (1 H, m) 7.41 (1 H, t, J = 7.60 Hz) 7.33 (1 H, t, J = 6.23 Hz) 7.22-7.29 (2 H, m) 6.75 (2 H, s) 5.86 (1 H, d, J = 5.13 Hz) 2.29 (3 H, s) 1.40 (9 H, s) |

| Ex | Structure | m/z [M+H]+ | 1H NMR |
|---|---|---|---|
| 146 | 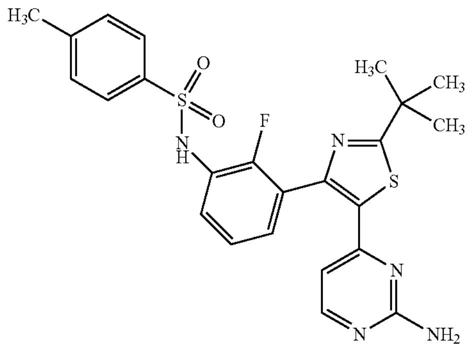 [SMILES: Cc1ccc(S(=O)(=O)Nc2cccc(-c3nc(C(C)(C)C)sc3-c3ccnc(N)n3)c2F)cc1] | 498 | 1H NMR (400 MHz, DMSO-d6) δ ppm 10.23 (1 H, s) 7.95 (1 H, d, J = 5.31 Hz) 7.61 (2 H, m, J = 8.06 Hz) 7.43 (1 H, td, J = 7.37, 1.92 Hz) 7.33 (2 H, m, J = 8.06 Hz) 7.18-7.30 (2 H, m) 6.75 (2 H, s) 5.78 (1 H, d, J = 5.13 Hz) 2.32 (3 H, s) 1.39 (9 H, s) |
| 147 | 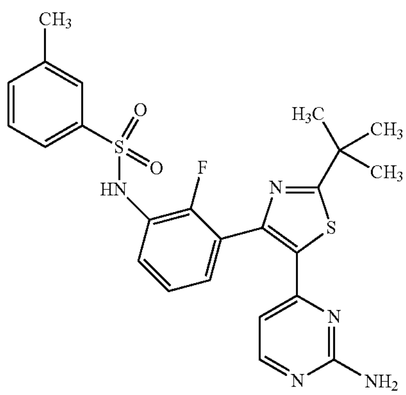 [SMILES: Cc1cccc(S(=O)(=O)Nc2cccc(-c3nc(C(C)(C)C)sc3-c3ccnc(N)n3)c2F)c1] | 498 | 1H NMR (400 MHz, DMSO-d6) δ ppm 10.26 (1 H, s) 7.96 (1 H, d, J = 5.31 Hz) 7.49-7.60 (2 H, m) 7.36-7.47 (3 H, m) 7.17-7.33 (2 H, m) 6.75 (2 H, s) 5.84 (1 H, d, J = 5.13 Hz) 2.32 (3 H, s) 1.40 (9 H, s) |
| 148 | 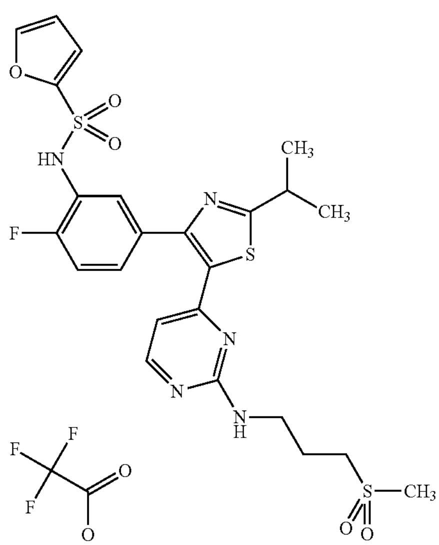 [SMILES: CC(C)c1nc(-c2ccc(F)c(NS(=O)(=O)c3ccco3)c2)c(-c2ccnc(NCCCS(C)(=O)=O)n2)s1 ; O=C(O)C(F)(F)F] | 580 free base | 1H NMR (400 MHz, DMSO-d6) δ ppm 10.59 (s, 1 H) 8.10 (d, J = 5.2 Hz, 1 H) 7.82-7.99 (m, 1 H) 7.30-7.48 (m, 3 H) 7.26 (t, J = 9.3 Hz, 1 H) 6.97 (d, J = 3.5 Hz, 1 H) 6.57 (dd, J = 3.3, 1.60 Hz, 1 H) 6.14-6.25 (m, 1 H) 3.17-3.44 (m, 3 H) 3.03-3.17 (m, 2 H) 2.92 (s, 3 H) 1.80-1.97 (m, 2 H) 1.32 (d, J = 6.9 Hz, 6 H) |

| Ex | Structure | m/z [M+H]+ | 1H NMR |
|---|---|---|---|
| 149 | 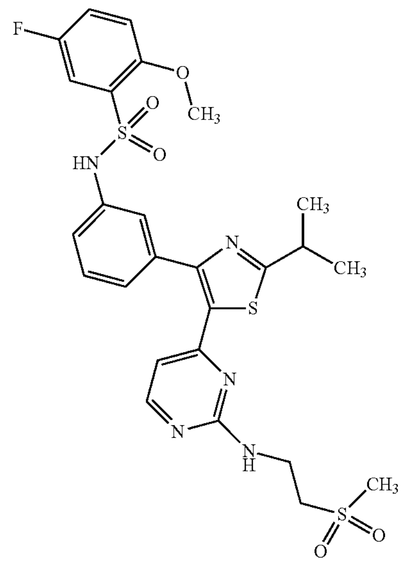 [SMILES: COc1ccc(F)cc1S(=O)(=O)Nc1cccc(-c2nc(C(C)C)sc2-c2ccnc(NCCS(C)(=O)=O)n2)c1] | 606 | 1H NMR (400 MHz, DMSO-d6) δ ppm 10.33 (s, 1 H) 8.03 (d, J = 5.1 Hz, 1 H) 7.39-7.56 (m, 3 H) 7.28 (t, J = 7.9 Hz, 1 H) 7.04-7.26 (m, 4 H) 6.06 (dd, J = 2.5, 1.45 Hz, 1 H) 3.83 (s, 3 H) 3.54-3.75 (m, 2 H) 3.38 (s, 2 H) 3.22-3.31 (m, 1 H) 3.01 (s, 3 H) 1.35 (d, J = 6.8 Hz, 6 H) |
| 150 | 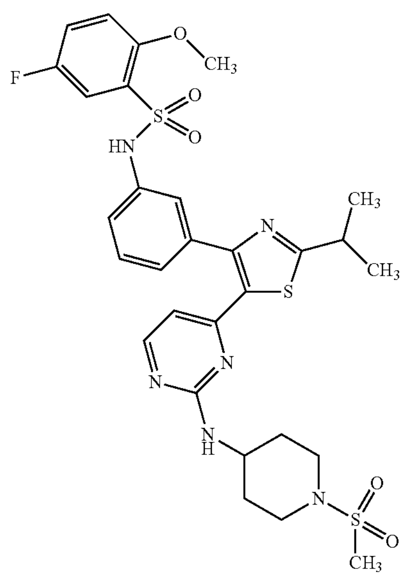 [SMILES: COc1ccc(F)cc1S(=O)(=O)Nc1cccc(-c2nc(C(C)C)sc2-c2ccnc(NC3CCN(S(C)(=O)=O)CC3)n2)c1] | 661 | 1H NMR (400 MHz, DMSO-d6) δ ppm 10.28 (s, 1 H) 7.98 (d, J = 0.8 Hz, 1 H) 7.37-7.49 (m, 2 H) 7.23-7.30 (m, 1 H) 7.21 (s, 1 H) 7.08-7.21 (m, 3 H) 7.06 (d, J = 7.5 Hz, 1 H) 5.85-6.18 (m, 1 H) 3.79 (s, 3 H) 3.47 (d, J = 10.7 Hz, 2 H) 3.24-3.25 (m, 1 H) 3.13-3.25 (m, 1 H) 2.83 (s, 3 H) 2.69-2.82 (m, 2 H) 1.78-1.93 (m, 2 H) 1.40-1.57 (m, 2 H) 1.31 (d, J = 6.9 Hz, 6 H) |

-continued

| Ex | Structure | m/z [M + H]+ | 1H NMR |
|---|---|---|---|
| 151 | 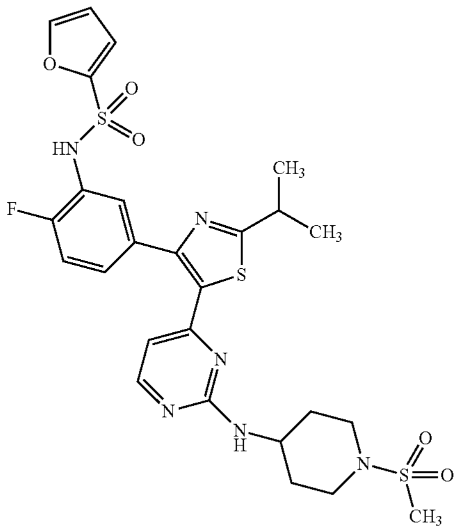 [SMILES: CC(C)c1nc(-c2ccc(F)c(NS(=O)(=O)c3ccco3)c2)c(-c2ccnc(NC3CCN(S(C)(=O)=O)CC3)n2)s1] | 621 | 1H NMR (400 MHz, DMSO-d6) δ ppm 10.60 (s, 1 H) 8.12 (d, J = 5.0 Hz, 1 H) 7.92 (s, 1 H) 7.14-7.44 (m, 4 H) 6.96 (d, J = 3.2 Hz, 1 H) 6.57 (dd, J = 3.0, 1.46 Hz, 1 H) 6.07-6.36 (m, 1 H) 3.53-3.88 (m, 1 H) 3.37-3.53 (m, 2 H) 3.17-3.25 (m, 1 H) 2.63-2.86 (m, 5 H) 1.85 (ddd, J = 4.7, 2.2, 1.0 Hz, 2 H) 1.42-1.60 (m, 2 H) 1.32 (d, J = 6.9 Hz, 6 H) |
| 152 | 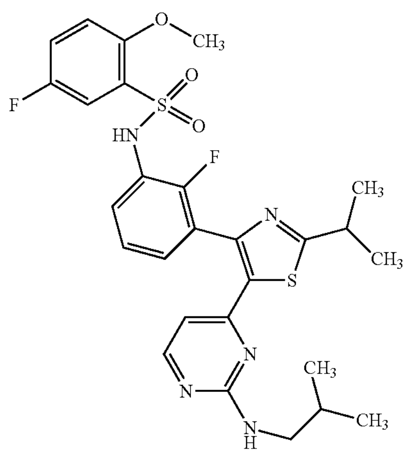 [SMILES: COc1ccc(F)cc1S(=O)(=O)Nc1cccc(-c2nc(C(C)C)sc2-c2ccnc(NCC(C)C)n2)c1F] | 574 | 1H NMR (400 MHz, DMSO-d6) δ ppm 10.04 (s, 1 H) 7.91 (d, J = 5.1 Hz, 1 H) 7.37-7.47 (m, 2 H) 7.30-7.38 (m, 1 H) 7.27 (t, J = 6.0 Hz, 1 H) 7.05-7.26 (m, 3 H) 5.64-5.86 (m, 1 H) 3.71 (s, 3 H) 3.17-3.26 (m, 1 H) 2.78-3.12 (m, 2 H) 1.66-1.85 (m, 1 H) 1.30 (d, J = 6.9 Hz, 6 H) 0.75-0.87 (m, 6 H) |
| 153 | 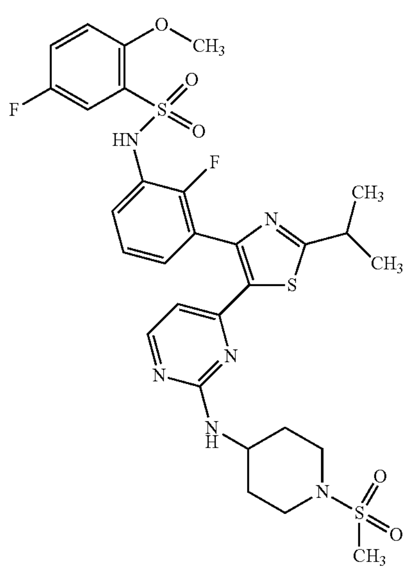 [SMILES: COc1ccc(F)cc1S(=O)(=O)Nc1cccc(-c2nc(C(C)C)sc2-c2ccnc(NC3CCN(S(C)(=O)=O)CC3)n2)c1F] | 679 | 1H NMR (400 MHz, DMSO-d6) δ ppm 10.09 (s, 1 H) 8.00 (br. s., 1 H) 7.38-7.51 (m, 2 H) 7.35 (t, J = 6.9 Hz, 1 H) 7.10-7.32 (m, 4 H) 5.70-6.09 (m, 1 H) 3.67-3.82 (m, 3 H) 3.48 (dd, J = 1.7, 1.1 Hz, 3 H) 3.26 (d, J = 6.8 Hz, 1 H) 2.85 (s, 3 H) 2.64-2.82 (m, 2 H) 1.74-1.95 (m, 2 H) 1.39-1.59 (m, 2 H) 1.32 (d, J = 6.8 Hz, 6 H) |

| Ex | Structure | m/z [M + H]+ | 1H NMR |
|---|---|---|---|
| 154 | 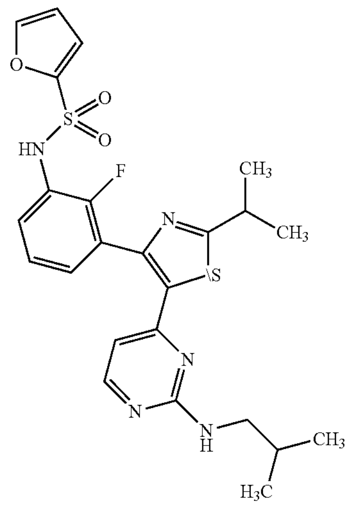 | 516 | 1H NMR (400 MHz, DMSO-d6) δ ppm 10.59 (s, 1 H) 8.06 (d, J = 5.1 Hz, 1 H) 7.91 (s, 1 H) 7.27-7.40 (m, 3 H) 7.24 (t, J = 7.8 Hz, 1 H) 7.04 (d, J = 3.2 Hz, 1 H) 6.56 (dd, J = 3.2, 1.7 Hz, 1 H) 5.77-6.01 (m, 1 H) 3.22-3.27 (m, 1 H) 2.83-3.12 (m, 2 H) 1.64-1.95 (m, 1 H) 1.33 (d, J = 6.9 Hz, 6 H) 0.74-0.91 (m, 6 H) |
| 155 | 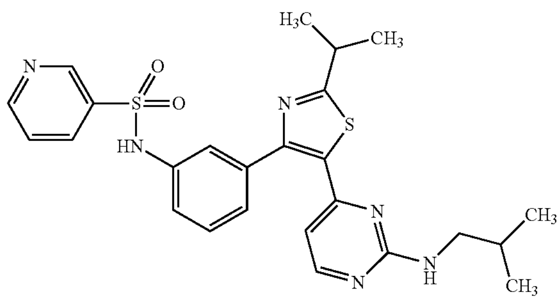 [SMILES: CC(C)CNc1nccc(-c2sc(C(C)C)nc2-c2cccc(NS(=O)(=O)c3cccnc3)c2)n1] | 509 | 1H NMR (400 MHz, DMSO-d6) δ ppm 10.56 (s, 1 H) 8.83 (d, J = 2.3 Hz, 1 H) 8.74 (dd, J = 4.8, 1.0 Hz, 1 H) 8.04-8.15 (m, 1 H) 7.98 (d, J = 5.1 Hz, 1 H) 7.56 (dd, J = 8.1, 4.9 Hz, 1 H) 7.25-7.38 (m, 2 H) 7.04-7.25 (m, 3 H) 5.91-6.05 (m, 1 H) 3.17-3.27 (m, 1 H) 2.87-3.11 (m, 2 H) 1.65-1.86 (m, 1 H) 1.22-1.38 (m, 6 H) 0.71-0.89 (m, 6 H) |
| 156 | 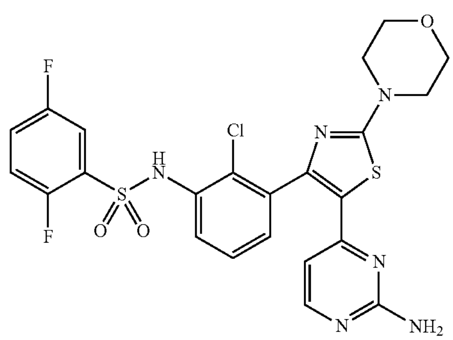 [SMILES: Nc1nccc(-c2sc(N3CCOCC3)nc2-c2cccc(NS(=O)(=O)c3cc(F)ccc3F)c2Cl)n1] | 565 | 1H NMR (400 MHz, DMSO-d6) δ ppm 10.76 (br. s., 1 H) 7.91 (d, J = 6.5 Hz, 1 H), 7.52-7.60 (m, 3 H), 7.47-7.52 (m, 3 H), 7.39 (dd, J = 5.8, 3.5 Hz, 1 H), 5.60 (d, J = 6.5 Hz, 1 H), 3.68-3.77 (m, 4 H), 3.55 (d, J = 4.3 Hz, 4 H) |
| 157 | 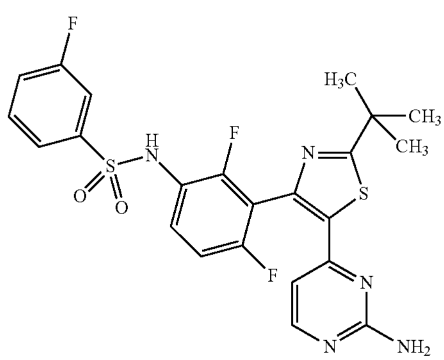 [SMILES: CC(C)(C)c1nc(-c2c(F)ccc(NS(=O)(=O)c3cccc(F)c3)c2F)c(-c2ccnc(N)n2)s1] | 520 | 1H NMR (400 MHz, DMSO-d6) δ ppm 10.43 (s, 1 H), 8.05 (d, J = 5.1 Hz, 1 H), 7.37-7.67 (m, 5 H), 7.23 (t, J = 8.8 Hz, 1 H) 6.77 (br. s., 2 H), 5.82 (d, J = 5.1 Hz, 1 H), 1.37 (s, 9 H). |

| Ex | Structure | m/z [M + H]+ | 1H NMR |
|---|---|---|---|
| 158 | 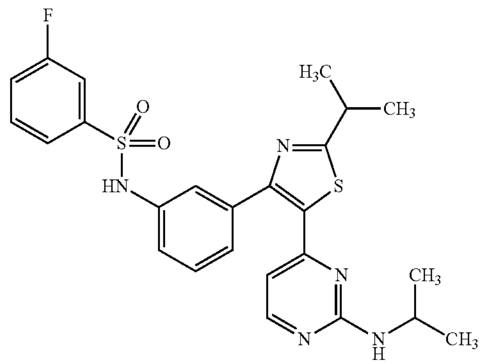 [SMILES: CC(C)Nc1nccc(-c2sc(C(C)C)nc2-c2cccc(NS(=O)(=O)c3cccc(F)c3)c2)n1] | 512.1 | 1H NMR (400 MHz, DMSO-d6) δ ppm 10.47 (s, 1 H), 7.96 (d, J = 4.8 Hz, 1 H), 7.44-7.58 (m, 4 H), 7.28 (t, J = 7.6 Hz, 1 H), 7.15-7.18 (m, 4 H), 7.08 (d, J = 7.3 Hz, 1 H), 5.97 (s, 1 H), 3.93 (bs, 1 H), 3.23 (m, 1 H), 1.30 (d, J = 6.6 Hz, 6 H), 1.09 (d, J = 7.1 Hz, 6 H) |
| 159 | 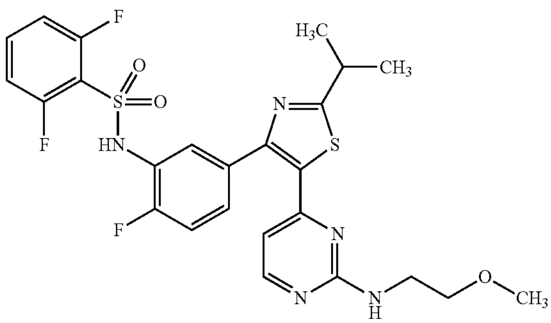 [SMILES: COCCNc1nccc(-c2sc(C(C)C)nc2-c2ccc(F)c(NS(=O)(=O)c3c(F)cccc3F)c2)n1] | 564.2 | 1H NMR (400 MHz, DMSO-d6) δ ppm 10.88 (s, 1 H), 8.00 (d, J = 4.4 Hz, 1 H), 7.60 (bs, 1 H), 7.35 (d, J = 7.9 Hz, 1 H), 7.06-7.21 (m, 5 H), 6.12 (s, 1 H), 3.34-3.41 (m, 4 H), 3.22-3.26 (m, 1 H), 3.21 (s, 3 H), 1.31 (d, J = 6.9 Hz, 6 H) |
| 160 | 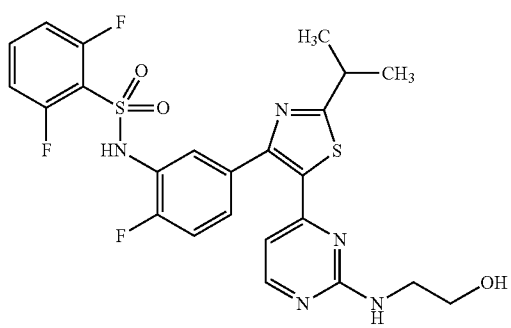 [SMILES: CC(C)c1nc(-c2ccc(F)c(NS(=O)(=O)c3c(F)cccc3F)c2)c(-c2ccnc(NCCO)n2)s1] | 550.2 | 1H NMR (400 MHz, DMSO-d6) δ ppm 10.93 (s, 1 H), 8.02 (d, J = 5.9 Hz, 1 H), 7.60 (s, 1 H), 7.39 (d, J = 7.9 Hz, 1 H), 7.05-7.25 (m, 5 H), 6.14 (s, 1 H), 4.66 (s, 1 H), 3.51 (bs, 2 H), 3.23-3.30 (m, 1 H), 1.36 (d, J = 7.0 Hz, 6 H) |
| 161 | 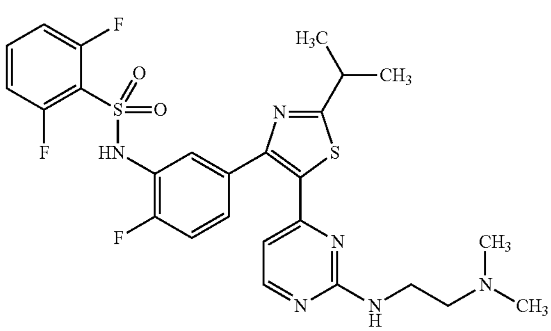 [SMILES: CC(C)c1nc(-c2ccc(F)c(NS(=O)(=O)c3c(F)cccc3F)c2)c(-c2ccnc(NCCN(C)C)n2)s1] | 577.2 | 1H NMR (400 MHz, DMSO-d6) δ ppm 8.00 (d, J = 5.3 Hz, 1 H), 7.40-7.48 (m,1 H), 7.35 (d, J = 7.5 Hz, 1 H), 7.22 (t, J = 5.4 Hz, 1 H), 6.98-7.07 (m, 3 H), 6.88 (s, 1 H), 6.22 (s, 1 H), 3.24-3.31 (m, 1 H), 2.85 (bs, 2 H), 2.53 (s, 6 H), 1.35 (d, J = 6.9 Hz, 6 H) |

| Ex | Structure | m/z [M + H]+ | 1H NMR |
|---|---|---|---|
| 162 | 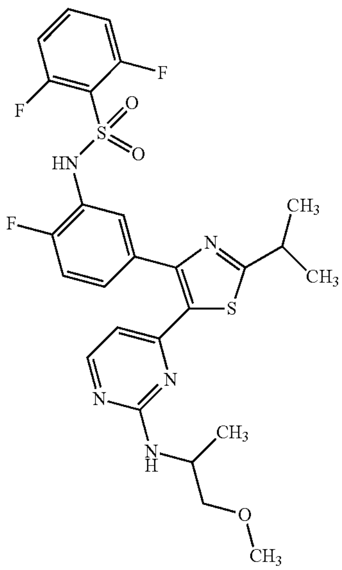 [SMILES: COCC(C)Nc1nccc(-c2sc(C(C)C)nc2-c2ccc(F)c(NS(=O)(=O)c3c(F)cccc3F)c2)n1] | 578.2 | 1H NMR (400 MHz, DMSO-d6) δ ppm 10.93 (s, 1 H), 8.08 (d, J = 5.1 Hz, 1 H), 7.72 (t, J = 4.4 Hz, 1 H), 7.39-7.45 (m, 2 H), 7.24-7.30 (m, 3 H), 7.11 (d, J = 8.0 Hz, 1 H), 6.17 (s, 1 H), 3.38-3.41 (m, 1 H), 3.27-3.31 (m, 2 H), 3.26 (s, 3 H), 1.36 (d, J = 6.8 Hz, 6 H), 1.12 (d, J = 6.6 Hz, 3 H) |
| 163 | 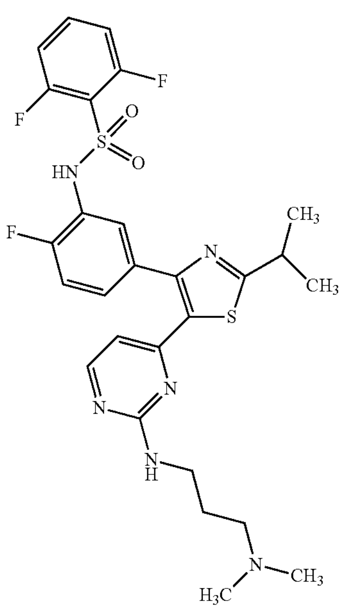 [SMILES: CC(C)c1nc(-c2ccc(F)c(NS(=O)(=O)c3c(F)cccc3F)c2)c(-c2ccnc(NCCCN(C)C)n2)s1] | 591.2 | 1H NMR (400 MHz, DMSO-d6) δ ppm 8.02 (s, 1 H), 7.40 (t, J = 8.4 Hz, 1 H), 7.26-7.32 (m, 2 H), 6.92-7.05 (m, 4 H), 6.28 (bs, 1 H), 3.25-3.30 (m, 1 H), 2.84 (t, J = 7.2 Hz, 2 H), 2.60 (s, 6 H), 1.76 (bs, 2 H), 1.36 (d, J = 6.9 Hz, 6 H) |

| Ex | Structure | m/z [M+H]+ | 1H NMR |
|---|---|---|---|
| 164 | 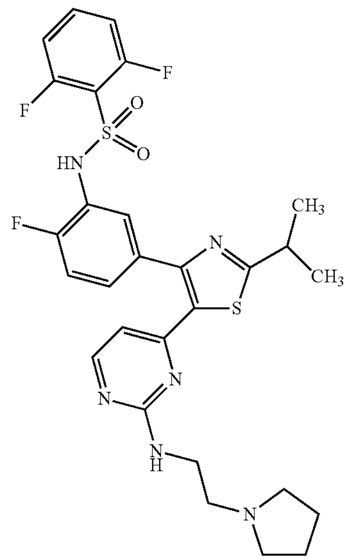 [SMILES: CC(C)c1nc(-c2ccc(F)c(NS(=O)(=O)c3c(F)cccc3F)c2)c(-c2ccnc(NCCN3CCCC3)n2)s1] | 603.3 | 1H NMR (400 MHz, DMSO-d6) δ ppm 8.01 (d, J = 5.1 Hz, 1 H), 7.33-7.41 (m, 2 H), 7.28 (s, 1 H), 6.95-7.03 (m, 4 H), 6.80 (s, 1 H), 6.24 (bs, 1 H), 3.48 (s, 2 H), 3.23-3.30 (m, 1 H), 3.04 (s, 4 H), 1.85 (s, 4 H), 1.36 (d, J = 6.8 Hz, 6 H) |
| 165 | 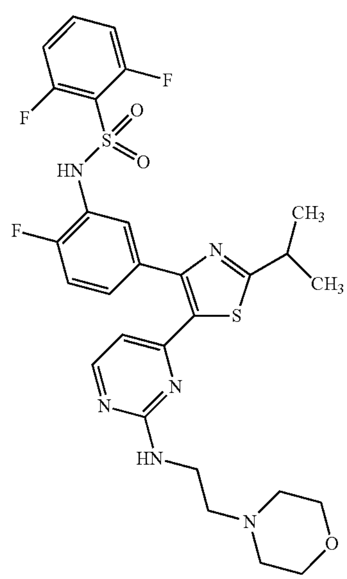 [SMILES: CC(C)c1nc(-c2ccc(F)c(NS(=O)(=O)c3c(F)cccc3F)c2)c(-c2ccnc(NCCN3CCOCC3)n2)s1] | 619.3 | 1H NMR (400 MHz, DMSO-d6) δ ppm 8.05 (d, J = 5.1 Hz, 1 H), 7.61-7.68 (m, 1 H), 7.42 (d, J = 6.1 Hz, 1 H), 7.17-7.25 (m, 5 H), 7.13 (t, J = 5.3 Hz, 1 H), 6.18 (s, 1 H), 3.58 (t, J = 4.3 Hz, 4 H), 3.25-3.32 (m, 1 H), 2.52 (s, 2 H), 2.47 (s, 4 H), 1.36 (d, J = 7.0 Hz, 6 H) |

| Ex | Structure | m/z [M + H]+ | 1H NMR |
|---|---|---|---|
| 166 | 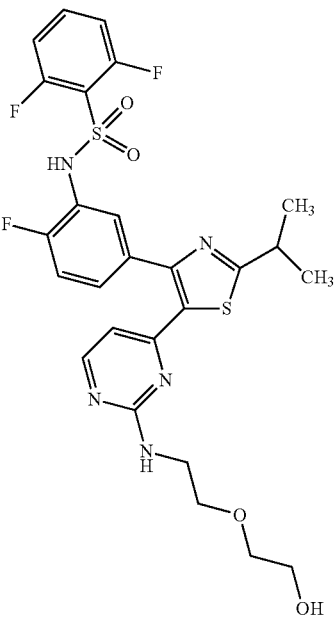 [SMILES: CC(C)c1nc(-c2ccc(F)c(NS(=O)(=O)c3c(F)cccc3F)c2)c(-c2ccnc(NCCOCCO)n2)s1] | 594.2 | 1H NMR (400 MHz, DMSO-d6) δ ppm 10.93 (s, 1 H), 8.06 (d, J = 5.1 Hz, 1 H), 7.67 (bs, 1 H), 7.41 (d, J = 7.7 Hz, 1 H), 7.17-7.32 (m, 4 H), 6.18 (s, 1 H), 4.62 (t, J = 5.3 Hz, 1 H), 3.41-3.54 (m, 8 H), 3.25-3.32 (m, 1 H), 1.36 (d, J = 6.6 Hz, 6 H) |
| 167 | 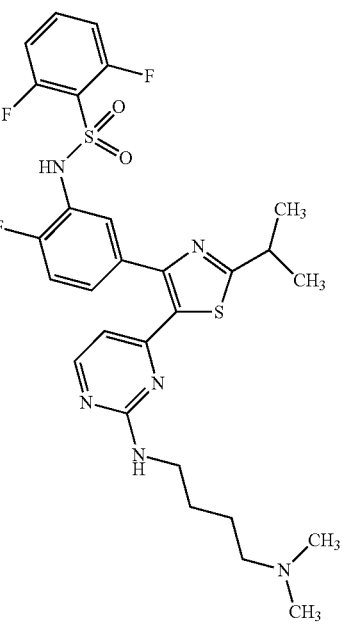 | 605.3 | 1H NMR (400 MHz, DMSO-d6) δ ppm 7.98 (d, J = 5.2 Hz, 1 H), 7.39 (t, J = 7.4 Hz, 1 H), 7.24-7.31 (m, 2 H), 6.93-7.02 (m, 3 H), 6.80 (bs, 1 H), 6.22 (bs, 1 H), 3.23-3.30 (m, 1 H), 3.19 (bs, 4 H), 2.84 (t, J = 7.6 Hz, 2 H), 2.61 (s, 6 H), 1.56 (bs, 2 H), 1.49 (bs, 2 H), 1.35 (d, J = 7.0 Hz, 6 H) |

| Ex | Structure | m/z [M+H]+ | 1H NMR |
|---|---|---|---|
| 168 | 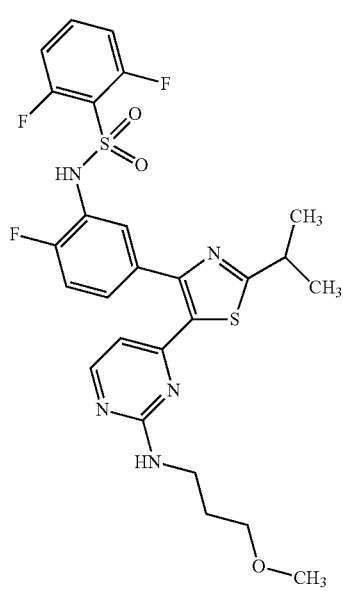 [SMILES: COCCCNc1nccc(-c2sc(C(C)C)nc2-c2ccc(F)c(NS(=O)(=O)c3c(F)cccc3F)c2)n1] | 578.2 | 1H NMR (400 MHz, DMSO-d6) δ ppm 10.93 (s, 1 H), 8.06 (d, J = 5.1 Hz, 1 H), 7.67 (t, J = 6.6 Hz, 1 H), 7.42 (dd, J = 2.1, 7.6 Hz, 1 H), 7.20-7.31 (m, 5 H), 6.17 (s, 1 H), 3.25-3.38 (m, 5 H), 3.13 (s, 3 H), 1.75 (t, J = 6.6 Hz, 2 H), 1.36 (d, J = 7.0 Hz, 6 H) |
| 169 | 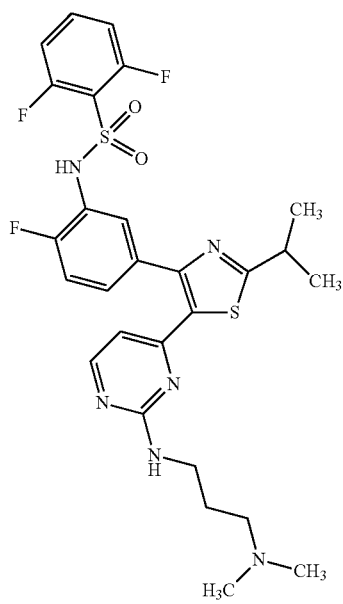 [SMILES: CC(C)c1nc(-c2ccc(F)c(NS(=O)(=O)c3c(F)cccc3F)c2)c(-c2ccnc(NCCCN(C)C)n2)s1] | 591.2 | 1H NMR (400 MHz, DMSO-d6) δ ppm 8.02 (s, 1 H), 7.40 (t, J = 8.4 Hz, 1 H), 7.26-7.32 (m, 2 H), 6.92-7.05 (m, 4 H), 6.28 (bs, 1 H), 3.25-3.30 (m, 1 H), 2.84 (t, J = 7.2 Hz, 2 H), 2.60 (s, 6 H), 1.76 (bs, 2 H), 1.36 (d, J = 6.9 Hz, 6 H) |

| Ex | Structure | m/z [M+H]+ | 1H NMR |
|---|---|---|---|
| 170 | 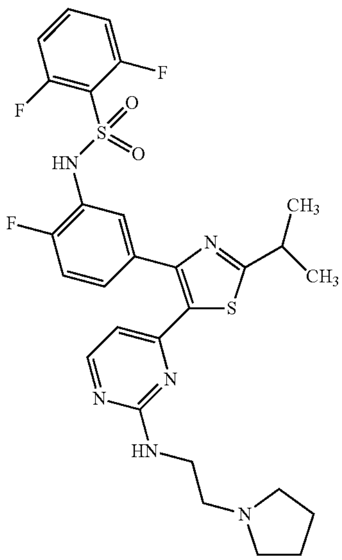 [SMILES: CC(C)c1nc(-c2ccc(F)c(NS(=O)(=O)c3c(F)cccc3F)c2)c(-c2ccnc(NCCN3CCCC3)n2)s1] | 603.3 | 1H NMR (400 MHz, DMSO-d6) δ ppm 8.01 (d, J = 5.1 Hz, 1 H), 7.33-7.41 (m, 2 H), 7.28 (s, 1 H), 6.95-7.03 (m, 4 H), 6.80 (s, 1 H), 6.24 (bs, 1 H), 3.48 (s, 2 H), 3.23-3.30 (m, 1 H), 3.04 (s, 4 H), 1.85 (s, 4 H), 1.36 (d, J = 6.8 Hz, 6 H) |
| 171 | 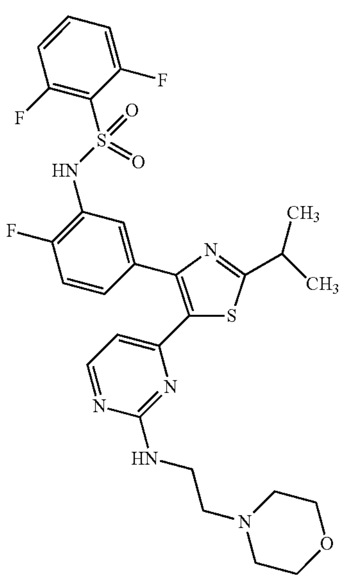 [SMILES: CC(C)c1nc(-c2ccc(F)c(NS(=O)(=O)c3c(F)cccc3F)c2)c(-c2ccnc(NCCN3CCOCC3)n2)s1] | 619.3 | 1H NMR (400 MHz, DMSO-d6) δ ppm 8.05 (d, J = 5.1 Hz, 1 H), 7.61-7.68 (m, 1 H), 7.42 (d, J = 6.1 Hz, 1 H), 7.17-7.25 (m, 5 H), 7.13 (t, J = 5.3 Hz, 1 H), 6.18 (s, 1 H), 3.58 (t, J = 4.3 Hz, 4 H), 3.25-3.32 (m, 1 H), 2.52 (s, 2 H), 2.47 (s, 4 H), 1.36 (d, J = 7.0 Hz, 6 H) |

| Ex | Structure | m/z [M + H]+ | 1H NMR |
|---|---|---|---|
| 172 | 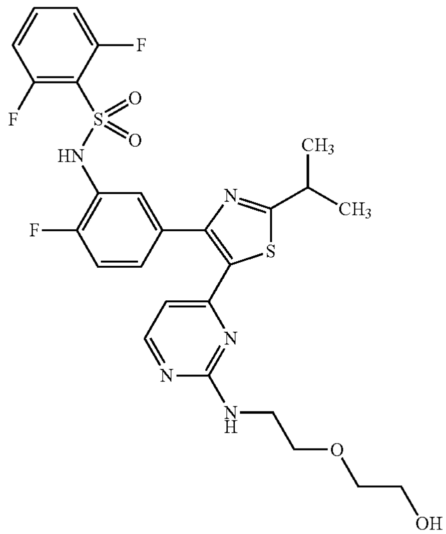 [SMILES: CC(C)c1nc(-c2ccc(F)c(NS(=O)(=O)c3c(F)cccc3F)c2)c(-c2ccnc(NCCOCCO)n2)s1] | 594.2 | 1H NMR (400 MHz, DMSO-d6) δ ppm 10.93 (s, 1 H), 8.06 (d, J = 5.1 Hz, 1 H), 7.67 (bs, 1 H), 7.41 (d, J = 7.7 Hz, 1 H), 7.17-7.32 (m, 4 H), 6.18 (s, 1 H), 4.62 (t, J = 5.3 Hz, 1 H), 3.41-3.54 (m, 8 H), 3.25-3.32 (m, 1 H), 1.36 (d, J = 6.6 Hz, 6 H) |
| 173 | 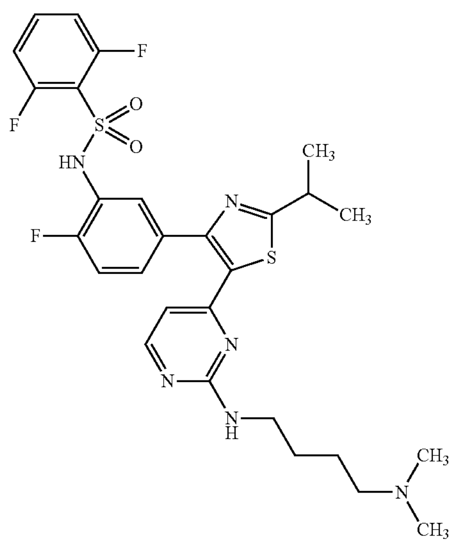 [SMILES: CC(C)c1nc(-c2ccc(F)c(NS(=O)(=O)c3c(F)cccc3F)c2)c(-c2ccnc(NCCCCN(C)C)n2)s1] | 605.3 | 1H NMR (400 MHz, DMSO-d6) δ ppm 7.98 (d, J = 5.2 Hz, 1 H), 7.39 (t, J = 7.4 Hz, 1 H), 7.24-7.31 (m, 2 H), 6.93-7.02 (m, 3 H), 6.80 (bs, 1 H), 6.22 (s, 1 H), 3.23-3.30 (m, 1 H), 3.19 (bs, 4 H), 2.84 (t, J = 7.6 Hz, 2 H), 2.61 (s, 6 H), 1.56 (bs, 2 H), 1.49 (bs, 2 H), 1.35 (d, J = 7.0 Hz, 6 H) |
| 174 | 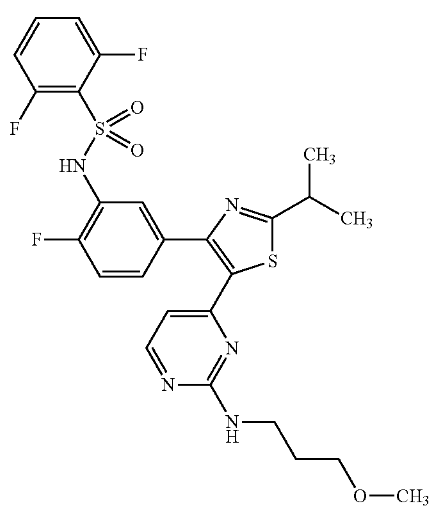 [SMILES: COCCCNc1nccc(-c2sc(C(C)C)nc2-c2ccc(F)c(NS(=O)(=O)c3c(F)cccc3F)c2)n1] | 578.2 | 1H NMR (400 MHz, DMSO-d6) δ ppm 10.93 (s, 1 H), 8.06 (d, J = 5.1 Hz, 1 H), 7.67 (t, J = 6.6 Hz, 1 H), 7.42 (dd, J = 2.1, 7.6 Hz, 1 H), 7.20-7.31 (m, 5 H), 6.17 (s, 1 H), 3.25-3.38 (m, 5 H), 3.13 (s, 3 H), 1.75 (t, J = 6.6 Hz, 2 H), 1.36 (d, J = 7.0 Hz, 6 H) |

| Ex | Structure | m/z [M + H]+ | 1H NMR |
|---|---|---|---|
| 175 | 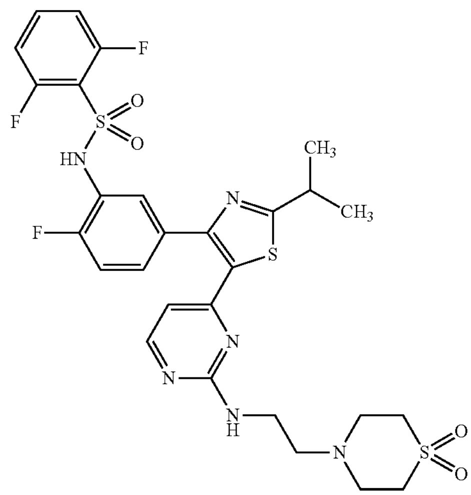 [SMILES: CC(C)c1nc(-c2ccc(F)c(NS(=O)(=O)c3c(F)cccc3F)c2)c(-c2ccnc(NCCN3CCS(=O)(=O)CC3)n2)s1] | 667.1 | 1H NMR (400 MHz, DMSO-d6) δ ppm 10.94 (s, 1 H), 8.06 (d, J = 5.0 Hz, 1 H), 7.66 (t, J = 6.9 Hz, 1 H), 7.42 (d, J = 6.8 Hz, 1 H), 7.18-7.27 (m, 5 H), 6.19 (s, 1 H), 3.24-3.31 (m, 1 H), 3.07 (s, 4 H), 2.96 (s, 4 H), 2.65 (t, J = 6.1 Hz, 2 H), 1.36 (d, J = 6.8 Hz, 6 H) |
| 176 | 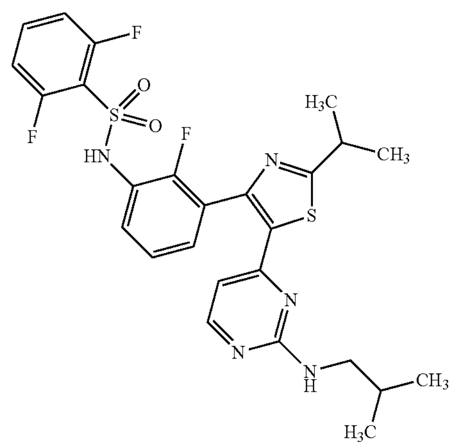 [SMILES: CC(C)CNc1nccc(-c2sc(C(C)C)nc2-c2cccc(NS(=O)(=O)c3c(F)cccc3F)c2F)n1] | 562.2 | 1H NMR (400 MHz, DMSO-d6) δ ppm 10.88 (s, 1 H), 8.02 (d, J = 5.3 Hz, 1 H), 7.67 (t, J = 8.4 Hz, 1 H), 7.42 (t, J = 7.3 Hz, 1 H), 7.21-7.36 (m, 5 H), 5.92 (bs, 1 H), 3.25-3.31 (m, 1 H), 3.05 (bs,1 1 H), 2.96 (bs, 1 H), 1.81 (bs, 1 H), 1.35 (d, J = 6.9 Hz, 6 H), 0.86 (d, J = 6.6 Hz, 6 H) |
| 177 | 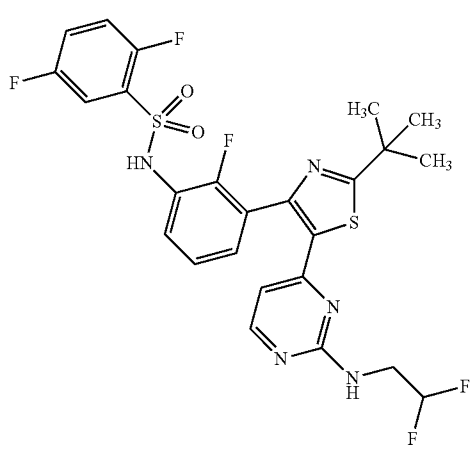 [SMILES: CC(C)(C)c1nc(-c2cccc(NS(=O)(=O)c3cc(F)ccc3F)c2F)c(-c2ccnc(NCC(F)F)n2)s1] | 584.0 | 1H NMR (400 MHz, DMSO-d6) δ ppm 10.76 (s, 1 H), 8.12 (d, J = 5.1 Hz, 1 H), 7.63 (t, J = 6.2 Hz, 1 H), 7.36-7.59 (m, 5 H), 7.28 (t, J = 7.9 Hz, 1 H), 6.04 (bs, 2 H), 3.55 (bs, 2 H), 1.41 (s, 9 H) |

-continued

| Ex | Structure | m/z [M + H]+ | 1H NMR |
|---|---|---|---|
| 178 | 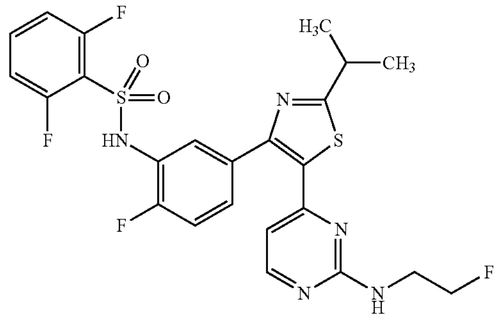 [SMILES: CC(C)c1nc(-c2ccc(F)c(NS(=O)(=O)c3c(F)cccc3F)c2)c(-c2ccnc(NCCF)n2)s1] | 552.1 | 1H NMR (400 MHz, DMSO-d6) δ ppm 10.93 (s, 1 H), 8.11 (d, J = 5.2 Hz, 1 H), 7.72 (t, J = 7.4 Hz, 1 H), 7.48 (t, J = 5.7 Hz, 1 H), 7.38-7.44 (m, 2 H), 7.24-7.30 (m, 3 H), 6.23 (bs, 1 H), 4.56 (bs, 1 H), 4.45 (bs, 1 H), 3.57 (bs, 1 H), 3.51 (bs, 1 H), 3.26-3.31 (m, 1 H), 1.36 (d, J = 6.9 Hz, 6 H) |
| 179 | 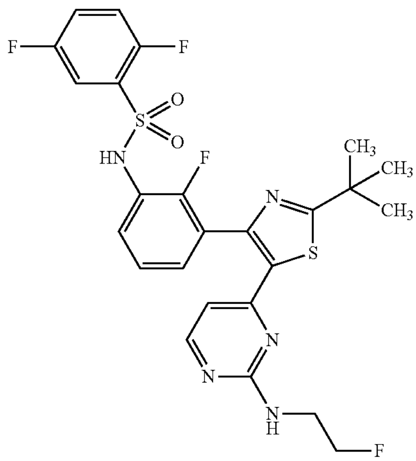 [SMILES: CC(C)(C)c1nc(-c2cccc(NS(=O)(=O)c3cc(F)ccc3F)c2F)c(-c2ccnc(NCCF)n2)s1] | 566.2 | 1H NMR (400 MHz, DMSO-d6) δ ppm 10.76 (s, 1 H), 8.07 (d, J = 5.1 Hz, 1 H), 7.35-7.57 (m, 6 H), 7.28 (t, J = 7.8 Hz, 1 H), 6.01 (bs, 1 H), 4.53 (bs, 1 H), 4.41 (bs, 1 H), 3.47 (bs, 2 H), 1.40 (s, 9 H) |
| 180 | 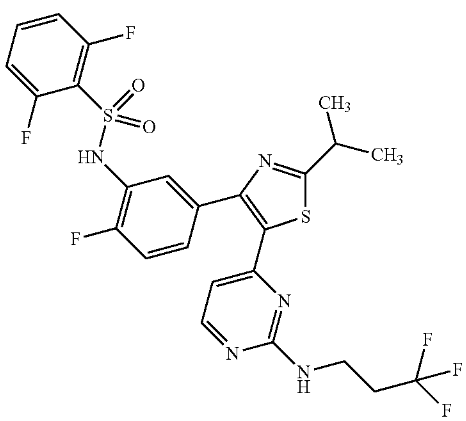 [SMILES: CC(C)c1nc(-c2ccc(F)c(NS(=O)(=O)c3c(F)cccc3F)c2)c(-c2ccnc(NCCC(F)(F)F)n2)s1] | 602.1 | 1H NMR (400 MHz, DMSO-d6) δ ppm 10.93 (s, 1 H), 8.13 (d, J = 5.1 Hz, 1 H), 7.72 (t, J = 8.5 Hz, 1 H), 7.38-7.48 (m, 3 H), 7.24-7.30 (m, 3 H), 6.26 (bs, 1 H), 3.46 (bs, 2 H), 3.25-3.32 (m, 1 H), 2.51 (bs, 2 H), 1.36 (d, J = 6.8 Hz, 6 H) |
| 181 | 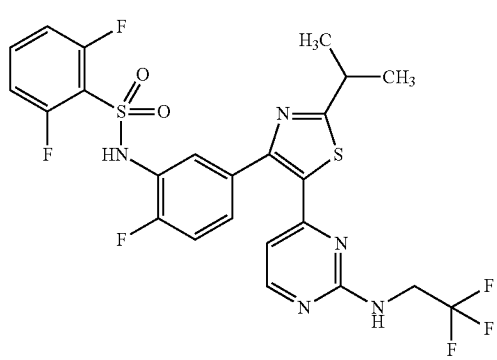 [SMILES: CC(C)c1nc(-c2ccc(F)c(NS(=O)(=O)c3c(F)cccc3F)c2)c(-c2ccnc(NCC(F)(F)F)n2)s1] | 589.1 | 1H NMR (400 MHz, DMSO-d6) δ ppm 10.98 (s, 1 H), 8.45 (d, J = 5.2 Hz, 1 H), 7.67 (t, J = 6.7 Hz, 6 H), 7.41 (d, J = 7.6 Hz, 1 H), 7.35 (bs, 1 H), 7.28 (t, J = 9.4 Hz, 1 H), 7.24 (t, J = 9.0 Hz, 2 H), 6.84 (d, J = 5.2 Hz, 1 H), 4.94 (q, J = 8.9 Hz, 2 H), 3.28-3.31 (m, 1 H), 1.38 (d, J = 7.1 Hz, 9 H) |

| Ex | Structure | m/z [M+H]+ | ¹H NMR |
|---|---|---|---|
| 182 | 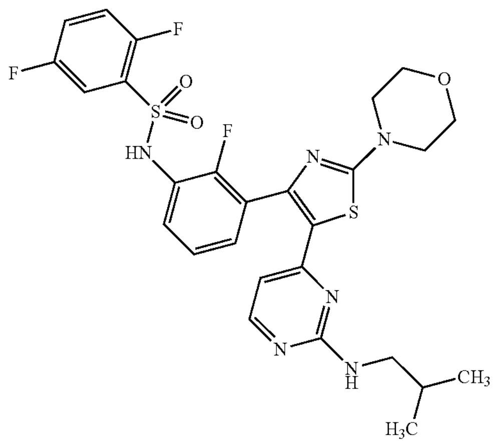 [SMILES: CC(C)CNc1nccc(-c2sc(N3CCOCC3)nc2-c2cccc(NS(=O)(=O)c3cc(F)ccc3F)c2F)n1] | 605.3 | ¹H NMR (400 MHz, DMSO-d₆) δ ppm 10.76 (s, 1 H), 7.86 (d, J = 3.2 Hz, 1 H), 7.46-7.59 (m, 3 H), 7.41 (t, J = 7.4 Hz, 1 H), 7.23-7.31 (m, 2 H), 7.15 (bs, 1 H), 5.62 (s, 1 H), 3.71 (s, 4 H), 3.45 (s, 4 H), 3.01 (bs, 2 H), 1.79-1.85 (m, 1 H), 0.87 (d, J = 6.4 Hz, 6 H) |
| 183 | 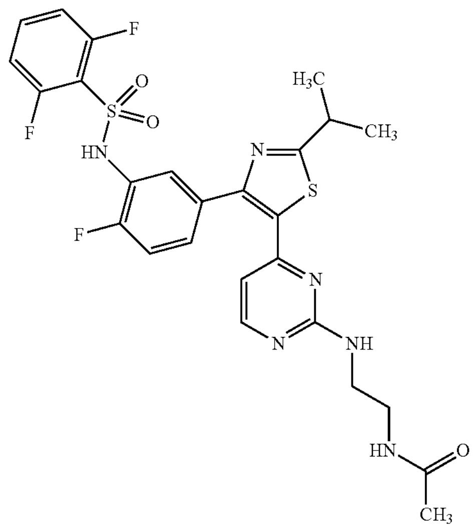 [SMILES: CC(=O)NCCNc1nccc(-c2sc(C(C)C)nc2-c2ccc(F)c(NS(=O)(=O)c3c(F)cccc3F)c2)n1] | 591 | ¹H NMR (400 MHz, DMSO-d₆) δ ppm 10.93 (s, 1 H), 8.08 (d, J = 5.1 Hz, 1 H), 7.87-8.00 (m, 1 H), 7.64-7.79 (m, 1 H), 7.34-7.50 (m, 2 H), 7.21-7.33 (m, 4 H), 6.12-6.28 (m, 1 H), 3.25-3.32 (m, 3 H), 3.17-3.24 (m, 2 H), 1.80 (s, 3 H), 1.36 (d, J = 6.9 Hz, 6 H) |
| 184 | 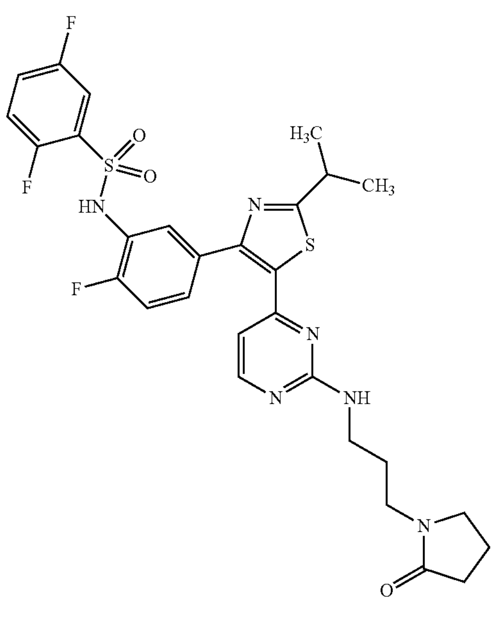 [SMILES: CC(C)c1nc(-c2ccc(F)c(NS(=O)(=O)c3cc(F)ccc3F)c2)c(-c2ccnc(NCCCN3CCCC3=O)n2)s1] | 631 | ¹H NMR (400 MHz, DMSO-d₆) δ ppm 10.80 (s, 1 H), 8.10 (d, J = 4.7 Hz, 1 H), 7.46-7.68 (m, 3 H), 7.39 (d, J = 6.5 Hz, 2 H), 7.20-7.33 (m, 2 H), 6.19 (br. s., 1 H), 3.16-3.25 (m, 4 H), 2.21 (t, 2 H), 1.85-1.97 (m, 2 H), 1.63-1.74 (m, 2 H), 1.36 (d, J = 6.8 Hz, 6 H) |

| Ex | Structure | m/z [M + H]+ | 1H NMR |
|---|---|---|---|
| 185 | 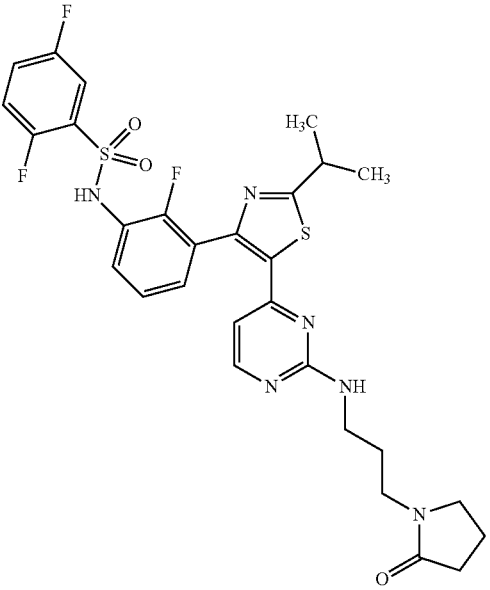 [SMILES: CC(C)c1nc(-c2cccc(NS(=O)(=O)c3cc(F)ccc3F)c2F)c(-c2ccnc(NCCCN3CCCC3=O)n2)s1] | 631 | 1H NMR (400 MHz, DMSO-d6) δ ppm 10.76 (s, 1 H), 8.03 (d, J = 5.1 Hz, 1 H), 7.45-7.61 (m, 3 H), 7.32-7.45 (m, 2 H), 7.18-7.32 (m, 2 H), 5.87 (br. s., 1 H), 3.08-3.25 (m, 4 H), 2.22 (t, J = 8.0 Hz, 2 H), 1.85-1.98 (m, 2 H), 1.66 (br. s., 2 H), 1.35 (d, J = 6.9 Hz, 6 H) |
| 186 | 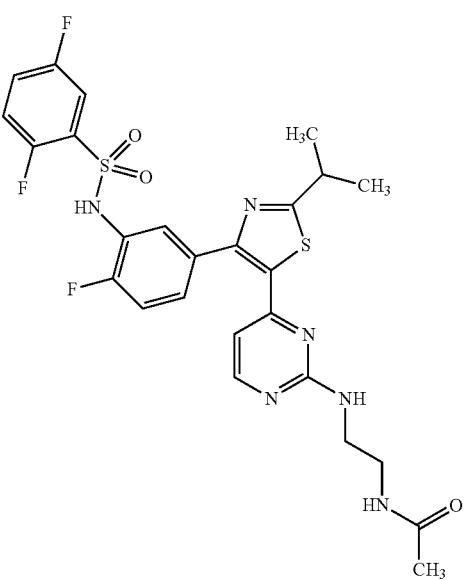 [SMILES: CC(=O)NCCNc1nccc(-c2sc(C(C)C)nc2-c2ccc(F)c(NS(=O)(=O)c3cc(F)ccc3F)c2)n1] | 591 | 1H NMR (400 MHz, DMSO-d6) δ ppm 10.80 (s, 1 H), 8.10 (d, J =4.7 Hz, 1 H), 7.92 (br. s., 1 H), 7.45-7.67 (m, 3 H), 7.39 (d, J = 6.7 Hz, 2 H), 7.23-7.33 (m, 2 H), 6.20 (br. s., 1 H), 3.25-3.32 (m, 2 H), 3.13-3.25 (m, 2 H), 1.80 (s, 3 H), 1.36 (d, J = 6.9 Hz, 6 H) |

| Ex | Structure | m/z [M + H]+ | 1H NMR |
|---|---|---|---|
| 187 | 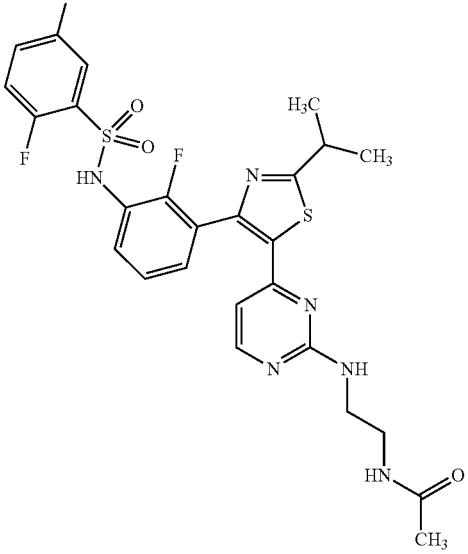 | 591 | 1H NMR (400 MHz, DMSO-d6) δ ppm 10.76 (s, 1 H), 8.04 (d, J = 5.2 Hz, 1 H), 7.91 (br. s., 1 H), 7.45-7.63 (m, 3 H), 7.32-7.45 (m, 2 H), 7.22-7.31 (m, 2 H), 5.90 (br. s., 1 H), 3.14-3.31 (m, 5 H), 1.80 (s, 3 H), 1.35 (d, J = 6.9 Hz, 6 H) |
| 188 | 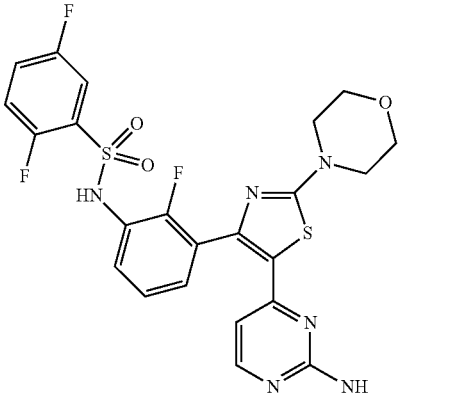 | 674 | 1H NMR (400 MHz, DMSO-d6) δ ppm 10.76 (s, 1 H), 7.87 (d, J = 5.1 Hz, 1 H), 7.45-7.63 (m, 3 H), 7.37-7.45 (m, 1 H), 7.22-7.33 (m, 2 H), 7.06 (br. s., 1 H), 5.60-5.68 (m, 2 H), 3.66-3.75 (m, 4 H), 3.41-3.52 (m, 4 H), 3.11-3.26 (m, 4 H), 2.21 (t, J =8.1 Hz, 2 H), 1.84-1.98 (m, 2 H), 1.59-1.74 (m, 2 H) |

| Ex | Structure | m/z [M+H]+ | ¹H NMR |
|---|---|---|---|
| 189 | 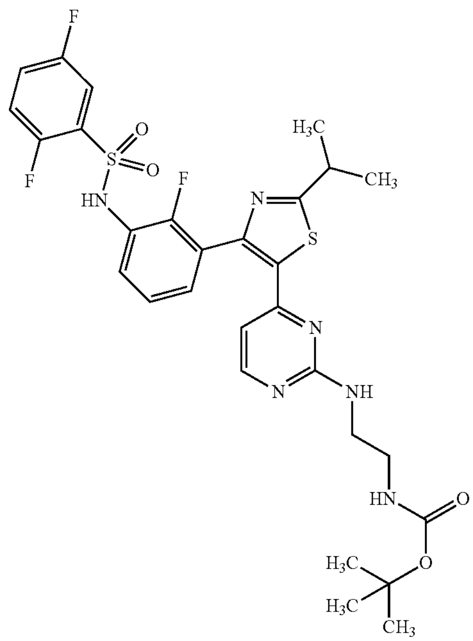 [SMILES: CC(C)c1nc(-c2cccc(NS(=O)(=O)c3cc(F)ccc3F)c2F)c(-c2ccnc(NCCNC(=O)OC(C)(C)C)n2)s1] | 649 | ¹H NMR (400 MHz, DMSO-d₆) δ ppm 10.75 (s, 1 H), 8.03 (d, J = 5.1 Hz, 1 H), 7.13-7.66 (m, 7 H), 6.84 (br. s., 1 H), 5.80-6.02 (m, 1 H), 3.19-3.31 (m, 3 H), 3.02-3.13 (m, 2 H), 1.30-1.41 (m, 15 H) |
| 190 | 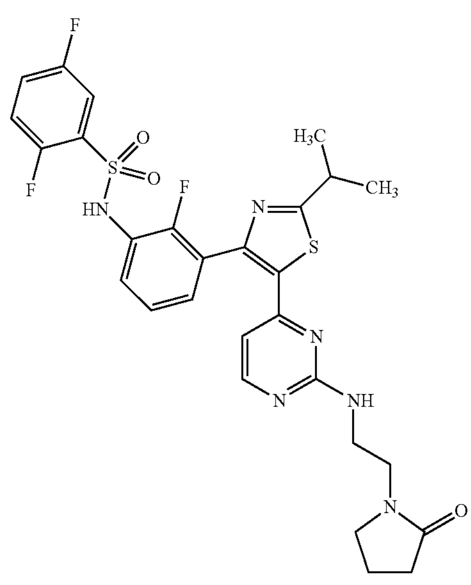 [SMILES: CC(C)c1nc(-c2cccc(NS(=O)(=O)c3cc(F)ccc3F)c2F)c(-c2ccnc(NCCN3CCCC3=O)n2)s1] | 617 | ¹H NMR (400 MHz, DMSO-d₆) δ ppm 10.77 (s, 1 H), 8.04 (d, J = 4.6 Hz, 1 H), 7.14-7.69 (m, 7 H), 5.90 (br. s., 1 H), 3.39 (t, J = 6.7 Hz, 2 H), 2.17 (t, J = 7.8 Hz, 2 H), 1.81-1.94 (m, 2 H), 1.35 (d, J = 6.8 Hz, 6 H) |

| Ex | Structure | m/z [M + H]+ | 1H NMR |
|---|---|---|---|
| 191 | 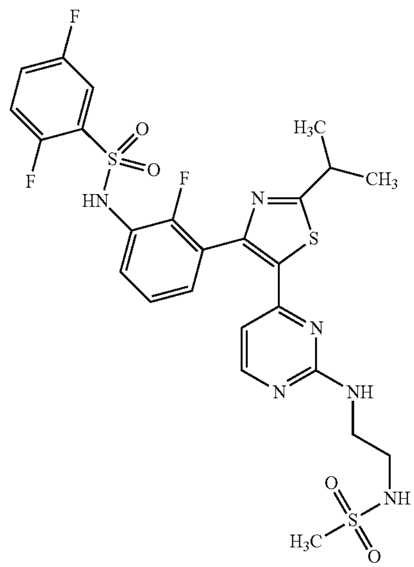 [SMILES: CC(C)c1nc(-c2cccc(NS(=O)(=O)c3cc(F)ccc3F)c2F)c(-c2ccnc(NCCNS(C)(=O)=O)n2)s1] | 627 | 1H NMR (400 MHz, DMSO-d6) δ ppm 10.76 (s, 1 H), 8.05 (d, J = 5.1 Hz, 1 H), 7.19-7.64 (m, 7 H), 7.10 (t, J = 5.5 Hz, 1 H), 5.91 (br. S., 1 H), 3.24-3.31 (m, 2 H), 3.04-3.16 (m, 2 H), 2.90 (s, 3 H), 1.35 (d, J = 7.0 Hz, 6 H) |
| 192 | 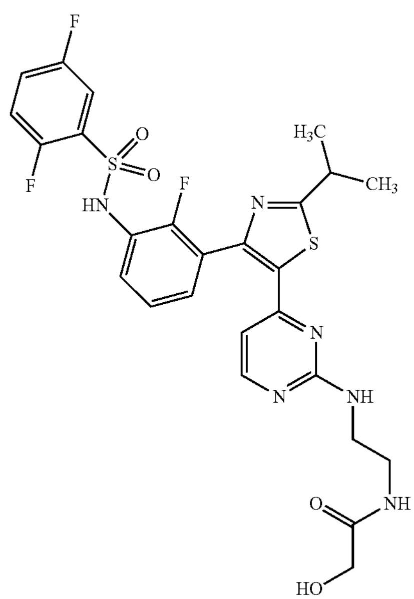 [SMILES: CC(C)c1nc(-c2cccc(NS(=O)(=O)c3cc(F)ccc3F)c2F)c(-c2ccnc(NCCNC(=O)CO)n2)s1] | 607 | 1H NMR (400 MHz, DMSO-d6) δ ppm 10.76 (br. s., 1 H), 8.04 (d, J = 5.1 Hz, 1 H), 7.77-7.98 (m, 1 H), 7.18-7.62 (m, 7 H), 5.82-6.02 (m, 1 H), 5.49 (t, J = 5.5 Hz, 1 H), 3.80 (d, J = 5.3 Hz, 2 H), 3.18-3.32 (m, 4 H), 1.35 (d, J = 7.0 Hz, 6 H) |

| Ex | Structure | m/z [M + H]+ | 1H NMR |
|---|---|---|---|
| 193 | 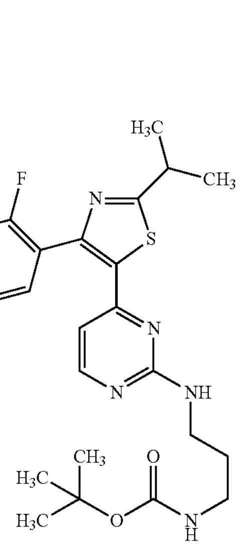 | 663 | 1H NMR (400 MHz, DMSO-d6) δ ppm 10.75 (s, 1 H), 8.02 (d, J = 4.9 Hz, 1 H), 7.14-7.66 (m, 8 H), 6.79 (br. s., 1 H), 5.79-5.97 (m, 1 H), 3.10-3.31 (m, 3 H), 2.91-3.01 (m, 2 H), 1.59 (br. s., 2 H), 1.32-1.40 (m, 15 H) |
| 194 | 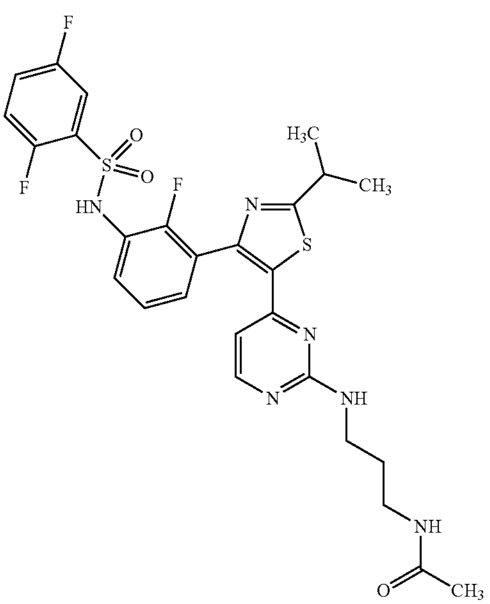 [SMILES: CC(=O)NCCCNc1nccc(-c2sc(C(C)C)nc2-c2cccc(NS(=O)(=O)c3cc(F)ccc3F)c2F)n1] | 605 | 1H NMR (400 MHz, DMSO-d6) δ ppm 10.76 (s, 1 H), 8.03 (d, J = 4.9 Hz, 1 H), 7.83 (br. s., 1 H), 7.16-7.64 (m, 7 H), 5.87 (br. s., 1 H), 3.13-3.30 (m, 3 H), 3.02-3.10 (m, 2 H), 1.80 (s, 3 H), 1.60 (br. s., 2 H), 1.35 (d, J = 6.8 Hz, 6 H) |

| Ex | Structure | m/z [M + H]+ | 1H NMR |
|---|---|---|---|
| 195 | 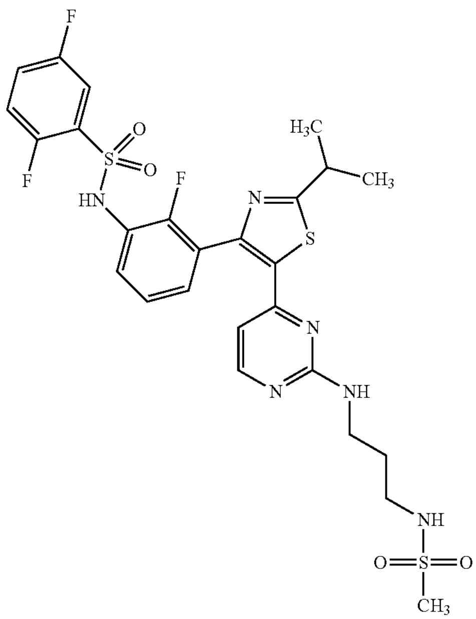 [SMILES: CC(C)c1nc(-c2cccc(NS(=O)(=O)c3cc(F)ccc3F)c2F)c(-c2ccnc(NCCCNS(C)(=O)=O)n2)s1] | 641 | 1H NMR (400 MHz, DMSO-d6) δ ppm 10.76 (s, 1 H), 8.03 (d, J = 5.1 Hz, 1 H), 7.21-7.61 (m, 7 H), 6.97 (d, J = 4.9 Hz, 1 H), 5.89 (br. s., 1 H), 3.16-3.30 (m, 3 H), 2.94-3.02 (m, 2 H), 2.88 (s, 3 H), 1.70 (br. s., 2 H), 1.35 (d, J = 6.8 Hz, 6 H) |
| 196 | 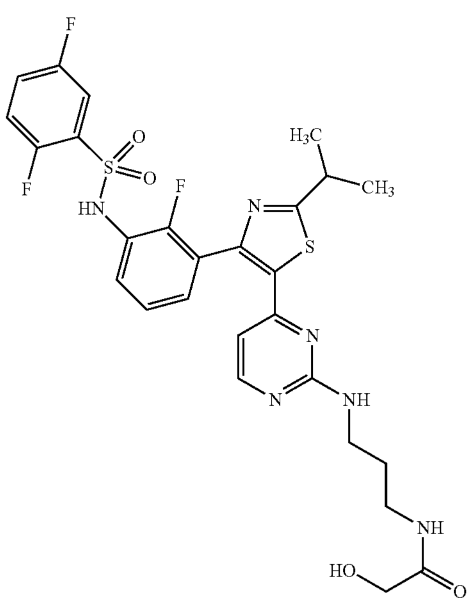 [SMILES: CC(C)c1nc(-c2cccc(NS(=O)(=O)c3cc(F)ccc3F)c2F)c(-c2ccnc(NCCCNC(=O)CO)n2)s1] | 621 | 1H NMR (400 MHz, DMSO-d6) δ ppm 10.76 (s, 1 H), 8.02 (d, J = 5.1 Hz, 1 H), 7.73-7.91 (m, 1 H), 7.20-7.64 (m, 8 H), 5.80-5.96 (m, 1 H), 3.79 (s, 2 H), 3.22-3.31 (m, 3 H), 3.07-3.20 (m, 3 H), 1.63 (br. s., 2 H), 1.35 (d, J = 6.8 Hz, 6 H) |

| Ex | Structure | m/z [M + H]⁺ | ¹H NMR |
|---|---|---|---|
| 197 | 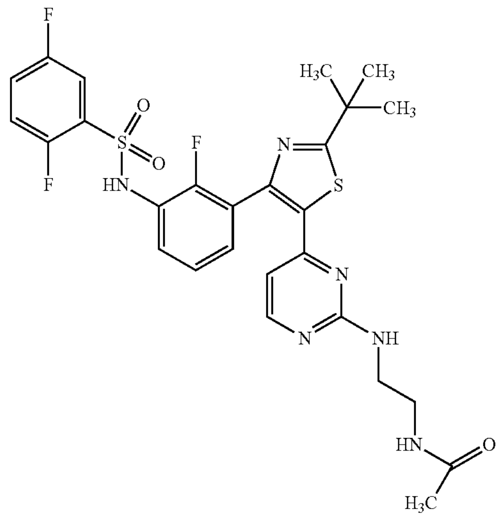 [SMILES: CC(=O)NCCNc1nccc(-c2sc(C(C)(C)C)nc2-c2cccc(NS(=O)(=O)c3cc(F)ccc3F)c2F)n1] | 605 | ¹H NMR (400 MHz, DMSO-d₆) δ ppm 10.71 (br. s., 1 H), 8.04 (d, mJ = 5.1 Hz, 1 H), 7.91 (d, J = 1.5 Hz, 1 H), 7.12-7.67 (m, 7 H), 5.83-6.09 (m, 1 H), 3.08-3.28 (m, 4 H), 1.80 (s, 3 H), 1.41 (s, 9 H) |
| 198 | 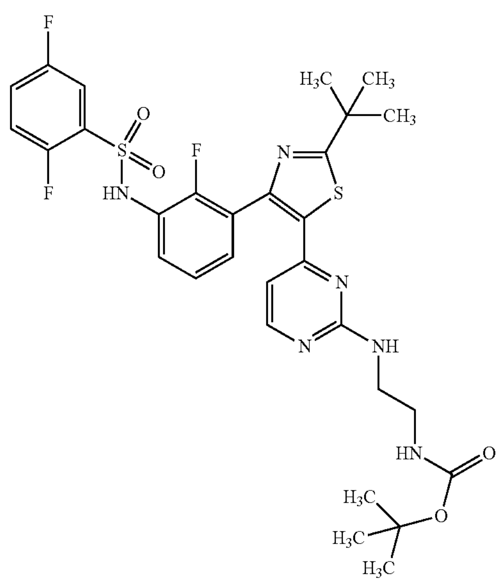 [SMILES: CC(C)(C)OC(=O)NCCNc1nccc(-c2sc(C(C)(C)C)nc2-c2cccc(NS(=O)(=O)c3cc(F)ccc3F)c2F)n1] | 663 | ¹H NMR (400 MHz, DMSO-d₆) δ ppm 10.75 (s, 1 H), 8.03 (d, J = 5.1 Hz, 1 H), 7.13-7.67 (m, 7 H), 6.85 (br. s., 1 H), 5.80-6.02 (m, 1 H), 3.16-3.28 (m, 2 H), 2.99-3.13 (m, 2 H), 1.40 (s, 9 H), 1.37 (s, 9 H) |

| Ex | Structure | m/z [M + H]⁺ | ¹H NMR |
|---|---|---|---|
| 199 | 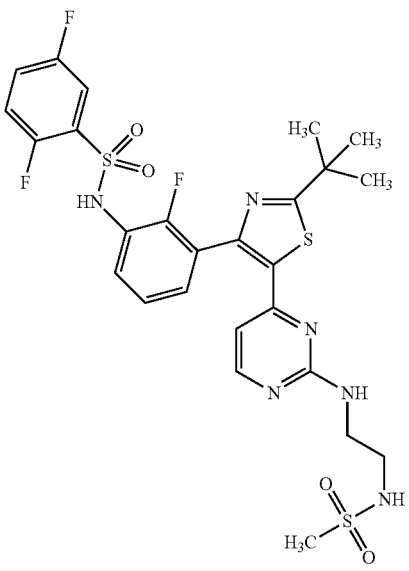 [SMILES: CC(C)(C)c1nc(-c2cccc(NS(=O)(=O)c3cc(F)ccc3F)c2F)c(-c2ccnc(NCCNS(C)(=O)=O)n2)s1] | 641 | ¹H NMR (400 MHz, DMSO-d₆) δ ppm 10.75 (s, 1 H), 8.05 (d, J = 5.1 Hz, 1 H), 7.23-7.64 (m, 7 H), 7.10 (t, J = 5.7 Hz, 1 H), 5.91 (br. s., 1 H), 3.05-3.15 (m, 2 H), 2.91 (s, 3 H), 1.40 (s, 9 H) |
| 200 | 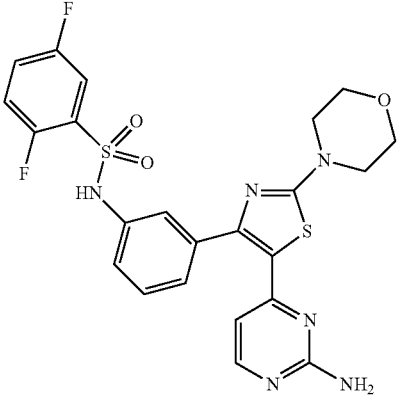 [SMILES: Nc1nccc(-c2sc(N3CCOCC3)nc2-c2cccc(NS(=O)(=O)c3cc(F)ccc3F)c2)n1] | 531 | ¹H NMR (400 MHz, DMSO-d₆) δ ppm 10.85 (s, 1 H), 7.74 (d, J = 5.3 Hz, 1 H), 7.40-7.63 (m, 3 H), 7.29 (t, J = 8.2 Hz, 1 H), 7.04-7.19 (m, 3 H), 6.52 (s, 2 H), 5.75 (d, J = 5.3 Hz, 1 H), 3.67 (t, J = 4.6 Hz, 4 H), 3.40 (t, J = 4.6 Hz, 4 H) |
| 201 | 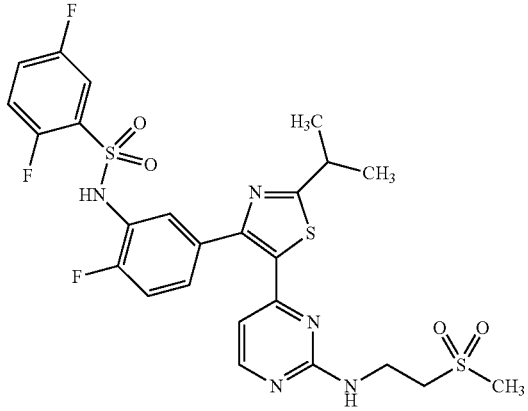 [SMILES: CC(C)c1nc(-c2ccc(F)c(NS(=O)(=O)c3cc(F)ccc3F)c2)c(-c2ccnc(NCCS(C)(=O)=O)n2)s1] | 612 | ¹H NMR (400 MHz, DMSO-d₆) δ ppm 10.81 (br. s., 1 H), 8.15 (d, J = 5.0 Hz, 1 H), 7.45-7.67 (m, 4 H), 7.36-7.45 (m, 2 H), 7.29 (dd, J = 10.0, 8.6 Hz, 1 H), 6.22-6.32 (m, 1 H), 3.59-3.77 (m, 2 H), 3.34-3.40 (m, 2 H), 3.30 (s, 1 H), 3.02 (s, 3 H), 1.36 (d, J = 6.9 Hz, 6 H) |

| Ex | Structure | m/z [M + H]+ | 1H NMR |
|---|---|---|---|
| 202 | 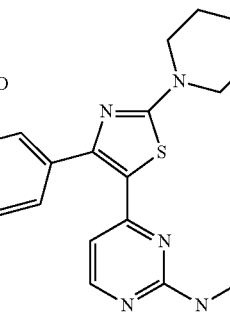 | 655 | 1H NMR (400 MHz, DMSO-d6) δ ppm 10.93 (s, 1 H), 7.96 (d, J = 5.2 Hz, 1 H), 7.66-7.78 (m, 1 H), 7.38 (d, J = 6.4 Hz, 2 H), 7.28 (q, J = 9.0 Hz, 4 H), 6.06 (d, J = 5.0 Hz, 1 H), 3.72 (t, J = 4.6 Hz, 4 H), 3.66 (q, J = 6.6 Hz, 2 H), 3.46 (t, J = 4.6 Hz, 4 H), 3.02 (s, 3 H) |
| 203 | 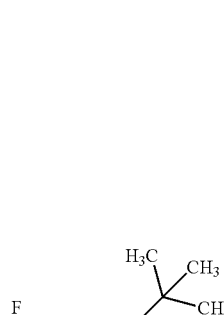 | 626 | 1H NMR (400 MHz, DMSO-d6) δ ppm 10.87 (s, 1 H), 8.09 (d, J = 5.2 Hz, 1 H), 7.61-7.75 (m, 1 H), 7.40-7.47 (m, 2 H), 7.37 (t, J = 6.2 Hz, 1 H), 7.30 (d, J = 7.9 Hz, 1 H), 7.24 (t, J = 9.1 Hz, 2 H), 5.98 (br. s., 1 H), 3.54-3.74 (m, 2 H), 3.34-3.39 (m, 2 H), 2.37-2.55 (m, 3 H), 1.41 (s, 9 H) |
| 204 | 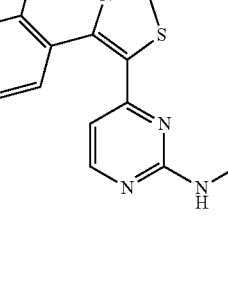 | 626 | 1H NMR (400 MHz, DMSO-d6) δ ppm 10.81 (s, 1 H), 8.11 (d, J = 5.1 Hz, 1 H), 7.35-7.67 (m, 6 H), 7.29 (t, J = 9.3 Hz, 1 H), 6.21 (br. s., 1 H), 3.36-3.46 (m, 1 H), 3.24-3.32 (m, 2 H), 3.10-3.21 (m, 2 H), 2.97 (s, 3 H), 1.87-2.02 (m, 2 H), 1.36 (d, J = 6.9 Hz, 6 H) |

| Ex | Structure | m/z [M + H]+ | 1H NMR |
|---|---|---|---|
| 205 | 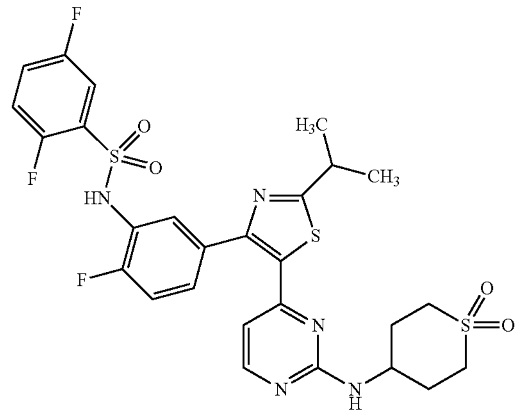 [SMILES: CC(C)c1nc(-c2ccc(F)c(NS(=O)(=O)c3cc(F)ccc3F)c2)c(-c2ccnc(NC3CCS(=O)(=O)CC3)n2)s1] | 638 | 1H NMR (400 MHz, DMSO-d6) δ ppm 10.83 (s, 1 H), 8.16 (d, J = 5.1 Hz, 1 H), 7.46-7.70 (m, 4 H), 7.35-7.47 (m, 2 H), 7.30 (dd, J = 10.0, 8.6 Hz, 1 H), 6.28 (br. s., 1 H), 3.25-3.33 (m, 1 H), 3.05-3.27 (m, 4 H), 1.93-2.25 (m, 5 H), 1.38 (d, J = 6.8 Hz, 6 H) |
| 206 | 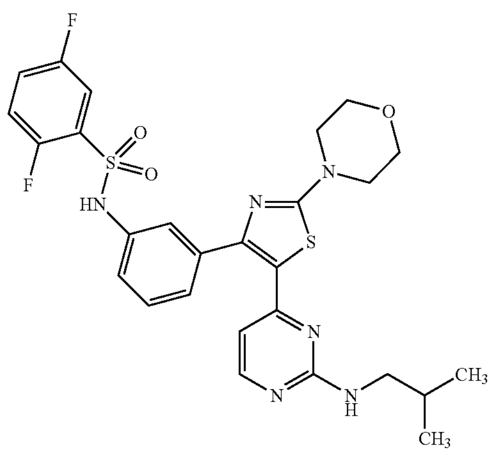 [SMILES: CC(C)CNc1nccc(-c2sc(N3CCOCC3)nc2-c2cccc(NS(=O)(=O)c3cc(F)ccc3F)c2)n1] | 587 | 1H NMR (400 MHz, DMSO-d6) δ ppm 10.85 (s, 1 H), 7.76 (d, J = 5.3 Hz, 1 H), 7.39-7.61 (m, 3 H), 7.29 (t, J = 8.2 Hz, 1 H), 7.02-7.22 (m, 4 H), 5.74 (d, J = 4.1 Hz, 1 H), 3.67 (t, J = 4.6 Hz, 4 H), 3.40 (t, J = 4.5 Hz, 4 H), 2.99 (t, J = 6.3 Hz, 2 H), 1.79 (dt, J = 13.4, 6.7 Hz, 1 H), 0.83 (d, J = 6.7 Hz, 6 H) |
| 207 | 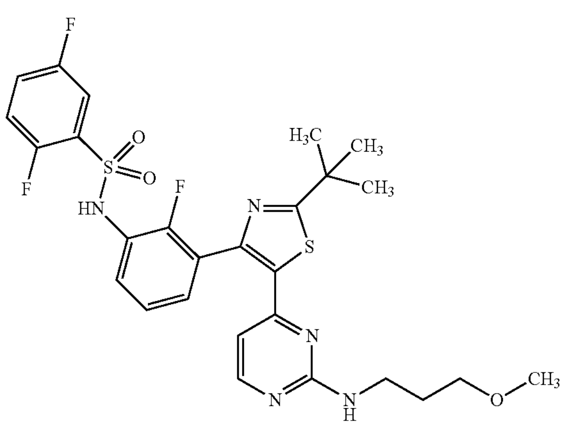 [SMILES: COCCCNc1nccc(-c2sc(C(C)(C)C)nc2-c2cccc(NS(=O)(=O)c3cc(F)ccc3F)c2F)n1] | 621 | 1H NMR (400 MHz, DMSO-d6) δ ppm 10.70 (s, 1 H), 7.82 (d, J = 5.2 Hz, 1 H), 7.40-7.57 (m, 3 H), 7.32-7.40 (m, 1 H), 7.16-7.29 (m, 2 H), 7.03 (br. s., 1 H), 5.60 (d, J = 4.3 Hz, 1 H), 3.66 (t, J = 4.6 Hz, 4 H), 3.40 (t, J = 4.4 Hz, 4 H), 3.24-3.36 (m, 4 H), 3.18 (s, 3 H), 1.68 (quin, J = 6.6 Hz, 2 H) |

| Ex | Structure | m/z [M + H]+ | ¹H NMR |
|---|---|---|---|
| 208 | 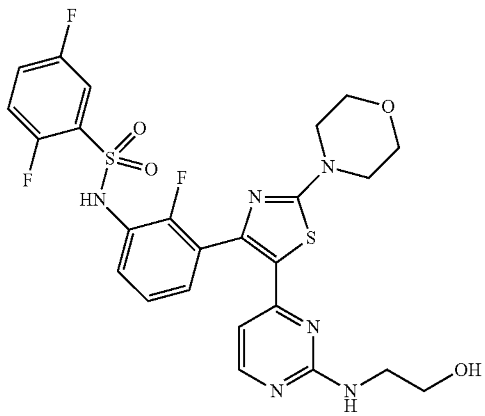 [SMILES: O=S(=O)(Nc1cccc(-c2nc(N3CCOCC3)sc2-c2ccnc(NCCO)n2)c1F)c1cc(F)ccc1F] | 593 | ¹H NMR (400 MHz, DMSO-d₆) δ ppm 10.70 (s, 1 H), 7.82 (d, J = 5.3 Hz, 1 H), 7.40-7.58 (m, 2 H), 7.37 (td, J = 7.3, 1.9 Hz, 1 H), 7.16-7.30 (m, 2 H), 6.89 (br. s., 1 H), 5.59 (d, J = 5.1 Hz, 1 H), 4.60 (t, J = 4.7 Hz, 1 H), 4.05 (q, J = 5.0 Hz, 1 H), 3.66 (t, J = 4.6 Hz, 4 H), 3.36-3.51 (m, 5 H), 3.23 (d, J = 5.7 Hz, 1 H), 3.12 (d, J = 4.8 Hz, 2 H) |
| 209 | 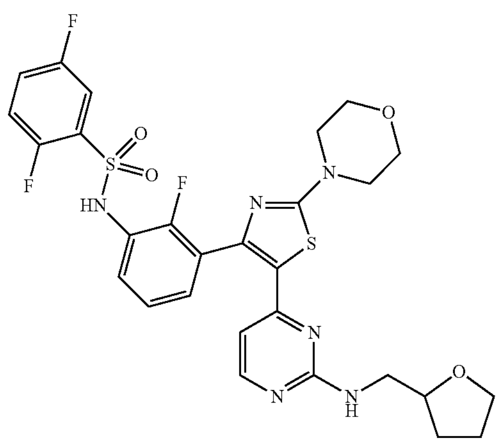 [SMILES: O=S(=O)(Nc1cccc(-c2nc(N3CCOCC3)sc2-c2ccnc(NCC3CCCO3)n2)c1F)c1cc(F)ccc1F] | 631 [M − H]⁻ | ¹H NMR (400 MHz, DMSO-d₆) δ ppm 10.70 (s, 1 H), 7.82 (d, J = 5.22 Hz, 1 H), 7.40-7.59 (m, 3 H), 7.31-7.41 (m, 1 H), 7.15-7.30 (m, 2 H), 6.99 (br. s., 1 H), 5.61 (d, J = 4.67 Hz, 1 H), 3.86-3.97 (m, 1 H), 3.61-3.78 (m, 5 H), 3.56 (q, J = 7.20 Hz, 1 H), 3.41 (t, J = 4.39 Hz, 4 H), 3.06-3.21 (m, 2 H), 1.63-1.92 (m, 3 H), 1.39-1.61 (m, 1 H) |
| 210 | 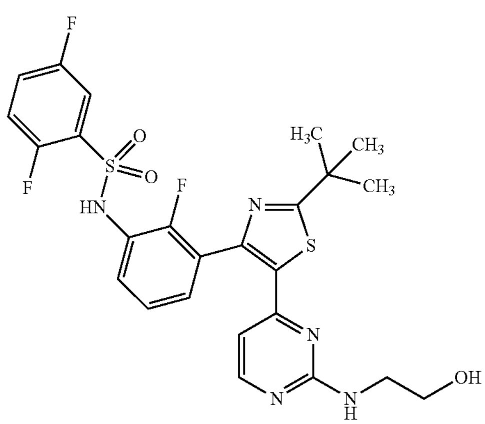 [SMILES: CC(C)(C)c1nc(-c2cccc(NS(=O)(=O)c3cc(F)ccc3F)c2F)c(-c2ccnc(NCCO)n2)s1] | 564 | ¹H NMR (400 MHz, DMSO-d₆) δ ppm 10.74 (s, 1 H), 8.03 (d, J = 5.1 Hz, 1 H), 7.52-7.63 (m, 1 H), 7.50 (dd, J = 9.0, 4.1 Hz, 2 H), 7.41 (t, J = 7.5 Hz, 1 H), 7.36 (t, J = 6.4 Hz, 1 H), 7.28 (t, J = 7.8 Hz, 1 H), 7.12 (t, J = 5.6 Hz, 1 H), 5.89 (d, J = 1.7 Hz, 1 H), 4.65 (br. s., 1 H), 3.49 (d, J = 4.3 Hz, 2 H), 3.33 (s, 2 H), 1.40 (s, 9 H) |

| Ex | Structure | m/z [M + H]+ | 1H NMR |
|---|---|---|---|
| 211 | 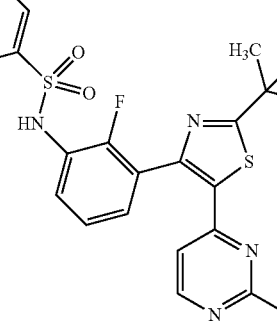 | 593 | 1H NMR (400 MHz, DMSO-d6) δ ppm 10.70 (s, 1 H), 7.98 (d, J = 5.1 Hz, 1 H), 7.40-7.57 (m, 3 H), 7.36 (t, J = 7.4 Hz, 1 H), 7.31 (t, J = 6.5 Hz, 1 H), 7.14-7.27 (m, 2 H), 5.58-6.16 (m, 1 H), 3.25-3.40 (m, 4 H), 3.18 (s, 3 H) 1.67 (br. s., 2 H), 1.36 (s, 9 H) |
| 212 | 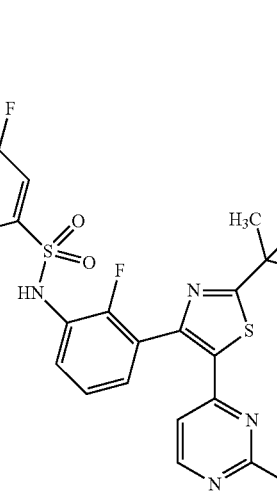 | 592 | 1H NMR (400 MHz, DMSO-d6) δ ppm 10.75 (s, 1 H), 8.04 (d, J = 5.1 Hz, 1 H), 7.53-7.63 (m, 1 H), 7.44-7.53 (m, 2 H), 7.41 (t, J = 7.5 Hz, 1 H), 7.36 (t, J = 6.3 Hz, 1 H), 7.28 (t, J = 7.8 Hz, 1 H), 7.21 (t, J = 5.6 Hz, 1 H), 5.75-6.06 (m, 1 H), 3.44 (q, J = 7.0 Hz, 4 H), 3.27-3.40 (m, 2 H), 1.40 (s, 9 H), 1.10 (t, J = 7.0 Hz, 3 H) |
| 213 | 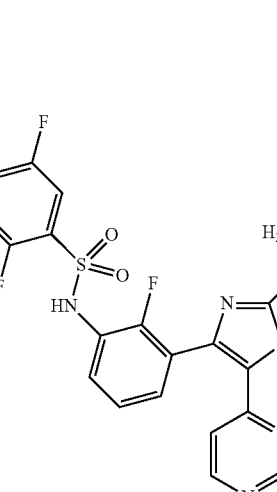 | 604 | 1H NMR (400 MHz, DMSO-d6) δ ppm 10.75 (s, 1 H), 8.03 (d, J = 5.13 Hz, 1 H), 7.45-7.62 (m, 23 H), 7.41 (t, J = 7.37 Hz, 1 H), 7.36 (t, J = 6.41 Hz, 1 H), 7.28 (d, J = 7.78 Hz, 1 H), 7.15-7.26 (m, 1 H), 5.64-6.16 (m, 1 H), 3.94 (br. s., 1 H), 3.69-3.82 (m, 1 H), 3.61 (q, J = 7.26 Hz, 1 H), 3.33 (s, 2 H), 3.02-3.30 (m, 1 H), 1.91 (s, 1 H), 1.71-1.90 (m, 2 H), 1.46-1.64 (m, 1 H), 1.40 (s, 9 H) |

| Ex | Structure | m/z [M + H]+ | 1H NMR |
|---|---|---|---|
| 214 | 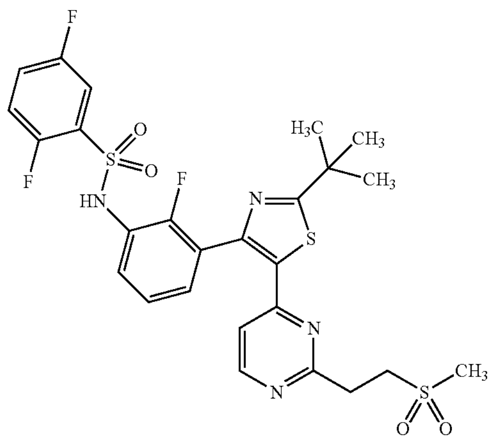 [SMILES: CC(C)(C)c1nc(-c2cccc(NS(=O)(=O)c3cc(F)ccc3F)c2F)c(-c2ccnc(CCS(C)(=O)=O)n2)s1] | 611 | 1H NMR (400 MHz, DMSO-d6) d ppm 10.70 (s, 1 H) 8.51 (d, J = 5.3 Hz, 1 H) 7.47-7.56 (m, 1 H) 7.33-7.47 (m, 4 H) 7.27 (t, J = 7.8 Hz, 1 H) 6.72 (d, J = 5.5 Hz, 1 H) 3.42-3.52 (m, 2 H) 3.20-3.26 (m, 2 H) 2.99 (s, 3 H) 1.38 (s, 9 H) |
| 215 | 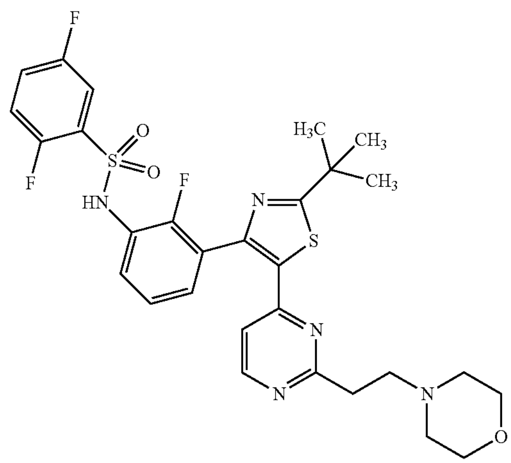 [SMILES: CC(C)(C)c1nc(-c2cccc(NS(=O)(=O)c3cc(F)ccc3F)c2F)c(-c2ccnc(CCN3CCOCC3)n2)s1] | 618 | 1H NMR (400 MHz, DMSO-d6) d ppm 8.47 (d, J = 5.3 Hz, 1 H) 7.26-7.54 (m, 6 H) 7.22 (t, J = 7.9 Hz, 1 H) 6.69 (d, J = 5.3 Hz, 1 H) 3.52 (t, J = 4.2 Hz, 4 H) 3.27 (br. s., 4 H) 2.96 (t, J = 7.5 Hz, 2 H) 2.72 (br. s., 2 H) 1.38 (s, 9 H) |
| 216 | 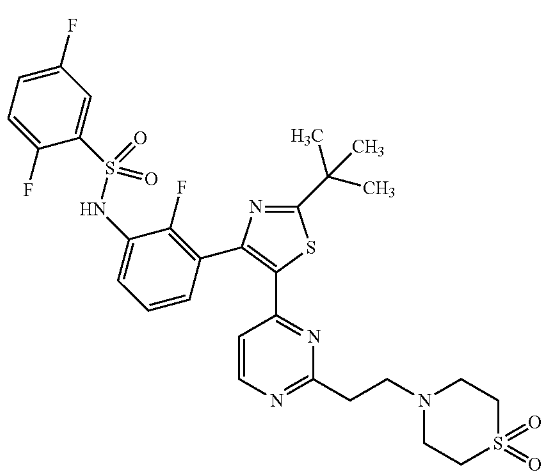 [SMILES: CC(C)(C)c1nc(-c2cccc(NS(=O)(=O)c3cc(F)ccc3F)c2F)c(-c2ccnc(CCN3CCS(=O)(=O)CC3)n2)s1] | 666 | 1H NMR (400 MHz, DMSO-d6) d ppm 10.75 (br. s., 1 H), 8.52 (d, J = 5.5 Hz, 1 H), 7.45-7.53 (m, 2 H), 7.53-7.62 (m, 1 H), 7.42 (t, J = 7.7 Hz, 2 H), 6.73 (d, 1 H), 7.31 (m, 1 H), 2.98 (m, 2 H), 3.05 (m, 4 H), 2.85-2.95 (m, 6 H), 1.42 (s, 6 H) |

-continued

| Ex | Structure | m/z [M+H]⁺ | ¹H NMR |
|---|---|---|---|
| 217 | 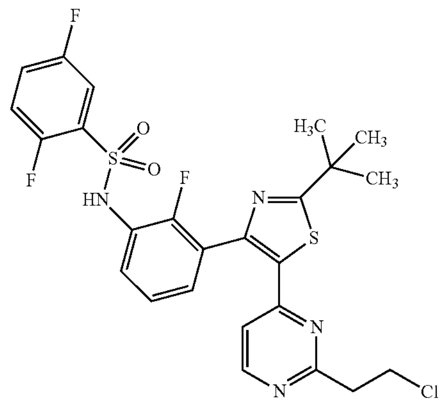 [SMILES: CC(C)(C)c1nc(-c2cccc(NS(=O)(=O)c3cc(F)ccc3F)c2F)c(-c2ccnc(CCCl)n2)s1] | 567 | 1H NMR (400 MHz, DMSO-d$_6$) d ppm 10.75 (s, 1 H), 8.56 (d, J = 5.31 Hz, 1 H), 7.46 (m, 4 H), 7.54 (m, 1 H), 7.31 (t, J = 7.78 Hz, 1 H), 6.76 (d, J = 5.31 Hz, 1 H), 4.00 (t, J = 6.50 Hz, 2 H), 3.29 (m, 2 H), 1.43 (s, 9 H). |

Example 218

N-{3-[5-(2-amino-4-pyrimidinyl)-2-(1,1-dimethylethyl)-1,3-thiazol-4-yl]-2-fluorophenyl}-3-fluorobenzenesulfonamide

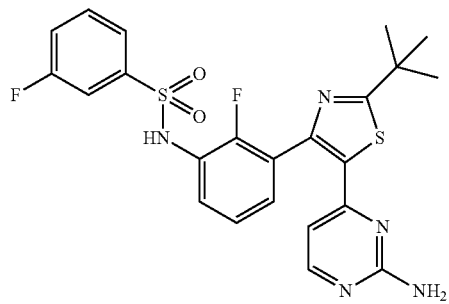 [SMILES: CC(C)(C)c1nc(-c2cccc(NS(=O)(=O)c3cccc(F)c3)c2F)c(-c2ccnc(N)n2)s1]

Following a procedure analogous to the procedure described in Intermediate 14 using 4-[4-(3-amino-2-fluorophenyl)-2-(1,1-dimethylethyl)-1,3-thiazol-5-yl]-2-pyrimidinamine (65 mg, 0.189 mmol) and 3-fluorobenzenesulfonyl chloride (0.030 mL, 0.227 mmol), the title compound was obtained as an off white solid (64 mg, 67% yield). MS (ESI): 502.2 [M+H]⁺.

Example 219

N-{3-[5-(2-amino-4-pyrimidinyl)-2-(1,1-dimethylethyl)-1,3-thiazol-4-yl]-2-fluorophenyl}benzenesulfonamide

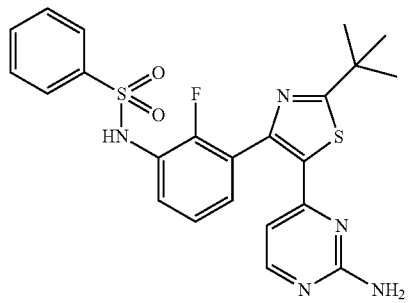 [SMILES: CC(C)(C)c1nc(-c2cccc(NS(=O)(=O)c3ccccc3)c2F)c(-c2ccnc(N)n2)s1]

Following a procedure analogous to the procedure described in Intermediate 14 using 4-[4-(3-amino-2-fluorophenyl)-2-(1,1-dimethylethyl)-1,3-thiazol-5-yl]-2-pyrimidinamine (65 mg, 0.189 mmol) and benzenesulfonyl chloride (0.029 mL, 0.227 mmol), the title compound was obtained as an off white solid (60 mg, 65% yield). MS (ESI): 484 [M+H]⁺.

Example 220

N-{3-[2-(1,1-dimethylethyl)-5-(2-methyl-4-pyrimidinyl)-1,3-thiazol-4-yl]-2,4-difluorophenyl}-3-fluorobenzenesulfonamide

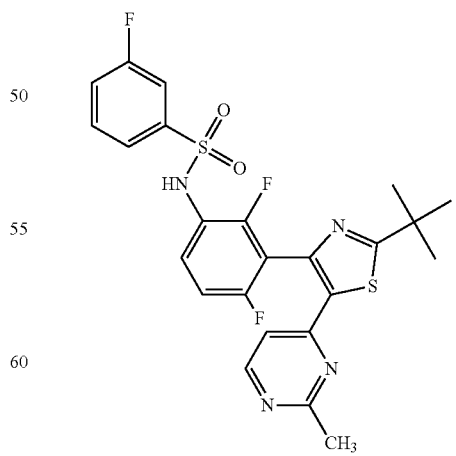

Step A: N-{3-[5-(2-chloro-4-pyrimidinyl)-2-(1,1-dimethylethyl)-1,3-thiazol-4-yl]-2,4-difluorophenyl}-3-fluorobenzenesulfonamide

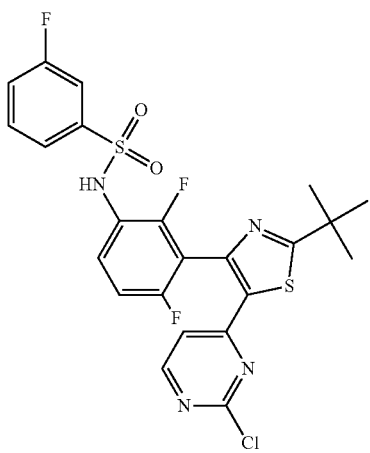 [SMILES: CC(C)(C)c1nc(-c2c(F)ccc(NS(=O)(=O)c3cccc(F)c3)c2F)c(-c2ccnc(Cl)n2)s1]

Following a procedure analogous to the procedure described in Intermediate 14 using {3-[5-(2-chloro-4-pyrimidinyl)-2-(1,1-dimethylethyl)-1,3-thiazol-4-yl]-2,4-difluorophenyl}amine (500 mg, 1.313 mmol) and 3-fluorobenzenesulfonyl chloride (0.210 mL, 1.575 mmol), the title compound was obtained as an yellow foam (690 mg, 98% yield).

Step B: N-{3-[2-(1,1-dimethylethyl)-5-(2-methyl-4-pyrimidinyl)-1,3-thiazol-4-yl]-2,4-difluorophenyl}-3-fluorobenzenesulfonamide Following a procedure analogous to the procedure described in Example 25 using N-{3-[5-(2-chloro-4-pyrimidinyl)-2-(1,1-dimethylethyl)-1,3-thiazol-4-yl]-2,4-difluorophenyl}-3-fluorobenzenesulfonamide (100 mg, 0.186 mmol) and dimethylzinc (0.186 mL, 0.371 mmol), the title compound was obtained as an off white solid (90 mg, 94% yield). MS (ESI): 519.1 [M+H]+.

Example 221

N-{3-[2-(1,1-dimethylethyl)-5-(4-pyrimidinyl)-1,3-thiazol-4-yl]-2,4-difluorophenyl}-3-fluorobenzenesulfonamide

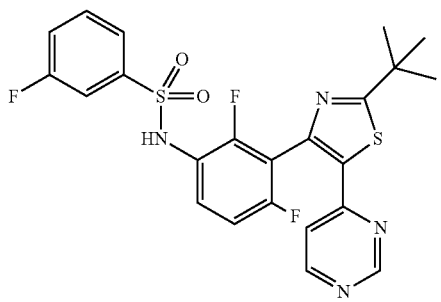 [SMILES: CC(C)(C)c1nc(-c2c(F)ccc(NS(=O)(=O)c3cccc(F)c3)c2F)c(-c2ccncn2)s1]

Following a procedure analogous to the procedure described in Example 26 using N-{3-[5-(2-chloro-4-pyrimidinyl)-2-(1,1-dimethylethyl)-1,3-thiazol-4-yl]-2,4-difluorophenyl}-3-fluorobenzenesulfonamide (150 mg, 0.278 mmol), the title compound was obtained as a yellow solid (85 mg, 60% yield). MS (ESI): 505.1 [M+H]+.

Example 222

N-{3-[2-(1,1-dimethylethyl)-5-(2-methyl-4-pyrimidinyl)-1,3-thiazol-4-yl]-2-fluorophenyl}-3-fluorobenzenesulfonamide

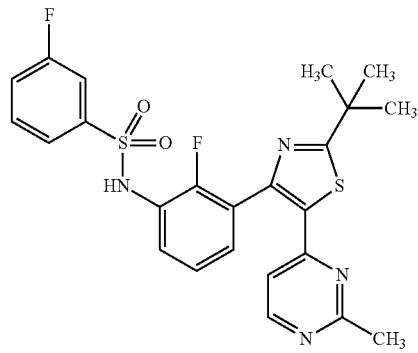 [SMILES: Cc1nccc(-c2sc(C(C)(C)C)nc2-c2cccc(NS(=O)(=O)c3cccc(F)c3)c2F)n1]

Step A: 3-[2-(1,1-dimethylethyl)-5-(4-pyrimidinyl)-1,3-thiazol-4-yl]-2-fluoroaniline

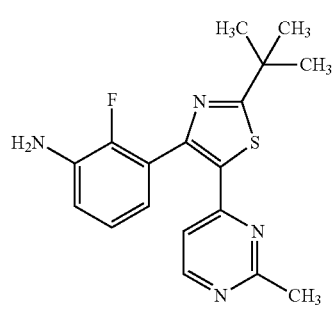 [SMILES: Cc1nccc(-c2sc(C(C)(C)C)nc2-c2cccc(N)c2F)n1]

Step A: 3-[2-(1,1-dimethylethyl)-5-(2-methyl-4-pyrimidinyl)-1,3-thiazol-4-yl]-2-fluoroaniline Following a procedure analogous to the procedure described in Example 25 using 3-[5-(2-chloro-4-pyrimidinyl)-2-(1,1-dimethylethyl)-1,3-thiazol-4-yl]-2-fluoroaniline (1.0 g, 2.76 mmol) and dimethylzinc (2.76 mL, 5.51 mmol), the title compound was obtained as an off white solid (0.8 g, 85% yield). MS (ESI): 343 [M+H]+.

Step B: N-{3-[2-(1,1-dimethylethyl)-5-(2-methyl-4-pyrimidinyl)-1,3-thiazol-4-yl]-2-fluorophenyl}-3-fluorobenzenesulfonamide

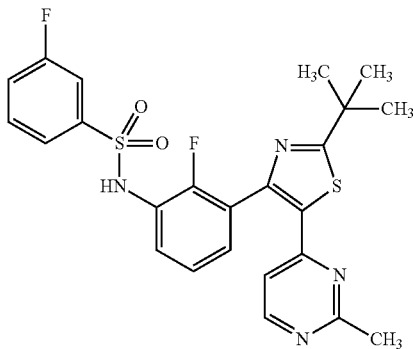 [SMILES: Cc1nccc(-c2sc(C(C)(C)C)nc2-c2cccc(NS(=O)(=O)c3cccc(F)c3)c2F)n1]

3-[2-(1,1-dimethylethyl)-5-(2-methyl-4-pyrimidinyl)-1,3-thiazol-4-yl]-2-fluoroaniline (70 mg, 0.204 mmol), 3-fluorobenzenesulfonyl chloride (40 mg, 0.204 mmol), and pyridine (0.162 mg, 2.04 mmol) were dissolved in dichloromethane (2 mL). After 2 h stirring, the reaction mixture was placed on silica gel and chromatography (0 to 30% EtOAc/Hexanes over 25 min.) to obtain N-{3-[2-(1,1-dimethylethyl)-5-(2-methyl-4-pyrimidinyl)-1,3-thiazol-4-yl]-2-fluorophenyl}-3-fluorobenzenesulfonamide (83 mg, 81%). $^1$H NMR (400 MHz, DMSO-d6) δ ppm 10.41 (s, 1H), 8.42 (d, J=5.49 Hz, 1H), 7.58-7.52 (m, 2H), 7.50-7.42 (m, 2H), 7.39-7.31 (m, 2H), 7.24 (t, J=7.87 Hz, 1H), 6.57 (d, J=5.31 Hz, 1H), 2.52 (s, 3H), 1.37 (s, 9H); MS (ESI); 499 (M−H)⁻.

Example 223

N-{3-[2-(1,1-dimethylethyl)-5-(4-pyrimidinyl)-1,3-thiazol-4-yl]-2-fluorophenyl}-3-fluorobenzenesulfonamide

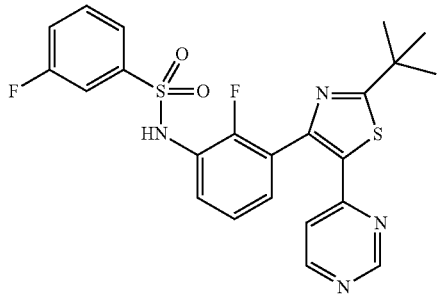

Step A: 3-[2-(1,1-dimethylethyl)-5-(4-pyrimidinyl)-1,3-thiazol-4-yl]-2-fluoroaniline

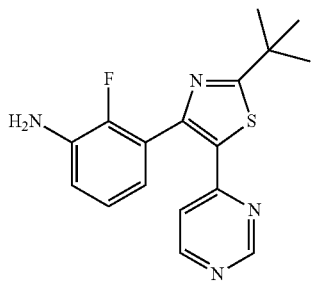 [SMILES: CC(C)(C)c1nc(-c2cccc(N)c2F)c(-c2ccncn2)s1]

Following a procedure analogous to the procedure described in Example 26 using 3-[5-(2-chloro-4-pyrimidinyl)-2-(1,1-dimethylethyl)-1,3-thiazol-4-yl]-2-fluoroaniline (964 mg, 2.66 mmol), the title compound was obtained as a solid (764 mg, 88% yield). MS (ESI): 329 [M+H]⁺.

Step B: N-{3-[2-(1,1-dimethylethyl)-5-(4-pyrimidinyl)-1,3-thiazol-4-yl]-2-fluorophenyl}-3-fluorobenzenesulfonamide Following a procedure analogous to the procedure described in Intermediate 14 using 3-[2-(1,1-dimethylethyl)-5-(4-pyrimidinyl)-1,3-thiazol-4-yl]-2-fluoroaniline (70 mg, 0.213 mmol) and 3-fluorobenzenesulfonyl chloride (124 mg, 0.639 mmol), the title compound was obtained as a solid (76 mg, 73% yield). MS (ESI): 488 [M+H]⁺.

Example 224

N-{3-[2-(1,1-dimethylethyl)-5-(4-pyrimidinyl)-1,3-thiazol-4-yl]-2-fluorophenyl}-2-fluorobenzenesulfonamide

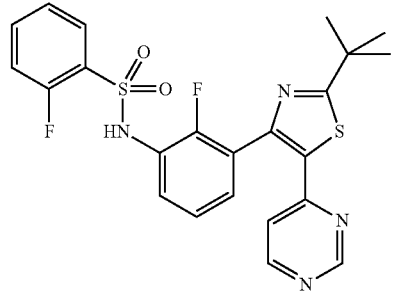

Following a procedure analogous to the procedure described in Example 223, Step A using 3-[2-(1,1-dimethylethyl)-5-(4-pyrimidinyl)-1,3-thiazol-4-yl]-2-fluoroaniline (70 mg, 0.213 mmol) and 2-fluorobenzenesulfonyl chloride (0.124 mg, 0.639 mmol), the title compound was obtained as an off white solid (60 mg, 57% yield). MS (ESI): 488 [M+H]⁺.

Example 225

N-{3-[2-(1,1-dimethylethyl)-5-(2-methyl-4-pyrimidinyl)-1,3-thiazol-4-yl]-2-fluorophenyl}-2-fluorobenzenesulfonamide

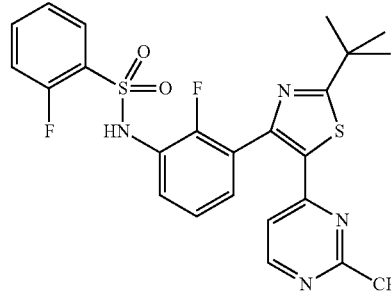 [SMILES: CC(C)(C)c1nc(-c2cccc(NS(=O)(=O)c3ccccc3F)c2F)c(-c2ccncn2)s1]

Following a procedure analogous to the procedure described in Example 222, Step A using 3-[2-(1,1-dimethylethyl)-5-(2-methyl-4-pyrimidinyl)-1,3-thiazol-4-yl]-2-fluoroaniline (70 mg, 0.204 mmol) and 2-fluorobenzenesulfonyl chloride (0.119 mL, 0.613 mmol), the title compound was obtained as a solid (77 mg, 75% yield). $^1$H NMR (400 MHz, DMSO-d$_6$) ppm 10.53 (s, 1H), 8.42 (d, J=5.31 Hz, 1H), 7.64-7.69 (m, 1H), 7.59-7.64 (m, 1H), 7.31-7.39 (m, 3H), 7.25 (dt, J=15.29, 7.74 Hz, 2H), 6.51 (d, J=5.31 Hz, 1H), 2.53 (s, 3H), 1.37 (s, 9H). MS (ESI): 502.2 [M+H]$^+$.

Example 226

Ethyl 3-{4-[4-(3-{[(2,6-difluorophenyl)sulfonyl]amino}-2-fluorophenyl)-2-(1,1-dimethylethyl)-1,3-thiazol-5-yl]-2-pyrimidinyl}propanoate

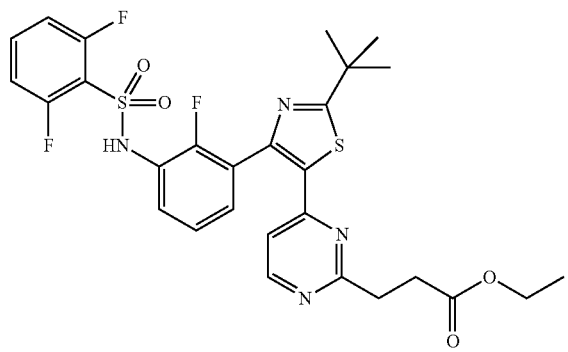 [SMILES: CCOC(=O)CCc1nccc(-c2sc(C(C)(C)C)nc2-c2cccc(NS(=O)(=O)c3c(F)cccc3F)c2F)n1]

To solid N-{3-[5-(2-chloro-4-pyrimidinyl)-2-(1,1-dimethylethyl)-1,3-thiazol-4-yl]-2-fluorophenyl}-2,6-difluorobenzenesulfonamide (1 g, 1.85 mmol) was added 3-ethoxy-3-oxopropylzinc bromide 0.5M solution in THF (31.5 ml, 15.77 mmol) at RT. Bis(tri-t-butylphosphine)palladium (0) (0.095 g, 0.186 mmol) was added to reaction mixture. The reaction was stirred at RT for several hours. The reaction was check by LCMS. The reaction mixture was quenched into sat'd NH$_4$Cl and stirred for several hours. A white/grey ppt was filtered. The EtOAc was added to filtrate. The EtOAc was separed contained form the water layer. The water layer was rewashed with EtOAc and the organic extracts combined, dried over MgSO$_4$, filtered, and concentrated to dryness to give an orange oil. The crude product was added to a silica gel column and eluted with EtOAc with DCM (20% to 60%) and collected fractions to obtain ethyl 3-{4-[4-(3-{[(2,6-difluorophenyl)sulfonyl]amino}-2-fluorophenyl)-2-(1,1-dimethylethyl)-1,3-thiazol-5-yl]-2-pyrimidinyl}propanoate (1.12 g, 64%). MS (ESI): 605 [M+H]$^+$.

Example 227

2,5-difluoro-N-{2-fluoro-3-[2-(4-morpholinyl)-5-(4-pyrimidinyl)-1,3-thiazol-4-yl]phenyl}benzenesulfonamide

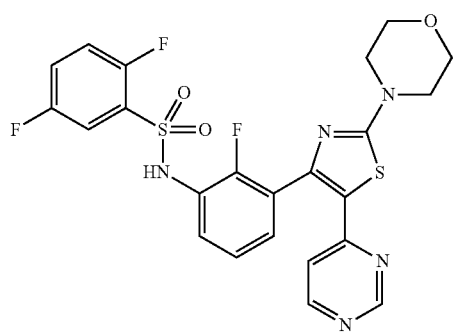 [SMILES: O=S(=O)(Nc1cccc(-c2nc(N3CCOCC3)sc2-c2ccncn2)c1F)c1cc(F)ccc1F]

Following a procedure analogous to the procedure described in Example 26 using N-{3-[5-(2-chloro-4-pyrimidinyl)-2-(4-morpholinyl)-1,3-thiazol-4-yl]-2-fluorophenyl}-2,5-difluorobenzenesulfonamide (109 mg, 0.192 mmol), the title compound was obtained as a yellow solid (83 mg, 81% yield). MS (ESI): 534.1 [M+H]$^+$.

Example 228

N-{2-chloro-3-[2-(1,1-dimethylethyl)-5-(4-pyrimidinyl)-1,3-thiazol-4-yl]phenyl}-2,5-difluorobenzenesulfonamide

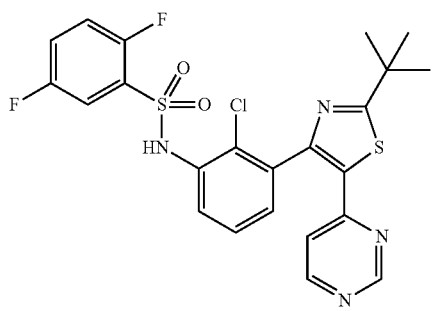 [SMILES: CC(C)(C)c1nc(-c2cccc(NS(=O)(=O)c3cc(F)ccc3F)c2Cl)c(-c2ccncn2)s1]

Following a procedure analogous to the procedure described in Example 26 using N-{2-chloro-3-[5-(2-chloro-4-pyrimidinyl)-2-(1,1-dimethylethyl)-1,3-thiazol-4-yl]phenyl}-2,5-difluorobenzenesulfonamide (100 mg, 0.180 mmol), the title compound was obtained as a yellow solid (45 mg, 48% yield). MS (ESI): 521 [M+H]$^+$.

Example 229

N-{2-chloro-3-[2-(1,1-dimethylethyl)-5-(2-methyl-4-pyrimidinyl)-1,3-thiazol-4-yl]phenyl}-2,5-difluorobenzenesulfonamide

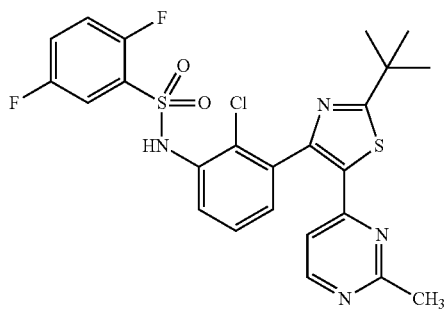 [SMILES: Cc1nccc(-c2sc(C(C)(C)C)nc2-c2cccc(NS(=O)(=O)c3cc(F)ccc3F)c2Cl)n1]

Following a procedure analogous to the procedure described in Example 25 using N-{2-chloro-3-[5-(2-chloro-4-pyrimidinyl)-2-(1,1-dimethylethyl)-1,3-thiazol-4-yl]phenyl}-2,5-difluorobenzenesulfonamide (200 mg, 0.360 mmol) and dimethyl zinc in toluene (0.360 mL, 0.720 mmol), the title compound was obtained as a yellow solid (161 mg, 84% yield). MS (ESI): 535.0 [M+H]$^+$.

Example 230

N-{3-[5-(2-amino-4-pyrimidinyl)-2-(1,1-dimethylethyl)-1,3-thiazol-4-yl]-2-fluorophenyl}-3-pyridinesulfonamide

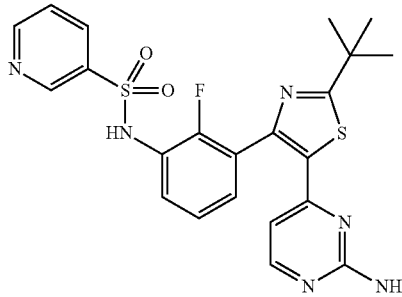

Following a procedure analogous to the procedure described in Intermediate 14 using 4-[4-(3-amino-2-fluorophenyl)-2-(1,1-dimethylethyl)-1,3-thiazol-5-yl]-2-pyrimidinamine (100 mg, 0.291 mmol) and 3-pyridinesulfonyl chloride (94 mL, 0.430 mmol), the title compound was obtained as a tan solid (34 mg, 24% yield). MS (ESI): 485.0 [M+H]$^+$.

Example 231

N-{3-[5-(2-amino-4-pyrimidinyl)-2-(1,1-dimethylethyl)-1,3-thiazol-4-yl]-2-fluorophenyl}-2-furansulfonamide

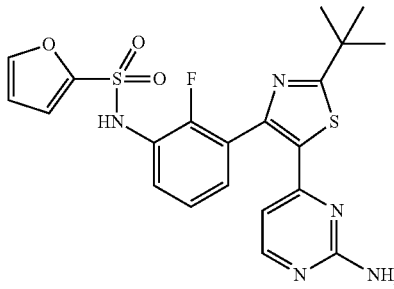

Following a procedure analogous to the procedure described in Intermediate 14 using 4-[4-(3-amino-2-fluorophenyl)-2-(1,1-dimethylethyl)-1,3-thiazol-5-yl]-2-pyrimidinamine (100 mg, 0.291 mmol) and furan-2-sulfonyl chloride (72 mg, 0.437 mmol), the title compound was obtained as a white solid (87 mg, 63% yield). MS (ESI): 474 [M+H]$^+$.

Example 232

N-{3-[5-(2-amino-4-pyrimidinyl)-2-(1,1-dimethylethyl)-1,3-thiazol-4-yl]-2-fluorophenyl}-2-thiophenesulfonamide

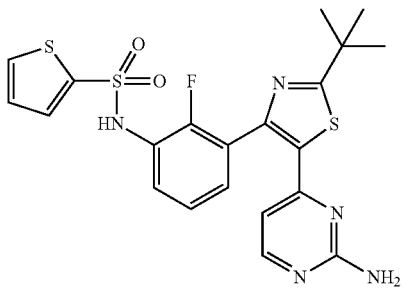 [SMILES: CC(C)(C)c1nc(-c2cccc(NS(=O)(=O)c3ccco3)c2F)c(-c2ccnc(N)n2)s1]

Following a procedure analogous to the procedure described in Intermediate 14 using 4-[4-(3-amino-2-fluorophenyl)-2-(1,1-dimethylethyl)-1,3-thiazol-5-yl]-2-pyrimidinamine (100 mg, 0.291 mmol) and thiophene-2-sulfonyl chloride (80 mg, 0.437 mmol), the title compound was obtained as a white solid (93 mg, 65% yield). MS (ESI): 489.9 [M+H]$^+$.

Example 233

N-{3-[5-(2-amino-4-pyrimidinyl)-2-(1,1-dimethylethyl)-1,3-thiazol-4-yl]-2-fluorophenyl}-3-thiophenesulfonamide

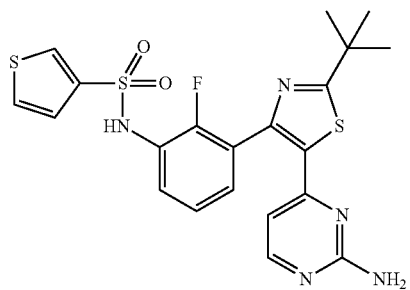 [SMILES: CC(C)(C)c1nc(-c2cccc(NS(=O)(=O)c3ccsc3)c2F)c(-c2ccnc(N)n2)s1]

Following a procedure analogous to the procedure described in Intermediate 14 using 4-[4-(3-amino-2-fluorophenyl)-2-(1,1-dimethylethyl)-1,3-thiazol-5-yl]-2-pyrimidinamine (80 mg, 0.233 mmol) and 3-thiophenesulfonyl chloride (47 mg, 0.256 mmol), the title compound was obtained as a white solid (68 mg, 56% yield). MS (ESI): 490.0 [M+H]$^+$.

Example 234

N-{3-[5-(2-amino-4-pyrimidinyl)-2-(1,1-dimethylethyl)-1,3-thiazol-4-yl]-2-fluorophenyl}-3-furansulfonamide

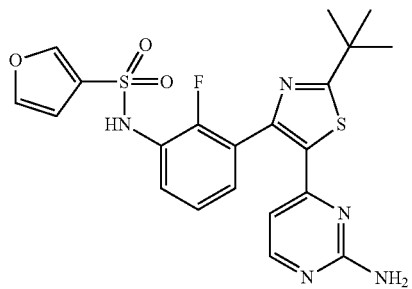 [SMILES: CC(C)(C)c1nc(-c2cccc(NS(=O)(=O)c3ccoc3)c2F)c(-c2ccnc(N)n2)s1]

Following a procedure analogous to the procedure described in Intermediate 14 using 4-[4-(3-amino-2-fluorophenyl)-2-(1,1-dimethylethyl)-1,3-thiazol-5-yl]-2-pyrimidinamine (80 mg, 0.233 mmol) and 3-furansulfonyl chloride (43 mg, 0.256 mmol), the title compound was obtained as a white solid (71 mg, 61% yield). MS (ESI): 474.0 [M+H]$^+$.

Example 235

N-{3-[5-(2-amino-4-pyrimidinyl)-2-(1,1-dimethylethyl)-1,3-thiazol-4-yl]-2-fluorophenyl}-4-methyl-2-thiophenesulfonamide

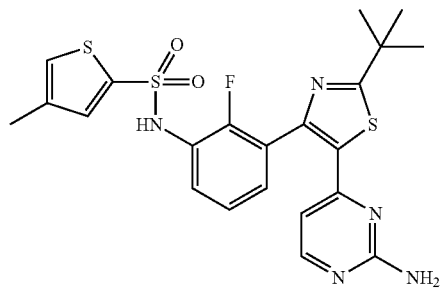 [SMILES: Cc1csc(S(=O)(=O)Nc2cccc(-c3nc(C(C)(C)C)sc3-c3ccnc(N)n3)c2F)c1]

Following a procedure analogous to the procedure described in Intermediate 14 using 4-[4-(3-amino-2-fluorophenyl)-2-(1,1-dimethylethyl)-1,3-thiazol-5-yl]-2-pyrimidinamine (80 mg, 0.233 mmol) and 4-methyl-2-thiophenesulfonyl chloride (50 mg, 0.256 mmol), the title compound was obtained as a white solid (59 mg, 47% yield). MS (ESI): 504 [M+H]$^+$.

Example 236

N-{3-[5-(2-amino-4-pyrimidinyl)-2-(1,1-dimethylethyl)-1,3-thiazol-4-yl]-2-chlorophenyl}-2,6-difluorobenzenesulfonamide

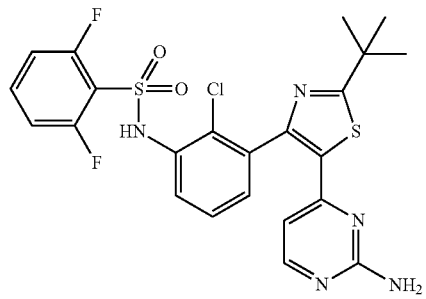 [SMILES: CC(C)(C)c1nc(-c2cccc(NS(=O)(=O)c3c(F)cccc3F)c2Cl)c(-c2ccnc(N)n2)s1]

Following a procedure analogous to the procedure described in Example 52, Step B using N-{2-chloro-3-[5-(2-chloro-4-pyrimidinyl)-2-(1,1-dimethylethyl)-1,3-thiazol-4-yl]phenyl}-2,6-difluorobenzenesulfonamide (156 mg, 0.281 mmol) and ammonia in isopropanol (15 mL, 30 mmol), the title compound was obtained as a white solid (56 mg, 35% yield). MS (ESI): 536 [M+H]$^+$.

Example 237

N-{2-chloro-3-[2-(1,1-dimethylethyl)-5-(4-pyrimidinyl)-1,3-thiazol-4-yl]phenyl}-2,6-difluorobenzenesulfonamide

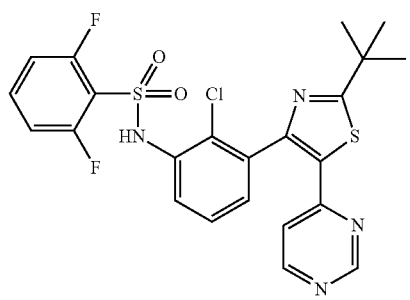 [SMILES: CC(C)(C)c1nc(-c2cccc(NS(=O)(=O)c3c(F)cccc3F)c2Cl)c(-c2ccncn2)s1]

Following a procedure analogous to the procedure described in Example 26 using N-{2-chloro-3-[5-(2-chloro-4-pyrimidinyl)-2-(1,1-dimethylethyl)-1,3-thiazol-4-yl]phenyl}-2,6-difluorobenzenesulfonamide (152 mg, 0.274 mmol), the title compound was obtained as a yellow solid (37 mg, 25% yield). MS (ESI): 521 [M+H]$^+$.

Example 238

N-{3-[5-(2-amino-4-pyrimidinyl)-2-(tetrahydro-2H-pyran-4-yl)-1,3-thiazol-4-yl]-2-chlorophenyl}-2,6-difluorobenzenesulfonamide

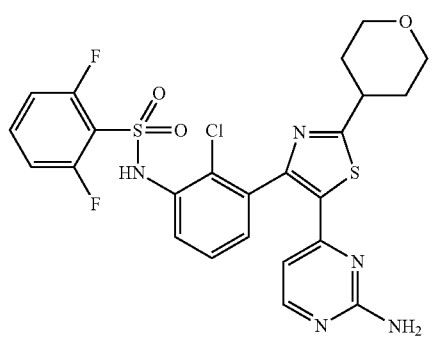 [SMILES: Nc1nccc(-c2sc(C3CCOCC3)nc2-c2cccc(NS(=O)(=O)c3c(F)cccc3F)c2Cl)n1]

Following a procedure analogous to the procedure described in Example 52, Step B using N-{2-chloro-3-[5-(2-chloro-4-pyrimidinyl)-2-(tetrahydro-2H-pyran-4-yl)-1,3-thiazol-4-yl]phenyl}-2,6-difluorobenzenesulfonamide (156 mg, 0.267 mmol) and ammonia in methanol (10 mL, 70 mmol), the title compound was obtained as a yellow solid (53 mg, 33% yield). MS (ESI): 564 [M+H]$^+$.

Example 239

N-{2-chloro-3-[2-(1,1-dimethylethyl)-5-(2-methyl-4-pyrimidinyl)-1,3-thiazol-4-yl]phenyl}-2,6-difluorobenzenesulfonamide

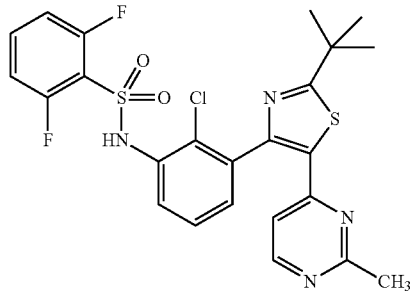 [SMILES: Cc1nccc(-c2sc(C(C)(C)C)nc2-c2cccc(NS(=O)(=O)c3c(F)cccc3F)c2Cl)n1]

Following a procedure analogous to the procedure described in Example 25 using N-{2-chloro-3-[5-(2-chloro-4-pyrimidinyl)-2-(1,1-dimethylethyl)-1,3-thiazol-4-yl]phenyl}-2,6-difluorobenzenesulfonamide (150 mg, 0.270 mmol) and 2N dimethylzinc in toluene (0.27 mL, 0.540 mmol), the title compound was obtained as a solid (75 mg, 47% yield). MS (ESI): 535 [M+H]$^+$.

Example 240

N-{2-chloro-3-[2-(4-morpholinyl)-5-(4-pyrimidinyl)-1,3-thiazol-4-yl]phenyl}-2,5-difluorobenzenesulfonamide

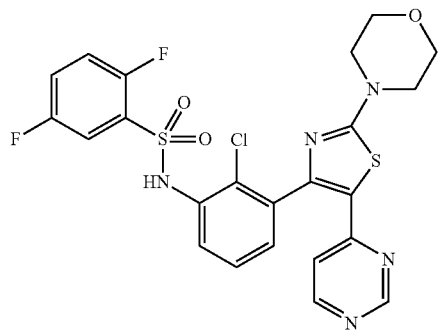 [SMILES: O=S(=O)(Nc1cccc(-c2nc(N3CCOCC3)sc2-c2ccncn2)c1Cl)c1cc(F)ccc1F]

Following a procedure analogous to the procedure described in Example 26 using N-{2-chloro-3-[5-(2-chloro-4-pyrimidinyl)-2-(4-morpholinyl)-1,3-thiazol-4-yl]phenyl}-2,5-difluorobenzenesulfonamide (150 mg, 0.257 mmol), the title compound was obtained as a yellow solid (65 mg, 43% yield). MS (ESI): 550 [M+H]$^+$.

Example 241

N-{3-[5-(2-amino-4-pyrimidinyl)-2-(1,1-dimethylethyl)-1,3-thiazol-4-yl]-2-chlorophenyl}-2,5-difluorobenzenesulfonamide

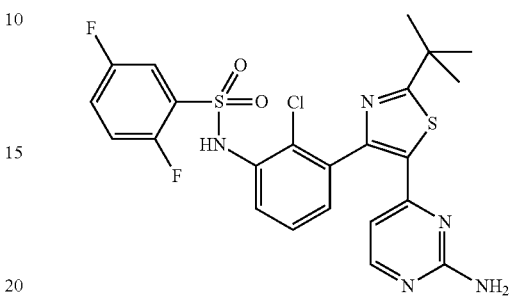

Following a procedure analogous to the procedure described in Example 52, Step B using N-{2-chloro-3-[5-(2-chloro-4-pyrimidinyl)-2-(1,1-dimethylethyl)-1,3-thiazol-4-yl]phenyl}-2,5-difluorobenzenesulfonamide (100 mg, 0.180 mmol) and ammonium hydroxide (3 mL, 77 mmol), the title compound was obtained as an off white solid (88 mg, 87% yield). MS (ESI): 536 [M+H]$^+$.

Example 242

N-{3-[5-(2-amino-4-pyrimidinyl)-2-(tetrahydro-2H-pyran-4-yl)-1,3-thiazol-4-yl]-2-chlorophenyl}-2,5-difluorobenzenesulfonamide

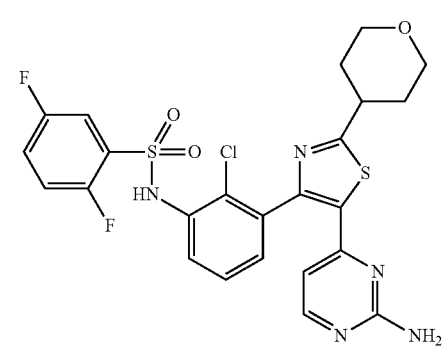 [SMILES: Nc1nccc(-c2sc(C3CCOCC3)nc2-c2cccc(NS(=O)(=O)c3cc(F)ccc3F)c2Cl)n1]

Following a procedure analogous to the procedure described in Example 52, Step B using N-{2-chloro-3-[5-(2-chloro-4-pyrimidinyl)-2-(tetrahydro-2H-pyran-4-yl)-1,3-thiazol-4-yl]phenyl}-2,5-difluorobenzenesulfonamide (150 mg, 0.257 mmol) and ammonium hydroxide (3 mL, 77 mmol), the title compound was obtained as a tan solid (47 mg, 31% yield). MS (ESI): 565 [M+H]+.

Example 243

N-{2-chloro-3-[5-(4-pyrimidinyl)-2-(tetrahydro-2H-pyran-4-yl)-1,3-thiazol-4-yl]phenyl}-2,5-difluorobenzenesulfonamide

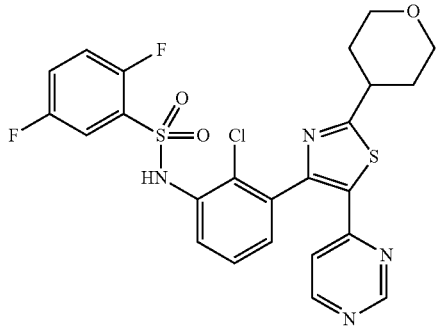

Following a procedure analogous to the procedure described in Example 26 using N-{2-chloro-3-[5-(2-chloro-4-pyrimidinyl)-2-(tetrahydro-2H-pyran-4-yl)-1,3-thiazol-4-yl]phenyl}-2,5-difluorobenzenesulfonamide (150 mg, 0.257 mmol), the title compound was obtained as a yellow solid (62 mg, 42% yield). MS (ESI): 549 [M+H]+.

Example 244

2,5-difluoro-N-{2-fluoro-3-[5-(4-pyrimidinyl)-2-(tetrahydro-2H-pyran-4-yl)-1,3-thiazol-4-yl]phenyl}benzenesulfonamide

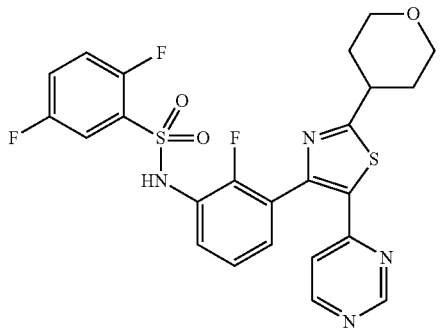

Following a procedure analogous to the procedure described in Example 26 using N-{3-[5-(2-chloro-4-pyrimidinyl)-2-(tetrahydro-2H-pyran-4-yl)-1,3-thiazol-4-yl]-2-fluorophenyl}-2,5-difluorobenzenesulfonamide (150 mg, 0.265 mmol) and ammonium formate (89 mg, 2.65 mmol), the title compound was obtained as a light yellow solid (89 mg, 63% yield). MS (ESI): 533.1 [M+H]+.

Example 245

N-{3-[5-(2-amino-4-pyrimidinyl)-2-(tetrahydro-2H-pyran-4-yl)-1,3-thiazol-4-yl]-2-fluorophenyl}-2,5-difluorobenzenesulfonamide

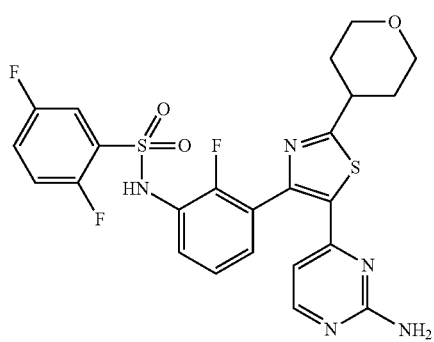

Following a procedure analogous to the procedure described in Example 52, Step B using N-{3-[5-(2-chloro-4-pyrimidinyl)-2-(tetrahydro-2H-pyran-4-yl)-1,3-thiazol-4-yl]-2-fluorophenyl}-2,5-difluorobenzenesulfonamide (0.150 g, 0.265 mmol) and 7N ammonia in methanol (5.67 mL, 39.7 mmol), the title compound was obtained as a white solid (93 mg, 64% yield). MS (ESI): 548 [M+H]+.

Example 246

2,5-difluoro-N-{2-fluoro-3-[5-(2-methyl-4-pyrimidinyl)-2-(tetrahydro-2H-pyran-4-yl)-1,3-thiazol-4-yl]phenyl}benzenesulfonamide

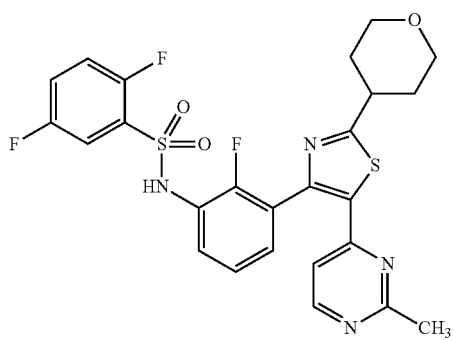 [SMILES: Cc1nccc(-c2sc(C3CCOCC3)nc2-c2cccc(NS(=O)(=O)c3cc(F)ccc3F)c2F)n1]

Following a procedure analogous to the procedure described in Example 25 using N-{3-[5-(2-chloro-4-pyrimidinyl)-2-(tetrahydro-2H-pyran-4-yl)-1,3-thiazol-4-yl]-2-fluorophenyl}-2,5-difluorobenzenesulfonamide (150 mg, 0.265 mmol) and 2N dimethylzinc in toluene ((0.265 mL,

Example 247

N-(3-{2-(1,1-dimethylethyl)-5-[2-(3-hydroxypropyl)-4-pyrimidinyl]-1,3-thiazol-4-yl}-2-fluorophenyl)-2,6-difluorobenzenesulfonamide

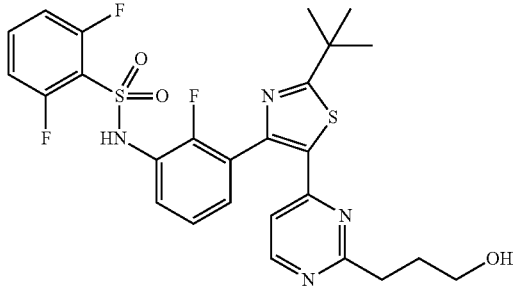 [SMILES: CC(C)(C)c1nc(-c2cccc(NS(=O)(=O)c3c(F)cccc3F)c2F)c(-c2ccnc(CCCO)n2)s1]

To a stirring solution of 2-propen-1-ol (0.038 ml, 0.557 mmol) in tetrahydrofuran (1 ml) at 0° C. was added 9-BBN (3.34 ml, 1.670 mmol). The reaction mixture taken out of the ice bath and stirred for 2 h and added a solution of N-{3-[5-(2-chloro-4-pyrimidinyl)-2-(1,1-dimethylethyl)-1,3-thiazol-4-yl]-2-fluorophenyl}-2,6-difluorobenzenesulfonamide (0.15 g, 0.278 mmol), K$_2$CO$_3$ (0.742 ml, 2.226 mmol), and bis(tri-t-butylphosphine)palladium (0) (0.014 g, 0.028 mmol) in N,N-dimethylformamide (1 ml) and stirred for 30 minutes. The reaction mixture was heated to 50° C. After 4 h, the reaction was diluted with EtOAc and saturated NH$_4$Cl. The mixture was extracted 2× with EtOAc, dried over MgSO$_4$, filtered, and concentrated. The crude mixture was placed on silica gel and chromatography (0 to 80% DCM/MeOH, gradient) to obtain the title compound (157 mg, 42%. $^1$H NMR (400 MHz, DMSO-d$_6$) ppm 10.88 (s, 1H), 8.47 (d, J=5.49 Hz, 1H), 7.67 (m, 1H), 7.43 (m, 2H), 7.31 (t, J=7.78 Hz, 1H), 7.23 (t, J=9.06 Hz, 2H), 6.62 (d, J=5.31 Hz, 1H), 4.51 (m, 1H), 3.46 (m, 2H), 2.86 (m, 2H), 1.87 (m, 2H), 1.41 (m, 9H); MS (ESI): 563 [M+H]$^+$.

Example 248

2,5-difluoro-N-{2-fluoro-3-[5-[2-(3-hydroxy-3-methylbutyl)-4-pyrimidinyl]-2-(4-morpholinyl)-1,3-thiazol-4-yl]phenyl}benzenesulfonamide

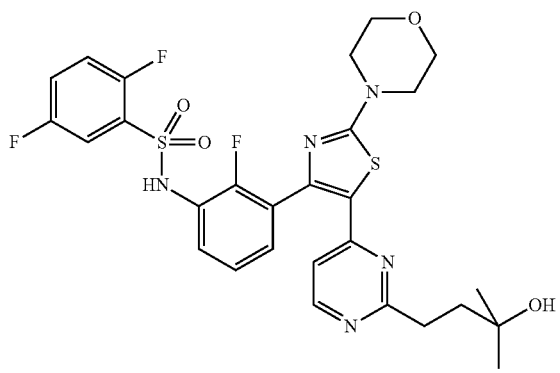 [SMILES: CC(C)(O)CCc1nccc(-c2sc(N3CCOCC3)nc2-c2cccc(NS(=O)(=O)c3cc(F)ccc3F)c2F)n1]

Following a procedure analogous to the procedure described in Example 247 using N-{3-[5-(2-chloro-4-pyrimidinyl)-2-(4-morpholinyl)-1,3-thiazol-4-yl]-2-fluorophenyl}-2,5-difluorobenzenesulfonamide (0.2 g, 0.352 mmol) and 2-Methyl-3-buten-2-ol (0.110 ml, 1.056 mmol), the title compound was obtained as a solid (83 mg, 38% yield). $^1$H NMR (400 MHz, DMSO-d$_6$) d ppm 10.76 (s, 1H), 8.28 (d, J=5.49 Hz, 1H), 7.53 (m, 3H), 7.43 (m, 1H), 7.35 (d, J=6.04 Hz, 1H), 7.29 (t, J=7.69 Hz, 1H), 6.31 (d, J=5.49 Hz, 1H), 4.28 (s, 1H), 3.71 (m, 4H), 3.50 (m, 4H), 2.81 (m, 2H), 1.77 (m, 2H), 1.12 (s, 6H); MS (ESI): 620 [M+H]$^+$.

Example 249

N-(3-{2-(1,1-dimethylethyl)-5-[2-(3-hydroxy-3-methylbutyl)-4-pyrimidinyl]-1,3-thiazol-4-yl}-2-fluorophenyl)-2,6-difluorobenzenesulfonamide

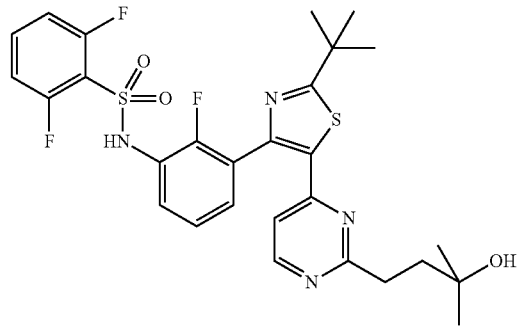 [SMILES: CC(C)(O)CCc1nccc(-c2sc(C(C)(C)C)nc2-c2cccc(NS(=O)(=O)c3c(F)cccc3F)c2F)n1]

Following a procedure analogous to the procedure described in Example 247 using N-{3-[5-(2-chloro-4-pyrimidinyl)-2-(1,1-dimethylethyl)-1,3-thiazol-4-yl]-2-fluorophenyl}-2,6-difluorobenzenesulfonamide (0.15 g, 0.278 mmol) and 2-Methyl-3-buten-2-ol (0.087 ml, 0.835 mmol), the title compound was obtained as a solid (86 mg, 52% yield). $^1$H NMR (400 MHz, DMSO-d$_6$) ppm 10.88 (s, 1H), 8.47 (dd, J=5.31, 1.46 Hz, 1H), 7.67 (m, 1H), 7.43 (m, 2H), 7.31 (t, J=8.15 Hz, 1H), 7.23 (t, J=9.61 Hz, 2H), 6.63 (d, J=4.94 Hz, 1H), 4.29 (s, 1H), 2.87 (m, 2H), 1.78 (d, J=8.42 Hz, 2H), 1.43 (d, J=1.46 Hz, 9H), 1.13 (d, J=1.28 Hz, 6H); MS (ESI): 591 [M+H]$^+$.

Example 250

N-(3-{2-(1,1-dimethylethyl)-5-[2-(3-hydroxy-3-methylbutyl)-4-pyrimidinyl]-1,3-thiazol-4-yl}-2-fluorophenyl)-2,5-difluorobenzenesulfonamide

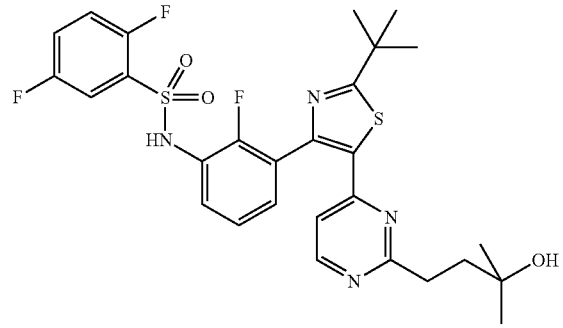 [SMILES: CC(C)(O)CCc1nccc(-c2sc(C(C)(C)C)nc2-c2cccc(NS(=O)(=O)c3cc(F)ccc3F)c2F)n1]

Following a procedure analogous to the procedure described in Example 247 using N-{3-[5-(2-chloro-4-pyrimidinyl)-2-(1,1-dimethylethyl)-1,3-thiazol-4-yl]-2-fluorophenyl}-2,5-difluorobenzenesulfonamide (0.15 g, 0.278 mmol) and 2-methyl-3-buten-2-ol (0.087 ml, 0.835 mmol), the title compound was obtained as a solid (164 mg, 57% yield); $^1$H NMR (400 MHz, DMSO-$d_6$) ppm 10.75 (s, 1H), 8.48 (d, J=5.31 Hz, 1H), 7.55 (m, 1H), 7.46 (m, 4H), 7.30 (t, J=8.33 Hz, 1H), 6.64 (d, J=5.31 Hz, 1H), 4.29 (s, 1H), 2.87 (m, 2H), 1.76 (m, 2H), 1.42 (s, 9H), 1.12 (s, 6H); MS (ESI): 592 [M+H]$^+$.

Example 251

N-[3-(2-(1,1-dimethylethyl)-5-{2-[2-(methylsulfonyl)ethyl]-4-pyrimidinyl}-1,3-thiazol-4-yl)-2-fluorophenyl]-2,6-difluorobenzenesulfonamide

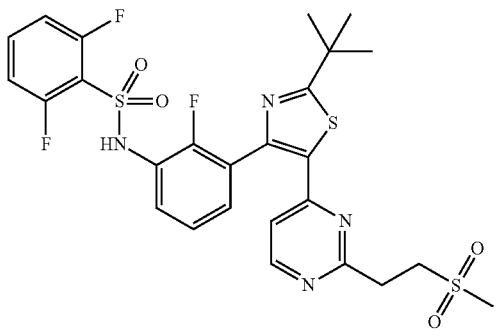 [SMILES: CC(C)(C)c1nc(-c2cccc(NS(=O)(=O)c3c(F)cccc3F)c2F)c(-c2ccnc(CCS(C)(=O)=O)n2)s1]

Step A: N-{3-[2-(1,1-dimethylethyl)-5-(2-ethenyl-4-pyrimidinyl)-1,3-thiazol-4-yl]-2-fluorophenyl}-2,6-difluorobenzenesulfonamide

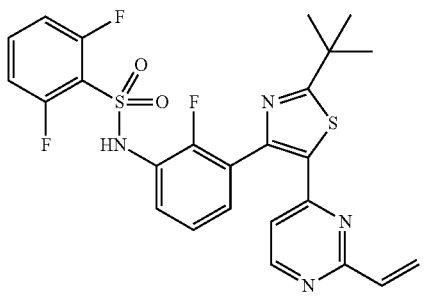 [SMILES: C=Cc1nccc(-c2sc(C(C)(C)C)nc2-c2cccc(NS(=O)(=O)c3c(F)cccc3F)c2F)n1]

N-{3-[5-(2-chloro-4-pyrimidinyl)-2-(1,1-dimethylethyl)-1,3-thiazol-4-yl]-2-fluorophenyl}-2,6-difluorobenzenesulfonamide (0.421 g, 0.781 mmol), potassium vinyl trifluoroborate (0.262 g, 1.953 mmol), PdCl$_2$(dppf)$_2$ (0.057 g, 0.078 mmol), and triethylamine (1.089 ml, 7.81 mmol) in n-propanol (7.81 ml) were heated at 100° C. in a screw-top vial overnight. The reaction mixture was filtered through celite and the celite rinsed with EtOAc. The combined organic portions were washed with water, dried over MgSO$_4$, filtered and concentrated to dryness. The crude mixture was placed on silica gel and chromatography (0 to 80% DCM/EtOAc, gradient) to obtain the title compound (350 mg, 84%). $^1$H NMR (400 MHz, DMSO-$d_6$) d ppm 10.88 (s, 1H), 8.56 (d, J=5.31 Hz, 1H), 7.67 (ddd, J=14.28, 8.15, 6.13 Hz, 1H), 7.43 (t, J=7.60 Hz, 2H), 7.31 (t, J=7.69 Hz, 1H), 7.22 (t, J=9.25 Hz, 2H), 6.74 (m, 2H), 6.44 (dd, J=17.58, 1.65 Hz, 1H), 5.75 (dd, J=10.62, 2.01 Hz, 1H), 1.43 (m, 9H); MS (ESI): 531 [M+H]$^+$.

Step B: N-[3-(2-(1,1-dimethylethyl)-5-{2-[2-(methylsulfonyl)ethyl]-4-pyrimidinyl}-1,3-thiazol-4-yl)-2-fluorophenyl]-2,6-difluorobenzenesulfonamide

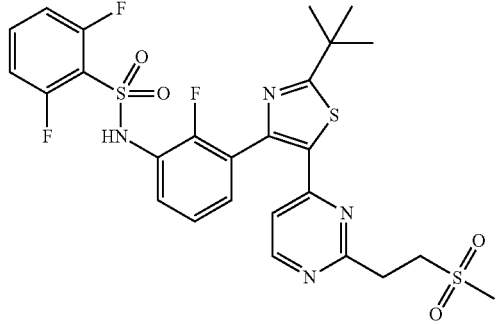 [SMILES: CC(C)(C)c1nc(-c2cccc(NS(=O)(=O)c3c(F)cccc3F)c2F)c(-c2ccnc(CCS(C)(=O)=O)n2)s1]

N-{3-[2-(1,1-dimethylethyl)-5-(2-ethenyl-4-pyrimidinyl)-1,3-thiazol-4-yl]-2-fluorophenyl}-2,6-difluorobenzenesulfonamide (0.15 g, 0.283 mmol) and methane sulfinic acid, sodium salt (0.144 g, 1.414 mmol) were stirred in acetic acid (1.5 ml) and ethanol (1.5 ml) at RT in a screw-top vial overnight. The reaction mixture is diluted with water and extracted 2× with EtOAc. The EtOAc is washed with brine, dried over MgSO4, filtered, and concentrated. The crude mixture was placed on silica gel and chromatography (0 to 80% DCM/EtOAc, gradient) to obtain the title compound (173 mg, 81%). $^1$H NMR (400 MHz, DMSO-$d_6$) ppm 10.87 (s, 1H), 8.54 (d, J=5.31 Hz, 1H), 7.68 (ddd, J=14.56, 8.42, 6.13 Hz, 1H), 7.43 (t, J=7.32 Hz, 2H), 7.32 (t, J=7.97 Hz, 1H), 7.23 (t, J=9.06 Hz, 2H), 6.75 (d, J=5.31 Hz, 1H), 3.53 (m, 2H), 3.29 (m, 2H), 3.03 (s, 3H), 1.44 (m, 9H); MS (ESI): 611 [M+H]$^+$.

Example 252

N-[2-chloro-3-(2-(1,1-dimethylethyl)-5-{2-[2-(methylsulfonyl)ethyl]-4-pyrimidinyl}-1,3-thiazol-4-yl)phenyl]-2,5-difluorobenzenesulfonamide

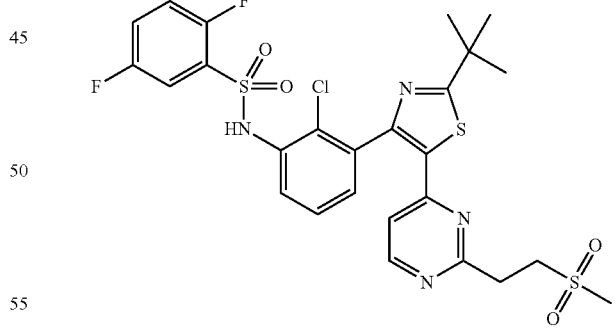

Following a procedure analogous to the procedure described in Example 251 using N-{2-chloro-3-[2-(1,1-dimethylethyl)-5-(2-ethenyl-4-pyrimidinyl)-1,3-thiazol-4-yl]phenyl}-2,5-difluorobenzenesulfonamide (0.135 g, 0.247 mmol) and methane sulfinic acid, sodium salt (0.126 g, 1.234 mmol), the title compound was obtained as a solid (127 mg, 82% yield). $^1$H NMR (400 MHz, DMSO-$d_6$) d ppm 10.72 (s, 1H), 8.54 (d, J=5.49 Hz, 1H), 7.52 (m, 3H), 7.44 (m, 2H), 6.48 (d, J=5.49 Hz, 1H), 3.54 (m, 2H), 3.28 (m, 2H), 3.04 (s, 3H), 1.42 (s, 9H); MS (ESI): 627 [M+H]$^+$.

Example 253

N-{3-[2-(1,1-dioxido-4-thiomorpholinyl)-5-(2-methyl-4-pyrimidinyl)-1,3-thiazol-4-yl]-2-fluorophenyl}-2,5-difluorobenzenesulfonamide

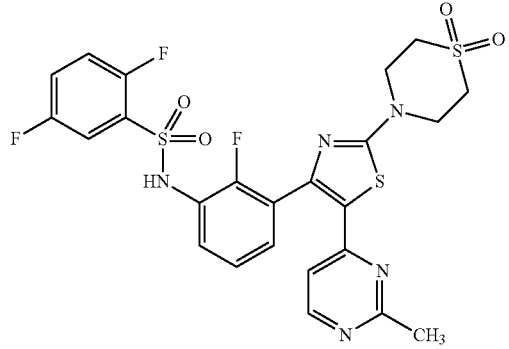 [SMILES: Cc1nccc(-c2sc(N3CCS(=O)(=O)CC3)nc2-c2cccc(NS(=O)(=O)c3cc(F)ccc3F)c2F)n1]

Step A: N-{3-[5-(2-chloro-4-pyrimidinyl)-2-(1,1-dioxido-4-thiomorpholinyl)-1,3-thiazol-4-yl]-2-fluorophenyl}-2,5-difluorobenzenesulfonamide Following a procedure analogous to the procedure described in intermediate 9 using N-{3-[5-(2-chloro-4-pyrimidinyl)-2-(1,1-dioxido-4-thiomorpholinyl)-1,3-thiazol-4-yl]-2-fluorophenyl}-2,5-difluorobenzenesulfonamide (1.5 g, 3.40 mmol) and 4-thiomorpholinecarbothioamide 1,1-dioxide (0.792 mL, 4.07 mmol), the title compound was obtained as a solid (2.06 mg, 98% yield). MS (ESI): 616 [M+H]$^+$.

Step B: N-{3-[2-(1,1-dioxido-4-thiomorpholinyl)-5-(2-methyl-4-pyrimidinyl)-1,3-thiazol-4-yl]-2-fluorophenyl}-2,5-difluorobenzenesulfonamide Following a procedure analogous to the procedure described in Example 25 using N-{3-[5-(2-chloro-4-pyrimidinyl)-2-(1,1-dioxido-4-thiomorpholinyl)-1,3-thiazol-4-yl]-2-fluorophenyl}-2,5-difluorobenzenesulfonamide (200 mg, 0.325 mmol) and 2N dimethylzinc in toluene (0.325 mL, 0.649 mmol), the title compound was obtained as a solid (110 mg, 59% yield). MS (ESI): 596 [M+H]$^+$.

Example 254

N-[3-(2-(1,1-dimethylethyl)-5-{2-[3-(4-morpholinyl)-3-oxopropyl]-4-pyrimidinyl}-1,3-thiazol-4-yl)-2-fluorophenyl]-2,5-difluorobenzenesulfonamide

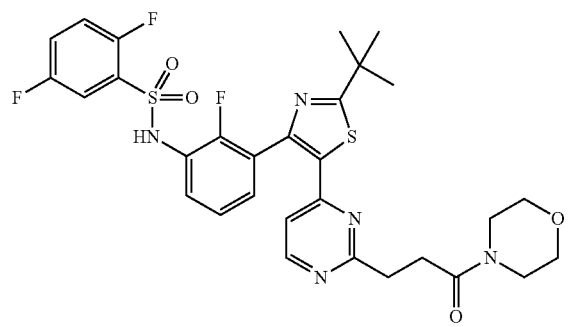 [SMILES: CC(C)(C)c1nc(-c2cccc(NS(=O)(=O)c3cc(F)ccc3F)c2F)c(-c2ccnc(CCC(=O)N3CCOCC3)n2)s1]

3-{4-[4-(3-{[(2,5-difluorophenyl)sulfonyl]amino}-2-fluorophenyl)-2-(1,1-dimethylethyl)-1,3-thiazol-5-yl]-2-pyrimidinyl}propanoic acid (200 mg, 0.347 mmol) was taken up in N,N-dimethylformamide (DMF) (2 ml). HATU (0.158 g, 0.416), DIEA (0.134 g, 1.041 mmol), and morpholine (0.060 g, 0.694) were added. After 30 min, the reaction mixture was concentrated and residue was purified via Gilson Acidic HPLC (10 to 90% gradient, Acetonitrile/H$_2$O+TFA; C18 column) to obtain the title compound (147 mg, 53%) as white solid. MS (ESI): 646 [M+H]$^+$.

Example 255

N-[3-(2-(1,1-dimethylethyl)-5-{2-[3-(1,1-dioxido-4-thiomorpholinyl)-3-oxopropyl]-4-pyrimidinyl}-1,3-thiazol-4-yl)-2-fluorophenyl]-2,5-difluorobenzenesulfonamide

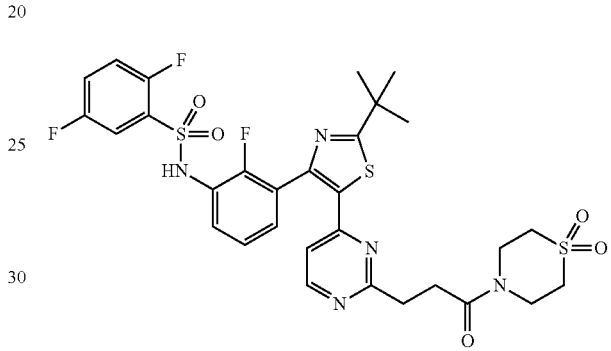

Following a procedure analogous to the procedure described in Example 254 using 3-{4-[4-(3-{[(2,5-difluorophenyl)sulfonyl]amino}-2-fluorophenyl)-2-(1,1-dimethylethyl)-1,3-thiazol-5-yl]-2-pyrimidinyl}propanoic acid (200 mg, 0.347 mmol) and thiomorpholine 1,1-dioxide (0.094 g, 0.694 mmol), the title compound was obtained as a white solid (108 mg, 36% yield). MS (ESI): 694 [M+H]$^+$.

Example 256

N-{3-[2-(1,1-dimethylethyl)-5-(4-pyrimidinyl)-1,3-thiazol-4-yl]-2-fluorophenyl}-3-furansulfonamide

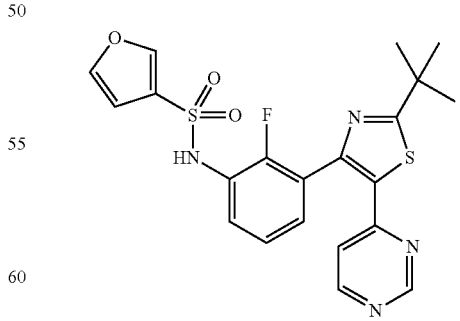

Following a procedure analogous to the procedure described in Example 26 using N-{3-[5-(2-chloro-4-pyrimidinyl)-2-(1,1-dimethylethyl)-1,3-thiazol-4-yl]-2-fluorophenyl}-3-furansulfonamide (77 mg, 0.156 mmol) and ammo-

Example 257

N-{3-[5-(2-amino-4-pyrimidinyl)-2-ethyl-1,3-thiazol-4-yl]-2-fluorophenyl}-2,6-difluorobenzenesulfonamide

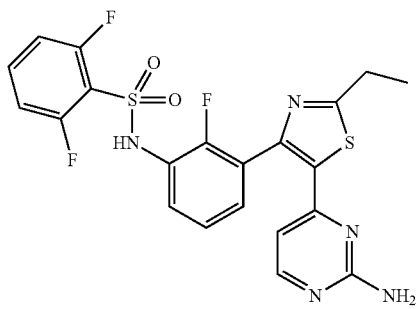 [SMILES: CCc1nc(-c2cccc(NS(=O)(=O)c3c(F)cccc3F)c2F)c(-c2ccnc(N)n2)s1]

Following a procedure analogous to the procedure described in Example 52, Step B using N-{3-[5-(2-chloro-4-pyrimidinyl)-2-ethyl-1,3-thiazol-4-yl]-2-fluorophenyl}-2,6-difluorobenzenesulfonamide (100 mg, 0.196 mmol) and ammonium hydroxide (3 mL, 77 mmol), the title compound was obtained as an off-white solid (52 mg, 51% yield). MS (ESI): 492 [M+H]$^+$.

Example 258

N-{3-[5-(2-amino-4-pyrimidinyl)-2-(1,1-dimethylethyl)-1,3-thiazol-4-yl]-2,4-difluorophenyl}-2,5-difluorobenzenesulfonamide

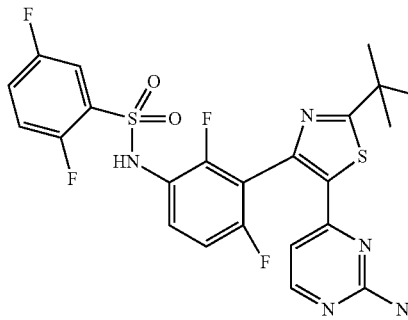

Following a procedure analogous to the procedure described in Example 52, Step B using N-{3-[5-(2-chloro-4-pyrimidinyl)-2-(1,1-dimethylethyl)-1,3-thiazol-4-yl]-2,4-difluorophenyl}-2,5-difluorobenzenesulfonamide (75 mg, 0.135 mmol) and ammonium hydroxide (3 mL), the title compound was obtained as an off-white solid (50 mg, 69% yield). MS (ESI): 538 [M+H]$^+$.

Example 259

N-{3-[5-(2-amino-4-pyrimidinyl)-2-(1,1-dimethylethyl)-1,3-thiazol-4-yl]-2-chlorophenyl}-2-furansulfonamide

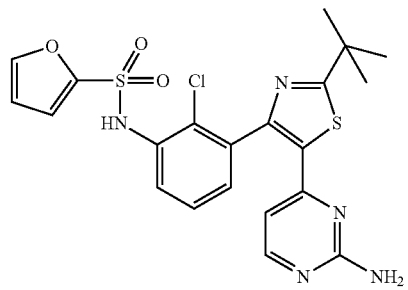 [SMILES: CC(C)(C)c1nc(-c2cccc(NS(=O)(=O)c3ccco3)c2Cl)c(-c2ccnc(N)n2)s1]

Following a procedure analogous to the procedure described in Example 52, Step B using N-{2-chloro-3-[5-(2-chloro-4-pyrimidinyl)-2-(1,1-dimethylethyl)-1,3-thiazol-4-yl]phenyl}-2-furansulfonamide (75 mg, 0.147 mmol) and ammonium hydroxide (3 mL), the title compound was obtained as an off-white solid (49 mg, 68% yield). MS (ESI): 490 [M+H]$^+$.

Example 260

N-{3-[2-(1,1-dimethylethyl)-5-(4-pyrimidinyl)-1,3-thiazol-4-yl]-2,4-difluorophenyl}-2,5-difluorobenzenesulfonamide

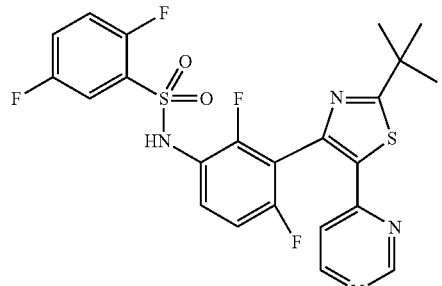

Following a procedure analogous to the procedure described in Example 26 using N-{3-[5-(2-chloro-4-pyrimidinyl)-2-(1,1-dimethylethyl)-1,3-thiazol-4-yl]-2,4-difluorophenyl}-2,5-difluorobenzenesulfonamide (75 mg, 0.135 mmol) and ammonium formate (85 mg, 1.347 mmol), the title compound was obtained as a yellow solid (21 mg, 29% yield). MS (ESI): 523 [M+H]$^+$.

Example 261

N-{2-chloro-3-[2-(1,1-dimethylethyl)-5-(4-pyrimidinyl)-1,3-thiazol-4-yl]phenyl}-2-furansulfonamide

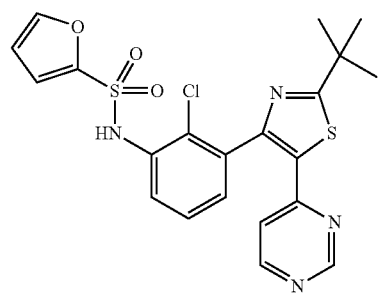 [SMILES: CC(C)(C)c1nc(-c2cccc(NS(=O)(=O)c3ccco3)c2Cl)c(-c2ccncn2)s1]

--- nium formate (98 mg, 1.562 mmol), the title compound was obtained as a yellow solid (23 mg, 30% yield). MS (ESI): 459 [M+H]$^+$.

Following a procedure analogous to the procedure described in Example 26 using N-{2-chloro-3-[5-(2-chloro-4-pyrimidinyl)-2-(1,1-dimethylethyl)-1,3-thiazol-4-yl]phenyl}-2-furansulfonamide (75 mg, 0.147 mmol) and ammonium formate (93 mg, 1.47 mmol), the title compound was obtained as a yellow solid (23 mg, 34% yield). MS (ESI): 475 [M+H]⁺.

Example 262

N-{3-[2-(1,1-dimethylethyl)-5-(2-methyl-4-pyrimidinyl)-1,3-thiazol-4-yl]-2,4-difluorophenyl}-2,5-difluorobenzenesulfonamide

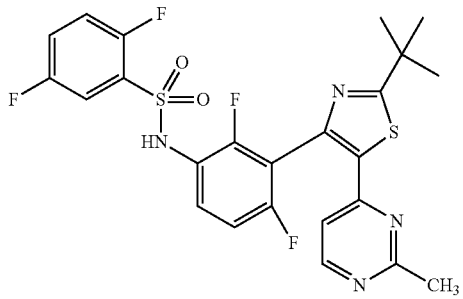 [SMILES: Cc1nccc(-c2sc(C(C)(C)C)nc2-c2c(F)ccc(NS(=O)(=O)c3cc(F)ccc3F)c2F)n1]

Following a procedure analogous to the procedure described in Example 25 using N-{3-[5-(2-chloro-4-pyrimidinyl)-2-(1,1-dimethylethyl)-1,3-thiazol-4-yl]-2,4-difluorophenyl}-2,5-difluorobenzenesulfonamide (150 mg, 0.269 mmol) and dimethyl zinc in toluene (0.269 mL, 0.539 mmol), the title compound was obtained as a yellow solid (105 mg, 72% yield). MS (ESI): 537 [M+H]⁺.

Example 263

N-{2-chloro-3-[2-(1,1-dimethylethyl)-5-(2-methyl-4-pyrimidinyl)-1,3-thiazol-4-yl]phenyl}-2-furansulfonamide

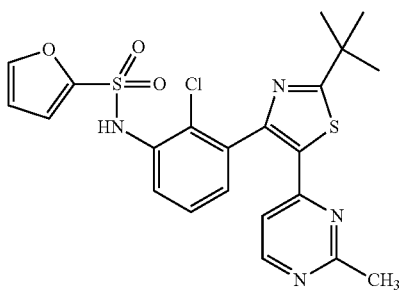 [SMILES: Cc1nccc(-c2sc(C(C)(C)C)nc2-c2cccc(NS(=O)(=O)c3ccco3)c2Cl)n1]

Following a procedure analogous to the procedure described in Example 25 using N-{2-chloro-3-[5-(2-chloro-4-pyrimidinyl)-2-(1,1-dimethylethyl)-1,3-thiazol-4-yl]phenyl}-2-furansulfonamide (150 mg, 0.294 mmol) and dimethyl zinc in toluene (0.294 mL, 0.589 mmol), the title compound was obtained as a yellow solid (113 mg, 78% yield). MS (ESI): 489 [M+H]⁺.

Example 264

N-{3-[5-(2-amino-4-pyrimidinyl)-2-(1,1-dimethylethyl)-1,3-thiazol-4-yl]-2-chlorophenyl}-3-furansulfonamide

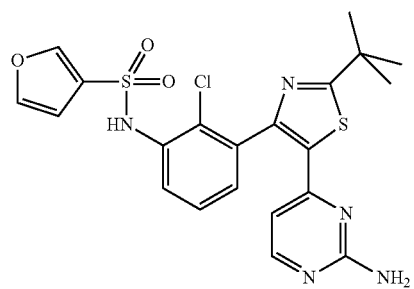 [SMILES: CC(C)(C)c1nc(-c2cccc(NS(=O)(=O)c3ccoc3)c2Cl)c(-c2ccnc(N)n2)s1]

Following a procedure analogous to the procedure described in Example 52, Step B using N-{2-chloro-3-[5-(2-chloro-4-pyrimidinyl)-2-(1,1-dimethylethyl)-1,3-thiazol-4-yl]phenyl}-3-furansulfonamide (130 mg, 0.255 mmol) and ammonium hydroxide (3 mL), the title compound was obtained as an off-white solid (48 mg, 38% yield). MS (ESI): 490 [M+H]⁺.

Example 265

N-{3-[5-(2-amino-4-pyrimidinyl)-2-(tetrahydro-2H-pyran-4-yl)-1,3-thiazol-4-yl]-2-chlorophenyl}-3-furansulfonamide

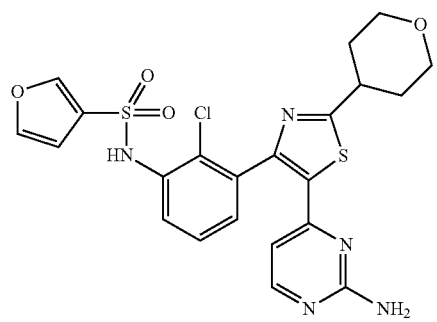 [SMILES: Nc1nccc(-c2sc(C3CCOCC3)nc2-c2cccc(NS(=O)(=O)c3ccoc3)c2Cl)n1]

Following a procedure analogous to the procedure described in Example 52, Step B using N-{2-chloro-3-[5-(2-chloro-4-pyrimidinyl)-2-(tetrahydro-2H-pyran-4-yl)-1,3-thiazol-4-yl]phenyl}-3-furansulfonamide (95 mg, 0.177 mmol) and ammonium hydroxide (4 mL), the title compound was obtained as an off-white solid (59 mg, 61% yield). MS (ESI): 519 [M+H]⁺.

Example 266

N-{3-[5-(2-amino-4-pyrimidinyl)-2-(4-morpholinyl)-1,3-thiazol-4-yl]-2-chlorophenyl}-3-furansulfonamide

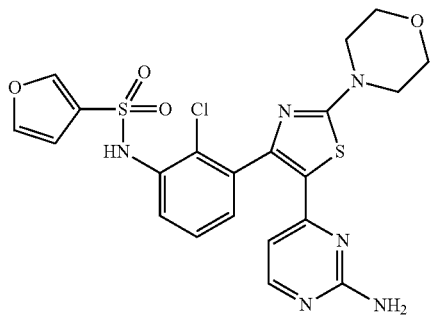

Following a procedure analogous to the procedure described in Example 52, Step B using N-{2-chloro-3-[5-(2-chloro-4-pyrimidinyl)-2-(4-morpholinyl)-1,3-thiazol-4-yl]phenyl}-3-furansulfonamide (114 mg, 0.212 mmol) and ammonium hydroxide (4 mL) and 1,4-Dioxane (1 mL), the title compound was obtained as an off-white solid (82 mg, 70% yield). MS (ESI): 519 [M+H]⁺.

Example 267

N-{3-[5-(2-amino-4-pyrimidinyl)-2-(4-morpholinyl)-1,3-thiazol-4-yl]-2-fluorophenyl}-3-furansulfonamide

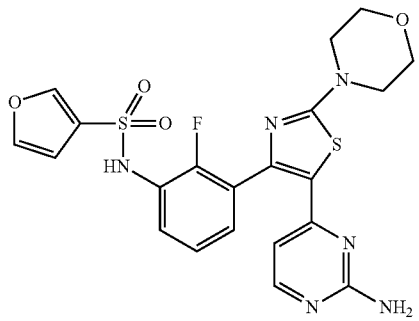 [SMILES: Nc1nccc(-c2sc(N3CCOCC3)nc2-c2cccc(NS(=O)(=O)c3ccoc3)c2F)n1]

Following a procedure analogous to the procedure described in Example 52, Step B using N-{3-[5-(2-chloro-4-pyrimidinyl)-2-(4-morpholinyl)-1,3-thiazol-4-yl]-2-fluorophenyl}-3-furansulfonamide (100 mg, 0.192 mmol) and ammonium hydroxide (4 mL) and 1,4-Dioxane (1 mL), the title compound was obtained as an off-white solid (65 mg, 64% yield). MS (ESI): 503 [M+H]⁺.

Example 268

N-{2-chloro-3-[2-(1,1-dimethylethyl)-5-(4-pyrimidinyl)-1,3-thiazol-4-yl]phenyl}-3-furansulfonamide

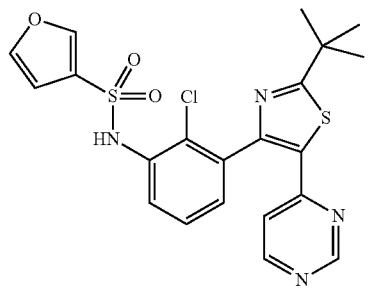 [SMILES: CC(C)(C)c1nc(-c2cccc(NS(=O)(=O)c3ccoc3)c2Cl)c(-c2ccncn2)s1]

Following a procedure analogous to the procedure described in Example 26 using N-{2-chloro-3-[5-(2-chloro-4-pyrimidinyl)-2-(1,1-dimethylethyl)-1,3-thiazol-4-yl]phenyl}-3-furansulfonamide (130 mg, 0.255 mmol) and ammonium formate (161 mg, 2.55 mmol), the title compound was obtained as a white solid (50 mg, 39% yield). MS (ESI): 474 [M+H]⁺.

Example 269

N-{2-chloro-3-[2-(4-morpholinyl)-5-(4-pyrimidinyl)-1,3-thiazol-4-yl]phenyl}-3-furansulfonamide

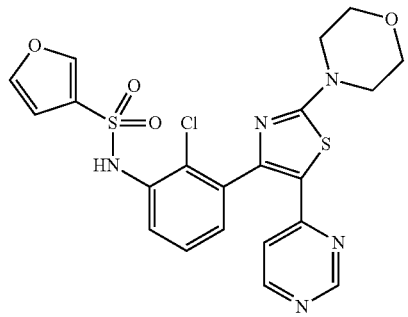 [SMILES: O=S(=O)(Nc1cccc(-c2nc(N3CCOCC3)sc2-c2ccncn2)c1Cl)c1ccoc1]

Following a procedure analogous to the procedure described in Example 26 using N-{2-chloro-3-[5-(2-chloro-4-pyrimidinyl)-2-(4-morpholinyl)-1,3-thiazol-4-yl]phenyl}-3-furansulfonamide (114 mg, 0.212 mmol) and ammonium formate (134 mg, 2.11 mmol), the title compound was obtained as a white solid (33 mg, 29% yield). MS (ESI): 503 [M+H]⁺.

Example 270

N-{2-chloro-3-[2-(1,1-dimethylethyl)-5-(2-methyl-4-pyrimidinyl)-1,3-thiazol-4-yl]phenyl}-3-furansulfonamide

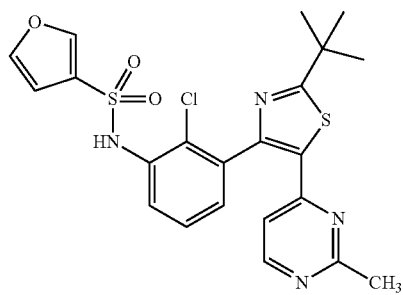 [SMILES: Cc1nccc(-c2sc(C(C)(C)C)nc2-c2cccc(NS(=O)(=O)c3ccoc3)c2Cl)n1]

Following a procedure analogous to the procedure described in Example 25 using N-{2-chloro-3-[5-(2-chloro-4-pyrimidinyl)-2-(1,1-dimethylethyl)-1,3-thiazol-4-yl]phenyl}-3-furansulfonamide (130 mg, 0.255 mmol) and dimethyl zinc in toluene (0.255 mL, 0.510 mmol), the title compound was obtained as a solid (35 mg, 26% yield). MS (ESI): 489 [M+H]+.

Example 271

N-{2-chloro-3-[5-(2-methyl-4-pyrimidinyl)-2-(4-morpholinyl)-1,3-thiazol-4-yl]phenyl}-3-furansulfonamide

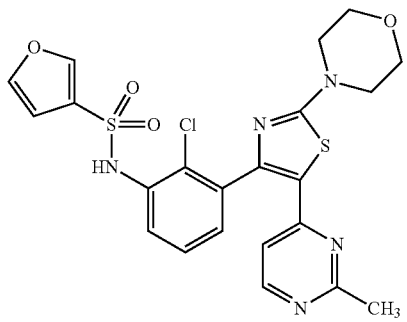 [SMILES: Cc1nccc(-c2sc(N3CCOCC3)nc2-c2cccc(NS(=O)(=O)c3ccoc3)c2Cl)n1]

Following a procedure analogous to the procedure described in Example 25 using N-{2-chloro-3-[5-(2-chloro-4-pyrimidinyl)-2-(4-morpholinyl)-1,3-thiazol-4-yl]phenyl}-3-furansulfonamide (115 mg, 0.214 mmol) and dimethyl zinc in toluene (0.214 mL, 0.427 mmol), the title compound was obtained as a solid (60 mg, 51% yield). MS (ESI): 519 [M+H]+.

Example 272

N-{2-fluoro-3-[5-(2-methyl-4-pyrimidinyl)-2-(4-morpholinyl)-1,3-thiazol-4-yl]phenyl}-3-furansulfonamide

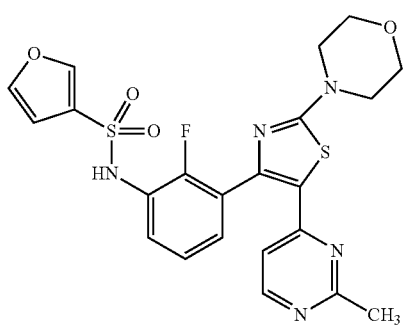 [SMILES: Cc1nccc(-c2sc(N3CCOCC3)nc2-c2cccc(NS(=O)(=O)c3ccoc3)c2F)n1]

Following a procedure analogous to the procedure described in Example 25 using N-{3-[5-(2-chloro-4-pyrimidinyl)-2-(4-morpholinyl)-1,3-thiazol-4-yl]-2-fluorophenyl}-3-furansulfonamide (100 mg, 0.192 mmol) and dimethyl zinc in toluene (0.192 mL, 0.383 mmol), the title compound was obtained as a solid (50 mg, 49% yield). MS (ESI): 502 [M+H]+.

Example 273

2,5-difluoro-N-{2-fluoro-3-[5-(2-{[(methylsulfonyl)amino]methyl}-4-pyrimidinyl)-2-(4-morpholinyl)-1,3-thiazol-4-yl]phenyl}benzenesulfonamide

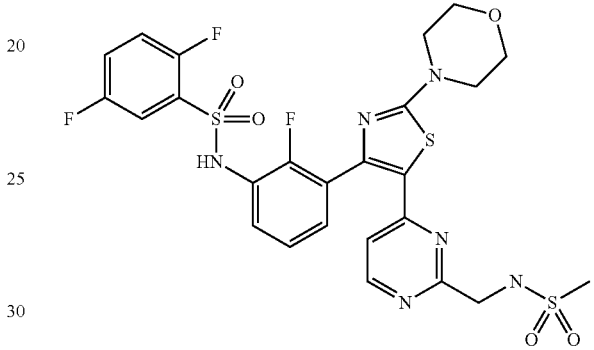

Step A: N-{3-[5-(2-cyano-4-pyrimidinyl)-2-(4-morpholinyl)-1,3-thiazol-4-yl]-2-fluorophenyl}-2,5-difluorobenzenesulfonamide

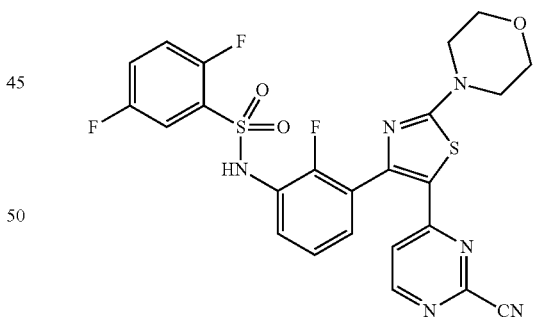

N-{3-[5-(2-chloro-4-pyrimidinyl)-2-(4-morpholinyl)-1,3-thiazol-4-yl]-2-fluorophenyl}-2,5-difluorobenzenesulfonamide (3.54 g, 6.23 mmol), zinc cyanide (0.805 g, 6.86 mmol), and tetrakis(triphenylphosphine)palladium (0) (0.720 g, 0.623 mmol) were stirred in N,N-dimethylformamide (DMF) (27.1 ml) overnight at 80° C. The reaction mixture was added dropwise into water to give a solid. The solids were filtered and dried in a vacuum oven overnight. DCM and MeOH (5:1) were added to solid and heat at 60° C. The mixture was cooled and filtered to obtain N-{3-[5-(2-cyano-4-pyrimidinyl)-2-(4- morpholinyl)-1,3-thiazol-4-yl]-2-fluorophenyl}-2,5-difluorobenzenesulfonamide (2.06, 60%). MS (ESI): 559 [M+H]+.

Step B: N-{3-[5-[2-(aminomethyl)-4-pyrimidinyl]-2-(4-morpholinyl)-1,3-thiazol-4-yl]-2-fluorophenyl}-2,5-difluorobenzenesulfonamide

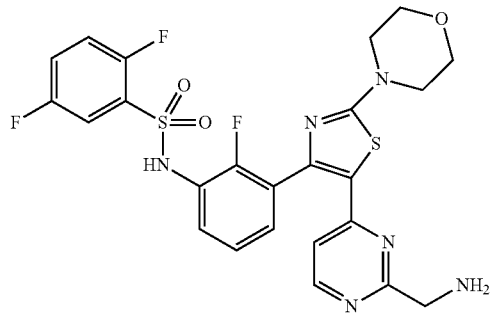 [SMILES: NCc1nccc(-c2sc(N3CCOCC3)nc2-c2cccc(NS(=O)(=O)c3cc(F)ccc3F)c2F)n1]

To a suspension of N-{3-[5-(2-cyano-4-pyrimidinyl)-2-(4-morpholinyl)-1,3-thiazol-4-yl]-2-fluorophenyl}-2,5-difluorobenzenesulfonamide (2.12 g, 3.80 mmol) in dichloromethane (DCM) (38.0 ml) at −78° C. was added DIBAL-H (18.98 ml, 18.98 mmol). The yellow suspension was slowly warmed to RT and stirred 1 hr. The reaction was quenched with Rochelle's salts and stirred about 1 hr. 4N HCl was added to clear the emulsion. The HCl solution was extracted with DCM (3×). The aqueous was passed through celite and neutralize with 6N NaOH. Solid formed during neutralizing and was filtered to obtain N-{3-[5-[2-(aminomethyl)-4-pyrimidinyl]-2-(4-morpholinyl)-1,3-thiazol-4-yl]-2-fluorophenyl}-2,5-difluorobenzenesulfonamide (1.57 g, 73%). MS (ESI): 563 [M+H]+.

Step C: 2,5-difluoro-N-{2-fluoro-3-[5-(2-{[(methylsulfonyl)amino]methyl}-4-pyrimidinyl)-2-(4-morpholinyl)-1,3-thiazol-4-yl]phenyl}benzenesulfonamide To a suspension of N-{3-[5-[2-(aminomethyl)-4-pyrimidinyl]-2-(4-morpholinyl)-1,3-thiazol-4-yl]-2-fluorophenyl}-2,5-difluorobenzenesulfonamide (0.1 g, 0.178 mmol) in dichloromethane (0.500 ml) was added pyridine (0.036 ml, 0.444 mmol) and a solution of methane sulphonyl chloride (0.025 g, 0.222 mmol) in dichloromethane (0.2 ml) and stirred overnight. The reaction was concentrated. The crude product was added to a silica gel column and eluted with DCM with MeOH (0% to 10%) and collected fractions to obtain crude product. The crude product was treated with EtOAc and hexanes and sonicated to form a white solid. The solid was filtered to obtain 2,5-difluoro-N-{2-fluoro-3-[5-(2-{[(methylsulfonyl)amino]methyl}-4-pyrimidinyl)-2-(4-morpholinyl)-1,3-thiazol-4-yl]phenyl}benzenesulfonamide (38 mg, 33%) as white solid. MS (ESI): 641 [M+H]+.

Example 274

N-({4-[4-(3-{[(2,5-difluorophenyl)sulfonyl]amino}-2-fluorophenyl)-2-(4-morpholinyl)-1,3-thiazol-5-yl]-2-pyrimidinyl}methyl)cyclopentanecarboxamide

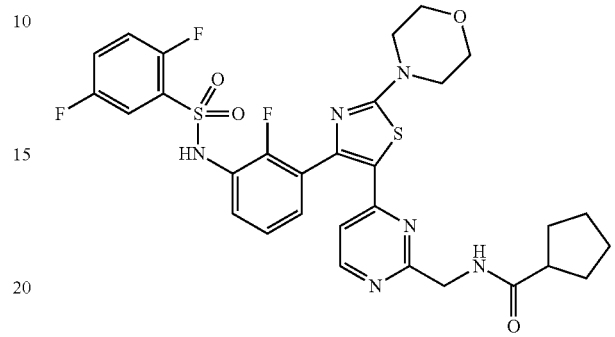

To a suspension of N-{3-[5-[2-(aminomethyl)-4-pyrimidinyl]-2-(4-morpholinyl)-1,3-thiazol-4-yl]-2-fluorophenyl}-2,5-difluorobenzenesulfonamide (0.1 g, 0.178 mmol) in dichloromethane (1.270 ml) was added triethylamine (0.062 ml, 0.444 mmol). A solution of cyclopentanecarbonyl chloride (0.024 g, 0.178 mmol) in dichloromethane (0.508 ml) was added dropwise and stirred. The reaction was quenched with water, extracted 2× with DCM, the organic extracts dried over MgSO4, filtered, and concentrated. The crude product was added to a silica gel column and eluted with DCM with MeOH (0% to 10%) and collected fractions to obtain the title compound as a solid (30 mg, 25% yield). MS (ESI): 659 [M+H]+.

Example 275

N-({4-[4-(3-{[(2,5-difluorophenyl)sulfonyl]amino}-2-fluorophenyl)-2-(4-morpholinyl)-1,3-thiazol-5-yl]-2-pyrimidinyl}methyl)-2-methylpropanamide

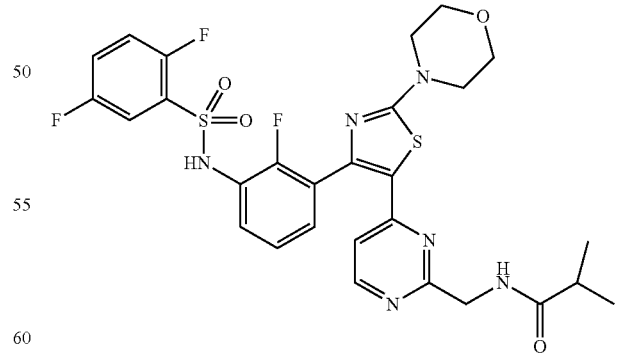

To suspension of N-{3-[5-[2-(aminomethyl)-4-pyrimidinyl]-2-(4-morpholinyl)-1,3-thiazol-4-yl]-2-fluorophenyl}-2,5-difluorobenzenesulfonamide (0.1 g, 0.178 mmol) in dichloromethane (1.778 ml) was added HATU (0.084 g, 0.222 mmol) and 2-methylpropanoic acid (0.047 g, 0.533 mmol).

The reaction mixture was stirred and heated at 55° C. After 16 h, the reaction mixture was quenched with water, extracted with DCM (2×), dried over MgSO₄, filtered, and concentrated. The crude product was added to a silica gel column and eluted with DCM with 10% MeOH in DCM (5% to 40%) and collected fractions to obtain the title compound as a solid (48 mg, 42% yield). MS (ESI): 633 [M+H]⁺.

Example 276

N-({4-[4-(3-{[(2,5-difluorophenyl)sulfonyl]amino}-2-fluorophenyl)-2-(4-morpholinyl)-1,3-thiazol-5-yl]-2-pyrimidinyl}methyl)acetamide

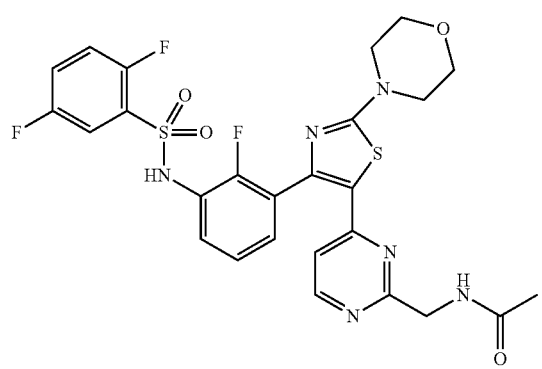 [SMILES: CC(=O)NCc1nccc(-c2sc(N3CCOCC3)nc2-c2cccc(NS(=O)(=O)c3cc(F)ccc3F)c2F)n1]

Following a procedure analogous to the procedure described in Example 275 using N-{3-[5-[2-(aminomethyl)-4-pyrimidinyl]-2-(4-morpholinyl)-1,3-thiazol-4-yl]-2-fluorophenyl}-2,5-difluorobenzenesulfonamide (0.1 g, 0.178 mmol) and acetic acid (0.053 g, 0.889 mmol), the title compound was obtained as a solid (30 mg, 27% yield). MS (ESI): 605 [M+H]⁺.

Example 277

N-{3-[5-(2-ethenyl-4-pyrimidinyl)-2-(4-morpholinyl)-1,3-thiazol-4-yl]-2-fluorophenyl}-2,5-difluorobenzenesulfonamide

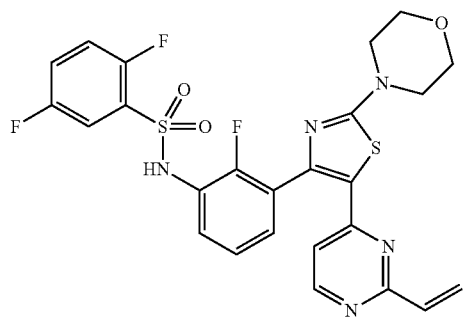 [SMILES: C=Cc1nccc(-c2sc(N3CCOCC3)nc2-c2cccc(NS(=O)(=O)c3cc(F)ccc3F)c2F)n1]

Following a procedure analogous to the procedure described in Example 251 using N-{3-[5-(2-chloro-4-pyrimidinyl)-2-(4-morpholinyl)-1,3-thiazol-4-yl]-2-fluorophenyl}-2,5-difluorobenzenesulfonamide (0.82 g, 1.444 mmol) and potassium vinyl trifluoroborate (0.483 g, 3.61 mmol), the title compound was obtained as a solid (481 mg, 59% yield). MS (ESI): 588 [M−H]⁻.

Example 278

N-{3-[5-(2-amino-4-pyrimidinyl)-2-(1,1-dimethylethyl)-1,3-thiazol-4-yl]-2-fluorophenyl}-2-pyridinesulfonamide

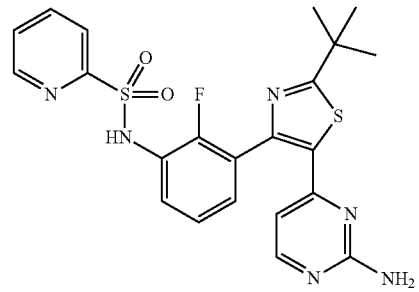 [SMILES: CC(C)(C)c1nc(-c2cccc(NS(=O)(=O)c3ccccn3)c2F)c(-c2ccnc(N)n2)s1]

To a suspension of sodium 2-pyridinesulfinate (48.4 mg, 0.291 mmol) in dichloromethane (3 ml) was added N-chlorosuccinimide (38.9 mg, 0.291 mmol). After 1 hour, the reaction mixture was filtered through a short Celite plug. To the crude sulfonyl chloride solution was added the 4-[4-(3-amino-2-fluorophenyl)-2-(1,1-dimethylethyl)-1,3-thiazol-5-yl]-2-pyrimidinamine (50 mg, 0.146 mmol) and pyridine (0.035 ml, 0.437 mmol), and the mixture was stirred for 3 hours at ambient temperature. After 3 hours, the reaction was quenched with methanol, and the crude reaction mixture was concentrated, redissolved in methanol, and purified via reversed-phase HPLC chromatography, eluting with 30-60% acetonitrile/0.1% aqueous trifluoroacetic acid. The desired fractions were combined, neutralized with aqueous saturated sodium bicarbonate, and extracted with ethyl acetate. The organic layer was washed with brine, dried over anhydrous sodium sulfate, filtered, and concentrated to obtain the title compound (8.8 mg, 12%) as tan solid. MS (ESI): 485 [M+H]⁺.

Example 279

N-{3-[5-(2-amino-4-pyrimidinyl)-2-(tetrahydro-2H-pyran-4-yl)-1,3-thiazol-4-yl]-2-fluorophenyl}-2-pyridinesulfonamide

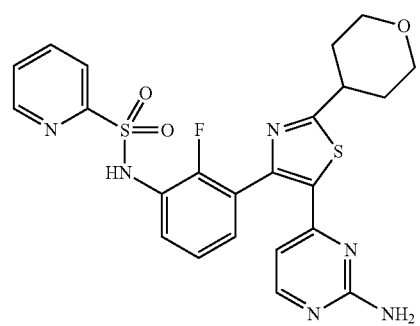 [SMILES: Nc1nccc(-c2sc(C3CCOCC3)nc2-c2cccc(NS(=O)(=O)c3ccccn3)c2F)n1]

Following a procedure analogous to the procedure described in Example 278 using 4-[4-(3-amino-2-fluorophenyl)-2-(tetrahydro-2H-pyran-4-yl)-1,3-thiazol-5-yl]-2-pyrimidinamine (100 mg, 0.269 mmol) and sodium 2-pyridinesulfinate (224 mg, 1.346 mmol), the title compound was obtained as a yellow solid (58 mg, 42% yield). MS (ESI): 513 [M–H]+.

Example 280

N-{3-[5-(2-amino-4-pyrimidinyl)-2-(tetrahydro-2H-pyran-4-yl)-1,3-thiazol-4-yl]-2-fluorophenyl}-2-pyrazinesulfonamide

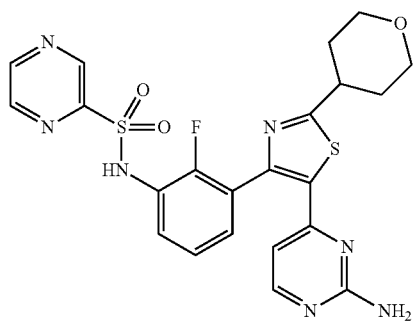 [SMILES: Nc1nccc(-c2sc(C3CCOCC3)nc2-c2cccc(NS(=O)(=O)c3cnccn3)c2F)n1]

Following a procedure analogous to the procedure described in Example 278 using 4-[4-(3-amino-2-fluorophenyl)-2-(tetrahydro-2H-pyran-4-yl)-1,3-thiazol-5-yl]-2-pyrimidinamine (100 mg, 0.269 mmol) and sodium 2-pyrazinesulfinate (135 mg, 0.808 mmol), the title compound was obtained as a yellow solid (30 mg, 21% yield). MS (ESI): 514 [M–H]+.

Example 281

N-{3-[5-(2-amino-4-pyrimidinyl)-2-(tetrahydro-2H-pyran-4-yl)-1,3-thiazol-4-yl]-2-fluorophenyl}-3-furansulfonamide

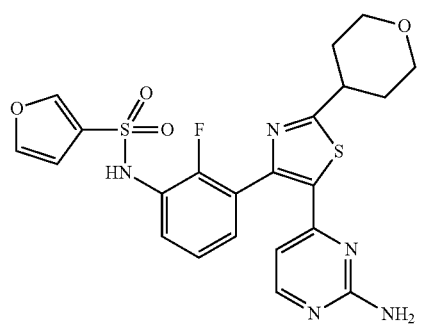 [SMILES: Nc1nccc(-c2sc(C3CCOCC3)nc2-c2cccc(NS(=O)(=O)c3ccoc3)c2F)n1]

Following a procedure analogous to the procedure described in Example 52, Step B using N-{3-[5-(2-chloro-4-pyrimidinyl)-2-(tetrahydro-2H-pyran-4-yl)-1,3-thiazol-4-yl]-2-fluorophenyl}-3-furansulfonamide (1.03 g×3, 5.95 mmol) and ammonium hydroxide (15 mL), the title compound was obtained as a white solid (1.86 g, 61% yield). MS (ESI): 502 [M+H]+.

Example 282

N-{3-[5-(2-amino-4-pyrimidinyl)-2-(1,1-dimethylethyl)-1,3-thiazol-4-yl]-2-fluorophenyl}-1-methyl-1H-pyrazole-5-sulfonamide hydrochloride

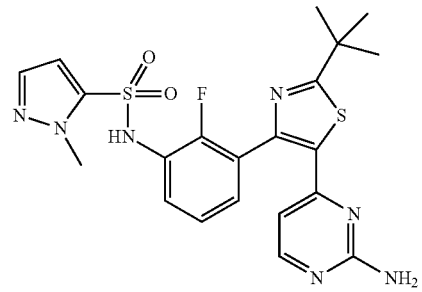 [SMILES: Cn1nccc1S(=O)(=O)Nc1cccc(-c2nc(C(C)(C)C)sc2-c2ccnc(N)n2)c1F]

N-{3-[5-(2-Chloro-4-pyrimidinyl)-2-(1,1-dimethylethyl)-1,3-thiazol-4-yl]-2-fluorophenyl}-1-methyl-1H-pyrazole-5-sulfonamide (530 mg, 1.04 mmol) and ammonium hydroxide (26%, 15 ml) was heated in a steal reactor to 100° C. for 3 h. The reaction mixture was cooled and concentrated under reduced pressure, the residue was dissolved in methanol, and purified by Pre-HPLC (A=10 m MNH$_4$HCO$_3$/H$_2$O, B=Acetonitrile), then the white solid obtained was dissolved in EtOAc, treated with HCl (g) for 30 min. The mixture was concentrated under reduced pressure, and then the residue was suspended in ether (20 ml), treated with ultrasonic for 3 min, filtered, the solid was suspended in ether (20 ml) again, treated with ultrasonic for 3 min, filtered to afford the title compound was obtained as a white solid (142 mg, 26%). $^1$HNMR (MEOD-d$^4$): δ ppm 8.05 (br s, 1H), 7.61-7.65 (ddd, J$_1$=7.7 Hz, J$_2$=1.6 Hz, 1H), 7.42-7.46 (m, 2H), 7.32-7.36 (t, J=8.0 Hz, 1H), 6.70-6.71 (d, J=2.0 Hz, 1H), 6.25-6.27 (d, J=6.4 Hz, 1H), 4.04 (s, 3H), 1.50 (s, 9H). MS: 488.2 [M+H]+.

Example 283

N-{3-[5-(2-amino-4-pyrimidinyl)-2-(1,1-dimethylethyl)-1,3-thiazol-4-yl]-2-fluorophenyl}-1-methyl-1H-pyrazole-4-sulfonamide hydrochloride

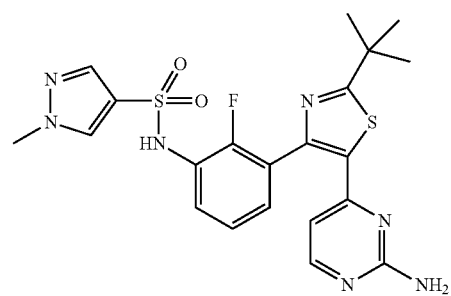 [SMILES: Cn1cc(S(=O)(=O)Nc2cccc(-c3nc(C(C)(C)C)sc3-c3ccnc(N)n3)c2F)cn1]

Following a procedure analogous to the procedure described in Example 282 using N-{3-[5-(2-chloro-4-pyrimidinyl)-2-(1,1-dimethylethyl)-1,3-thiazol-4-yl]-2-fluorophenyl}-1-methyl-1H-pyrazole-4-sulfonamide (750 mg, 1.47 mmol) and ammonium hydroxide (12 ml) the title compound was obtained as a white solid (183 mg, 23%). $^1$HNMR (DMSO-d$^6$): δ ppm 10.13 (s, 1H), 8.23 (s, 1H), 8.11 (br s, 1.5H), 7.68 (s, 1.5H), 7.46-7.49 (dd, $J_1$=7.6 Hz, $J_2$=0.8 Hz, 1H), 7.35 (br s, 1H), 7.27-7.31 (t, J=8.0 Hz, 1H), 6.06 (br s, 2H), 3.82 (s, 3H), 1.42 (s, 9H); MS: 488 [M$^+$H]$^+$.

Example 284

N-{3-[5-(2-amino-4-pyrimidinyl)-2-(1,1-dimethylethyl)-1,3-thiazol-4-yl]-2-fluorophenyl}-1-methyl-1H-pyrrole-3-sulfonamide hydrochloride

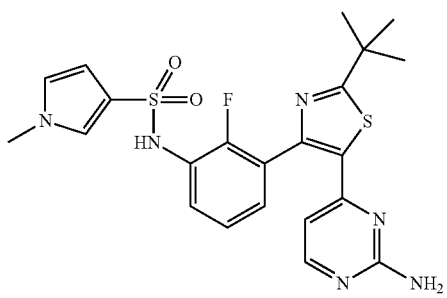 [SMILES: Cn1ccc(S(=O)(=O)Nc2cccc(-c3nc(C(C)(C)C)sc3-c3ccnc(N)n3)c2F)c1]

Following a procedure analogous to the procedure described in Example 282 using N-{3-[5-(2-chloro-4-pyrimidinyl)-2-(1,1-dimethylethyl)-1,3-thiazol-4-yl]-2-fluorophenyl}-1-methyl-1H-pyrrole-3-sulfonamide (230 mg, 0.45 mmol) and ammonium hydroxide (5 ml), the title compound was obtained as a white solid (130 mg, 54.8%). $^1$HNMR (DMSO-d$^6$): δ ppm 9.80 (s, 1H), 8.13-8.15 (d, J=5.6 Hz, 1H), 7.87 (br s, 2H), 7.47-7.51 (dd, $J_1$=7.6 Hz, $J_2$=2.0 Hz, 1H), 7.23-7.29 (m, 3H), 6.80-6.82 (t, J=2.4 Hz, 1H), 6.23-6.24 (dd, $J_1$=2.0H, $J_2$=2.8 Hz, 1H), 6.13-6.14 (d, J=6.0 Hz, 1H), 3.61 (s, 3H), 1.42 (s, 9H); MS: 487.1 [M$^+$H]$^+$.

Example 285

N-{3-[5-(2-amino-4-pyrimidinyl)-2-(tetrahydro-2H-pyran-4-yl)-1,3-thiazol-4-yl]-2-fluorophenyl}-1-methyl-1H-pyrrole-3-sulfonamide hydrochloride

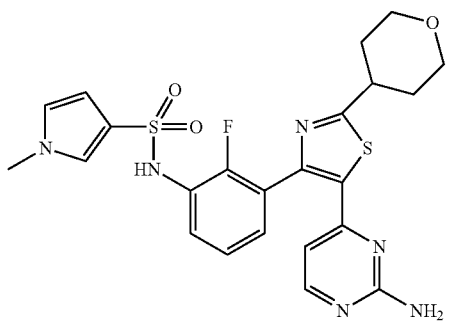

Following a procedure analogous to the procedure described in Example 282 using N-{3-[5-(2-chloro-4-pyrimidinyl)-2-(tetrahydro-2H-pyran-4-yl)-1,3-thiazol-4-yl]-2-fluorophenyl}-1-methyl-1H-pyrrole-3-sulfonamide (260 mg, 0.487 mmol) and ammonium hydroxide (10 ml), the title compound was obtained as a white solid (132 mg, 49.2%). $^1$HNMR (MEOD-d$^4$): δ ppm 7.92-7.93 (d, J=6.4 Hz, 1H), 7.50-7.54 (t, J=7.6 Hz, 1H), 7.16-7.23 (m, 2H), 7.12 (s, 1H), 6.31-6.64 (t, J=2.4 Hz, 1H), 6.30-6.32 (d, J=6.0 Hz, 1H), 6.23 (s, 1H), 3.94-3.97 (dd, $J_1$=11.4 Hz, $J_2$=2.4 Hz, 2H), 3.57 (s, 3H), 3.47-3.53 (t, $J_1$=11.4 Hz, 2H), 3.26-3.28 (m, 1H), 1.98-2.01 (dd, $J_1$=11.8 Hz, $J_2$=1.2 Hz, 2H), 1.76-1.86 (dd, $J_1$=12.1 Hz, $J_2$=4.4 Hz, 2H); MS: 515.2 [M$^+$H]$^+$.

Example 286

N-{3-[5-(2-amino-4-pyrimidinyl)-2-(tetrahydro-2H-pyran-4-yl)-1,3-thiazol-4-yl]-2-fluorophenyl}-1-methyl-1H-pyrazole-4-sulfonamide hydrochloride

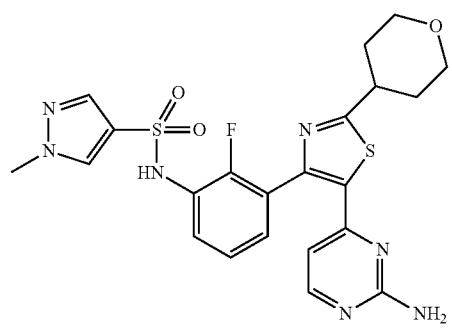 [SMILES: Cn1cc(S(=O)(=O)Nc2cccc(-c3nc(C4CCOCC4)sc3-c3ccnc(N)n3)c2F)cn1]

Following a procedure analogous to the procedure described in Example 282 using N-{3-[5-(2-chloro-4-pyrimidinyl)-2-(tetrahydro-2H-pyran-4-yl)-1,3-thiazol-4-yl]-2-fluorophenyl}-1-methyl-1H-pyrazole-4-sulfonamide (720 mg, 1.34 mmol) and ammonium hydroxide (15 ml), the title compound was obtained as a white solid (122 mg, 16%). $^1$HNMR (MEOD-d$^4$): δ ppm 7.95-7.97 (d, J=8.0 Hz, 2H), 7.52-7.56 (m, 2H), 7.29-7.32 (t, J=6.0 Hz, 1H), 7.21-7.25 (t, J=8.0 Hz, 1H), 6.32-6.33 (d, J=6.4 Hz, 1H), 3.92-3.96 (dd, $J_1$=11.8 Hz, $J_2$=3.2 Hz, 2H), 3.77 (s, 3H), 3.45-3.51 (dd, $J_1$=11.4 Hz, $J_2$=1.2 Hz, 2H), 3.23-3.31 (m, 1H), 1.97-1.99 (d, J=11.2 Hz, 2H), 1.75-1.85 (dd, $J_1$=12.2 Hz, $J_2$=4.0 Hz, 2H); MS: 516 [M$^+$H]$^+$.

Example 287

N-{3-[5-(2-amino-4-pyrimidinyl)-2-(1,1-dimethylethyl)-1,3-thiazol-4-yl]-2-fluorophenyl}-1-methyl-1H-imidazole-2-sulfonamide hydrochloride

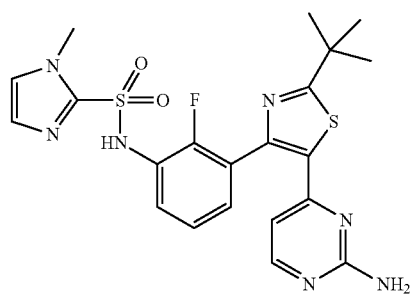 [SMILES: Cn1ccnc1S(=O)(=O)Nc1cccc(-c2nc(C(C)(C)C)sc2-c2ccnc(N)n2)c1F]

Following a procedure analogous to the procedure described in Example 282 using N-{3-[5-(2-chloro-4-pyrimidinyl)-2-(1,1-dimethylethyl)-1,3-thiazol-4-yl]-2-fluorophenyl}-1-methyl-1H-imidazole-2-sulfonamide (560 mg, 1.10 mmol) and ammonium hydroxide (15 ml), the title compound was obtained as a white solid (156 mg, 27%). $^1$HNMR (MEOD-d$^4$): δ ppm 8.06 (br s, 1H), 7.66 (s, 1H), 7.53-7.58 (m, 2H), 7.44 (s, 1H), 7.36-7.40 (t, J=8.0 Hz, 1H), 6.47-6.51 (m, 1H), 4.06 (s, 3H), 1.50 (s, 9H). MS: 488 [M$^+$H]$^+$.

Example 288

N-{3-[5-(2-amino-4-pyrimidinyl)-2-(1,1-dimethylethyl)-1,3-thiazol-4-yl]-2-fluorophenyl}-1-methyl-1H-pyrazole-3-sulfonamide hydrochloride

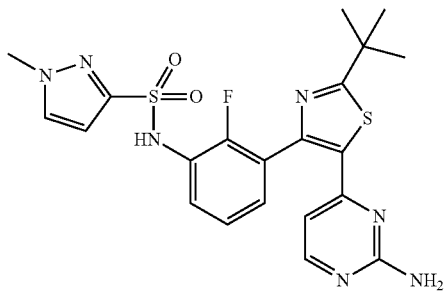 [SMILES: Cn1ccc(S(=O)(=O)Nc2cccc(-c3nc(C(C)(C)C)sc3-c3ccnc(N)n3)c2F)n1]

Following a procedure analogous to the procedure described in Example 282 using N-{3-[5-(2-chloro-4-pyrimidinyl)-2-(1,1-dimethylethyl)-1,3-thiazol-4-yl]-2-fluorophenyl}-1-methyl-1H-pyrazole-3-sulfonamide (760 mg, 1.50 mmol) and ammonium hydroxide (15 ml), the title compound was obtained as a white solid (130 mg, 54%). $^1$HNMR (MEOD-d$^4$): δ ppm 7.94-7.96 (d, J=6.4 Hz, 1H), 7.60-7.60 (d, J=2.4 Hz, 1H), 7.44-7.49 (dd, J$_1$=7.7 Hz, J$_2$=1.2 Hz, 1H), 7.27-7.30 (t, J=6.4 Hz, 1H), 7.15-7.19 (t, J=8.0 Hz, 1H), 6.56-6.56 (t, J=2.4 Hz, 1H), 6.41-6.43 (d, J=6.8 Hz, 1H), 3.81 (s, 3H), 1.39 (s, 9H); MS: 488 [M$^+$H]$^+$:

Example 289

N-{3-[5-(2-amino-4-pyrimidinyl)-2-(tetrahydro-2H-pyran-4-yl)-1,3-thiazol-4-yl]-2-fluorophenyl}-1-methyl-1H-pyrazole-3-sulfonamide hydrochloride

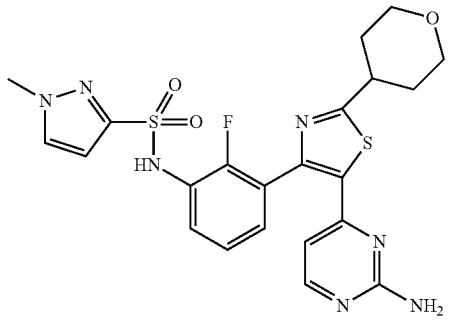 [SMILES: Cn1ccc(S(=O)(=O)Nc2cccc(-c3nc(C4CCOCC4)sc3-c3ccnc(N)n3)c2F)n1]

Following a procedure analogous to the procedure described in Example 282 using N-{3-[5-(2-chloro-4-pyrimidinyl)-2-(tetrahydro-2H-pyran-4-yl)-1,3-thiazol-4-yl]-2-fluorophenyl}-1-methyl-1H-pyrazole-3-sulfonamide (640 mg, 1.19 mmol) and ammonium hydroxide (15 ml), the title compound was obtained as a white solid (340 mg, 51.5%). $^1$HNMR (MEOD-d$^4$): δ ppm 7.93-7.95 (d, J=6.0 Hz, 1H), 7.59-7.59 (d, J=2.0 Hz, 1H), 7.46-7.50 (dd, J$_1$=7.8 Hz, J$_2$=1.6 Hz, 1H), 7.24-7.28 (dd, J$_1$=6.8 Hz, J$_2$=1.6 Hz, 1H), 7.15-7.18 (t, J=7.8 Hz, 1H), 6.54-6.55 (d, J=2.4 Hz, 1H), 6.32-6.34 (d, J=6.0 Hz, 1H), 3.92-3.96 (dd, J$_1$=11.6 Hz, J$_2$=2.4 Hz, 1H), 3.80 (s, 3H), 3.45-3.51 (dd, J$_1$=11.6 Hz, J$_2$=2.0 Hz, 2H), 3.21-3.28 (m, 1H), 1.96-2.00 (dd, J$_1$=12.8 Hz, J$_2$=2.4 Hz, 2H), 1.75-1.85 (dd, J$_1$=12.2 Hz, J$_2$=4.4 Hz, 2H); MS: 516 [M$^+$H]$^+$.

Example 290

N-{3-[2-(1,1-dimethylethyl)-5-(2-{[(2R)-2-hydroxypropyl]amino}-4-pyrimidinyl)-1,3-thiazol-4-yl]-2-fluorophenyl}-2,6-difluorobenzenesulfonamide

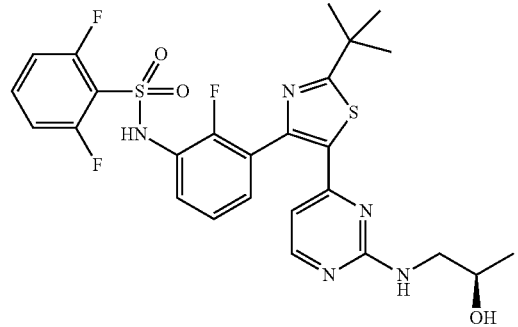 [SMILES: C[C@@H](O)CNc1nccc(-c2sc(C(C)(C)C)nc2-c2cccc(NS(=O)(=O)c3c(F)cccc3F)c2F)n1]

A 5 mL microwave tube was charged with N-{3-[5-(2-chloro-4-pyrimidinyl)-2-(1,1-dimethylethyl)-1,3-thiazol-4-yl]-2-fluorophenyl}-2,6-difluorobenzenesulfonamide (250 mg, 0.464 mmol) and (R)-(−)-1 amino-2-propanol (348 mg, 4.64 mmol) in toluene (3 mL) to give a colorless solution at rt under nitrogen. The sealed reaction mixture was microwaved at 90° C. for 30 min. The reaction mixture was concentrated. The residue was chromatographed on silica gel column and eluted with CH$_2$Cl$_2$ with chloroform/methanol/ammonium hydroxide (90:9:1) (5% to 75%) and collected fractions to obtain ammonium salt of the product. The ammonium salt was diluted with ethyl acetate (10 mL) and water (10 mL) and stirred. 1N HCl was added until pH=6. After stirring, the EtOAc layer was separated from the water layer. The EtOAc layer was dried over Na$_2$SO$_4$, filtered, and concentrated to obtain N-{3-[2-(1,1-dimethylethyl)-5-(2-{[(2R)-2-hydroxypropyl]amino}-4-pyrimidinyl)-1,3-thiazol-4-yl]-2-fluorophenyl}-2,6-difluorobenzenesulfonamide (180 mg, 65.8% yield). MS (ESI): 578 [M+H]$^+$.

Example 291

N-{3-[2-(1,1-dimethylethyl)-5-(2-{[(2S)-2-hydroxypropyl]amino}-4-pyrimidinyl)-1,3-thiazol-4-yl]-2-fluorophenyl}-2,6-difluorobenzenesulfonamide

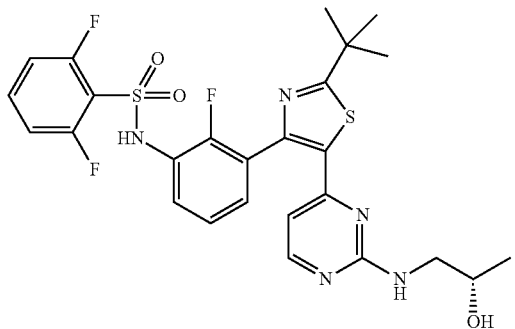 [SMILES: C[C@H](O)CNc1nccc(-c2sc(C(C)(C)C)nc2-c2cccc(NS(=O)(=O)c3c(F)cccc3F)c2F)n1]

Following a procedure analogous to the procedure described in Example 291 using N-{3-[5-(2-chloro-4-pyrimidinyl)-2-(1,1-dimethylethyl)-1,3-thiazol-4-yl]-2-fluorophenyl}-2,6-difluorobenzenesulfonamide (250 mg, 0.464 mmol) and (S)-(+)-1-amino-2-propanol (348 mg, 4.64 mmol), the title compound was obtained as an off white solid (40 mg, 14%). MS (ESI): 578 [M+H]+.

Example 292

N-{3-[5-{2-[(2-cyanoethyl)amino]-4-pyrimidinyl}-2-(1,1-dimethylethyl)-1,3-thiazol-4-yl]-2-fluorophenyl}-2,6-difluorobenzenesulfonamide

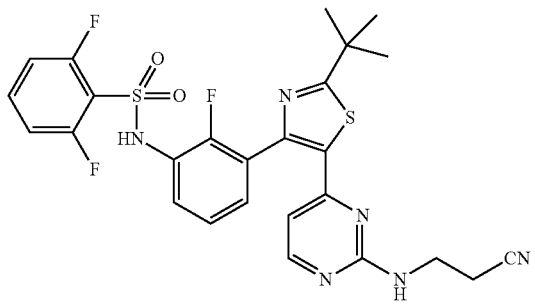

A 5 mL microwave tube was charged with N-{3-[5-(2-chloro-4-pyrimidinyl)-2-(1,1-dimethylethyl)-1,3-thiazol-4-yl]-2-fluorophenyl}-2,6-difluorobenzenesulfonamide (250 mg, 0.464 mmol) and 3-aminopropionitrile (163 mg, 2.319 mmol) and CsF (70.5 mg, 0.464 mmol) in dimethyl sulfoxide (3.00 mL) to give a yellow solution at rt under nitrogen. The sealed reaction mixture was microwaved at 90° C. for 30 min. For second time, the sealed reaction mixture was microwaved at 100° C. for 1 h. The reaction was diluted with water and a white solid formed. The reaction was filtered and washed with water. The crude product was chromatographed on silica gel column and eluted with CH2Cl2 with chloroform/methanol/ammonium hydroxide (90:9:1) (5% to 100%) and collected fractions. Water and DCM were added to solid and take to a pH=6 and extracted with DCM (3×). The CH2Cl2 layers were dried over Na2SO4, filtered, and concentrated to obtain N-{3-[5-{2-[(2-cyanoethyl)amino]-4-pyrimidinyl}-2-(1,1-dimethylethyl)-1,3-thiazol-4-yl]-2-fluorophenyl}-2,6-difluorobenzenesulfonamide (35 mg, 12%). MS (ESI): 573 [M+H]+.

Example 293

N-[3-(2-(1,1-dimethylethyl)-5-{2-[(2-hydroxyethyl)amino]-4-pyrimidinyl}-1,3-thiazol-4-yl)-2-fluorophenyl]-2,6-difluorobenzenesulfonamide

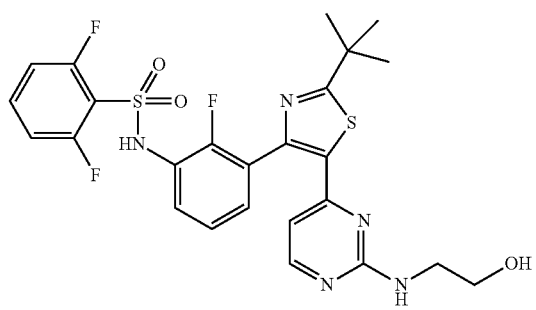 [SMILES: CC(C)(C)c1nc(-c2cccc(NS(=O)(=O)c3c(F)cccc3F)c2F)c(-c2ccnc(NCCC#N)n2)s1]

Following a procedure analogous to the procedure described in Example 290 using N-{3-[5-(2-chloro-4-pyrimidinyl)-2-(1,1-dimethylethyl)-1,3-thiazol-4-yl]-2-fluorophenyl}-2,6-difluorobenzenesulfonamide (250 mg, 0.464 mmol) and 2-aminoethanol (142 mg, 2.31 mmol), the title compound was obtained as a white solid (110 mg, 39%). MS (ESI): 564 [M+H]+.

Example 294

N-{3-[5-[2-(cyclopropylamino)-4-pyrimidinyl]-2-(1,1-dimethylethyl)-1,3-thiazol-4-yl]-2-fluorophenyl}-2,6-difluorobenzenesulfonamide

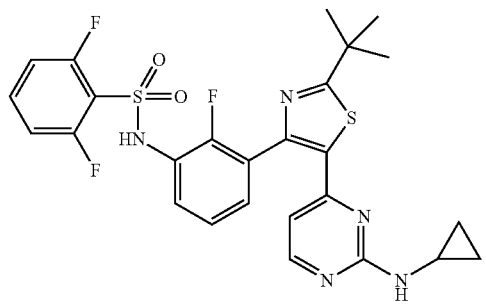 [SMILES: CC(C)(C)c1nc(-c2cccc(NS(=O)(=O)c3c(F)cccc3F)c2F)c(-c2ccnc(NC3CC3)n2)s1]

Following a procedure analogous to the procedure described in Example 290 using N-{3-[5-(2-chloro-4-pyrimidinyl)-2-(1,1-dimethylethyl)-1,3-thiazol-4-yl]-2-fluorophenyl}-2,6-difluorobenzenesulfonamide (250 mg, 0.464 mmol) and cyclopropylamine (0.163 mL, 2.31 mmol), the title compound was obtained as a white solid (40 mg, 14%). MS (ESI): 560 [M+H]+.

Example 295

N-{3-[5-(2-amino-4-pyrimidinyl)-2-(2-hydroxy-1,1-dimethylethyl)-1,3-thiazol-4-yl]-2-fluorophenyl}-2,6-difluorobenzenesulfonamide

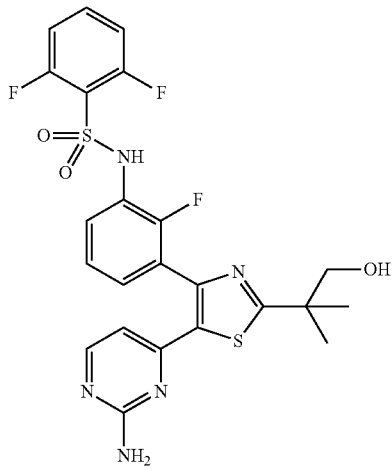 [SMILES: CC(C)(CO)c1nc(-c2cccc(NS(=O)(=O)c3c(F)cccc3F)c2F)c(-c2ccnc(N)n2)s1]

Step A: 3-Hydroxy-2,2-dimethylpropanethioamide

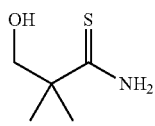

1M-tert-Butylammonium fluoride (2 mL of 1M) in THF was added to a suspension of 3-{[(1,1-dimethylethyl)(diphenyl)silyl]oxy}-2,2-dimethylpropanamide (prepared according to Eur. J. Org. Chem., 2007, 934) (150 mg, 0.404 mmol) in THF (2 mL) at ambient temperature. The mixture was heated to effect dissolution of all solids and the solution stirred at ambient temperature for 1 hour. The solvent was evaporated and residue partitioned between EtOAc (50 mL) and water (25 mL). The separated organic phase was dried (MgSO$_4$), filtered and filtrate evaporated to a clear gum which was flash chromatographed to give the title compound as a white solid (49 mg, 89%). $^1$H NMR (400 MHz, DMSO-d6) δ ppm 9.50 (br s, 1H), 8.70 (br s, 1H), 4.86 (t, J=14 Hz, 1H), 3.45 (d, J=14 Hz), 1.42 (s, 6H). MS (ESI) 134.1 [M+H]$^+$.

Step B: N-{3-[5-(2-chloro-4-pyrimidinyl)-2-(2-hydroxy-1,1-dimethylethyl)-1,3-thiazol-4-yl]-2-fluorophenyl}-2,6-difluorobenzenesulfonamide

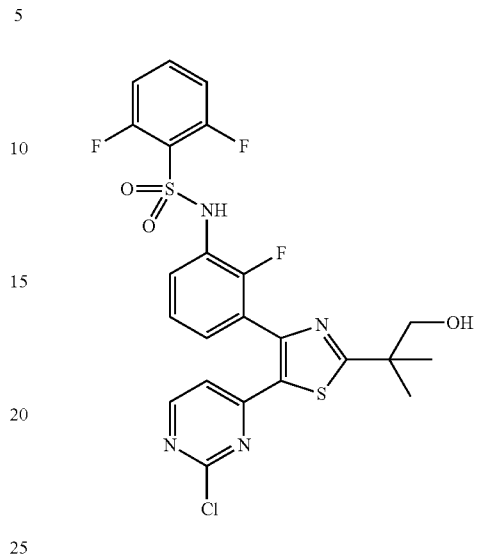

Following a procedure analogous to the procedure described for Intermediate 9 using N-{3-[(2-chloro-4-pyrimidinyl)acetyl]-2-fluorophenyl}-2,6-difluorobenzenesulfonamide (750 mg, 1.7 mmol), NBS (317 mg, 1.782 mmol), and 3-hydroxy-2,2-dimethylpropanethioamide (248 mg, 1.86 mmol), the title compound was obtained as an yellow foam (460 mg, 45%). A portion of the sample was crystallized from ethyl acetate hexanes. $^1$H NMR (400 MHz, DMSO-d$_6$) δ ppm 10.92 (s, 1H) 8.54 (d, J=5.31 Hz, 1H) 7.64-7.74 (m, 1H) 7.41-7.50 (m, 2H) 7.31-7.36 (m, 1H) 7.24 (t, J=8.97 Hz, 2H) 6.87 (d, J=5.31 Hz, 1H) 5.2-5.4 (br s, 1H) 3.54 (s, 2H) 1.36 (s, 6H). MS (ESI): 555.0 [M+H]$^+$.

Step C: N-{3-[5-(2-amino-4-pyrimidinyl)-2-(2-hydroxy-1,1-dimethylethyl)-1,3-thiazol-4-yl]-2-fluorophenyl}-2,6-difluorobenzenesulfonamide N-{3-[5-(2-chloro-4-pyrimidinyl)-2-(2-hydroxy-1,1-dimethylethyl)-1,3-thiazol-4-yl]-2-fluorophenyl}-2,6-difluorobenzenesulfonamide (450 mg, 0.811 mmol) and saturated aqueous ammonium hydroxide (6.0 mL) were heated in a microwave reactor to 90° C. for 90 minutes. The reaction mixture was diluted with water, solution layered with ethyl acetate and pH of the mixture adjusted to 7 giving a gummy residue. The liquors were decanted and set aside; the gum was dissolved in mixture of warm ethyl acetate, dichloromethane and methanol and the solution added to the earlier liquors. The pH of this mixture was re-adjusted to 7.0. Organic phase was separated, dried (MgSO$_4$), filtered and evaporated to give an orange colored foam which was dissolved in ethyl acetate (5 mL). Drop-wise addition of this solution to rapidly stirring hexanes (100 mL) gave a creamy white suspension which was filtered, filter pad washed with fresh hexanes, then air-dried to afford the title compound as a light yellow solid (370 mg, 81% yield). $^1$H NMR (400 MHz, DMSO-d$_6$) d ppm 10.88 (s, 1H) 7.97 (d, J=5.05 Hz, 1H) 7.64-7.77 (m, 1H) 7.40-7.48 (m, 1H) 7.33-7.39 (m, 1H) 7.18-7.32 (m, 4H) 6.75 (s, 2H) 5.84 (d, J=5.05 Hz, 1H) 5.09 (t, J=5.43 Hz, 1H) 3.51 (d, J=5.31 Hz, 2H) 1.33 (s, 6H). MS (ESI): 536.0 [M+H]+.

Example 296

N-{3-[5-(2-amino-4-pyrimidinyl)-2-(1,1-dimethylethyl)-1,3-oxazol-4-yl]-2-fluorophenyl}-2,6-difluorobenzenesulfonamide

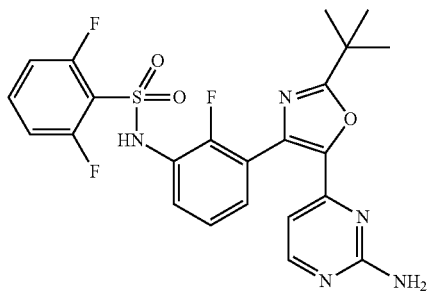 [SMILES: CC(C)(C)c1nc(-c2cccc(NS(=O)(=O)c3c(F)cccc3F)c2F)c(-c2ccnc(N)n2)o1]

Step A: 2-propen-1-yl {3-[bromo(2-chloro-4-pyrimidinyl)acetyl]-2-fluorophenyl}carbamate

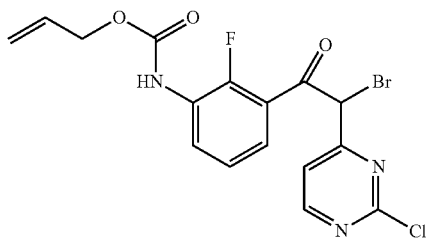 [SMILES: C=CCOC(=O)Nc1cccc(C(=O)C(Br)c2ccnc(Cl)n2)c1F]

To a stirring mixture of 2-propen-1-yl {3-[(2-chloro-4-pyrimidinyl)acetyl]-2-fluorophenyl}carbamate (5 g, 14.30 mmol) in DMA (100 ml) was added NBS (2.54 g, 14.30 mmol) and mixture was stirred at 25° C. overnight. The reaction mixture was poured into water (400 ml) and extracted with EtOAc (100 ml×3). The combined organic layers were dried over Na₂SO₄ and evaporated to afford the title compound as a yellow oil (6.1 g, 99%). MS (ES): 427 [M+H]+.

Step B: 2-propen-1-yl {3-[5-(2-chloro-4-pyrimidinyl)-2-(1,1-dimethylethyl)-1,3-oxazol-4-yl]-2-fluorophenyl}carbamate

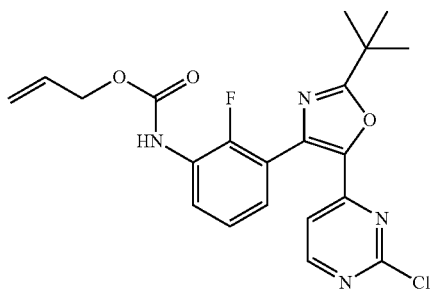 [SMILES: C=CCOC(=O)Nc1cccc(-c2nc(C(C)(C)C)oc2-c2ccnc(Cl)n2)c1F]

A stirring mixture of 2-propen-1-yl {3-[bromo(2-chloro-4-pyrimidinyl)acetyl]-2-fluorophenyl}carbamate (6.1 g, 14.23 mmol) and 2,2-dimethylpropanamide (2.16 g, 21.35 mmol) in DMA (200 ml) was heated to 80° C. for 2 days. Upon cooling, the reaction mixture was poured into water (500 ml) and extracted with EtOAc (100 ml×5). The combined organic layers were washed with brine, separated, dried over Na₂SO₄, filtered, and concentrated. The crude product was added to a silica gel column and eluted with petroleum ether with EtOAc (10% to 16%) and collected fractions to obtain title compound as yellow solid (1.21 g, 19%). MS (ES): 431 [M+H]+.

Step C: 3-[5-(2-chloro-4-pyrimidinyl)-2-(1,1-dimethylethyl)-1,3-oxazol-4-yl]-2-fluoroaniline

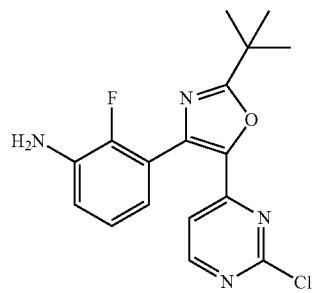 [SMILES: CC(C)(C)c1nc(-c2cccc(N)c2F)c(-c2ccnc(Cl)n2)o1]

Following a procedure analogous to the procedure described in Intermediate 13 using 2-propen-1-yl {3-[5-(2-chloro-4-pyrimidinyl)-2-(1,1-dimethylethyl)-1,3-oxazol-4-yl]-2-fluorophenyl}carbamate (1.2 g, 2.78 mmol) and tri-n-butyltin hydride (1.21 g, 4.17 mmol), the title compound was obtained as a yellow solid (530 mg, 55%). MS (ESI): 347 [M+H]+.

Step D: N-{3-[5-(2-chloro-4-pyrimidinyl)-2-(1,1-dimethylethyl)-1,3-oxazol-4-yl]-2-fluorophenyl}-2,6-difluorobenzenesulfonamide

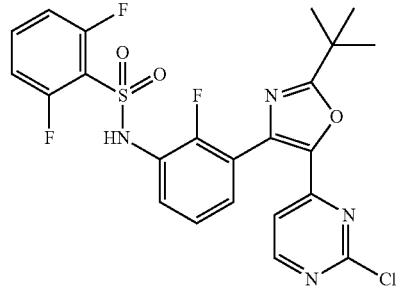 [SMILES: CC(C)(C)c1nc(-c2cccc(NS(=O)(=O)c3c(F)cccc3F)c2F)c(-c2ccnc(Cl)n2)o1]

Following a procedure analogous to the procedure described in Intermediate 14 using 3-[5-(2-chloro-4-pyrimidinyl)-2-(1,1-dimethylethyl)-1,3-oxazol-4-yl]-2-fluoroaniline (150 mg, 0.433 mmol) and 2,6-difluorobenzenesulfonyl chloride (184 mg, 0.865 mmol), the title compound was obtained as a white solid (135 mg, 59%). MS (ES): 522 [M+H]+.

Step E: N-{3-[5-(2-amino-4-pyrimidinyl)-2-(1,1-dimethylethyl)-1,3-oxazol-4-yl]-2-fluorophenyl}-2,6-difluorobenzenesulfonamide Following a procedure analogous to the procedure described in Example 52, Step B using N-{3-[5-(2-chloro-4- pyrimidinyl)-2-(1,1-dimethylethyl)-1,3-oxazol-4-yl]-2-fluorophenyl}-2,6-difluorobenzenesulfonamide (94 mg, 0.179 mmol) and ammonium hydroxide (5 mL), the title compound was obtained as a white solid (30 mg, 33%). $^1$H-NMR (DMSO-d6): δ ppm 10.34 (br s, 1H), 8.18-8.19 (d, J=5.2 Hz, 1H), 7.65 (br s, 1H), 7.30-7.34 (t, J=7.4 Hz, 2H), 7.21-7.24 (m, 3H), 6.56 (br s, 2H), 6.45 (d, J=5.2 Hz, 1H), 1.40 (s, 9H); MS: 504 [M$^+$H]$^+$.

Example 297

N-{3-[5-(2-amino-4-pyrimidinyl)-2-(1,1-dimethylethyl)-1,3-oxazol-4-yl]-2-fluorophenyl}-2,5-difluorobenzenesulfonamide

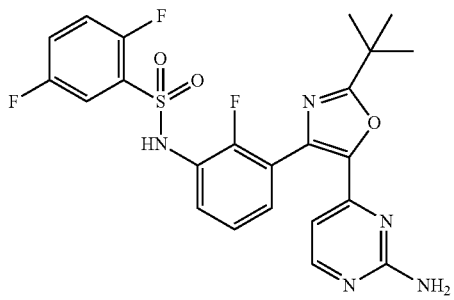 [SMILES: CC(C)(C)c1nc(-c2cccc(NS(=O)(=O)c3cc(F)ccc3F)c2F)c(-c2ccnc(N)n2)o1]

Following a procedure analogous to the procedure described in Example 52, Step B using N-{3-[5-(2-chloro-4-pyrimidinyl)-2-(1,1-dimethylethyl)-1,3-oxazol-4-yl]-2-fluorophenyl}-2,5-difluorobenzenesulfonamide (135 mg, 0.258 mmol) and ammonium hydroxide (5 mL), the title compound was obtained as an off-white solid (75 mg, 58%). $^1$H-NMR (DMSO-d6): δ ppm 10.74 (br s, 1H), 8.26 (d, J=5.6 Hz, 1H), 7.45-7.61 (m, 4H), 7.28-7.37 (m, 1H), 6.63-7.26 (m, 1H), 6.62 (d, J=5.6 Hz, 1H), 1.40 (s, 9H); MS: 504 [M$^+$H]$^+$.

Example 298

N-{3-[5-(2-amino-4-pyrimidinyl)-2-(1,1-dimethylethyl)-1,3-oxazol-4-yl]-2-fluorophenyl}-2-furansulfonamide

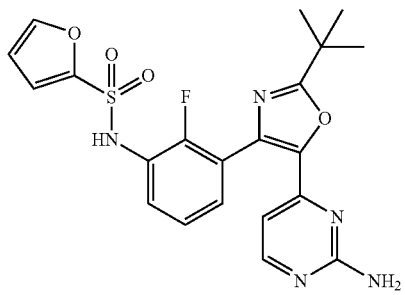 [SMILES: CC(C)(C)c1nc(-c2cccc(NS(=O)(=O)c3ccco3)c2F)c(-c2ccnc(N)n2)o1]

Following a procedure analogous to the procedure described in Example 52, Step B using N-{3-[5-(2-chloro-4-pyrimidinyl)-2-(1,1-dimethylethyl)-1,3-oxazol-4-yl]-2-fluorophenyl}-2-furansulfonamide (72 mg, 0.151 mmol) and ammonium hydroxide (5 mL), the title compound was obtained as a white solid (62 mg, 89%). $^1$H-NMR (DMSO-d6): δ ppm 10.57 (br s, 1H), 8.26 (d, J=5.6 Hz, 1H), 7.97 (m, 1H), 7.44-7.48 (m, 1H), 7.23-7.32 (m, 2H), 7.08 (m, 1H), 6.63 (m, 1H) 6.57 (d, J=5.2 Hz, 1H), 1.41 (s, 9H); MS: 458 [M$^+$H]$^+$.

Example 299

N-{3-[5-(2-amino-4-pyrimidinyl)-2-(1,1-dimethylethyl)-1,3-oxazol-4-yl]-2-fluorophenyl}-3-furansulfonamide

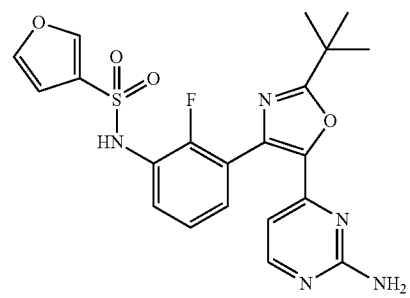 [SMILES: CC(C)(C)c1nc(-c2cccc(NS(=O)(=O)c3ccoc3)c2F)c(-c2ccnc(N)n2)o1]

Following a procedure analogous to the procedure described in Example 52, Step B using N-{3-[5-(2-chloro-4-pyrimidinyl)-2-(1,1-dimethylethyl)-1,3-oxazol-4-yl]-2-fluorophenyl}-3-furansulfonamide (85 mg, 0.178 mmol) and ammonium hydroxide (5 mL), the title compound was obtained as an off-white solid (74 mg, 91%). $^1$H-NMR (DMSO-d6): δ ppm 10.25 (br s, 1H), 8.27 (s, 1H), 8.25 (d, J=5.2 Hz, 1H), 7.83 (t, J=2.0 Hz, 1H), 7.44-7.36 (m, 2H), 7.25 (t, J=8.4 Hz, 1H), 6.69 (s, 1H), 6.63 (br s, 2H), 6.50 (d, J=5.2 Hz, 1H), 1.41 (s, 9H); MS: 458 [M$^+$H]$^+$.

Example 300

N-{2-fluoro-3-[5-{2-[(2-hydroxyethyl)amino]-4-pyrimidinyl}-2-(tetrahydro-2H-pyran-4-yl)-1,3-thiazol-4-yl]phenyl}-3-furansulfonamide

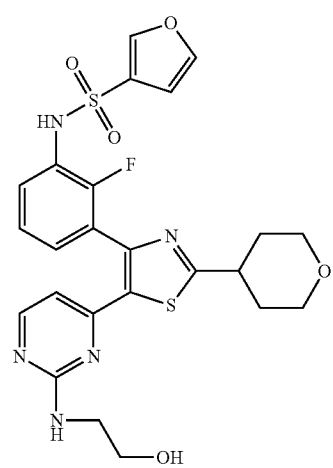 [SMILES: O=S(=O)(Nc1cccc(-c2nc(C3CCOCC3)sc2-c2ccnc(NCCO)n2)c1F)c1ccoc1]

To the solution of N-{3-[5-(2-chloro-4-pyrimidinyl)-2-(tetrahydro-2H-pyran-4-yl)-1,3-thiazol-4-yl]-2-fluorophenyl}-3-furansulfonamide (110 mg, 0.211 mmol) in toluene (2 ml) was added ethanol amine (64.5 mg, 1.056 mmol) and the reaction mixture heated in MW for 30 min at 140° C. Methanol (1 ml) was added and solution was purified by chromatography (100% EtOAc to 20% MeOH:EtOAc). N-{2-fluoro-3-[5-{2-[(2-hydroxyethyl)amino]-4-pyrimidinyl}-2-(tetrahydro-2H-pyran-4-yl)-1,3-thiazol-4-yl]phenyl}-3-furansulfonamide (53 mg, 43.7%) was isolated as white powder. $^1$H NMR (400 MHz, DMSO-$d_6$) ppm 1.74 (qd, J=12.19, 4.48 Hz, 2H), 2.01 (dd, J=12.66, 2.12 Hz, 2H), 3.21-3.34 (m, 4H), 3.42-3.57 (m, 4H), 3.93 (dt, J=9.58, 2.22 Hz, 2H), 4.67 (t, J=6.00 Hz, 1H), 6.66 (t, J=1.29 Hz, 1H), 7.17 (t, J=5.75 Hz, 1H), 7.24-7.40 (m, 2H), 7.46 (td, J=7.69, 1.99 Hz, 1H), 7.82 (t, J=1.80 Hz, 1H), 8.08 (d, J=5.18 Hz, 1H), 8.28 (t, J=1.20 Hz, 1H), 10.31 (s, 1H); MS (ESI): 546.1 [M+H]$^+$.

Example 301

N-{3-[5-(2-{[2-(diethylamino)ethyl]amino}-4-pyrimidinyl)-2-(tetrahydro-2H-pyran-4-yl)-1,3-thiazol-4-yl]-2-fluorophenyl}-3-furansulfonamide

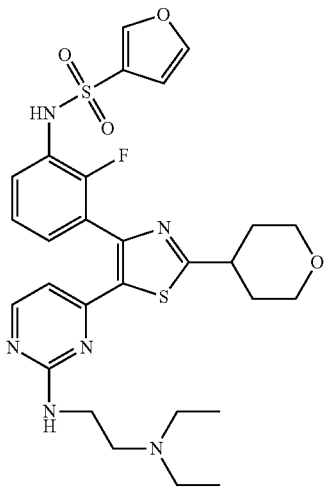 [SMILES: CCN(CC)CCNc1nccc(-c2sc(C3CCOCC3)nc2-c2cccc(NS(=O)(=O)c3ccoc3)c2F)n1]

Following a procedure analogous to the procedure described in example 300 using N-{3-[5-(2-chloro-4-pyrimidinyl)-2-(tetrahydro-2H-pyran-4-yl)-1,3-thiazol-4-yl]-2-fluorophenyl}-3-furansulfonamide (110 mg, 0.211 mmol), N,N-diethyl-1,2-ethanediamine (123 mg, 1.056 mmol) in 1,4-dioxane (2 mL), the title compound was obtained as a yellow foam (30 mg, 22.47%). $^1$H NMR (400 MHz, DMSO-$d_6$) ppm 1.01 (t, J=6.44 Hz, 6H), 1.65-1.83 (m, 2H), 2.01 (dd, J=12.76, 1.89 Hz, 2H), 2.58-2.73 (m, 6H), 3.27-3.41 (m, 5H), 3.42-3.58 (m, 2H), 3.93 (dt, J=9.54, 2.18 Hz, 2H), 5.78-6.17 (m, 1H), 6.60 (d, J=1.26 Hz, 1H), 6.97-7.28 (m, 3H), 7.43 (td, J=7.77, 1.64 Hz, 1H), 7.75 (s, 1H), 7.96-8.30 (m, 2H); MS (ESI): 601.2 [M+H]$^+$.

Example 302

N-{2-fluoro-3-[5-(2-{[(2R)-2-hydroxypropyl]amino}-4-pyrimidinyl)-2-(tetrahydro-2H-pyran-4-yl)-1,3-thiazol-4-yl]phenyl}-3-furansulfonamide

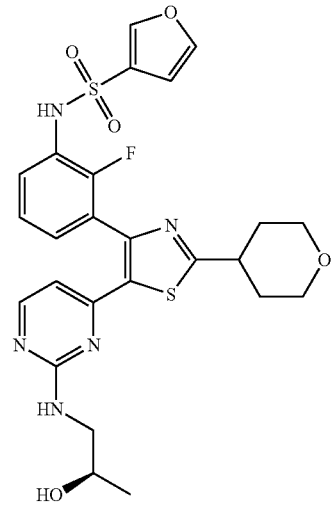 [SMILES: C[C@@H](O)CNc1nccc(-c2sc(C3CCOCC3)nc2-c2cccc(NS(=O)(=O)c3ccoc3)c2F)n1]

Following a procedure analogous to the procedure described in example 300 using N-{3-[5-(2-chloro-4-pyrimidinyl)-2-(tetrahydro-2H-pyran-4-yl)-1,3-thiazol-4-yl]-2-fluorophenyl}-3-furansulfonamide (110 mg, 0.211 mmol), (R)-(-)-1-aminopropanol (79 mg, 1.056 mmol) in 1,4-dioxane (2 mL), the title compound was obtained as a yellow foam (48 mg, 0.081 mmol, 38.6%). $^1$H NMR (400 MHz, DMSO-$d_6$) ppm 0.93-1.12 (m, 3H), 1.75 (qd, J=12.13, 4.29 Hz, 2H), 2.02 (d, J=1.77 Hz, 1H), 3.00-3.24 (m, 2H), 3.24-3.33 (m, 1H), 3.40-3.59 (m, 2H), 3.78 (dt, J=10.67, 5.65 Hz, 1H), 3.93 (dd, J=11.24, 2.15 Hz, 2H), 4.69 (d, J=1.26 Hz, 1H), 5.79-6.06 (m, 1H), 6.66 (d, J=1.26 Hz, 1H), 7.13 (t, J=5.81 Hz, 1H), 7.20-7.40 (m, 2H), 7.40-7.53 (m, 1H), 7.81 (t, J=1.77 Hz, 1H), 8.08 (d, J=5.05 Hz, 1H), 8.27 (s, 1H), 10.30 (br. s., 1H); MS (ESI): 560.1 [M+H]$^+$.

Example 303

N-{2-fluoro-3-[5-(2-{[(2S)-2-hydroxypropyl]amino}-4-pyrimidinyl)-2-(tetrahydro-2H-pyran-4-yl)-1,3-thiazol-4-yl]phenyl}-3-furansulfonamide

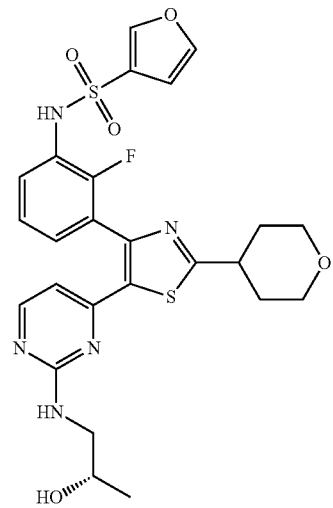 [SMILES: C[C@H](O)CNc1nccc(-c2sc(C3CCOCC3)nc2-c2cccc(NS(=O)(=O)c3ccoc3)c2F)n1]

Following a procedure analogous to the procedure described in example 300 using N-{3-[5-(2-chloro-4-pyrimidinyl)-2-(tetrahydro-2H-pyran-4-yl)-1,3-thiazol-4-yl]-2-fluorophenyl}-3-furansulfonamide (110 mg, 0.211 mmol), (S)-(+)-1-amino-2-propanol (79 mg, 1.056 mmol) in 1,4-dioxane (2 mL), the title compound was obtained as a white foam (44 mg, 0.075 mmol, 35.4%). $^1$H NMR (400 MHz, DMSO-$d_6$) ppm 1.05 (d, J=6.32 Hz, 3H), 1.75 (qd, J=12.13, 4.04 Hz, 2H), 1.99-2.09 (m, 2H), 2.98-3.24 (m, 2H), 3.29 (tt, J=11.49, 3.92 Hz, 1H), 3.39-3.53 (m, 2H), 3.78 (dt, J=11.31, 5.84 Hz, 1H), 3.93 (dd, J=11.49, 2.15 Hz, 2H), 4.69 (br s., 1H), 5.94 (d, J=1.26 Hz, 1H), 6.66 (d, J=1.01 Hz, 1H), 7.13 (t, J=5.81 Hz, 1H), 7.23-7.39 (m, 2H) 7.46 (t, J=6.95 Hz, 1H), 7.82 (t, J=1.77 Hz, 1H), 8.08 (d, J=5.05 Hz, 1H), 8.28 (s, 1H), 10.32 (s, 1H); MS (ESI): 560.0 [M+H]$^+$.

Example 304

N-{2-fluoro-3-[5-{2-[(2-methylpropyl)amino]-4-pyrimidinyl}-2-(tetrahydro-2H-pyran-4-yl)-1,3-thiazol-4-yl]phenyl}-3-furansulfonamide

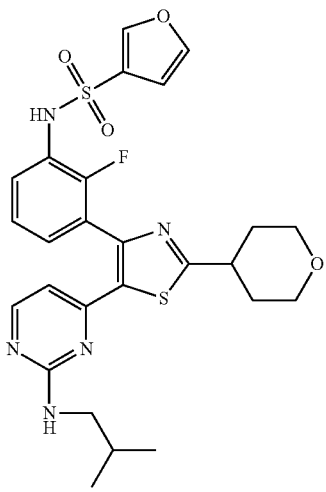 [SMILES: CC(C)CNc1nccc(-c2sc(C3CCOCC3)nc2-c2cccc(NS(=O)(=O)c3ccoc3)c2F)n1]

Following a procedure analogous to the procedure described in example 300 using N-{3-[5-(2-chloro-4-pyrimidinyl)-2-(tetrahydro-2H-pyran-4-yl)-1,3-thiazol-4-yl]-2-fluorophenyl}-3-furansulfonamide (110 mg, 0.211 mmol), isobutylamine (77 mg, 1.056 mmol) in 1,4-dioxane (2 mL), the title compound was obtained as a yellow foam (28 mg, 0.048 mmol, 22.59%). $^1$H NMR (400 MHz, DMSO-$d_6$) ppm 0.87 (d, J=6.57 Hz, 7H), 1.76 (td, J=12.00, 3.79 Hz, 3H), 1.94-2.06 (m, 2H), 3.25-3.34 (m, 2H), 3.41-3.50 (m, 2H), 3.93 (dt, J=9.66, 2.12 Hz, 2H), 5.79-6.04 (m, 1H), 6.66 (d, J=1.26 Hz, 1H), 7.20-7.41 (m, 3H), 7.41-7.56 (m, 1H), 7.81 (t, J=1.77 Hz, 1H), 8.08 (d, J=5.30 Hz, 1H), 8.28 (s, 1H), 10.31 (s, 1H); MS (ESI): 558.0 [M+H]$^+$.

Example 305

N-(2-fluoro-3-{2-(tetrahydro-2H-pyran-4-yl)-5-[2-(tetrahydro-2H-pyran-4-ylamino)-4-pyrimidinyl]-1,3-thiazol-4-yl}phenyl)-3-furansulfonamide

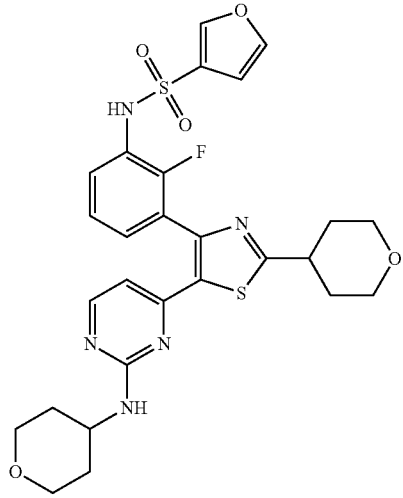 [SMILES: O=S(=O)(Nc1cccc(-c2nc(C3CCOCC3)sc2-c2ccnc(NC3CCOCC3)n2)c1F)c1ccoc1]

Following a procedure analogous to the procedure described in example 300 using N-{3-[5-(2-chloro-4-pyrimidinyl)-2-(tetrahydro-2H-pyran-4-yl)-1,3-thiazol-4-yl]-2-fluorophenyl}-3-furansulfonamide (110 mg, 0.211 mmol), 4-aminotetrahydropyrane (107 mg, 1.056 mmol) in 1,4-dioxane (2 mL), the title compound was obtained as a brown foam (20 mg, 0.032 mmol, 15%). $^1$H NMR (400 MHz, DMSO-$d_6$) ppm 1.33-1.63 (m, 2H), 1.75 (qd, J=11.96, 4.29 Hz, 4H), 1.99-2.05 (m, 2H), 3.19-3.39 (m, 5H), 3.47 (td, J=11.62, 1.77 Hz, 2H), 3.78-3.90 (m, 2H), 3.90-3.98 (m, 2H), 6.66 (d, J=1.26 Hz, 1H), 7.23-7.38 (m, 3H), 7.45 (t, J=6.95 Hz, 1H), 7.82 (t, J=1.77 Hz, 1H), 8.11 (d, J=4.55 Hz, 1H), 8.28 (s, 1H), 10.32 (s, 1H); MS (ESI): 586.0 [M+H]$^+$.

Example 306

N-{2-fluoro-3-[5-(2-{[2-(1-pyrrolidinyl)ethyl]amino}-4-pyrimidinyl)-2-(tetrahydro-2H-pyran-4-yl)-1,3-thiazol-4-yl]phenyl}-3-furansulfonamide

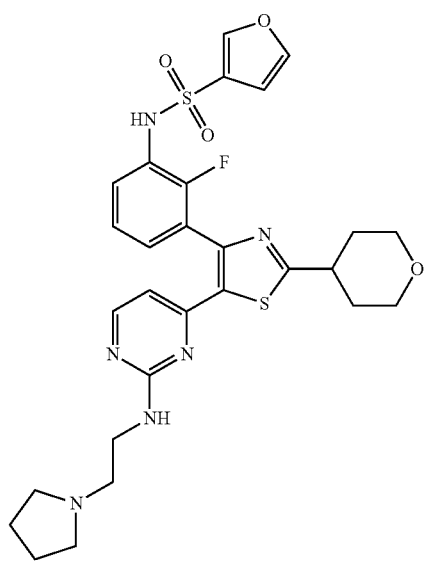 [SMILES: O=S(=O)(Nc1cccc(-c2nc(C3CCOCC3)sc2-c2ccnc(NCCN3CCCC3)n2)c1F)c1ccoc1]

Following a procedure analogous to the procedure described in example 300 using N-{3-[5-(2-chloro-4-pyrimidinyl)-2-(tetrahydro-2H-pyran-4-yl)-1,3-thiazol-4-yl]-2-fluorophenyl}-3-furansulfonamide (110 mg, 0.211 mmol), [2-(1-pyrrolidinyl)ethyl]amine (121 mg, 1.056 mmol) in 1,4-dioxane (2 mL)), the title compound was obtained as a white foam (30 mg, 22%). $^1$H NMR (400 MHz, DMSO-d$_6$) ppm 1.58-1.87 (m, 6H), 2.01 (dd, J=12.88, 2.02 Hz, 2H), 2.54-2.88 (m, 6H), 3.12-3.43 (m, 3H), 3.47 (td, J=11.62, 2.02 Hz, 2H), 3.93 (dt, J=9.47, 2.21 Hz, 2H), 5.77 (s, 1H), 5.91-6.31 (m, 1H), 6.56 (d, J=1.26 Hz, 1H), 6.92 (br. s., 1H), 7.07 (t, J=7.71 Hz, 1H), 7.18 (br. s., 1H), 7.41 (td, J=8.02, 1.64 Hz, 1H), 7.70 (t, J=1.77 Hz, 1H), 8.05 (s, 1H), 8.11 (d, J=5.05 Hz, 1H); MS (ESI): 599.1 [M+H]$^+$.

Example 307

N-{2-fluoro-3-[5-(2-{[2-(4-morpholinyl)ethyl]amino}-4-pyrimidinyl)-2-(tetrahydro-2H-pyran-4-yl)-1,3-thiazol-4-yl]phenyl}-3-furansulfonamide

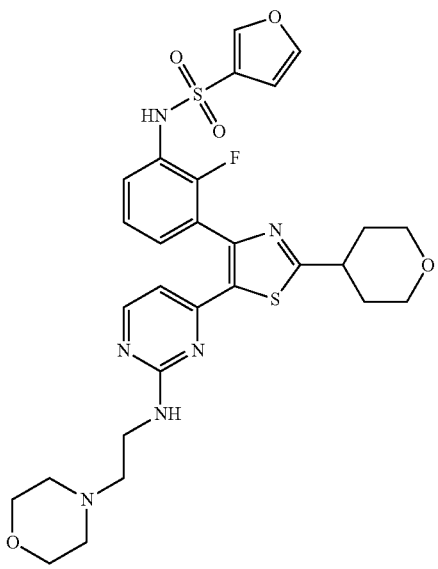 [SMILES: O=S(=O)(Nc1cccc(-c2nc(C3CCOCC3)sc2-c2ccnc(NCCN3CCOCC3)n2)c1F)c1ccoc1]

Following a procedure analogous to the procedure described in example 300 using N-{3-[5-(2-chloro-4-pyrimidinyl)-2-(tetrahydro-2H-pyran-4-yl)-1,3-thiazol-4-yl]-2-fluorophenyl}-3-furansulfonamide (110 mg, 0.211 mmol), [2-(4-morpholinyl)ethyl]amine (137 mg, 1.056 mmol) in 1,4-dioxane (2 mL), the title compound was obtained as a white foam (35 mg, 25.6%. $^1$H NMR (400 MHz, DMSO-d$_6$) ppm 1.62-1.83 (m, 2H), 2.01 (dd, J=12.76, 2.15 Hz, 2H), 2.35-2.47 (m, 7H), 3.23-3.32 (m, 2H), 3.47 (td, J=11.56, 1.89 Hz, 2H), 3.57 (t, J=4.42 Hz, 4H), 3.93 (dt, J=9.35, 2.27 Hz, 2H), 5.81-6.11 (m, 1H), 6.64 (s, 1H), 7.13 (t, J=5.31 Hz, 1H), 7.24 (d, J=5.56 Hz, 2H), 7.44 (dt, J=9.66, 3.76 Hz, 1H), 7.79 (s, 1H), 8.09 (d, J=5.30 Hz, 1H), 8.23 (s, 1H), 10.32 (d, J=1.01 Hz, 1H); MS (ESI): 615.1 [M+H]$^+$.

Example 308 and Example 309

2-[5-(2-Amino-4-pyrimidinyl)-4-(3-{[(2,6-difluorophenyl)sulfonyl]amino}-2-fluorophenyl)-1,3-thiazol-2-yl]-2-methylpropanoic acid and 2-[5-(2-Amino-4-pyrimidinyl)-4-(3-{[(2,6-difluorophenyl)sulfonyl]amino}-2-fluorophenyl)-1,3-thiazol-2-yl]-2-methylpropanamide Step A: 3-Hydroxy-2,2-dimethylpropanethioamide

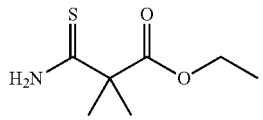

ethyl 2-cyano-2-methylpropanoate (2.5 g, 17.71 mmol) and diphenylphosphinodithioic acid (8.86 g, 35.4 mmol) in isopropanol (150 mL) were heated to reflux overnight, then cooled to ambient temperature. The mixture was transferred in a freezer for 50 minutes then filtered rapidly (white deposit produced during freezer storage was left behind). The filtrate was evaporated, residue dissolved in DCM (250 mL) and the solution washed sequentially with 100 mL each of water, 1N—NaOH and sat. aq. sodium bicarbonate. After drying (MgSO4), the solution was filtered and filtrate evaporated to give clear liquid which was flash chromatographed on silica gel to afford the title compound as a yellow liquid (0.43 g, 14%). $^1$H NMR (400 MHz, DMSO-d$_6$) d ppm 9.73 (br s, 1H) 8.82 (br s, 1H) 3.96-4.15 (q, J=7.07 Hz, 2H) 1.40 (s, 6H) 1.16 (t, J=7.07 Hz, 3H), MS (ESI) 175.0 [M+H]$^+$.

Step B: Ethyl 2-[5-(2-chloro-4-pyrimidinyl)-4-(3-{[(2,6-difluorophenyl)sulfonyl]amino}-2-fluorophenyl)-1,3-thiazol-2-yl]-2-methylpropanoate

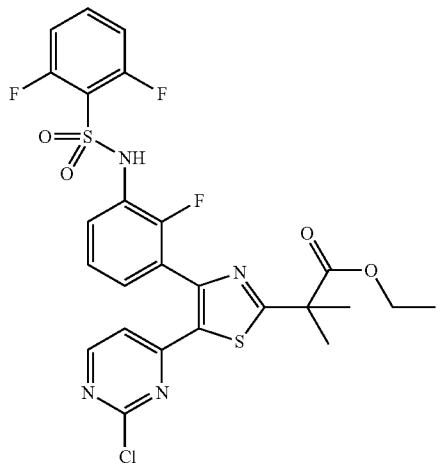 [SMILES: CCOC(=O)C(C)(C)c1nc(-c2cccc(NS(=O)(=O)c3c(F)cccc3F)c2F)c(-c2ccnc(Cl)n2)s1]

Following a procedure analogous to the procedure described for Intermediate 9 using N-{3-[(2-chloro-4-pyrimidinyl)acetyl]-2-fluorophenyl}-2,6-difluorobenzenesulfonamide (962 mg, 2.18 mmol) and 3-hydroxy-2,2-dimethylpropanethioamide (394 mg, 2.26 mmol), the title compound was obtained as a white foam (940 mg, 72% yield). A portion of the sample was crystallized from ethyl acetate hexanes. $^1$H NMR (400 MHz, DMSO-d$_6$) d ppm 10.93 (s, 1H), 8.58 (d, J=5.31 Hz, 1H), 7.63-7.76 (m, 1H), 7.41-7.52 (m, 2H), 7.29-7.38 (m, 1H), 7.24 (t, J=8.97 Hz, 2H), 6.91 (d, J=5.31 Hz, 1H), 4.14 (q, J=7.07 Hz, 2H), 1.67 (s, 6H), 1.15 (t, J=7.07 Hz, 3H). MS (ESI): 597.0, 598.5 [M+H]$^+$.

Step C: 2-[5-(2-Amino-4-pyrimidinyl)-4-(3-{[(2,6-difluorophenyl)sulfonyl]amino}-2-fluorophenyl)-1,3-thiazol-2-yl]-2-methylpropanoic acid and 2-[5-(2-Amino-4-pyrimidinyl)-4-(3-{[(2,6-difluorophenyl)sulfonyl]amino}-2-fluorophenyl)-1,3-thiazol-2-yl]-2-methylpropanamide

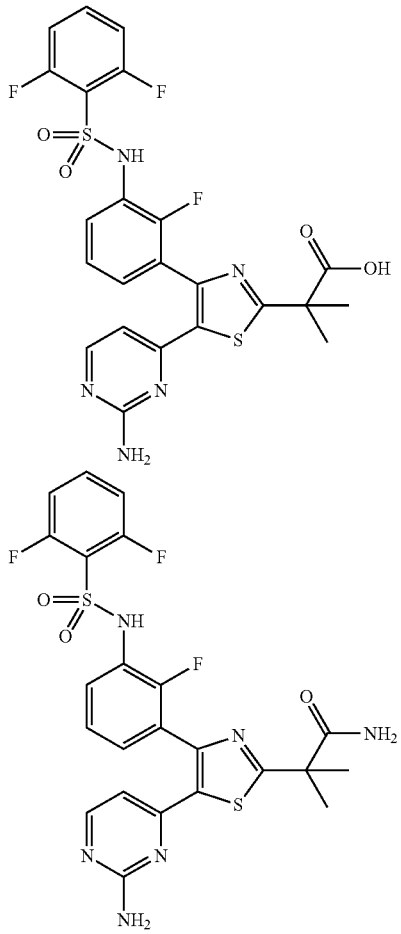

A solution of ethyl 2-[5-(2-chloro-4-pyrimidinyl)-4-(3-{[(2,6-difluorophenyl)sulfonyl]amino}-2-fluorophenyl)-1,3-thiazol-2-yl]-2-methylpropanoate (75 mg, 0.126 mmol) and saturated aqueous ammonium hydroxide (16.0 mL) were heated in a microwave reactor to 90° C. for 15 minutes.

The reaction mixture was concentrated, diluted with water, and extracted with ethyl acetate (6×25 mL) and chloroform (1×25 mL). The combined organics were dried (MgSO4), filtered and filtrate evaporated; the residue was set aside. The pH of the aqueous phase was adjusted to ~13 with 1N—NaOH (total vol. ~8 mL) and the solution passed through "Diaion HP20SS" resin eluting first with water, then acetone-water mixtures. Product-containing fraction (IL-CMS monitoring) was, concentrated, adjusted to pH 12 and lyophilized to give 2-[5-(2-amino-4-pyrimidinyl)-4-(3-{[(2,6-difluorophenyl)sulfonyl]amino}-2-fluorophenyl)-1,3-thiazol-2-yl]-2-methylpropanoic acid, disodium salt (4.9 mg). $^1$H NMR (400 MHz, DMSO-d$_6$) δ ppm 7.95 (d, J=5.05 Hz, 1H) 7.30-7.40 (m, 1H) 7.21-7.28 (m, 1H) 6.92-7.03 (m, 2H) 6.80 (t, J=7.83 Hz, 1H) 6.58 (s, 2H) 6.46-6.52 (m, 1H) 6.09 (d, J=4.55 Hz, 1H) 1.44 (s, 6H). MS (ESI): 550.0 [M+H]$^+$.

Organic residue from above work-up was chromatographed on silica gel eluting with an ethyl acetate/hexanes gradient. The second-eluting fraction was 2-[5-(2-amino-4-pyrimidinyl)-4-(3-{[(2,6-difluorophenyl)sulfonyl]amino}-2-fluorophenyl)-1,3-thiazol-2-yl]-2-methylpropanamide. Fractions containing this material were combined and evaporated to white foam (35 mg) which was crystallized from ethyl acetate-hexanes. $^1$H NMR (400 MHz, chloroform-d) δ ppm 8.03 (d, J=5.31 Hz, 1H), 7.72-7.80 (m, 1H), 7.49-7.59 (m, 1H), 7.27-7.35 (m, 2H), 7.15 (br s, 1H), 7.02 (t, J=8.46 Hz, 2H), 6.16 (d, J=5.05 Hz, 1H), 5.35 (br. s., 1H), 5.07 (br. s, 2H), 1.77 (s, 6H). MS (ESI): 549.0 [M+H]$^+$.

Example 310

N-{3-[2-(1-amino-1-methylethyl)-5-(2-methyl-4-pyrimidinyl)-1,3-thiazol-4-yl]-2-fluorophenyl}-2,6-difluorobenzenesulfonamide

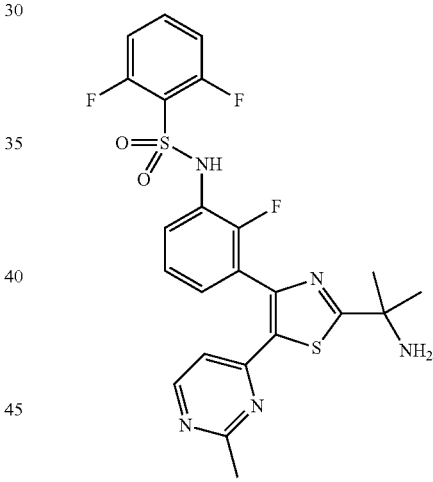

Step A: 1,1-dimethylethyl (2-amino-1,1-dimethyl-2-thioxoethyl)carbamate

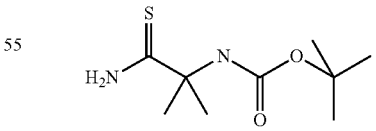

N$^2$-{[(1,1-dimethylethyl)oxy]carbonyl}-2-methylalaninamide (3.87 g, 19.13 mmol), Lawesson's reagent (7.74 g, 19.13 mmol) and tetrahydrofuran (THF) (100 mL) was heated to 50° C. for 3 hours. The reaction was concentrated, added 150 cc of EtOAc and washed with sat'd NaHCO$_3$ (3×100 cc), water and brine. The EtOAc layer was concentrated and the residue was purified via chromatography on silica gel eluted Hex to 1:1 Hex/EtOAc to obtain the title compound (2.04 g, 48% yield).

Step B: 2-propen-1-yl (3-{5-(2-chloro-4-pyrimidinyl)-2-[1-({[(1,1-dimethylethyl)oxy]carbonyl}amino)-1-methylethyl]-1,3-thiazol-4-yl}-2-fluorophenyl)carbamate

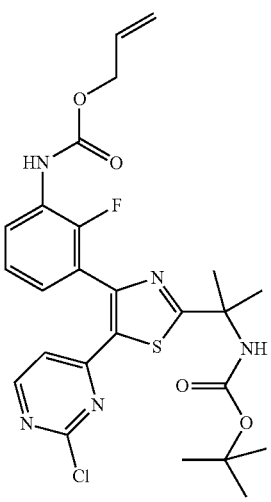 [SMILES: C=CCOC(=O)Nc1cccc(-c2nc(C(C)(C)NC(=O)OC(C)(C)C)sc2-c2ccnc(Cl)n2)c1F]

N-Bromosuccinimide (0.763 g, 4.29 mmol) was added to a solution of 2-propen-1-yl {3-[(2-chloro-4-pyrimidinyl)acetyl]-2-fluorophenyl}carbamate (1.5 g, 4.29 mmol) in dichloromethane (DCM) (50 mL). After 1 h of stirring, 1,1-dimethylethyl (2-amino-1,1-dimethyl-2-thioxoethyl)carbamate (0.936 g, 4.29 mmol) was added to the reaction mixture and heated to 80° C. for 2 h. The reaction mixture was diluted with 150 cc of EtOAc and washed with water (5×100 cc). The EtOAc layer was dried over MgSO₄ and filtered and concentrated in vacuo. The residue was purified via chromatography on silica gel using Hex to 25% EtOAc in Hex to obtain the title compound (1.28 g, 54% yield). MS (ESI): 548.3 [M+H]+

Step C: 1,1-dimethylethyl {1-[4-(3-amino-2-fluorophenyl)-5-(2-chloro-4-pyrimidinyl)-1,3-thiazol-2-yl]-1-methylethyl}carbamate

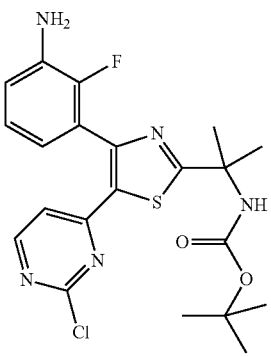 [SMILES: CC(C)(C)OC(=O)NC(C)(C)c1nc(-c2cccc(N)c2F)c(-c2ccnc(Cl)n2)s1]

To a solution of 2-propen-1-yl (3-{5-(2-chloro-4-pyrimidinyl)-2-[1-({[(1,1-dimethylethyl)oxy]carbonyl}amino)-1-methylethyl]-1,3-thiazol-4-yl}-2-fluorophenyl)carbamate (1.28 g, 2.336 mmol). tri-n-butyltin hydride (0.624 mL, 2.336 mmol) in dichloromethane (DCM) (50 mL) was added tetrakis(triphenylphosphine)palladium(0) (0.135 g, 0.117 mmol) followed by water (0.2 mL). After 30 min, the reaction was concentrated. The residue was purified via chromatography on silica gel to obtain the title compound (0.81 g 74% yield). MS (ESI): 464.1 [M+H]+

Step D: 1,1-dimethylethyl {1-[5-(2-chloro-4-pyrimidinyl)-4-(3-{[(2,6-difluorophenyl)sulfonyl]amino}-2-fluorophenyl)-1,3-thiazol-2-yl]-1-methylethyl}carbamate

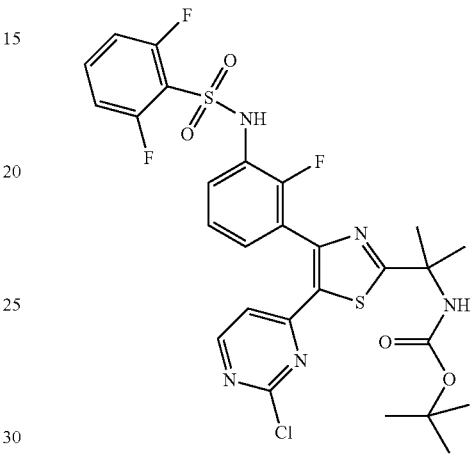

To a solution of 1,1-dimethylethyl {1-[4-(3-amino-2-fluorophenyl)-5-(2-chloro-4-pyrimidinyl)-1,3-thiazol-2-yl]-1-methylethyl}carbamate (400 mg, 0.862 mmol) in pyridine (50 mL) was added dropwise 2,6-difluorobenzenesulfonyl chloride (238 mg, 1.121 mmol). After 4 h, 2,6-difluorobenzenesulfonyl chloride (0.20 g) was added to the reaction mixture and stirred at rt overnight. The reaction mixture was concentrated. The residue was purified via chromatography on silica gel to obtain the title compound (330 mg 59% yield). MS (ESI): 639.9 [M+H]+

Step E: N-{3-[2-(1-amino-1-methylethyl)-5-(2-methyl-4-pyrimidinyl)-1,3-thiazol-4-yl]-2-fluorophenyl}-2,6-difluorobenzenesulfonamide N-{3-[2-(1-amino-1-methylethyl)-5-(2-methyl-4-pyrimidinyl)-1,3-thiazol-4-yl]-2-fluorophenyl}-2,6-difluorobenzenesulfonamide was dissolved in 1,4-dioxane (40 mL) and was degassed for 10 minutes. To this solution was added 1,1'-bis(diphenylphosphino)ferrocene-palladium(II)dichloride dichloromethane complex (0.017 g, 0.020 mmol) followed by dimethylzinc (0.406 mL, 0.812 mmol) and was heated to 80° C. for 3 hours. The reaction mixture was quenched by addition of 1 ml of MeOH. The reaction was diluted with 50 ml of DCM and 50 ml of water, filtered and separated phases. The water was extracted with 50 cc of DCM (2×). The combined organic phases were washed with water. The DCM layers were dried over MgSO₄, filtered and concentrated in vacuo. The residue was chromatographed on silica gel (Hex:EtOAc). The residue was dissolved in 3 ml of DCM and added 3 ml of TFA and stirred stir at rt for 30 minutes. The reaction mixture was concentrated in vacuo. The residue was dissolved in 10 ml of MeOH. Conc. HCl (2 cc) was added to the reaction mixture and concentrated in vacuo. The residue was dissolved in MeOH, added HCl and concentrated to give conc. HCl salt of product. Free base was obtained by addition of sat'd NaHCO₃ (22 cc) to the HCl salt and extracted with DCM (3×30 cc). DCM extracts were washed with brine and dried over MgSO$_4$, filtered and concentrated in vacuo to obtain the title compound (43 mg 20% yield). MS (ESI): 520.1 [M+H]+

Example 311

N-{3-[2-(1-amino-1-methylethyl)-5-(2-methyl-4-pyrimidinyl)-1,3-thiazol-4-yl]-2-fluorophenyl}-3-furansulfonamide

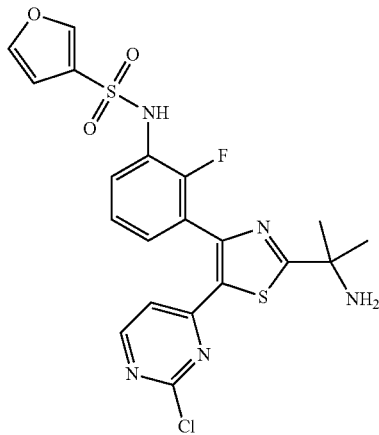 [SMILES: CC(C)(N)c1nc(-c2cccc(NS(=O)(=O)c3ccoc3)c2F)c(-c2ccnc(Cl)n2)s1]

Step A: 1,1-dimethylethyl [1-(5-(2-chloro-4-pyrimidinyl)-4-{2-fluoro-3-[(3-furanylsulfonyl)amino]phenyl}-1,3-thiazol-2-yl)-1-methylethyl]carbamate

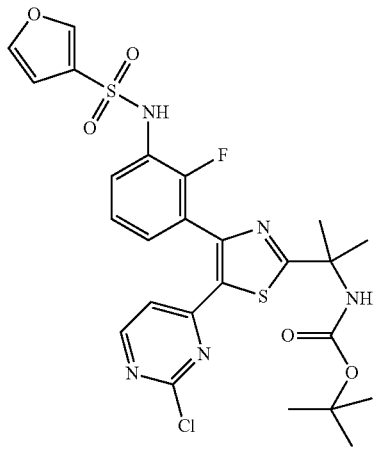 [SMILES: CC(C)(C)OC(=O)NC(C)(C)c1nc(-c2cccc(NS(=O)(=O)c3ccoc3)c2F)c(-c2ccnc(Cl)n2)s1]

To a solution of 1,1-dimethylethyl {1-[4-(3-amino-2-fluorophenyl)-5-(2-chloro-4-pyrimidinyl)-1,3-thiazol-2-yl]-1-methylethyl}carbamate (400 mg, 0.862 mmol) in pyridine (50 mL) was added 3-furansulfonyl chloride (144 mg, 0.862 mmol) (in 5 cc DCM). After 4 h, 3-furansulfonyl chloride (0.20 g) was to the reaction mixture and stirred at rt overnight. The reaction mixture was concentrated in vacuo. The residue was purified via Biotage (3:1-Hex/EtOAc; 25M silica gel column) to obtain the title compound (460 mg 90% yield). MS (ESI): 594.2 [M+H]+

N-{3-[2-(1-amino-1-methylethyl)-5-(2-methyl-4-pyrimidinyl)-1,3-thiazol-4-yl]-2-fluorophenyl}-3-furansulfonamide 1,1-dimethylethyl [1-(5-(2-chloro-4-pyrimidinyl)-4-{2-fluoro-3-[(3-furanylsulfonyl)amino]phenyl}-1,3-thiazol-2-yl)-1-methylethyl]carbamate (310 mg, 0.522 mmol) was dissolved in 1,4-dioxane (40 mL) and was degassed for 10 minutes. To this solution was added 1,1'-bis(diphenylphosphino)ferrocene-palladium(II)dichloride dichloromethane complex (21.31 mg, 0.026 mmol) followed by dimethylzinc (0.522 mL, 1.044 mmol) and heated to 80° C. for 3 hours. The reaction mixture was quenched by addition of 1 ml of MeOH. The reaction mixture was diluted with 50 ml of DCM and 50 ml of water, filtered and separated phases. The aqueous layer was extracted 50 cc of DCM (2×). The combined organic phases were washed with water and dried over MgSO$_4$, filtered, and concentrated in vacuo. The residue was chromatographed on silica gel (Hex:EtOAc). The residue was dissolved in 3 ml of DCM and added 3 ml of TFA and stirred at rt for 30 minutes. The reaction was concentrated in vacuo. The residue was dissolved in 10 ml of MeOH and added 3 cc of conc. HCl and concentrated in vacuo. The residue was dissolved in MeOH, added HCl, and concentrated to give HCl salt of product. Free base was obtained by adding 20 cc of sat'd NaHCO$_3$ to the HCl salt and extracted with DCM (3×30 cc). DCM extracts was washed with brine and dried over MgSO$_4$, filtered and concentrated in vacuo to obtain the title compound (68 mg 24% yield). MS (ESI): 574.1 [M+H]+

Example 312

N-{3-[2-(1-amino-1-methylethyl)-5-(2-amino-4-pyrimidinyl)-1,3-thiazol-4-yl]-2-fluorophenyl}-3-furansulfonamide

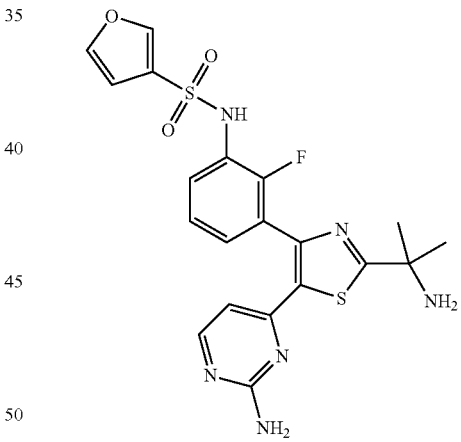

1,1-dimethylethyl [1-(5-(2-chloro-4-pyrimidinyl)-4-{2-fluoro-3-[(3-furanylsulfonyl)amino]phenyl}-1,3-thiazol-2-yl)-1-methylethyl]carbamate (100 mg, 0.168 mmol) and ammonium hydroxide (2 ml, 51.4 mmol) was microwaved at 90° C. for 3 hours. The reaction was cooled in ice water bath before opening microwave vial to relieve pressure. The reaction was concentrated to dryness in vacuo. The residue was diluted with 50 ml of DCM and 50 ml of water and adjusted pH to about 4 to 5 by addition of 1N HCl and separated phases. The water was extracted with 50 cc of DCM (3×50 cc). The combined DCM phases were washed with water and dried over MgSO$_4$, filtered, and concentrated in vacuo. The residue was dissolved in 3 ml of DCM and added 3 ml of TFA and stirred at rt for 30 minutes. The reaction mixture was concentrated in vacuo. The residue was dissolved in 10 ml of MeOH and added 3 ml of conc. HCl and concentrated in vacuo. The residue again was dissolved in MeOH, added conc. HCl and concentrated in vacuo to yield the HCl salt of the product. Free base was obtained by addition of 20 cc of sat'd NaHCO$_3$ to the HCl salt and extracted with DCM (3×30 cc). DCM extracts was washed with brine and dried over MgSO$_4$, filtered, and concentrated in vacuo to obtain the title compound (48 mg 60% yield). MS (ESI): 474.8 [M+H]+

Example 313

N-{3-[2-(1-amino-1-methylethyl)-5-(2-amino-4-pyrimidinyl)-1,3-thiazol-4-yl]-2-fluorophenyl}-2,6-difluorobenzenesulfonamide

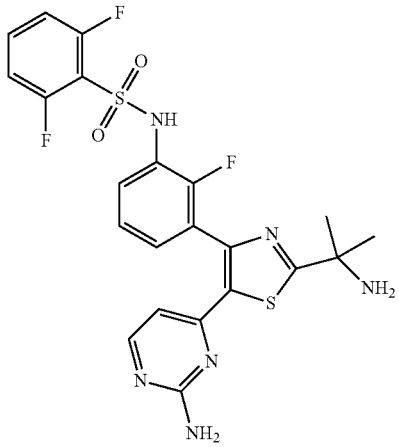 [SMILES: CC(C)(N)c1nc(-c2cccc(NS(=O)(=O)c3c(F)cccc3F)c2F)c(-c2ccnc(N)n2)s1]

Following a procedure analogous to the procedure described in Example 312 using 1,1-dimethylethyl {1-[5-(2-chloro-4-pyrimidinyl)-4-(3-{[(2,6-difluorophenyl)sulfonyl]amino}-2-fluorophenyl)-1,3-thiazol-2-yl]-1-methylethyl}carbamate (100 mg, 0.156 mmol) and ammonium hydroxide (2 mL, 51.4 mmol) at 90° C. for 3 hours, the title compound was obtained as a solid (37 mg 45% yield). MS (ESI): 521.2 [M+H]+

Example 314

N-{2-fluoro-3-[5-(2-methyl-4-pyrimidinyl)-2-(tetrahydro-2H-pyran-4-yl)-1,3-thiazol-4-yl]phenyl}-3-furansulfonamide

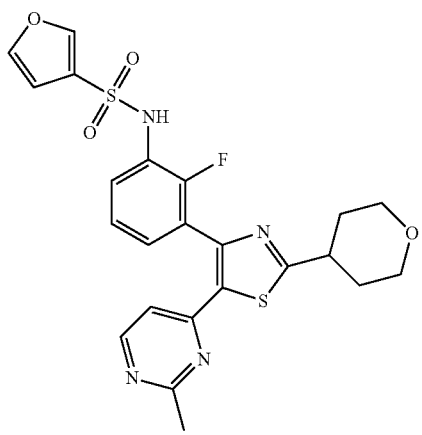 [SMILES: Cc1nccc(-c2sc(C3CCOCC3)nc2-c2cccc(NS(=O)(=O)c3ccoc3)c2F)n1]

Following a procedure analogous to the procedure described in Example 25 using N-{3-[5-(2-chloro-4-pyrim-idinyl)-2-(tetrahydro-2H-pyran-4-yl)-1,3-thiazol-4-yl]-2-fluorophenyl}-3-furansulfonamide (200 mg, 0.384 mmol) and dimethylzinc (384 µl, 0.768 mmol) at 80° C. for 3 hours, the title compound was obtained as a solid (60 mg, 31% yield). MS (ESI): 500.8 [M+H]+

Example 315

2,6-difluoro-N-{2-fluoro-3-[5-(2-methyl-4-pyrimidinyl)-2-(tetrahydro-2H-pyran-4-yl)-1,3-thiazol-4-yl]phenyl}benzenesulfonamide

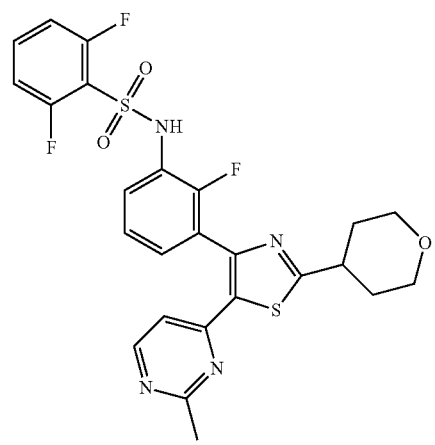 [SMILES: Cc1nccc(-c2sc(C3CCOCC3)nc2-c2cccc(NS(=O)(=O)c3c(F)cccc3F)c2F)n1]

Following a procedure analogous to the procedure described in Example 25 using N-{3-[5-(2-chloro-4-pyrimidinyl)-2-(tetrahydro-2H-pyran-4-yl)-1,3-thiazol-4-yl]-2-fluorophenyl}-2,6-difluorobenzenesulfonamide (300 mg, 0.529 mmol) and dimethylzinc (529 µl, 1.058 mmol) at 80° C. for 3 hours, the title compound was obtained as a solid (60 mg, 31% yield). MS (ESI): 547.1 [M+H]+

Example 316

2,6-difluoro-N-{2-fluoro-3-[2-(2-hydroxy-1,1-dimethylethyl)-5-(2-methyl-4-pyrimidinyl)-1,3-thiazol-4-yl]phenyl}benzenesulfonamide

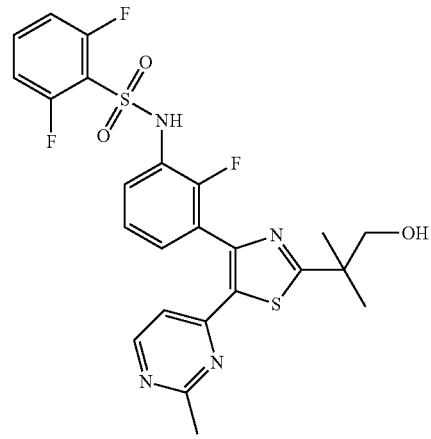 [SMILES: Cc1nccc(-c2sc(C(C)(C)CO)nc2-c2cccc(NS(=O)(=O)c3c(F)cccc3F)c2F)n1]

Following a procedure analogous to the procedure described in Example 25 using N-{3-[5-(2-chloro-4-pyrimidinyl)-2-(2-hydroxy-1,1-dimethylethyl)-1,3-thiazol-4-yl]-2-fluorophenyl}-2,6-difluorobenzenesulfonamide (200 mg, 0.360 mmol) and dimethylzinc (0.360 mL, 0.721 mmol) at 80° C. for 3 hours, the title compound was obtained as a solid (8 mg, 4% yield). MS (ESI): 534.9 [M+H]+

Example 317

2,6-difluoro-N-{2-fluoro-3-[2-(4-methyl-4-piperidinyl)-5-(2-methyl-4-pyrimidinyl)-1,3-thiazol-4-yl]phenyl}benzenesulfonamide

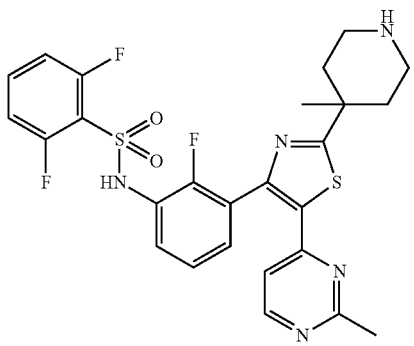 [SMILES: Cc1nccc(-c2sc(C3(C)CCNCC3)nc2-c2cccc(NS(=O)(=O)c3c(F)cccc3F)c2F)n1]

Step A: 1,1-dimethylethyl 4-[5-(2-chloro-4-pyrimidinyl)-4-(2-fluoro-3-{[(2-propen-1-yloxy)carbonyl]amino}phenyl)-1,3-thiazol-2-yl]-4-methyl-1-piperidinecarboxylate

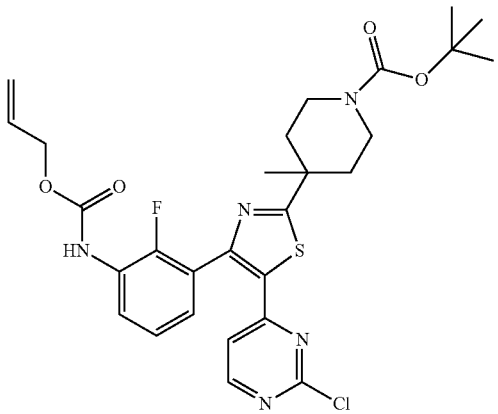 [SMILES: C=CCOC(=O)Nc1cccc(-c2nc(C3(C)CCN(C(=O)OC(C)(C)C)CC3)sc2-c2ccnc(Cl)n2)c1F]

To a solution of 2-propen-1-yl {3-[(2-chloro-4-pyrimidinyl)acetyl]-2-fluorophenyl}carbamate (0.738 g, 2.110 mmol) in N,N-dimethylacetamide (8 mL) was added NBS (0.376 g, 2.110 mmol), and the reaction mixture was stirred for 1.5 h. 1,1-Dimethylethyl 4-(aminocarbonothioyl)-4-methyl-1-piperidinecarboxylate (0.545 g, 2.110 mmol) was added and the mixture was heated to 80° C. for 30 min. The reaction mixture was cooled, quenched with water (20 mL), and extracted with EtOAc (3×). The extract was dried over Na₂SO₄, filtered and concentrated. The residue was purified using column chromatography (hexane/EtOAc, 0 to 100%) to obtain the title compound (670 mg). MS (ESI): 588.2 [M+1]+.

Step B: 1,1-dimethylethyl 4-[4-(3-amino-2-fluorophenyl)-5-(2-chloro-4-pyrimidinyl)-1,3-thiazol-2-yl]-4-methyl-1-piperidinecarboxylate

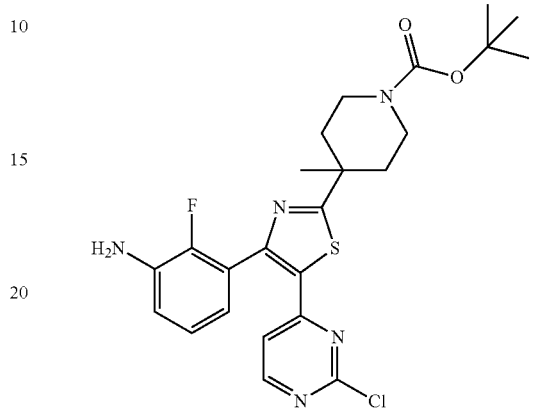

To a solution of 1,1-dimethylethyl 4-[5-(2-chloro-4-pyrimidinyl)-4-(2-fluoro-3-{[(2-propen-1-yloxy)carbonyl]amino}phenyl)-1,3-thiazol-2-yl]-4-methyl-1-piperidinecarboxylate (670 mg, 1.139 mmol) in dichloromethane (8 mL) were added tributylstannane (332 mg, 1.139 mmol), tetrakis (65.8 mg, 0.057 mmol) and water (66 μl, 3.66 mmol). The reaction mixture was stirred for 1 h. The reaction mixture was concentrated and residue was purified using column chromatography (hexane/EtOAc, 0 to 100%) to obtain the title compound (482 mg). MS (ESI): 504.2 [M+1]+.

Step C: 1,1-dimethylethyl 4-[5-(2-chloro-4-pyrimidinyl)-4-(3-{[(2,6-difluorophenyl)sulfonyl]amino}-2-fluorophenyl)-1,3-thiazol-2-yl]-4-methyl-1-piperidinecarboxylate

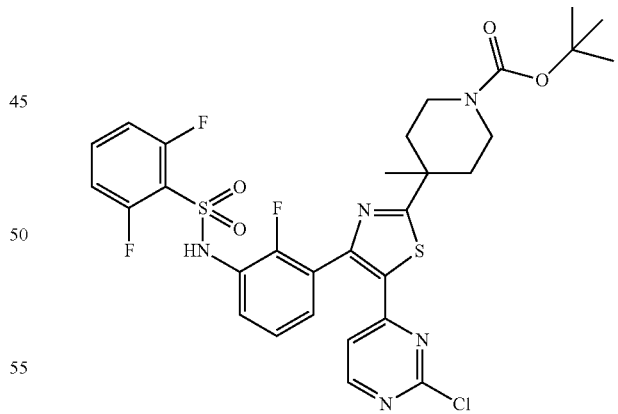

To a solution of 1,1-dimethylethyl 4-[4-(3-amino-2-fluorophenyl)-5-(2-chloro-4-pyrimidinyl)-1,3-thiazol-2-yl]-4-methyl-1-piperidinecarboxylate (200 mg, 0.397 mmol) in pyridine (2 mL) was added 2,6-difluorobenzenesulfonyl chloride (130 mg, 0.612 mmol) and the reaction mixture was stirred for 5 h. The reaction mixture was quenched with water (5 mL) and extracted with EtOAc (3×). The extract was dried, filtered and concentrated. The residue was purified using column chromatography (40 to 100% EtOAc/hexane) to obtain the title compound (220 mg). MS (ESI): 680.4 [M+1]+.

Step D: 1,1-dimethylethyl 4-[4-(3-{[(2,6-difluorophenyl)sulfonyl]amino}-2-fluorophenyl)-5-(2-methyl-4-pyrimidinyl)-1,3-thiazol-2-yl]-4-methyl-1-piperidinecarboxylate

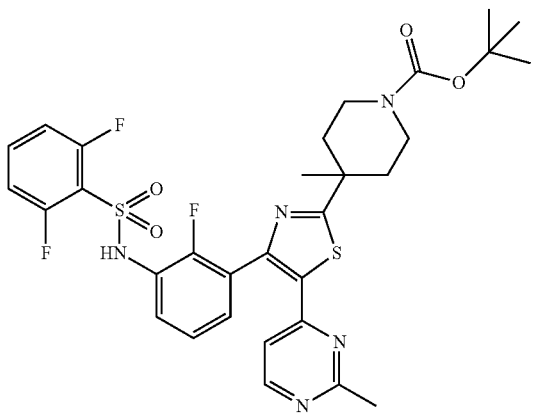 [SMILES: Cc1nccc(-c2sc(C3(C)CCN(C(=O)OC(C)(C)C)CC3)nc2-c2cccc(NS(=O)(=O)c3c(F)cccc3F)c2F)n1]

1,1-dimethylethyl 4-[5-(2-chloro-4-pyrimidinyl)-4-(3-{[(2,6-difluorophenyl)sulfonyl]amino}-2-fluorophenyl)-1,3-thiazol-2-yl]-4-methyl-1-piperidinecarboxylate (150 mg, 0.221 mmol) was dissolved into 1,4-dioxane (3 mL) and the solution was degassed for 10 min. PdCl$_2$(dppf)-CH$_2$Cl$_2$ adduct (9.00 mg, 0.011 mmol) and dimethylzinc (0.221 mL, 0.441 mmol) were then added. The reaction mixture was stirred at 80° C. for 1 h. The reaction mixture was quenched with methanol (3 mL) and water (10 mL) and extracted with EtOAc (3×). The extract was dried over Na$_2$SO$_4$, filtered, and concentrated. The residue was purified using column chromatography (40% to 100% EtOAc/hexane) to obtain the title compound (75 mg). MS (ESI): 660.5 [M+1]$^+$.

Step E: 2,6-difluoro-N-{2-fluoro-3-[2-(4-methyl-4-piperidinyl)-5-(2-methyl-4-pyrimidinyl)-1,3-thiazol-4-yl]phenyl}benzenesulfonamide To a solution of 1,1-dimethylethyl 4-[4-(3-{[(2,6-difluorophenyl)sulfonyl]amino}-2-fluorophenyl)-5-(2-methyl-4-pyrimidinyl)-1,3-thiazol-2-yl]-4-methyl-1-piperidinecarboxylate (72 mg, 0.109 mmol) in dichloromethane (2 mL) was added TFA (0.5 mL, 6.49 mmol), and the reaction mixture was stirred for 1 h. The reaction was concentrated and the residue was purified using RP-HPLC. The TFA salt was neutralized to obtain the title compound (38 mg). MS (ESI): 560.0 [M+1]$^+$.

Example 318

N-{3-[5-(2-amino-4-pyrimidinyl)-2-(4-piperidinyl)-1,3-thiazol-4-yl]-2-fluorophenyl}-2,6-difluorobenzenesulfonamide

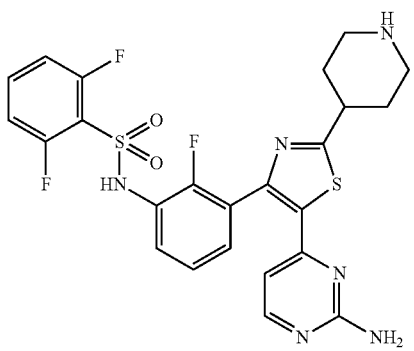 [SMILES: Nc1nccc(-c2sc(C3CCNCC3)nc2-c2cccc(NS(=O)(=O)c3c(F)cccc3F)c2F)n1]

Step A: 1,1-dimethylethyl 4-[5-(2-amino-4-pyrimidinyl)-4-(3-{[(2,6-difluorophenyl)sulfonyl]amino}-2-fluorophenyl)-1,3-thiazol-2-yl]-4-methyl-1-piperidinecarboxylate

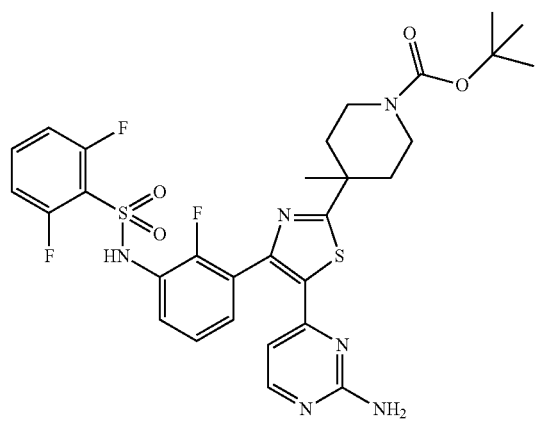 [SMILES: CC(C)(C)OC(=O)N1CCC(C)(c2nc(-c3cccc(NS(=O)(=O)c4c(F)cccc4F)c3F)c(-c3ccnc(N)n3)s2)CC1]

A suspension of 1,1-dimethylethyl 4-[5-(2-chloro-4-pyrimidinyl)-4-(3-{[(2,6-difluorophenyl)sulfonyl]amino}-2-fluorophenyl)-1,3-thiazol-2-yl]-4-methyl-1-piperidinecarboxylate (39 mg, 0.057 mmol) in ammonium hydroxide solution (28%, 2 mL, 51.4 mmol) sealed in a 5-mL microwave tube was heated at 90° C. for 3 h under the microwave conditions. The mixture was concentrated and dried under high vacuum to obtain the title compound (40 mg). MS (ESI): 661.4 [M+1]$^+$.

Step B: N-{3-[5-(2-amino-4-pyrimidinyl)-2-(4-piperidinyl)-1,3-thiazol-4-yl]-2-fluorophenyl}-2,6-difluorobenzenesulfonamide To a solution of 1,1-dimethylethyl 4-[5-(2-amino-4-pyrimidinyl)-4-(3-{[(2,6-difluorophenyl)sulfonyl]amino}-2-fluorophenyl)-1,3-thiazol-2-yl]-1-piperidinecarboxylate (94 mg, 0.145 mmol) in dichloromethane (2 mL) was added TFA (0.5 mL, 6.49 mmol), and the reaction mixture was stirred for 1 h. the reaction mixture was concentrated and the residue was purified using RP-HPLC. The TFA salt was neutralized to the title compound (56 mg). MS (ESI): 547.1 [M+1]$^+$.

Example 319

N-{3-[5-(2-amino-4-pyrimidinyl)-2-(4-methyl-4-piperidinyl)-1,3-thiazol-4-yl]-2-fluorophenyl}-3-furansulfonamide

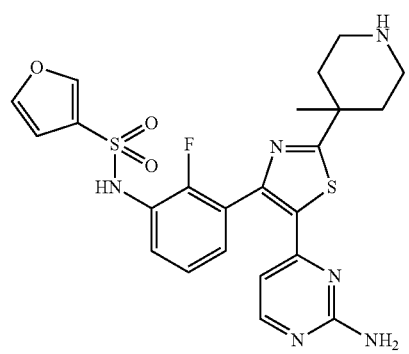 [SMILES: CC1(c2nc(-c3cccc(NS(=O)(=O)c4ccoc4)c3F)c(-c3ccnc(N)n3)s2)CCNCC1]

Step A: 1,1-dimethylethyl 4-(5-(2-chloro-4-pyrimidinyl)-4-{2-fluoro-3-[(3-furanylsulfonyl)amino]phenyl}-1,3-thiazol-2-yl)-4-methyl-1-piperidinecarboxylate

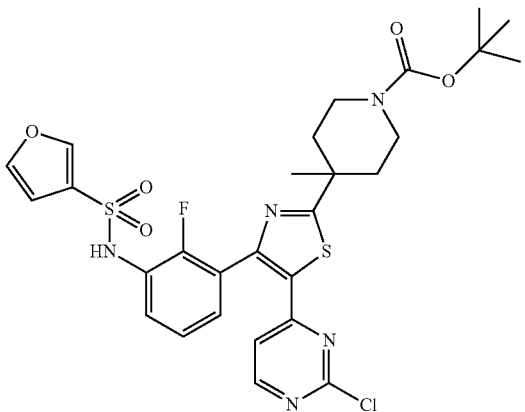 [SMILES: CC(C)(C)OC(=O)N1CCC(C)(c2nc(-c3cccc(NS(=O)(=O)c4ccoc4)c3F)c(-c3ccnc(Cl)n3)s2)CC1]

To a solution of 1,1-dimethylethyl 4-[4-(3-amino-2-fluorophenyl)-5-(2-chloro-4-pyrimidinyl)-1,3-thiazol-2-yl]-4-methyl-1-piperidinecarboxylate (280 mg, 0.556 mmol) in pyridine (3 mL) was added 3-furansulfonyl chloride (139 mg, 0.833 mmol), and the reaction mixture was stirred for 3 h. The reaction mixture was quenched with water (5 mL) and extracted with EtOAc (3×). The extract was dried, filtered and concentrated. The residue was purified using column chromatography (40 to 100% EtOAc/hexane) to the title compound (310 mg). MS (ESI): 634.1 [M+1]+.

Step B: 1,1-dimethylethyl 4-(5-(2-amino-4-pyrimidinyl)-4-{2-fluoro-3-[(3-furanylsulfonyl)amino]phenyl}-1,3-thiazol-2-yl)-4-methyl-1-piperidinecarboxylate

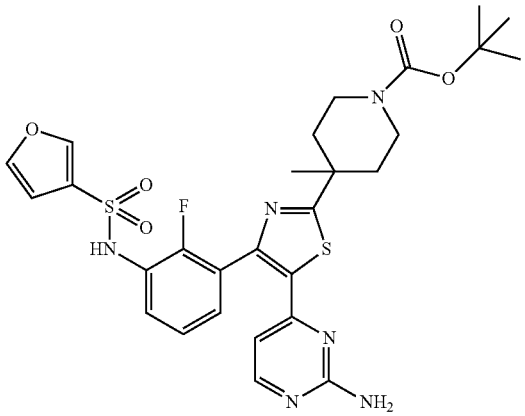 [SMILES: CC(C)(C)OC(=O)N1CCC(C)(c2nc(-c3cccc(NS(=O)(=O)c4ccoc4)c3F)c(-c3ccnc(N)n3)s2)CC1]

A suspension of 1,1-dimethylethyl 4-(5-(2-chloro-4-pyrimidinyl)-4-{2-fluoro-3-[(3-furanylsulfonyl)amino]phenyl}-1,3-thiazol-2-yl)-4-methyl-1-piperidinecarboxylate (65 mg, 0.103 mmol) in ammonium hydroxide solution (28%, 2 mL, 51.4 mmol) sealed in a 5-mL microwave tube was heated at 90° C. for 3 h under the microwave conditions. The mixture was concentrated and dried under high vacuum to the title compound (64 mg). MS (ESI): 558.6 [M+1-56]+.

Step C: N-{3-[5-(2-amino-4-pyrimidinyl)-2-(4-methyl-4-piperidinyl)-1,3-thiazol-4-yl]-2-fluorophenyl}-3-furansulfonamide To a solution of 1,1-dimethylethyl 4-(5-(2-amino-4-pyrimidinyl)-4-{2-fluoro-3-[(3-furanylsulfonyl)amino]phenyl}-1,3-thiazol-2-yl)-4-methyl-1-piperidinecarboxylate (64 mg, 0.104 mmol) in dichloromethane (DCM) (2 mL) was added TFA (500 µl, 6.49 mmol), and the reaction mixture was stirred for 1 h. The reaction mixture was concentrated and the residue was purified using RP-HPLC. The TFA salt was neutralized to the title compound (37 mg). MS (ESI): 515.2 [M+1]+.

Example 320

N-{2-fluoro-3-[2-(4-methyl-4-piperidinyl)-5-(2-methyl-4-pyrimidinyl)-1,3-thiazol-4-yl]phenyl}-3-furansulfonamide

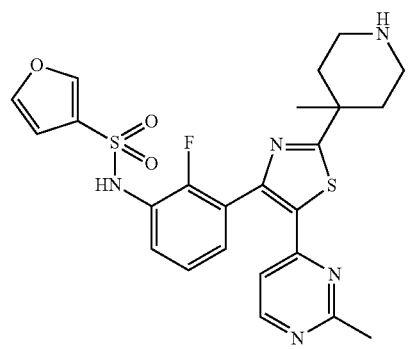 [SMILES: Cc1nccc(-c2sc(C3(C)CCNCC3)nc2-c2cccc(NS(=O)(=O)c3ccoc3)c2F)n1]

Step A: 1,1-dimethylethyl 4-[4-{2-fluoro-3-[(3-furanylsulfonyl)amino]phenyl}-5-(2-methyl-4-pyrimidinyl)-1,3-thiazol-2-yl]-4-methyl-1-piperidinecarboxylate

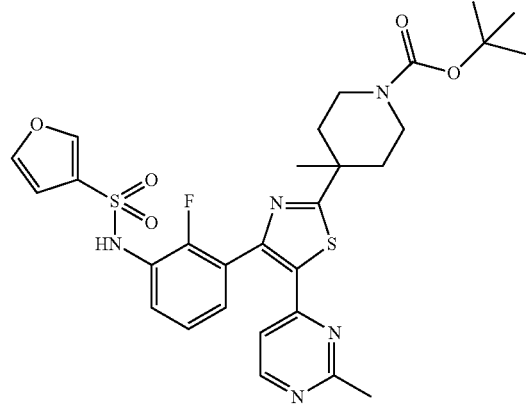 [SMILES: Cc1nccc(-c2sc(C3(C)CCN(C(=O)OC(C)(C)C)CC3)nc2-c2cccc(NS(=O)(=O)c3ccoc3)c2F)n1]

1,1-dimethylethyl 4-(5-(2-chloro-4-pyrimidinyl)-4-{2-fluoro-3-[(3-furanylsulfonyl)amino]phenyl}-1,3-thiazol-2-yl)-4-methyl-1-piperidinecarboxylate (130 mg, 0.205 mmol) was dissolved into 1,4-dioxane (3 mL) and the solution was degassed for 10 min. PdCl$_2$(dppf)-CH$_2$Cl$_2$ adduct (8.37 mg, 10.25 µmol) and dimethylzinc (0.205 mL, 0.410 mmol) were added the reaction mixture. The reaction mixture was stirred at 80° C. for 1 h. The reaction was quenched with methanol (3 mL) and water (10 mL) and extracted with EtOAc (3×). The extract was dried over Na$_2$SO$_4$, filtered, and concentrated. The residue was purified using column chromatography (40% to 100% EtOAc/hexane) to the title compound (100 mg). MS (ESI): 557.7 [M+1]+.

Step B: N-{2-fluoro-3-[2-(4-methyl-4-piperidinyl)-5-(2-methyl-4-pyrimidinyl)-1,3-thiazol-4-yl]phenyl}-3-furansulfonamide To a solution of 1,1-dimethylethyl 4-[4-{2-fluoro-3-[(3-furanylsulfonyl)amino]phenyl}-5-(2-methyl-4-pyrimidinyl)-1,3-thiazol-2-yl]-4-methyl-1-piperidinecarboxylate (98 mg, 0.160 mmol) in dichloromethane (DCM) (2 mL) was added TFA (0.5 mL, 6.49 mmol), and the reaction mixture was stirred for 1 h. The reaction mixture was concentrated and the residue was purified using RP-HPLC. The TFA salt was neutralized to the title compound (26 mg). MS (ESI): 514.2 [M+1]$^+$.

Example 321

2,6-difluoro-N-{2-fluoro-3-[5-(2-methyl-4-pyrimidinyl)-2-(4-piperidinyl)-1,3-thiazol-4-yl]phenyl}benzenesulfonamide

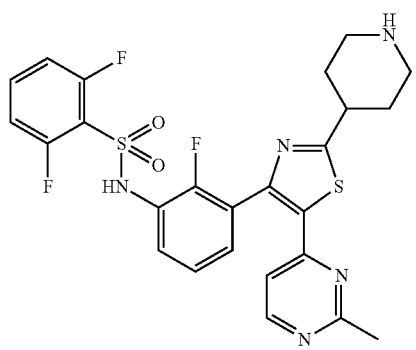 [SMILES: Cc1nccc(-c2sc(C3CCNCC3)nc2-c2cccc(NS(=O)(=O)c3c(F)cccc3F)c2F)n1]

Step A: 1,1-dimethylethyl 4-[5-(2-chloro-4-pyrimidinyl)-4-(2-fluoro-3-{[(2-propen-1-yloxy)carbonyl]amino}phenyl)-1,3-thiazol-2-yl]-1-piperidinecarboxylate

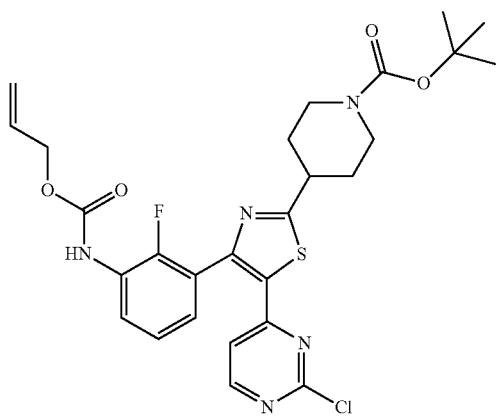 [SMILES: C=CCOC(=O)Nc1cccc(-c2nc(C3CCN(C(=O)OC(C)(C)C)CC3)sc2-c2ccnc(Cl)n2)c1F]

To a solution of 2-propen-1-yl {3-[(2-chloro-4-pyrimidinyl)acetyl]-2-fluorophenyl}-carbamate (1.43 g, 4.09 mmol) in N,N-dimethylacetamide (DMA) (15 mL) was added NBS (0.728 g, 4.09 mmol), and the reaction mixture was stirred for 1 h. 1,1-Dimethylethyl 4-(aminocarbonothioyl)-1-piperidinecarboxylate (0.999 g, 4.09 mmol) was added and the reaction mixture was heated to 80° C. for 25 min. The mixture was cooled, quenched with water (30 mL) and extract with EtOAc (3×). The extract was dried over Na2SO4, filtered and concentrated. The residue was purified using column chromatography (hexane/EtOAc, 0 to 100%) to give 1.34 g of the title compound. MS (ESI): 574.2 [M+1]$^+$.

Step B: 1,1-dimethylethyl 4-[4-(3-amino-2-fluorophenyl)-5-(2-chloro-4-pyrimidinyl)-1,3-thiazol-2-yl]-1-piperidinecarboxylate

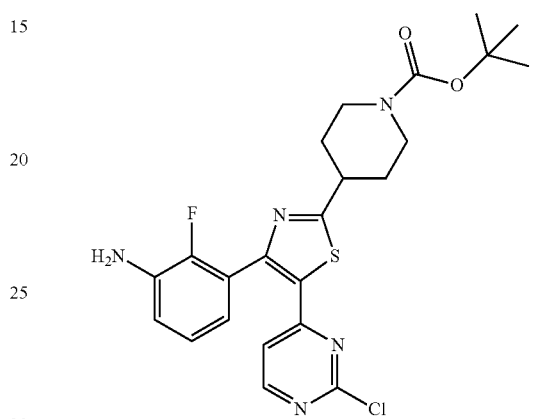

1,1-dimethylethyl 4-[5-(2-chloro-4-pyrimidinyl)-4-(2-fluoro-3-{[(2-propen-1-yloxy)carbonyl]amino}phenyl)-1,3-thiazol-2-yl]-1-piperidinecarboxylate (855 mg, 1.489 mmol) was dissolved into dichloromethane (DCM) (8 mL). To this solution were added tributylstannane (433 mg, 1.489 mmol), tetrakis (86 mg, 0.074 mmol) and water (0.083 mL, 4.62 mmol), and the reaction mixture was stirred for 1 h and concentrated. The residue was purified using column chromatography (0 to 100% EtOAc/hexane) to give 690 mg of the title compound. MS (ESI): 490.1 [M+1]$^+$.

Step C: 1,1-dimethylethyl 4-[5-(2-chloro-4-pyrimidinyl)-4-(3-{[(2,6-difluorophenyl)sulfonyl]amino}-2-fluorophenyl)-1,3-thiazol-2-yl]-1-piperidinecarboxylate

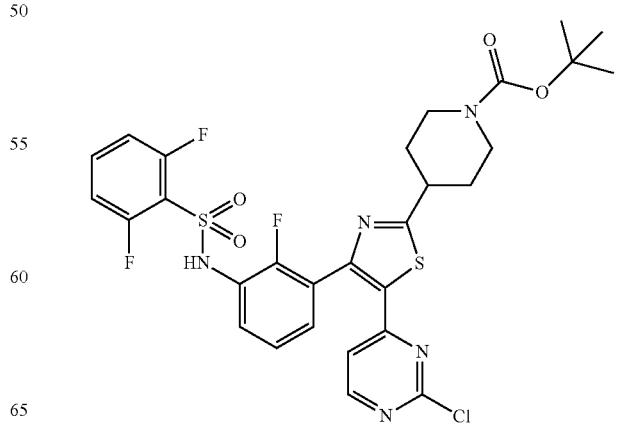

To a solution of 1,1-dimethylethyl 4-[4-(3-amino-2-fluorophenyl)-5-(2-chloro-4-pyrimidinyl)-1,3-thiazol-2-yl]-1-piperidinecarboxylate (300 mg, 0.612 mmol) in pyridine (3 mL) was added 2,6-difluorobenzenesulfonyl chloride (130 mg, 0.612 mmol), and the reaction mixture was stirred for 3 h. The reaction mixture was quenched with water (5 mL) and extracted with EtOAc (3×). The extracts were dried, filtered and concentrated. The residue was purified using column chromatography (40 to 100% EtOAc/hexane) to give 324 mg of the title compound. MS (ESI): 610.1 [M+1-56]⁺.

Step D: 1,1-dimethylethyl 4-[4-(3-{[(2,6-difluorophenyl)sulfonyl]amino}-2-fluorophenyl)-5-(2-methyl-4-pyrimidinyl)-1,3-thiazol-2-yl]-1-piperidinecarboxylate

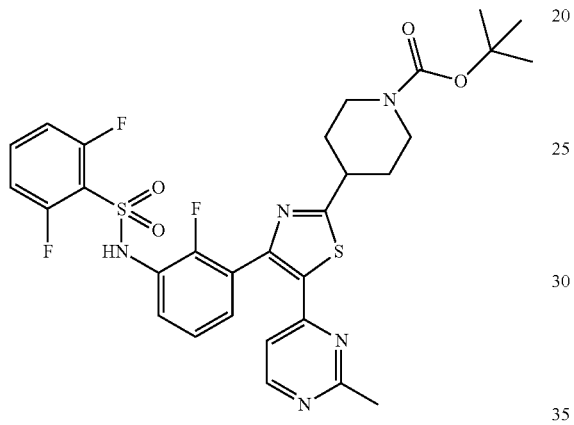

1,1-dimethylethyl 4-[5-(2-chloro-4-pyrimidinyl)-4-(3-{[(2,6-difluorophenyl)sulfonyl]amino}-2-fluorophenyl)-1,3-thiazol-2-yl]-1-piperidinecarboxylate (167 mg, 0.251 mmol) was dissolved into 1,4-dioxane (3 mL) and the solution was degassed for 10 min. PdCl₂(dppf)-CH₂Cl₂ adduct (10.24 mg, 0.013 mmol) and dimethylzinc (0.251 mL, 0.501 mmol) were added to the reaction mixture. The reaction mixture was stirred at 80° C. for 1 h. The reaction was quenched with methanol (3 mL) and water (10 mL) and extracted with EtOAc (3×). The extract was dried over Na₂SO₄, filtered, and concentrated. The residue was purified using column chromatography (40% to 100% EtOAc/hexane) to give the title compound (120 mg). MS (ESI): 646.3 [M+1]⁺.

Step D: 2,6-difluoro-N-{2-fluoro-3-[5-(2-methyl-4-pyrimidinyl)-2-(4-piperidinyl)-1,3-thiazol-4-yl]phenyl}benzenesulfonamide To a solution of 1,1-dimethylethyl 4-[4-(3-{[(2,6-difluorophenyl)sulfonyl]amino}-2-fluorophenyl)-5-(2-methyl-4-pyrimidinyl)-1,3-thiazol-2-yl]-1-piperidinecarboxylate (60 mg, 0.093 mmol) in dichloromethane (DCM) (2 mL) was added TFA (0.5 µL, 6.49 µmol), and the reaction mixture was stirred for 1 h. The reaction mixture was concentrated and the residue was purified using RP-HPLC. The TFA salt was neutralized to give 32 mg of title compound. MS (ESI): 546.1 [M+1]⁺.

Example 322

N-{3-[5-(2-amino-4-pyrimidinyl)-2-(4-piperidinyl)-1,3-thiazol-4-yl]-2-fluorophenyl}-2,6-difluorobenzenesulfonamide

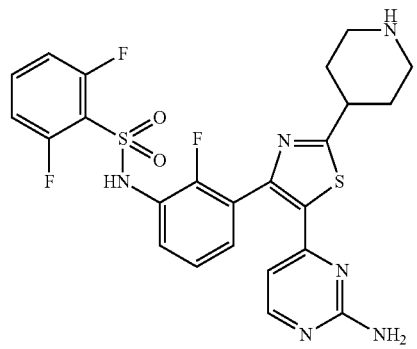 [SMILES: Nc1nccc(-c2sc(C3CCNCC3)nc2-c2cccc(NS(=O)(=O)c3c(F)cccc3F)c2F)n1]

Step A: 1,1-dimethylethyl 4-[5-(2-amino-4-pyrimidinyl)-4-(3-{[(2,6-difluorophenyl)sulfonyl]amino}-2-fluorophenyl)-1,3-thiazol-2-yl]-1-piperidinecarboxylate

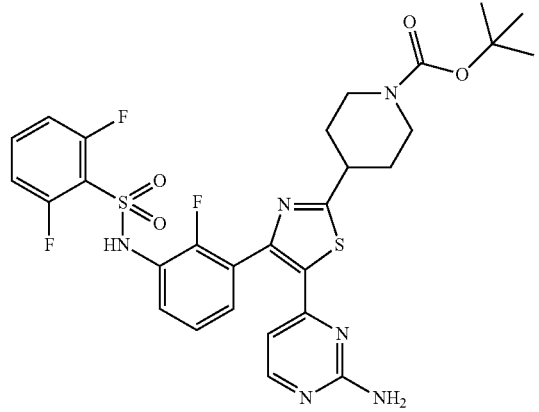 [SMILES: CC(C)(C)OC(=O)N1CCC(c2nc(-c3cccc(NS(=O)(=O)c4c(F)cccc4F)c3F)c(-c3ccnc(N)n3)s2)CC1]

A suspension of 1,1-dimethylethyl 4-[5-(2-chloro-4-pyrimidinyl)-4-(3-{[(2,6-difluorophenyl)sulfonyl]amino}-2-fluorophenyl)-1,3-thiazol-2-yl]-1-piperidinecarboxylate (110 mg, 0.165 mmol) in ammonium hydroxide solution (28%, 2 mL, 51.4 mmol) sealed in a 5-mL microwave tube was heated at 90° C. for 3 h under the microwave conditions. The mixture was concentrated and dried under high vacuum to give 98 mg of the title compound. MS (ESI): 647.3 [M+1]⁺.

Step B: N-{3-[5-(2-amino-4-pyrimidinyl)-2-(4-piperidinyl)-1,3-thiazol-4-yl]-2-fluorophenyl}-2,6-difluorobenzenesulfonamide To a solution of 1,1-dimethylethyl 4-[5-(2-amino-4-pyrimidinyl)-4-(3-{[(2,6-difluorophenyl)sulfonyl]amino}-2-fluorophenyl)-1,3-thiazol-2-yl]-1-piperidinecarboxylate (94 mg, 0.145 mmol) in dichloromethane (2 mL) was added TFA (0.5 mL, 6.49 mmol), and the reaction mixture was stirred for 1 h. The reaction mixture was concentrated and the residue was purified using RP-HPLC. The TFA salt was neutralized to give 52 mg of the title compound. MS (ESI): 547.1 [M+1]+.

Example 323

N-{2-fluoro-3-[5-(2-methyl-4-pyrimidinyl)-2-(4-piperidinyl)-1,3-thiazol-4-yl]phenyl}-3-furansulfonamide

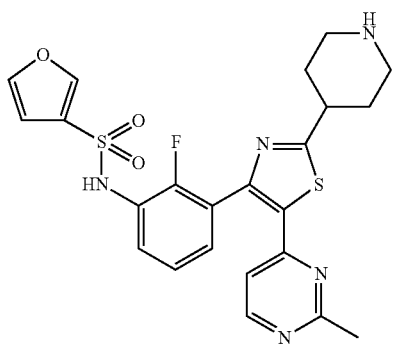 [SMILES: Cc1nccc(-c2sc(C3CCNCC3)nc2-c2cccc(NS(=O)(=O)c3ccoc3)c2F)n1]

Step A: 1,1-dimethylethyl 4-(5-(2-chloro-4-pyrimidinyl)-4-{2-fluoro-3-[(3-furanylsulfonyl)amino]phenyl}-1,3-thiazol-2-yl)-1-piperidinecarboxylate

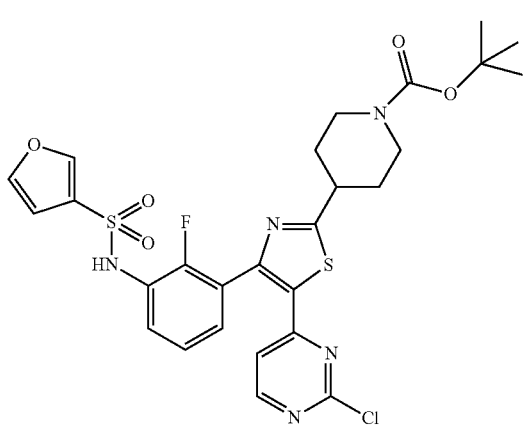 [SMILES: CC(C)(C)OC(=O)N1CCC(c2nc(-c3cccc(NS(=O)(=O)c4ccoc4)c3F)c(-c3ccnc(Cl)n3)s2)CC1]

To a solution of 1,1-dimethylethyl 4-[4-(3-amino-2-fluorophenyl)-5-(2-chloro-4-pyrimidinyl)-1,3-thiazol-2-yl]-1-piperidinecarboxylate (300 mg, 0.612 mmol) in pyridine (3 mL) was added 3-furansulfonyl chloride (153 mg, 0.918 mmol, and the reaction mixture was stirred for 3 h. The reaction mixture was quenched with water (5 mL) and extracted with EtOAc (3×). The extract was dried, filtered and concentrated. The residue was purified using column chromatography (40 to 100% EtOAc/hexane) to give 310 mg of the title compound. MS (ESI): 620.2, 622.2 [M+1]+.

Step B 1,1-dimethylethyl 4-[4-{2-fluoro-3-[(3-furanylsulfonyl)amino]phenyl}-5-(2-methyl-4-pyrimidinyl)-1,3-thiazol-2-yl]-1-piperidinecarboxylate

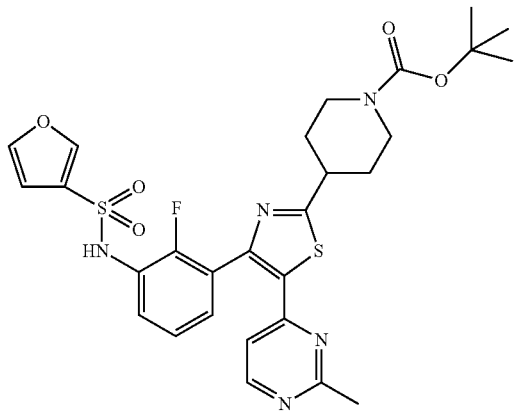 [SMILES: Cc1nccc(-c2sc(C3CCN(C(=O)OC(C)(C)C)CC3)nc2-c2cccc(NS(=O)(=O)c3ccoc3)c2F)n1]

1,1-dimethylethyl 4-(5-(2-chloro-4-pyrimidinyl)-4-{2-fluoro-3-[(3-furanylsulfonyl)-amino]phenyl}-1,3-thiazol-2-yl)-1-piperidinecarboxylate (150 mg, 0.242 mmol) was dissolved into 1,4-dioxane (3 mL) and the solution was degassed for 10 min. PdCl$_2$(dppf)-CH$_2$Cl$_2$ adduct (13.83 mg, 0.017 mmol) and dimethylzinc (0.242 mL, 0.484 mmol) were added to the reaction mixture. The reaction mixture was stirred at 80° C. for 1 h. The reaction was quenched with methanol (3 mL) and water (10 mL) and extracted with EtOAc (3×). The extract was dried over Na$_2$SO$_4$, filtered, and concentrated. The residue was purified using column chromatography (40% to 100% EtOAc/hexane) to give the title compound (118 mg). MS (ESI): 600.3 [M+1]+.

Step C: N-{2-fluoro-3-[5-(2-methyl-4-pyrimidinyl)-2-(4-piperidinyl)-1,3-thiazol-4-yl]phenyl}-3-furansulfonamide To a solution of 1,1-dimethylethyl 4-[4-{2-fluoro-3-[(3-furanylsulfonyl)amino]phenyl}-5-(2-methyl-4-pyrimidinyl)-1,3-thiazol-2-yl]-1-piperidinecarboxylate (115 mg, 0.192 mmol) in dichloromethane (2 mL) was added TFA (0.015 mL, 0.192 mmol), and the reaction mixture was stirred for 1 h. The reaction mixture was concentrated and the residue was purified using RP-HPLC. The TFA salt was neutralized to give 62 mg of the title compound. MS (ESI): 500.3 [M+1]+.

Example 324

N-{3-[5-(2-amino-4-pyrimidinyl)-2-(4-piperidinyl)-1,3-thiazol-4-yl]-2-fluorophenyl}-3-furansulfonamide

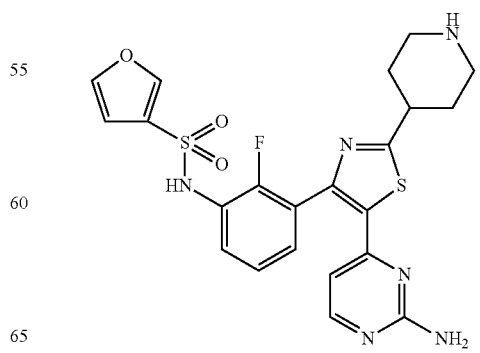

Step A: 1,1-dimethylethyl 4-(5-(2-amino-4-pyrimidinyl)-4-{2-fluoro-3-[(3-furanylsulfonyl)amino]phenyl}-1,3-thiazol-2-yl)-1-piperidinecarboxylate

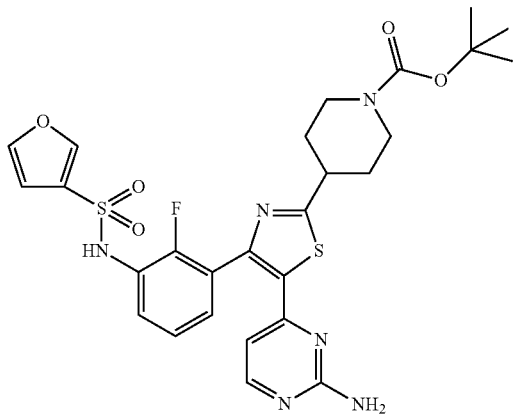 [SMILES: CC(C)(C)OC(=O)N1CCC(c2nc(-c3cccc(NS(=O)(=O)c4ccoc4)c3F)c(-c3ccnc(N)n3)s2)CC1]

A suspension of 1,1-dimethylethyl 4-(5-(2-chloro-4-pyrimidinyl)-4-{2-fluoro-3-[(3-furanylsulfonyl)amino]phenyl}-1,3-thiazol-2-yl)-1-piperidinecarboxylate (53 mg, 0.085 mmol) in ammonium hydroxide solution (28%, 2 mL, 51.4 mmol) sealed in a 5-mL microwave tube was heated at 90° C. for 3 h under the microwave conditions. The mixture was concentrated and dried under high vacuum to give 49 mg of the title compound. MS (ESI): 501.1 [M+1]+.

Step B: N-{3-[5-(2-amino-4-pyrimidinyl)-2-(4-piperidinyl)-1,3-thiazol-4-yl]-2-fluorophenyl}-3-furansulfonamide To a solution of 1,1-dimethylethyl 4-(5-(2-amino-4-pyrimidinyl)-4-{2-fluoro-3-[(3-furanylsulfonyl)amino]phenyl}-1,3-thiazol-2-yl)-1-piperidinecarboxylate (46 mg, 0.077 mmol) in dichloromethane (2 mL) was added TFA (0.5 mL, 6.49 mmol), and the reaction mixture was stirred for 1 h. The reaction mixture was concentrated and the residue was purified using RP-HPLC. The TFA salt was neutralized to give 22 mg of the title compound. MS (ESI): 501.1 [M+1]+.

Example 325

N-{3-[5-(2-amino-4-pyrimidinyl)-2-(4-morpholinyl)-1,3-thiazol-4-yl]-2-chlorophenyl}-2,5-difluorobenzenesulfonamide

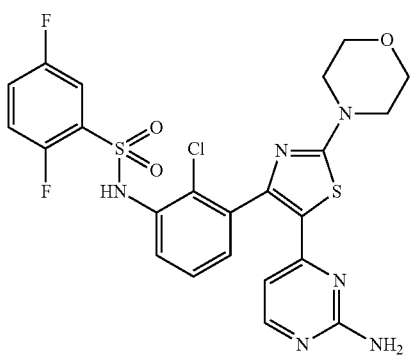

A suspension of N-{2-Chloro-3-[5-(2-chloro-4-pyrimidinyl)-2-(4-morpholinyl)-1,3-thiazol-4-yl]phenyl}-2,5-difluorobenzenesulfonamide (20 g, 34.3 mol) and saturated ammonium hydroxide (275 mL) was heated in a 1 L capacity Parr reactor @ 120° C. and 195-200 psi for 18 hrs. The mixture was cooled to ambient and the solid collected by filtration, washed with ethanol and dried to give ammonium salt of target compound (18.22 g). The mixture was suspended between ethyl acetate (1 L) and water (0.5 L), pH of the stirring mixture adjusted carefully at 60° C. to ~6.5 (first with 6N—HCl, then 1N—HCl) and the mixture filtered whilst still hot. The separated organic phase was washed with water, dried, and filtered. The filtrate was concentrated under reduced pressure to about ⅓ original volume during which time much solid crashed out; the pale yellow solid was filtered off, washed with more ethyl acetate and dried to give the title compound was obtained as a pale-yellow solid (12 g, 21.2 mol, 62% yield). (400 MHz, DMSO-$d_6$) δ ppm 10.76 (br. s., 1H), 7.91 (d, J=6.5 Hz, 1H), 7.60-7.40 (m, 5H), 7.47-7.52 (m, 3H), 7.39 (dd, J=5.8, 3.5 Hz, 1H), 6.56 (br. s, 2H), 5.60 (d, J=6.5 Hz, 1H), 3.68-3.77 (m, 4H), 3.55 (d, J=4.3 Hz, 4H), MS (ESI): 565.0 [M+H]+.

Biological Examples

Compounds of the present invention were tested for B-Raf protein kinase inhibitory activity in substrate phosphorylation assays and cell proliferation assays.

A. B-Raf Enzyme Assay:

Compounds of the present invention were tested for B-Raf protein serine kinase inhibitory activity in a B-Raf Accelerated MEK ATPase assay (BRAMA). Baculovirus-expressed His6-tagged BRAFV600E full-length (amino acids 2-766) was used in the BRAMA assay. The BRAMA assay is a high sensitivity assay which measures an intrinsic MEK-mediated ATP hydrolysis uncoupled from downstream ERK phosphorylation by coupling the formation of ADP to NADH oxidation through the enzymes pyruvate kinase and lactate dehydrogenase. When ADP production is initiated by addition of catalytic amounts of an activated Raf enzyme and non-phosphorylated MEK, one observes robust ADP production concomitant with Raf-mediated phosphorylation of MEK. The method is disclosed in: C. Rominger, M. Schaber, E. May. Assay for B-Raf Activity Based on Intrinsic MEK ATPase Activity. Statutory Invention Registration Ser. No. 11/084, 993 (March, 2005) but includes the following changes: 1) the assay was performed with a final MEK concentration of 150 nM and 2) the assay was read as single end point instead of a kinetic read.

Acceleration of MEK ATPase activity was determined from the data and plotted as a function of inhibitor concentration to give concentration response curves, from which the pIC50 values were generated following standard pIC50 fitting protocol.

Many of the exemplified compounds Examples 1-217 were run in the recited assay (A). The results are reported in the following Table 1a in which the highest pIC50 for the one or more runs of each assayed compound is categorized as indicated. In the following table:

"+" indicates no pIC50 measurement greater than 6 against B-Raf

"++" indicates at least one pIC50 measurement greater than 6 against B-Raf but no measurement greater than pIC50 of 7; and "+++" indicates at least one pIC50 measurement of greater than 7 against B-Raf.

TABLE 1a

| Example | B-Raf Activity |
|---|---|
| 1 | +++ |
| 2 | +++ |
| 3 | +++ |
| 4 | +++ |
| 5 | ++ |
| 6 | +++ |
| 7 | ++ |
| 8 | +++ |
| 9 | ++ |
| 10 | +++ |
| 11 | +++ |
| 12 | +++ |
| 13 | +++ |
| 14 | +++ |
| 15 | +++ |
| 16 | +++ |
| 17 | +++ |
| 18 | +++ |
| 19 | +++ |
| 20 | +++ |
| 21 | +++ |
| 22 | +++ |
| 23 | +++ |
| 24 | +++ |
| 25 | +++ |
| 26 | +++ |
| 27 | +++ |
| 28 | +++ |
| 29 | +++ |
| 30 | +++ |
| 31 | +++ |
| 32 | +++ |
| 33 | +++ |
| 34 | +++ |
| 35 | +++ |
| 36 | ++ |
| 37 | ++ |
| 38 | ++ |
| 39 | +++ |
| 40 | +++ |
| 41 | +++ |
| 42 | +++ |
| 43 | +++ |
| 44 | +++ |
| 45 | +++ |
| 46 | +++ |
| 47 | +++ |
| 48 | ++ |
| 49 | ++ |
| 50 | ++ |
| 51 | + |
| 52 | ++ |
| 53 | +++ |
| 54 | +++ |
| 55 | ++ |
| 56 | +++ |
| 57 | +++ |
| 58 | +++ |
| 59 | +++ |
| 60 | +++ |
| 61 | +++ |
| 62 | +++ |
| 63 | ++ |
| 64 | +++ |
| 65 | +++ |
| 66 | +++ |
| 67 | +++ |
| 68 | ++ |
| 69 | +++ |
| 70 | +++ |
| 71 | +++ |
| 72 | +++ |
| 73 | +++ |
| 74 | +++ |
| 75 | +++ |
| 76 | +++ |
| 77 | +++ |
| 78 | +++ |
| 79 | +++ |
| 80 | +++ |
| 81 | +++ |
| 82 | +++ |
| 83 | +++ |
| 84 | ++ |
| 85 | ++ |
| 86 | +++ |
| 87 | +++ |
| 88 | +++ |
| 89 | +++ |
| 90 | +++ |
| 91 | +++ |
| 92 | +++ |
| 93 | +++ |
| 94 | +++ |
| 95 | +++ |
| 96 | +++ |
| 97 | +++ |
| 98 | +++ |
| 99 | +++ |
| 100 | +++ |
| 101 | +++ |
| 102 | +++ |
| 103 | +++ |
| 104 | +++ |
| 105 | +++ |
| 106 | +++ |
| 107 | +++ |
| 108 | NT |
| 109 | +++ |
| 110 | ++ |
| 111 | +++ |
| 112 | ++ |
| 113 | +++ |
| 114 | ++ |
| 115 | + |
| 116 | +++ |
| 117 | +++ |
| 118 | +++ |
| 119 | ++ |
| 120 | +++ |
| 121 | +++ |
| 122 | +++ |
| 123 | +++ |
| 124 | +++ |
| 125 | +++ |
| 126 | +++ |
| 127 | +++ |
| 128 | +++ |
| 129 | +++ |
| 130 | +++ |
| 131 | +++ |
| 132 | +++ |
| 133 | ++ |
| 134 | +++ |
| 135 | +++ |
| 136 | +++ |
| 137 | +++ |
| 138 | +++ |
| 139 | +++ |
| 140 | +++ |
| 141 | +++ |
| 142 | +++ |
| 143 | +++ |
| 144 | +++ |
| 145 | +++ |
| 146 | +++ |
| 147 | +++ |
| 148 | +++ |
| 149 | +++ |
| 150 | ++ |
| 151 | +++ |
| 152 | +++ |

TABLE 1a-continued

B-Raf Activity

| Example | Activity |
|---|---|
| 153 | +++ |
| 154 | +++ |
| 155 | +++ |
| 156 | +++ |
| 157 | +++ |
| 158 | +++ |
| 159 | ++ |
| 160 | ++ |
| 161 | ++ |
| 162 | ++ |
| 163 | + |
| 164 | + |
| 165 | ++ |
| 166 | ++ |
| 167 | ++ |
| 168 | ++ |
| 169 | + |
| 170 | + |
| 171 | ++ |
| 172 | ++ |
| 173 | ++ |
| 174 | ++ |
| 175 | +++ |
| 176 | +++ |
| 177 | +++ |
| 178 | +++ |
| 179 | +++ |
| 180 | +++ |
| 181 | ++ |
| 182 | +++ |
| 183 | +++ |
| 184 | +++ |
| 185 | +++ |
| 186 | +++ |
| 187 | +++ |
| 188 | +++ |
| 189 | +++ |
| 190 | +++ |
| 191 | +++ |
| 192 | +++ |
| 193 | +++ |
| 194 | +++ |
| 195 | +++ |
| 196 | +++ |
| 197 | +++ |
| 198 | +++ |
| 199 | +++ |
| 200 | +++ |
| 201 | +++ |
| 202 | +++ |
| 203 | +++ |
| 204 | +++ |
| 205 | +++ |
| 206 | +++ |
| 207 | +++ |
| 208 | +++ |
| 209 | +++ |
| 210 | +++ |
| 211 | +++ |
| 212 | +++ |
| 213 | +++ |
| 214 | +++ |
| 215 | +++ |
| 216 | +++ |
| 217 | +++ |

At a time after the assay runs shown in Table 1a, above, many of the exemplified compounds Examples 1-217 were re-run and many of the exemplified compounds of Examples 218-325 were run one or more times in the recited assay (A). The results are reported in the following Table 1b in which the average pIC50 for the one or more runs of each assayed compound is categorized as indicated. In the following table: pIC50 values for the compounds of the examples were categorized by relative inhibition of B-Raf. The results are summarized in the tables below.

| B-Raf pIC50 | Example no. |
|---|---|
| 8.5 and over | 1, 2, 11-15, 18, 20, 21, 24, 26, 30-33, 40-43, 45, 54, 56, 57, 58a, 58d, 60, 61, 62, 64, 65, 66, 67, 69, 72, 74, 75, 78, 79, 81, 83, 91, 96-99, 101, 103, 104, 105, 107, 117, 118, 130, 132, 135, 137, 138, 142, 144, 154-157, 176, 177, 179, 182, 185, 187-192, 194-199, 201, 203, 207-214, 217, 218, 221, 223, 224, 226, 227, 228, 230, 231, 232, 233, 234, 236, 238, 240-245, 252, 256, 258-270, 273, 280, 281, 290-307, 309, 312, 319, 320, 322, and 324 |
| >7.5-<8.5 | 3, 8, 10, 16, 17, 19, 22, 23, 25, 27, 28, 29, 34, 35, 39, 44, 46, 47, 53, 59, 70, 71, 73, 76, 77, 80, 87, 88, 92, 93, 94, 100, 102, 106, 115, 116, 120, 121, 125, 128, 129, 134, 136, 139, 140, 141, 143, 148, 151, 152, 153, 180, 184, 186, 193, 200, 204, 205, 206, 215, 216, 219, 220, 222, 225, 229, 235, 237, 239, 246-251, 253, 254, 255, 257, 271, 272, 274-279, 283, 286, 287, 311, 313-315, 316, 321, and 323 |
| 6.0-7.5 | 4-7, 9, 36, 37, 38, 48, 49, 50, 52, 55, 63, 68, 68, 84, 85, 86, 89, 90, 95, 109-114, 119, 122, 123, 124, 126, 127, 131, 133, 145, 146, 147, 149, 150, 158-162, 165-168, 175, 178, 181, 183, 202, 282, 284, 285, 288, 289, and 310 |

B. Cellular Assays—Cell Growth Inhibition Assay

Human colon tumor cells (Colo205) were cultured in RPMI (Mediatech 50-020-PB) containing 10% FBS and 1% penicillin-streptomycin. Human melanoma cancer cells (SK-MEL-28) were cultured in EMEM with nonessential amino acids (Mediatech 50-011-PB) containing 10% FBS, 1% sodium pyruvate (JT Baker 3354-04), and 1% penicillin-streptomycin. All cell lines were maintained at 37° C. in a humidified 5% $CO_2$, 95% air incubator. Cells were harvested using trypsin/EDTA (Invitrogen 25200), counted using a haemocytometer, and plated. For 96-well assays (using white full-area NUNC plates cat. #136102), cells were plated in 105 µL at the following densities (cells/well): Colo205, 500; SK-MEL-28, 500. For 384-well assays (white full-area NUNC plates, cat. #781080), cells were plated in 48 µL at the following densities (cells/well): Colo205, 500; SK-MEL-28, 500.

The next day, compounds were diluted as follow: For 96-well assays, 13.5 µL of compound in DMSO were diluted using nine (9) serial 1:3 dilutions of 4.5 µL in 9 µL of DMSO. Medium (270 µL/well of RPMI with 10% FBS and 1% penicillin-streptomycin) was added to the plates. Aliquots (7 µL) were added to cells in the final assay giving a final DMSO concentration of 0.2%. For 384-well assays, 15 µL of compound in DMSO were diluted using nine (9) serial 1:3 dilutions of 5 µL in 10 µL of DMSO, followed by a further dilution of 5 µL of compound with 95 µL of medium, of which 2 µL were added to cells in the final assay giving a final DMSO concentration of 0.2%. Cells were incubated at 37° C., 5% $CO_2$ for 3 days.

Total ATP was measured (as a surrogate estimate of cell number) using CellTiter-Glo® reagent (Promega G7571). Briefly, plates were removed from the incubator and allowed to equilibrate to room temperature for 30 minutes. CellTiter-Glo® (25 µL or 55 µL for 384-well or 96-well assays, respectively) reagent was added to each well and plates were shaken on an orbital plate shaker for 2 minutes. Plates were incubated without shaking for a further 30 minutes and read on an LJL Analyst GT reader in luminometer mode with an integration time of 0.5 seconds per well. Percent inhibition of cell growth was calculated relative to DMSO vehicle-treated control wells. Concentration of compound required to give 50% inhibition of vehicle-treated control cell growth ($IC_{50}$) was interpolated using a 4-parameter fit for determining $IC_{50}$ using the following equation: $Y=A+((B-A)/(1+((C/X)^D)))$ where $X=IC_{50}$.

Many of the compounds of Examples 1-217 were run in the recited assay and the results are reported in the following Table 2a. In the following table:

"+" indicates that the compound showed activity of >1 µM in Colo205 tumor cells;

"++" indicates that the compound showed activity of between 100 nM and 1 µM in Colo205 tumor cells; and "+++" indicates that the compound showed activity of less than 100 nM in Colo205 tumor cells.

TABLE 2a

Activity in Colo205 Tumor Cells

| Example | Activity |
|---|---|
| 1 | +++ |
| 2 | +++ |
| 3 | +++ |
| 4 | ++ |
| 5 | ++ |
| 6 | + |
| 7 | + |
| 8 | ++ |
| 9 | + |
| 10 | +++ |
| 11 | +++ |
| 12 | +++ |
| 13 | +++ |
| 14 | +++ |
| 15 | +++ |
| 16 | +++ |
| 17 | +++ |
| 18 | +++ |
| 19 | +++ |
| 20 | +++ |
| 21 | ++ |
| 22 | +++ |
| 23 | ++ |
| 24 | +++ |
| 25 | ++ |
| 26 | +++ |
| 27 | ++ |
| 28 | +++ |
| 29 | ++ |
| 30 | +++ |
| 31 | +++ |
| 32 | +++ |
| 33 | +++ |
| 34 | + |
| 35 | ++ |
| 36 | + |
| 37 | ++ |
| 38 | + |
| 39 | ++ |
| 40 | ++ |
| 41 | +++ |
| 42 | +++ |
| 43 | ++ |
| 44 | + |
| 45 | ++ |
| 46 | ++ |
| 47 | ++ |
| 48 | ++ |
| 49 | ++ |
| 50 | + |
| 51 | + |

TABLE 2a-continued

Activity in Colo205 Tumor Cells

| Example | Activity |
|---|---|
| 52 | ++ |
| 53 | +++ |
| 54 | +++ |
| 55 | ++ |
| 56 | +++ |
| 57 | +++ |
| 58 | +++ |
| 59 | ++ |
| 60 | +++ |
| 61 | ++ |
| 62 | ++ |
| 63 | ++ |
| 64 | +++ |
| 65 | +++ |
| 66 | +++ |
| 67 | +++ |
| 68 | + |
| 69 | ++ |
| 70 | ++ |
| 71 | ++ |
| 72 | ++ |
| 73 | + |
| 74 | +++ |
| 75 | +++ |
| 76 | ++ |
| 77 | +++ |
| 78 | +++ |
| 79 | +++ |
| 80 | ++ |
| 81 | +++ |
| 82 | +++ |
| 83 | +++ |
| 84 | + |
| 85 | + |
| 86 | + |
| 87 | ++ |
| 88 | ++ |
| 89 | ++ |
| 90 | ++ |
| 91 | +++ |
| 92 | +++ |
| 93 | ++ |
| 94 | ++ |
| 95 | ++ |
| 96 | +++ |
| 97 | +++ |
| 98 | +++ |
| 99 | ++ |
| 100 | ++ |
| 101 | +++ |
| 102 | ++ |
| 103 | +++ |
| 104 | +++ |
| 105 | +++ |
| 106 | ++ |
| 107 | +++ |
| 108 | NT |
| 109 | + |
| 110 | NT |
| 111 | NT |
| 112 | NT |
| 113 | NT |
| 114 | NT |
| 115 | + |
| 116 | +++ |
| 117 | +++ |
| 118 | ++ |
| 119 | + |
| 120 | ++ |
| 121 | ++ |
| 122 | + |
| 123 | ++ |
| 124 | ++ |
| 125 | ++ |
| 126 | ++ |
| 127 | + |

TABLE 2a-continued

Activity in Colo205 Tumor Cells

| Example | Activity |
|---|---|
| 128 | + |
| 129 | ++ |
| 130 | +++ |
| 131 | + |
| 132 | ++ |
| 133 | + |
| 134 | ++ |
| 135 | ++ |
| 136 | ++ |
| 137 | +++ |
| 138 | +++ |
| 139 | +++ |
| 140 | +++ |
| 141 | +++ |
| 142 | +++ |
| 143 | ++ |
| 144 | +++ |
| 145 | ++ |
| 146 | ++ |
| 147 | ++ |
| 148 | + |
| 149 | ++ |
| 150 | ++ |
| 151 | ++ |
| 152 | +++ |
| 153 | +++ |
| 154 | ++ |
| 155 | ++ |
| 156 | +++ |
| 157 | +++ |
| 158 | + |
| 159 | ++ |
| 160 | ++ |
| 161 | + |
| 162 | ++ |
| 163 | + |
| 164 | + |
| 165 | ++ |
| 166 | ++ |
| 167 | ++ |
| 168 | ++ |
| 169 | + |
| 170 | + |
| 171 | ++ |
| 172 | ++ |
| 173 | ++ |
| 174 | ++ |
| 175 | ++ |
| 176 | +++ |
| 177 | +++ |
| 178 | ++ |
| 179 | +++ |
| 180 | ++ |
| 181 | + |
| 182 | +++ |
| 183 | + |
| 184 | +++ |
| 185 | +++ |
| 186 | ++ |
| 187 | +++ |
| 188 | +++ |
| 189 | +++ |
| 190 | +++ |
| 191 | +++ |
| 192 | ++ |
| 193 | ++ |
| 194 | +++ |
| 195 | +++ |
| 196 | +++ |
| 197 | +++ |
| 198 | ++ |
| 199 | +++ |
| 200 | ++ |
| 201 | +++ |
| 202 | + |
| 203 | +++ |
| 204 | +++ |
| 205 | ++ |
| 206 | +++ |
| 207 | +++ |
| 208 | +++ |
| 209 | +++ |
| 210 | +++ |
| 211 | +++ |
| 212 | +++ |
| 213 | +++ |
| 214 | +++ |
| 215 | +++ |
| 216 | NT |
| 217 | NT |

At a time after the assay runs shown in Table 2a, above, many of the exemplified compounds Examples 1-217 were re-run and many of the exemplified compounds of Examples 218-325 were run one or more times in the recited assay (B). The results are reported in the following Table 2b in which the average inhibition for the one or more runs of each assayed compound is categorized as indicated. In the following table:

IC50 (nM) values for compounds of select examples were categorized by relative inhibition of cell proliferation. The results are summarized in the tables below.

| IC50 for Colo205 | Example No. |
|---|---|
| <100 nM | 1, 2, 3, 10-20, 22, 26, 28, 30, 31, 32, 33, 41, 42, 53, 54, 56, 57, 58a, 58d, 60, 64, 65, 66, 67, 74, 75, 77, 78, 79, 81, 83, 91, 92, 96-98, 101, 103, 104, 105, 107, 116, 117, 130, 137, 138, 140, 141, 142, 144, 152, 153, 156, 157, 176, 179, 182, 184, 185, 188, 189, 190, 191, 195, 196, 197, 199, 201, 203, 204, 206-253, 255, 256, 258, 259, 262, 264, 266, 269, 281, and 295 |
| 100 nM to 1000 nM | 8, 21, 23, 24, 25, 27, 29, 35, 37, 39, 40, 43, 45-49, 52, 55, 59, 61, 62, 63, 69-72, 76, 80, 97, 88, 89, 90, 93, 94, 95, 99, 100, 102, 106, 113, 118, 120, 121, 123-126, 129, 132,134, 135, 136, 139, 143, 145, 146, 147, 149, 150, 151, 154, 155, 159, 160, 162, 165, 166, 167, 168, 175, 178, 180, 186, 192, 193, 198, 200, 205, 254, 263, 267, 270, 271, 272, 278, 280, and 282-287 |
| >1000 nM-10 µM | 4-7, 9, 34, 38, 44, 50, 51, 68, 73, 84, 86, 109, 110, 111, 112, 115, 122, 127, 128, 133, 148, 158, 161, 163, 164, 177, 181, 183, 187, and 202 |

Many of the compounds of Examples 1-217 were run in the recited assay and the results are reported in the following Table 3a. In the following table:

"+" indicates that the compound showed activity of >1 µM in SK-MEL-28 tumor cells;

"++" indicates that the compound showed activity of between 100 nM and 1 µM in SK-MEL-28 tumor cells; and "+++" indicates that the compound showed activity of less than 100 nM in SK-MEL-28 tumor cells.

TABLE 3a

Activity in SK-MEL-28 Tumor Cells

| Example | Activity |
|---|---|
| 1 | +++ |
| 2 | +++ |
| 3 | +++ |
| 4 | ++ |
| 5 | ++ |
| 6 | + |
| 7 | + |
| 8 | ++ |
| 9 | + |
| 10 | +++ |
| 11 | +++ |
| 12 | +++ |
| 13 | +++ |
| 14 | +++ |
| 15 | +++ |
| 16 | +++ |
| 17 | +++ |
| 18 | +++ |
| 19 | +++ |
| 20 | +++ |
| 21 | ++ |
| 22 | +++ |
| 23 | ++ |
| 24 | +++ |
| 25 | +++ |
| 26 | +++ |
| 27 | ++ |
| 28 | +++ |
| 29 | ++ |
| 30 | +++ |
| 31 | +++ |
| 32 | +++ |
| 33 | +++ |
| 34 | + |
| 35 | ++ |
| 36 | + |
| 37 | ++ |
| 38 | + |
| 39 | ++ |
| 40 | ++ |
| 41 | +++ |
| 42 | +++ |
| 43 | ++ |
| 44 | + |
| 45 | ++ |
| 46 | ++ |
| 47 | ++ |
| 48 | ++ |
| 49 | ++ |
| 50 | + |
| 51 | + |
| 52 | ++ |
| 53 | +++ |
| 54 | +++ |
| 55 | + |
| 56 | +++ |
| 57 | +++ |
| 58 | +++ |
| 59 | ++ |
| 60 | +++ |
| 61 | ++ |
| 62 | ++ |
| 63 | ++ |
| 64 | +++ |
| 65 | +++ |
| 66 | +++ |
| 67 | +++ |
| 68 | + |
| 69 | ++ |
| 70 | ++ |
| 71 | ++ |
| 72 | +++ |
| 73 | + |
| 74 | ++ |
| 75 | +++ |
| 76 | ++ |
| 77 | +++ |
| 78 | +++ |
| 79 | +++ |
| 80 | ++ |
| 81 | +++ |
| 82 | +++ |
| 83 | +++ |
| 84 | + |
| 85 | + |
| 86 | + |
| 87 | ++ |
| 88 | + |
| 89 | ++ |
| 90 | ++ |
| 91 | +++ |
| 92 | +++ |
| 93 | ++ |
| 94 | ++ |
| 95 | ++ |
| 96 | +++ |
| 97 | +++ |
| 98 | +++ |
| 99 | ++ |
| 100 | ++ |
| 101 | +++ |
| 102 | ++ |
| 103 | +++ |
| 104 | +++ |
| 105 | +++ |
| 106 | ++ |
| 107 | +++ |
| 108 | NT |
| 109 | + |
| 110 | NT |
| 111 | NT |
| 112 | NT |
| 113 | NT |
| 114 | NT |
| 115 | + |
| 116 | +++ |
| 117 | +++ |
| 118 | ++ |
| 119 | + |
| 120 | ++ |
| 121 | ++ |
| 122 | + |
| 123 | + |
| 124 | ++ |
| 125 | ++ |
| 126 | ++ |
| 127 | + |
| 128 | + |
| 129 | ++ |
| 130 | +++ |
| 131 | + |
| 132 | ++ |
| 133 | + |
| 134 | ++ |
| 135 | +++ |
| 136 | ++ |
| 137 | +++ |
| 138 | + |
| 139 | +++ |
| 140 | +++ |
| 141 | +++ |
| 142 | +++ |
| 143 | ++ |
| 144 | +++ |
| 145 | ++ |
| 146 | ++ |
| 147 | ++ |
| 148 | + |
| 149 | ++ |
| 150 | ++ |
| 151 | ++ |
| 152 | +++ |

TABLE 3a-continued

Activity in SK-MEL-28 Tumor Cells

| Example | Activity |
|---|---|
| 153 | +++ |
| 154 | ++ |
| 155 | ++ |
| 156 | +++ |
| 157 | +++ |
| 158 | + |
| 159 | ++ |
| 160 | ++ |
| 161 | + |
| 162 | ++ |
| 163 | + |
| 164 | + |
| 165 | ++ |
| 166 | ++ |
| 167 | + |
| 168 | ++ |
| 169 | + |
| 170 | + |
| 171 | ++ |
| 172 | ++ |
| 173 | + |
| 174 | ++ |
| 175 | ++ |
| 176 | +++ |
| 177 | +++ |
| 178 | ++ |
| 179 | +++ |
| 180 | ++ |
| 181 | + |
| 182 | +++ |
| 183 | + |
| 184 | +++ |
| 185 | +++ |
| 186 | ++ |
| 187 | +++ |
| 188 | +++ |
| 189 | +++ |
| 190 | +++ |
| 191 | +++ |
| 192 | ++ |
| 193 | ++ |
| 194 | +++ |
| 195 | +++ |
| 196 | +++ |
| 197 | +++ |
| 198 | ++ |
| 199 | +++ |
| 200 | ++ |
| 201 | +++ |
| 202 | ++ |
| 203 | +++ |
| 204 | +++ |
| 205 | ++ |
| 206 | +++ |
| 207 | +++ |
| 208 | +++ |
| 209 | +++ |
| 210 | +++ |
| 211 | +++ |
| 212 | +++ |
| 213 | +++ |
| 214 | +++ |
| 215 | +++ |
| 216 | NT |
| 217 | NT |

At a time after the assay runs shown in Table 3a, above, many of the exemplified compounds Examples 1-217 were re-run and many of the exemplified compounds of Examples 218-325 were run one or more times in the recited assay (B). The results are reported in the following Table 3b in which the average inhibition for the one or more runs of each assayed compound is categorized as indicated. In the following table:

IC50 (nM) values for compounds of select examples were categorized by relative inhibition of cell proliferation. The results are summarized in the tables below.

| IC50 for SK-MEL-28 | Example No. |
|---|---|
| <100 nM | 1, 2, 3, 10-20, 22, 25, 26, 28, 30, 31, 32, 33, 42, 53, 54, 56, 57, 58a, 58d, 60, 64, 65, 66, 67, 72, 75, 77, 78, 79, 81, 83, 91, 92, 96, 97, 98, 101, 103, 104, 105, 107, 116, 117, 130, 135, 137, 138, 140, 141, 142, 144, 152, 153, 156, 157, 176, 179, 182, 184, 185, 187, 188, 189, 190, 191, 192, 194, 195, 196, 197, 199, 201, 203, 204, 206-249, 251-256, 258, 259, 262, 264, 265, 266, 271, 272, 281, and 295 |
| 100 nM to 1000 nM | 4, 5, 8, 21, 23, 24, 27, 29, 35, 37, 39, 40, 41, 43, 45, 46, 47, 48, 49, 52, 59, 61, 62, 63, 69, 70, 71, 74, 76, 80, 87, 89, 90, 93, 94, 95, 99, 100, 102, 106, 113, 118, 120, 121, 124, 125, 126, 129, 132, 134, 136, 139, 143, 145, 146, 147, 149, 150, 151, 154, 155, 159, 160, 162, 165, 166, 168, 175, 178, 180, 186, 193, 198, 200, 202, 205, 250, 263, 267, 269, 270, 278, 280, 283, 284, 286, and 287 |
| >1000 nM-10 pM | 6, 7, 9, 34, 38, 44, 50, 51, 55, 68, 73, 86, 88, 109, 110, 111, 115, 119, 122, 123, 127, 131, 133, 148, 158, 161, 164, 167, 177, 181, 183, 282, and 285 |

C. Mutant Cancer Cell Lines

Twenty two (22) cancer cell lines encoding B-Raf V600E mutation, cultured generally according to instructions supplied by cell culture supplier American Type Culture Collection, Manassas, Va., were tested for sensitivity to the compound of example 58a in a 3 day proliferation assay. Data demonstrated that 16 out of 22 cancer cell lines encoding B-Raf V600E were sensitive with gIC50<100 nM while 2 out of 22 demonstrated an intermediate response (gIC50≥100 nM and <1000 nM) and 4 out of 22 were not sensitive (gIC50>1000M) to the compound. Activity of the compound of example 58a against B-Raf V600E mutant cancer cell lines is shown in Table 4.

TABLE 4

| CELL LINE | Tissue Origin | BRAF | Mean gIC$_{50}$ (nM) |
|---|---|---|---|
| MALME-3M | Skin | V600E | (+++) |
| UACC-62 | Skin | V600E | (+++) |
| C32TG | Skin | V600E | (+++) |
| SK-MEL-1 | Skin | V600E | (+++) |
| UCLA-SO-M14 | Skin | V600E | (+++) |
| SK-MEL-28 | Skin | V600E | (+++) |
| DU4475 | Breast | V600E | (+++) |
| WM115 | Skin | V600D, V600E | (+++) |
| UACC-257 | Skin | V600E | (+++) |
| COLO 205 | Colon | V600E | (+++) |
| SK-MEL-3 | Skin | V600E | (+++) |
| A375P F11s | Skin | V600E | (+++) |
| SH-4 | Skin | V600E | (+++) |
| A101D | Skin | V600E | (+++) |
| ES-2 | Ovary | V600E | (+++) |
| HT-29 | Colon | T119S, V600E | (+++) |
| SW1417 | Colon | V600E | (++) |
| SW872 | Connective tissue | V600E | (++) |

TABLE 4-continued

| CELL LINE | Tissue Origin | BRAF | Mean gIC$_{50}$ (nM) |
|---|---|---|---|
| RKO | Colon | V600E | (−) |
| A673 | Muscle | V600E | (−) |
| GCT | Skin | V600E | (−) |
| NCI-H292 | Lung | T119S, V600E | (−) |

(+++) gIC50 < 100 nM
(++) gIC50 ≥ 100 nM and <1000 nM
(−) gIC50 ≥ 1000 nM

D. In Vivo Experiments

1. Dose Dependent Tumor Inhibition Using Compound of Example 58a

A375P F11s were cultured in RPMI 1640 medium supplemented with 10% fetal bovine serum, 1% Penicillin-streptomycin and 1% sodium pyruvate. Tumor cells (2×10$^6$ A375P F11s) were implanted subcutaneously into the right flank of athymic mice on Day 1. To facilitate their growth, A375P F11s cells were suspended in Matrigel diluted 1:1 in phosphate-buffered saline before implantation. When tumors had reached approximately 200 mm$^3$ in volume (Day 19-22), tumor-bearing mice were randomized into study groups (n=7 or 8). Animals were dosed orally once or twice daily for a 14-day period. The compound of Example 58a was dosed in a 0.5% HPMC/0.2% Tween 80 pH 7-8 vehicle. Tumor growth was measured twice a week using calipers for the duration of the study. Tumor volumes were calculated as a product of (length×width×width)/2 and median values were used to compare groups. Complete regressions (CR) were defined as three consecutive tumor measurements of ≤13.5 mm$^3$. Partial regressions were defined as three consecutive measurements of ≤50% of starting tumor volume. Tumor growth delay was defined as the difference in time taken for treated and control groups to reach 1000 mm$^3$ (T-C1000).

In the following table:
"−" indicates no response
"+" indicates growth delay (1-2× doubling)
"++" indicates growth delay (>2× doubling)
"+++" indicates stable disease
"++++" indicates partial regression
"+++++" indicates complete regression

TABLE 5

| In vivo Evaluation | | |
|---|---|---|
| Tumor Line | Dosage | Response |
| A375P F11s | 300 mg/kg bid | ++++ (+) |
| A375P F11s | 300 mg/kg qd | ++++ (+) |
| A375P F11s | 100 mg/kg bid | ++++ (+) |
| A375P F11s | 100 mg/kg qd | ++++ (+) |
| A375P F11s | 10 mg/kg qd | ++ (+) |
| A375P F11s | 1 mg/kg qd | + |
| A375P F11s | 0.1 mg/kg qd | − |

2. Pharmacodynamic Effect of Various Compounds

Activity of select exemplified compounds was tested in vivo against A375PF11s (melanoma cell line encoding a B-Raf V600E mutation) xenograft mouse model. The A375P F11s cell line, encoding a mutation for BRAF$^{V600E}$, was subcloned from the A375P human melanoma cell line (obtained from ATCC, Cat #CRL-1619) by limiting dilution and selected based on high (90%) sensitivity to the BRAF inhibitor, SB-590885 (commercially available), in 3-day proliferation assays. The selected clone (A375P F11s) was isolated and mutation in B-Raf (T1799A) encoding the V600E amino acid change was reconfirmed.

Female CD-1 nu/nu mice of 8-10 weeks in age were used in these studies; all mice were obtained from Charles River Laboratories (Wilmington, Del.). Animals were housed in pathogen free conditions and handled with aseptic technique. A375P F11s were harvested from culture flasks by exposure to 0.25% trypsin/EDTA for 5 min at 37° C. Detached cells were collected, centrifuged (1500 rpm, 5 min, 4° C.) and rinsed to remove the trypsin solution. Cells were resuspended in PBS without magnesium or calcium and counted. Cells were spun as previously to remove PBS and a single cell suspension was created either in 50% Matrigel: 50% PBS (v:v) or 100% PBS so that a 100 µL subcutaneous injection would deliver the required number of cells per mouse. The A375P F11s melanoma line was injected with Matrigel at 4 million cells per mouse. Tumors were established (~150-300 mm$^3$) for all cell lines within 2-4 weeks post-injection.

Compounds of examples 24, 25, 26, 57, 58, 59, 64, 65, 66, and 156 were prepared in formulations of either 0.5% HPMC/0.2% TWEEN 80 ph 7-8 or 20% encapsin/1% DMSO. The preparations were administered orally to the mice as a single oral dose of 100 mg/kg.

At 2 h following oral administration of compound mice were euthanized using carbon dioxide. Tumors were carefully excised, homogenized using Medimachine (BD Bioscience) with 1 ml of lysis buffer (25 mM Tris-HCl (pH 7.5), 2 mM EDTA (pH 8.0), 2 mM EGTA (pH 8.0), 1% Triton X-100, 0.1% SDS, 50 mM Na—B—PO4, 2 mM NaVO4, 4 mM Na-Pyr-PO4, 2× phosphatase inhibitor cocktail. Crude homogenate was transferred to a 12 ml polypropylene tube containing 1.5 ml of lysis buffer and kept on ice. Following homogenization of all samples, 1 ml of homogenate was transferred to an eppendorf tube and centrifuged at 14,000 rpm for 15 min at 4° C. Five hundred microliter of clarified lysate was transferred to a new tube, flash frozen and processed for quantitation of pERK and tERK using western blot or Elisa (MSD) assays. Before the ratio of pERK/tERK was determined and to ensure linear range, a BSA standard curve was made by performing serial ⅓-fold dilution to reach concentrations of 20, 13.3, 8.9, 5.9, 3.9, 2.6, 1.7, 1.2, 0.8, 0.5, 0 µg/µl. BioRad dye was added to BSA dilutions and diluted test lysates. Samples were incubated at room temperature for 15 min and read on the SpectraMax plate reader at 595 nM. Comparison to the standard curve provides a relative measurement of protein concentration. For determination of pERK/tERK ratio by western blot analysis 50 µg microgram of tumor lysates were electrophoresed on Invitrogen 4-12% bis-Tris HCl SDS-PAGE. The gels were transferred onto nitro-cellulose membranes using the iBlot transfer apparatus, which were then blocked and incubated with different primary antibodies overnight at 4° C. Western blots dually probed against pERK and tERK were scanned using LI-COR Odyssey® reader. A ratio of the immunofluorescent density obtained for pERK/tERK is calculated and expressed as a ratio (in percentage) to control untreated samples. For determination of pERK/tERK ratio by ELISA, MesoScale Discovery (MSD) (cat #K15107) plate were used according to manufacturer's instructions. In brief, MSD plates were block with 150 µl/well of blocking buffer for 1 hr before being washed 4 times with 200 µl of washing buffer. Thirty microliter (30 µl) of serially diluted samples was added to wells and plates were incubated overnight at 4° C. under slow agitation (~500 rpm). Plates were washed 4 times in 200 µl 1× Tris wash buffer and 25 µl detection antibody solution was added to all wells and incubated at room temperature for 1 hr (~500 rpm). Plates were washed 4 times in 200 µl wash buffer and 1500 of read buffer was added to all wells. Plates were read on MSD.SI6000. In this assay vehicle and compound treated samples were tested at 4 different dilutions to allow linear range coverage of the assay. From pERK and tERK signal, background (BSA signal) was subtracted and ratio of pERK/tERK determined and normalized to untreated vehicle samples, arbitrarily set at 100%.

Inhibition of pERK by B-Raf inhibitors is a good pharmacodynamic marker (PD marker) for BRAF inhibition. The compounds of examples 24, 25, 26, 57, 58, 59, 64, 65, 66, and 156 exhibited inhibition of pERK (pERK/tERK) of equal to or greater than 30%.

3. Efficacy In Vivo Study in Mouse.

Of the 10 compounds tested for inhibition of pERK, in C.2 above, eight of the compounds (compounds described in example numbers 24, 26, 58, 59, 64, 65, 66, and 156) were tested in an efficacy study similar to study D.1 above. The results demonstrate that six of the eight tested compounds caused tumor regression (mean tumor volume smaller after 14 day treatment than initial tumor volume) or stable disease (mean tumor volume similar after 14 day treatment to initial mean tumor volume) compared to vehicle treated animals.

Pharmaceutical Formulation Example

Preparation of Capsules Containing a Compound of the Invention (Freebase)

Contents in each capsule:
=60 mg Active Pharmaceutical ingredient (API)+60 mg Avicel+13 mg SSG.
133 mg total powder in a size 0 hard gelatin capsule. The Avicel/SSG weight may be reasonably approximate.

Procedure:
1. Separate the halves of hard-gelatin capsule and mark/identify each as appropriate/needed.
2. Place the bottom capsule half in capsule filler with the filling funnel on top.
3. Weigh the components (Avicel, Sodium Starch Glycolate (SSG), API) onto a single weigh paper (tared on an analytical balance between each weighing).
4. Record weights of each component.
5. Carefully and thoroughly mix the dry powders on the weigh paper with a small spatula.
6. Carefully transfer the mixed powders into the capsule through the funnel.
7. Place the top half onto the capsule and close until secure, shake capsule to mix/distribute contents.
8. IF powder begins to near top of capsule, gently tap capsule and powder should settle.
9. Place the capsule into a small appropriately labeled bottle (but large enough to easily remove it).

Pharmaceutical Formulation Example

Preparation of Tablets Containing a Compound of the Invention (Freebase)

| Component | Quantity (mg/tablet) | % w/w |
|---|---|---|
| Core Tablet | | |
| API | 405.0 | 71.6 |
| Lactose monohydrate | 59.0 | 10.4 |
| Polysorbate 80 | 1.0 | 0.2 |
| Povidone | 40.0 | 7.1 |
| Colloidal Silicon Dioxide | 5.5 | 1.0 |
| Crospovidone | 51.0 | 9.0 |
| Magnesium Stearate | 4.5 | 0.8 |
| Purified Water | qs | |
| Film Coating | | |
| Opadry ® Orange, YS-1-13065-A | 17.0 | 3.0 |
| Purified water | qs | |

Procedure:
1. Sieve Lactose, Silicon dioxide, Crospovidone and half Povidone.
2. Add API.
3. Granulate in High Shear Granulator with granulating solution containing dissolved
Polysorbate 80 and other half of Povidone in Purified water.
4. Mill using Comil 197, 0.375" screen.
5. Dry using Fluid Bed Dryer
6. Mill using Comil 197, 0.075" screen
7. Add Crospofidone, magnesium stearate.
8. Blend 5 minute
9. Compress tablet
10. Aqueous film coat tablet X-Ray Crystallography of Example Nos. 58, 64 and 65:

The X-ray powder diffraction pattern of Form 1 of Example Nos. 58, 64 and 65 can be determined using conventional techniques and equipment known to those skilled in the art of analytical chemistry and physical characterization. The diffraction patterns of FIGS. 1, 3 and 5 were obtained with a PANalytical diffractometer system utilizing copper K X-radiation and equipped with automated divergent slits, nickel filter, and a real time multiple strip detector. The powder sample used to generate the X-ray powder diffraction data was mounted on a silicon zero background plate. In FIGS. 1, 3 and 5, 2 theta angles in degrees (x-axis) is plotted against peak intensity (y-axis). The XRD pattern for each form of Example No. 58, 64 and 65 is unique to the particular form; exhibiting a unique set of diffraction peaks which can be expressed in 2 theta angles ( ), d-spacings (Å) and/or relative peak intensities.

Since some margin of error is possible in the assignment of 2 theta angles and d-spacings, the preferred method of comparing XRD patterns in order to identify a particular form of a sample is to overlay the XRD pattern of the unknown sample over the XRD pattern of a known form. For example, one skilled in the art can overlay an XRD pattern of an unknown sample of Example No. 58, obtained using the methods described herein, over FIG. 1 and, using expertise and knowledge in the art, readily determine whether the XRD pattern of the unknown sample is substantially the same as the XRD pattern of Form 1 of Example No. 58. If the XRD pattern is substantially the same as FIG. 1, the previously unknown form can be readily and accurately identified as Form 1 of Example No. 58. The same method may be used to compare a sample of an unknown form of Example Nos. 64 and 65 with FIGS. 3 and 5.

Although 2 theta angles or d-spacings are the primary method of identifying a particular crystalline form, it may be desirable to also compare relative peak intensities. As noted above, relative peak intensities may vary depending upon the specific diffractometer employed and the analyst's sample preparation technique. The peak intensities are reported as intensities relative to the peak intensity of the strongest peak. The intensity units on the XRD are counts/sec. The absolute counts=counts/time×count time=counts/sec×10 sec.

Differential Scanning Calorimetry of Form 1 of Example Nos. 58, 64 and 65.

Figure 4:
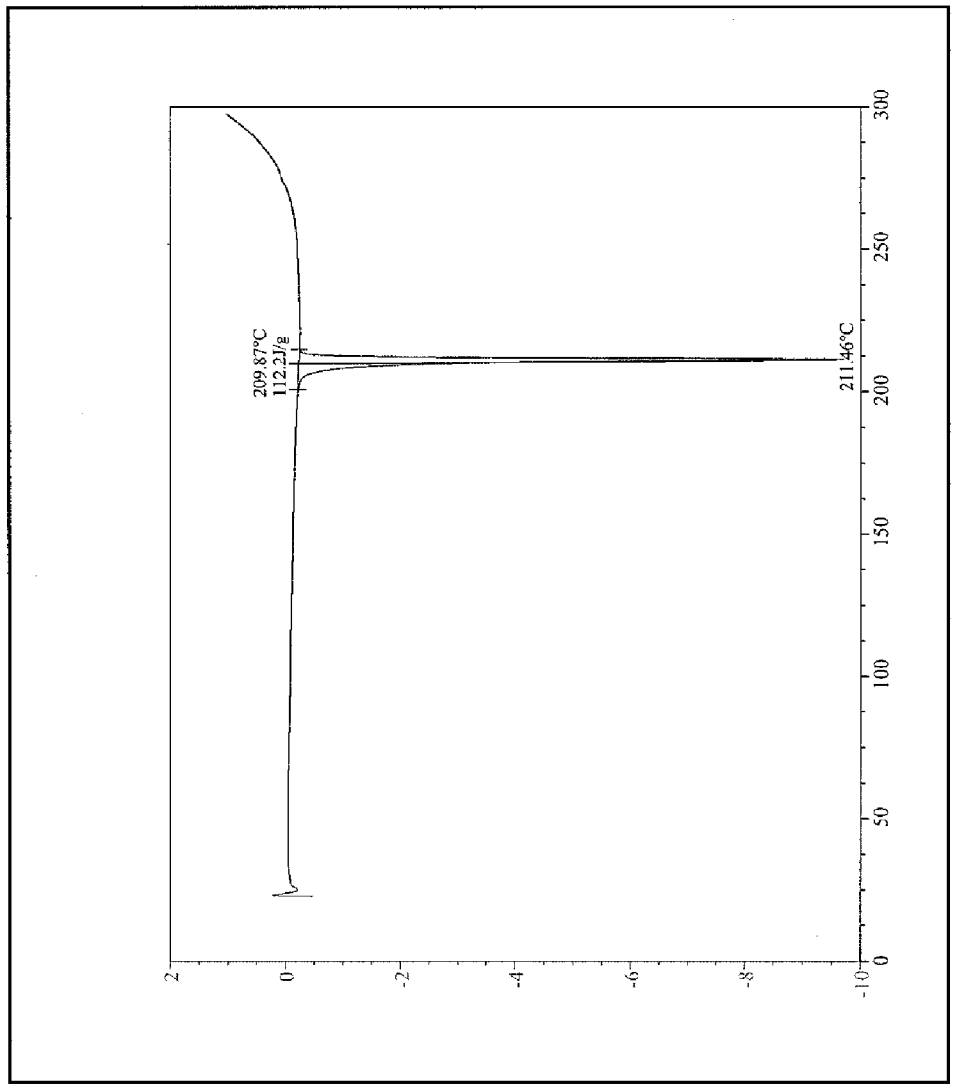
FIG. 4 is a differential scanning calorimetry (DSC) thermogram of a particular solid state form of N-{3-[5-(2-amino-4-pyrimidinyl)-2-(tetrahydro-2H-pyran-4-yl)-1,3-thiazol-4-yl]-2-fluorophenyl}-2,6-difluorobenzenesulfonamide. The DSC was carried out on a TA Instruments DSC Q100 system at a heating rate of 10° C. per minute, using a sample size of 0.4-1.5 mg, according to the procedures described herein.
Figure 5:
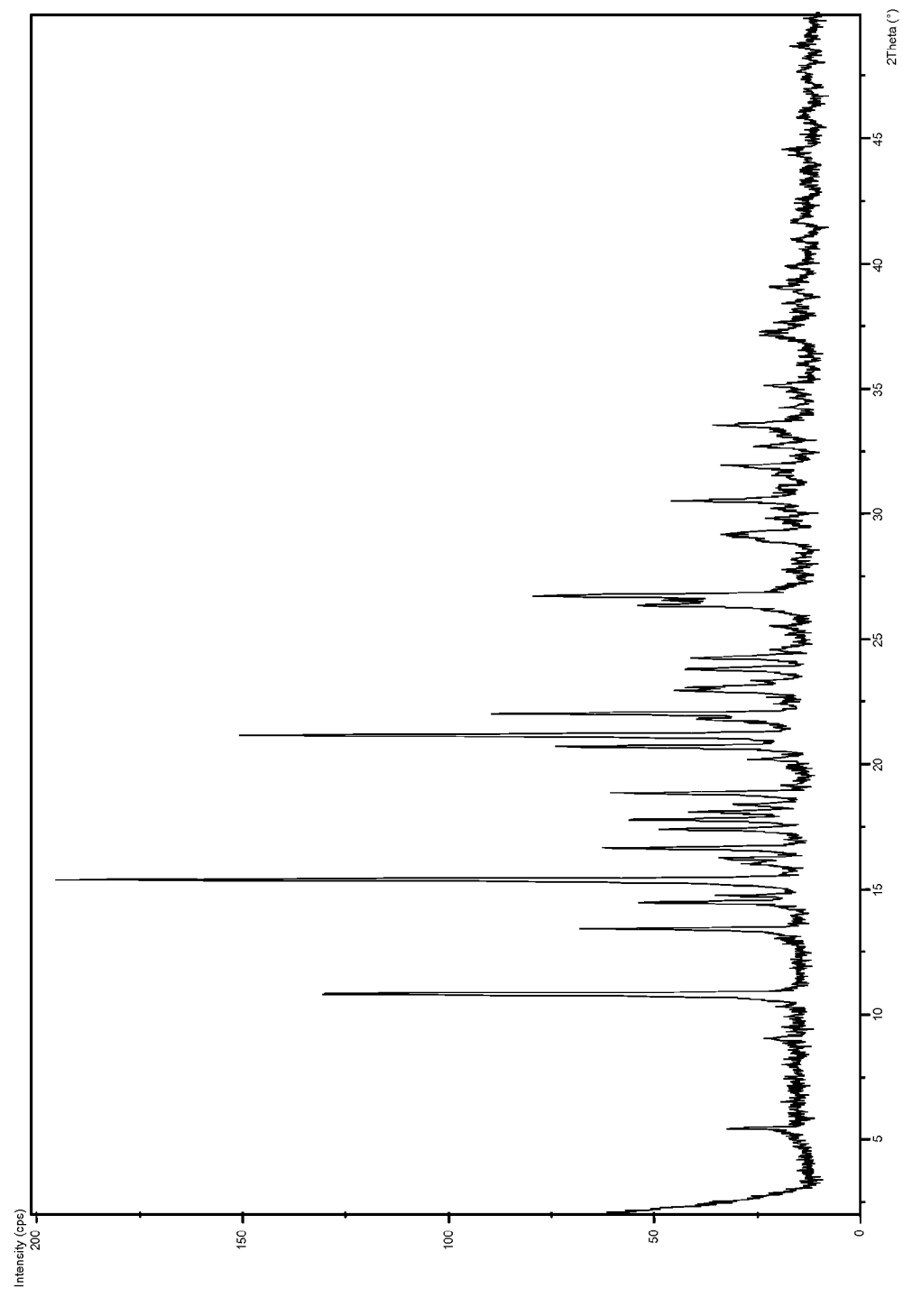
FIG. 5 is a is an X-Ray Powder Diffraction Pattern of a particular solid state form of N-{3-[2-(1,1-dimethylethyl)-5-(2-methyl-4-pyrimidinyl)-1,3-thiazol-4-yl]-2-fluorophenyl}-2,5-difluorobenzenesulfonamide. The XRD pattern is expressed in terms of 2 theta angles and obtained with a PANalytical diffractometer equipped with a diffracted beam nickel filter using copper Kα X-radiation, according to the procedures described herein.
Figure 6:
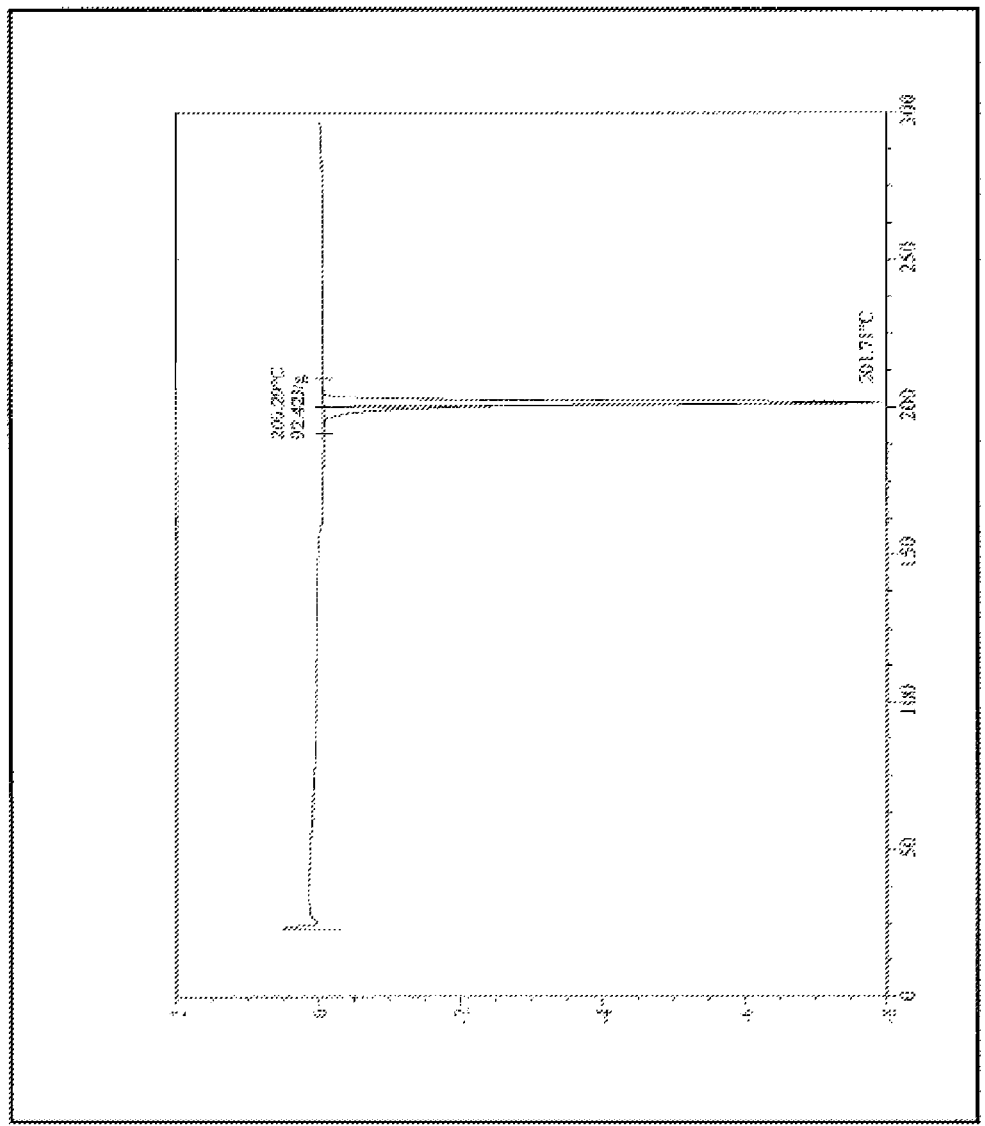
FIG. 6 is a differential scanning calorimetry (DSC) thermogram of a particular solid state form of N-{3-[2-(1,1-dimethylethyl)-5-(2-methyl-4-pyrimidinyl)-1,3-thiazol-4-yl]-2-fluorophenyl}-2,5-difluorobenzenesulfonamide. The DSC was carried out on a TA Instruments DSC Q100 system at a heating rate of 10° C. per minute, using a sample size of 0.4-1.5 mg, according to the procedures described herein.

Differential scanning calorimetry was carried out on TA Instruments DSC Q100 DSC system. Heating rate of 10° C. per minute. Sample size 0.4-1.5 mg. The thermograms are provided at FIGS. 2, 4, and 6, respectively.

As an additional aspects, the present invention provides a particular solid state form, identified as "Form 1" of N-{3-[5-(2-amino-4-pyrimidinyl)-2-(1,1-dimethylethyl)-1,3-thiazol-4-yl]-2-fluorophenyl}-2,6-difluorobenzenesulfonamide; a particular solid state form identified as "Form 1" of N-{3-[5-(2-amino-4-pyrimidinyl)-2-(tetrahydro-2H-pyran-4-yl)-1,3-thiazol-4-yl]-2-fluorophenyl}-2,6-difluorobenzenesulfonamide; and a particular solid state form identified as "Form 1" of N-{3-[2-(1,1-dimethylethyl)-5-(2-methyl-4-pyrimidinyl)-1,3-thiazol-4-yl]-2-fluorophenyl}-2,5-difluorobenzenesulfonamide.

That which is claimed is:

1. A compound of formula

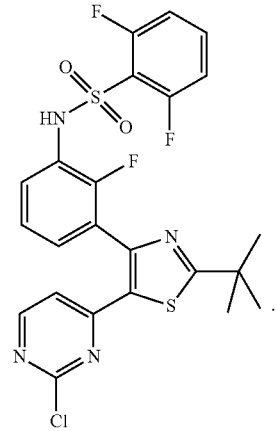 [SMILES: CC(C)(C)c1nc(-c2cccc(NS(=O)(=O)c3c(F)cccc3F)c2F)c(-c2ccnc(Cl)n2)s1]

* * * * *